US012760006B2

United States Patent

Park et al.

(12) United States Patent
(10) Patent No.: US 12,760,006 B2
(45) Date of Patent: Oct. 13, 2026

(54) HETEROCYCLIC COMPOUND, ORGANIC LIGHT EMITTING DEVICE COMPRISING THE SAME AND COMPOSITION FOR ORGANIC MATERIAL LAYER OF ORGANIC LIGHT EMITTING DEVICE

(71) Applicant: LT MATERIALS CO., LTD., Yongin-City (KR)

(72) Inventors: Seong-Jong Park, Yongin-City (KR); Hyung-Keun Jang, Yongin-City (KR); Young-Seok No, Yongin-City (KR); Dong-Jun Kim, Yongin-City (KR)

(73) Assignee: LT MATERIALS CO., LTD., Yongin-City (KE)

(*) Notice: Subject to any disclaimer, the term of this patent is extended or adjusted under 35 U.S.C. 154(b) by 1106 days.

(21) Appl. No.: 17/639,024

(22) PCT Filed: Sep. 9, 2021

(86) PCT No.: PCT/KR2021/012272

§ 371 (c)(1),
(2) Date: Feb. 28, 2022

(87) PCT Pub. No.: WO2022/065761

PCT Pub. Date: Mar. 31, 2022

(65) Prior Publication Data

US 2023/0165145 A1 May 25, 2023

(30) Foreign Application Priority Data

Sep. 28, 2020 (KR) ........................ 10-2020-0125761

(51) Int. Cl.

*C07D 405/10* (2006.01)
*C07D 209/82* (2006.01)
(Continued)

(52) U.S. Cl.

CPC ......... *C07D 405/10* (2013.01); *C07D 209/82* (2013.01); *C07D 405/04* (2013.01);
(Continued)

(58) Field of Classification Search

CPC ................ C07D 405/04; C07D 405/10; C07D 405/14; C07D 409/04; C07D 409/10;
(Continued)

(56) References Cited

U.S. PATENT DOCUMENTS 4,356,429 A 10/1982 Tang
9,397,307 B2 7/2016 Nishimura et al.
(Continued)

FOREIGN PATENT DOCUMENTS

CN 110642724 A 1/2020
CN 110724088 A * 1/2020
(Continued)

OTHER PUBLICATIONS

Kuwabara et al., "Thermally Stable Multilayered Organic Electroluminescent Devices Using Novel Starburst Molecules, 4,4'4"-Tri(N-carbazolyl)triphenylamine (TCTA) and 4,4',4"-Tris(3-methylphenylamino)triphenylamine (m-MTDATA), as Hole-Transport Materials", Advanced Materials, vol. 6, No. 9, 1994, pp. 677-679.
(Continued)

*Primary Examiner* — Vu A Nguyen
(74) *Attorney, Agent, or Firm* — The PL Law Group, PLLC

(57) ABSTRACT

The present specification relates to a heterocyclic compound represented by Chemical Formula 1, and an organic light emitting device and a composition for an organic material layer comprising the same.

12 Claims, 5 Drawing Sheets

(51) Int. Cl.

| | |
|---|---|
| ***C07D 405/04*** | (2006.01) |
| ***C07D 405/14*** | (2006.01) |
| ***C07D 409/04*** | (2006.01) |
| ***C07D 409/10*** | (2006.01) |
| ***C07D 409/14*** | (2006.01) |
| ***C07F 7/08*** | (2006.01) |
| ***H10K 50/11*** | (2023.01) |
| ***H10K 50/16*** | (2023.01) |
| ***H10K 71/16*** | (2023.01) |
| ***H10K 85/40*** | (2023.01) |
| ***H10K 85/60*** | (2023.01) |

(52) U.S. Cl.

CPC ......... *C07D 405/14* (2013.01); *C07D 409/04* (2013.01); *C07D 409/10* (2013.01); *C07D 409/14* (2013.01); *C07F 7/0812* (2013.01); *H10K 50/11* (2023.02); *H10K 50/16* (2023.02); *H10K 71/164* (2023.02); *H10K 85/40* (2023.02); *H10K 85/622* (2023.02); *H10K 85/654* (2023.02); *H10K 85/6572* (2023.02); *H10K 85/6574* (2023.02); *H10K 85/6576* (2023.02); *C07B 2200/05* (2013.01)

(58) Field of Classification Search

CPC ................ C07D 409/14; C07D 251/24; C07B 2200/05; H10K 85/6574; H10K 85/6576; H10K 85/654

See application file for complete search history.

(56) References Cited

U.S. PATENT DOCUMENTS

| | | | | |
|---|---|---|---|---|
| 10,505,121 | B2 | 12/2019 | Song et al. | |
| 2017/0054087 | A1 | 2/2017 | Zeng et al. | |
| 2018/0337348 | A1 | 11/2018 | Jung et al. | |
| 2019/0013490 | A1 | 1/2019 | Cho et al. | |
| 2019/0058131 | A1 | 2/2019 | Cho et al. | |
| 2019/0198772 | A1 | 6/2019 | Lui et al. | |
| 2019/0214570 | A1 | 7/2019 | Inayama et al. | |
| 2020/0161560 | A1 | 5/2020 | Jang et al. | |
| 2020/0168804 | A1* | 5/2020 | Song | H10K 85/636 |
| 2020/0203631 | A1 | 6/2020 | Gao et al. | |
| 2021/0009894 | A1 | 1/2021 | Ha et al. | |
| 2021/0028370 | A1* | 1/2021 | Mun | C07D 409/14 |
| 2021/0184129 | A1* | 6/2021 | Mun | C07D 405/14 |
| 2021/0184131 | A1 | 6/2021 | Jung et al. | |
| 2021/0340103 | A1* | 11/2021 | Mun | H10K 85/624 |
| 2022/0006022 | A1* | 1/2022 | Suh | H10K 85/6574 |
| 2022/0020932 | A1 | 1/2022 | Yun et al. | |
| 2022/0085300 | A1* | 3/2022 | Kim | C07D 409/14 |
| 2022/0298147 | A1 | 9/2022 | Yoshida et al. | |
| 2022/0306616 | A1 | 9/2022 | Suh et al. | |
| 2022/0359831 | A1 | 11/2022 | Kushida et al. | |
| 2022/0380387 | A1* | 12/2022 | Shiomi | C07D 413/10 |
| 2022/0384744 | A1 | 12/2022 | Lee et al. | |
| 2023/0117383 | A1 | 4/2023 | Kim et al. | |
| 2023/0172065 | A1* | 6/2023 | Park | C07D 487/04 257/40 |
| 2023/0172085 | P1 | 6/2023 | Bouchet et al. | |
| 2023/0263054 | A1 | 8/2023 | Hwang et al. | |
| 2024/0083878 | A1 | 3/2024 | Jung et al. | |
| 2024/0172560 | A1 | 5/2024 | Lee et al. | |
| 2024/0251668 | A1 | 7/2024 | Jung et al. | |

FOREIGN PATENT DOCUMENTS

| | | | | | |
|---|---|---|---|---|---|
| CN | 111354853 | A | | 6/2020 | |
| CN | 114206658 | A | | 3/2022 | |
| CN | 115398661 | A | | 11/2022 | |
| CN | 115804268 | A | | 3/2023 | |
| EP | 3 415 585 | A1 | | 12/2018 | |
| EP | 3 643 762 | A1 | | 4/2020 | |
| JP | 2014-157947 | A | | 8/2014 | |
| JP | 2022-183109 | A | | 12/2022 | |
| JP | 2024-500696 | A | | 1/2024 | |
| JP | 2024-504057 | A | | 1/2024 | |
| JP | 2024-504543 | A | | 2/2024 | |
| KR | 10-2018-0010130 | A | | 1/2018 | |
| KR | 10-2018-0055679 | A | | 5/2018 | |
| KR | 10-1857632 | B1 | | 5/2018 | |
| KR | 10-2018-0060991 | A | | 6/2018 | |
| KR | 10-2018-0112962 | A | | 10/2018 | |
| KR | 10-2019-0000185 | A | | 1/2019 | |
| KR | 10-2019-0086347 | A | | 7/2019 | |
| KR | 10-2019-0103765 | A | | 9/2019 | |
| KR | 10-2054806 | B1 | | 12/2019 | |
| KR | 2054806 | B1 | * | 12/2019 | C07D 487/04 |
| KR | 10-2020-0026083 | A | | 3/2020 | |
| KR | 10-2020-0056589 | A | | 5/2020 | |
| KR | 10-2020-0088172 | A | | 7/2020 | |
| KR | 20210053695 | A | * | 5/2021 | C07D 409/14 |
| KR | 10-2021-0080184 | A | | 6/2021 | |
| KR | 20210080184 | A | † | 6/2021 | |
| KR | 10-2021-0086524 | A | | 7/2021 | |
| KR | 10-2021-0100103 | A | | 8/2021 | |
| KR | 10-2021-0115596 | A | | 9/2021 | |
| KR | 10-2022-0009351 | A | | 1/2022 | |
| KR | 10-2022-0010455 | A | | 1/2022 | |
| KR | 20220010455 | A | † | 1/2022 | |
| KR | 10-2022-0015980 | A | | 2/2022 | |
| WO | WO 2019/117440 | A1 | | 6/2019 | |
| WO | WO 2019/231226 | A1 | | 12/2019 | |
| WO | WO 2020/022860 | A1 | | 1/2020 | |
| WO | WO 2020/235955 | A1 | | 11/2020 | |
| WO | WO 2021/033724 | A1 | | 2/2021 | |
| WO | WO 2021/033730 | A1 | | 2/2021 | |
| WO | WO 2021/033731 | A1 | | 2/2021 | |
| WO | WO 2021/125552 | A1 | | 6/2021 | |

OTHER PUBLICATIONS

Japanese Office Action for Japanese Application No. 2024-005632, dated Jan. 21, 2025, with an English translation.

Extended European Search Report for European Application No. 21872791.5, dated Oct. 8, 2024.

Partial Supplementary European Search Report for European Application No. 21854794.1, dated Oct. 7, 2024.

Japanese Office Action for Japanese Application No. 2024-005632, dated Jun. 24, 2025, with English translation.

Office action issued on Apr. 17, 2026 from Korean Patent Office in a counterpart Korean Patent Application No. 10-2023-0004789 (all the cited references are listed in this IDS.) (English translation is also submitted herewith.).

* cited by examiner
† cited by third party

【FIG. 1】
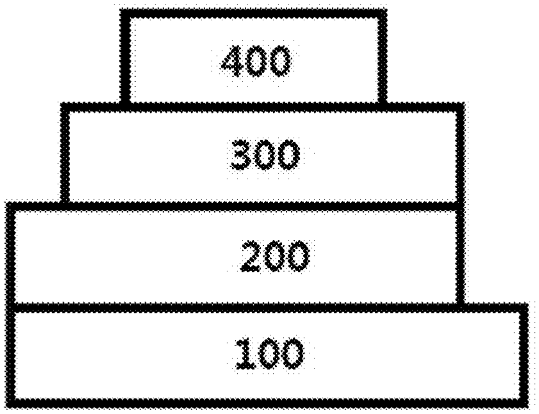
【FIG. 2】
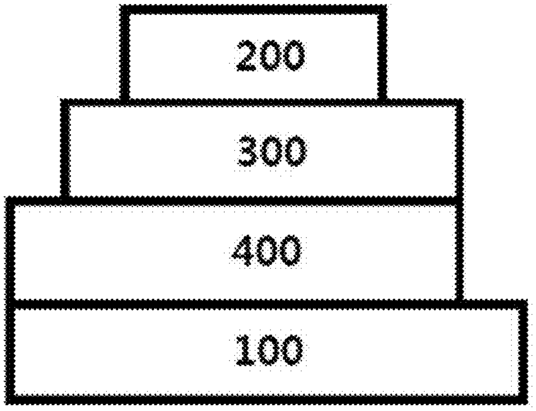

【FIG. 3】
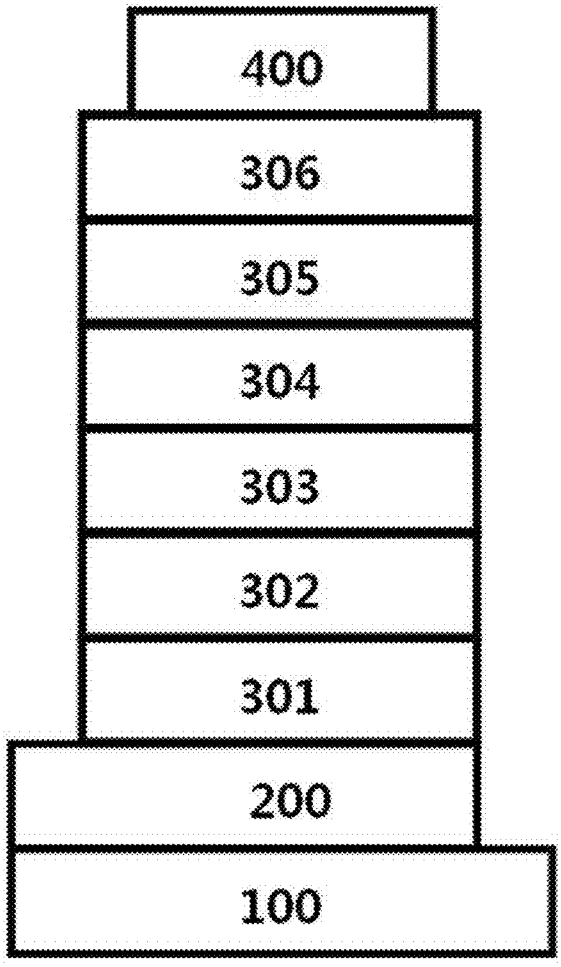

【FIG. 4】
| HOMO Electronic Distribution | LUMO Electronic Distribution |
| --- | --- |
| 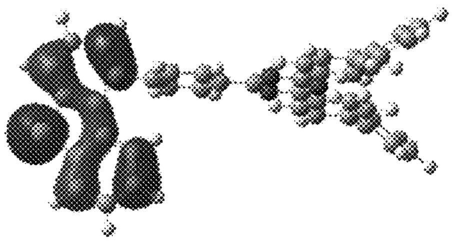 | 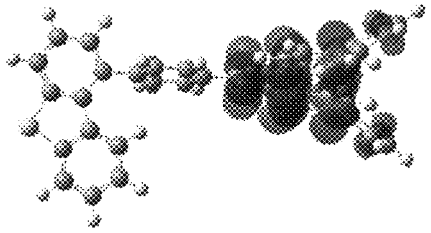 |

【FIG. 5】
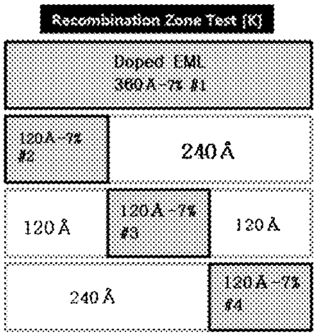
- IVL DATA [K]
| Sample | Op. V (V) | EL Eff. (cd/A) | x | y | $T_{95\%}$ |
|---|---|---|---|---|---|
| #1(Ref.) | 100% | 100% | 0.260 | 0.708 | 100% |
| #2 | 100% | 99% | 0.251 | 0.714 | 80% |
| #3 | 98% | 93% | 0.252 | 0.713 | 70% |
| #4 | 96% | 84% | 0.252 | 0.713 | 30% |
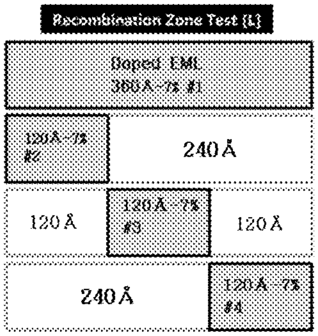
- IVL DATA [L]
| Sample | Op. V (V) | EL Eff. (cd/A) | x | y | $T_{95\%}$ |
|---|---|---|---|---|---|
| #1(Ref.) | 100% | 100% | 0.248 | 0.718 | 100% |
| #2 | 100% | 98% | 0.238 | 0.723 | 70% |
| #3 | 97% | 88% | 0.244 | 0.718 | 55% |
| #4 | 94% | 82% | 0.246 | 0.717 | 25% |
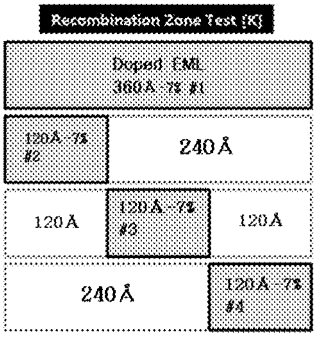
- IVL DATA [K]
| Sample | Op. V (V) | EL Eff. (cd/A) | x | y | $T_{95\%}$ |
|---|---|---|---|---|---|
| #1(Ref.) | 100% | 100% | 0.260 | 0.708 | 100% |
| #2 | 100% | 99% | 0.251 | 0.714 | 80% |
| #3 | 98% | 93% | 0.252 | 0.713 | 70% |
| #4 | 96% | 84% | 0.252 | 0.713 | 30% |
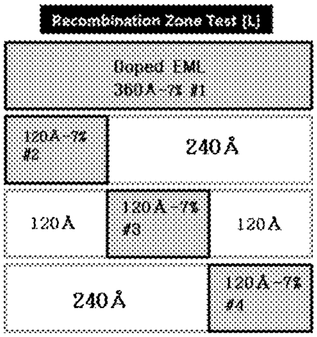
- IVL DATA [L]
| Sample | Op. V (V) | EL Eff. (cd/A) | x | y | $T_{95\%}$ |
|---|---|---|---|---|---|
| #1(Ref.) | 100% | 100% | 0.248 | 0.716 | 100% |
| #2 | 100% | 98% | 0.239 | 0.723 | 70% |
| #3 | 97% | 89% | 0.244 | 0.718 | 53% |
| #4 | 94% | 82% | 0.246 | 0.717 | 25% |

【FIG. 6】
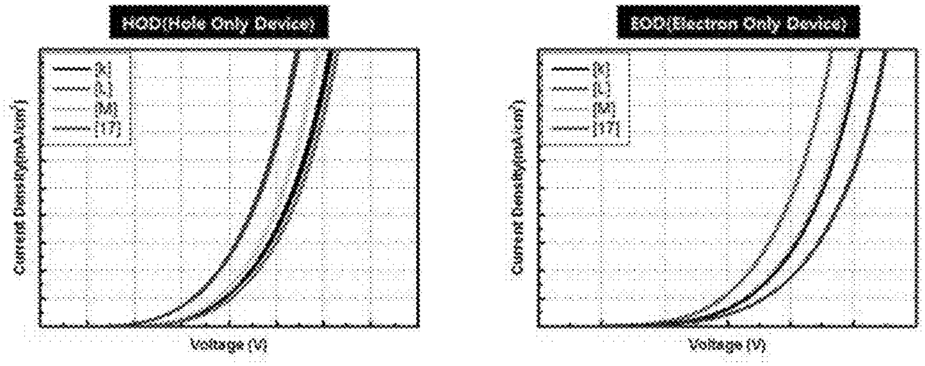

HETEROCYCLIC COMPOUND, ORGANIC LIGHT EMITTING DEVICE COMPRISING THE SAME AND COMPOSITION FOR ORGANIC MATERIAL LAYER OF ORGANIC LIGHT EMITTING DEVICE

TECHNICAL FIELD

This application claims priority to and the benefits of Korean Patent Application No. 10-2020-0125761, filed with the Korean Intellectual Property Office on Sep. 28, 2020, the entire contents of which are incorporated herein by reference.

The present specification relates to a heterocyclic compound, an organic light emitting device comprising the same, and a composition for an organic material layer.

BACKGROUND ART

An organic electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of forming a light emitting layer themselves alone may be used, or compounds capable of performing a role of a host or a dopant of a host-dopant-based light emitting layer may also be used. In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifetime or efficiency of an organic light emitting device.

PRIOR ART DOCUMENTS

Patent Documents

U.S. Pat. No. 4,356,429

DISCLOSURE

Technical Problem

The present disclosure is directed to providing a heterocyclic compound, an organic light emitting device comprising the same, and a composition for an organic material layer.

Technical Solution

One embodiment of the present application provides a heterocyclic compound represented by the following Chemical Formula 1.

[Chemical Formula 1]

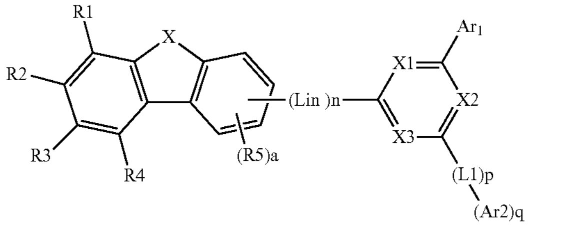

In Chemical Formula 1,

X is O; or S,

R1 to R5 are the same as or different from each other, and each independently selected from the group consisting of hydrogen; deuterium; halogen; a cyano group; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; —SiRR'R"; —P(═O)RR'; and —NRR', or two or more groups adjacent to each other bond to each other to form a substituted or unsubstituted aromatic hydrocarbon ring or a substituted or unsubstituted heteroring, X1 to X3 are N; or CRe, and at least one of X1 to X3 is N, L1 is a direct bond; a substituted or unsubstituted C6 to C60 arylene group; or a substituted or unsubstituted C2 to C60 heteroarylene group, Ar1 and Ar2 are the same as or different from each other, and each independently a substituted or unsubstituted C1 to C60 alkyl group; a substituted or unsubstituted C6 to C60 aryl group; or a substituted or unsubstituted C2 to C60 heteroaryl group, Lin is a substituted or unsubstituted C6 to C20 arylene group, Chemical Formula 1 has a deuterium content of greater than or equal to 20% and less than or equal to 100%, R, R', R" and Re are the same as or different from each other, and each independently hydrogen; deuterium; a substituted or unsubstituted C1 to C60 alkyl group; or a substituted or unsubstituted C6 to C60 aryl group, a and p are an integer of 0 to 3, q is an integer of 1 to 5, n is an integer of 0 to 2, and when n is an integer of 2 or p, a and q are 2 or greater, substituents in the parentheses are the same as or different from each other.

In addition, one embodiment of the present application provides an organic light emitting device comprising a first electrode; a second electrode provided opposite to the first electrode; and one or more organic material layers provided between the first electrode and the second electrode, wherein one or more layers of the organic material layers comprise the heterocyclic compound represented by Chemical Formula 1.

In addition, in the organic light emitting device provided in one embodiment of the present application, the organic material layer comprising the heterocyclic compound of Chemical Formula 1 further comprises a heterocyclic compound represented by the following Chemical Formula 2.

[Chemical Formula 2]

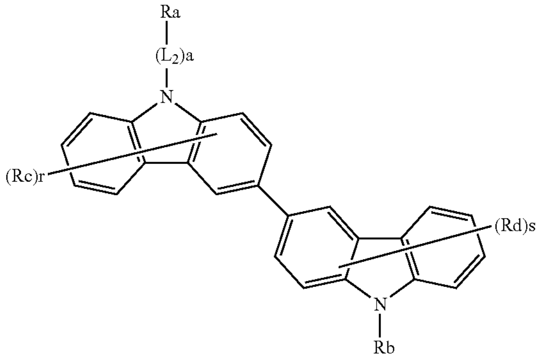

In Chemical Formula 2,

Rc and Rd are the same as or different from each other, and each independently selected from the group consisting of hydrogen; deuterium; halogen; a cyano group; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; —SiRR'R"; —P(═O)RR'; and —NRR', or two or more groups adjacent to each other bond to each other to form a substituted or unsubstituted aromatic hydrocarbon ring or a substituted or unsubstituted heteroring, L2 is a direct bond; a substituted or unsubstituted C6 to C60 arylene group; or a substituted or unsubstituted C2 to C60 heteroarylene group, Ra and Rb are the same as or different from each other, and each independently —CN; —SiRR'R"; a substituted or unsubstituted C6 to C60 aryl group; or a substituted or unsubstituted C2 to C60 heteroaryl group, R, R' and R" are the same as or different from each other, and each independently hydrogen; deuterium; a substituted or unsubstituted C1 to C60 alkyl group; or a substituted or unsubstituted C6 to C60 aryl group, a is an integer of 0 to 4, r and s are an integer of 0 to 7, and when a, s and r are 2 or greater, substituents in the parentheses are the same as or different from each other.

In addition, another embodiment of the present application provides a composition for an organic material layer of an organic light emitting device, the composition comprising the heterocyclic compound represented by Chemical Formula 1 and the heterocyclic compound represented by Chemical Formula 2.

Lastly, one embodiment of the present application provides a method for manufacturing an organic light emitting device, the method comprising preparing a substrate; forming a first electrode on the substrate; forming one or more organic material layers on the first electrode; and forming a second electrode on the organic material layers, wherein the foaming of organic material layers comprises forming one or more organic material layers using the composition for an organic material layer according to one embodiment of the present application.

Advantageous Effects

A heterocyclic compound according to one embodiment of the present application can be used as a material of an organic material layer of an organic light emitting device. The heterocyclic compound can be used as a material of a hole injection layer, a hole transfer layer, a light emitting layer, an electron transfer layer, an electron injection layer, a charge generation layer or the like in an organic light emitting device.

Specifically, the heterocyclic compound of Chemical Formula 1 is particularly effective when used as a light emitting layer host since HOMO is localized on dibenzofuran and dibenzothiophene effectively stabilizing holes, and LUMO is localized on an azine-based substituent effectively stabilizing electrons.

In addition, the heterocyclic compound represented by Chemical Formula 1 and the heterocyclic compound represented by Chemical Formula 2 can be used as a material of a light emitting layer of an organic light emitting device at the same time. In addition, using the heterocyclic compound represented by Chemical Formula 1 and the heterocyclic compound represented by Chemical Formula 2 at the same time in an organic light emitting device is capable of reducing a driving voltage of the device, enhancing light efficiency, and enhancing lifetime properties of the device by thermal stability of the compound.

Particularly, the heterocyclic compound represented by Chemical Formula 1 has a phenylene linking group in the core structure of dibenzofuran or dibenzothiophene and has an azine-based substituent, which strengthens n-type properties, and, by comprising the heterocyclic compound represented by Chemical Formula 2 corresponding to biscarbazoles having a specific substituent, the driving voltage can be reduced, and efficiency and lifetime can be maximized.

DESCRIPTION OF DRAWINGS

FIG. 1 to FIG. 3 are diagrams each schematically illustrating a lamination structure of an organic light emitting device according to one embodiment of the present application.

FIG. 4 is a diagram showing HOMO and LUMO distribution maps.

FIG. 5 and FIG. 6 are diagrams relating to identifying a recombination zone in an OLED.

REFERENCE NUMERAL

100: Substrate
200: Anode
300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode

MODE FOR DISCLOSURE

Hereinafter, the present application will be described in detail.

A term "substitution" means a hydrogen atom bonding to a carbon atom of a compound being changed to another substituent, and the position of substitution is not limited as long as it is a position at which the hydrogen atom is substituted, that is, a position at which a substituent is capable of substituting, and when two or more substituents substitute, the two or more substituents may be the same as or different from each other.

In the present specification, "substituted or unsubstituted" means being substituted with one or more substituents selected from the group consisting of deuterium; a cyano group; a halogen group; a C1 to C60 alkyl group; a C2 to C60 alkenyl group; a C2 to C60 alkynyl group; a C3 to C60 cycloalkyl group; a C2 to C60 heterocycloalkyl group; a C6 to C60 aryl group; a C2 to C60 heteroaryl group; a silyl group; a phosphine oxide group; and an amine group or being unsubstituted, or being substituted with a substituent linking two or more substituents selected from among the substituents illustrated above or being unsubstituted.

In the present specification, a "case of a substituent being not indicated in a chemical formula or compound structure" means that a hydrogen atom bonds to a carbon atom. However, since deuterium ($^2H$) is an isotope of hydrogen, some hydrogen atoms may be deuterium.

In one embodiment of the present application, a "case of a substituent being not indicated in a chemical formula or compound structure" may mean that positions that may come as a substituent may all be hydrogen or deuterium. In other words, since deuterium is an isotope of hydrogen, some hydrogen atoms may be deuterium that is an isotope, and herein, a content of the deuterium may be from 0% to 100%.

In one embodiment of the present application, in a "case of a substituent being not indicated in a chemical formula or compound structure", hydrogen and deuterium may be mixed in compounds when deuterium is not explicitly excluded such as a deuterium content being 0% or a hydrogen content being 100%. In other words, an expression of "substituent X is hydrogen" does not exclude deuterium unlike a hydrogen content being 100% or a deuterium content being 0%, and therefore, may mean a state in which hydrogen and deuterium are mixed.

In one embodiment of the present application, deuterium is one of isotopes of hydrogen, is an element having deuteron formed with one proton and one neutron as a nucleus, and may be expressed as hydrogen-2, and the elemental symbol may also be written as D or $^2H$.

In one embodiment of the present application, an isotope means an atom with the same atomic number (Z) but with a different mass number (A), and may also be interpreted as an element with the same number of protons but with a different number of neutrons.

In one embodiment of the present application, a meaning of a content T % of a specific substituent may be defined as T2/T1×100=T % when the total number of substituents that a basic compound may have is defined as T1, and the number of specific substituents among these is defined as T2.

In other words, in one example, having a deuterium content of 20% in a phenyl group represented by

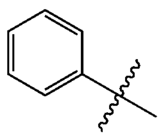 [SMILES: *c1ccccc1]

means that the total number of substituents that the phenyl group may have is 5 (T1 in the formula), and the number of deuterium among these is 1 (T2 in the formula). In other words, having a deuterium content of 20% in a phenyl group may be represented by the following structural formulae.

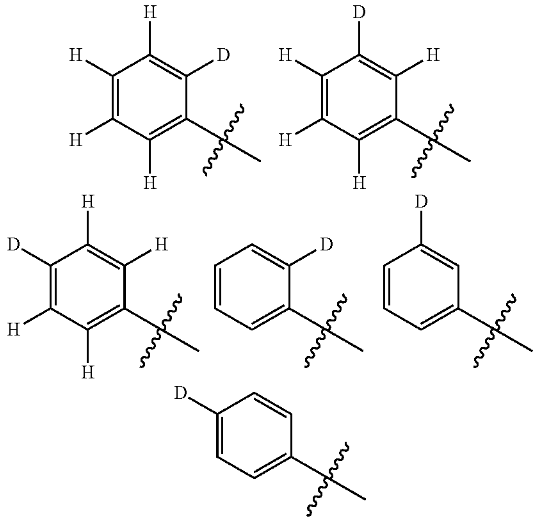

In addition, in one embodiment of the present application, "a phenyl group having a deuterium content of 0%" may mean a phenyl group that does not comprise a deuterium atom, that is, a phenyl group that has 5 hydrogen atoms.

In the present specification, the halogen may be fluorine, chlorine, bromine or iodine.

In the present specification, the alkyl group comprises linear or branched having 1 to 60 carbon atoms, and may be further substituted with other substituents. The number of carbon atoms of the alkyl group may be from 1 to 60, specifically from 1 to 40 and more specifically from 1 to 20. Specific examples thereof may comprise a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethyl-butyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 4-methylhexyl group, a 5-methylhexyl group and the like, but are not limited thereto.

In the present specification, the alkenyl group comprises linear or branched having 2 to 60 carbon atoms, and may be further substituted with other substituents. The number of carbon atoms of the alkenyl group may be from 2 to 60, specifically from 2 to 40 and more specifically from 2 to 20. Specific examples thereof may comprise a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenyl-vinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group comprises linear or branched having 2 to 60 carbon atoms, and may be further substituted with other substituents. The number of carbon atoms of the alkynyl group may be from 2 to 60, specifically from 2 to 40 and more specifically from 2 to 20.

In the present specification, the alkoxy group may be linear, branched or cyclic. The number of carbon atoms of the alkoxy group is not particularly limited, but is preferably from 1 to 20. Specific examples thereof may comprise methoxy, ethoxy, n-propoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the cycloalkyl group comprises a monocyclic or polycyclic aryl group having 3 to 60 carbon atoms, and may be further substituted with other substituents. Herein, the polycyclic means a group in which the cycloalkyl group is directly linked to or fused with other cyclic groups. Herein, the other cyclic groups may be a cycloalkyl group, but may also be different types of cyclic groups such as a heterocycloalkyl group, an aryl group and a heteroaryl group. The number of carbon groups of the cycloalkyl group may be from 3 to 60, specifically from 3 to 40 and more specifically from 5 to 20. Specific examples thereof may comprise a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the heterocycloalkyl group comprises O, S, Se, N or Si as a heteroatom, comprises monocyclic or polycyclic having 2 to 60 carbon atoms, and may be further substituted with other substituents. Herein, the polycyclic means a group in which the heterocycloalkyl group is directly linked to or fused with other cyclic groups. Herein, the other cyclic groups may be a heterocycloalkyl group, but may also be different types of cyclic groups such as a cycloalkyl group, an aryl group and a heteroaryl group. The number of carbon atoms of the heterocycloalkyl group may be from 2 to 60, specifically from 2 to 40 and more specifically from 3 to 20.

In the present specification, the aryl group comprises monocyclic or polycyclic having 6 to 60 carbon atoms, and may be further substituted with other substituents. Herein, the polycyclic means a group in which the aryl group is directly linked to or fused with other cyclic groups. Herein, the other cyclic groups may be an aryl group, but may also be different types of cyclic groups such as a cycloalkyl group, a heterocycloalkyl group and a heteroaryl group. The aryl group comprises a spiro group. The number of carbon atoms of the aryl group may be from 6 to 60, specifically from 6 to 40 and more specifically from 6 to 25. Specific examples of the aryl group may comprise a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused ring group thereof, and the like, but are not limited thereto.

In the present specification, the fluorenyl group may be substituted, and adjacent substituents may bond to each other to form a ring.

When the fluorenyl group is substituted,

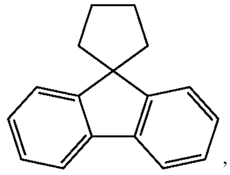
,
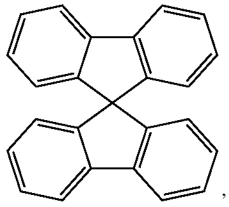
,
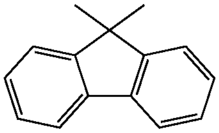
,
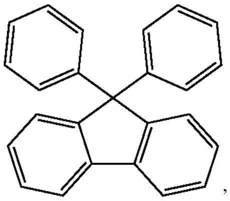
,
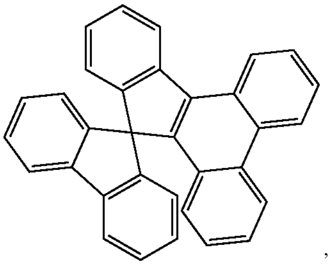
,
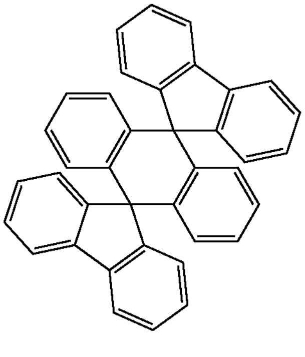

and the like may be included, however, the structure is not limited thereto.

In the present specification, the heteroaryl group comprises S, O, Se, N or Si as a heteroatom, comprises monocyclic or polycyclic having 2 to 60 carbon atoms, and may be further substituted with other substituents. Herein, the polycyclic means a group in which the heteroaryl group is directly linked to or fused with other cyclic groups. Herein, the other cyclic groups may be a heteroaryl group, but may also be different types of cyclic groups such as a cycloalkyl group, a heterocycloalkyl group and an aryl group. The number of carbon atoms of the heteroaryl group may be from 2 to 60, specifically from 2 to 40 and more specifically from 3 to 25. Specific examples of the heteroaryl group may comprise a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a triazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a triazinyl group, a dioxynyl group, a triazinyl group, a tetrazinyl group, a quinolyl group, an isoquinolyl group, a quinazolinyl group, an isoquinazolinyl group, a qninozolinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), a dihydrophenazinyl group, a phenoxazinyl group, a phenanthridyl group, an imidazopyridinyl group, a thienyl group, an indolo[2,3-a]carbazolyl group, an indolo[2,3-b]carbazolyl group, an indolinyl group, a 10,11-dihydrodibenzo[b,f]azepine group, a 9,10-dihydroacridinyl group, a phenanthrazinyl group, a phenothiathiazinyl group, a phthalazinyl group, a naphthylidinyl group, a phenanthrolinyl group, a benzo[c][1,2,5]thiadiazolyl group, a 5,10-dihydrobenzo[b,e][1,4]azasilinyl group, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group and the like, but are not limited thereto.

In the present specification, the amine group may be selected from the group consisting of a monoalkylamine group; a monoarylamine group; a monoheteroarylamine group; —$NH_2$; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may comprise a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, the arylene group means the aryl group having two bonding sites, that is, a divalent group. The descriptions on the aryl group provided above may be applied thereto except for those that are each a divalent group. In addition, the heteroarylene group means the heteroaryl group having two bonding sites, that is, a divalent group. The descriptions on the heteroaryl group provided above may be applied thereto except for those that are each a divalent group In the present specification, the phosphine oxide group is represented by —P(═O)R101R102, and R101 and R102 are the same as or different from each other and may be each independently a substituent formed with at least one of hydrogen; deuterium; a halogen group; an alkyl group; an alkenyl group; an alkoxy group; a cycloalkyl group; an aryl group; and a heterocyclic group. Specifically, the phosphine oxide group may be substituted with an aryl group, and as the aryl group, the examples described above may be used. Examples of the phosphine oxide group may comprise a diphenylphosphine oxide group, a dinaphthylphosphine oxide group and the like, but are not limited thereto.

In the present specification, the silyl group is a substituent comprising Si, having the Si atom directly linked as a radical, and is represented by —SiR104R105R106. R104 to R106 are the same as or different from each other, and may be each independently a substituent formed with at least one of hydrogen; deuterium; a halogen group; an alkyl group; an alkenyl group; an alkoxy group; a cycloalkyl group; an aryl group; and a heterocyclic group. Specific examples of the silyl group may comprise a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

As the aliphatic or aromatic hydrocarbon ring or heteroring that adjacent groups may form, the structures illustrated as the cycloalkyl group, the cycloheteroalkyl group, the aryl group and the heteroaryl group described above may be used except for those that are not a monovalent group.

One embodiment of the present application provides a heterocyclic compound represented by Chemical Formula 1.

In one embodiment of the present application, Chemical Formula 1 may be represented by any one of the following Chemical Formula 3 to Chemical Formula 7.

[Chemical Formula 3]

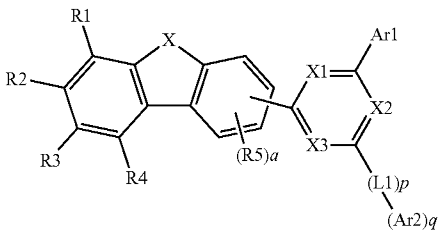

[Chemical Formula 4]

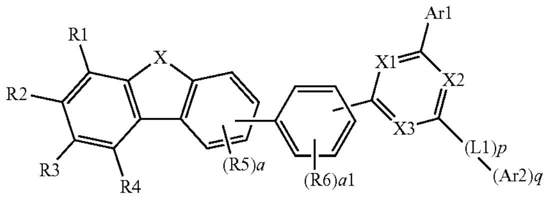

[Chemical Formula 5]

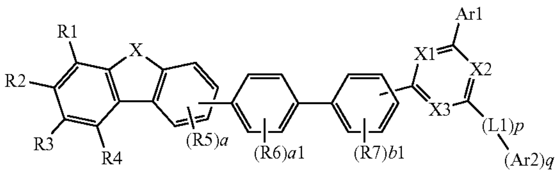

-continued

[Chemical Formula 6]

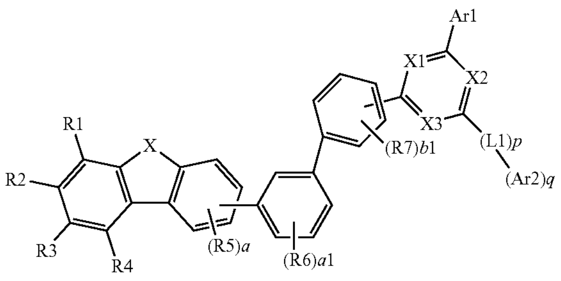

[Chemical Formula 7]

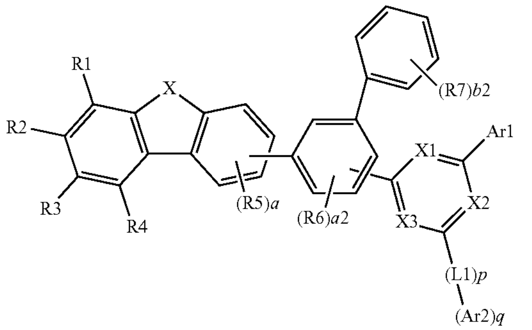

In Chemical Formulae 3 to 7,

X, R1 to R5, a, X1 to X3, Ar1, Ar2, L1, q and p have the same definitions as in Chemical Formula 1, R6 and R7 are the same as or different from each other, and each independently selected from the group consisting of hydrogen; deuterium; halogen; a cyano group; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; and a substituted or unsubstituted C2 to C60 heteroaryl group, or two or more groups adjacent to each other bond to each other to form a substituted or unsubstituted aromatic hydrocarbon ring or a substituted or unsubstituted heteroring, a1 and b1 are an integer of 0 to 4, b2 is an integer of 0 to 5, a2 is an integer of 0 to 3, and when a1, b1, a2 and b2 are 2 or greater, substituents in the parentheses are the same as or different from each other.

In one embodiment of the present application, Chemical Formula 1 may be represented by any one of the following Chemical Formula 8 to Chemical Formula 11.

[Chemical Formula 8]

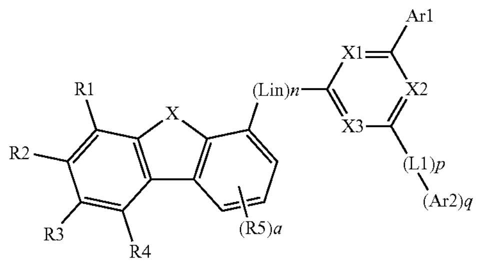

[Chemical Formula 9]

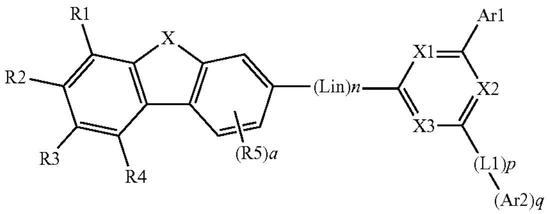

[Chemical Formula 10]

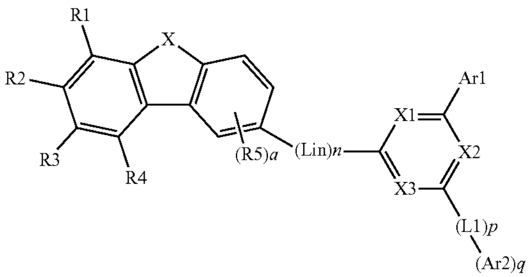

[Chemical Formula 11]

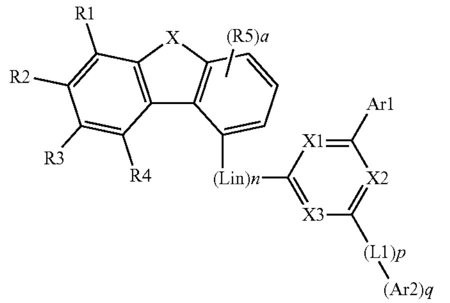

In Chemical Formulae 8 to 11, each substituent has the same definition as in Chemical Formula 1.

In one embodiment of the present application, X may be O; or S.

In one embodiment of the present application, X may be O.

In one embodiment of the present application, X may be S.

In one embodiment of the present application, X1 to X3 are N; or CRe, and at least one of X1 to X3 may be N.

In one embodiment of the present application, X1 to X3 may be N.

In one embodiment of the present application, X1 and X2 are N, and X3 may be CRe.

In one embodiment of the present application, X1 and X3 are N, and X2 may be CRe.

In one embodiment of the present application, R1 to R5 are the same as or different from each other, and each independently selected from the group consisting of hydrogen; deuterium; halogen; a cyano group; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; —SiRR'R"; —P(═O)RR'; and —NRR', or two or more groups adjacent to each other may bond to each other to form a substituted or unsubstituted aromatic hydrocarbon ring or a substituted or unsubstituted heteroring.

In another embodiment, R1 to R5 are the same as or different from each other, and may be each independently selected from the group consisting of hydrogen; deuterium; a substituted or unsubstituted C1 to C60 alkyl group; a substituted or unsubstituted C6 to C60 aryl group; a substituted or unsubstituted C2 to C60 heteroaryl group; —SiRR'R"; —P(═O)RR'; and —NRR'.

In another embodiment, R1 to R5 are the same as or different from each other, and may be each independently hydrogen; deuterium; a substituted or unsubstituted C1 to C60 alkyl group; a substituted or unsubstituted C6 to C60 aryl group; or a substituted or unsubstituted C2 to C60 heteroaryl group.

In another embodiment, R1 to R5 are the same as or different from each other, and may be each independently hydrogen; deuterium; a substituted or unsubstituted C1 to C40 alkyl group; a substituted or unsubstituted C6 to C40 aryl group; or a substituted or unsubstituted C2 to C40 heteroaryl group.

In another embodiment, R1 to R5 are the same as or different from each other, and may be each independently hydrogen; deuterium; or a substituted or unsubstituted C6 to C40 aryl group.

In another embodiment, R1 to R5 are the same as or different from each other, and may be each independently hydrogen; deuterium; or a C6 to C40 aryl group.

In another embodiment, R1 to R5 are the same as or different from each other, and may be each independently hydrogen; deuterium; or a C6 to C20 aryl group.

In another embodiment, R1 to R5 are the same as or different from each other, and may be each independently hydrogen; deuterium; a monocyclic C6 to C10 aryl group; or a polycyclic C10 to C20 aryl group.

In another embodiment, R1 to R5 are the same as or different from each other, and may be each independently hydrogen; deuterium; a substituted or unsubstituted phenyl group; or a substituted or unsubstituted biphenyl group.

In another embodiment, R1 to R5 are the same as or different from each other, and may be each independently hydrogen; deuterium; a phenyl group; or a biphenyl group.

In one embodiment of the present application, R1 to R5 may be substituted with deuterium.

In one embodiment of the present application, Ar1 may be a substituted or unsubstituted C1 to C60 alkyl group; a substituted or unsubstituted C6 to C60 aryl group; or a substituted or unsubstituted C2 to C60 heteroaryl group.

In another embodiment, Ar1 may be a substituted or unsubstituted C6 to C60 aryl group.

In another embodiment, Ar1 may be a substituted or unsubstituted C6 to C40 aryl group.

In another embodiment, Ar1 may be a C6 to C40 aryl group.

In another embodiment, Ar1 may be a monocyclic C6 to C10 aryl group; or a polycyclic C10 to C40 aryl group.

In another embodiment, Ar1 may be a monocyclic C6 to C10 aryl group; or a polycyclic C10 to C20 aryl group.

In another embodiment, Ar1 may be a substituted or unsubstituted phenyl group; or a substituted or unsubstituted biphenyl group.

In another embodiment, Ar1 may be a phenyl group; or a biphenyl group.

In one embodiment of the present application, when

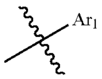
and
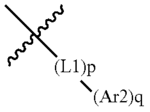

of Chemical Formula 1 are expressed as an unsubstituted biphenyl group, the biphenyl group may be represented by any one of the following structural formulae.

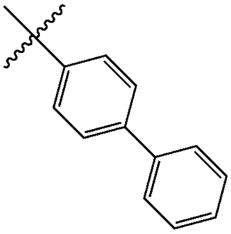
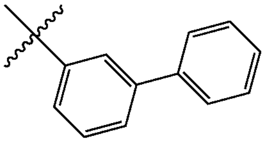

In one embodiment of the present application, when Ar1 is a biphenyl group, Ar1 may be represented by any one of the following structural formulae.

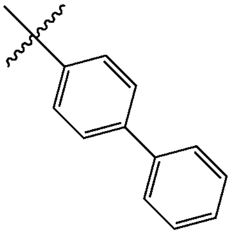
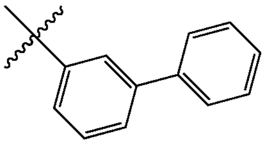

In another embodiment, Ar1 may be represented by any one of the following Chemical Formulae 1-1-1 to 1-1-3.

[Chemical Formula 1-1-1]

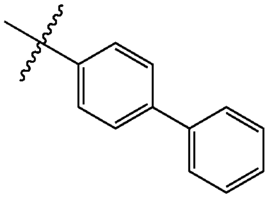

-continued

[Chemical Formula 1-1-2]

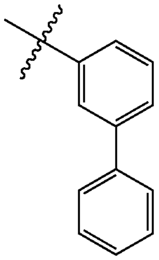

[Chemical Formula 1-1-3]

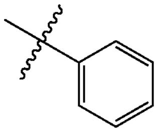

In Chemical Formulae 1-1-1 to 1-1-3,

means a position linked to Chemical Formula 1.

In one embodiment of the present application, L1 may be a direct bond; a substituted or unsubstituted C6 to C60 arylene group; or a substituted or unsubstituted C2 to C60 heteroarylene group.

In another embodiment, L1 may be a direct bond; a substituted or unsubstituted C6 to C40 arylene group; or a substituted or unsubstituted C2 to C40 heteroarylene group.

In another embodiment, L1 may be a direct bond; or a substituted or unsubstituted C6 to C40 arylene group.

In another embodiment, L1 may be a direct bond; or a C6 to C40 arylene group.

In another embodiment, L1 may be a direct bond; or a C6 to C20 arylene group.

In another embodiment, L1 may be a direct bond; or a substituted or unsubstituted phenylene group.

In another embodiment, L1 may be a direct bond; or a phenylene group.

In one embodiment of the present application, Ar2 may be a substituted or unsubstituted C1 to C60 alkyl group; a substituted or unsubstituted C6 to C60 aryl group; or a substituted or unsubstituted C2 to C60 heteroaryl group.

In another embodiment, Ar2 may be a substituted or unsubstituted C1 to C40 alkyl group; a substituted or unsubstituted C6 to C40 aryl group; or a substituted or unsubstituted C2 to C40 heteroaryl group.

In another embodiment, Ar2 may be a substituted or unsubstituted C6 to C40 aryl group; or a substituted or unsubstituted C2 to C40 heteroaryl group.

In another embodiment, Ar2 may be a C6 to C40 aryl group; or a C2 to C40 heteroaryl group.

In another embodiment, Ar2 may be a substituted or unsubstituted phenyl group; a substituted or unsubstituted biphenyl group; a substituted or unsubstituted terphenyl group; a substituted or unsubstituted triphenylenyl group; a substituted or unsubstituted dibenzofuran group; or a substituted or unsubstituted dibenzothiophene group.

In another embodiment, Ar2 may be a phenyl group; a biphenyl group; a terphenyl group; a triphenylenyl group; a dibenzofuran group; or a dibenzothiophene group.

In another embodiment, Ar2 may be represented by the following Chemical Formula 1-2-1 or 1-2-2.

[Chemical Formula 1-2-1]

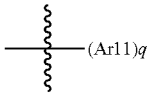

[Chemical Formula 1-2-2]

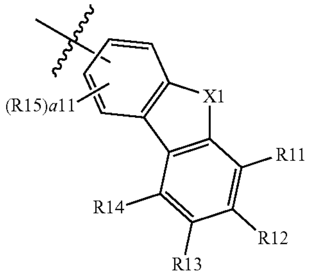

In Chemical Formulae 1-2-1 and 1-2-2,

means a position linked to Chemical Formula 1,

X1 is O; or S,

R11 to R15 are the same as or different from each other, and each independently selected from the group consisting of hydrogen; deuterium; halogen; a cyano group; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; —SiRR'R"; —P(═O)RR'; and —NRR', or two or more groups adjacent to each other bond to each other to form a substituted or unsubstituted aromatic hydrocarbon ring or a substituted or unsubstituted heteroring, a11 is an integer of 0 to 3, and when a11 is 2 or greater, substituents in the parentheses are the same as or different from each other, R, R' and R" have the same definitions as in Chemical Formula 1, and Ar11 is a substituted or unsubstituted C6 to C60 aryl group.

In one embodiment of the present application, R11 to R15 are the same as or different from each other, and each independently selected from the group consisting of hydrogen; deuterium; halogen; a cyano group; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; —SiRR'R"; —P(═O)RR'; and —NRR', or two or more groups adjacent to each other bond to each other to form a substituted or unsubstituted aromatic hydrocarbon ring or a substituted or unsubstituted heteroring.

In another embodiment, R11 to R15 are the same as or different from each other, and may be each independently hydrogen; deuterium; a substituted or unsubstituted C6 to C60 aryl group; or a substituted or unsubstituted C2 to C60 heteroaryl group.

In another embodiment, R11 to R15 are the same as or different from each other, and may be each independently hydrogen; deuterium; a substituted or unsubstituted C6 to C40 aryl group; or a substituted or unsubstituted C2 to C40 heteroaryl group.

In another embodiment, R11 to R15 are the same as or different from each other, and may be each independently hydrogen; deuterium; a substituted or unsubstituted C6 to C20 aryl group; or a substituted or unsubstituted C2 to C20 heteroaryl group.

In another embodiment, R11 to R15 are the same as or different from each other, and may be each independently hydrogen; deuterium; a C6 to C20 aryl group; or a C2 to C20 heteroaryl group.

In another embodiment, R11 to R15 are the same as or different from each other, and may be each independently hydrogen; deuterium; a C6 to C10 aryl group; or a C2 to C10 heteroaryl group.

In another embodiment, R11 to R15 are the same as or different from each other, and may be each independently hydrogen; or deuterium.

In one embodiment of the present application, Ar11 is a substituted or unsubstituted C6 to C60 aryl group.

In another embodiment, Ar11 is a substituted or unsubstituted C6 to C40 aryl group.

In another embodiment, Ar11 is a substituted or unsubstituted C6 to C20 aryl group.

In another embodiment, Ar11 is a C6 to C20 aryl group.

In another embodiment, Ar11 is a phenyl group; a biphenyl group; a terphenyl group; or a triphenylenyl group.

In one embodiment of the present application, Chemical Formula 1-2-2 may be represented by any one of the following Chemical Formulae 1-A to 1-D.

[Chemical Formula 1-A]

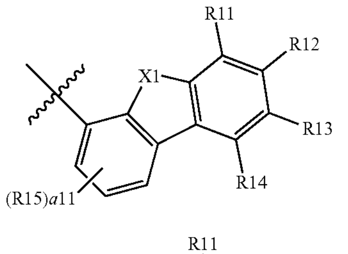

[Chemical Formula 1-B]

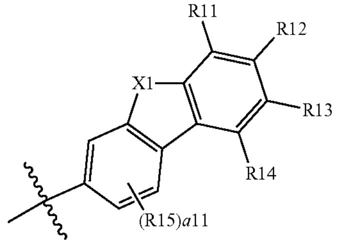

-continued

[Chemical Formula 1-C]

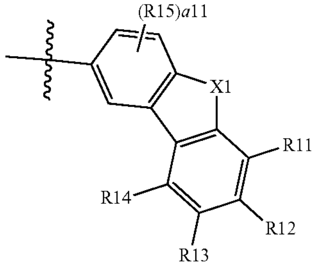

[Chemical Formula 1-D]

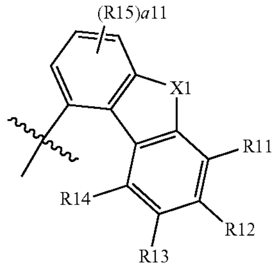

In Chemical Formulae 1-A to 1-D, each substituent has the same definition as in Chemical Formula 1-2-2.

In one embodiment of the present application, R, R' and R" are the same as or different from each other, and may be each independently a substituted or unsubstituted C1 to C60 alkyl group; a substituted or unsubstituted C6 to C60 aryl group; or a substituted or unsubstituted C2 to C60 heteroaryl group.

In another embodiment, R, R' and R" are the same as or different from each other, and may be each independently a substituted or unsubstituted C1 to C60 alkyl group; or a substituted or unsubstituted C6 to C60 aryl group.

In another embodiment, R, R' and R" are the same as or different from each other, and may be each independently a C1 to C60 alkyl group; or a C6 to C60 aryl group.

In another embodiment, R, R' and R" are the same as or different from each other, and may be each independently a methyl group; or a phenyl group.

In another embodiment, R, R' and R" may be a substituted or unsubstituted methyl group.

In another embodiment, R, R' and R" may be a substituted or unsubstituted phenyl group.

In another embodiment, R, R' and R" may be a phenyl group.

In one embodiment of the present application, Re may be hydrogen; deuterium; a substituted or unsubstituted C1 to C60 alkyl group; or a substituted or unsubstituted C6 to C60 aryl group.

In another embodiment, Re may be hydrogen.

In one embodiment of the present application, Lin may be a substituted or unsubstituted C6 to C20 arylene group.

In another embodiment, Lin may be a substituted or unsubstituted C6 to C15 arylene group.

In another embodiment, Lin may be a C6 to C15 arylene group.

In another embodiment, Lin may be a monocyclic C6 to C10 arylene group; or a polycyclic C10 to C15 arylene group.

In another embodiment, Lin may be a phenylene group; or a biphenylene group.

In one embodiment of the present application, n may be an integer of 0 or 1.

In being 0 means a substituent being linked without Lin bonding, that is, a direct bond.

In one embodiment of the present application, Lin may be represented by any one of the following structural formulae.

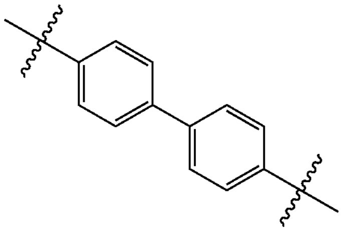

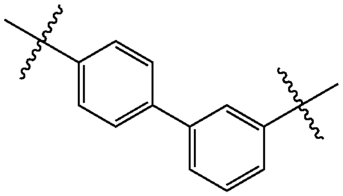

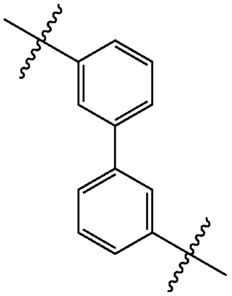

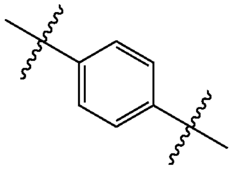

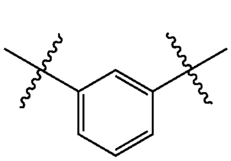

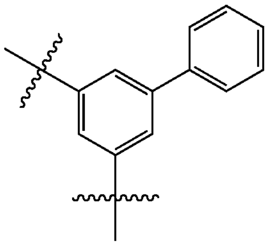

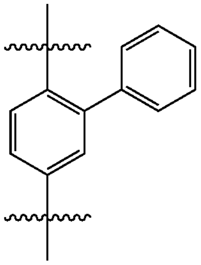

In the structural formulae,

means a position linked to the substituents of Chemical Formula 1.

In one embodiment of the present application, Lin may be substituted with deuterium.

In one embodiment of the present application, Chemical Formula 1 may be represented by a combination of the following Structural Formula A to the following Structural Formula C.

[Structural Formula A]

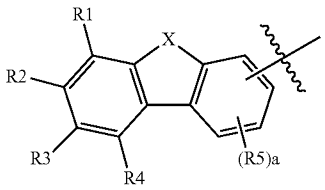

[Structural Formula B]

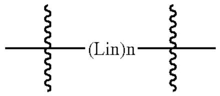

[Structural Formula C]

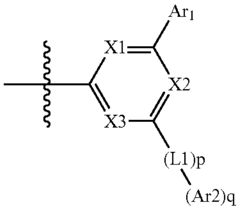

In Structural Formula A to Structural Formula C,

is a position to which Structural Formulae A to C each bond, and

Structural Formula A and Structural Formula B; or Structural Formula A has a deuterium content of 20% to 100%.

In one embodiment of the present application, Structural Formula A and Structural Formula B; or Structural Formula A has a deuterium content of 20% to 100%.

Molecules are thermally damaged by electron migration when driving an organic light emitting device. Particularly, structures comprising dibenzofuran and dibenzothiophene are highly likely to have defects in oxygen or sulfur, a most unstable site.

In the compound in which Structural Formula A and Structural Formula B; or Structural Formula A has a deuterium content of 20% to 100% as in the disclosure of the present application, the heterocyclic compound is substituted with deuterium having a larger molecular weight than hydrogen in order to prevent this phenomenon, and as a result, molecular energy is lowered by reducing changes in the vibrational frequency, which resultantly increases molecular stability. In addition, it is identified that, since single bond dissociation energy of carbon and deuterium is higher than single bond dissociation energy of carbon and hydrogen, thermal stability of the molecule increases, and a device lifetime is improved as a result.

A unipolar material that does not comprise carbazole such as the compound having triazine (Structural Formula C) bonding to a heteroring (Structural Formula A) has relatively faster electron migration compared to hole migration. A compound substituted with deuterium has higher packing density compared to a compound substituted with hydrogen. Accordingly, holes or electrons migrate faster when substituted with deuterium since the intermolecular distance is close. In the compound of the present disclosure, the HOMO region responsible for hole migration is mainly distributed in the heteroring (Structural Formula A) or the heteroring and the linker (Structural Formula B). Accordingly, when the compound is substituted deuterium, relatively slow hole migration becomes faster increasing probability of electrons and holes meeting in a light emitting layer, and as a result, light emission efficiency may increase.

In one embodiment of the present application, Structural Formula A has a deuterium content of 20% to 100%.

In another embodiment, Structural Formula A may have a deuterium content of 20% to 100%; 25% to 100%; or 30% to 100%.

In one embodiment of the present application, Structural Formula A may have a deuterium content of 100%.

In one embodiment of the present application, Structural Formula B has a deuterium content of 20% to 100%.

In another embodiment, Structural Formula B may have a deuterium content of 20% to 100%; 30% to 100%; or 60% to 100%.

In one embodiment of the present application, Structural Formula B may have a deuterium content of 100%.

In one embodiment of the present application, Structural Formula A has a deuterium content of 20% to 100%, and Structural Formula B and Structural Formula C may have a deuterium content of 0%.

In one embodiment of the present application, Structural Formula A and Structural Formula B have a deuterium content of 20% to 100%, and Structural Formula C may have a deuterium content of 0%.

In one embodiment of the present application, Structural Formula A and Structural Formula B have a deuterium content of 100%, and Structural Formula C may have a deuterium content of 0%.

In one embodiment of the present application, Structural Formula A has a deuterium content of 100%, and Structural Formula B and Structural Formula C may have a deuterium content of 0%.

In another embodiment, the deuterium content of each of Structural Formulae A, B and C may increase or decrease when additional substituents are further included depending on the deuterium substitution process.

In the heterocyclic compound provided in one embodiment of the present application, Chemical Formula 1 is represented by any one of the following compounds. In addition, in one embodiment of the present application, the following compounds are one example, and other compounds included in Chemical Formula 1 comprising additional substituents may be included without being limited to the following compounds.

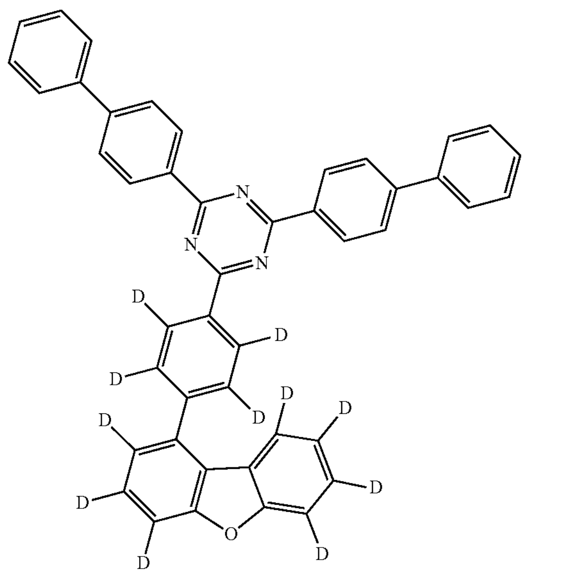

1

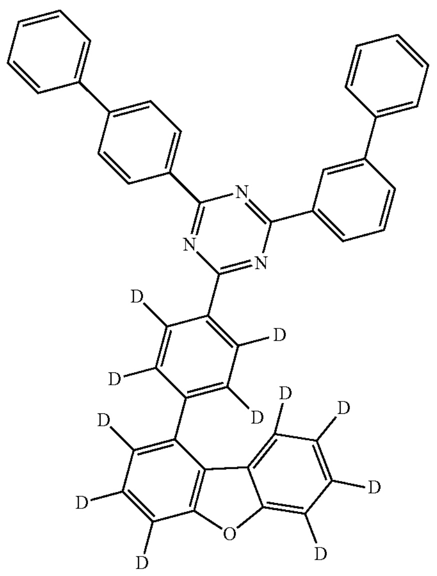

2

-continued
3
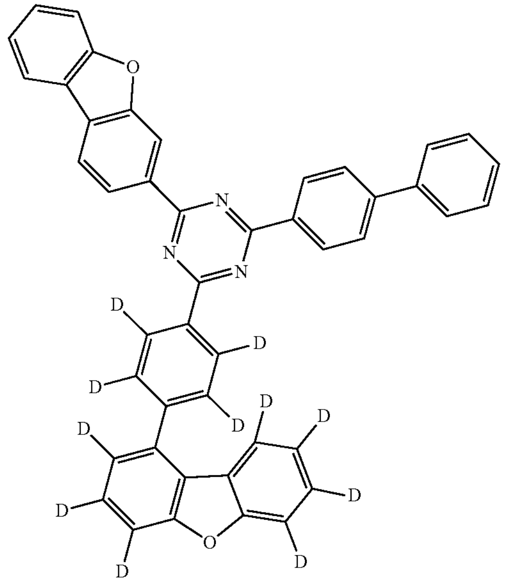
4
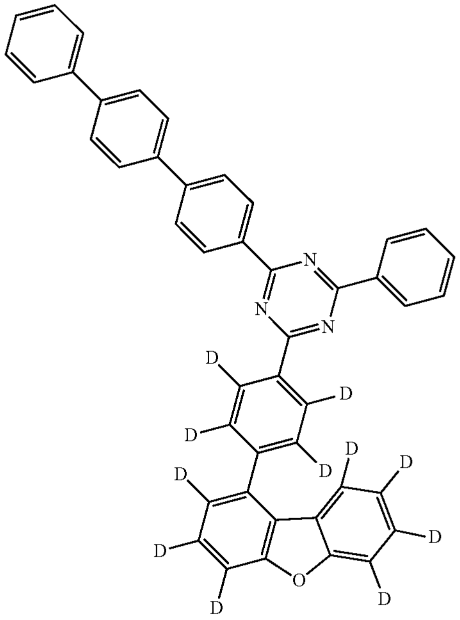
5
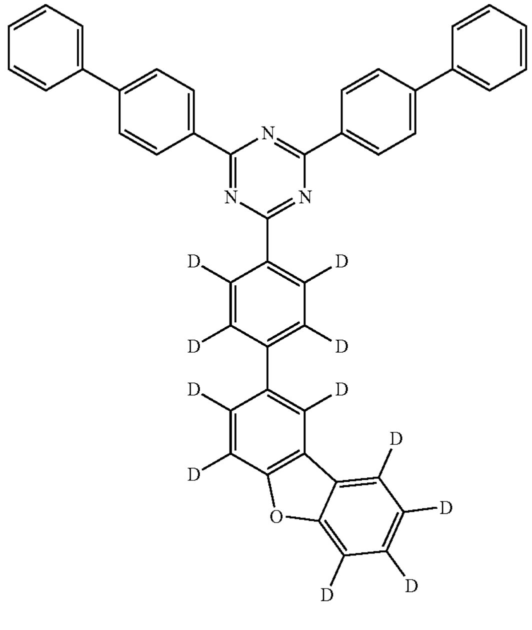
6
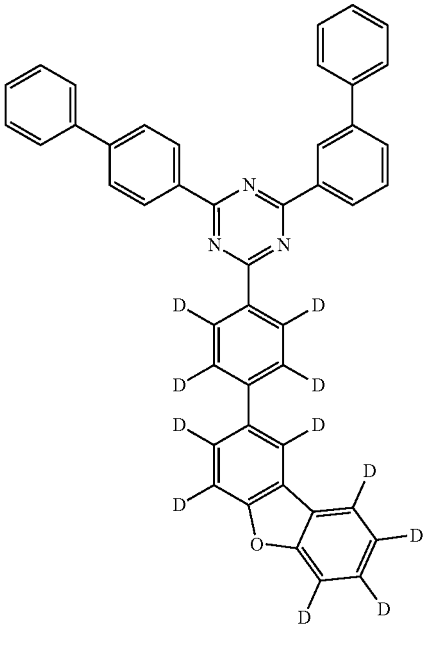

-continued
7
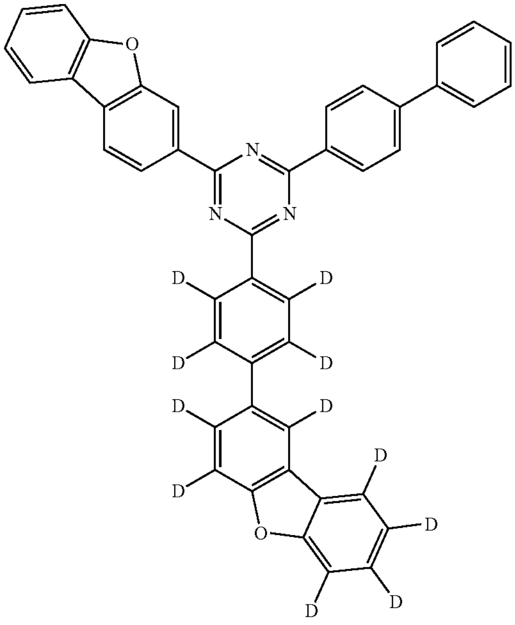
8
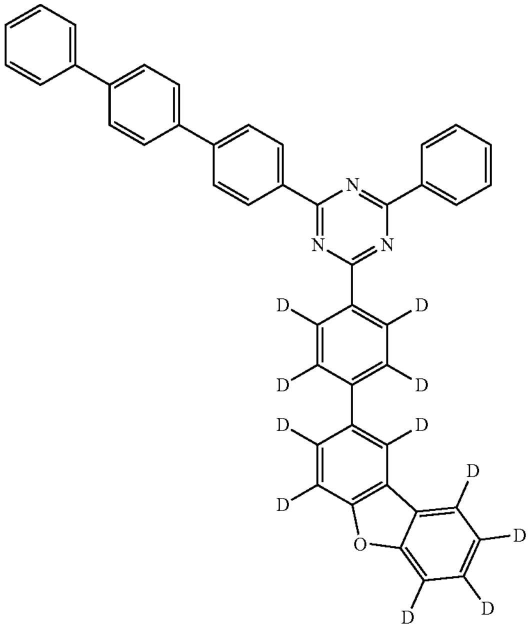
9
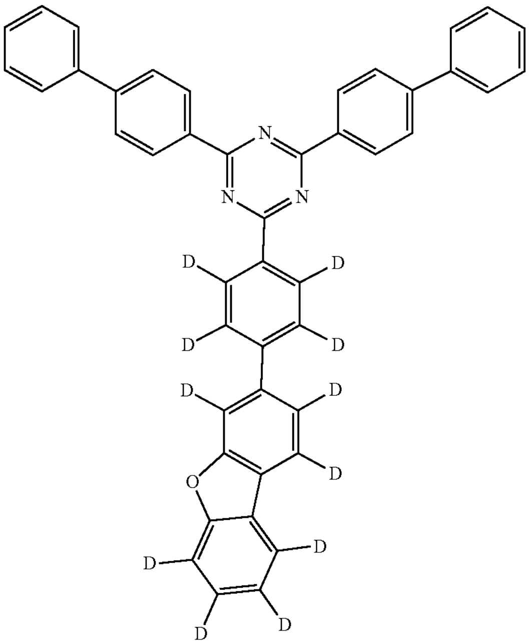
10
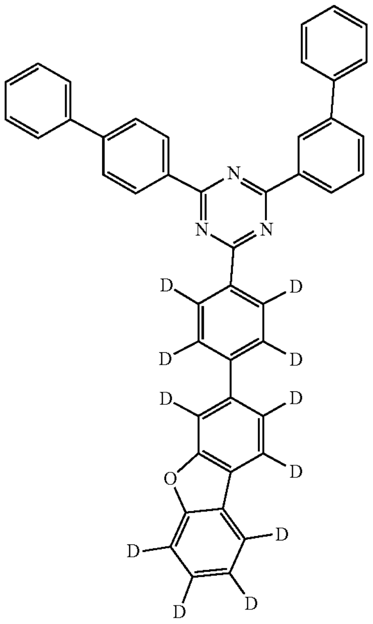

-continued
11
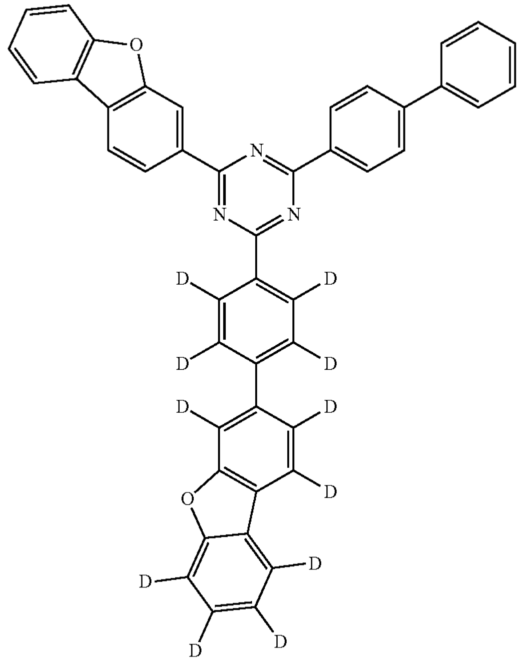
12
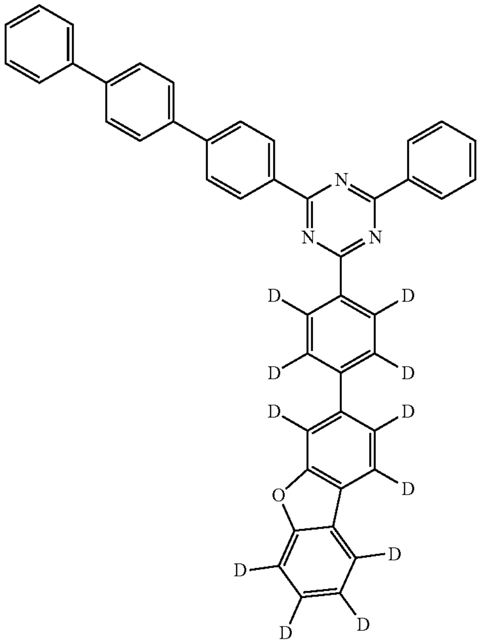
13
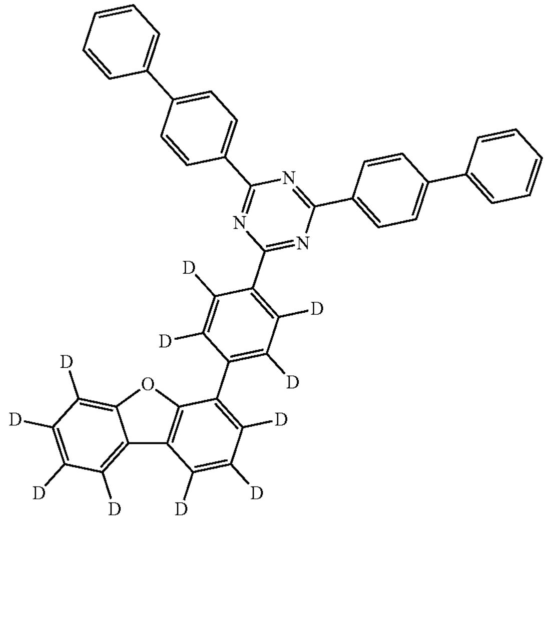
14
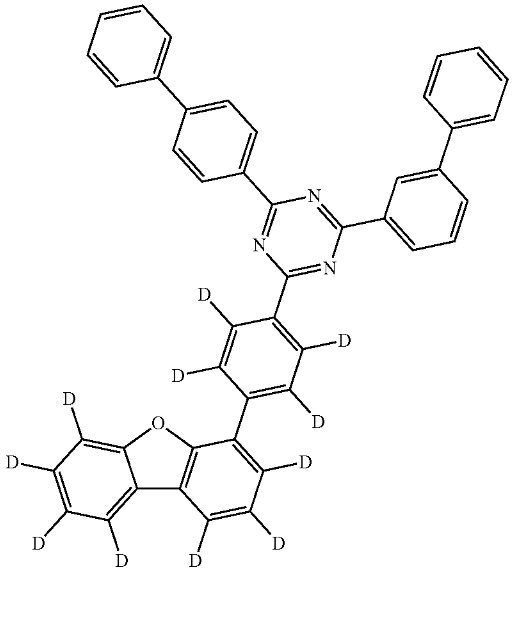

-continued
15
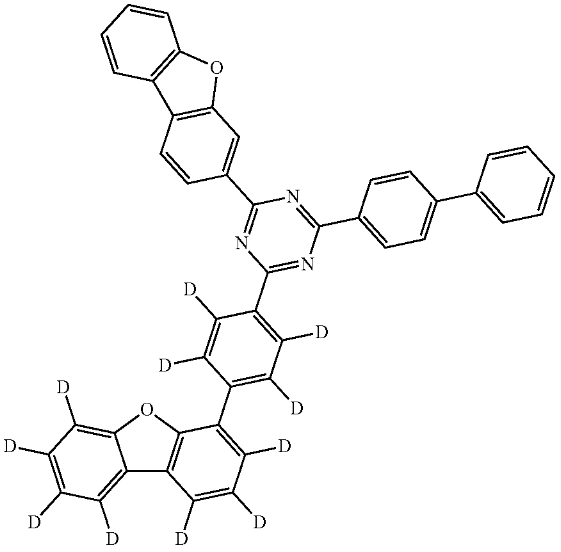
16
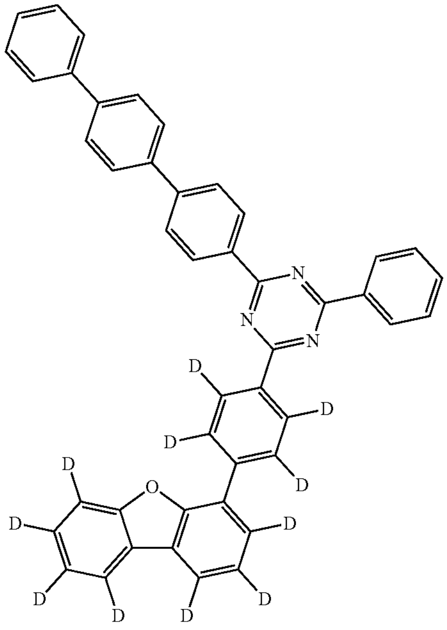
17
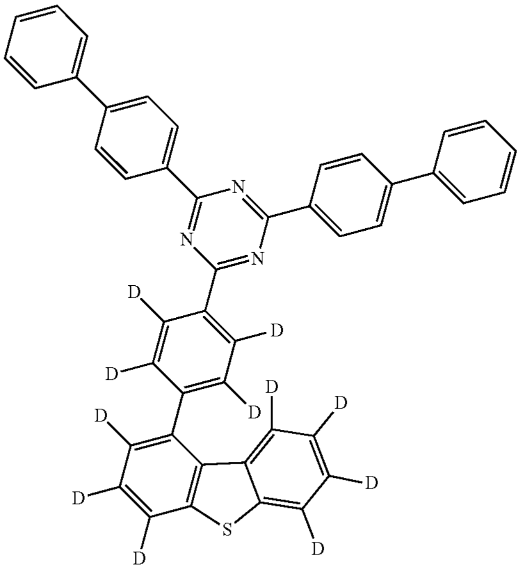
18
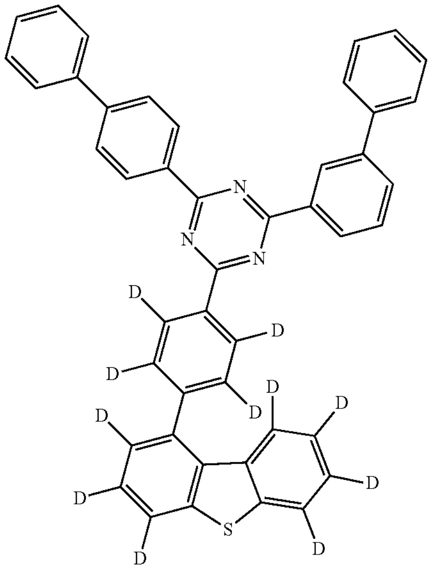

-continued
19
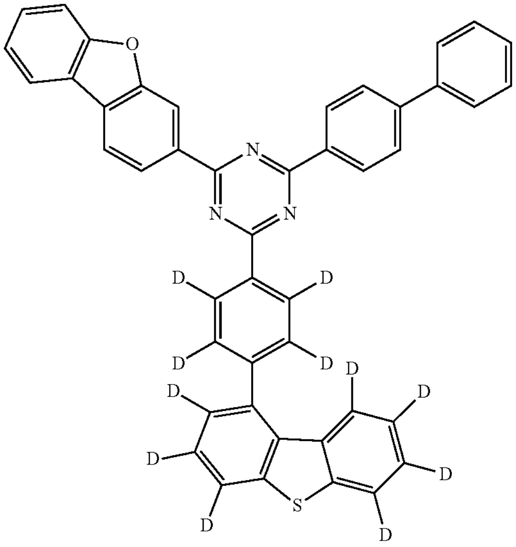
20
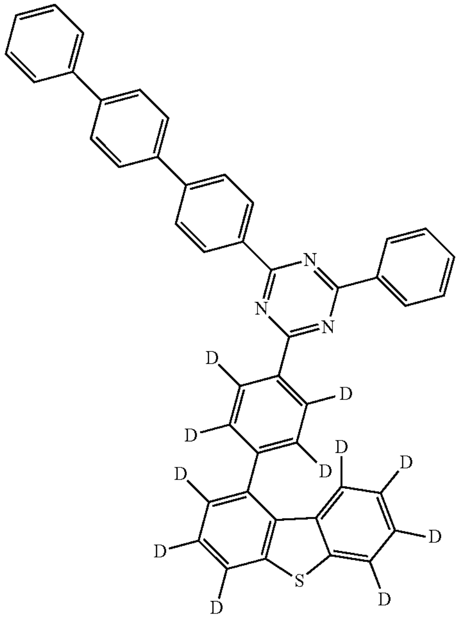
21
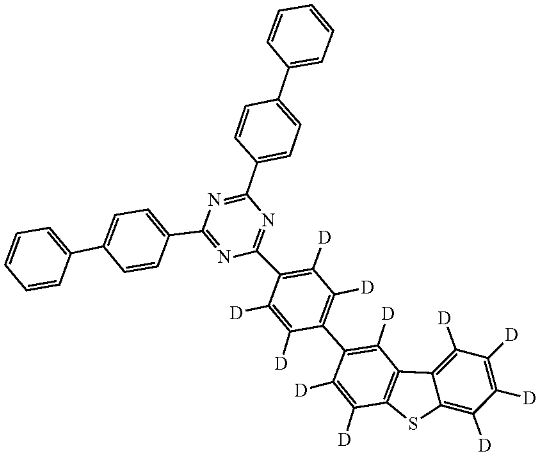
22
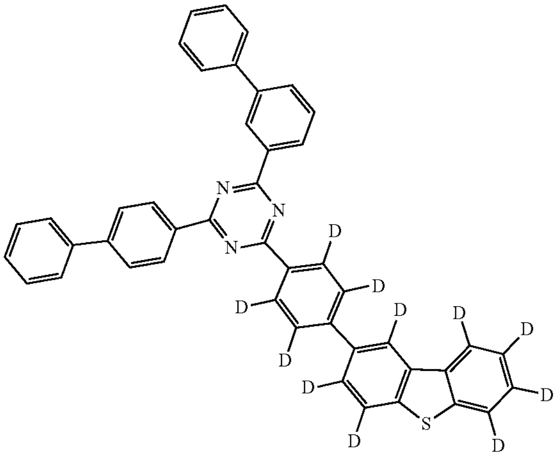

-continued
23
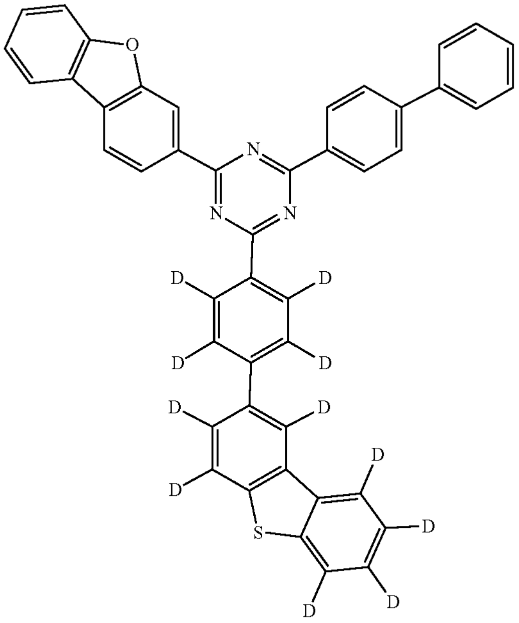
24
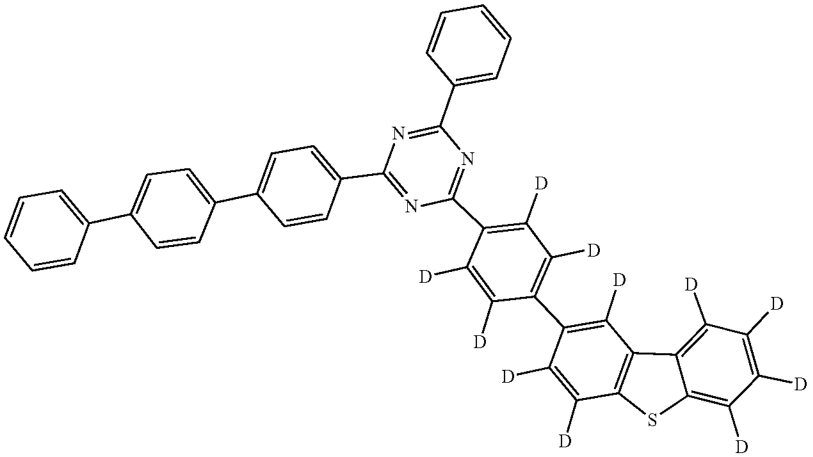

-continued
25
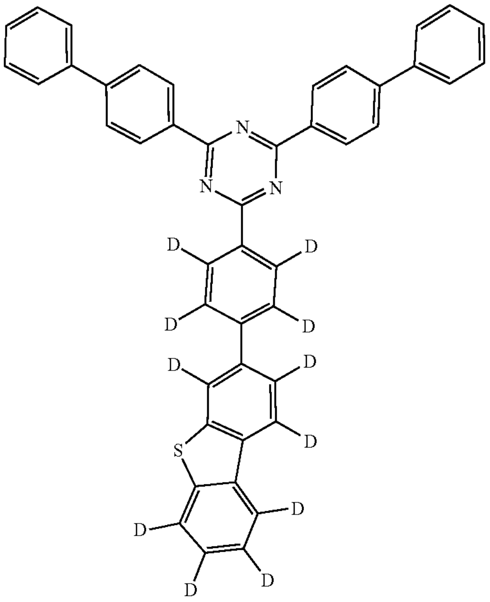
26
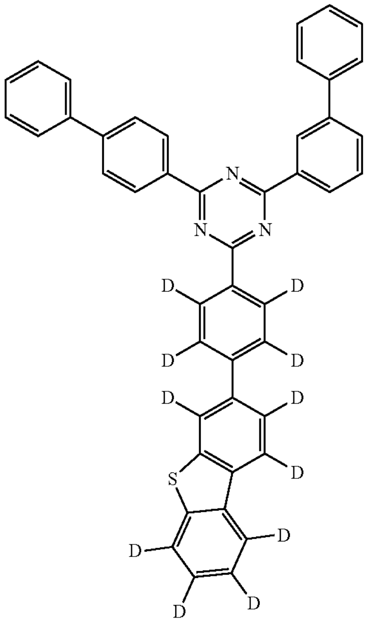
27
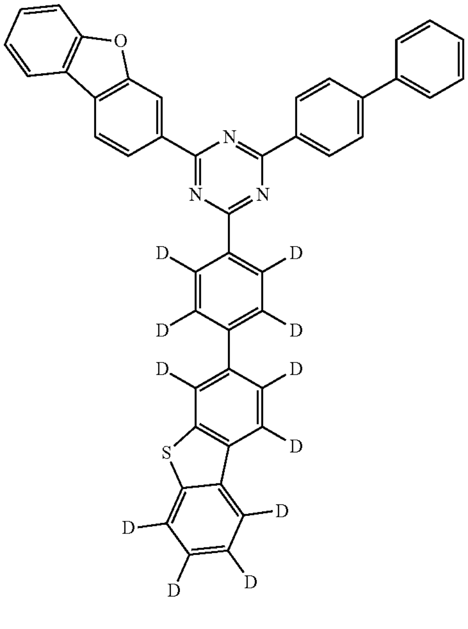
28
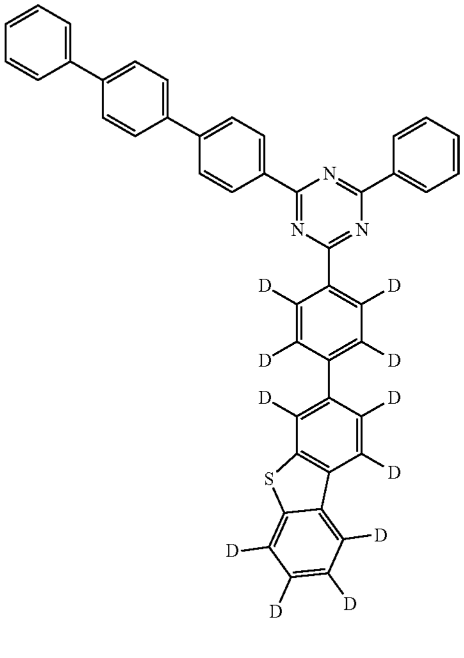

-continued
29
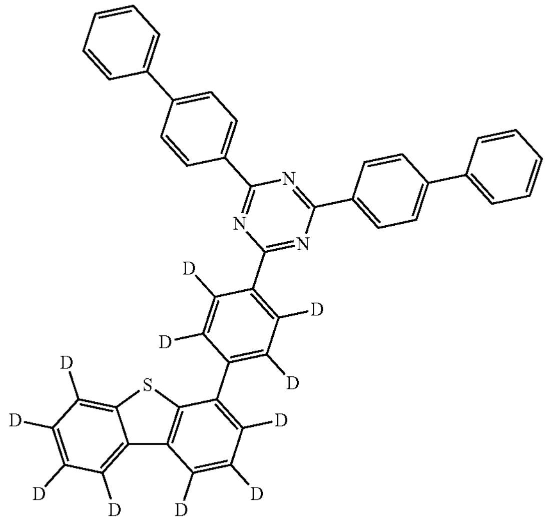
30
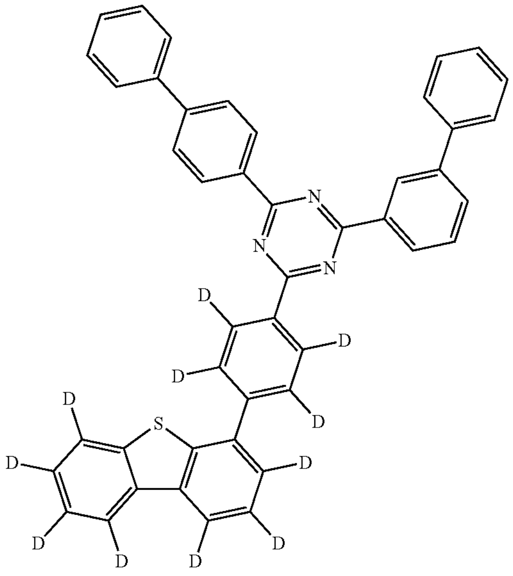
31
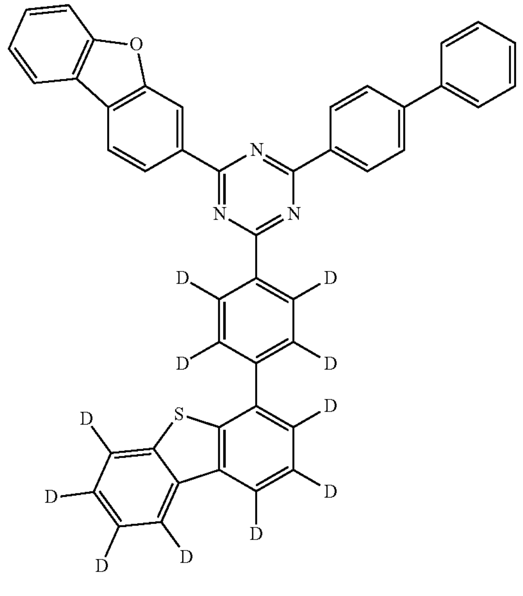
32
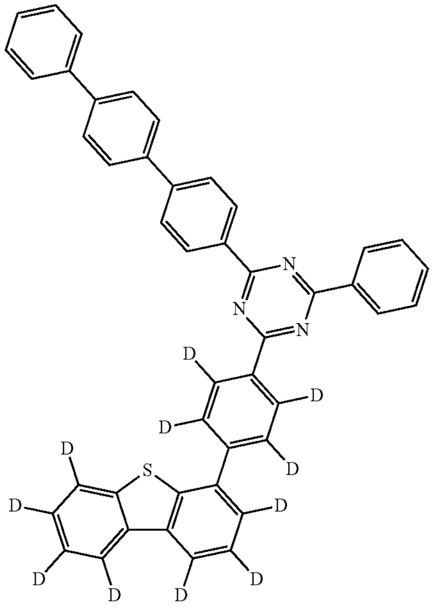

-continued
33
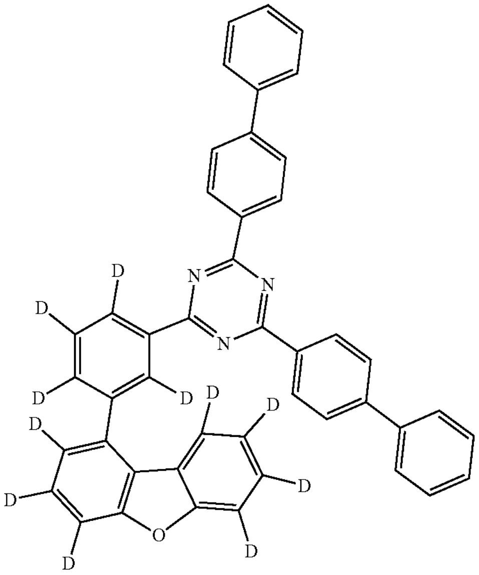
34
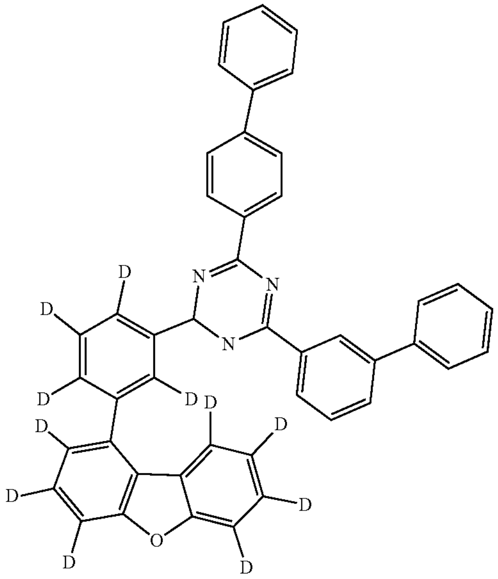
35
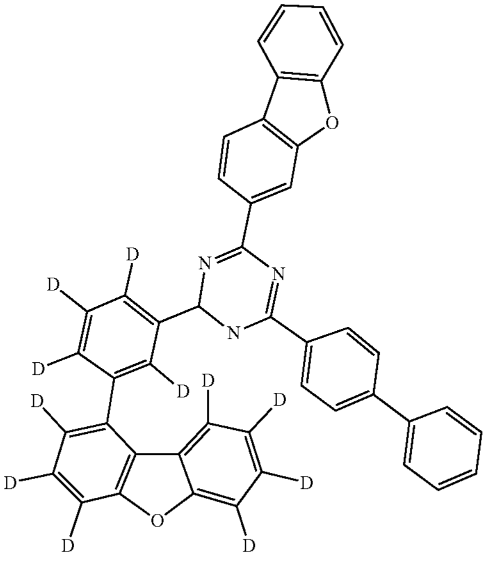
36
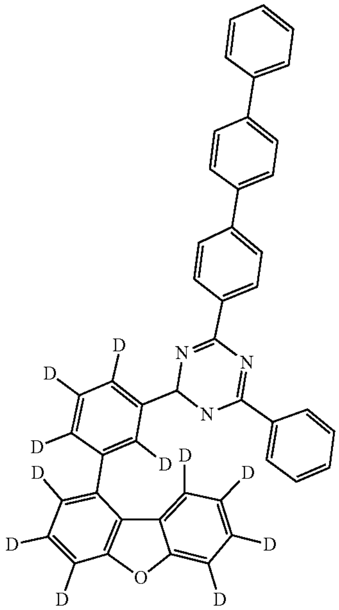

-continued
37
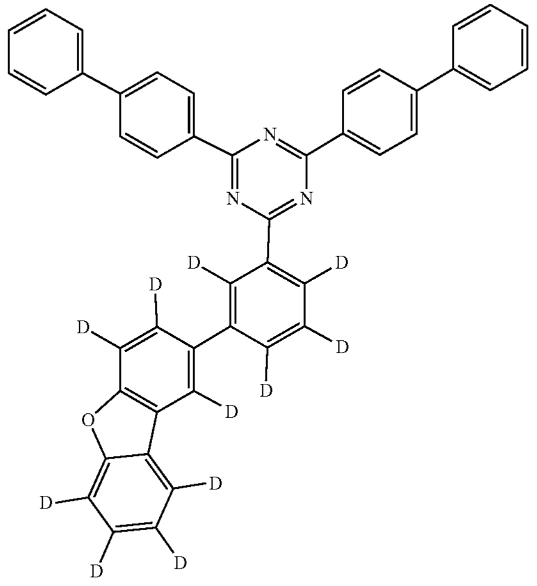
38
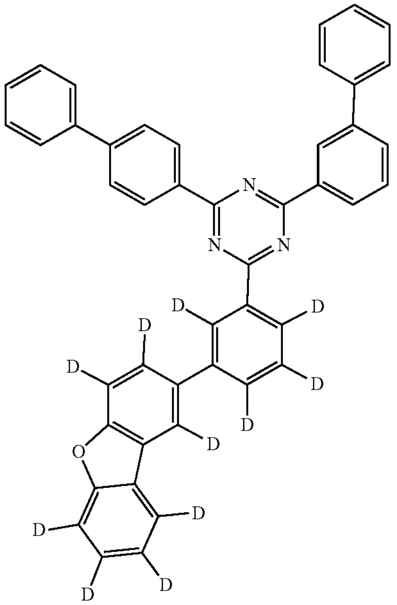
39
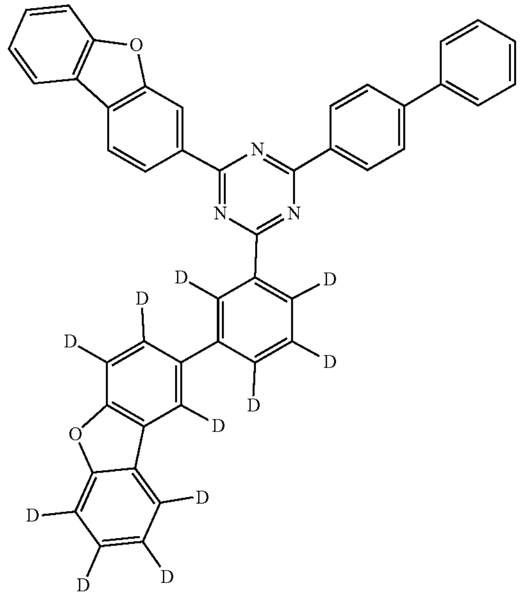
40
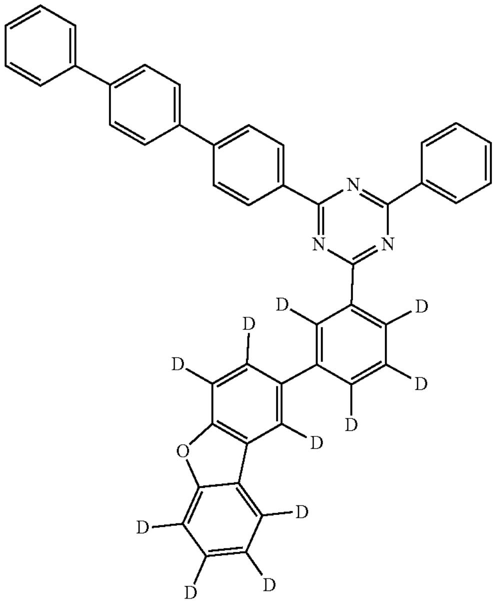

-continued
41
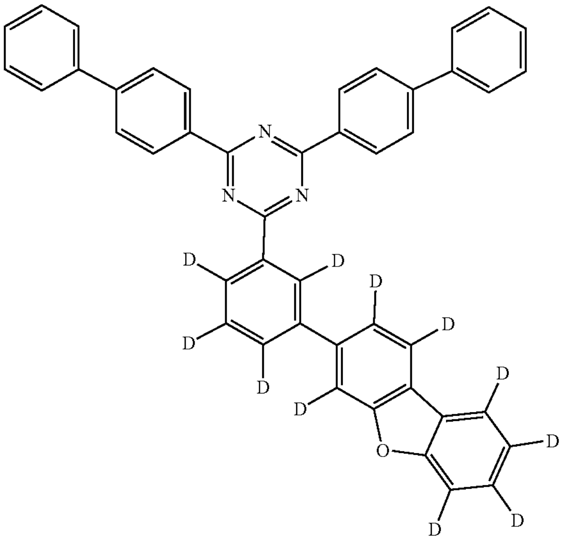
42
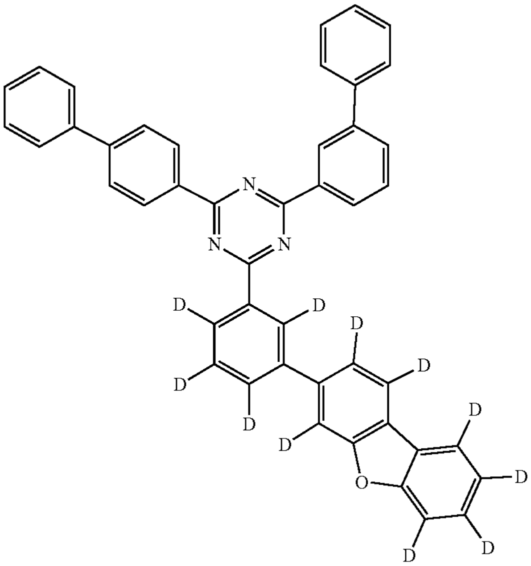
43
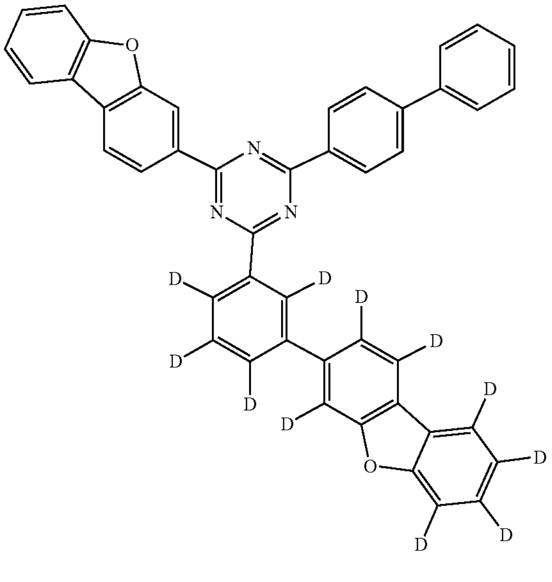
44
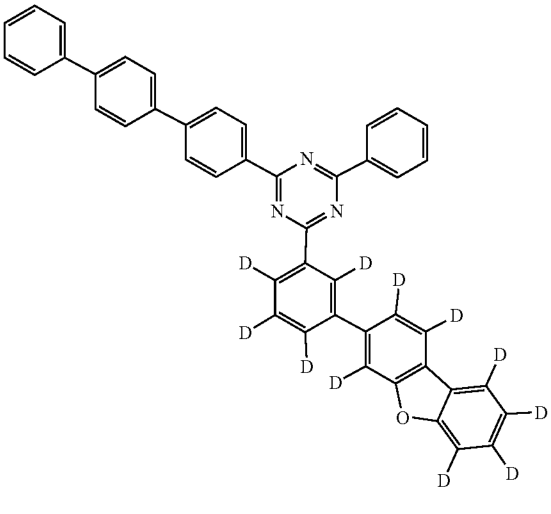

-continued
45
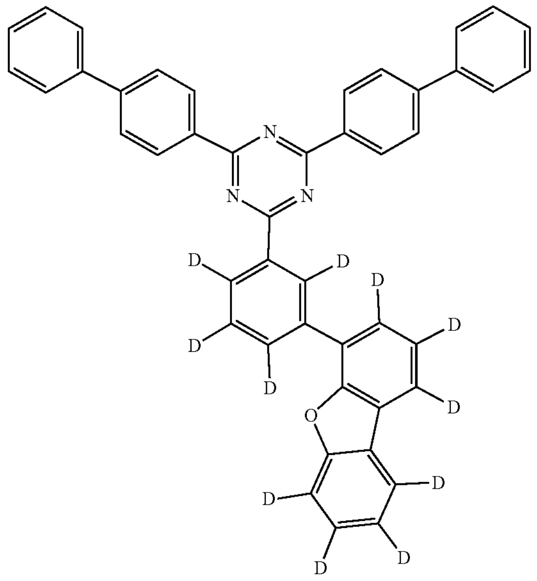
46
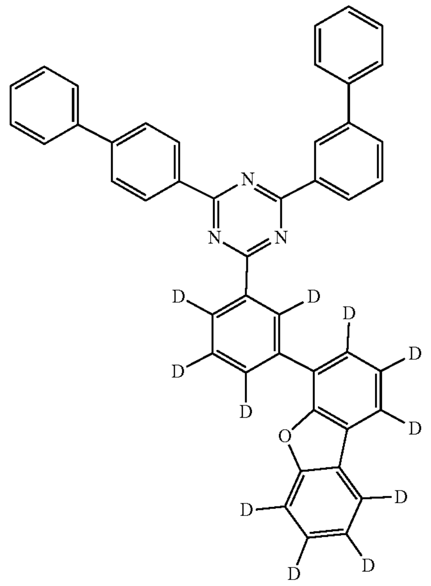
47
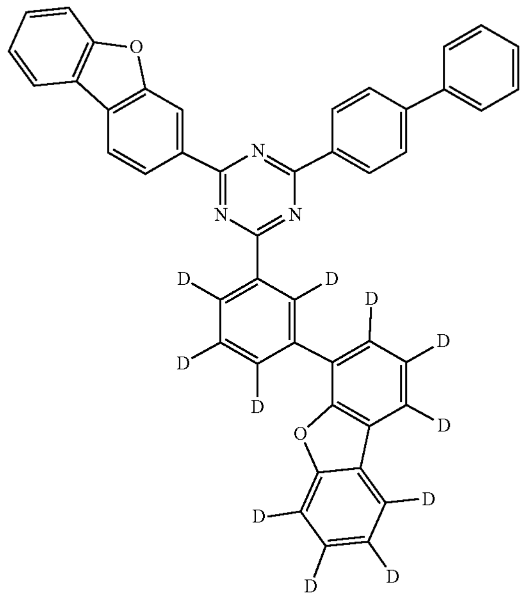
48
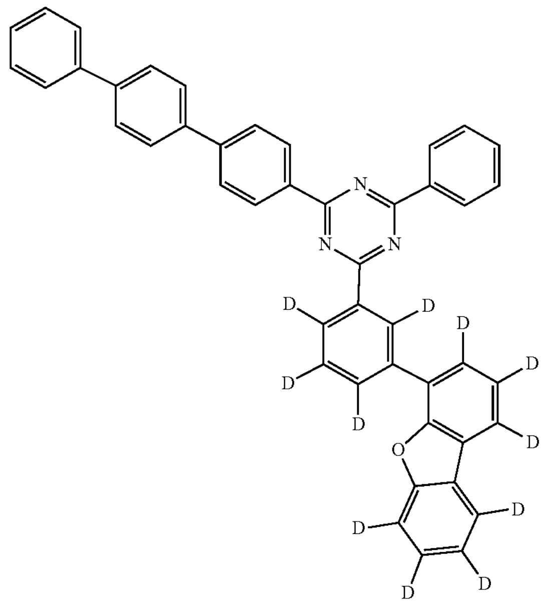

-continued
49
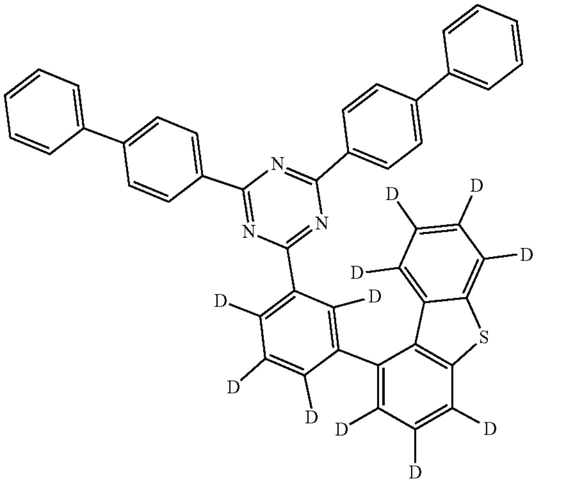
50
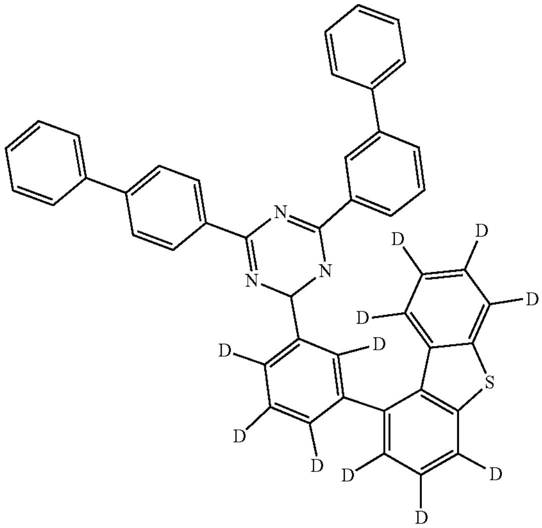
51
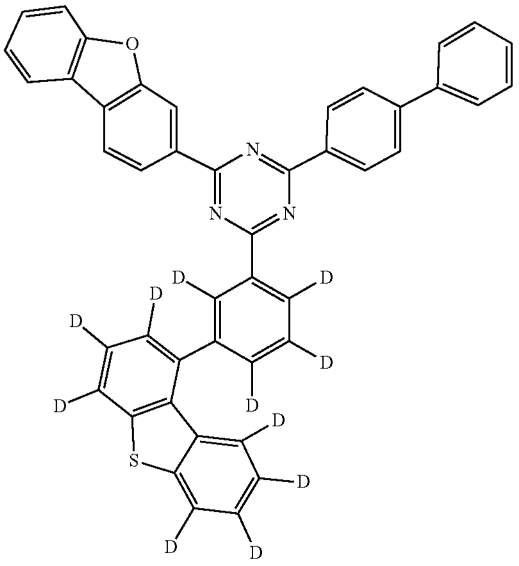
52
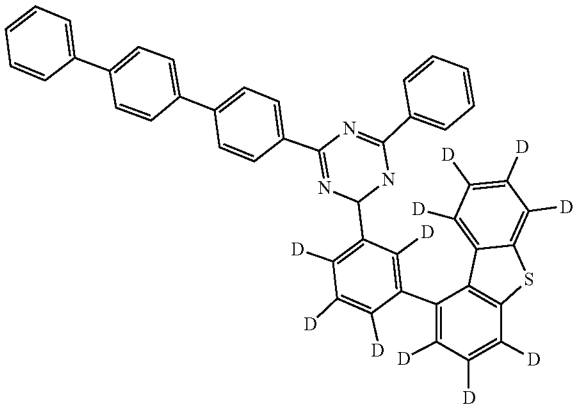

-continued
53
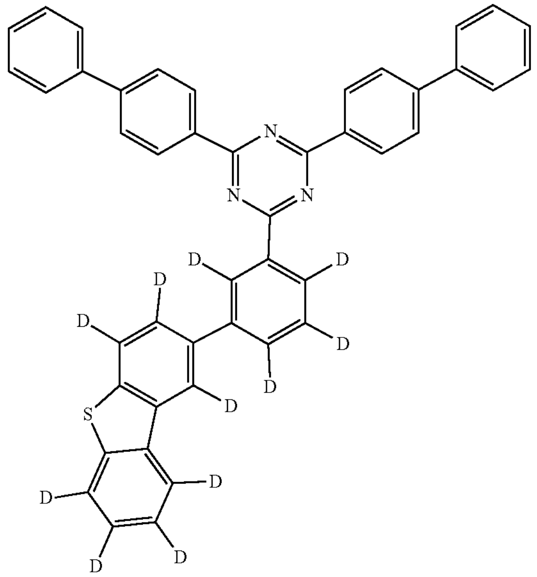
54
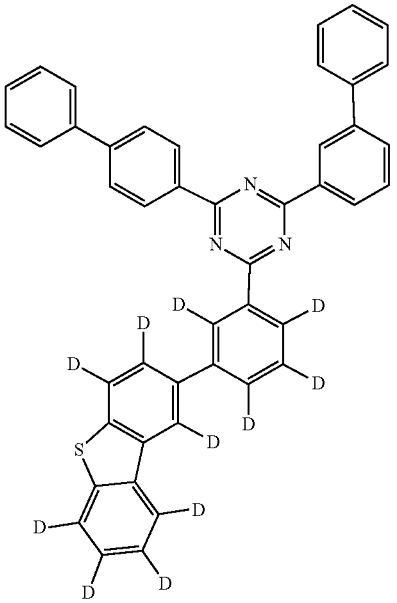
55
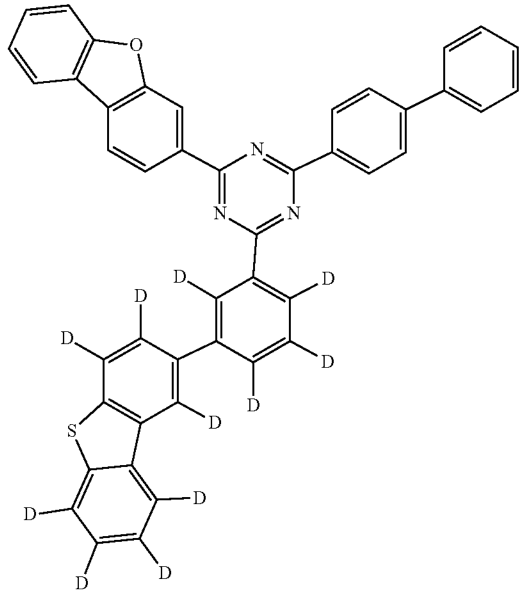
56
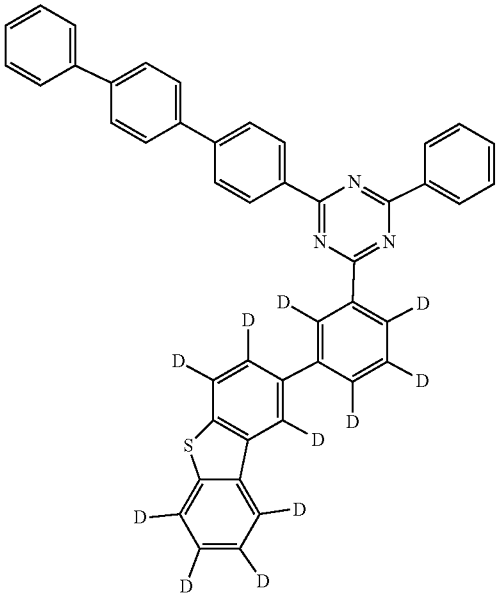

-continued
57
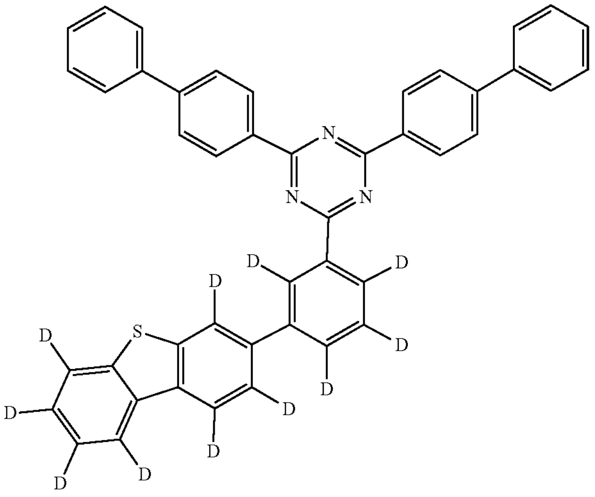
58
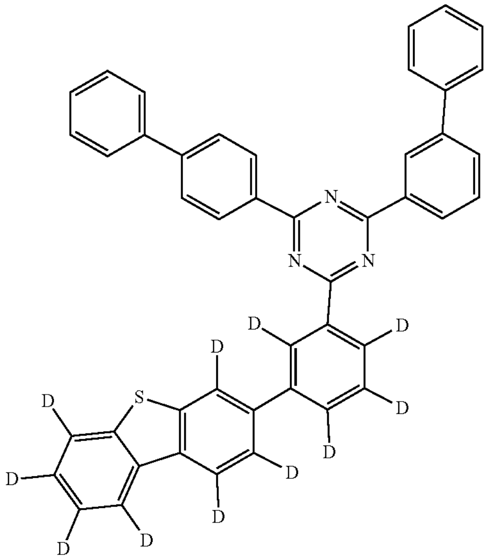
59
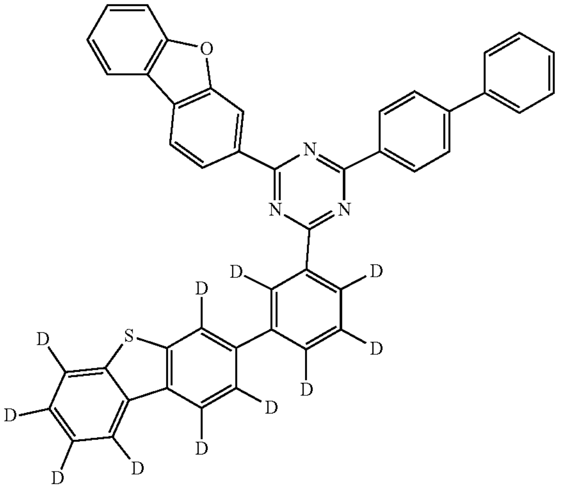
60
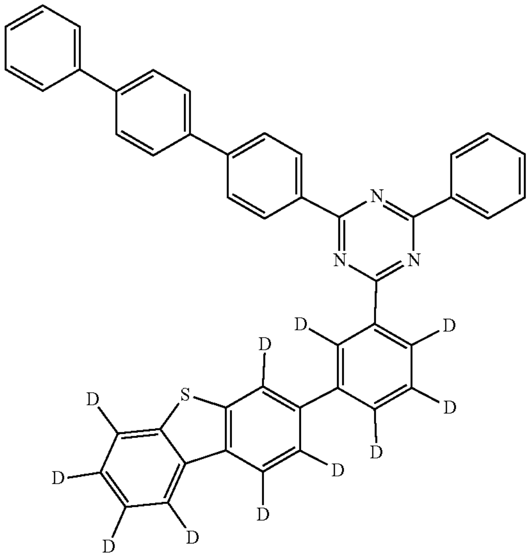

-continued
61
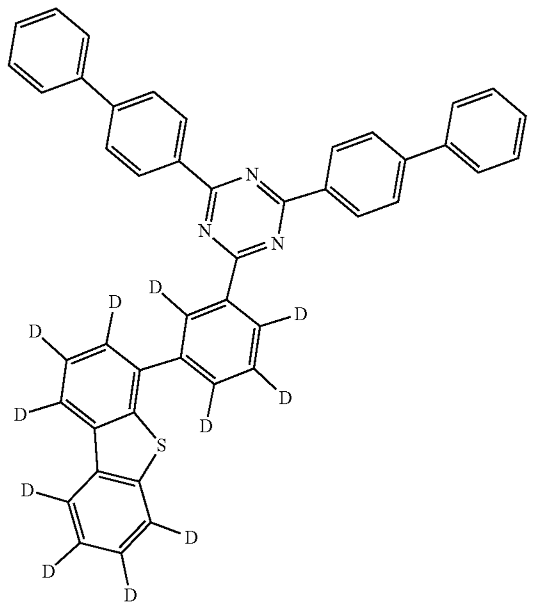
62
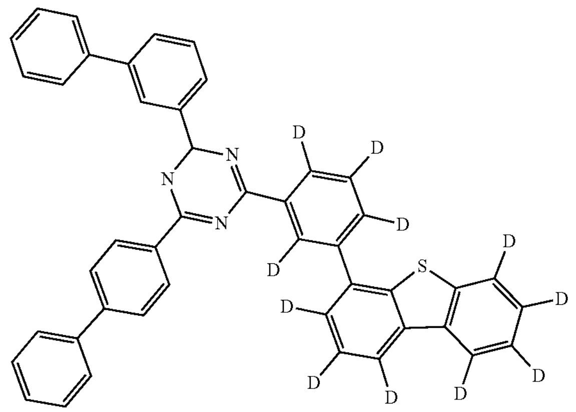
63
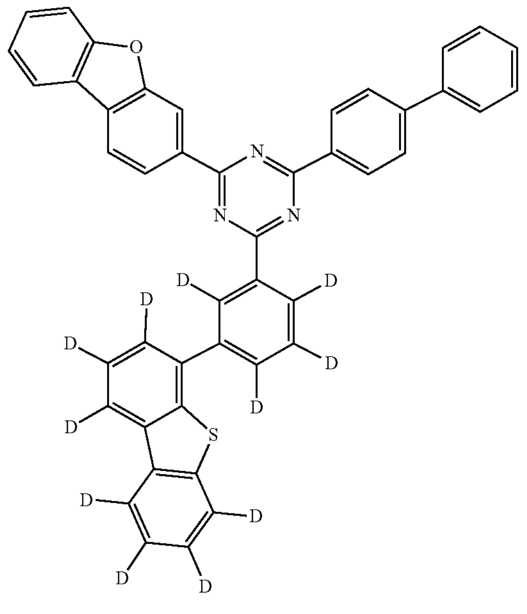
64
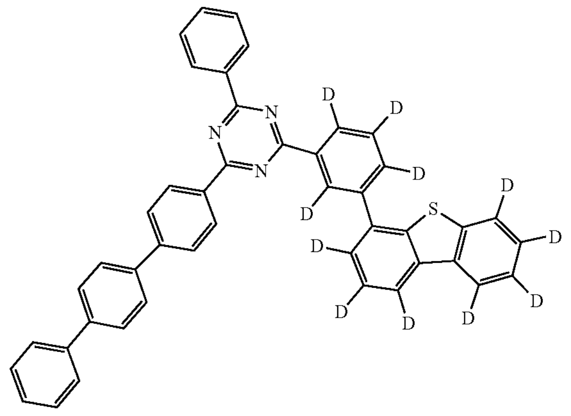

-continued
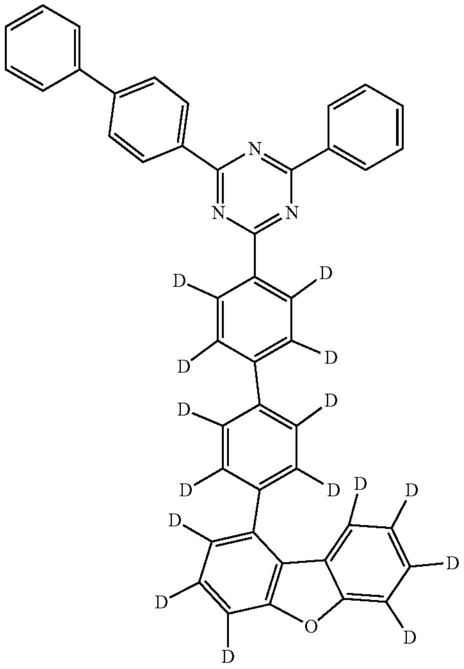
65
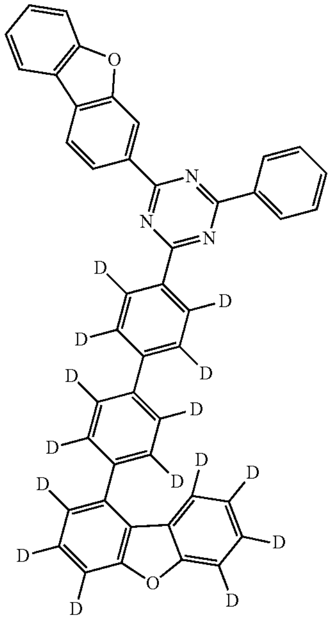
66
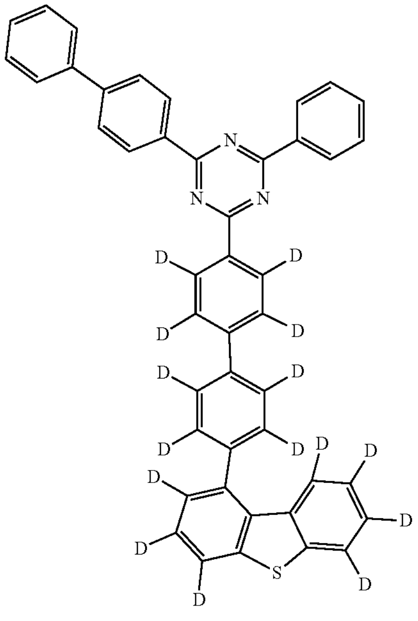
67
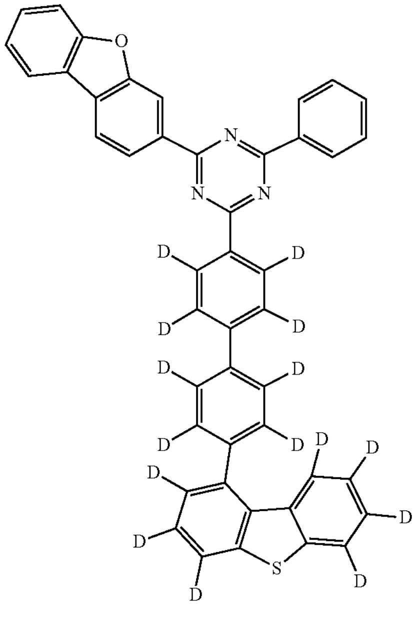
68

-continued
69
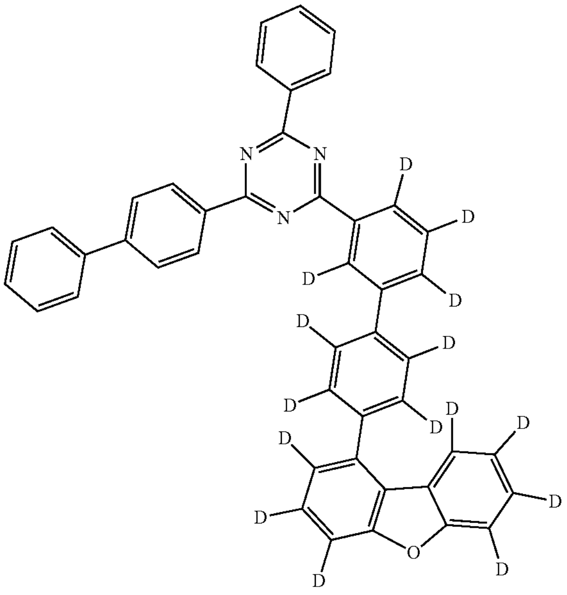
70
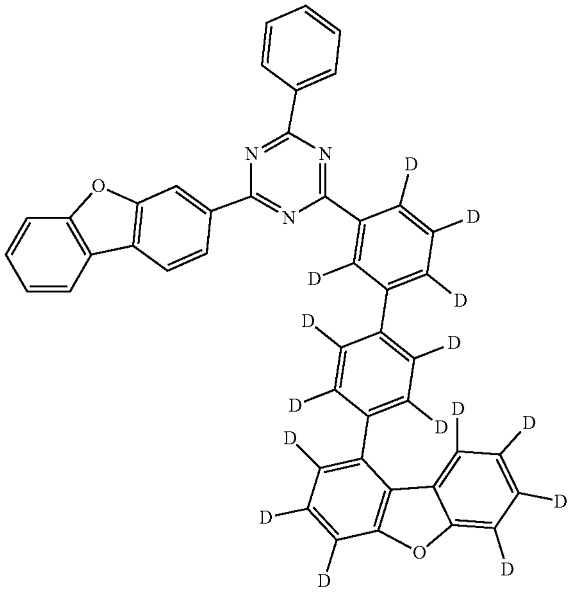
71
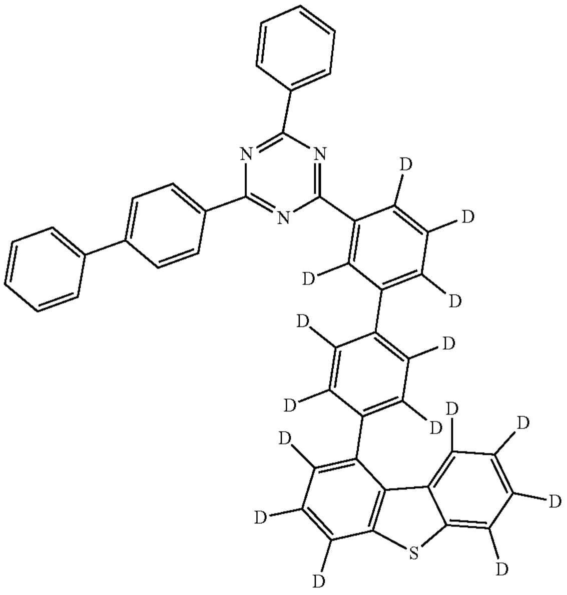
72
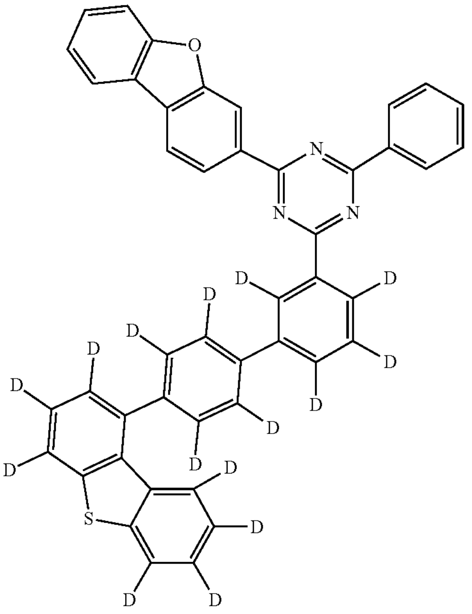

-continued
73
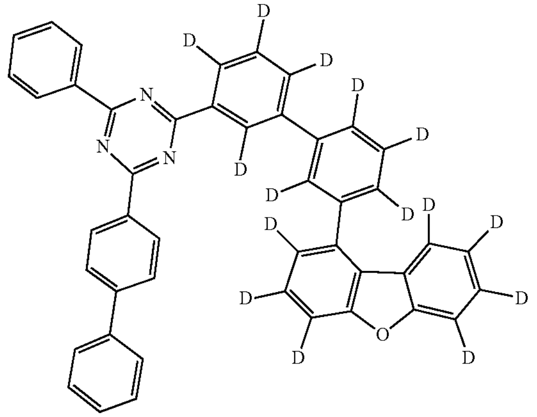
74
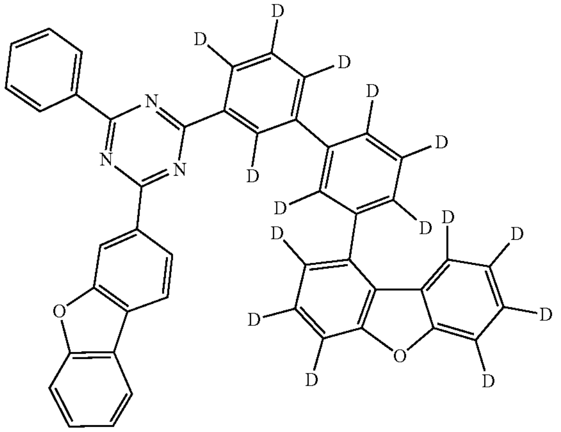
75
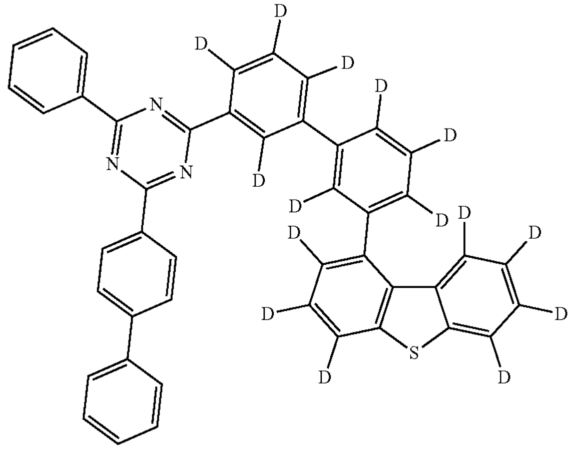
76
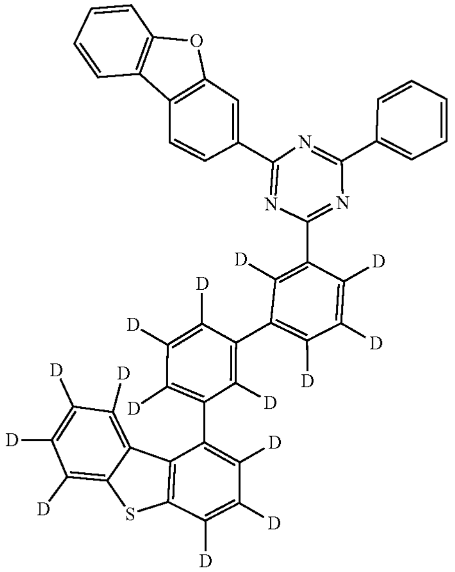
77
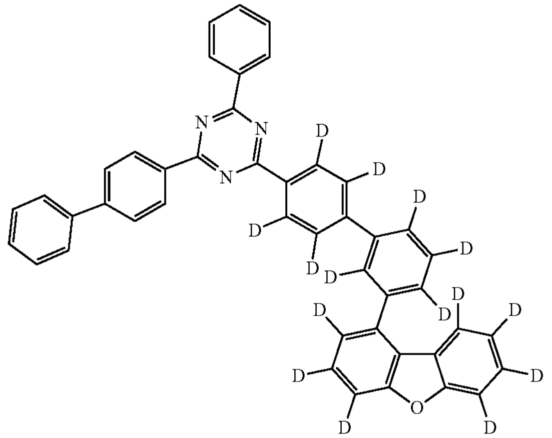
78
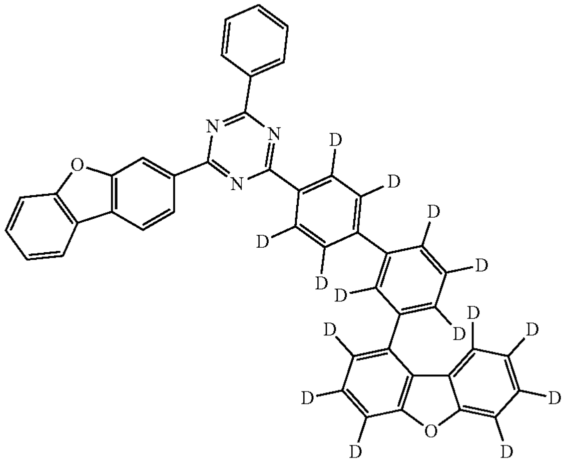

-continued
79
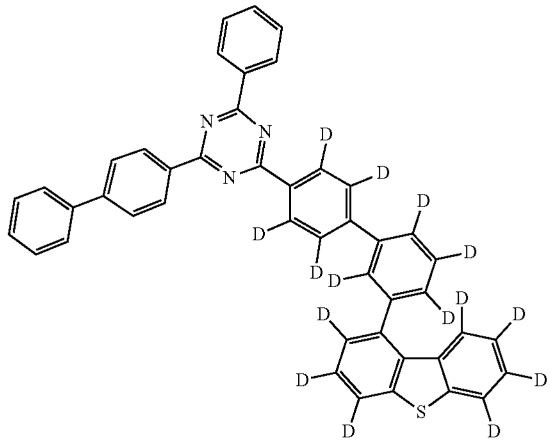
80
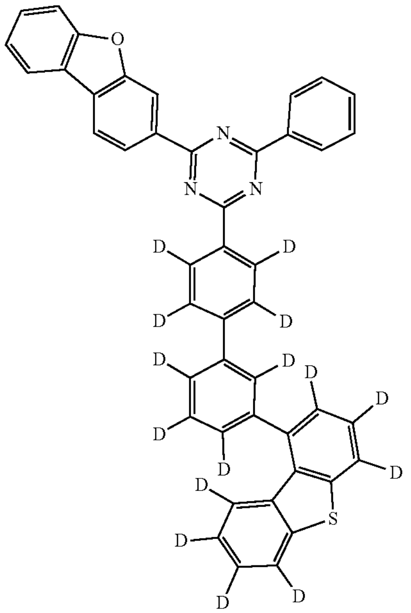
81
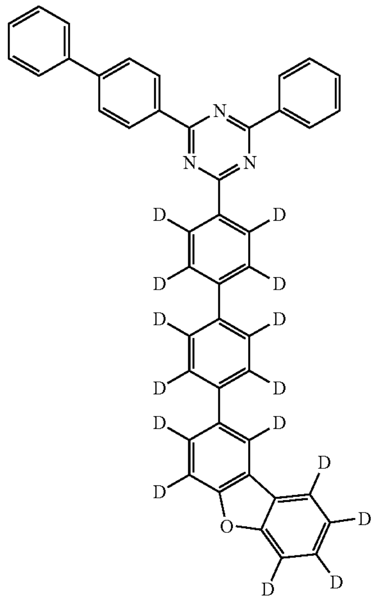
82
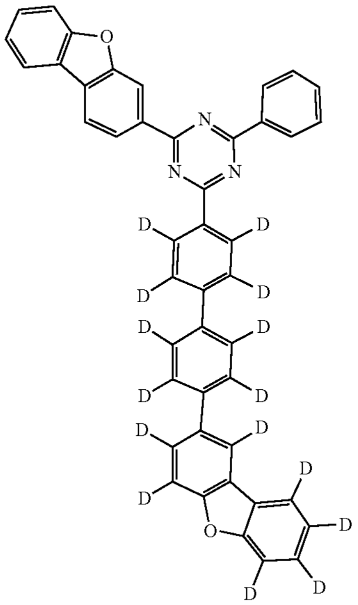

-continued
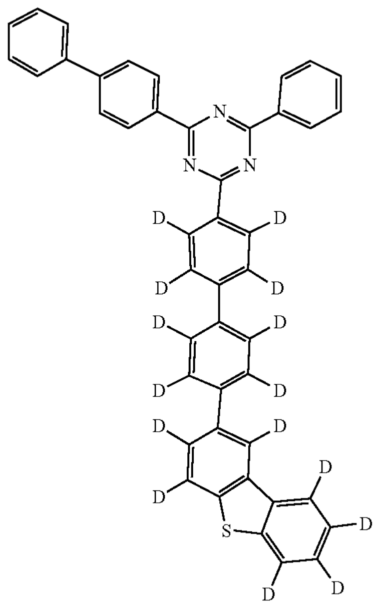
83
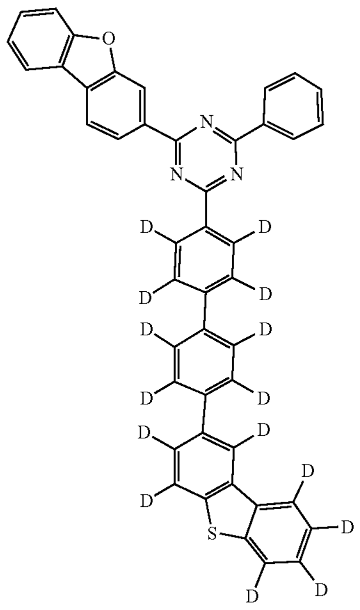
84
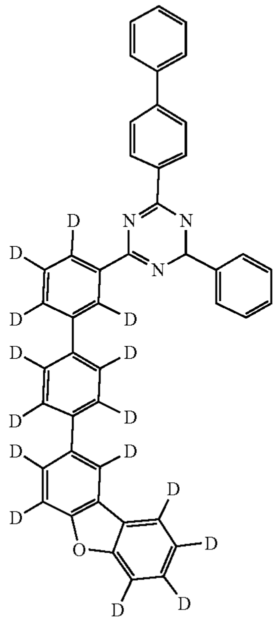
85
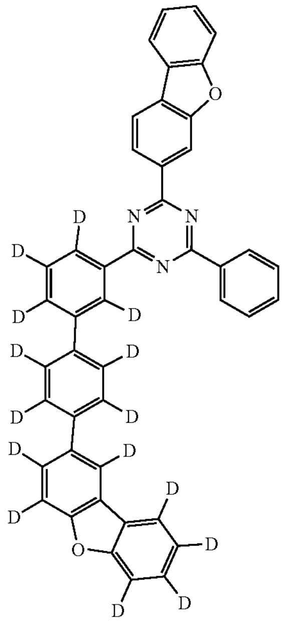
86

-continued
87
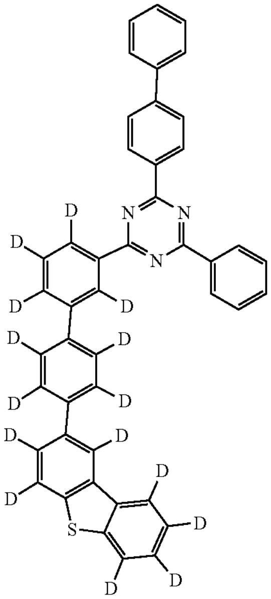
88
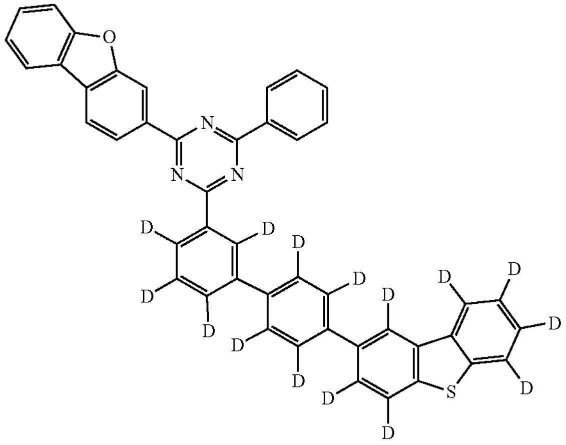
89
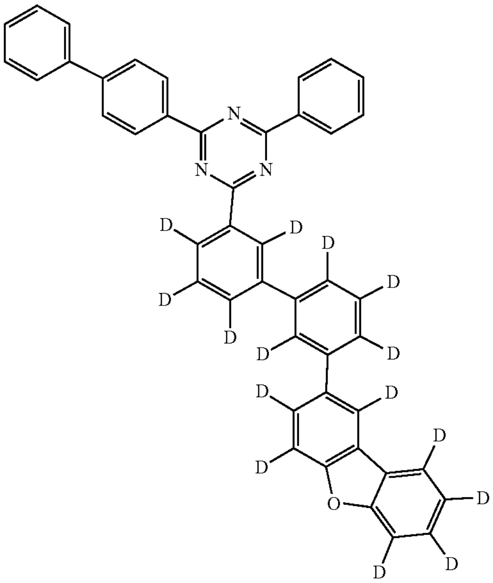
90
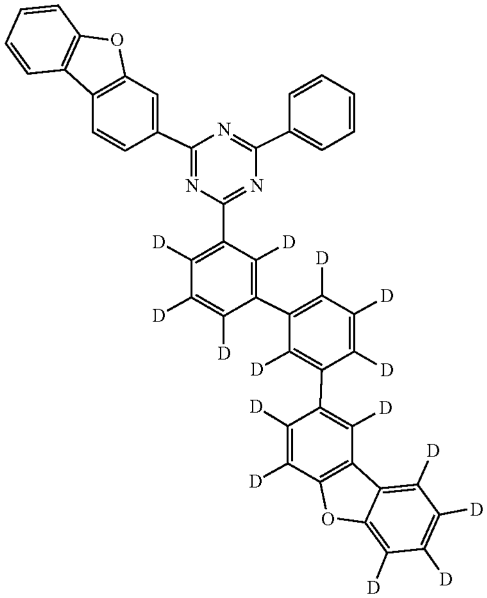

-continued
91
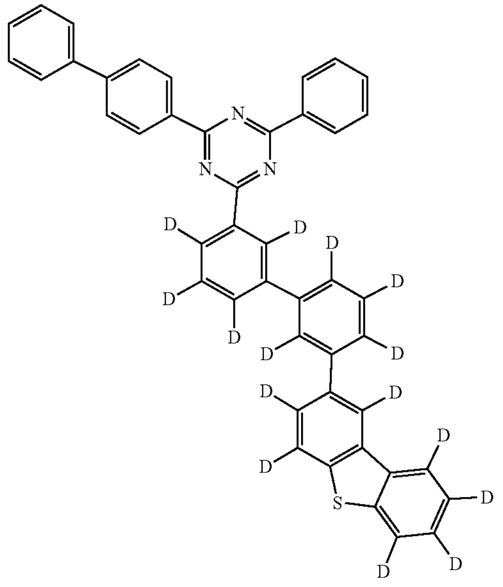
92
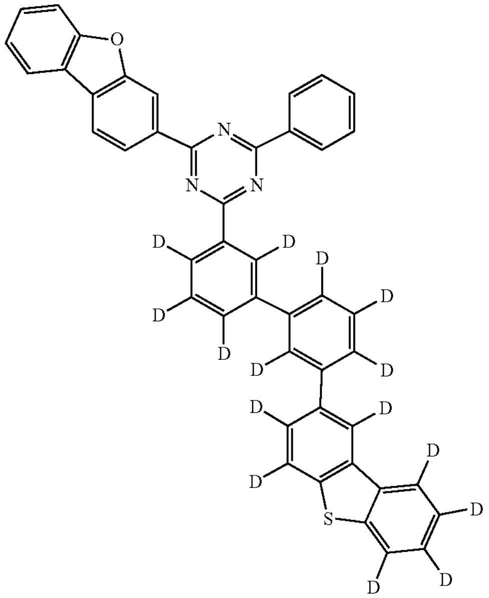
93
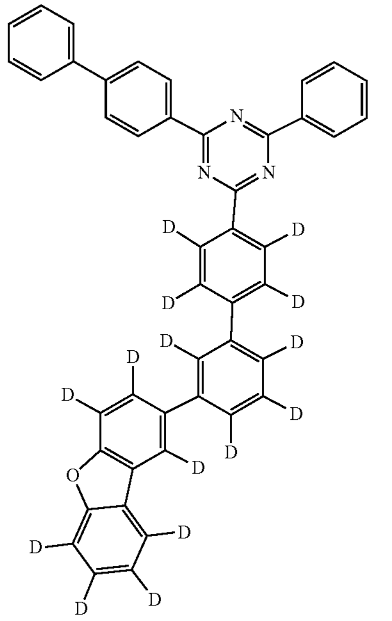
94
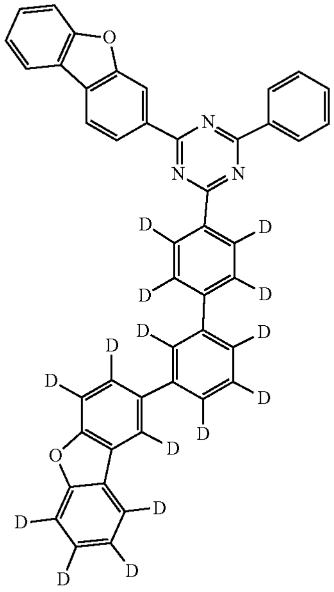

-continued
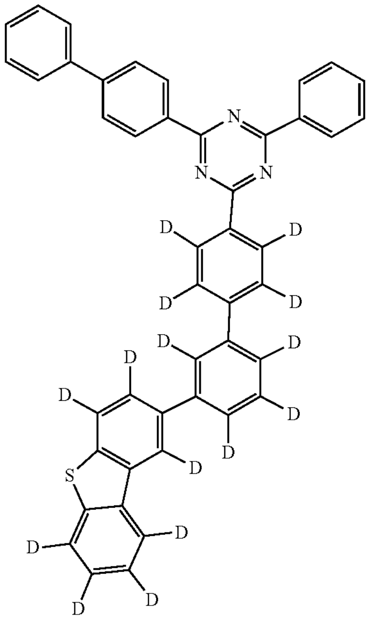
95
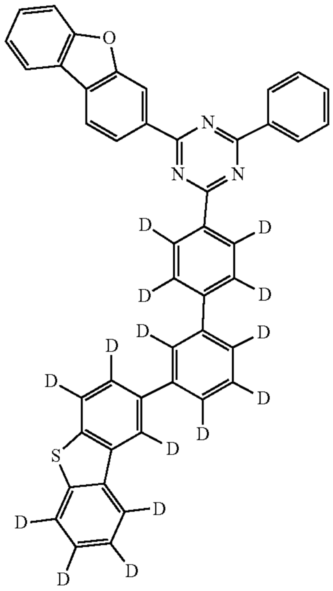
96
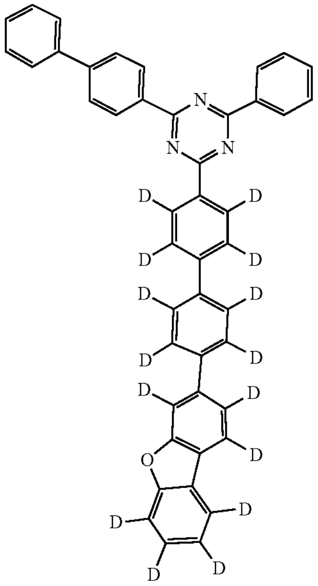
97
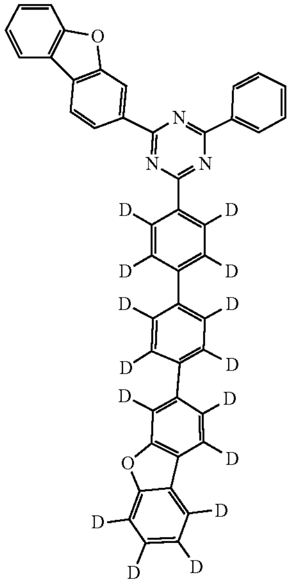
98

-continued
99
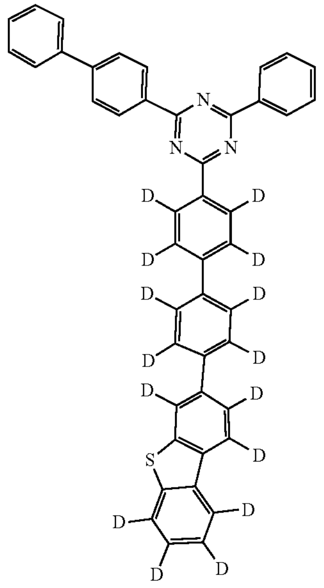
100
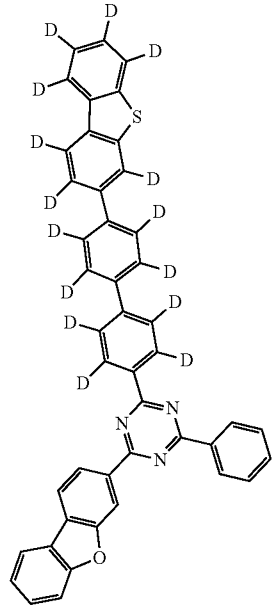
101
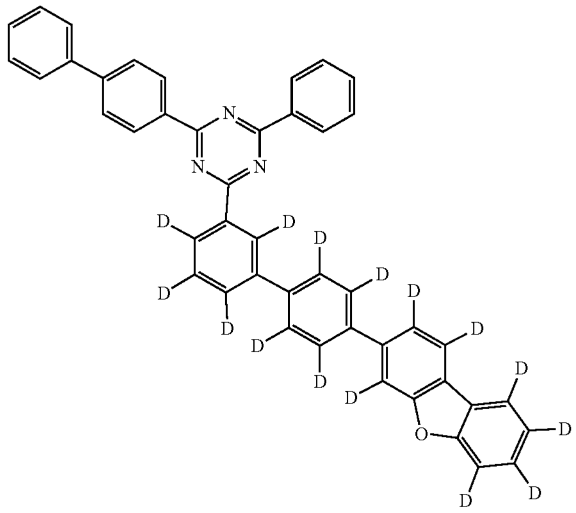
102
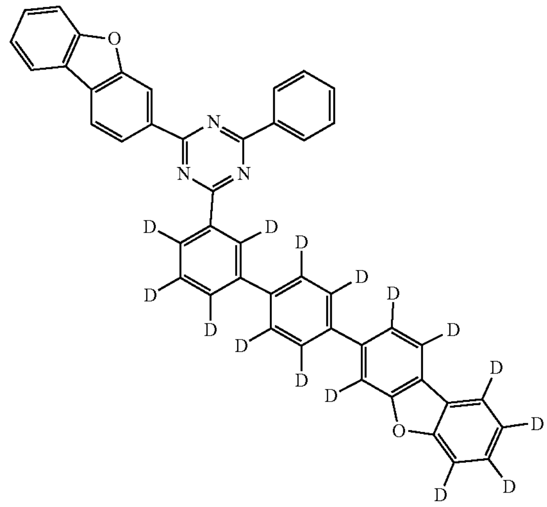
103
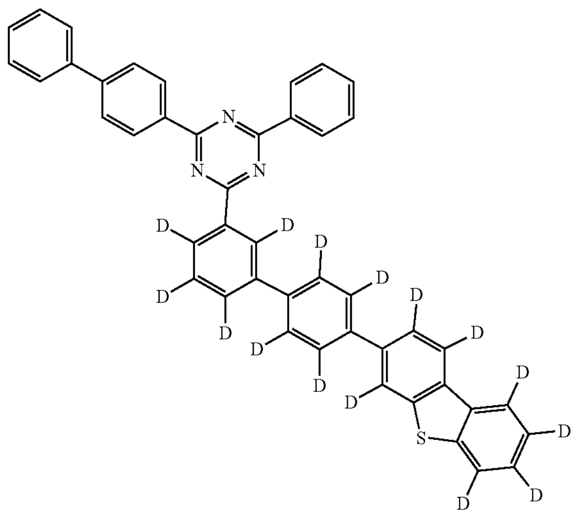
104
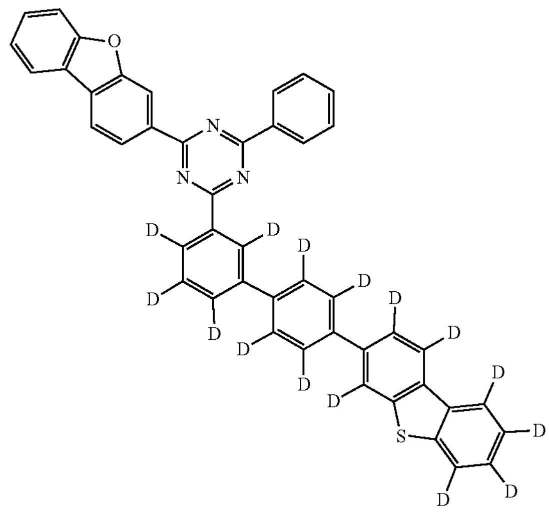

-continued
105
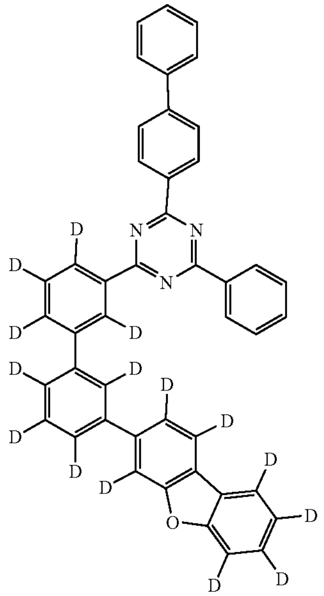
106
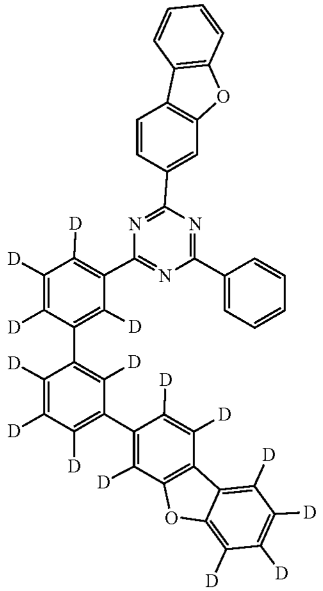
107
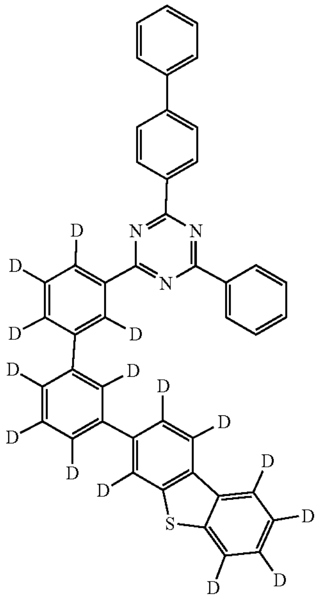
108
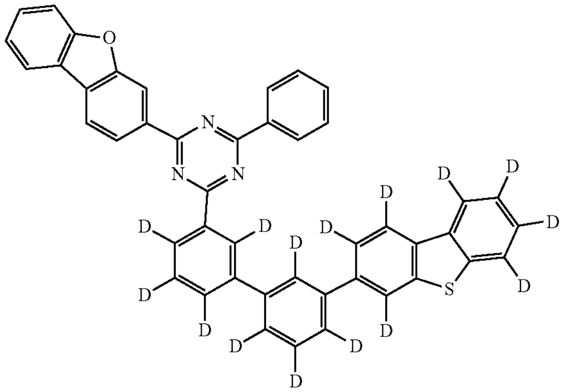

-continued
109
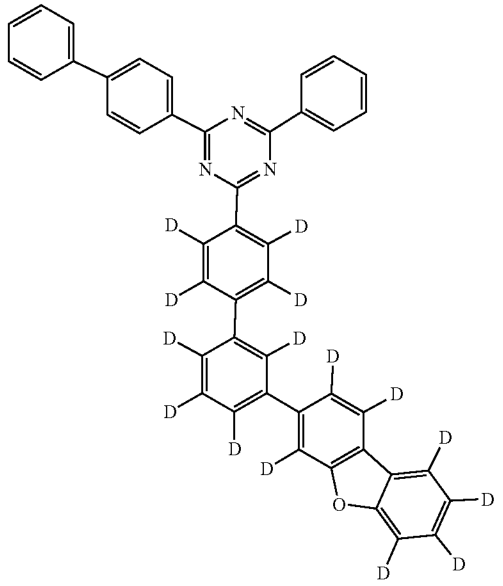
110
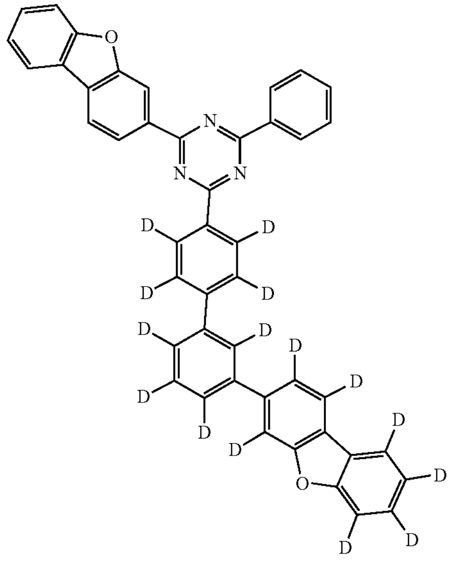
111
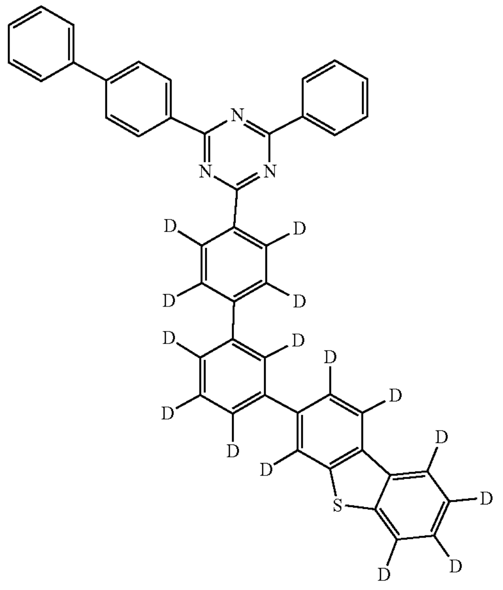
112
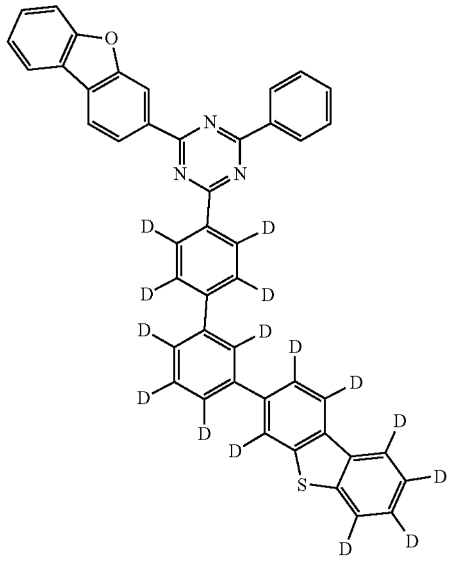

-continued
113
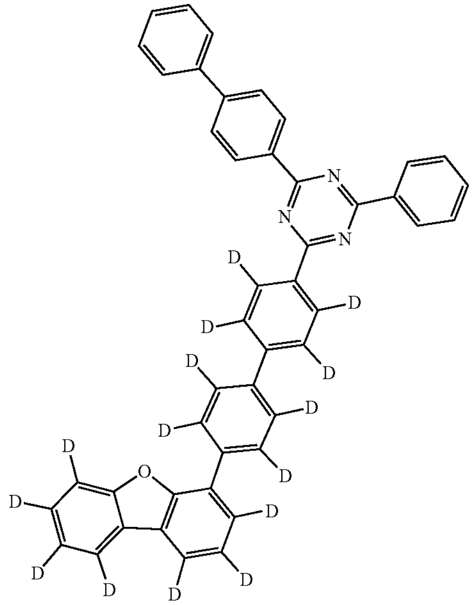
114
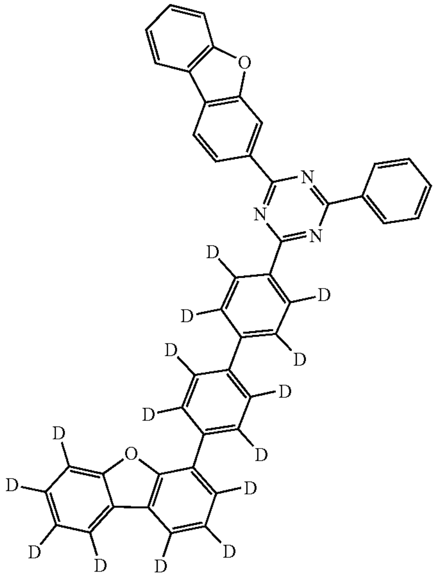
115
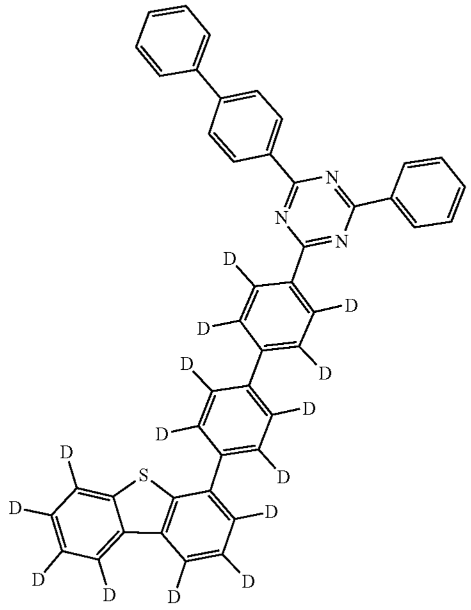
116
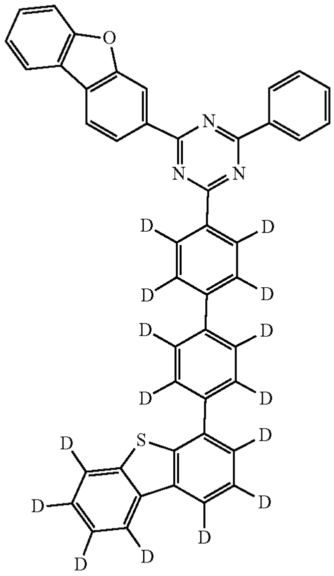

-continued
117
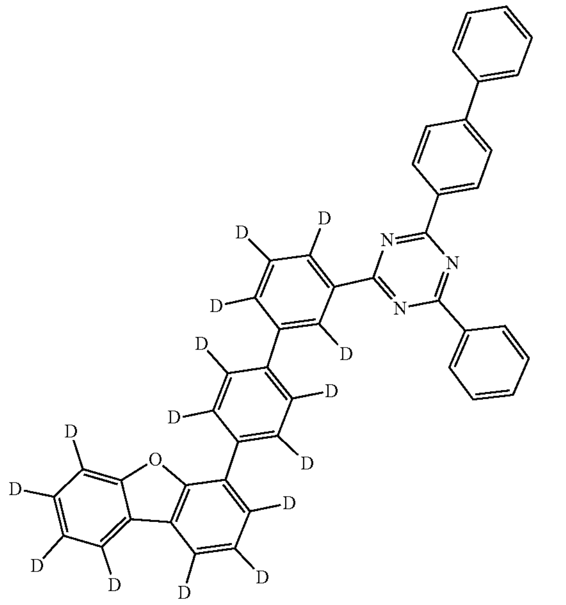
118
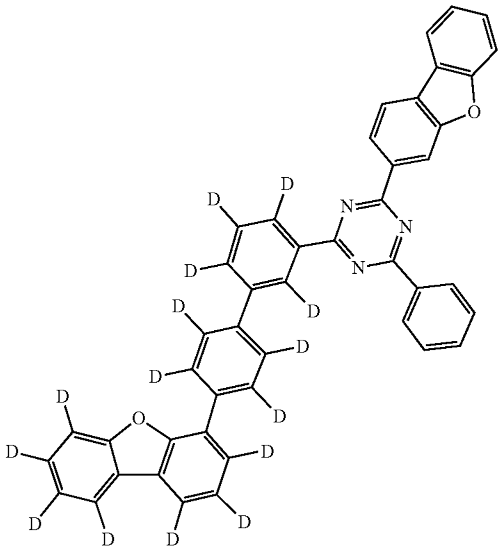
119
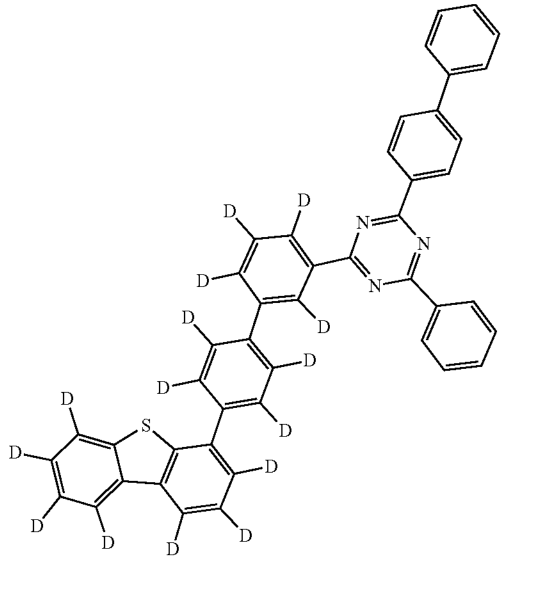
120
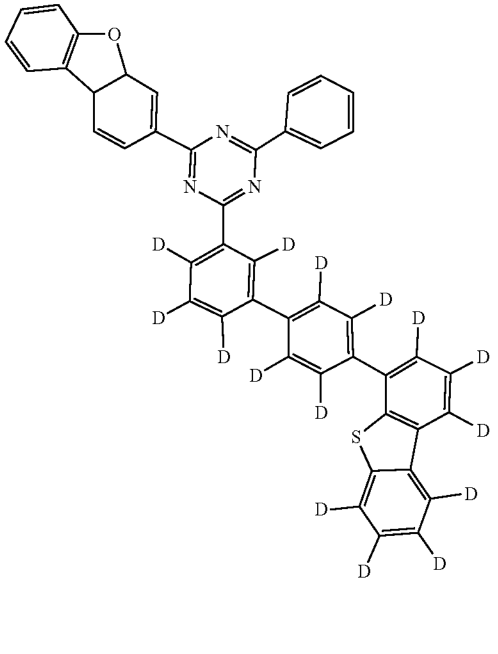

-continued
121
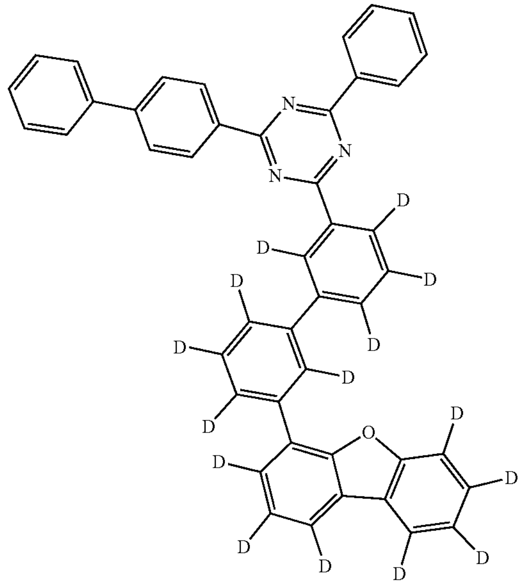
122
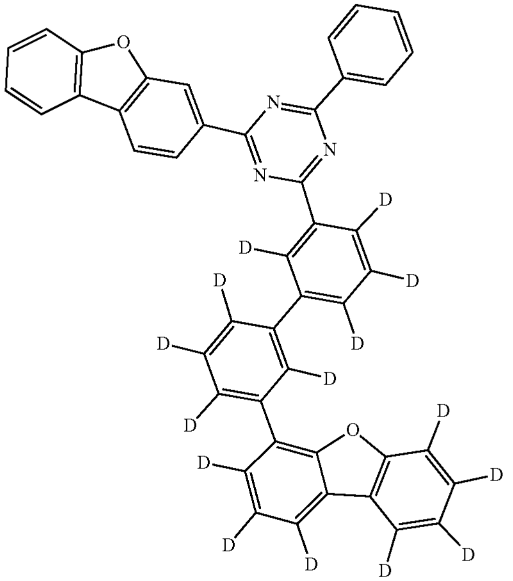
123
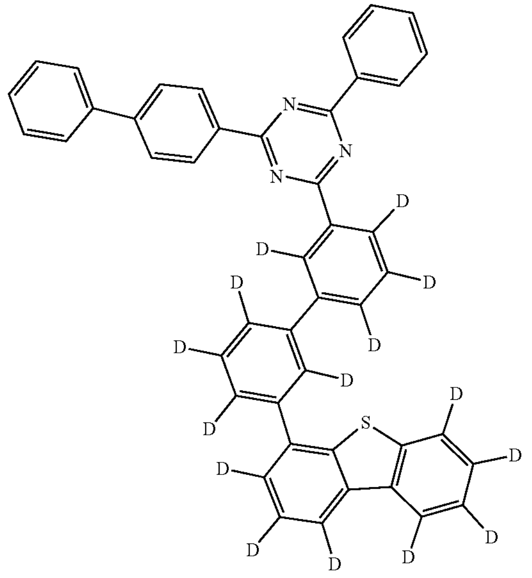
124
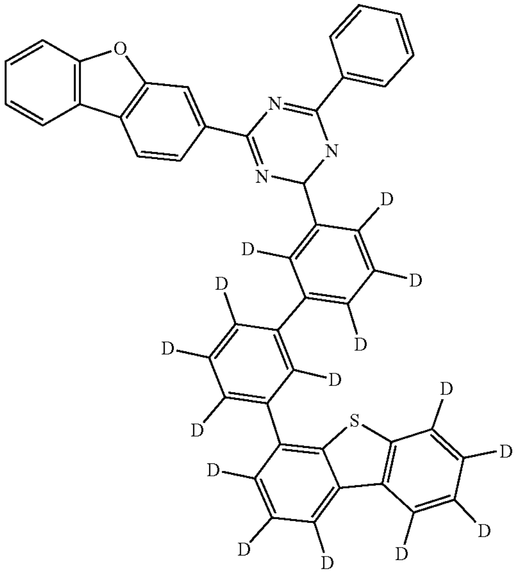

-continued
125
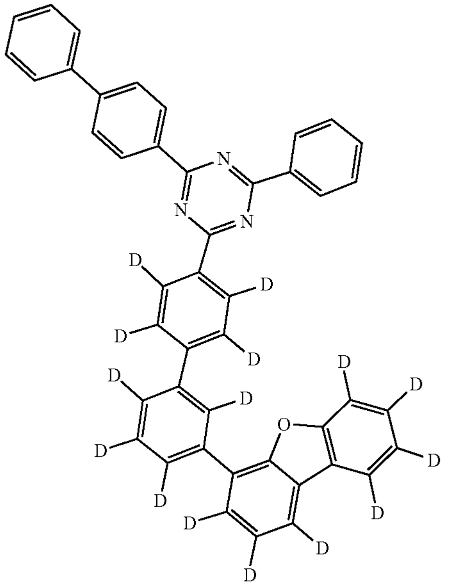
126
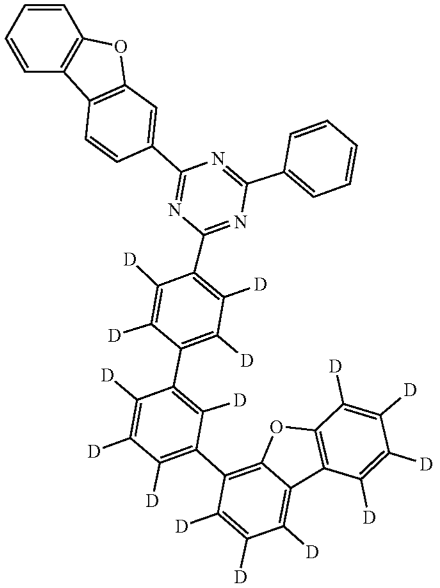
127
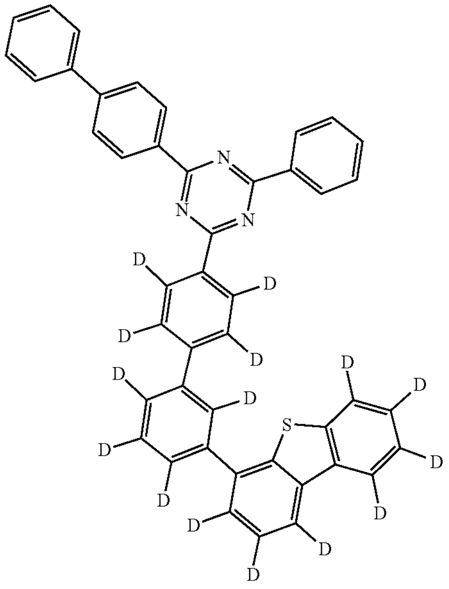
128
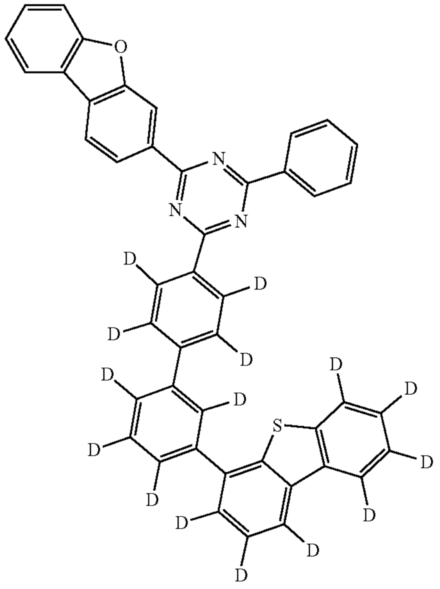
129
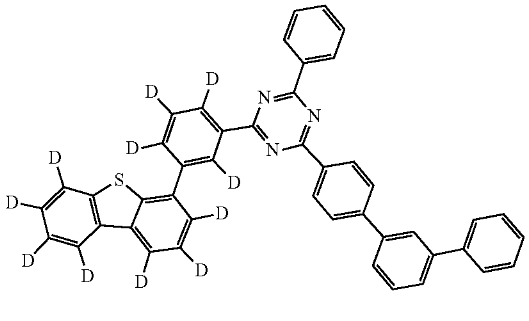
130
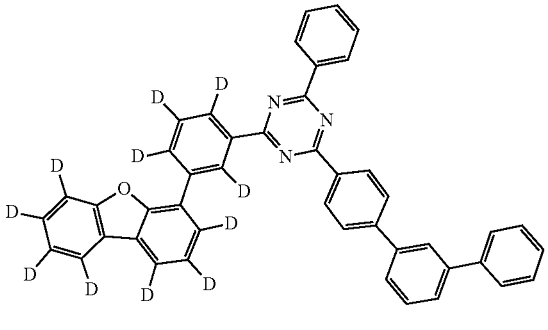

-continued
131
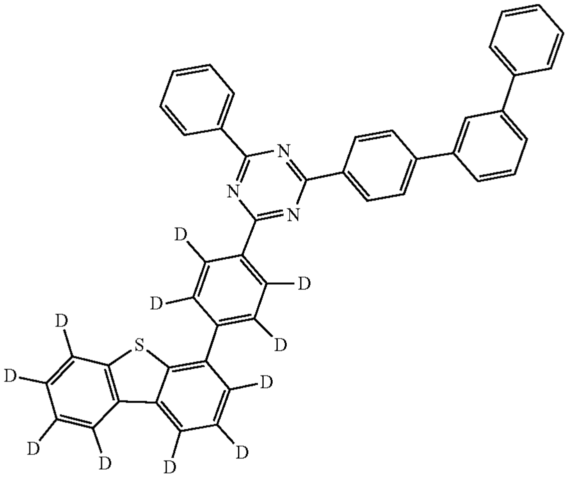
132
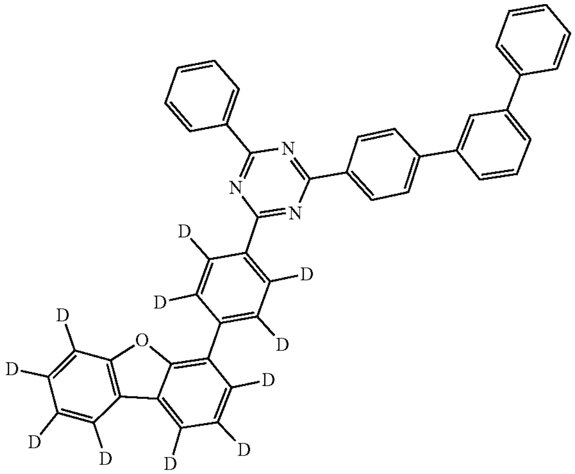
133
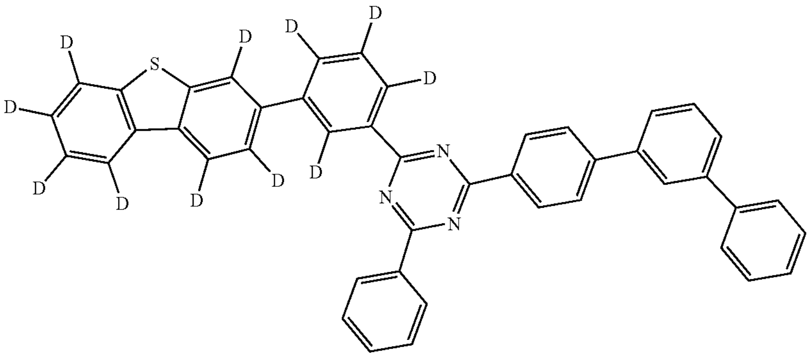
134
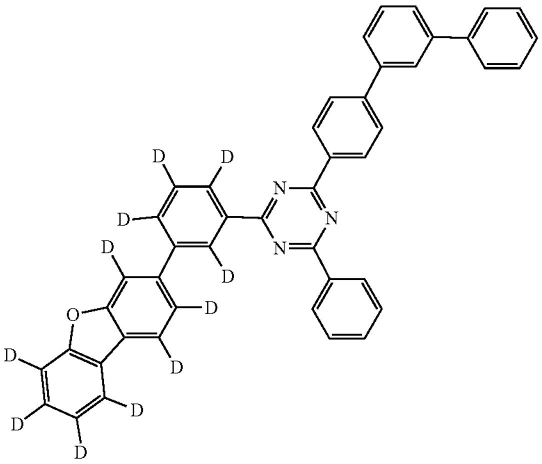
135
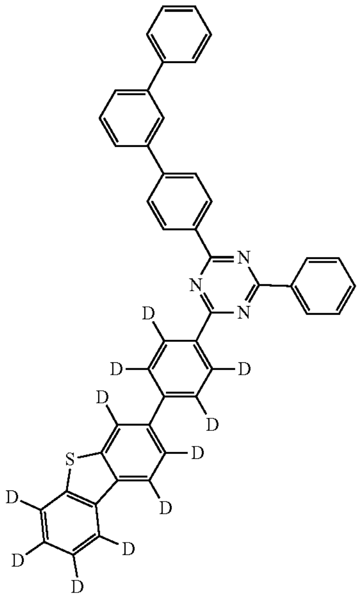

-continued
136
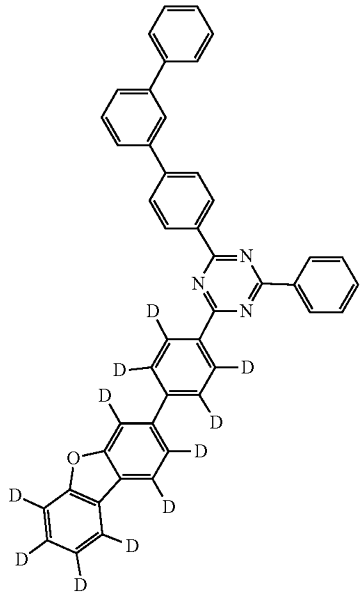
137
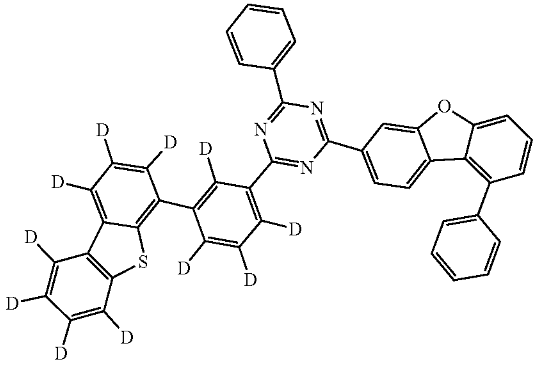
138
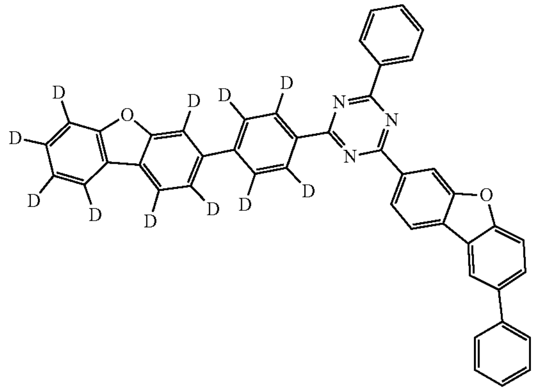
139
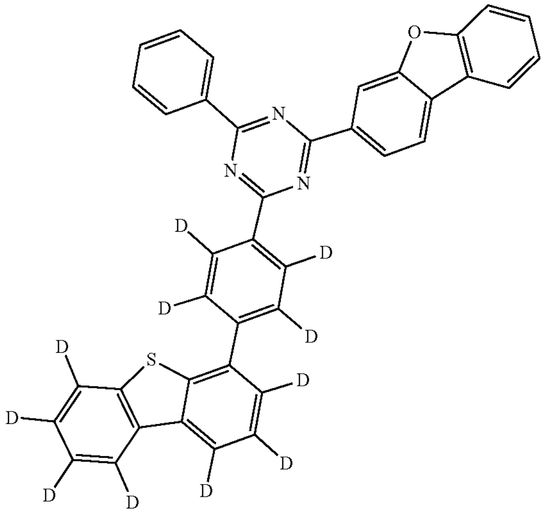

-continued
140
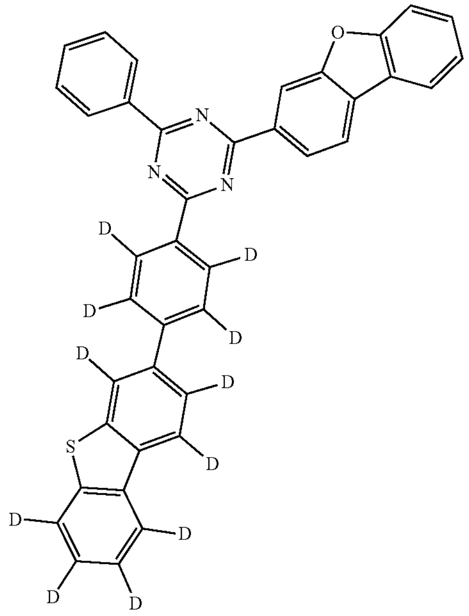
141
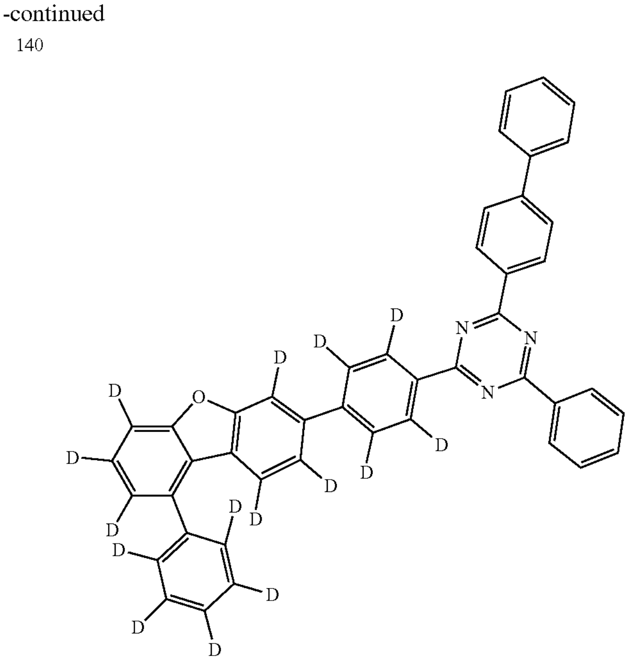
142
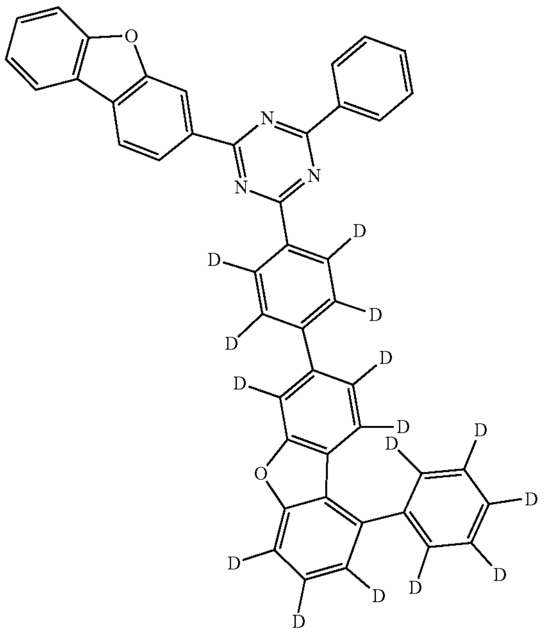
143
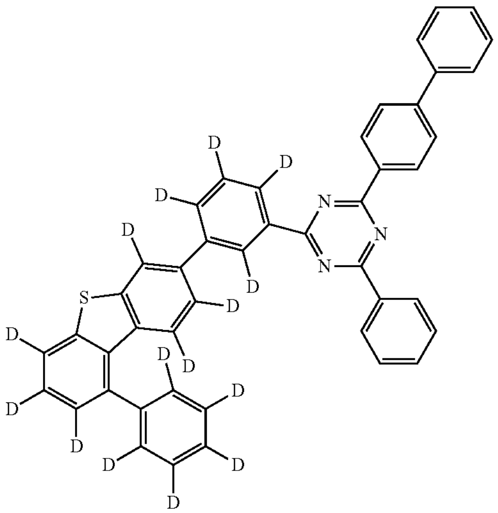

-continued
144
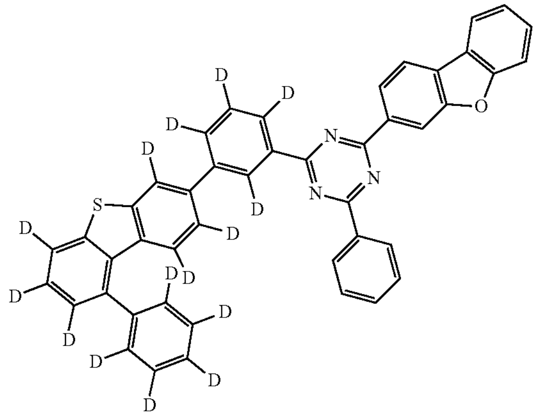
145
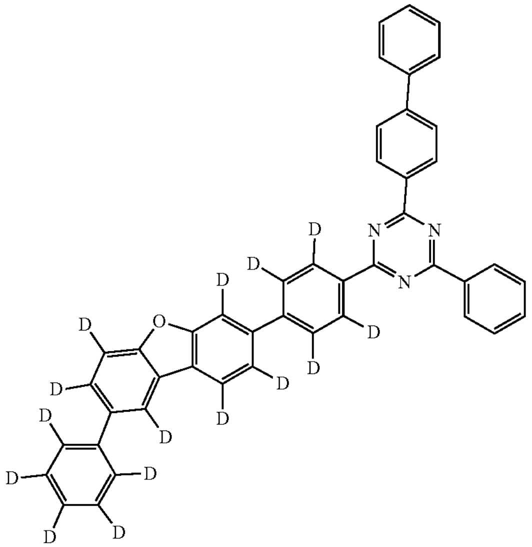
146
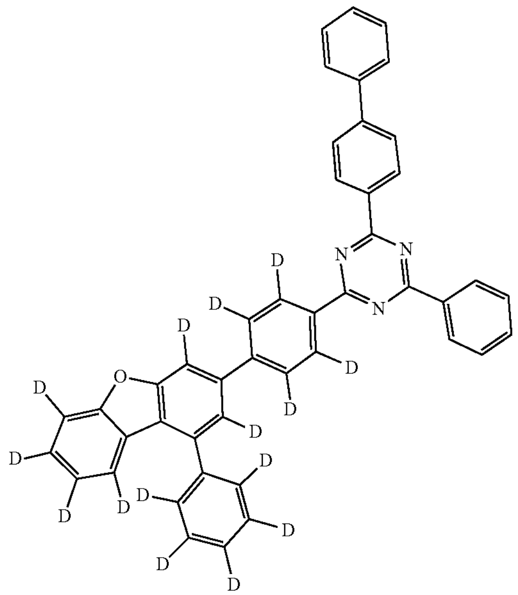
147
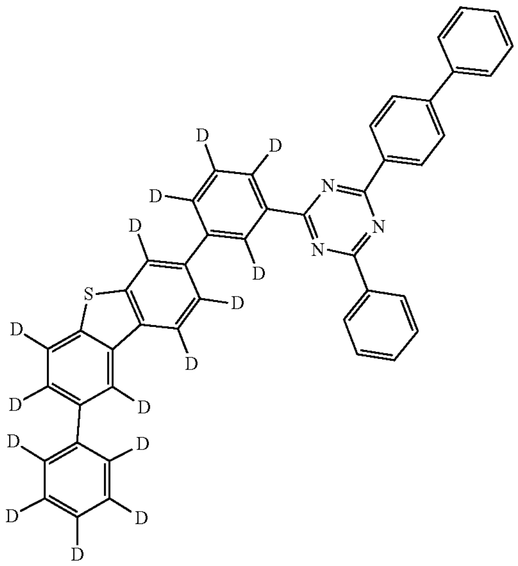

-continued
148
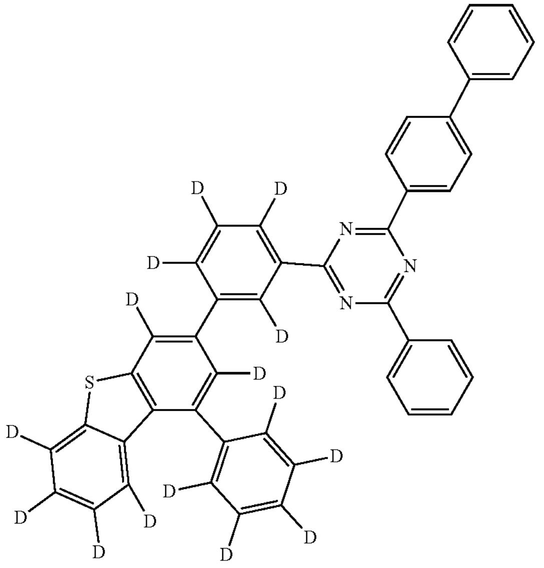
149
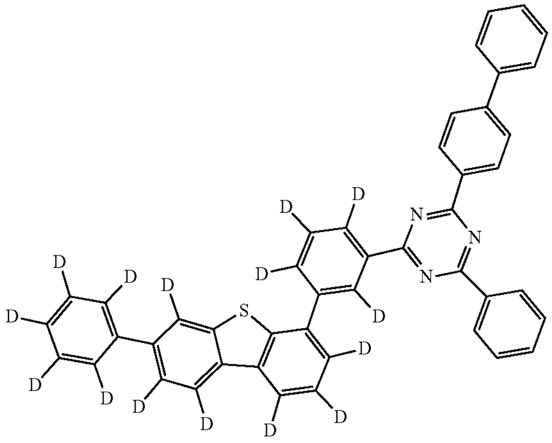
150
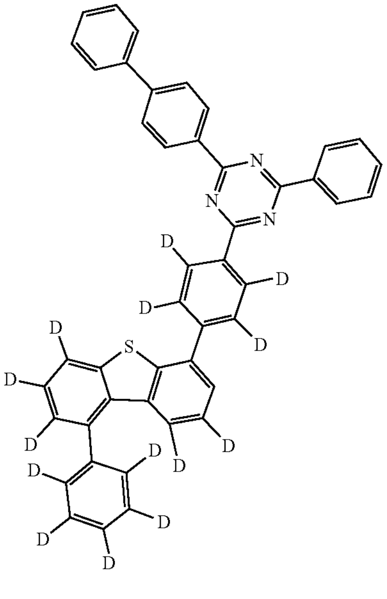
151
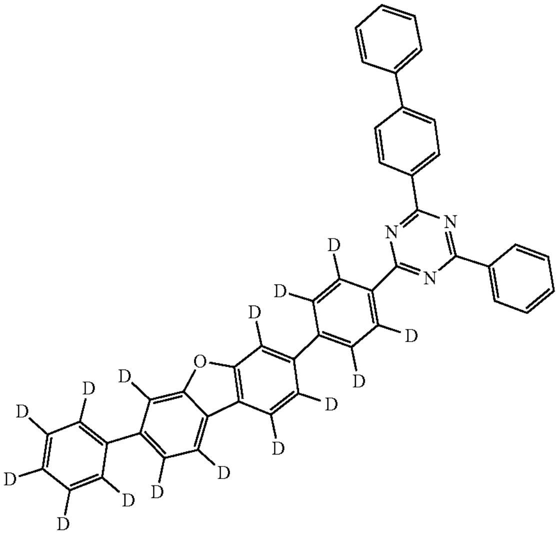

-continued
152
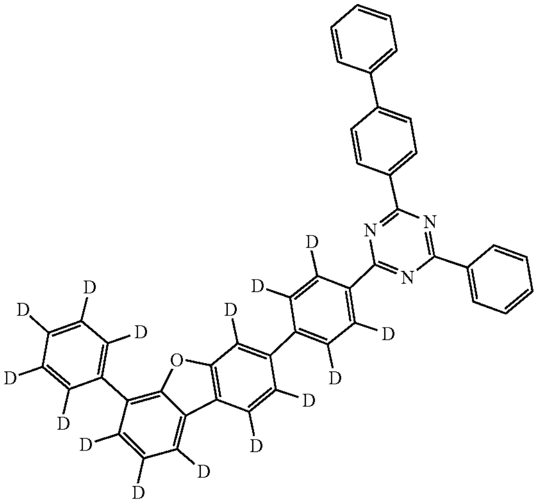
153
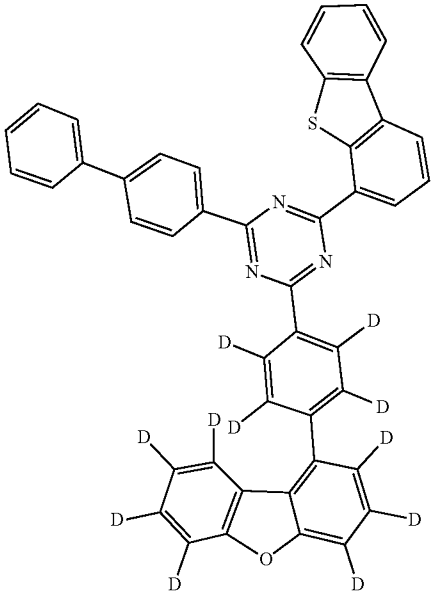
154
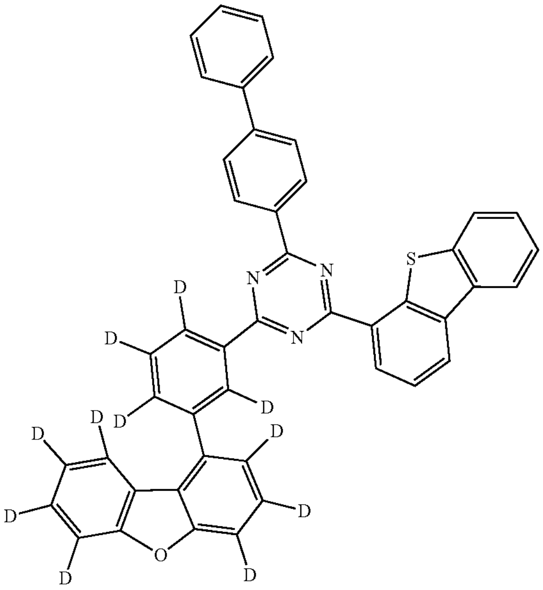
155
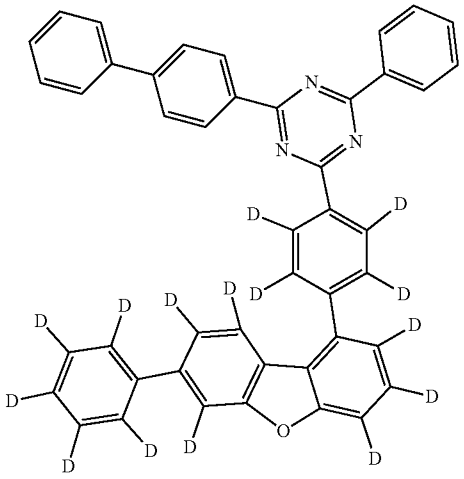

-continued
156
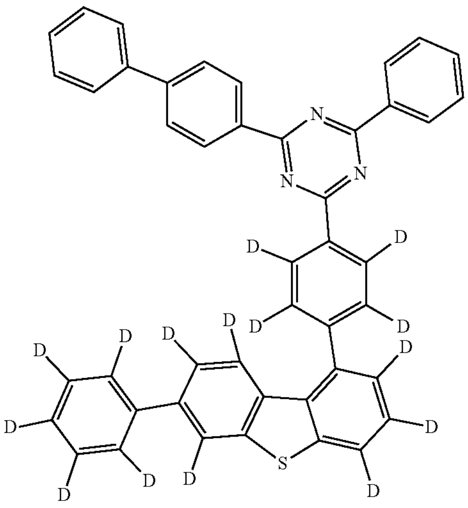
157
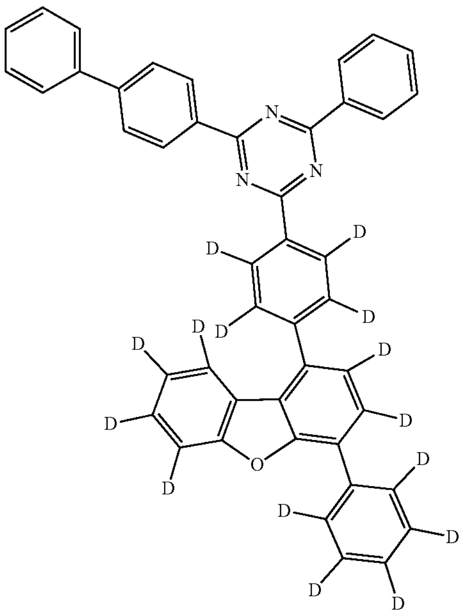
158
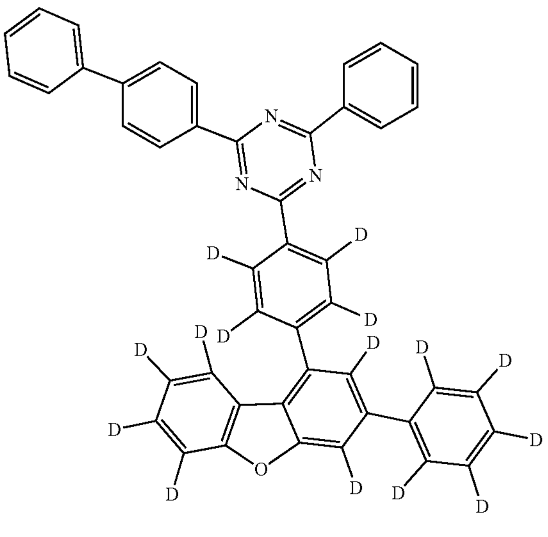
159
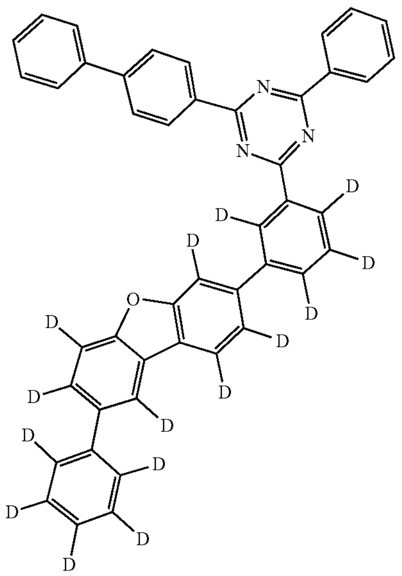

-continued
160
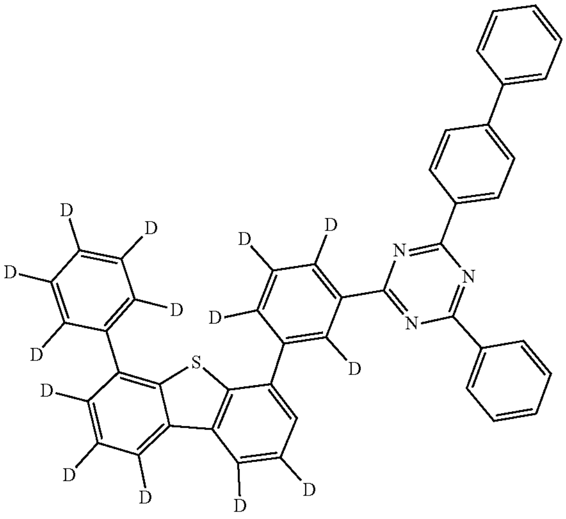
161
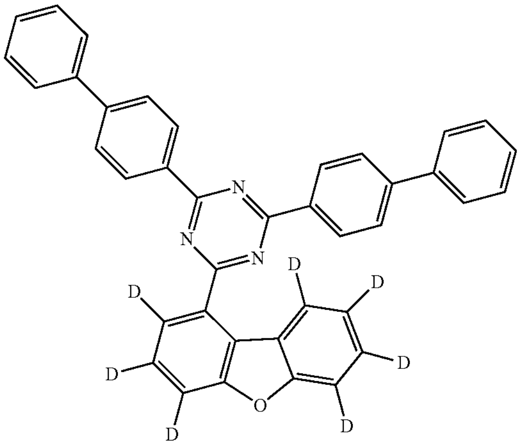
162
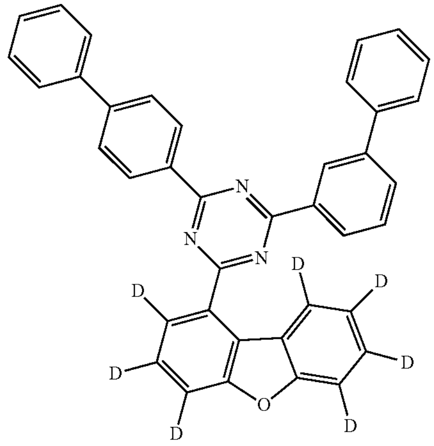
-continued
163
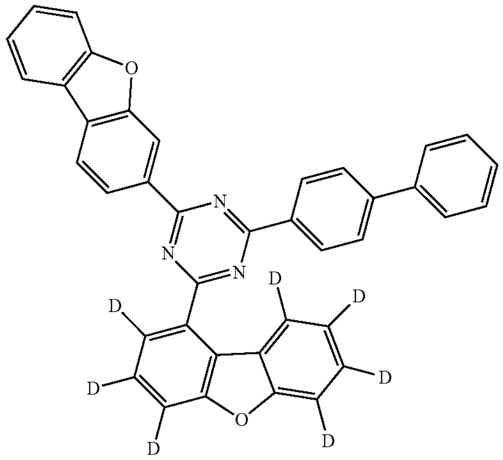
164
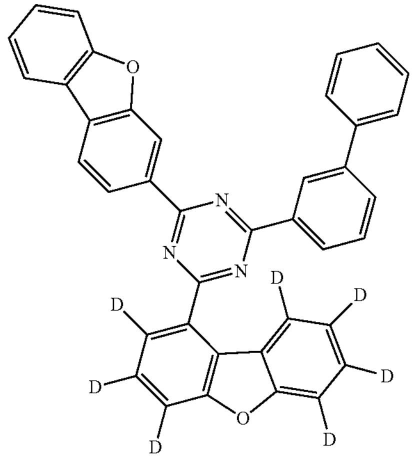

-continued
165
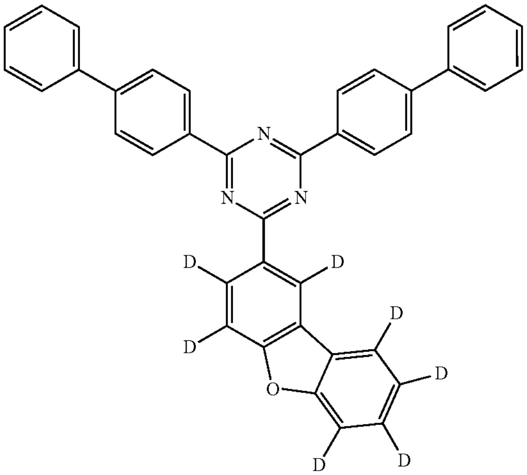
166
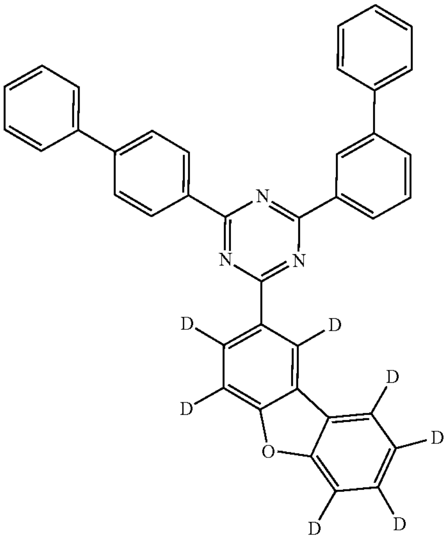
167
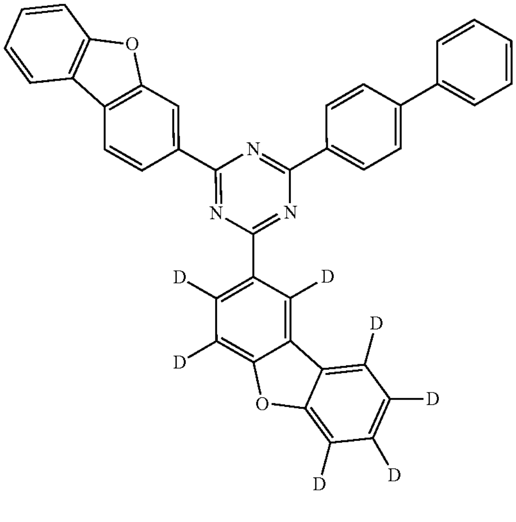
-continued
168
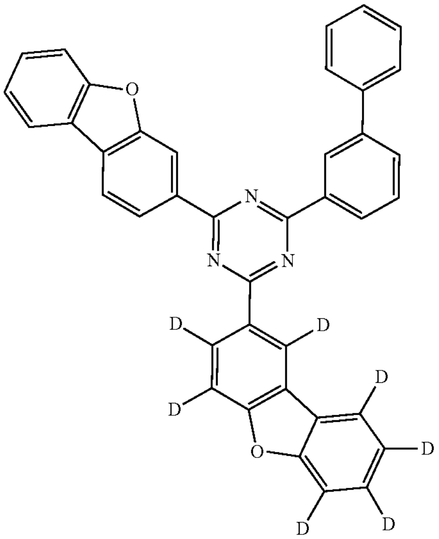
169
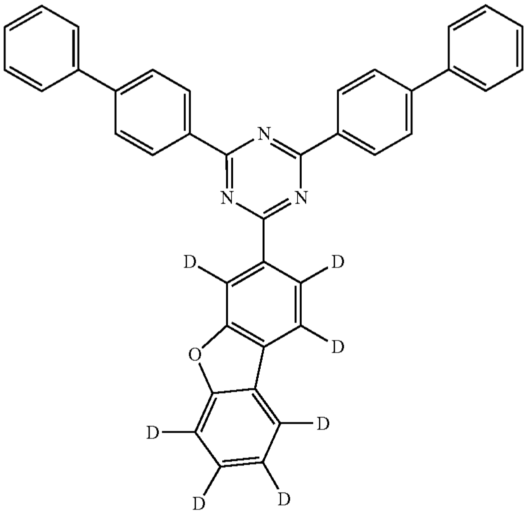
170
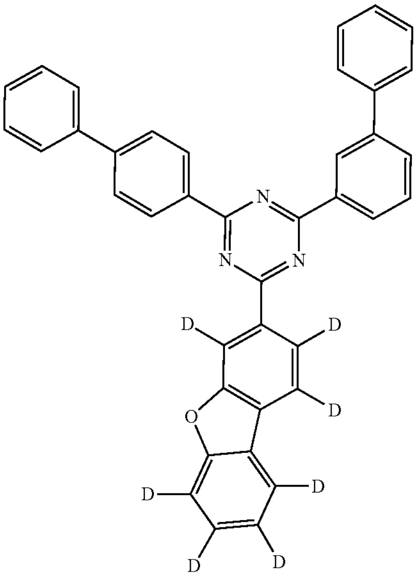

-continued
171
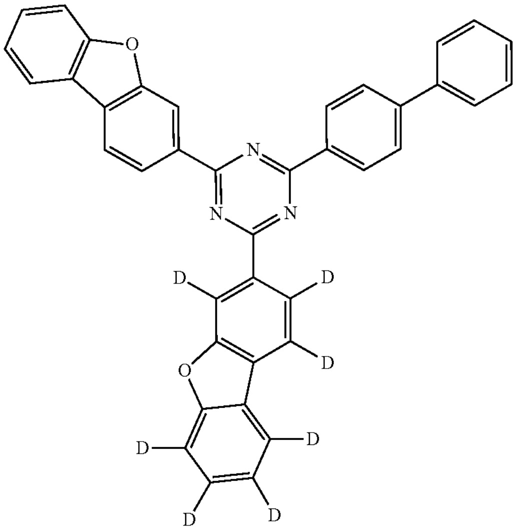
172
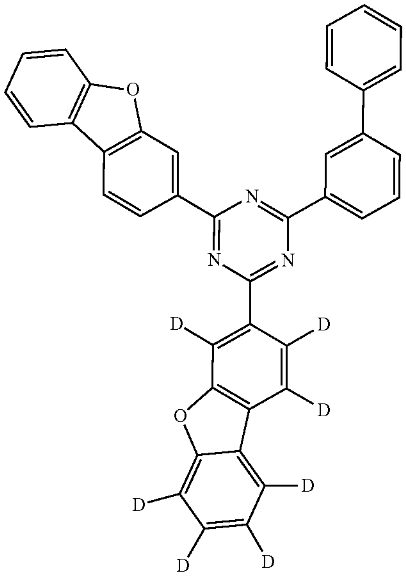
173
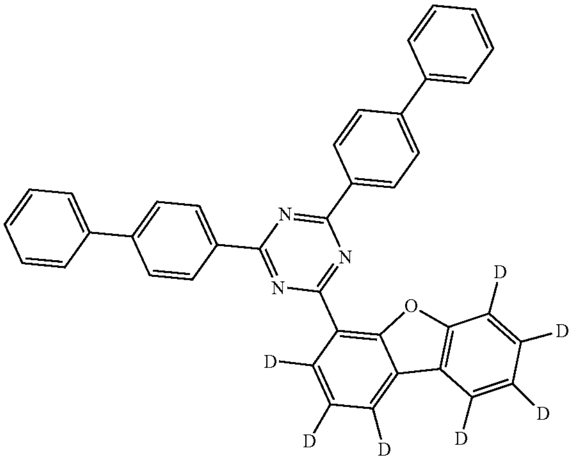
-continued
174
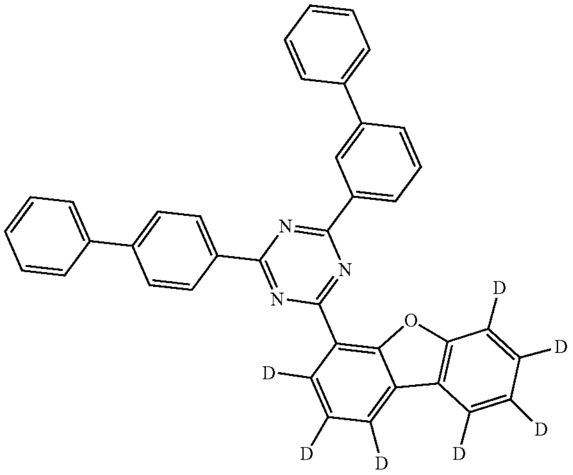
175
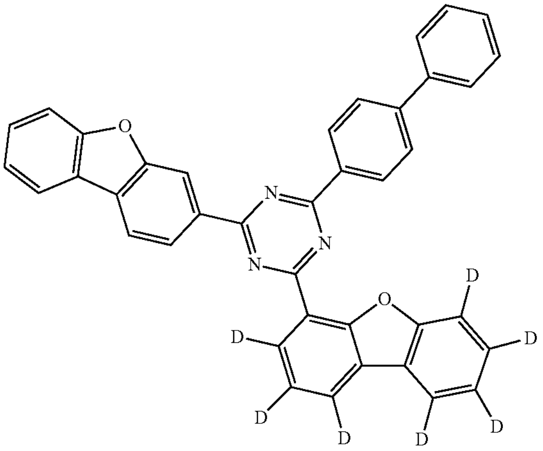
176
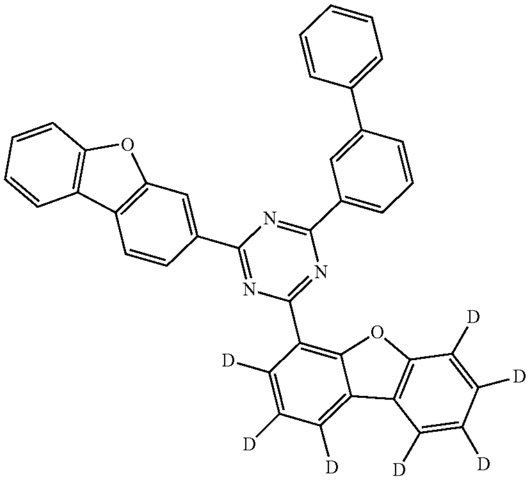

-continued
177
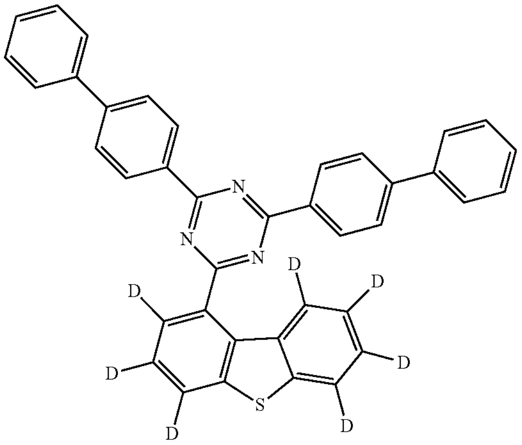
178
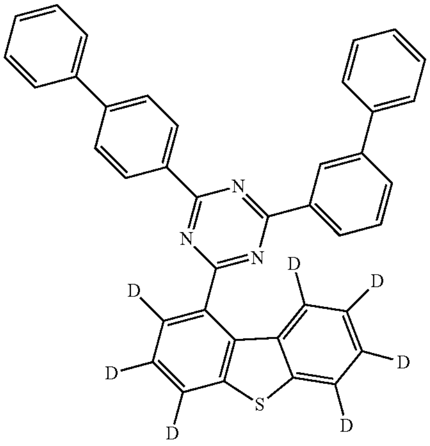
179
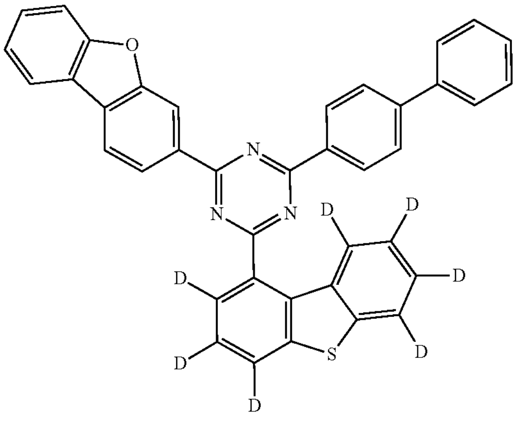
-continued
180
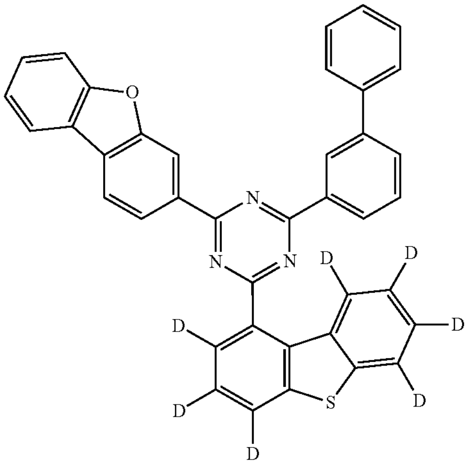
181
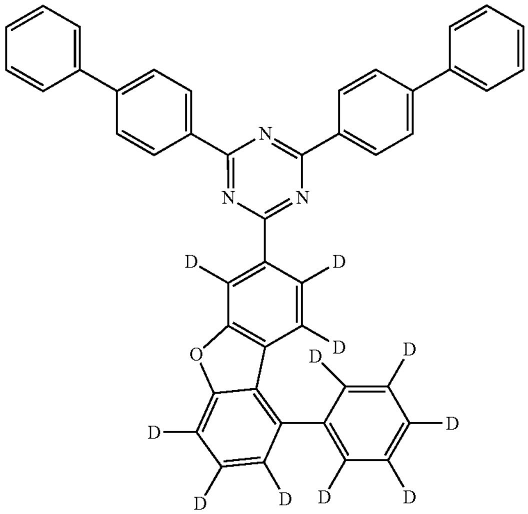
182
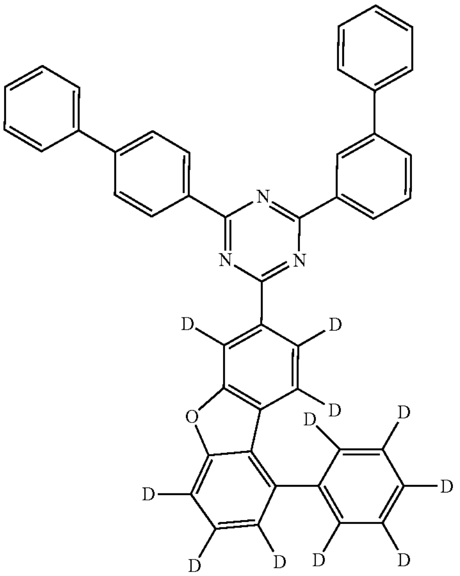

-continued
183
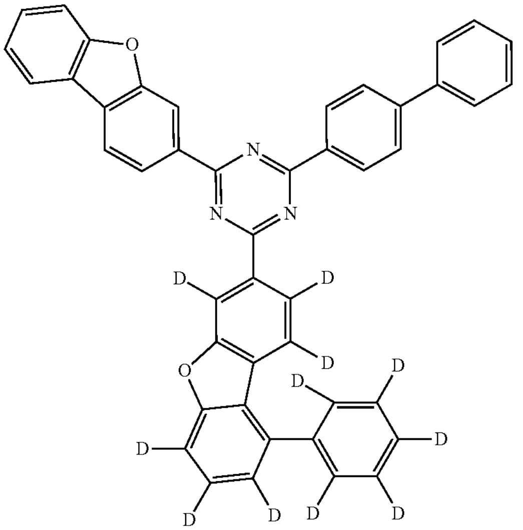
184
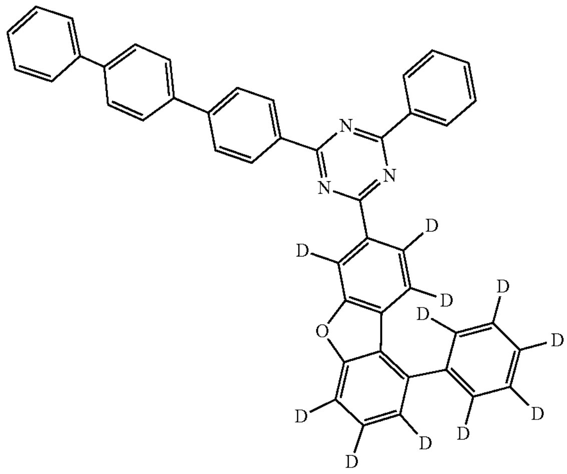
185
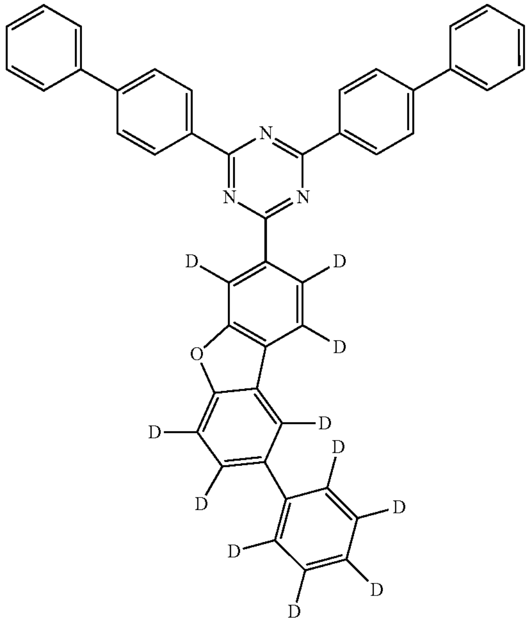
-continued
186
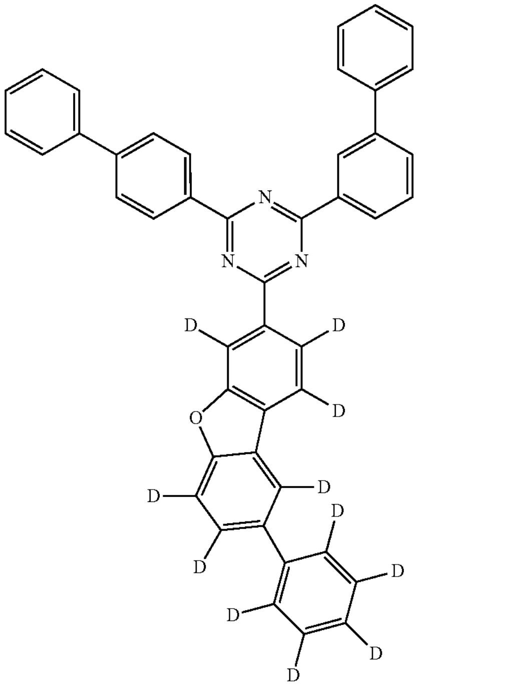
187
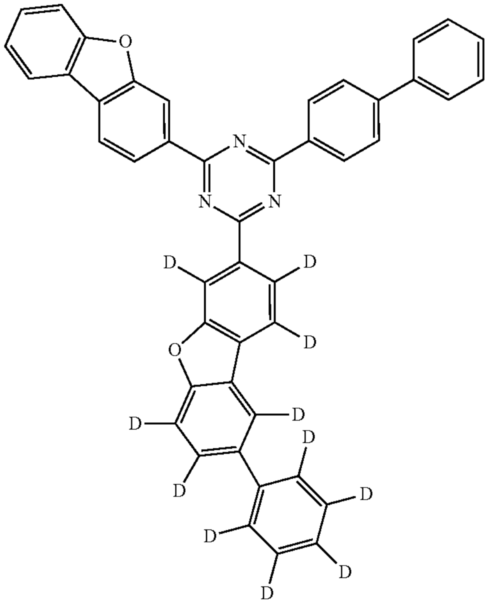

-continued
188
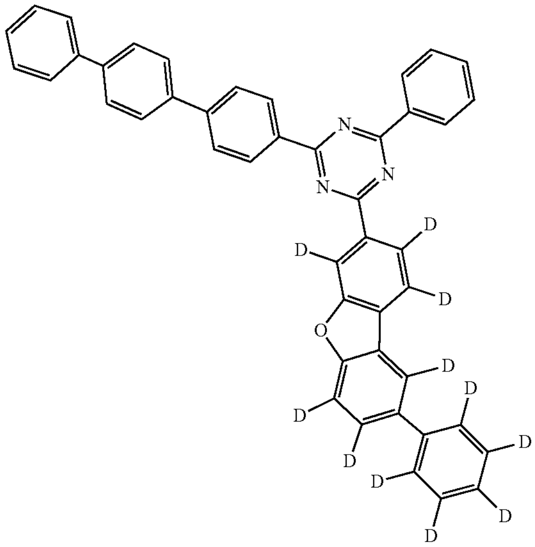
189
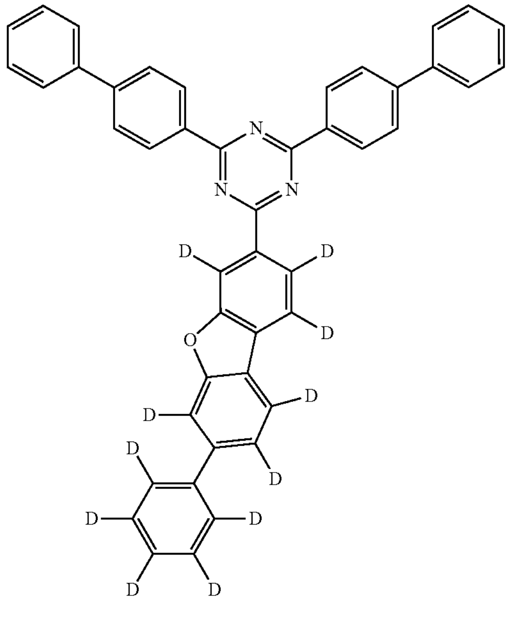
-continued
190
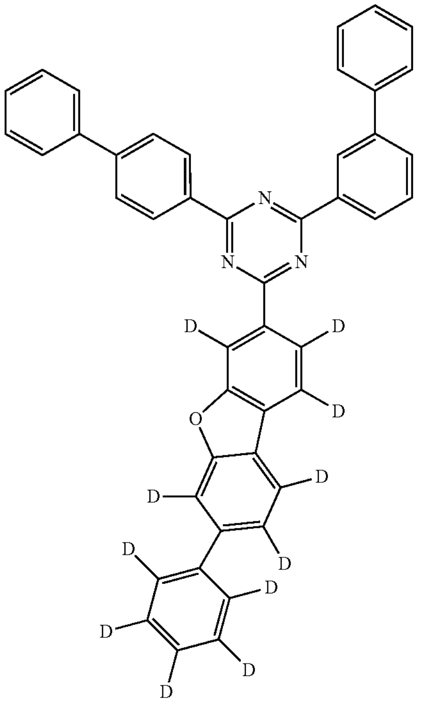
191
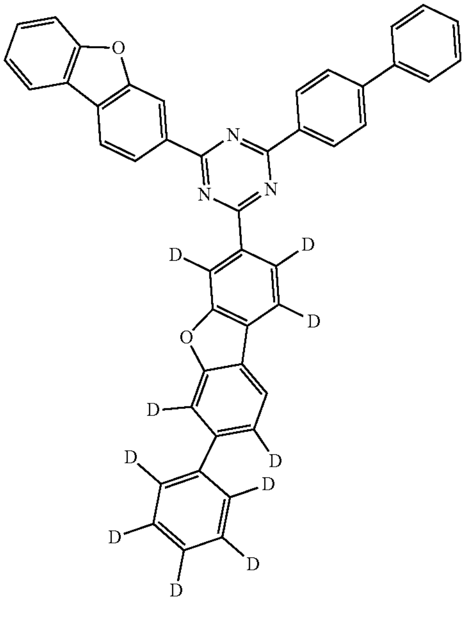

-continued
192
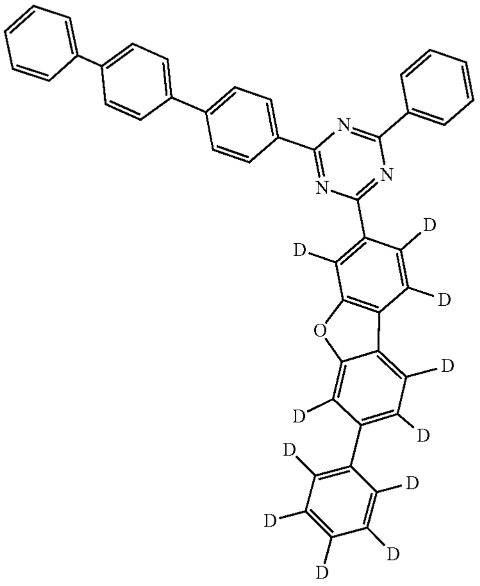
194
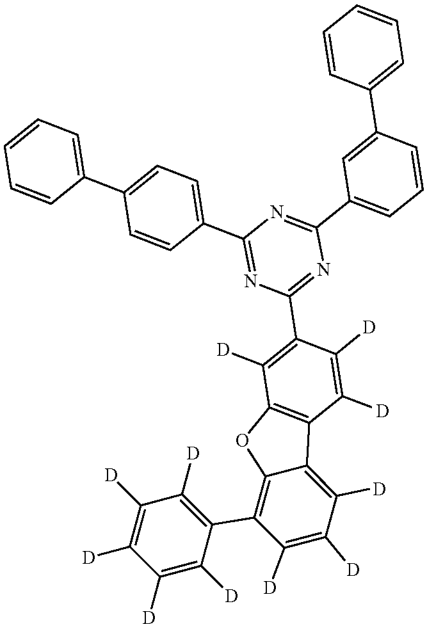
193
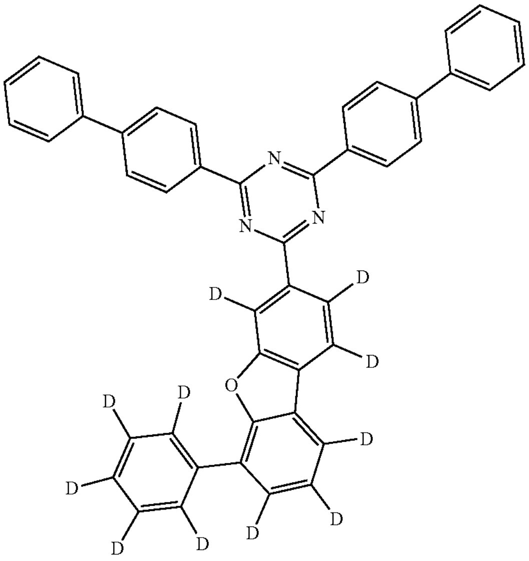
195
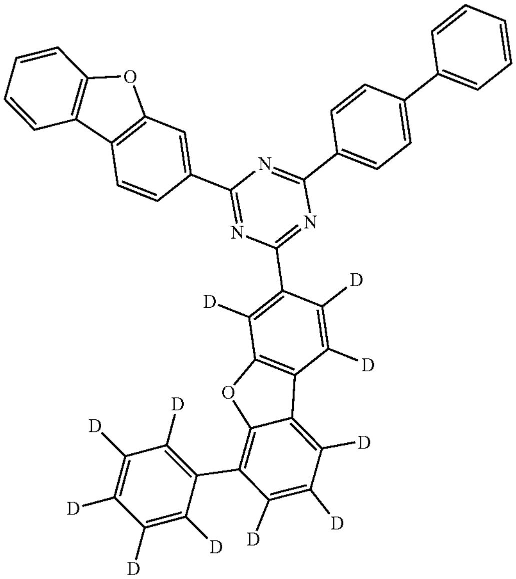

-continued
196
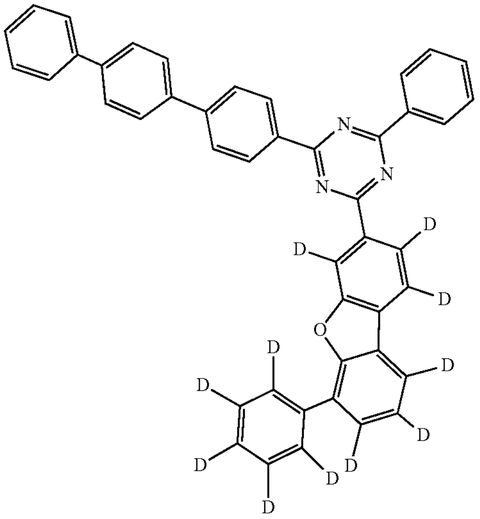
197
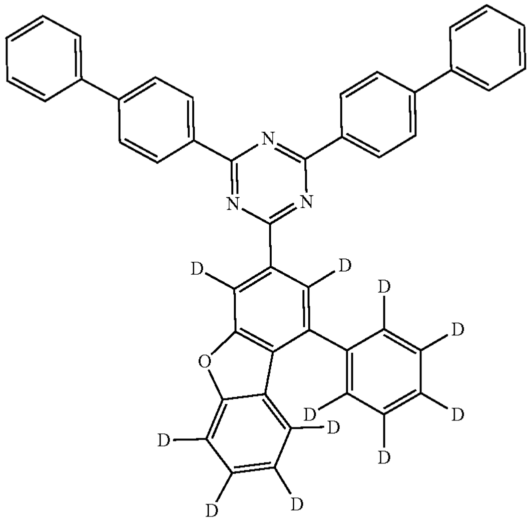
198
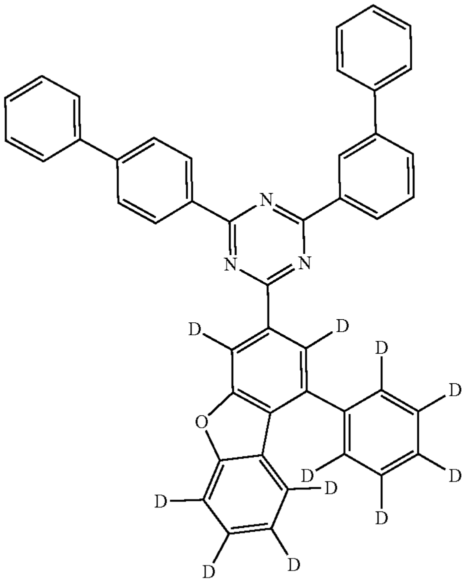
-continued
199
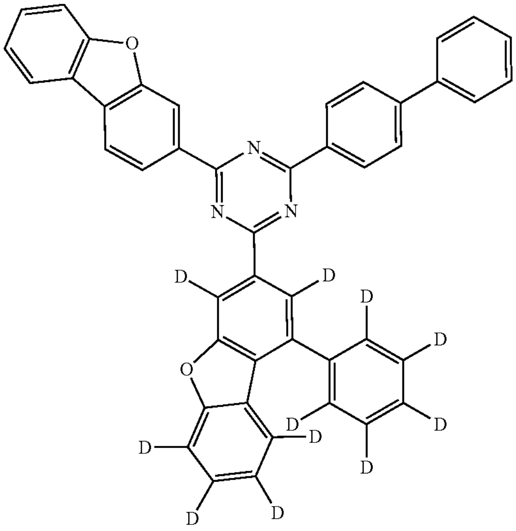
200
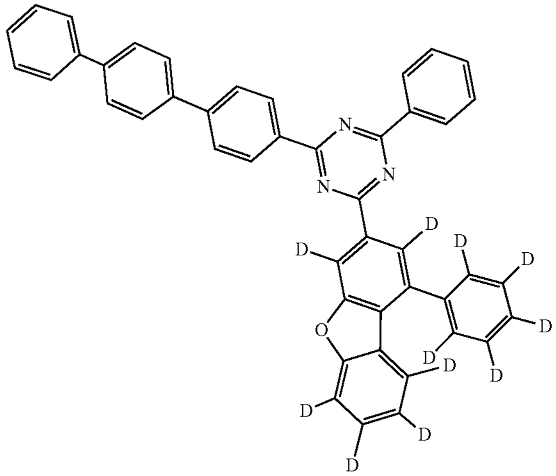
201
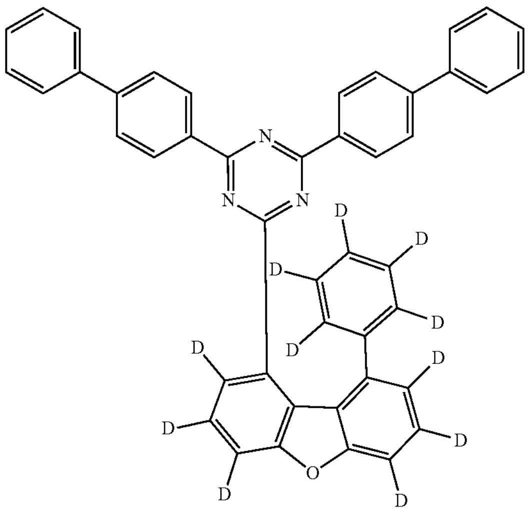

-continued
202
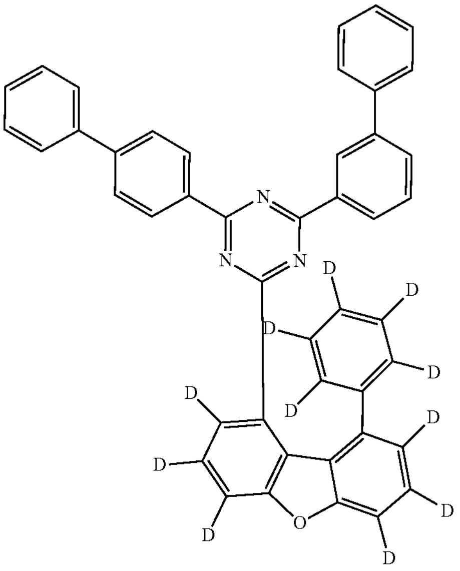
203
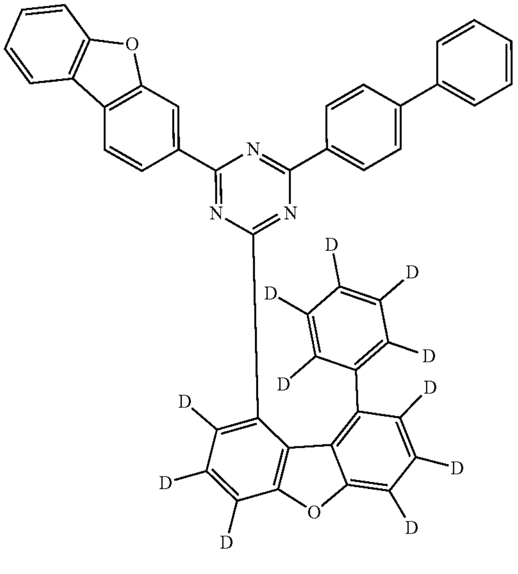
-continued
204
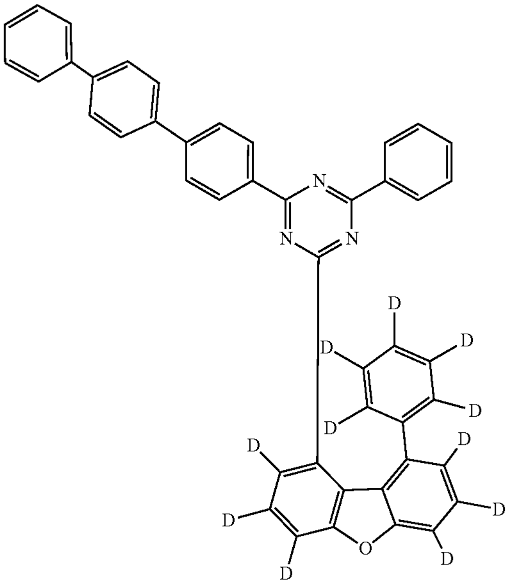
205
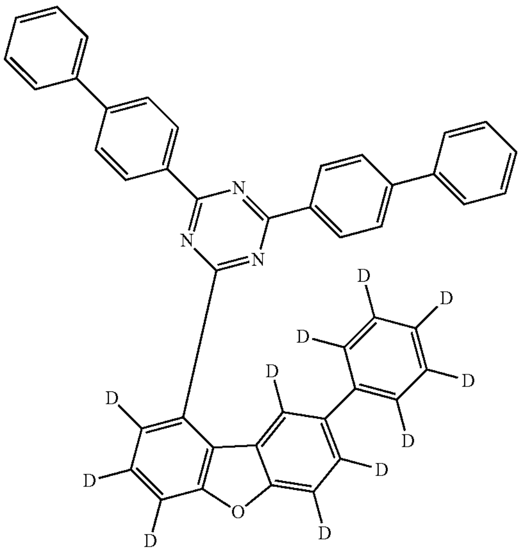

-continued
206
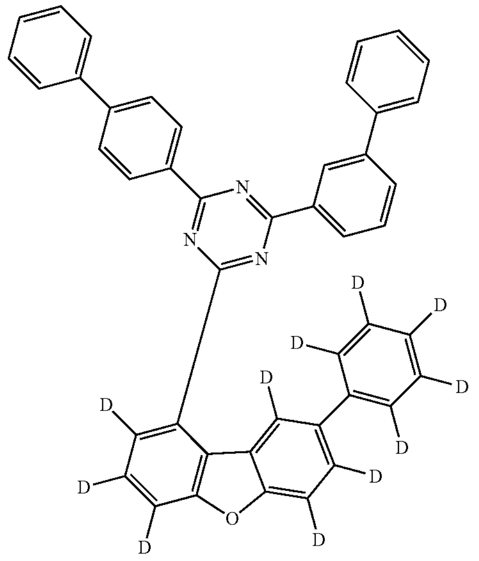
-continued
208
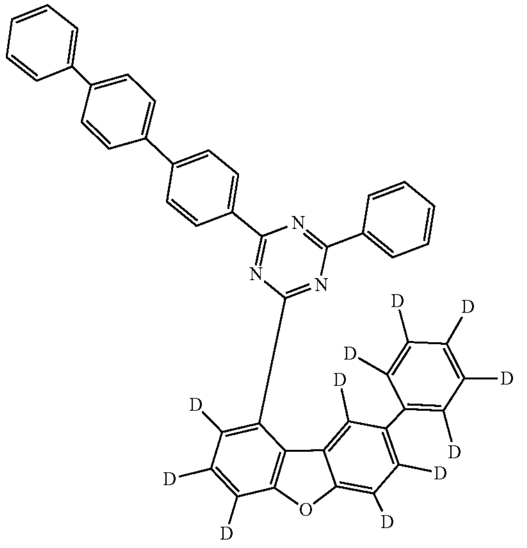
207
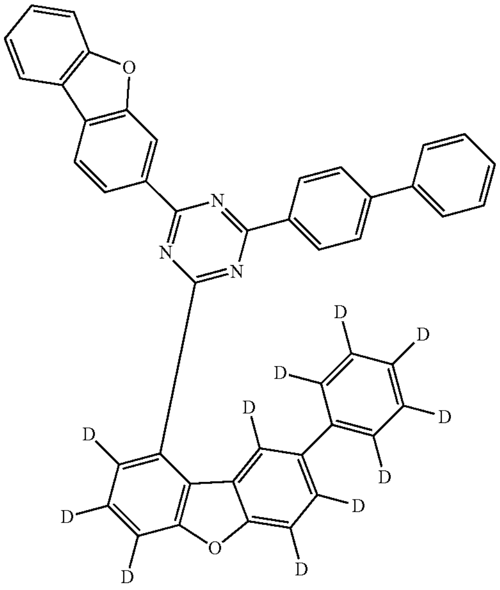
209
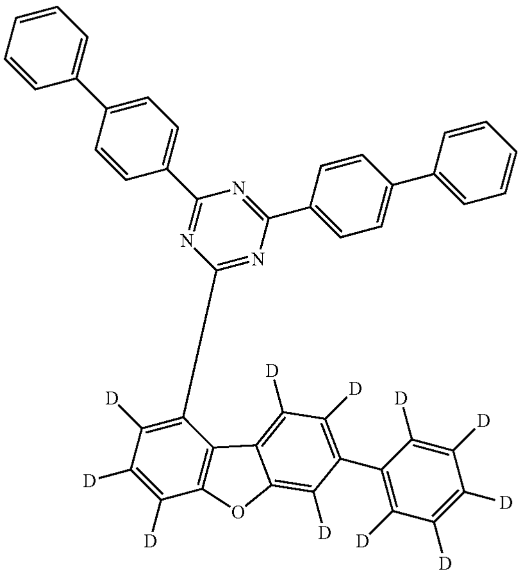

-continued
210
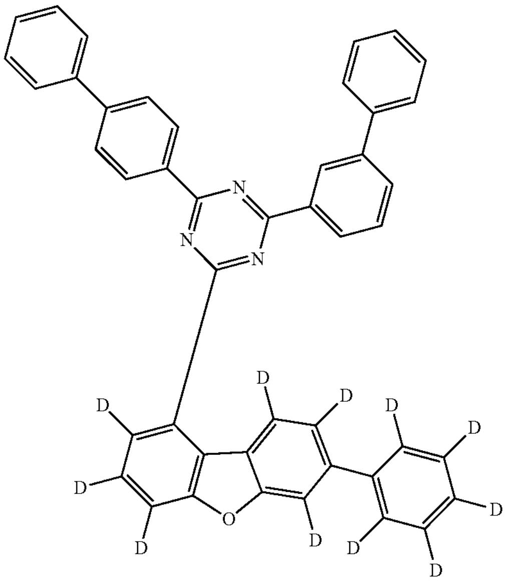
211
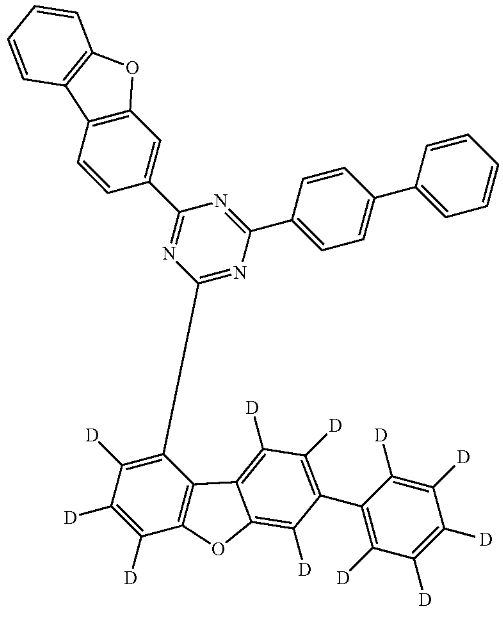
-continued
212
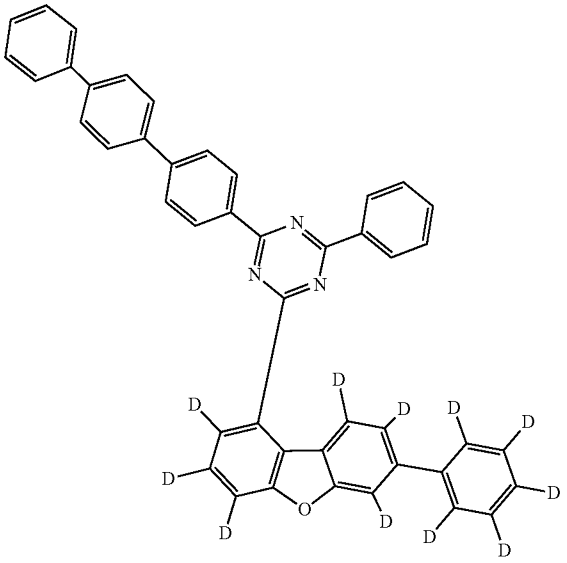
213
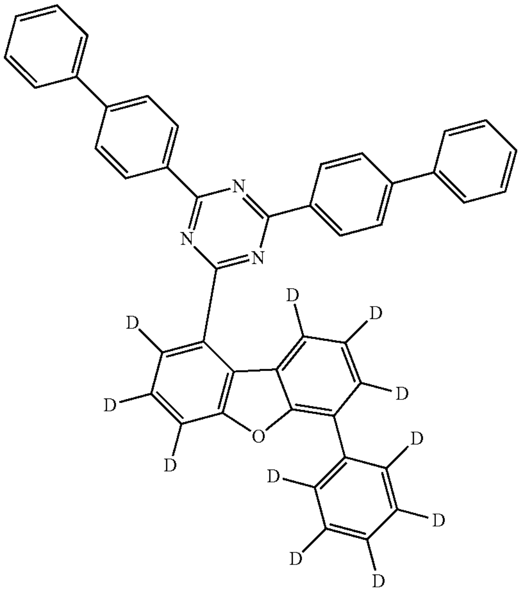

214
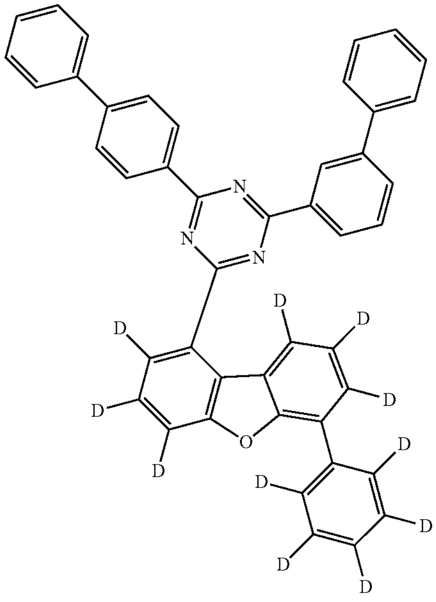
216
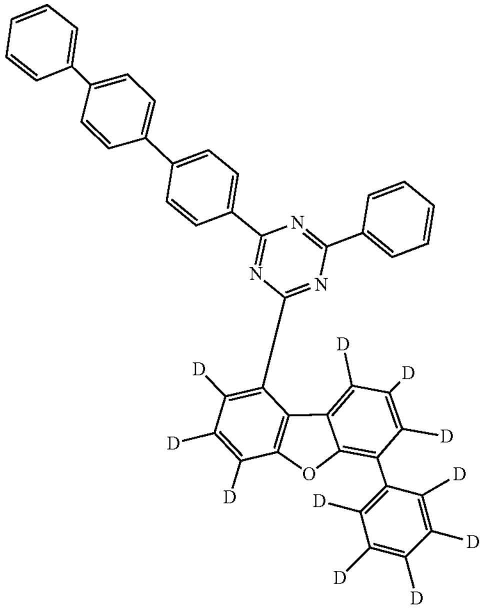
215
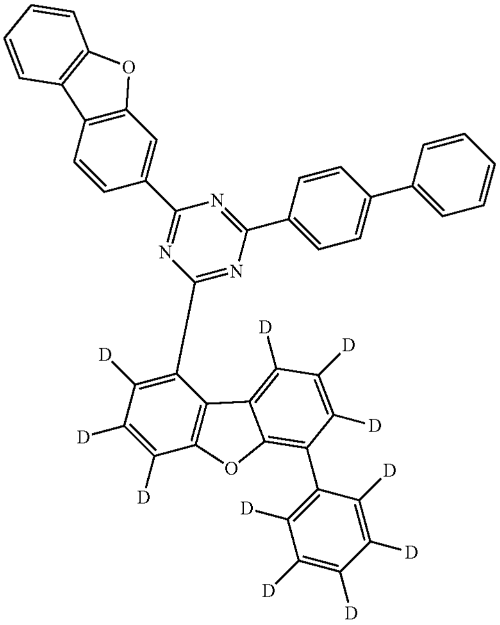
217
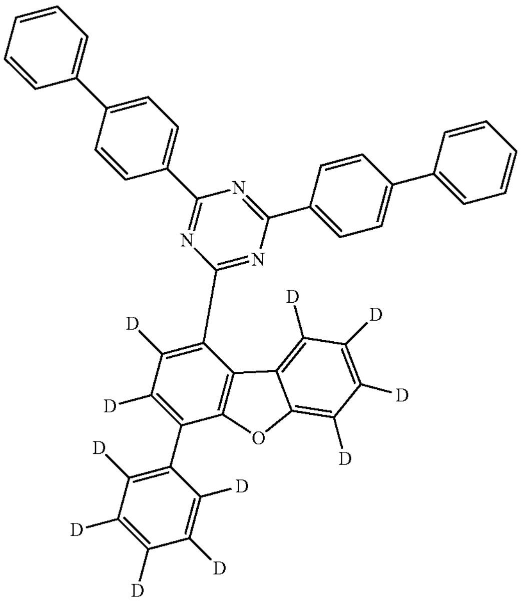

-continued
218
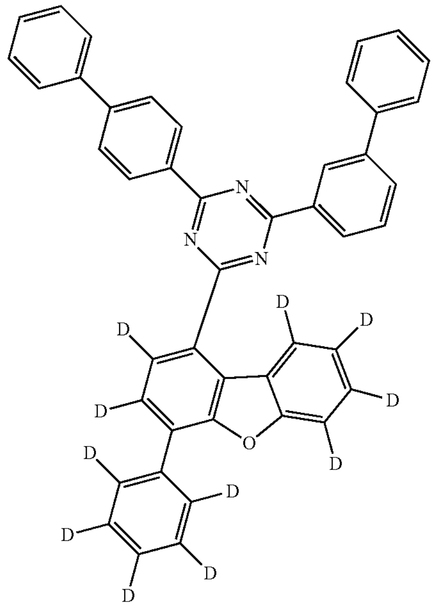
219
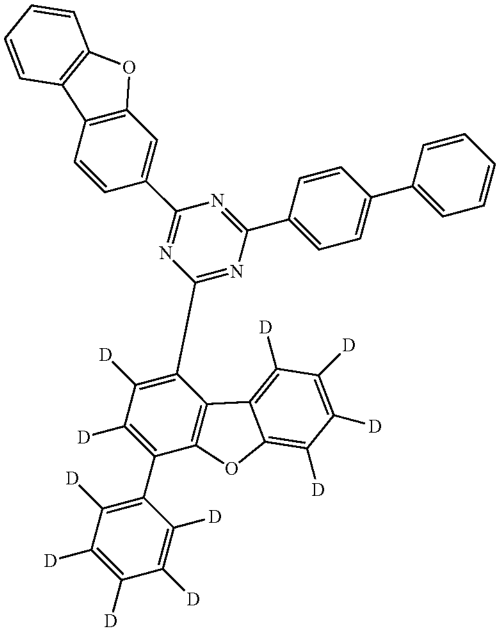
-continued
220
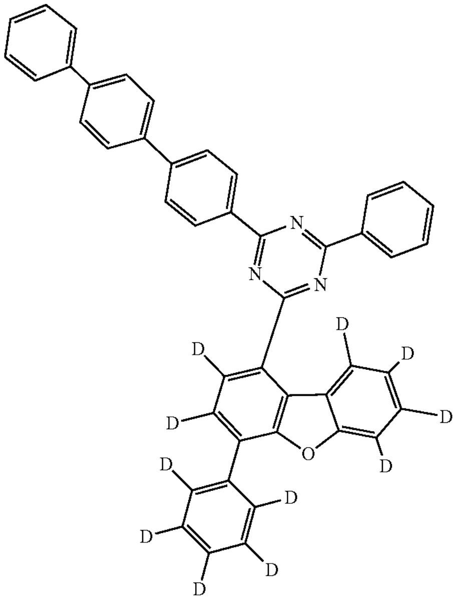
221
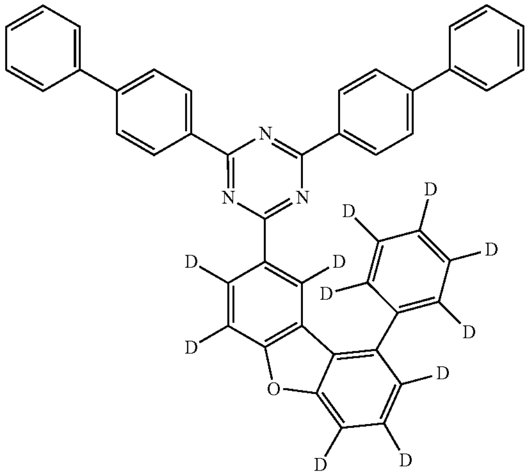
222
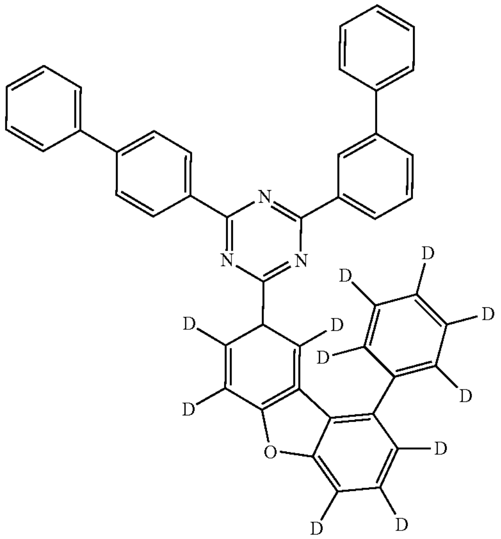

-continued
223
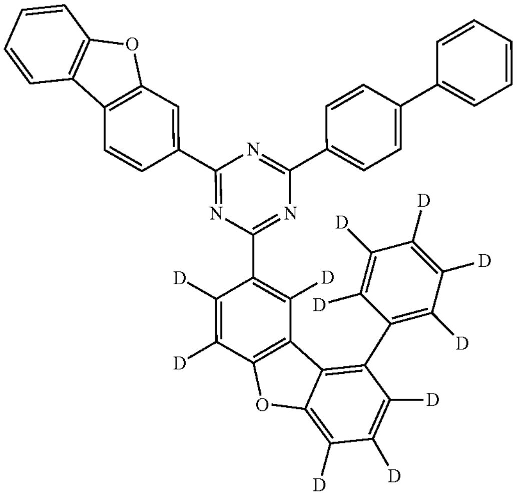
224
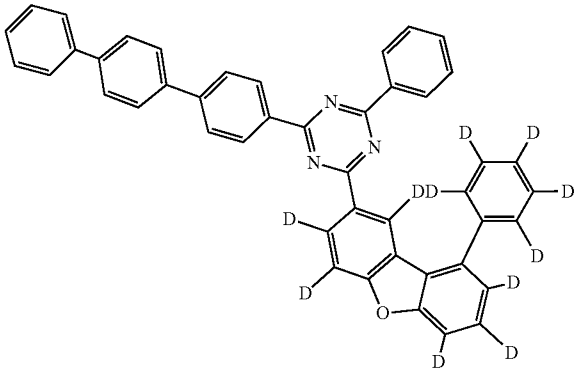
225
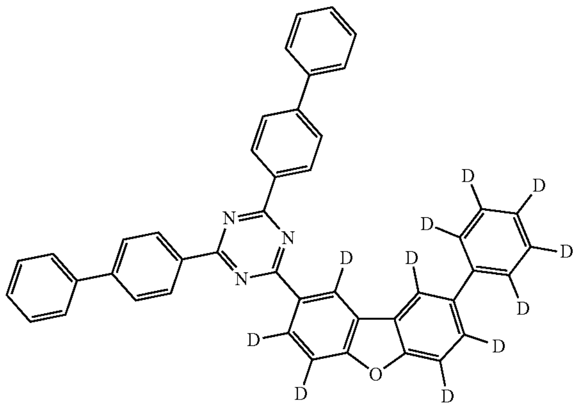
-continued
226
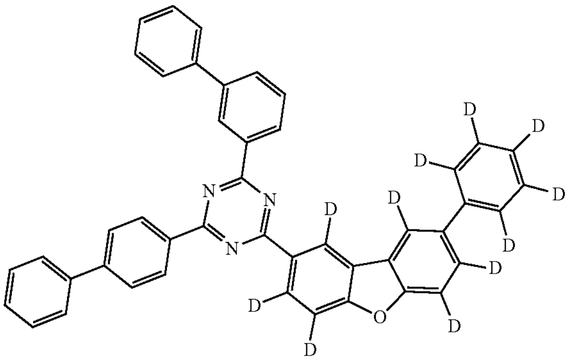
227
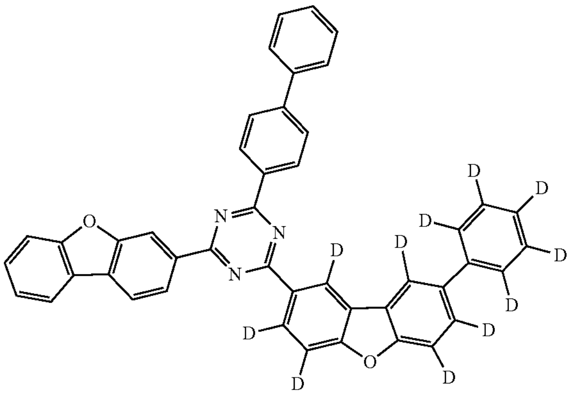
228
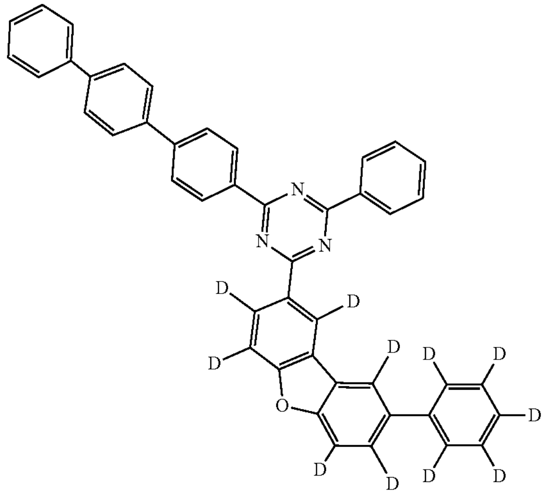

-continued
229
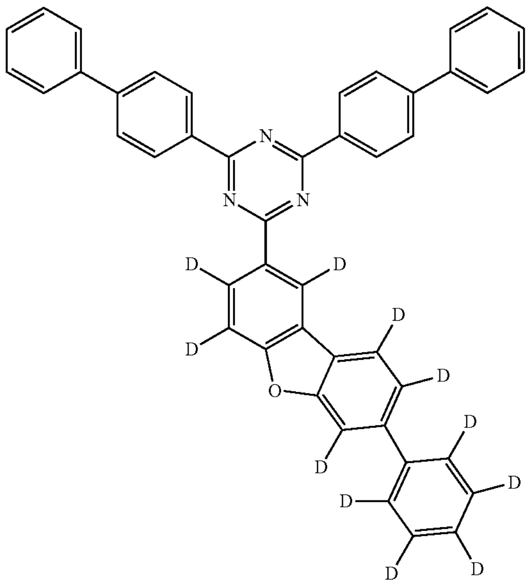
230
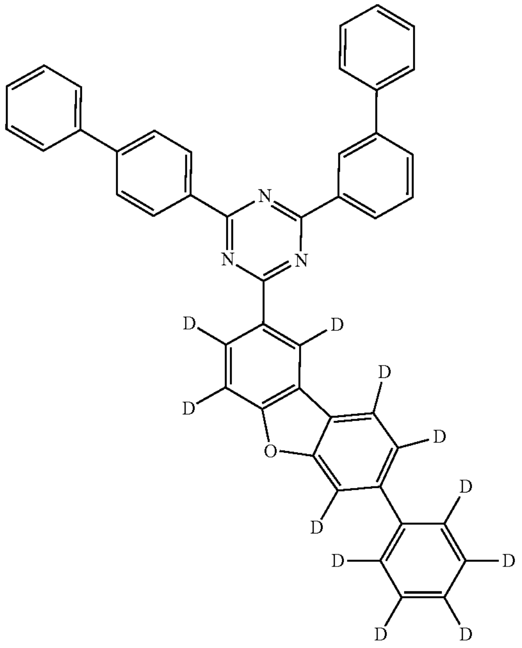
-continued
231
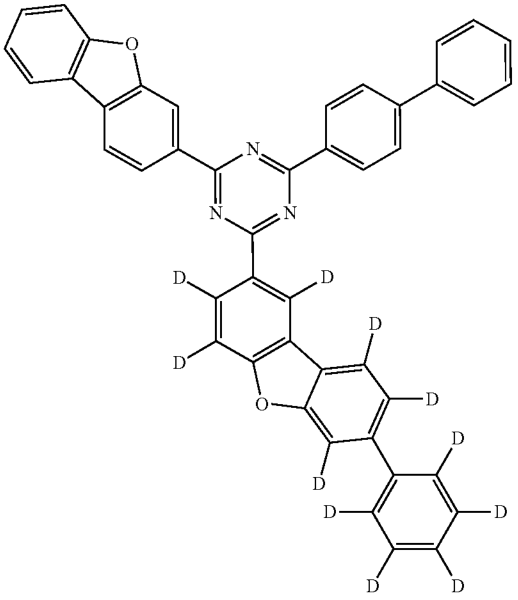
232
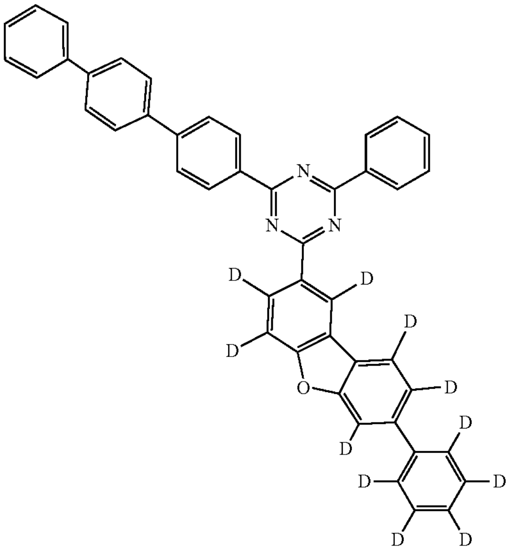

-continued
233
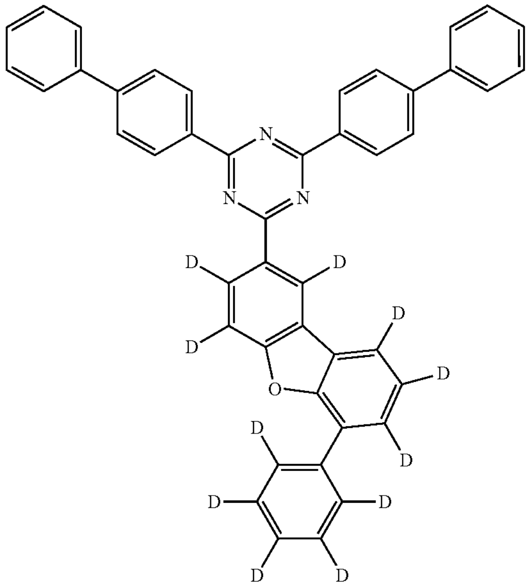
234
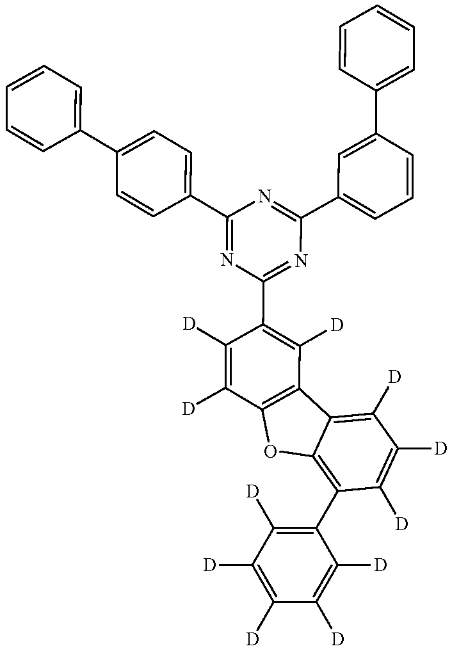
-continued
235
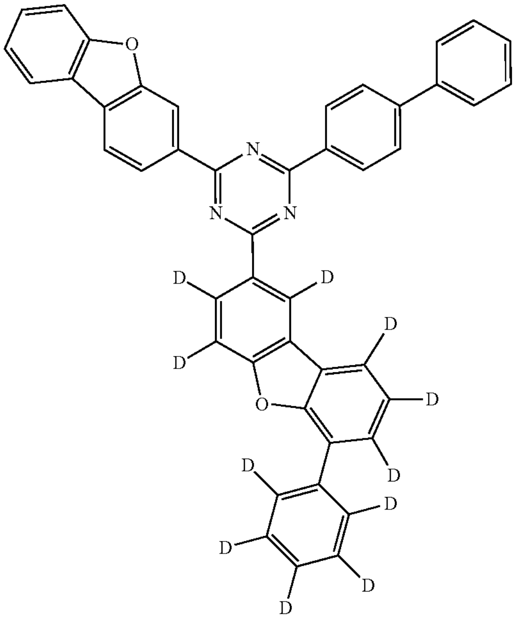
236
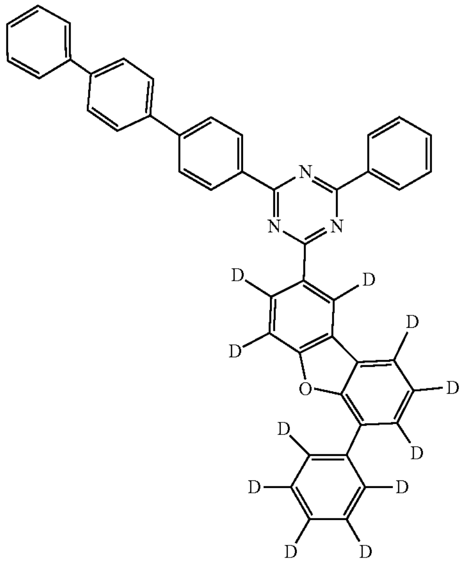

-continued
237
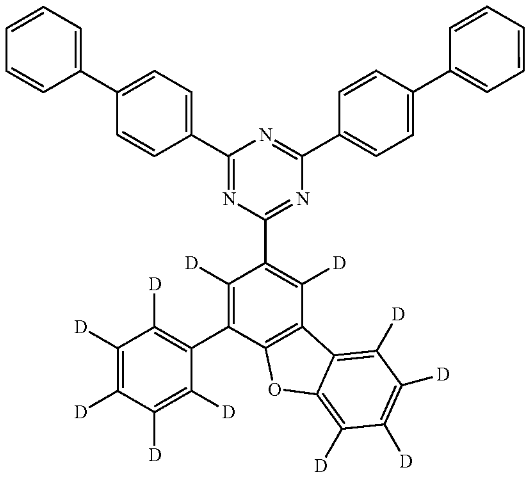
238
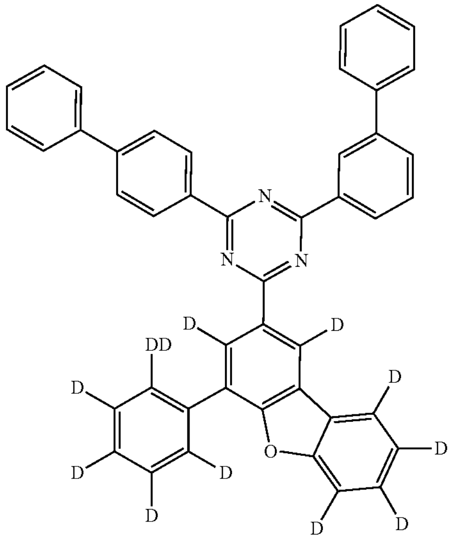
239
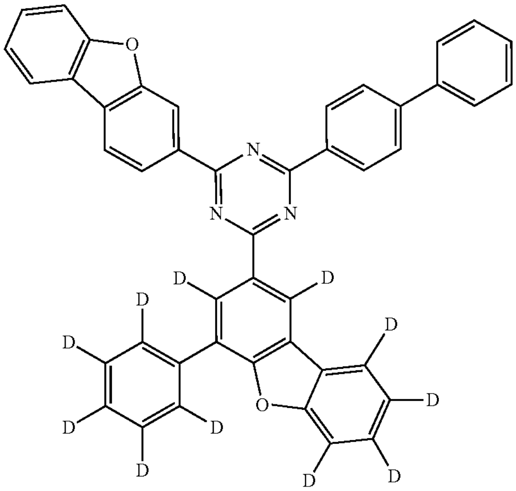
-continued
240
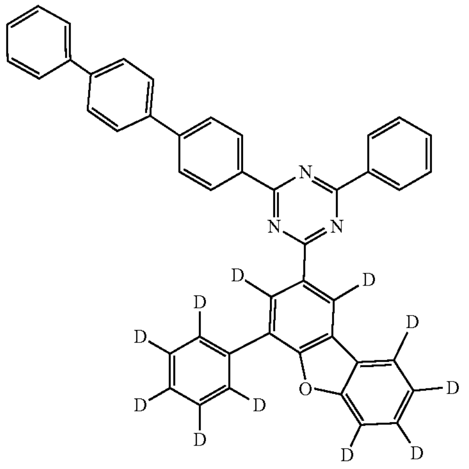
241
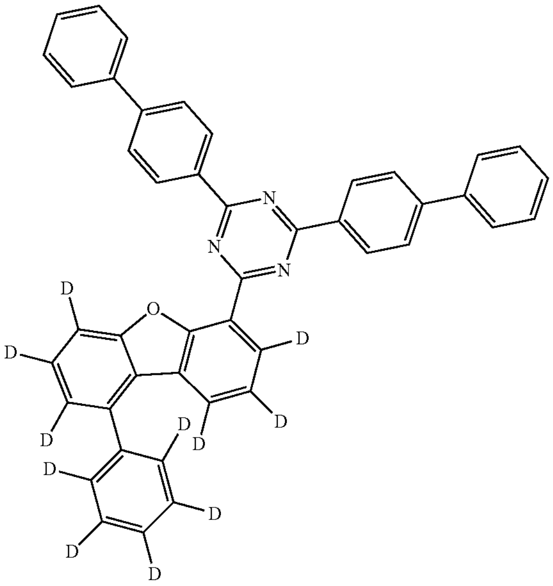
242
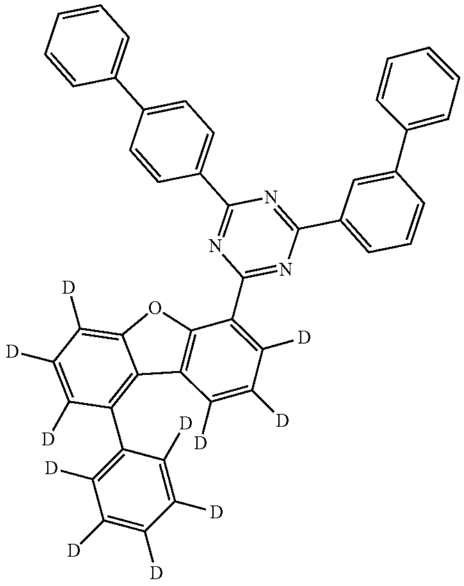

-continued
243
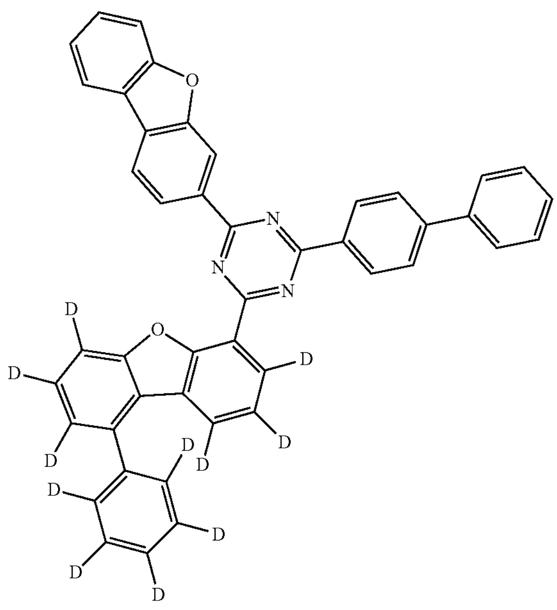
244
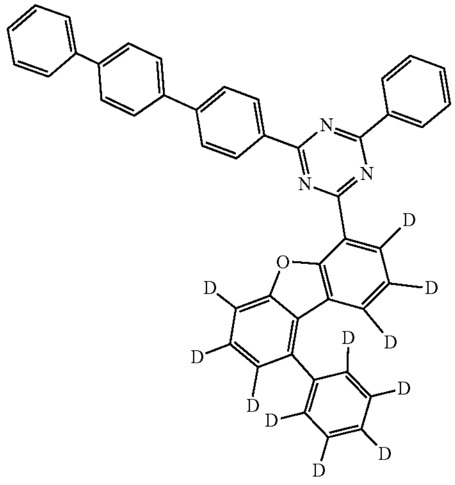
245
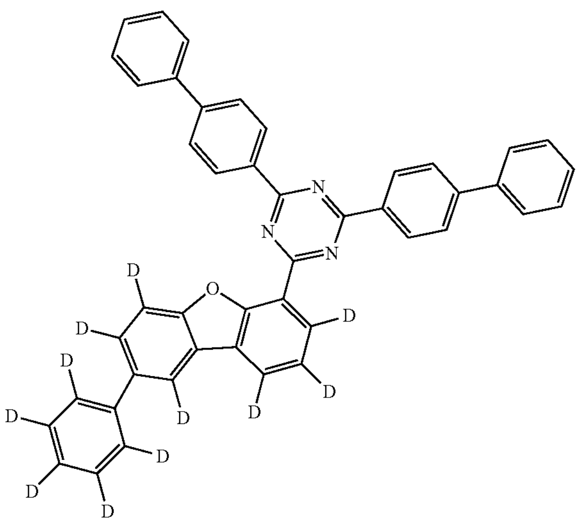
-continued
246
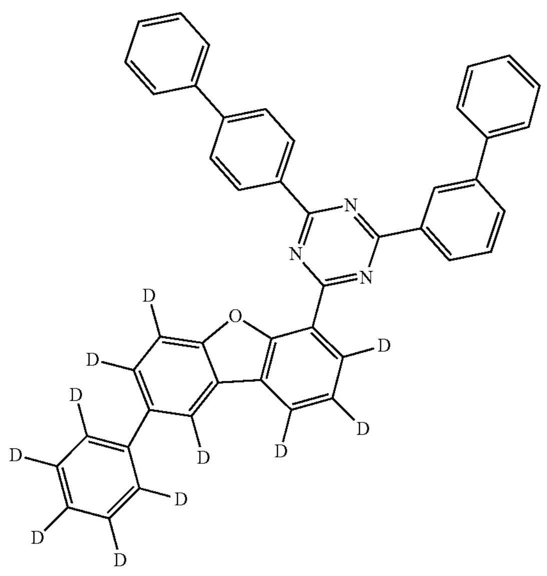
247
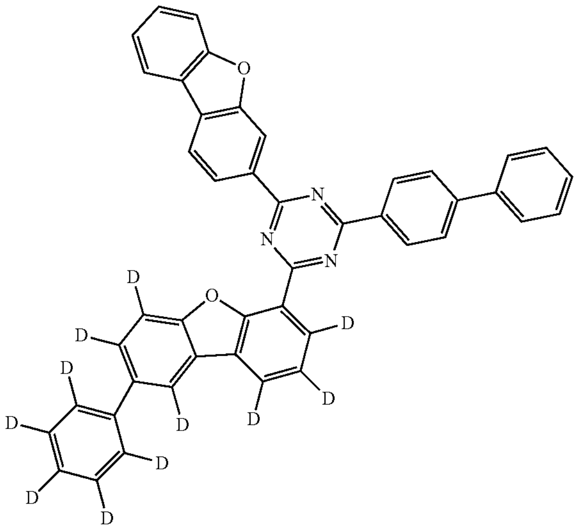

-continued
248
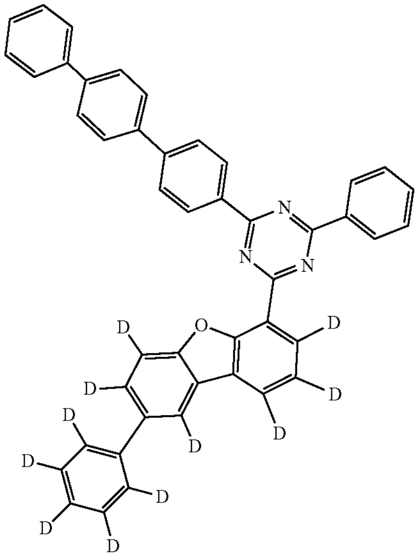
249
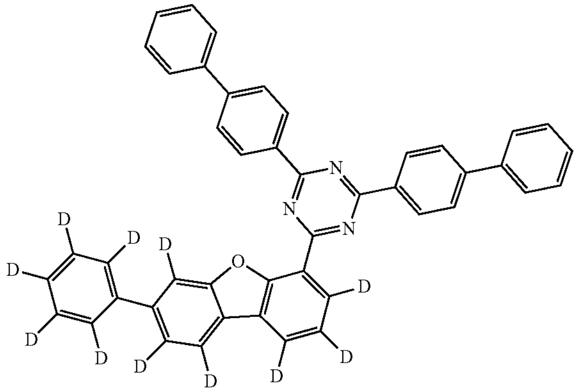
250
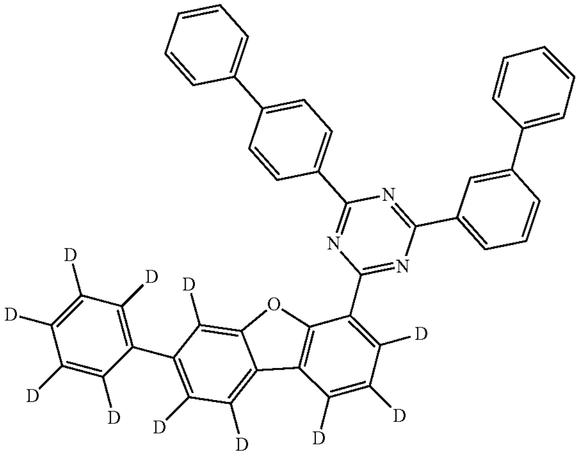
-continued
251
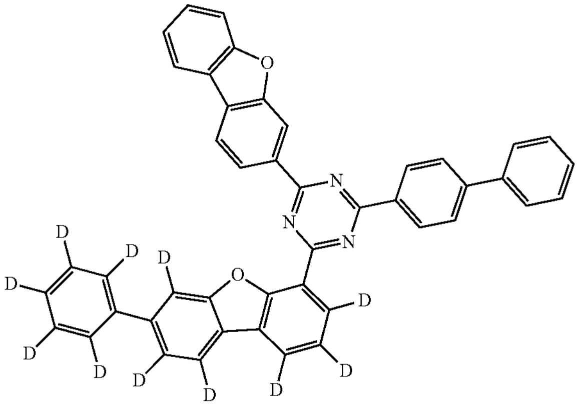
252
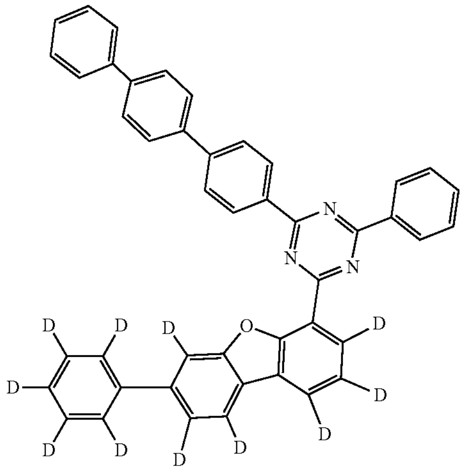
253
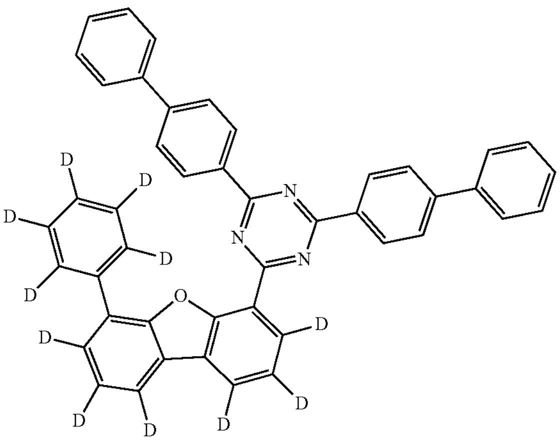

254
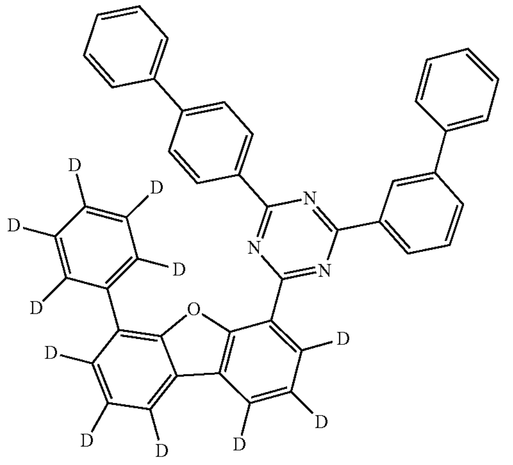
255
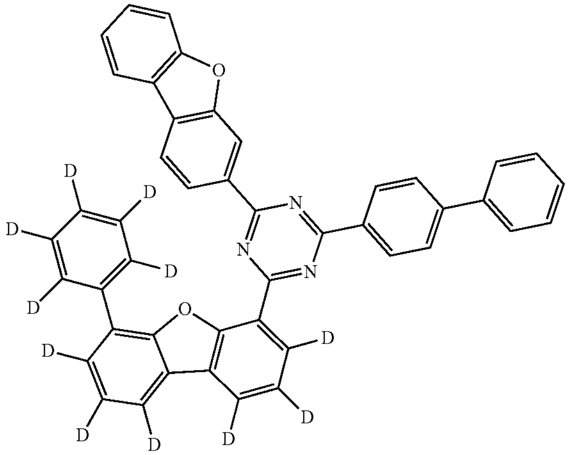
256
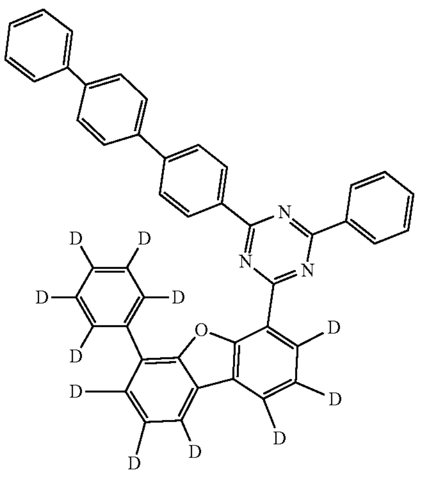
257
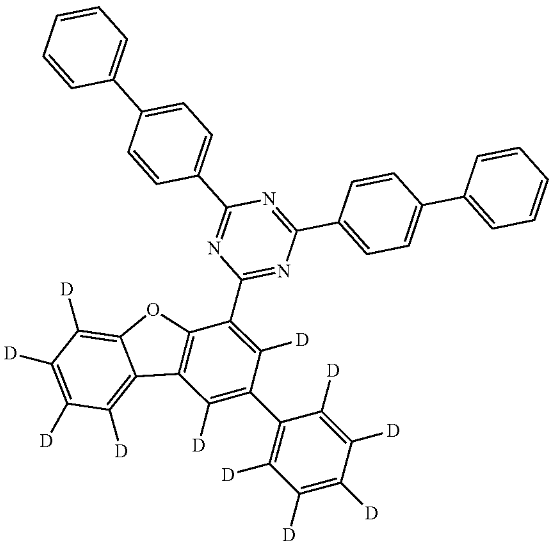
258
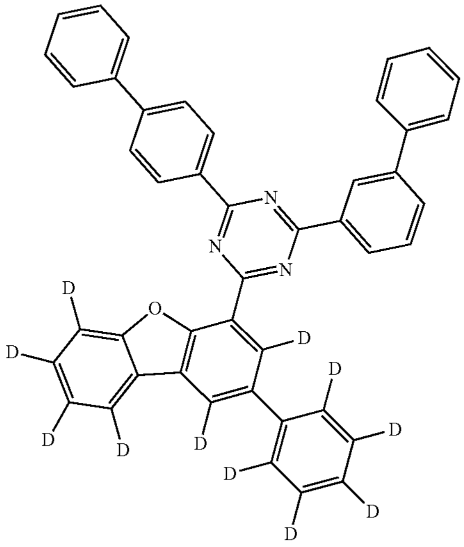

-continued
259
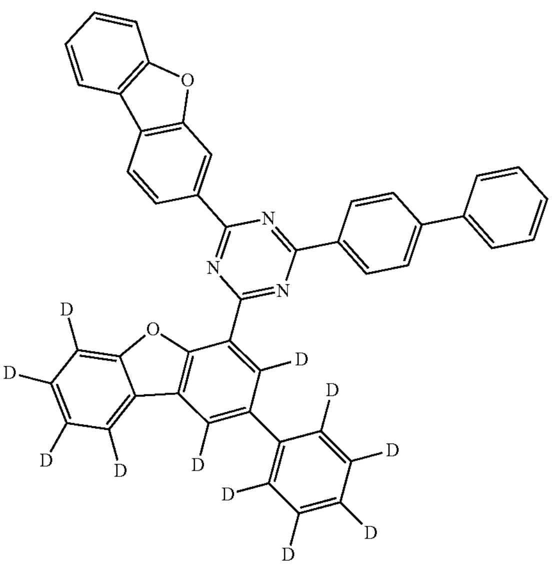
260
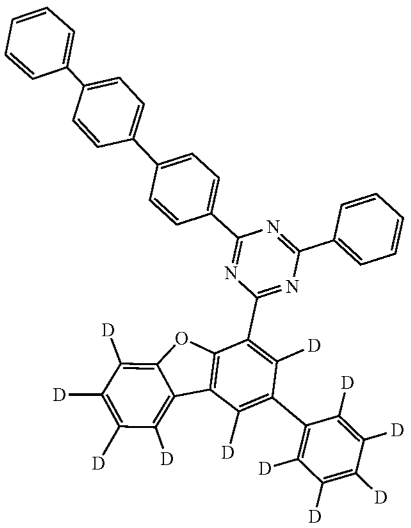
261
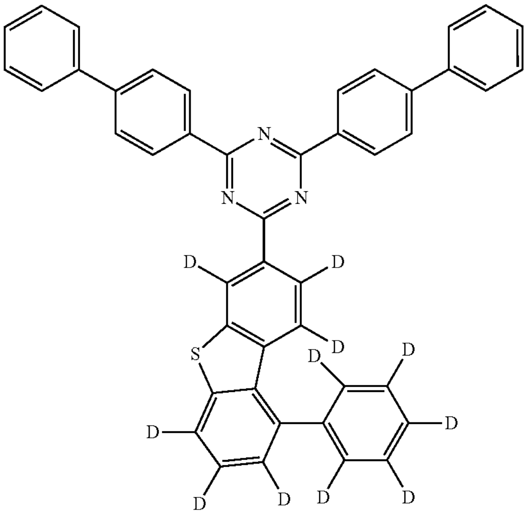
-continued
262
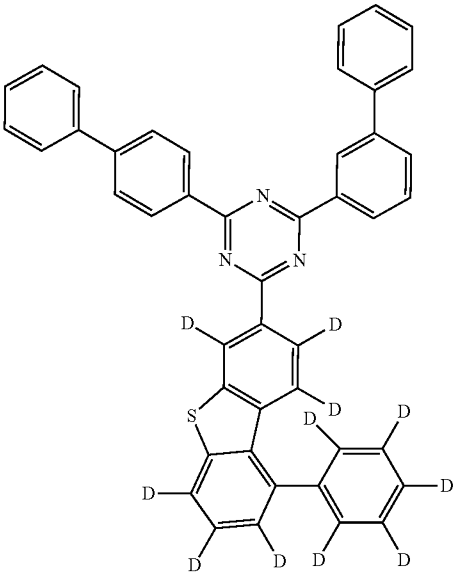
263
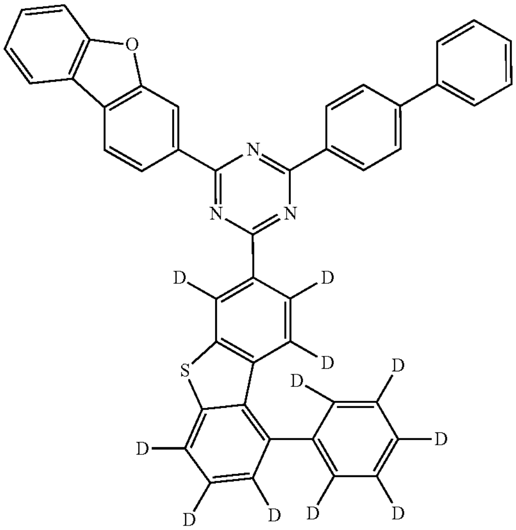
264
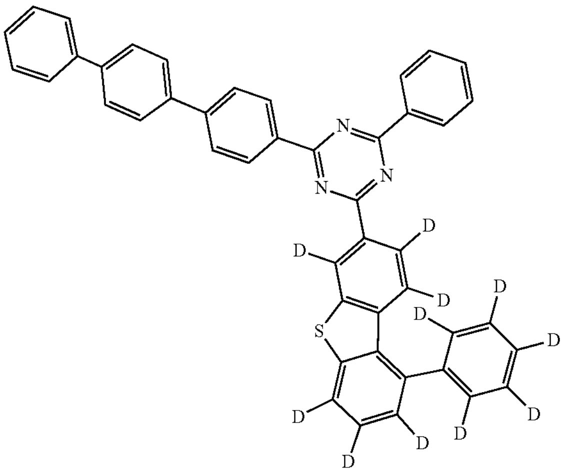

-continued
265
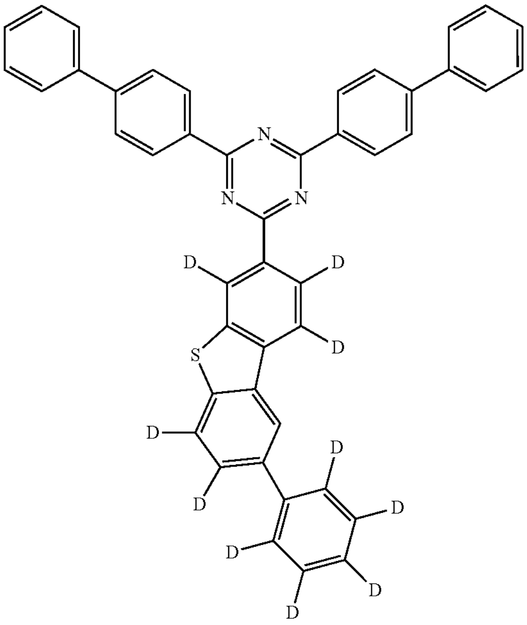
266
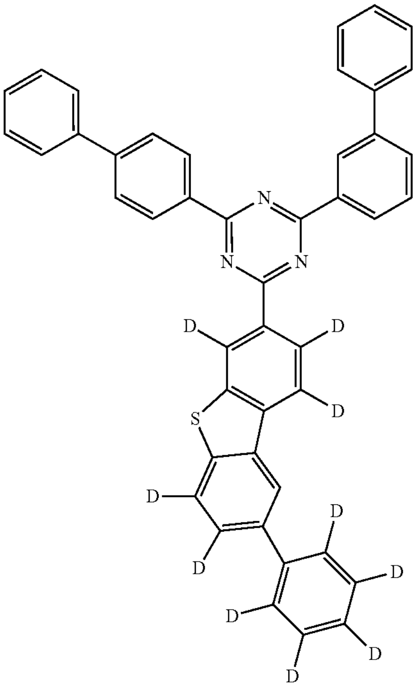
-continued
267
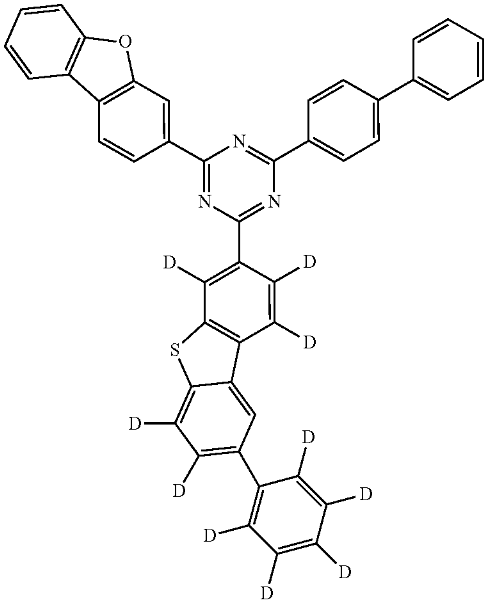
268
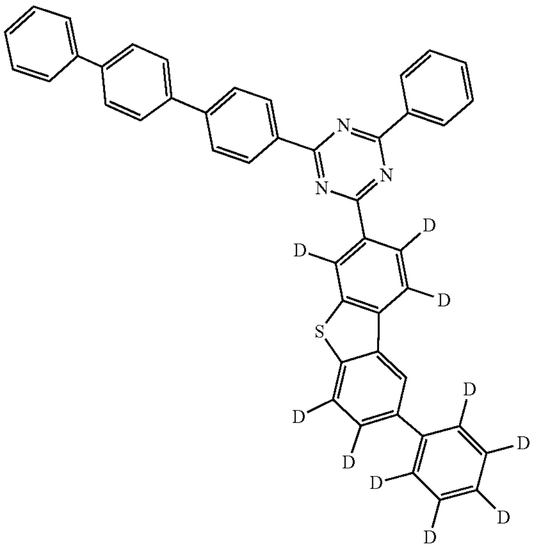

-continued
269
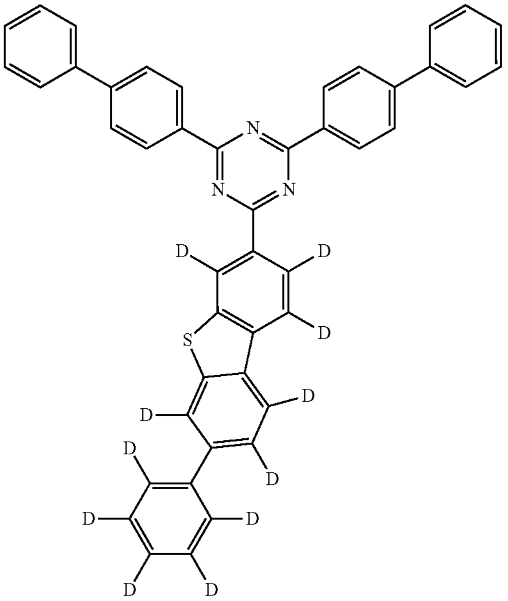
270
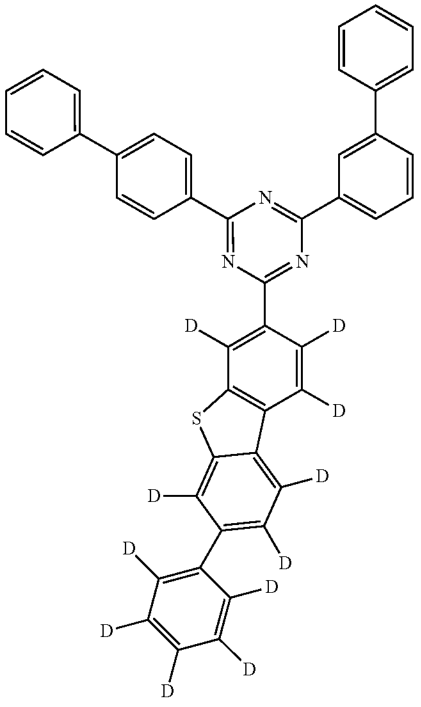
-continued
271
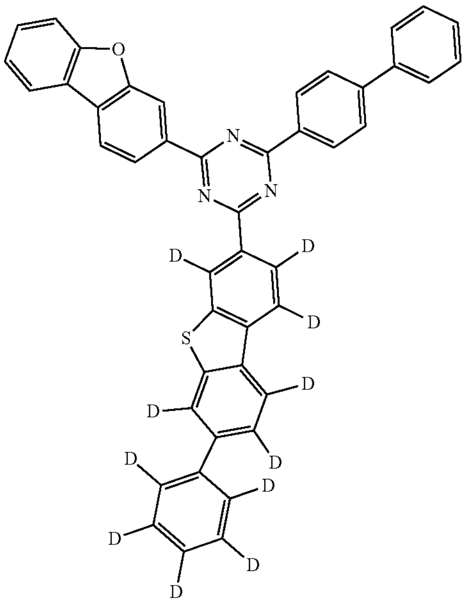
272
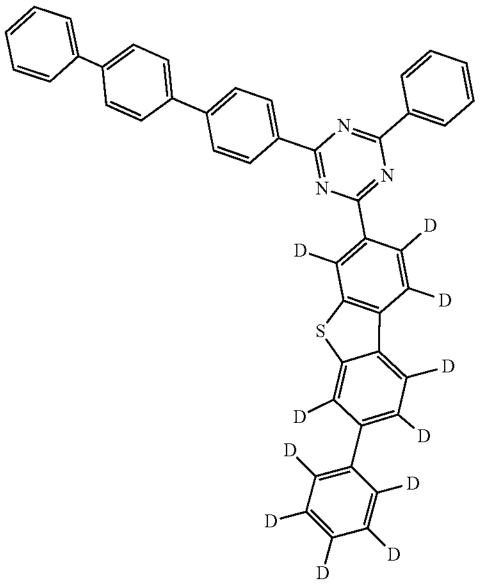

-continued
273
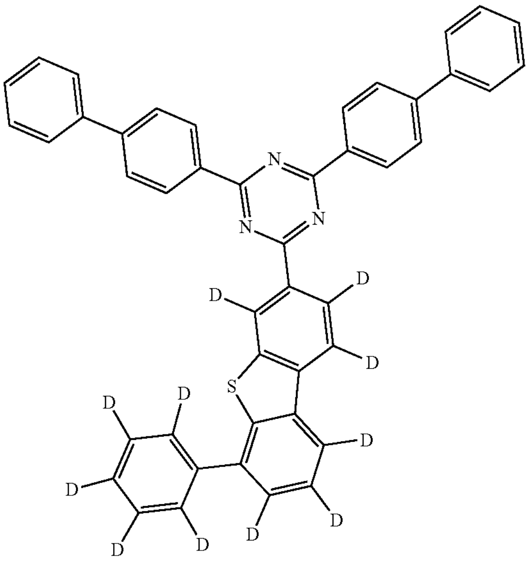
274
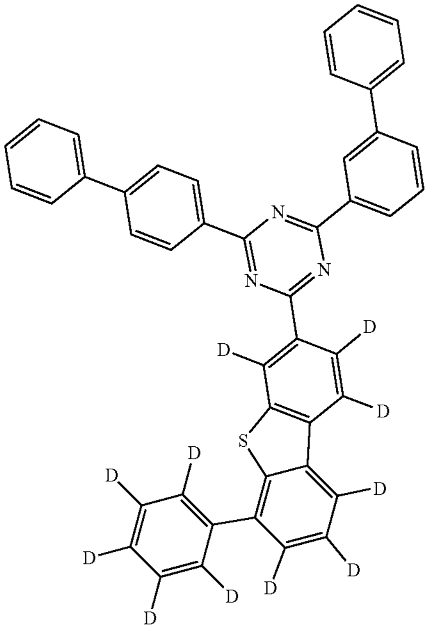
-continued
275
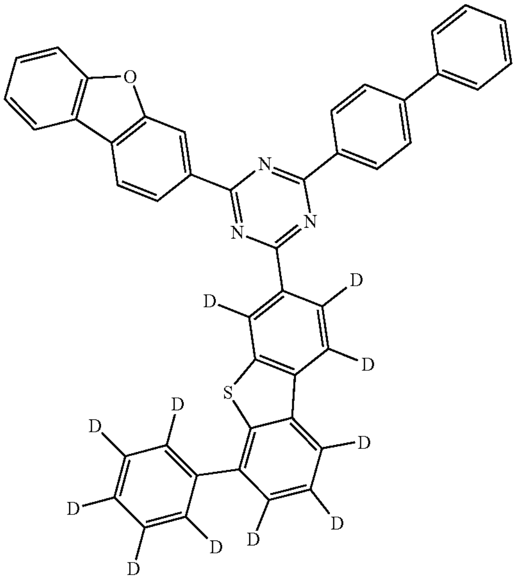
276
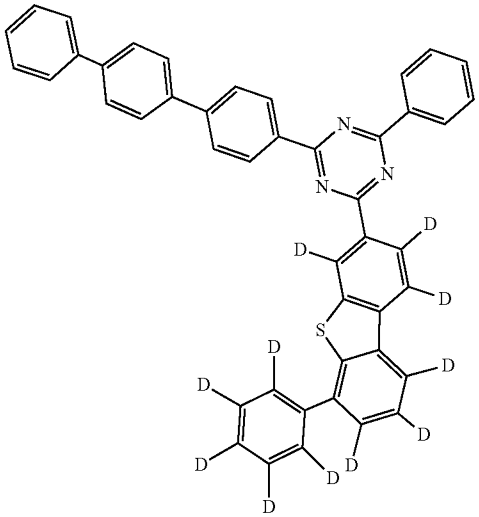
277
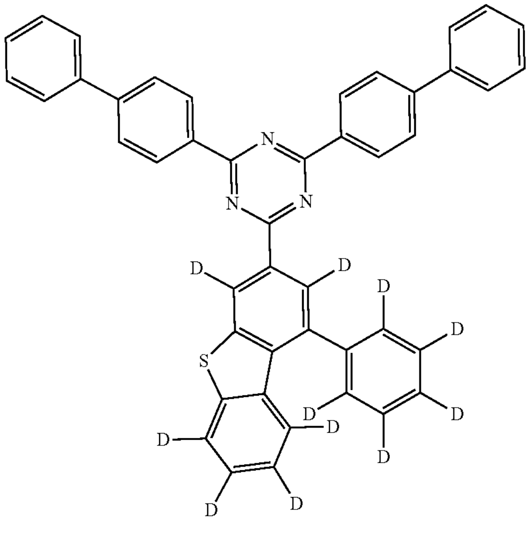

-continued
278
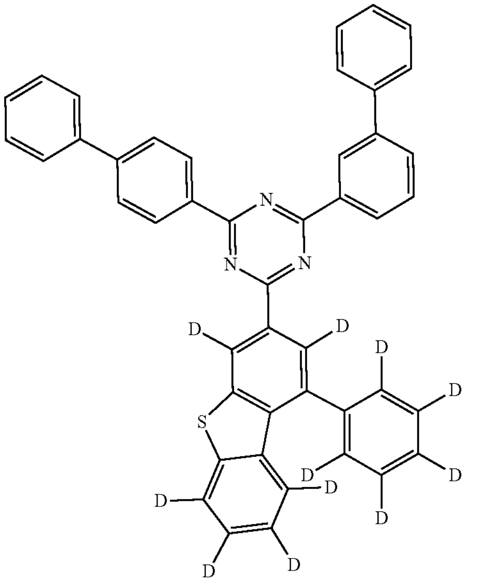
279
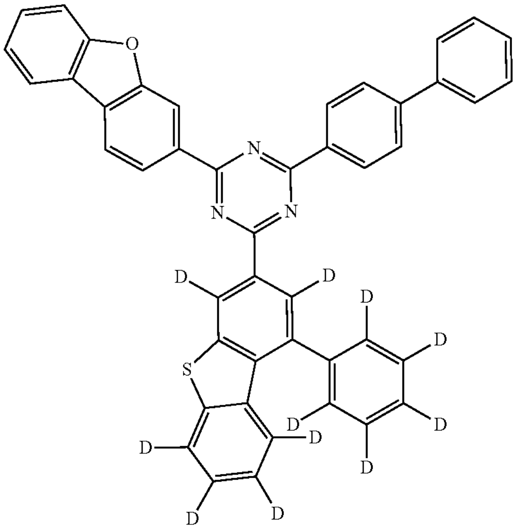
280
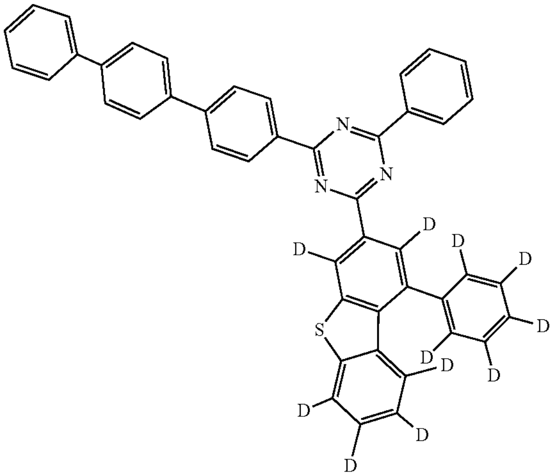
-continued
281
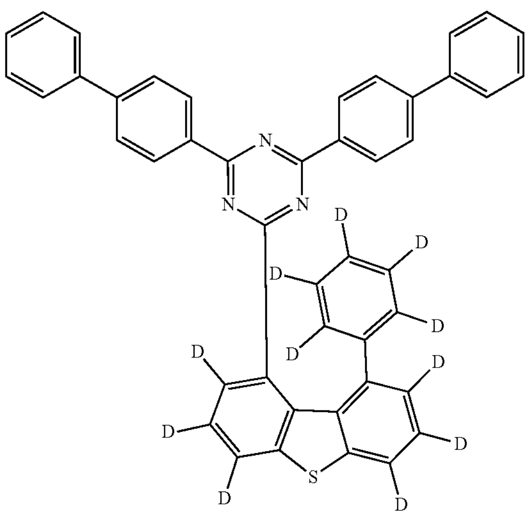
282
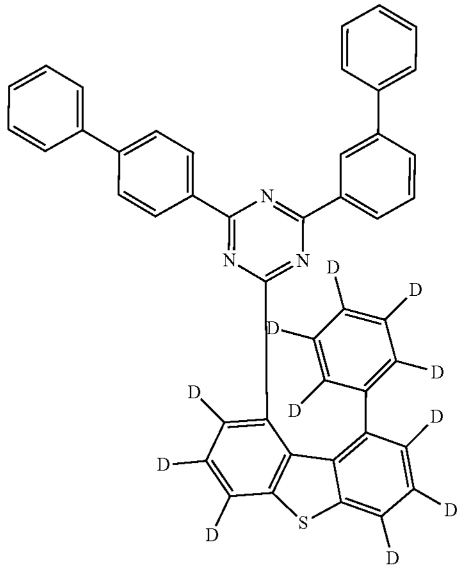
283
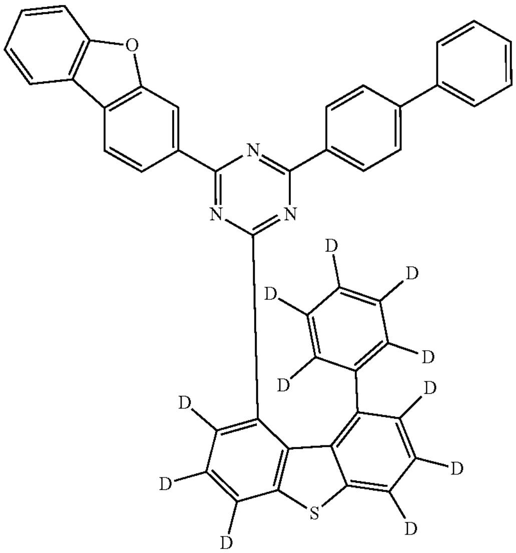

-continued
284
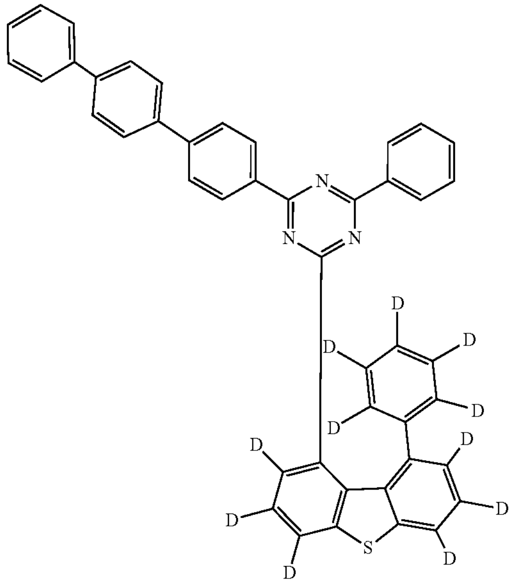
285
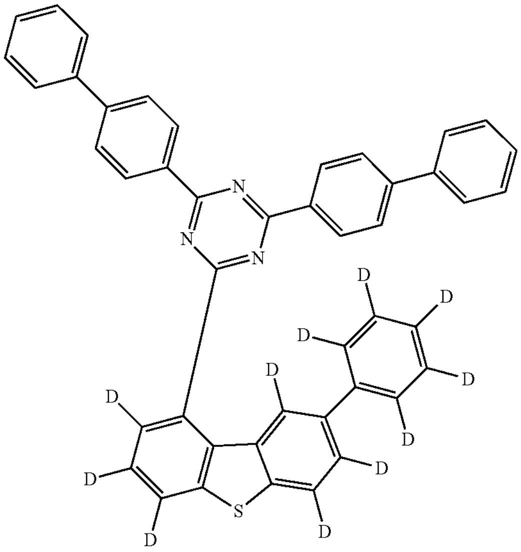
-continued
286
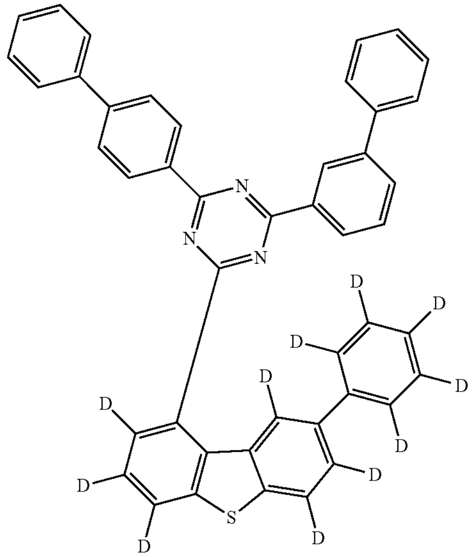
287
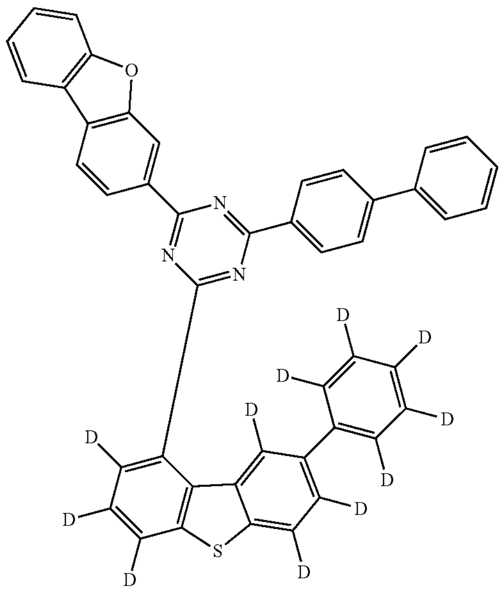

-continued
288
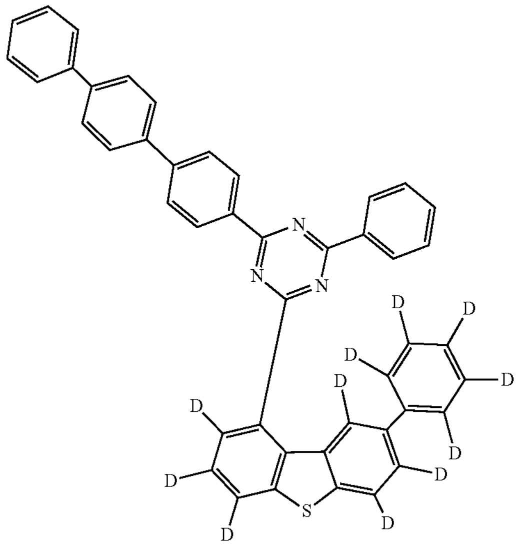
289
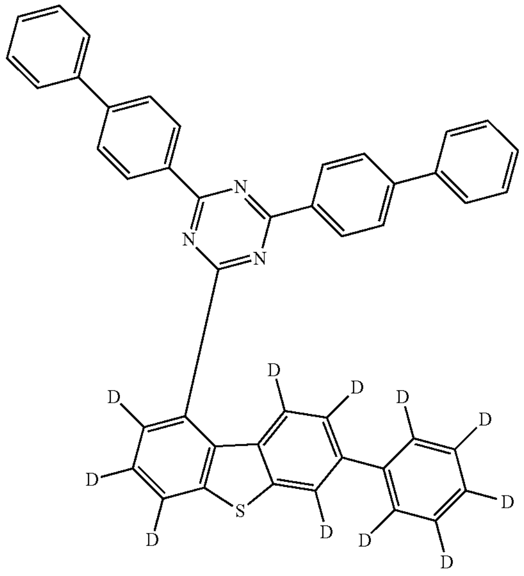
-continued
290
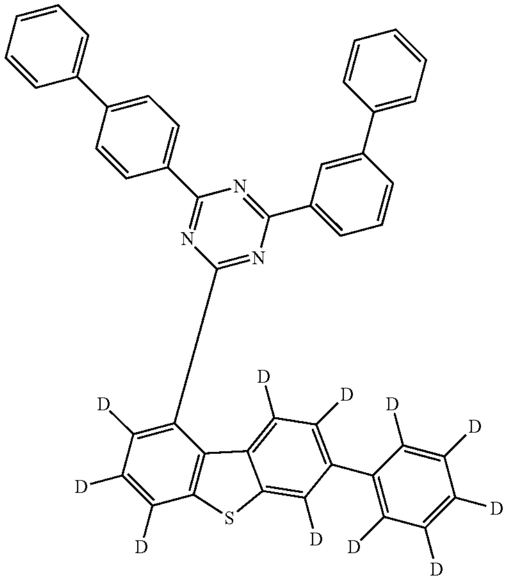
291
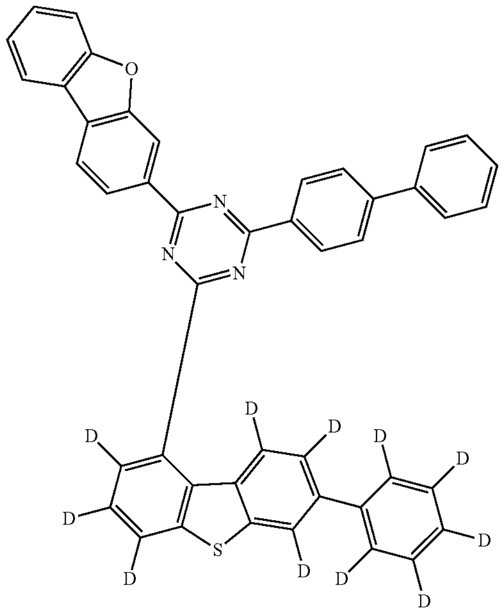

-continued
292
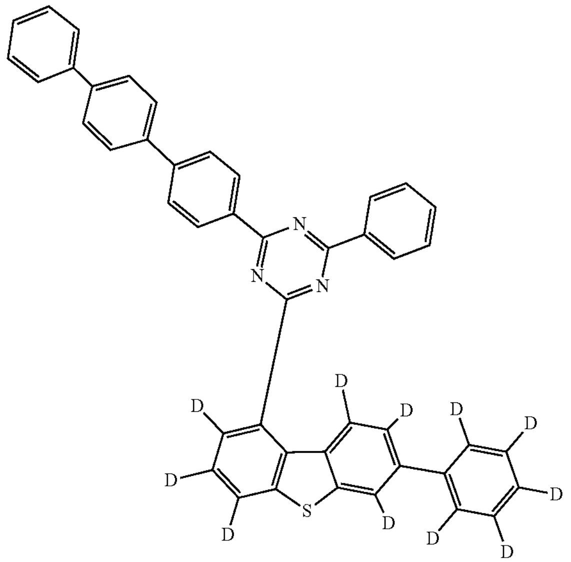
294
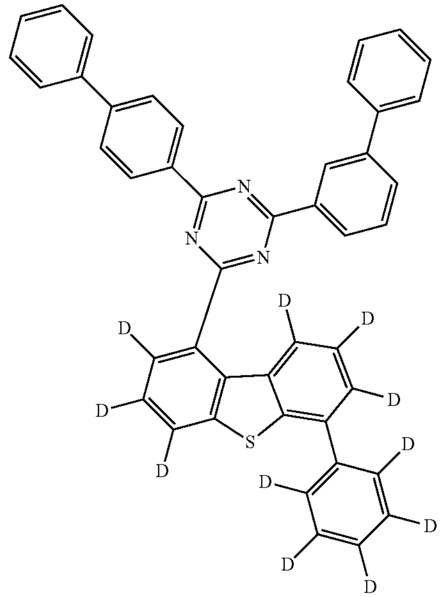
293
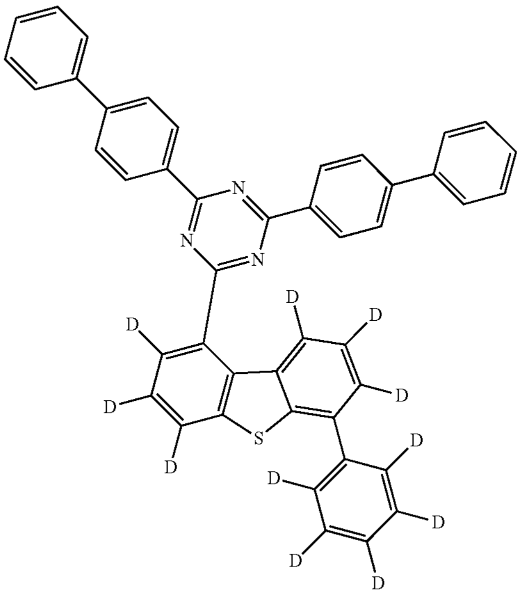
295
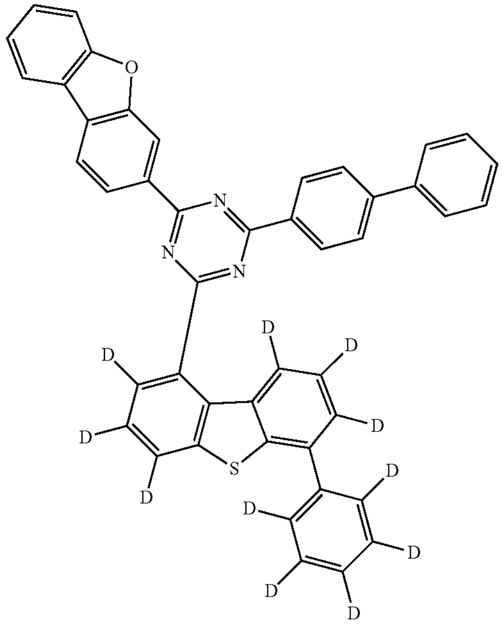

-continued
296
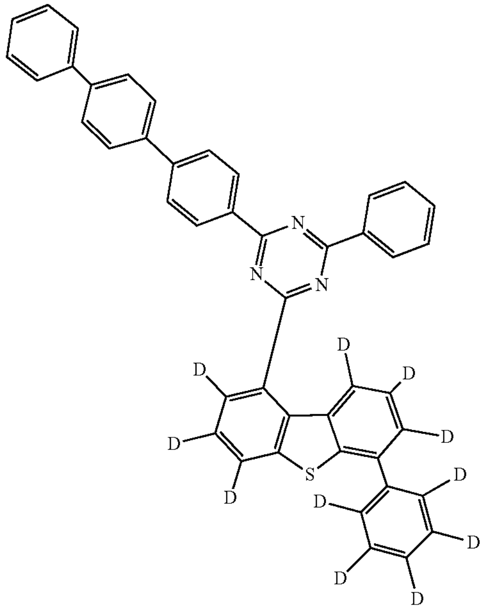
297
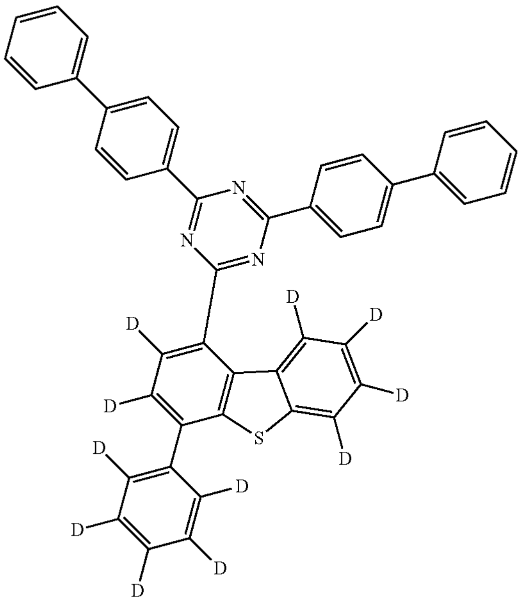
-continued
298
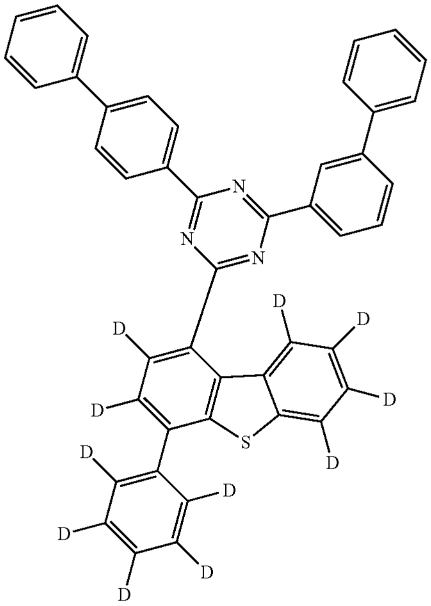
299
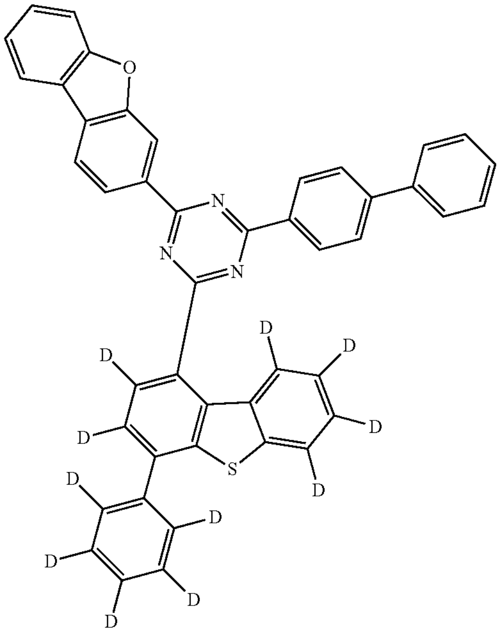

-continued
300
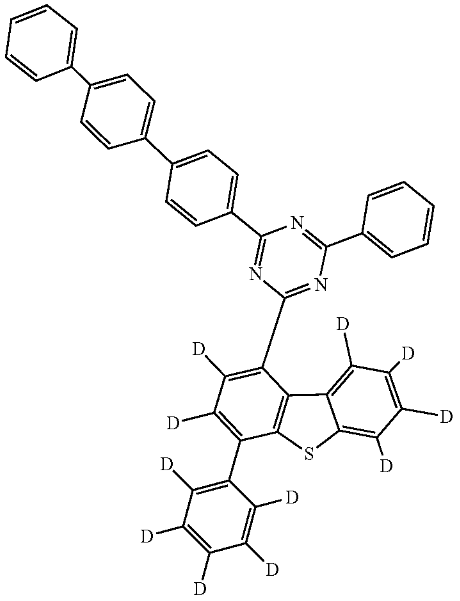
301
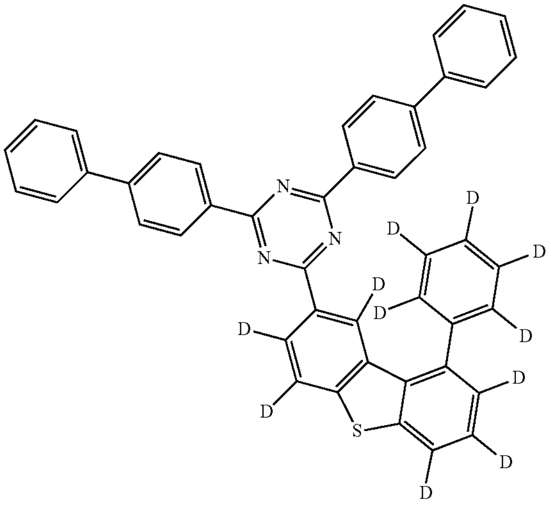
-continued
302
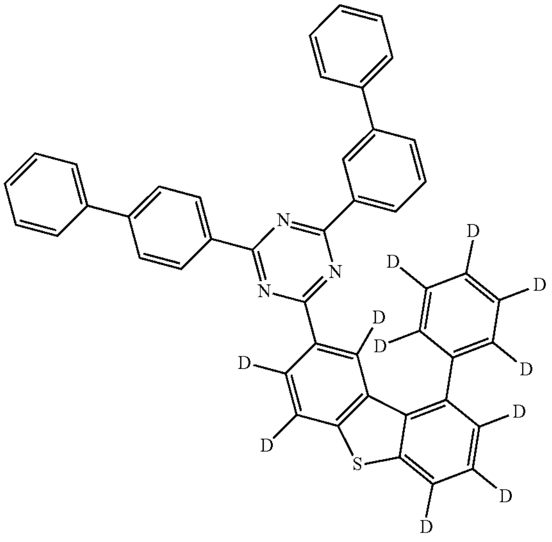
303
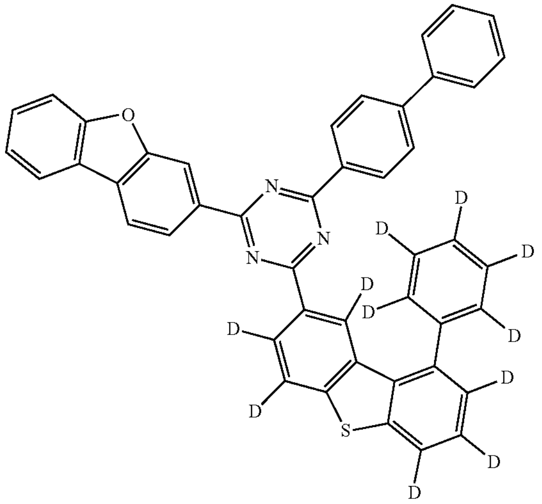
304
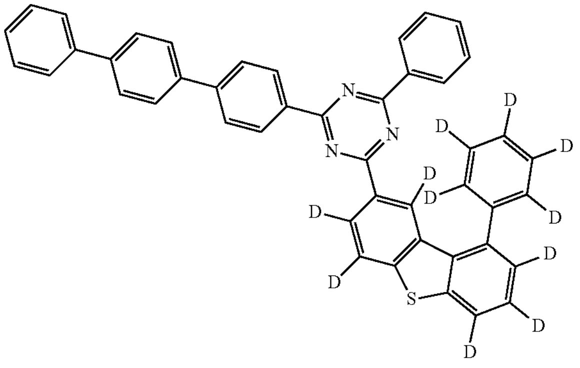

-continued
305
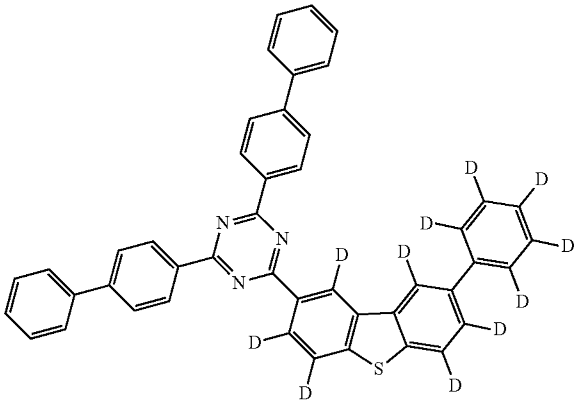
306
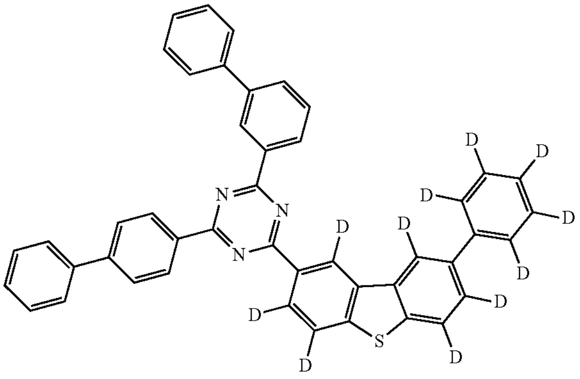
307
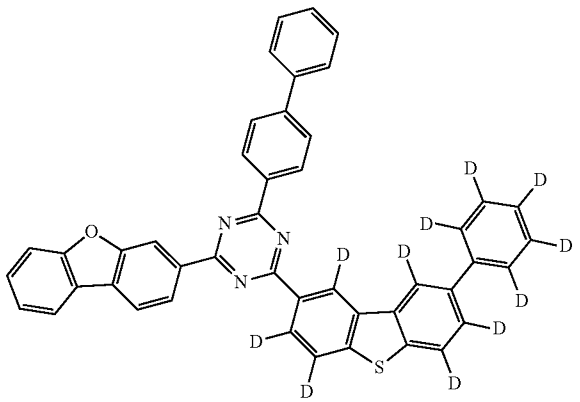
-continued
308
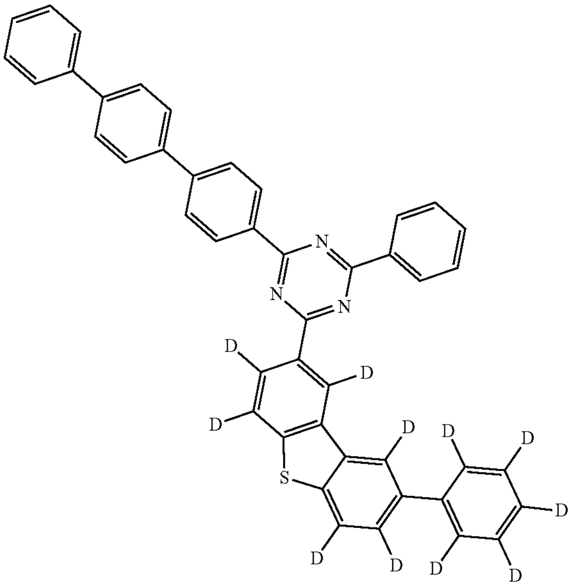
309
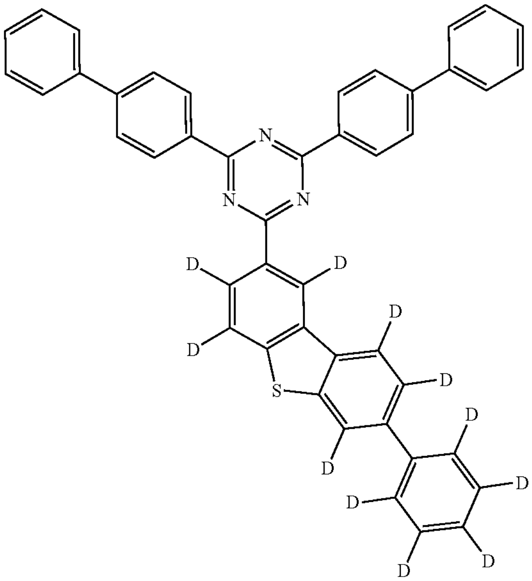

-continued
310
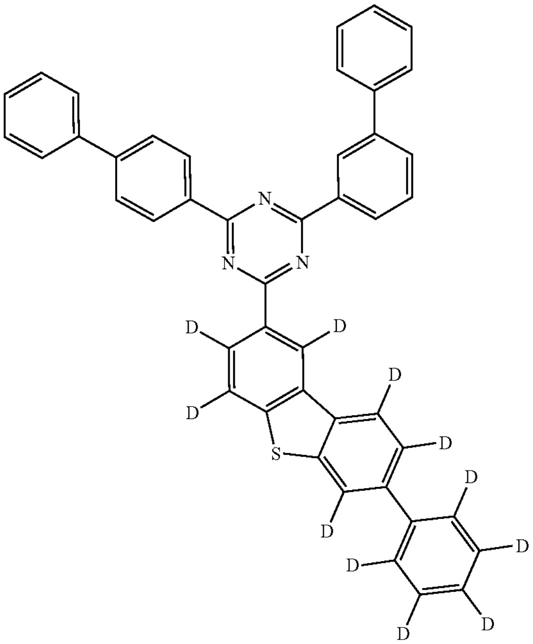
311
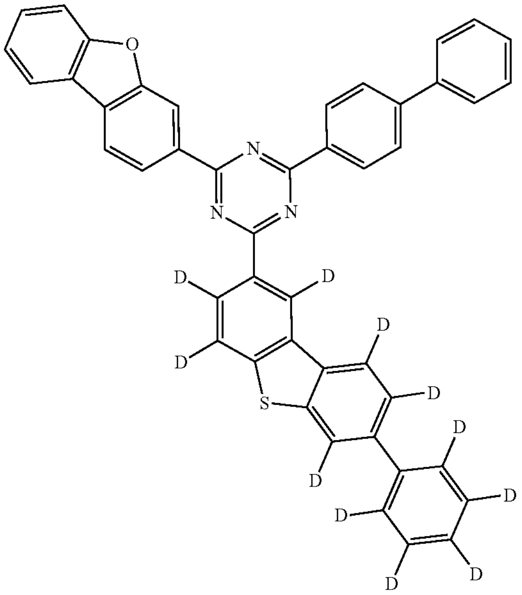
-continued
312
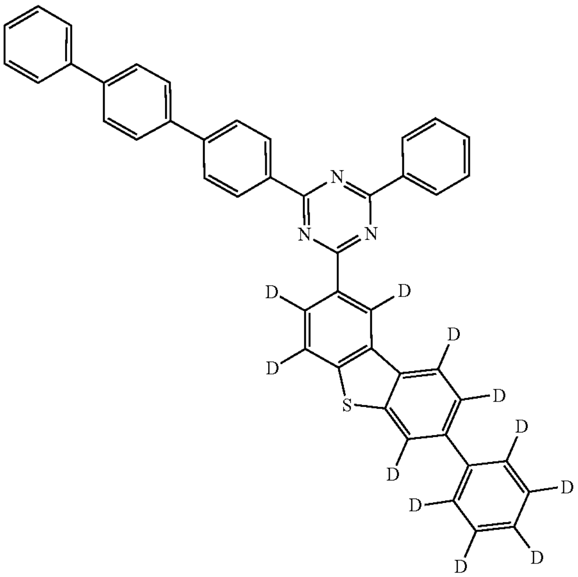
313
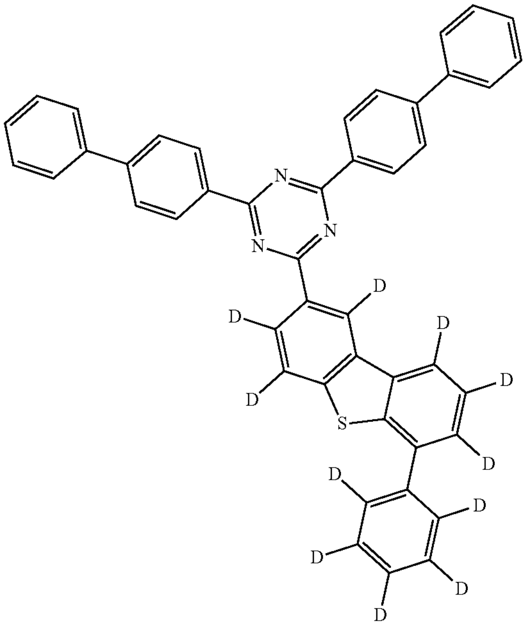

-continued
314
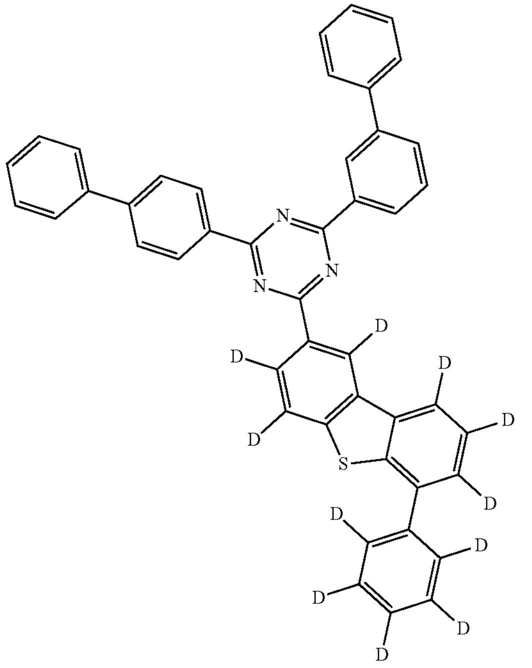
315
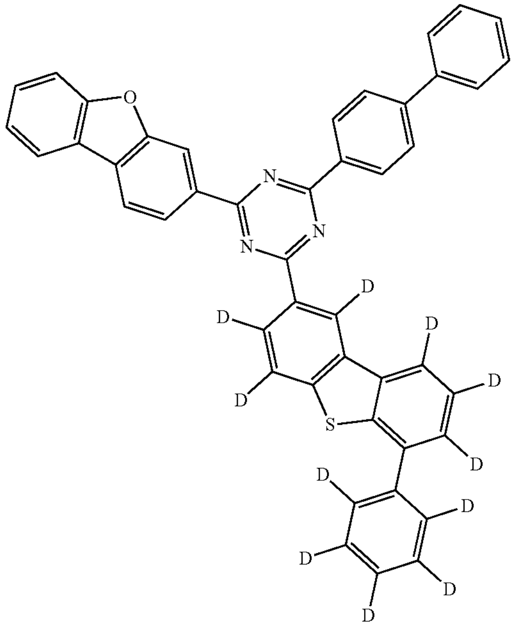
-continued
316
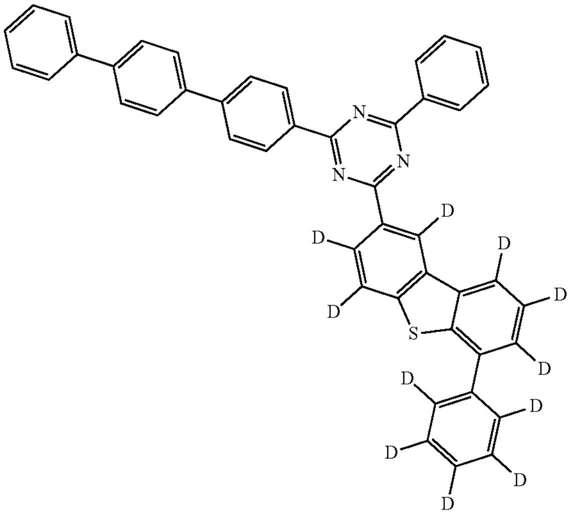
317
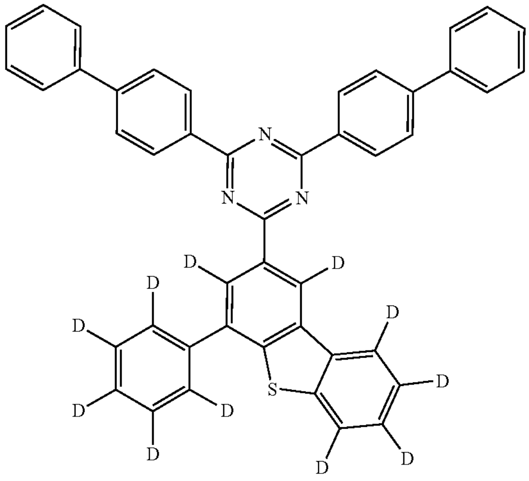
318
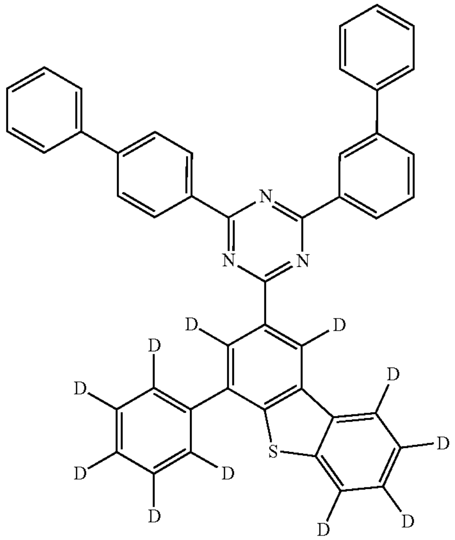

-continued
319
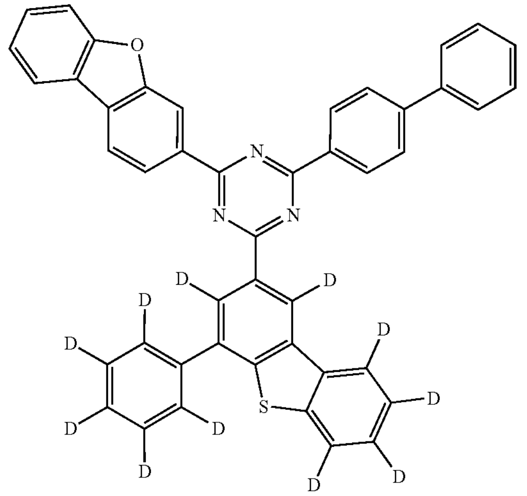
320
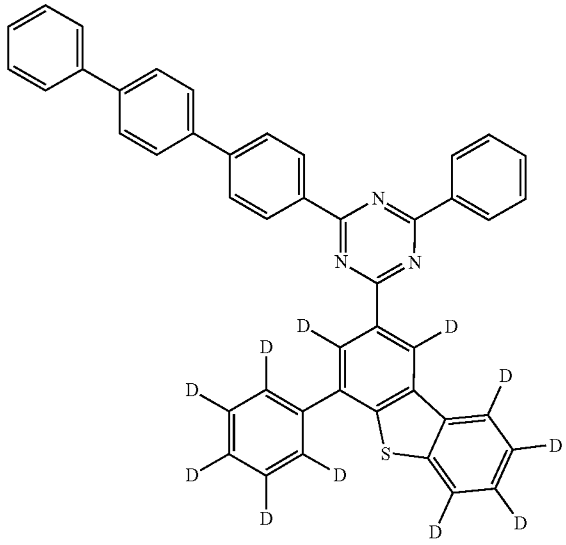
321
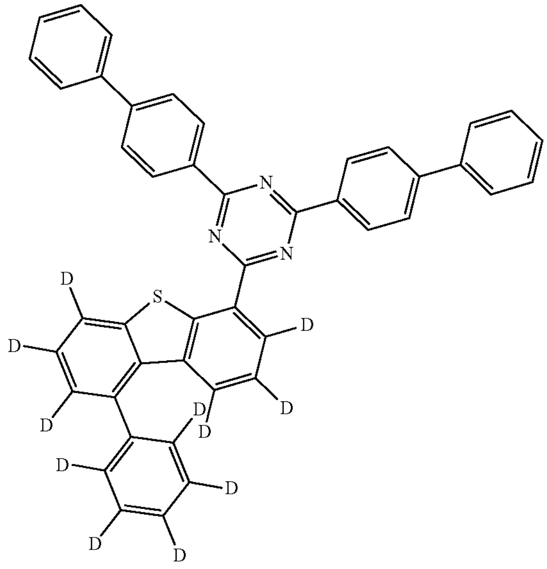
-continued
322
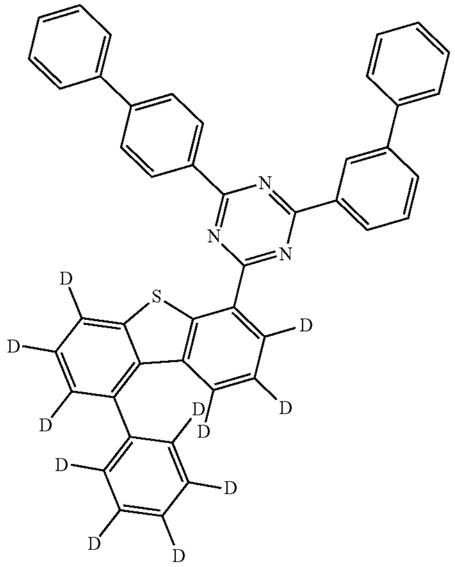
323
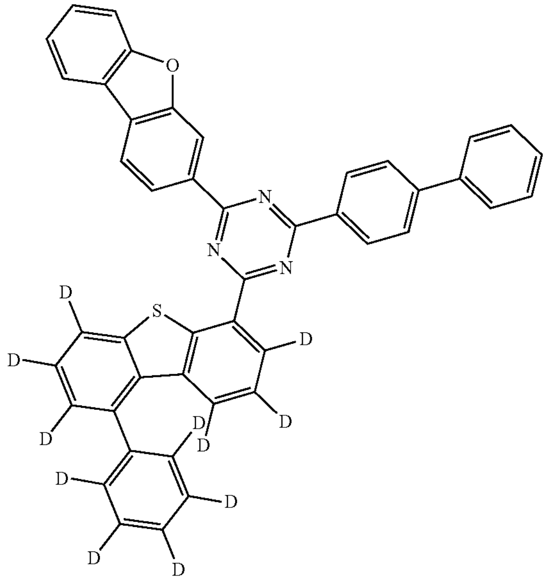

324
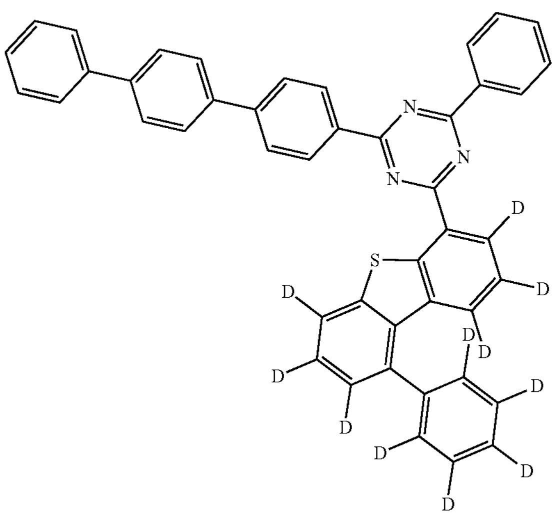
325
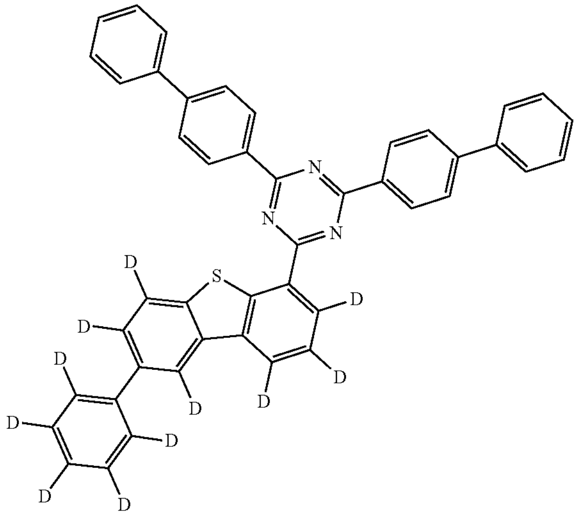
326
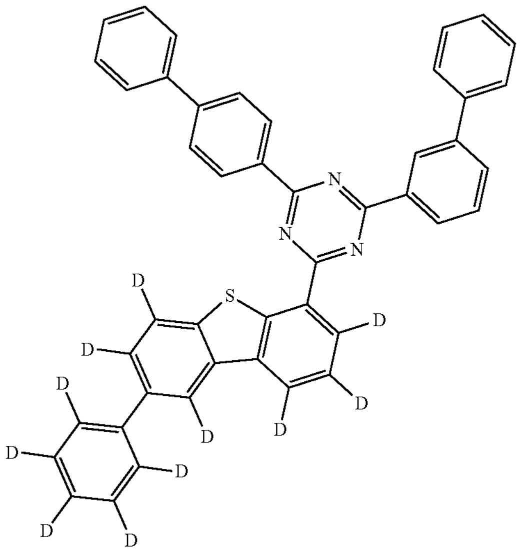
327
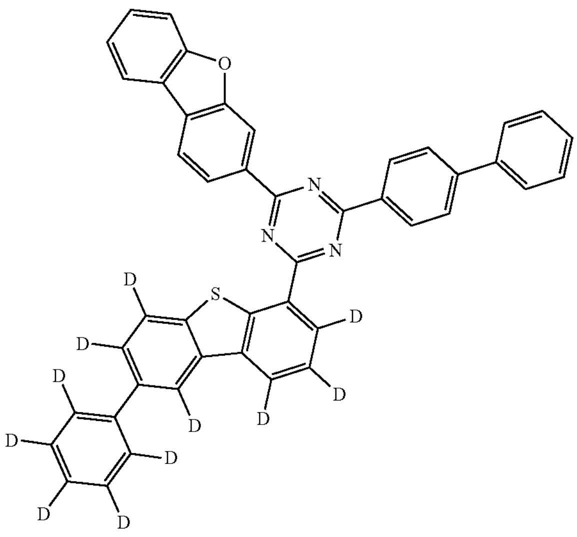
328
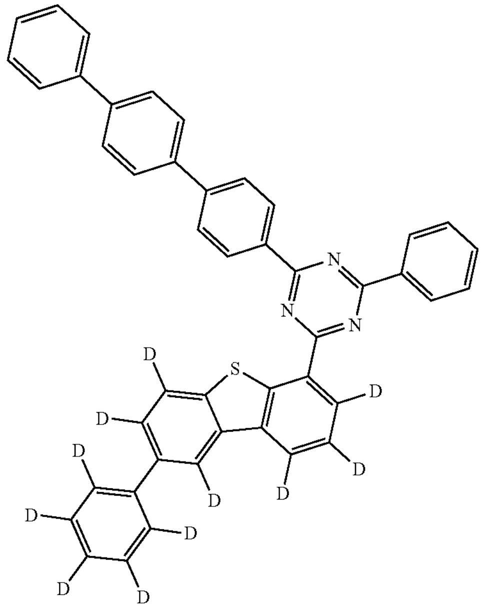
329
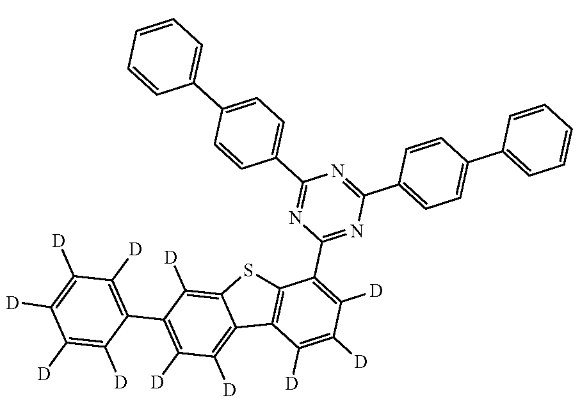

-continued
330
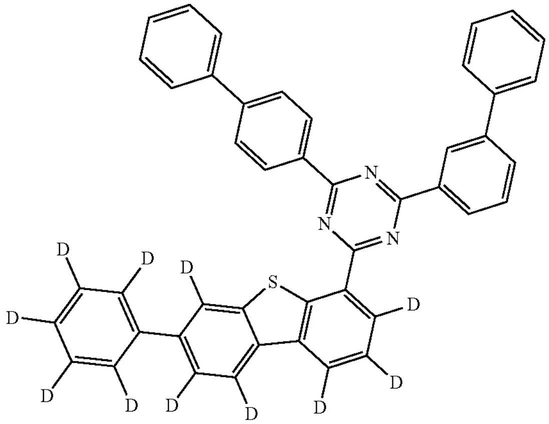
331
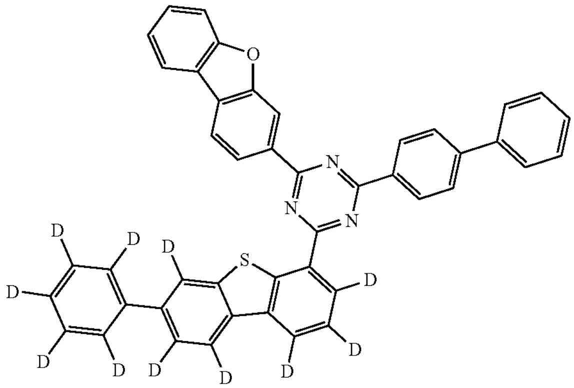
332
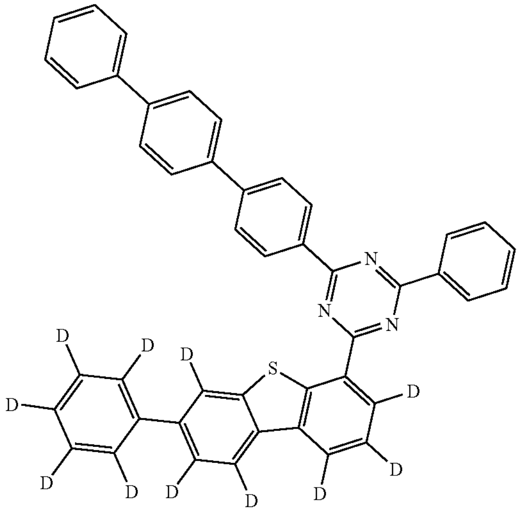
-continued
333
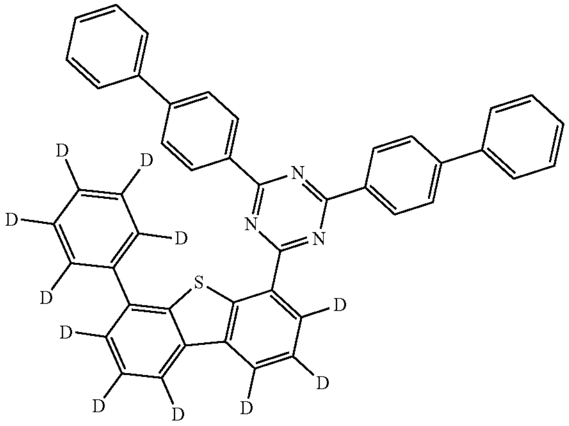
334
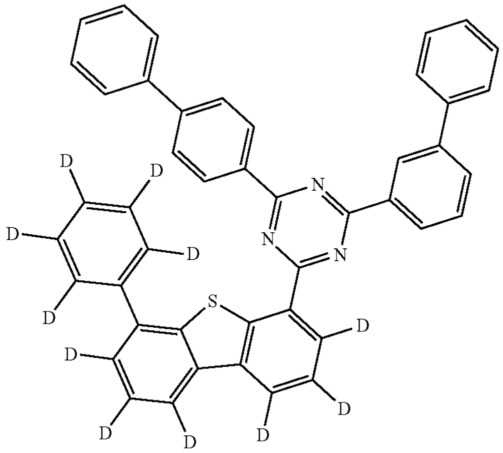
335
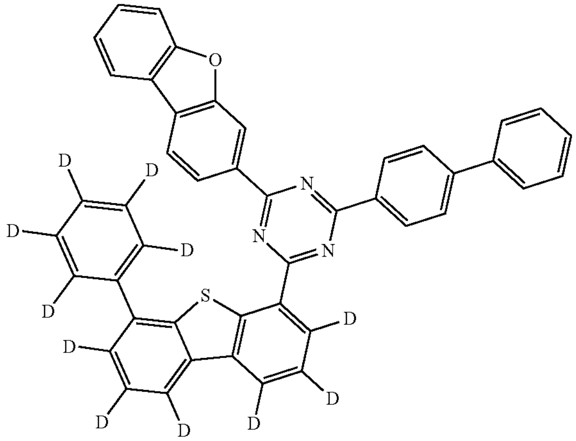

-continued
336
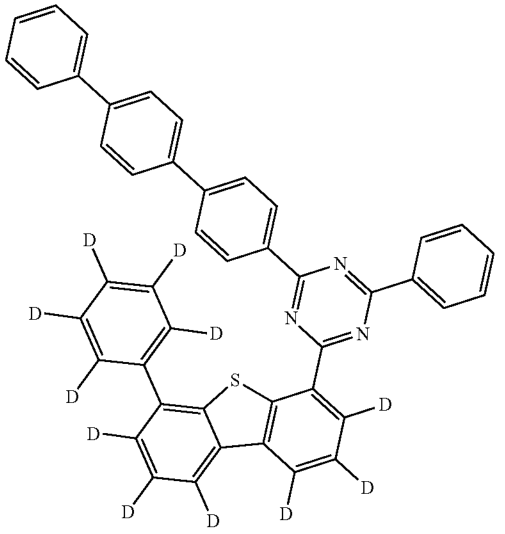
337
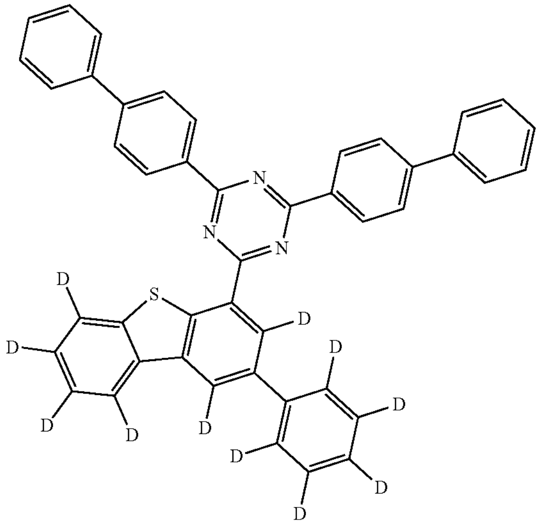
338
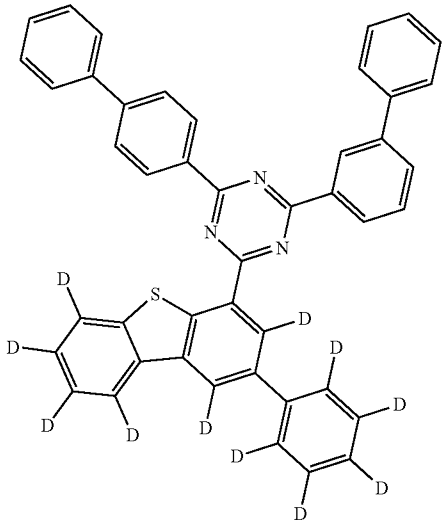
-continued
339
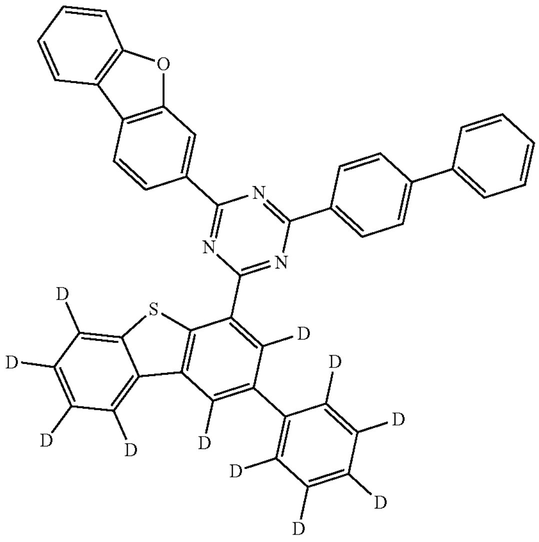
340
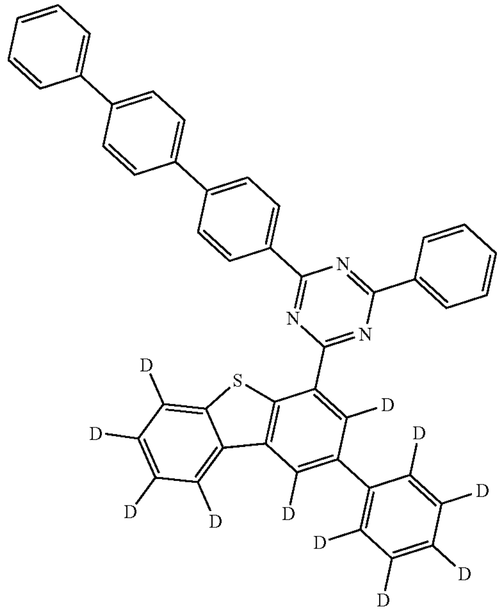
341
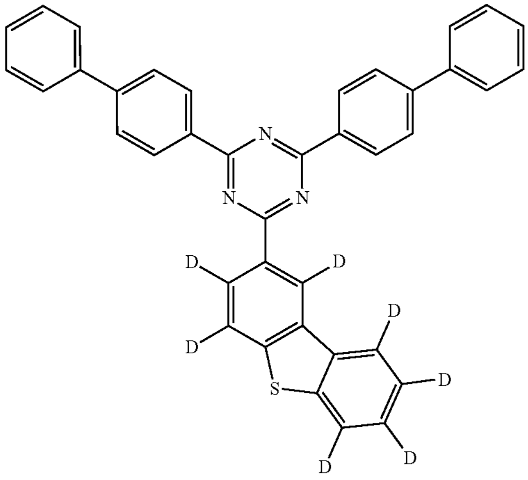

342
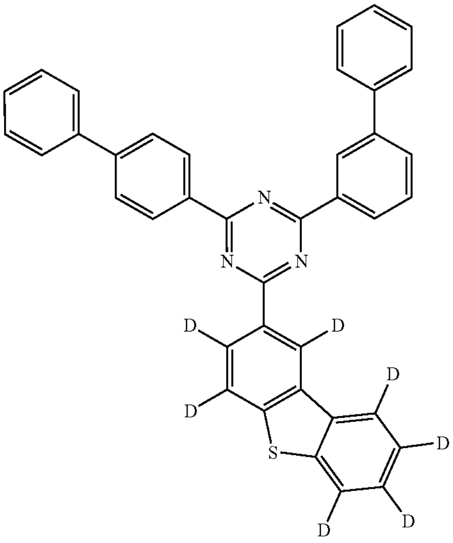
343
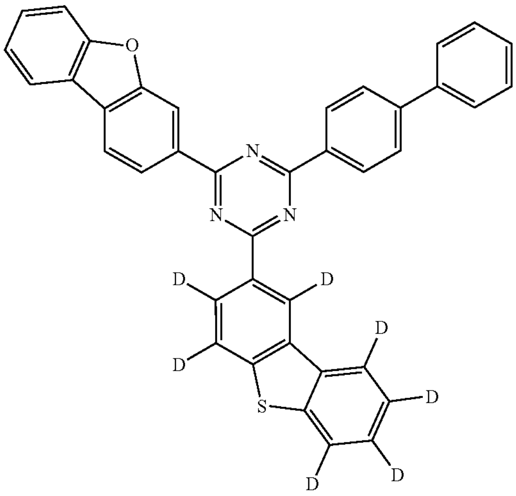
344
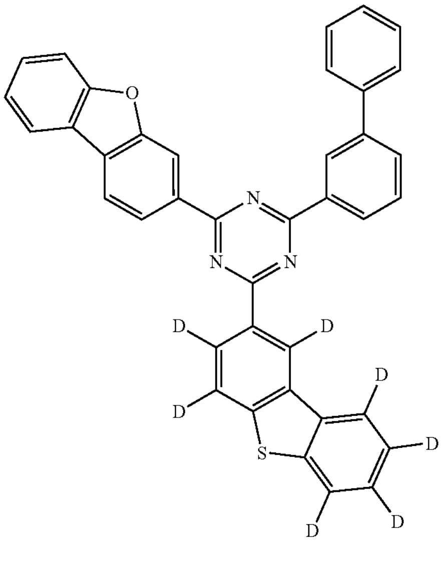
345
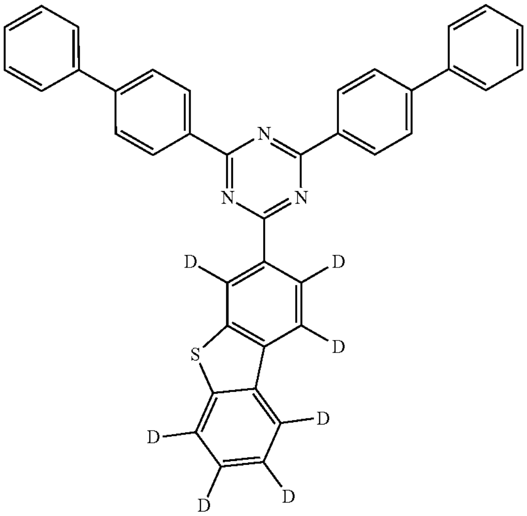
346
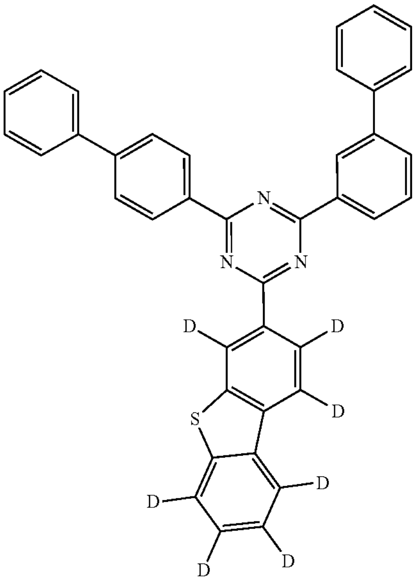
347
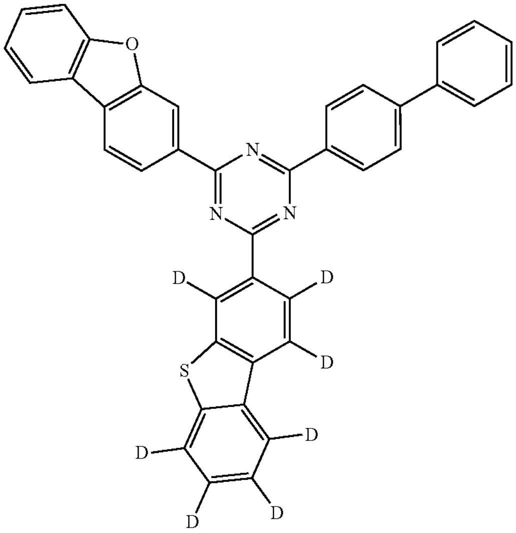

-continued
348
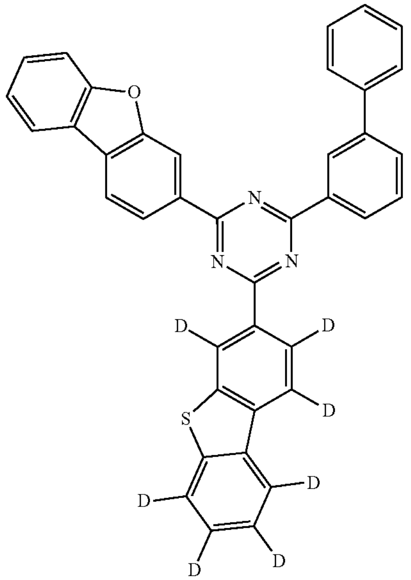
349
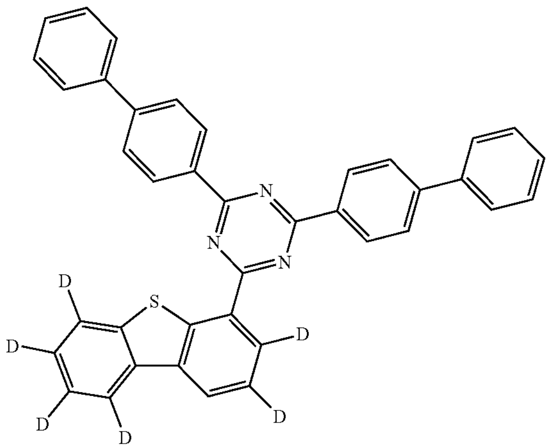
350
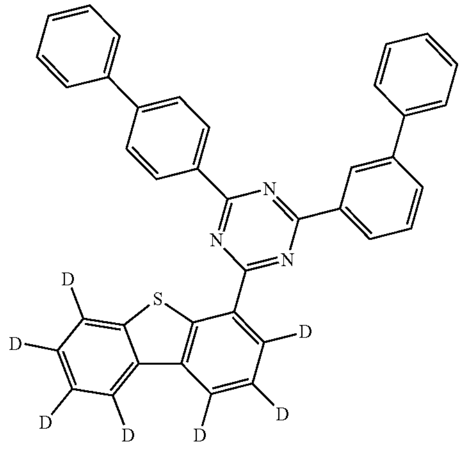
-continued
351
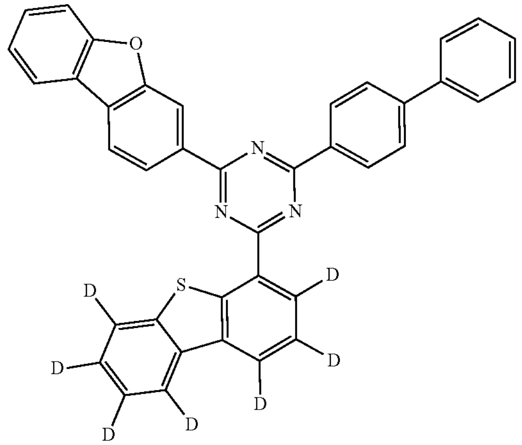
352
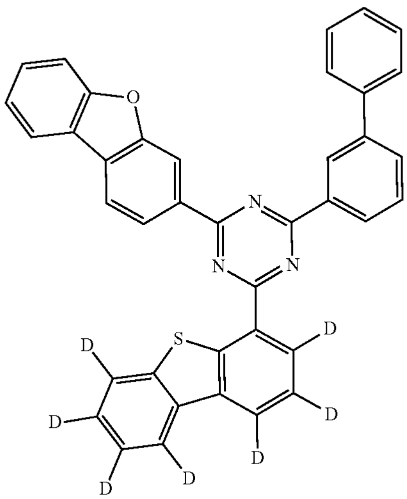
353
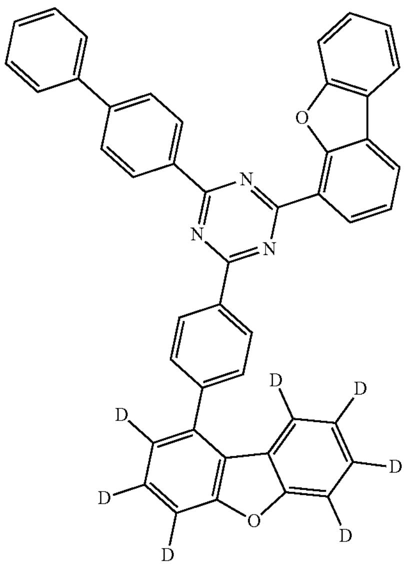

-continued
354
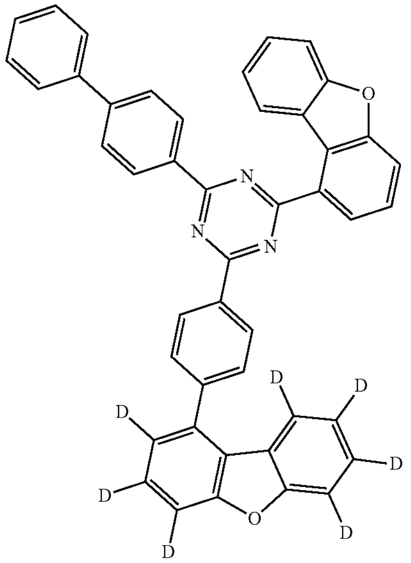
355
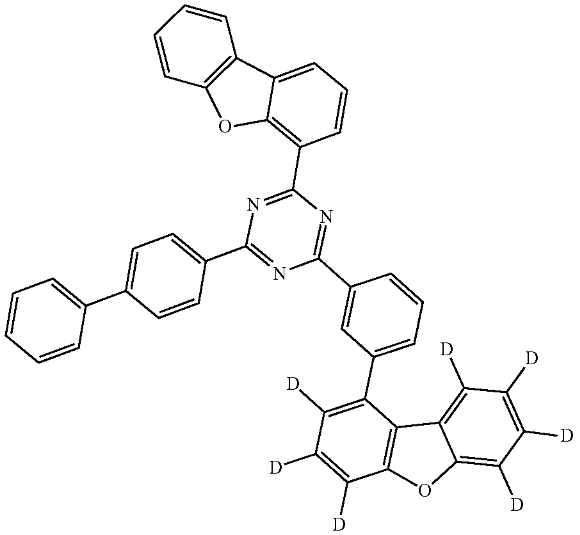
356
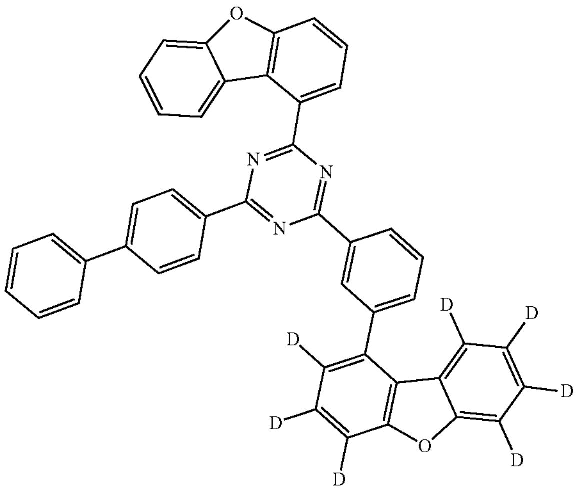
-continued
357
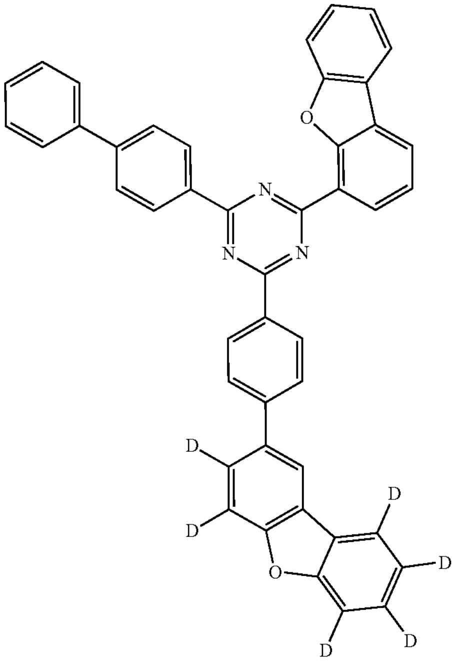
358
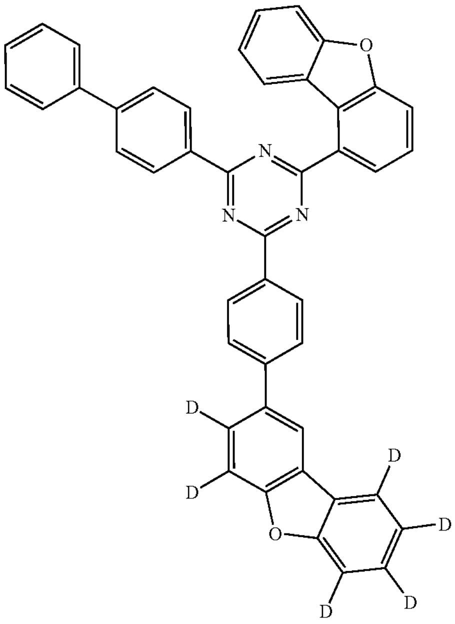

-continued
359
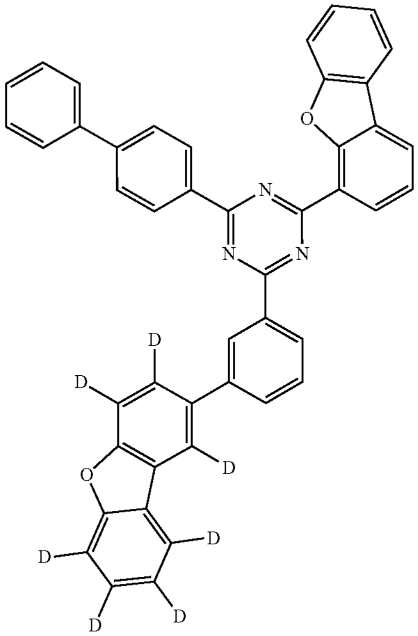
360
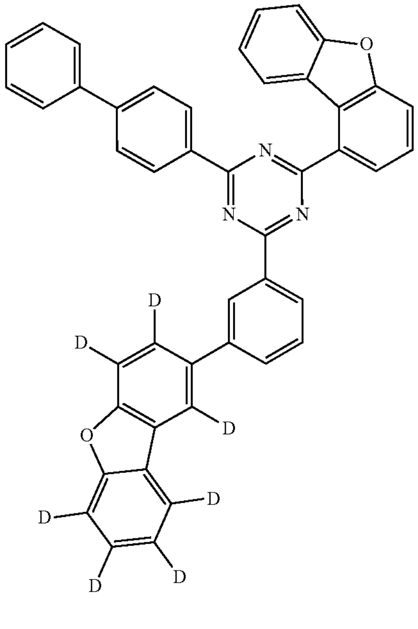
-continued
361
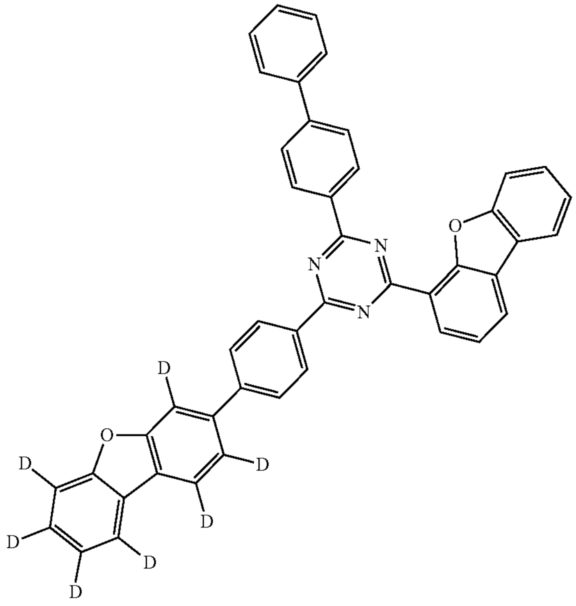
362
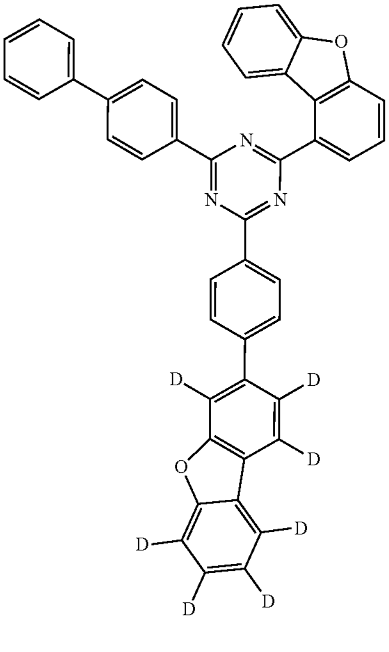

363
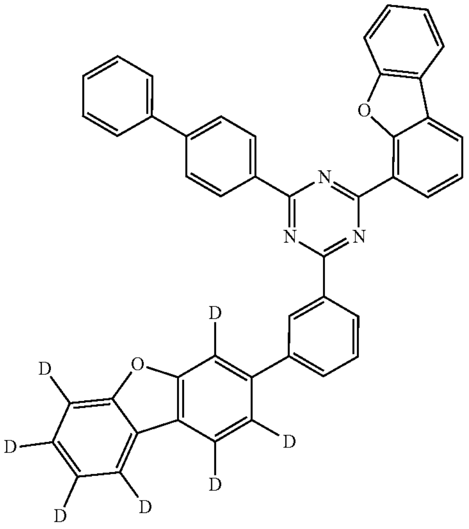
364
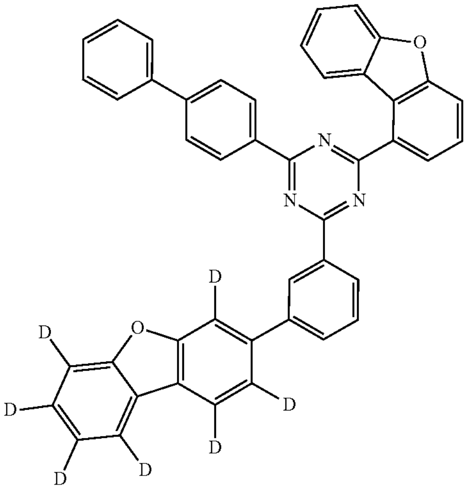
365
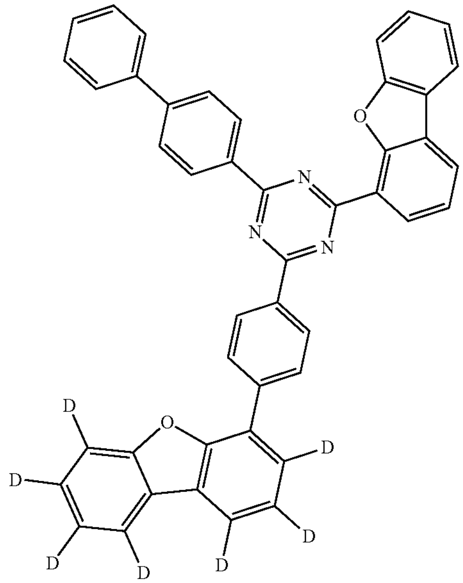
366
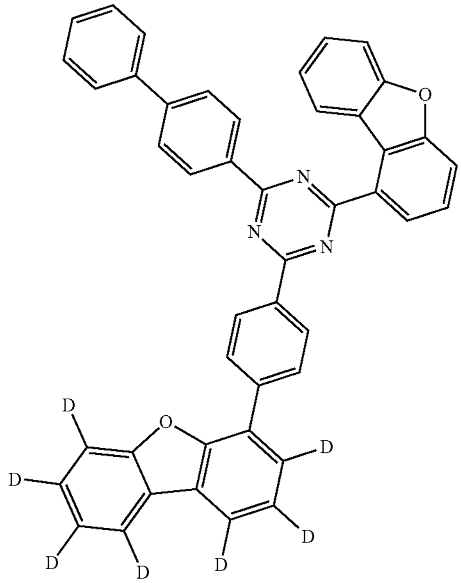
367
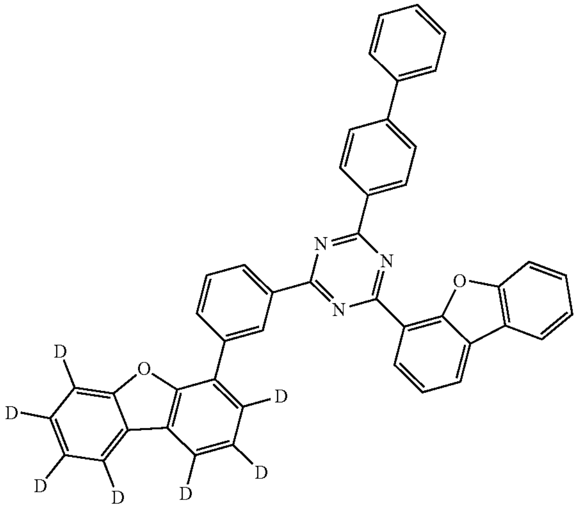

-continued
368
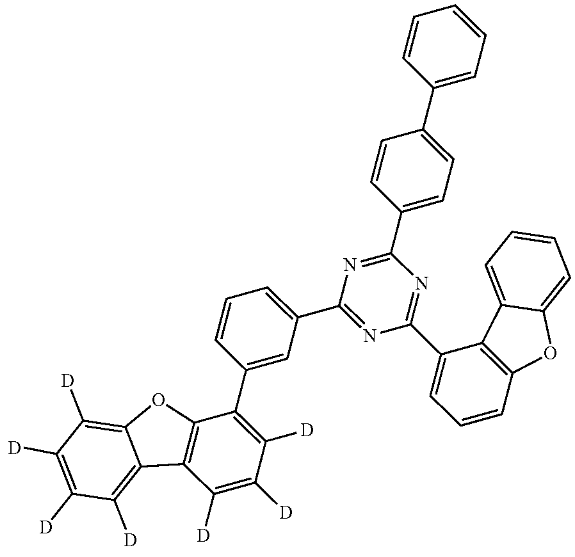
369
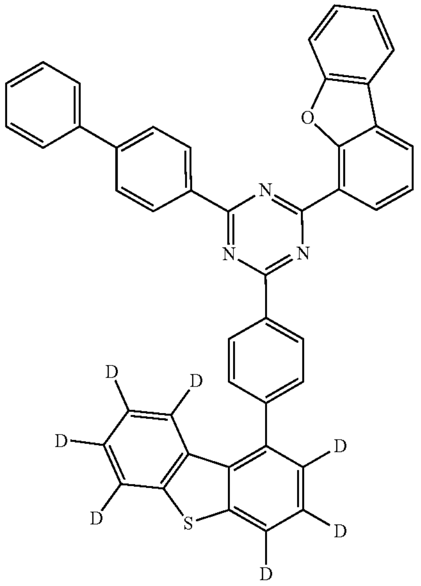
-continued
370
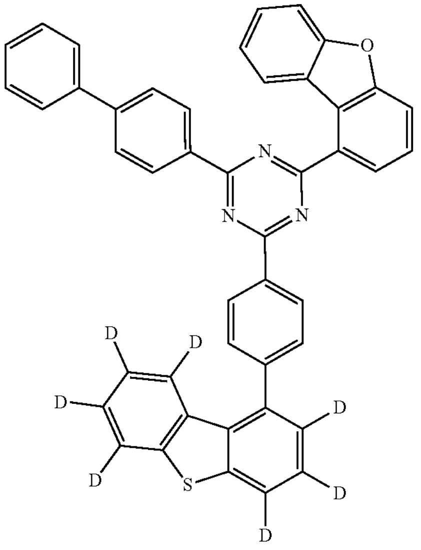
371
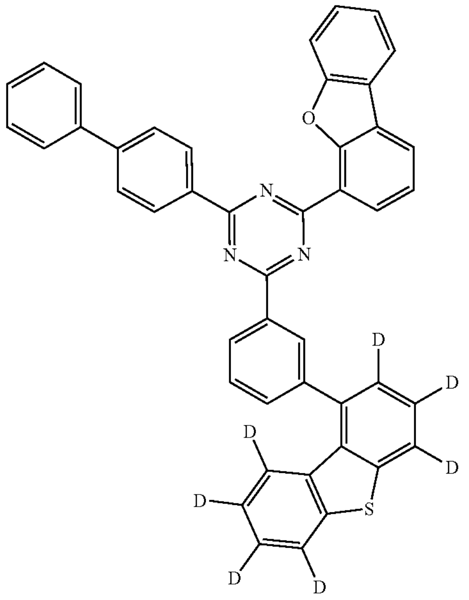

-continued
372
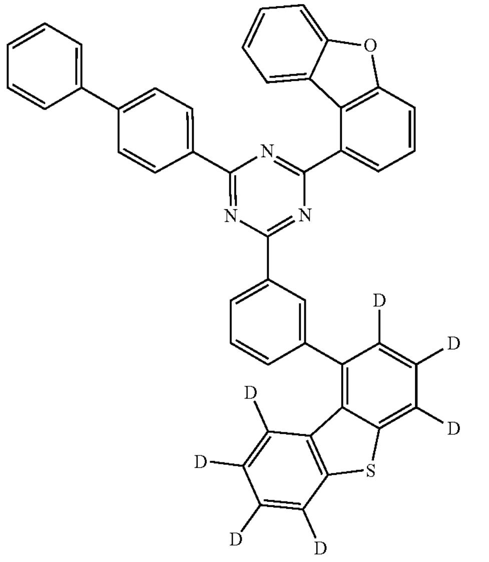
373
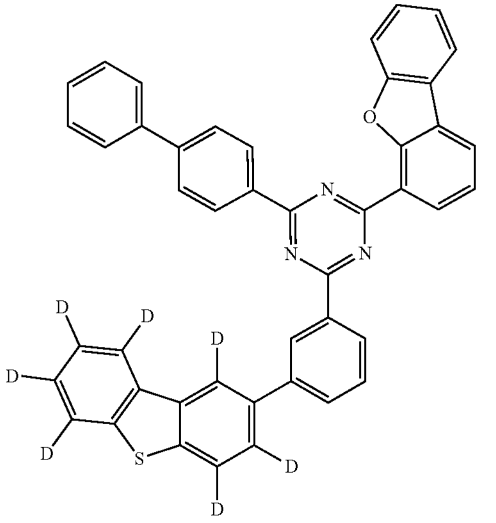
374
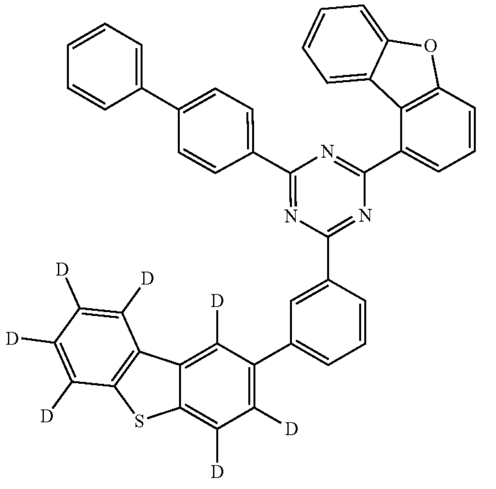
-continued
375
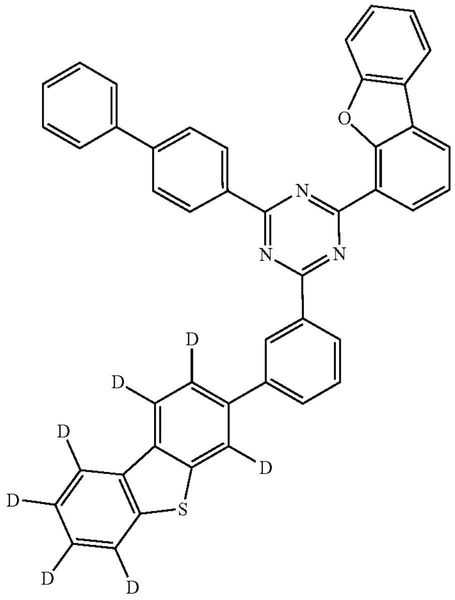
376
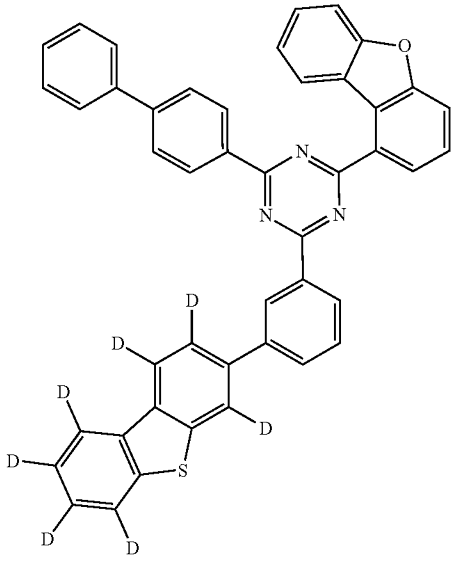

-continued
377
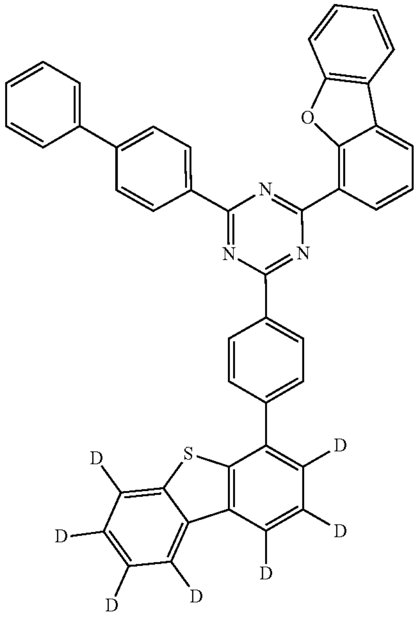
379
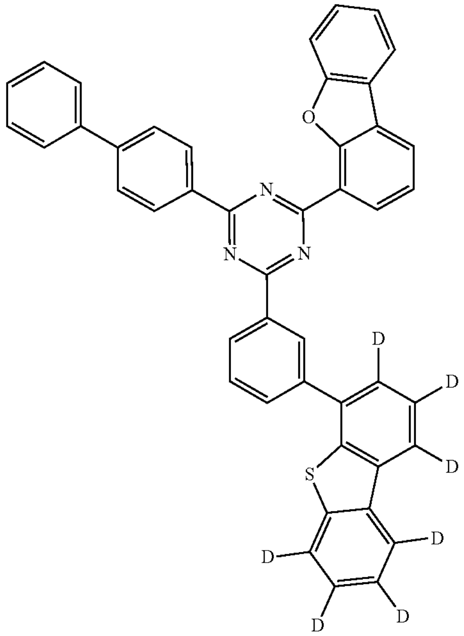
378
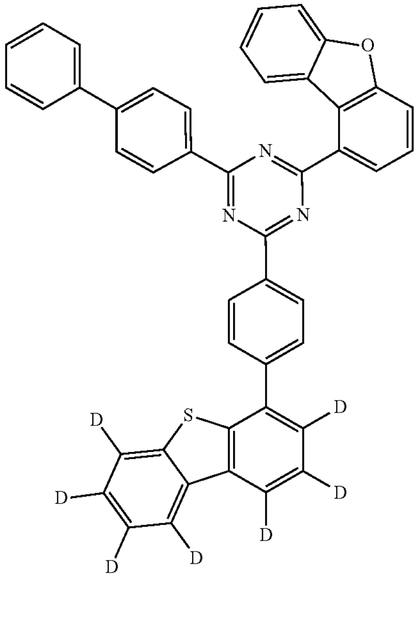
380
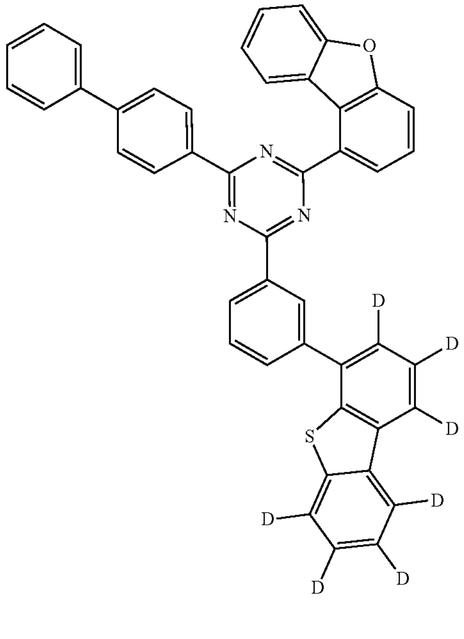

-continued
381
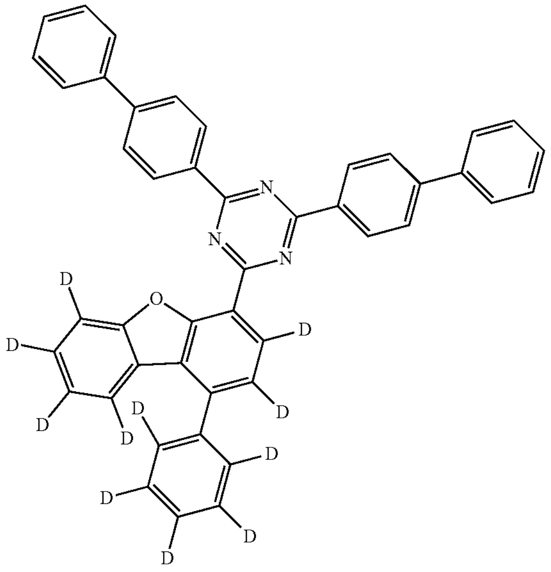
382
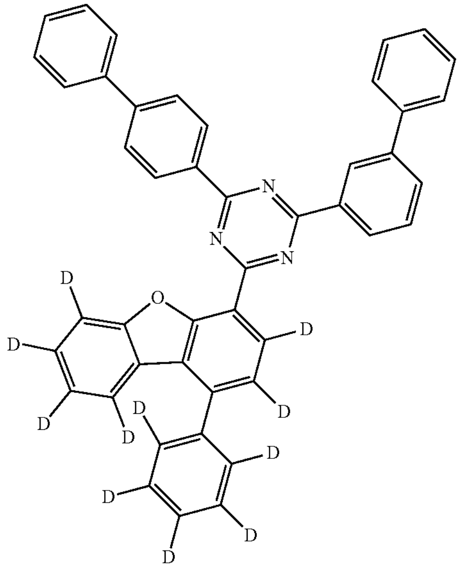
-continued
383
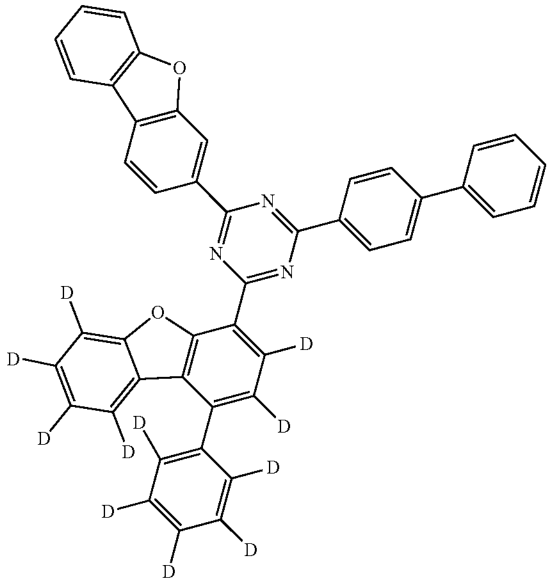
384
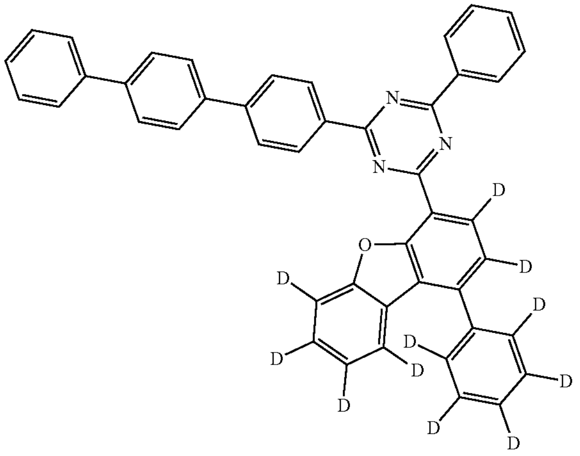
385
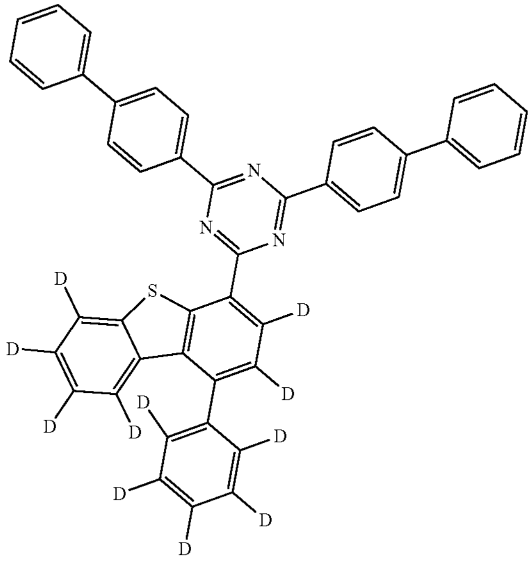

-continued
386
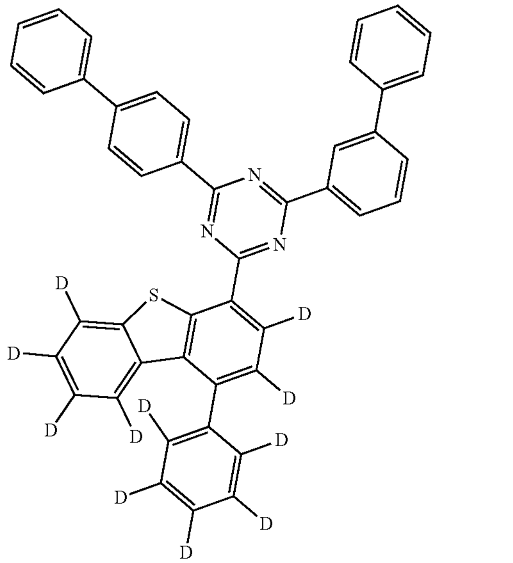
387
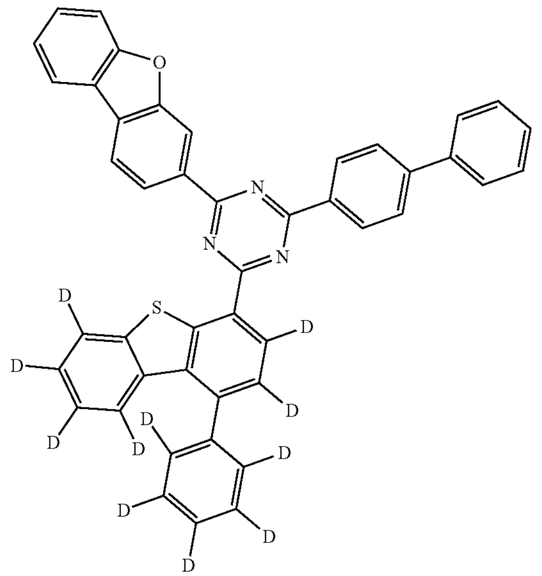
388
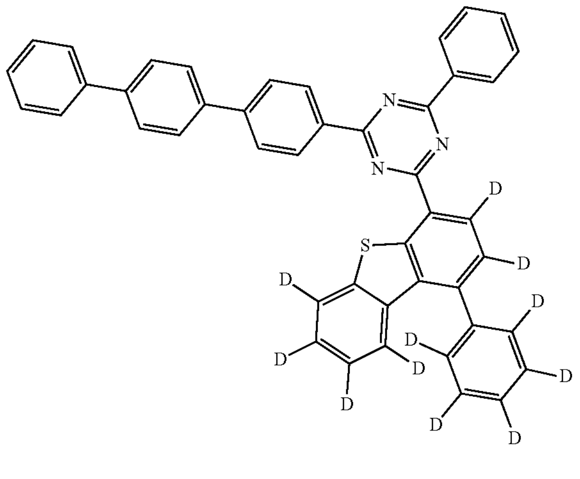
-continued
389
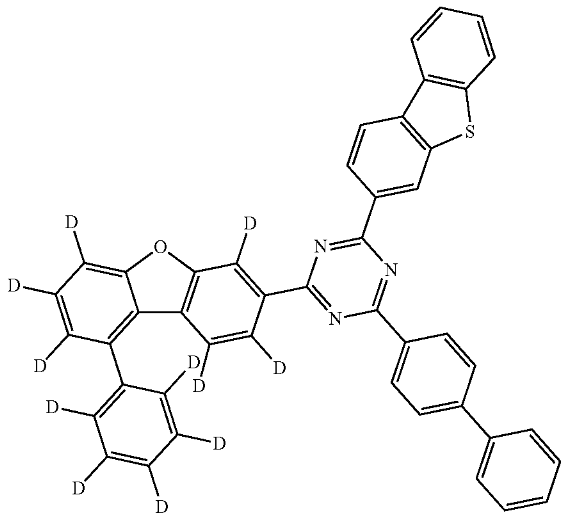
390
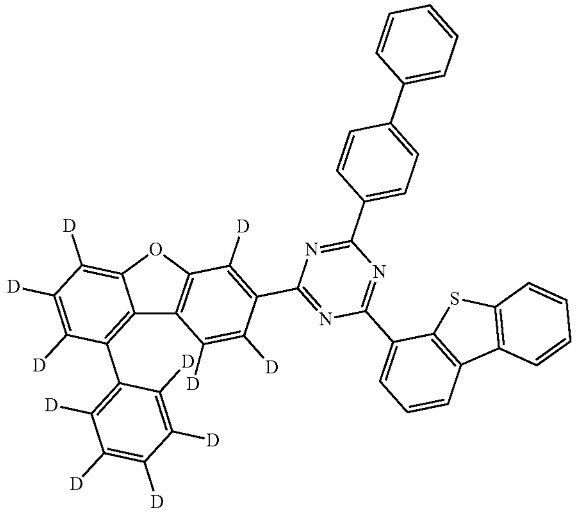
391
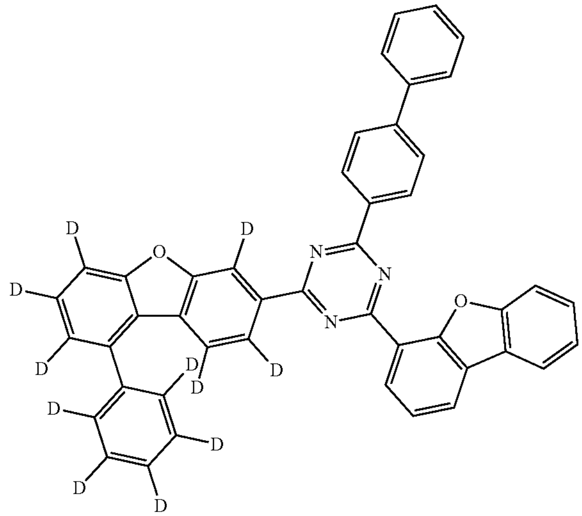

392
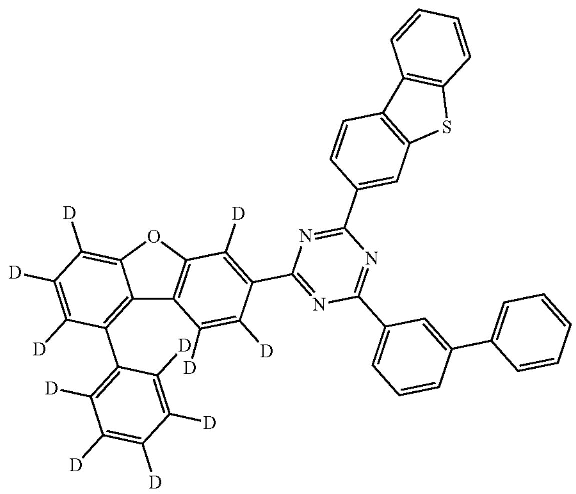
393
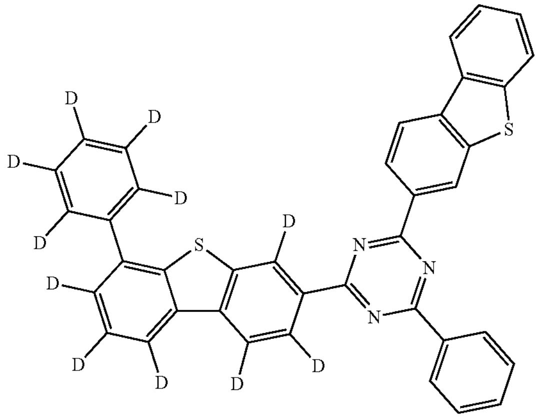
394
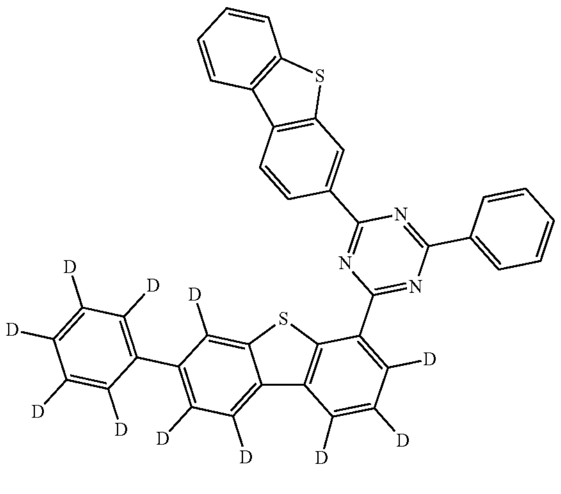
395
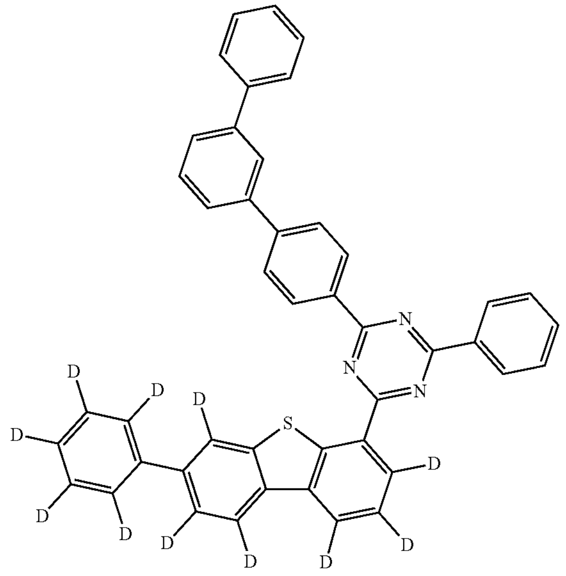
396
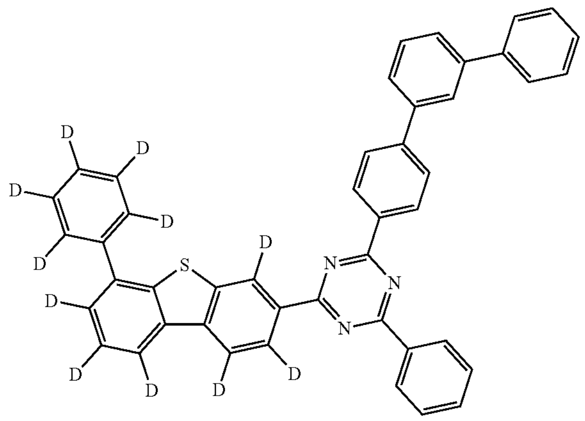
397
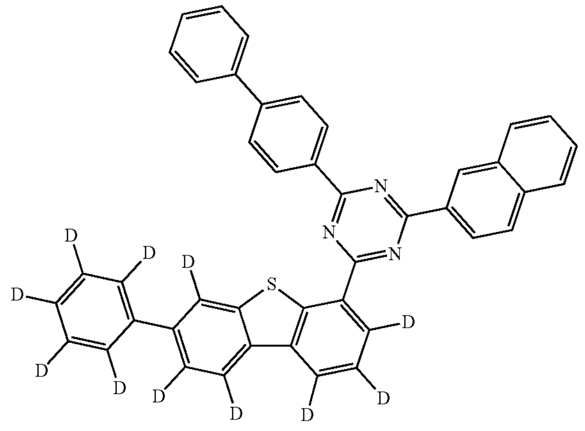

-continued
398
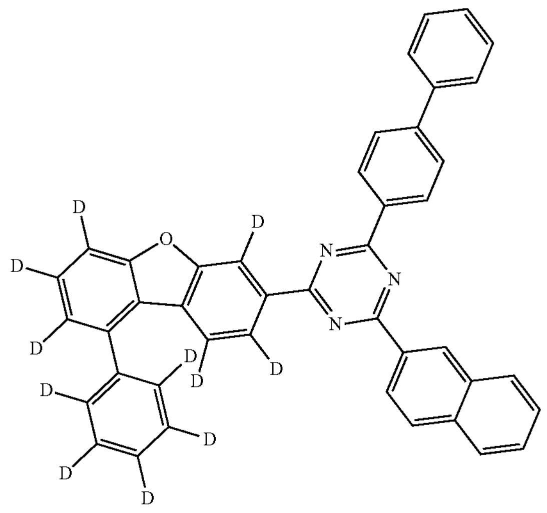
399
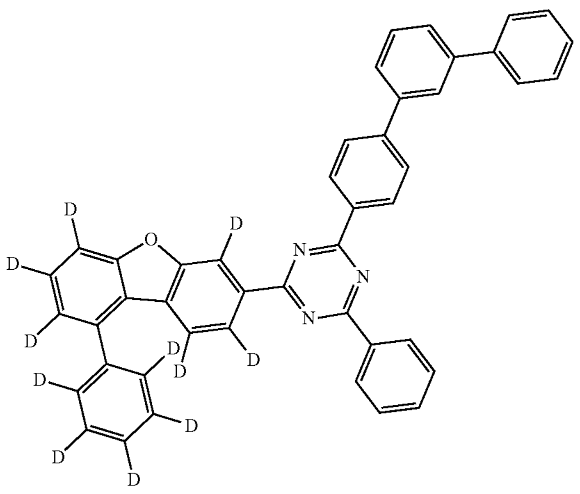
400
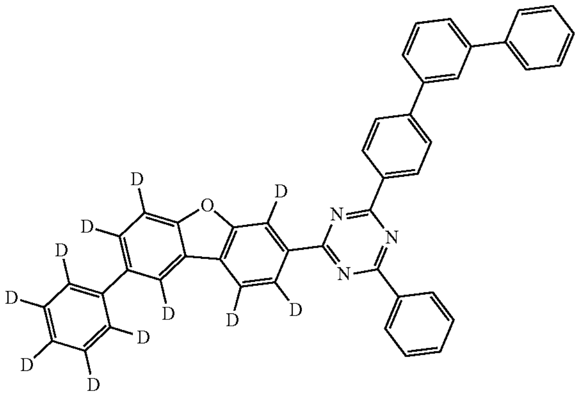
-continued
401
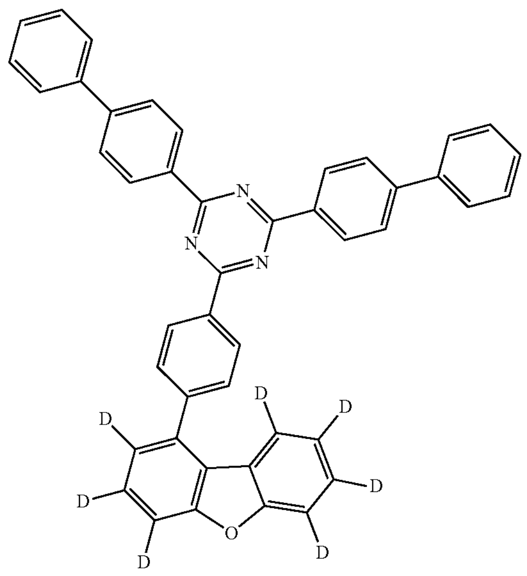
402
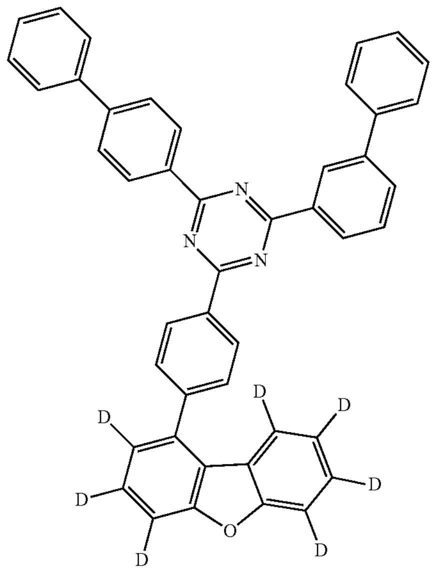

-continued
403
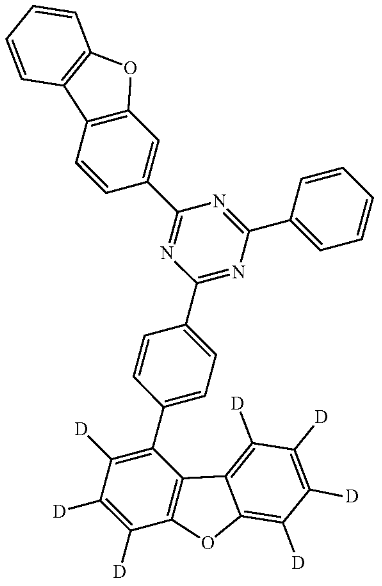
404
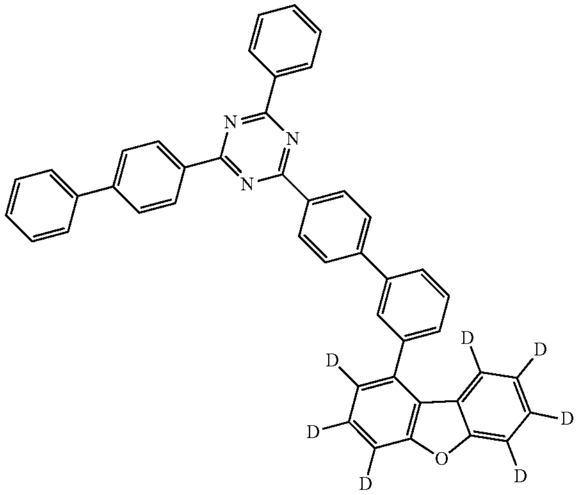
-continued
405
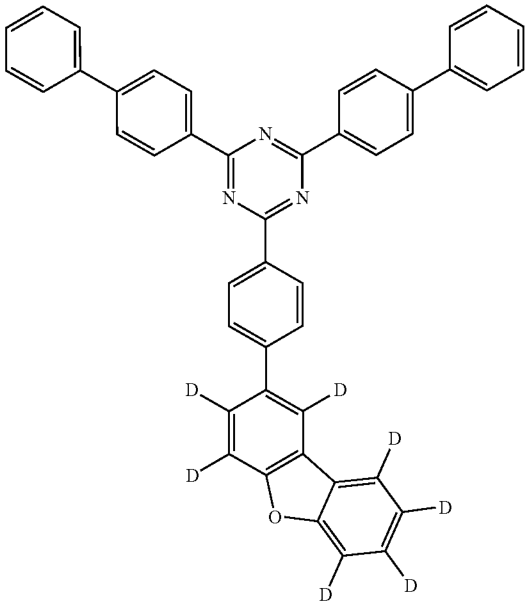
406
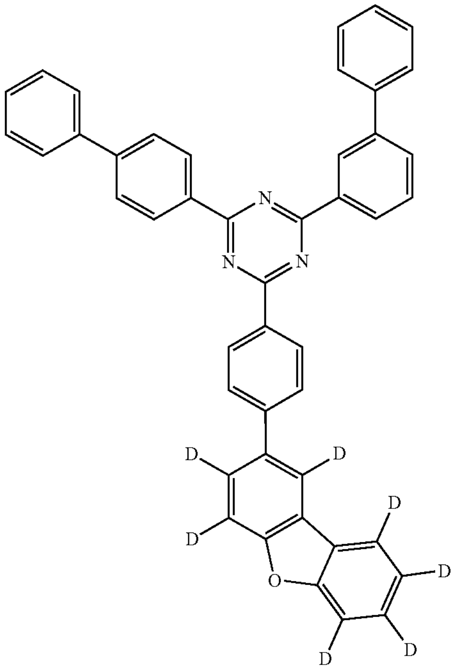

-continued
407
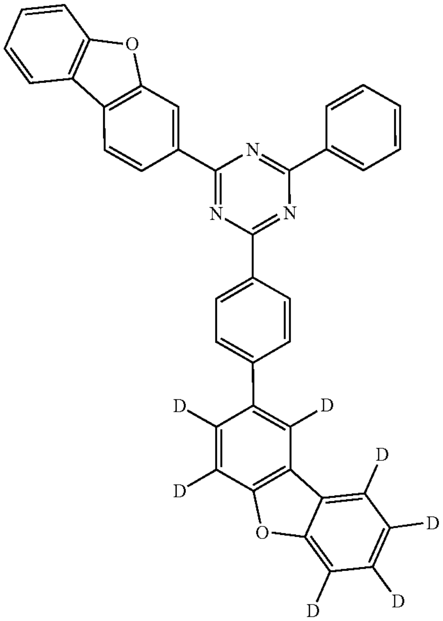
409
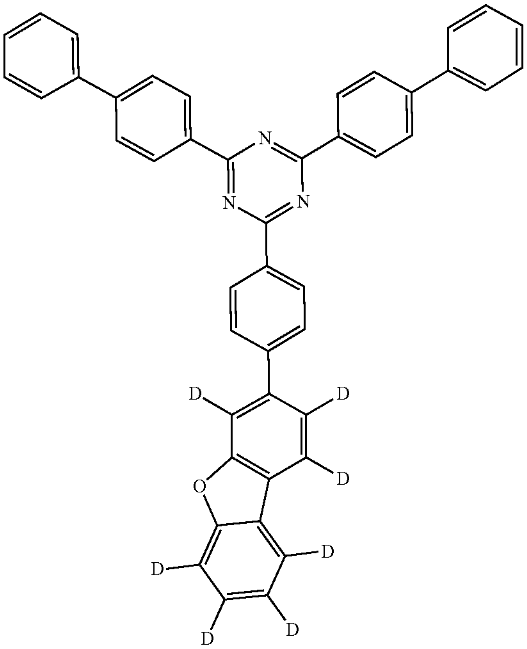
408
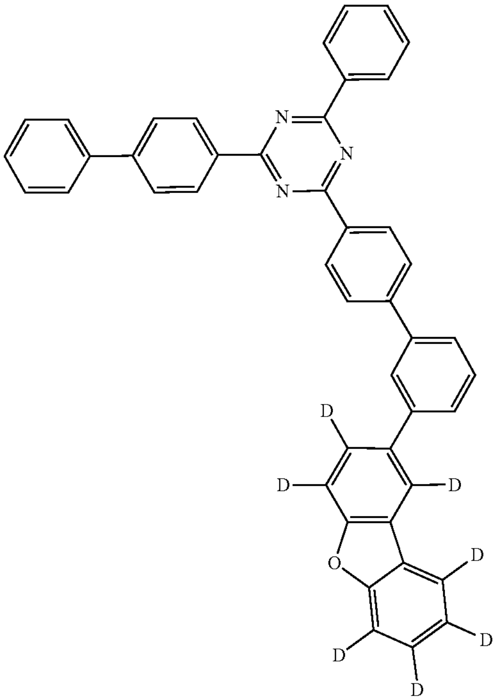
410
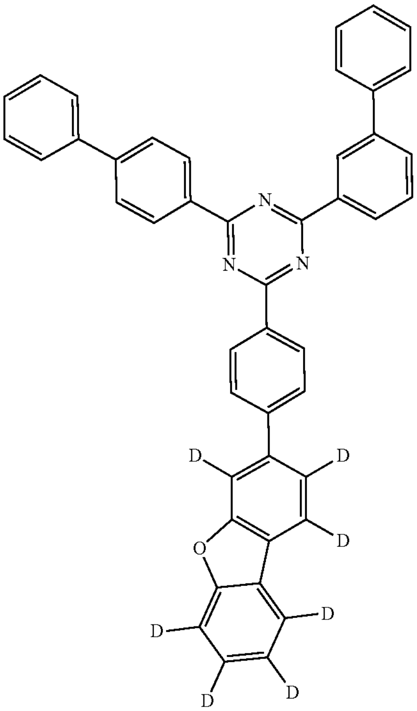

-continued
411
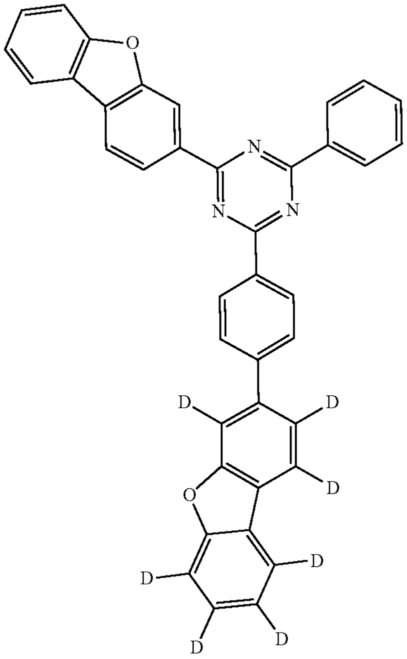
412
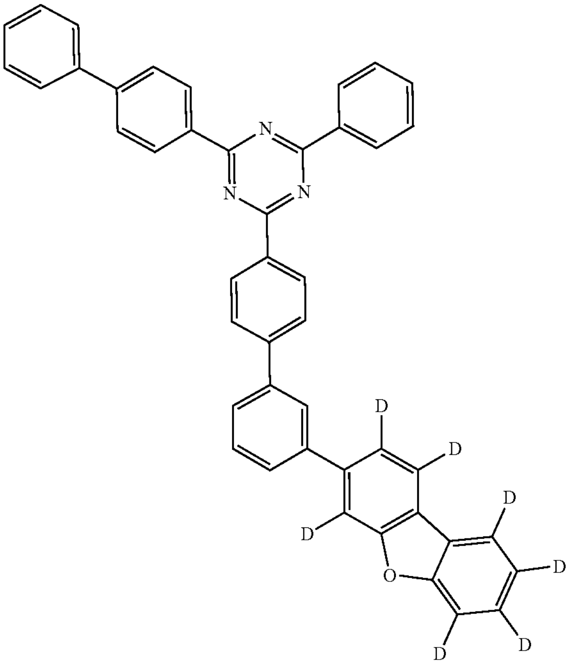
-continued
413
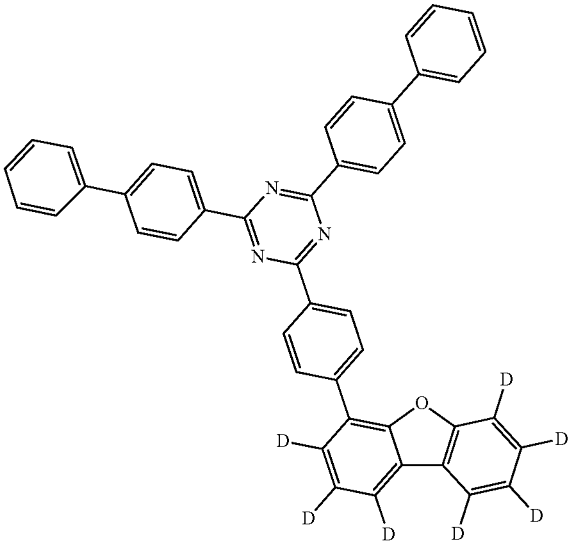
414
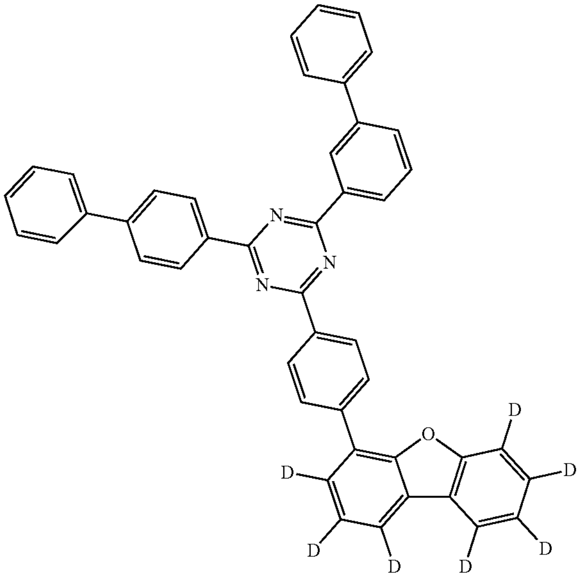
415
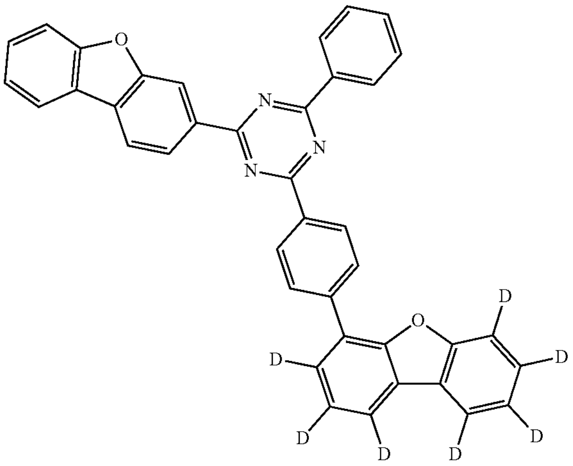

-continued
416
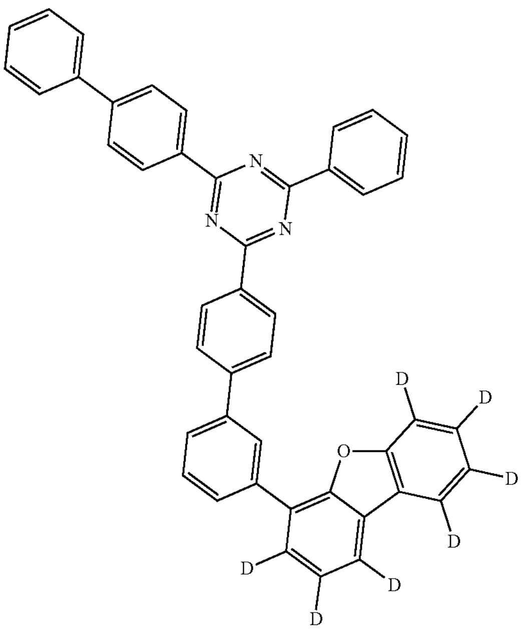
417
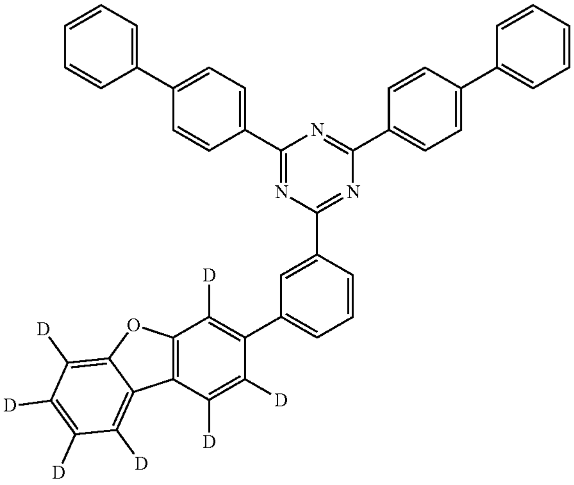
-continued
418
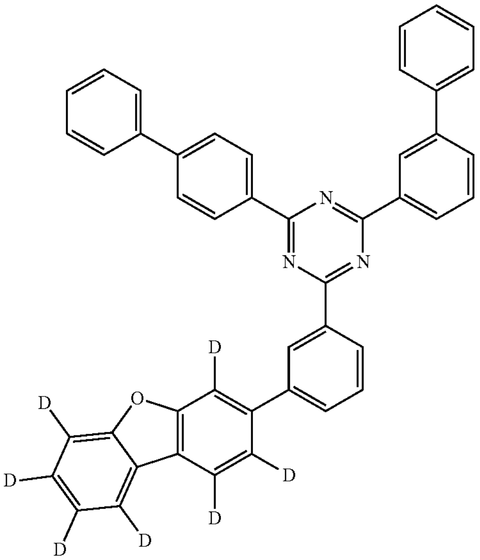
419
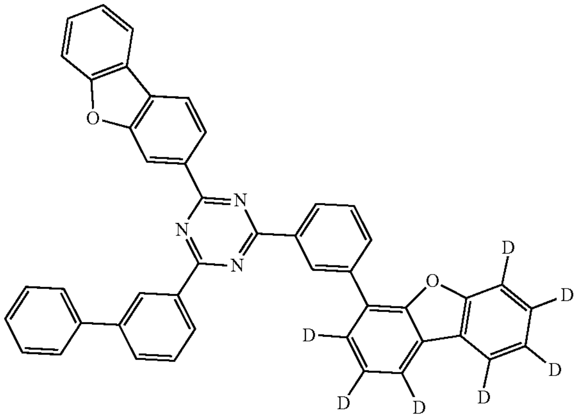

-continued
420
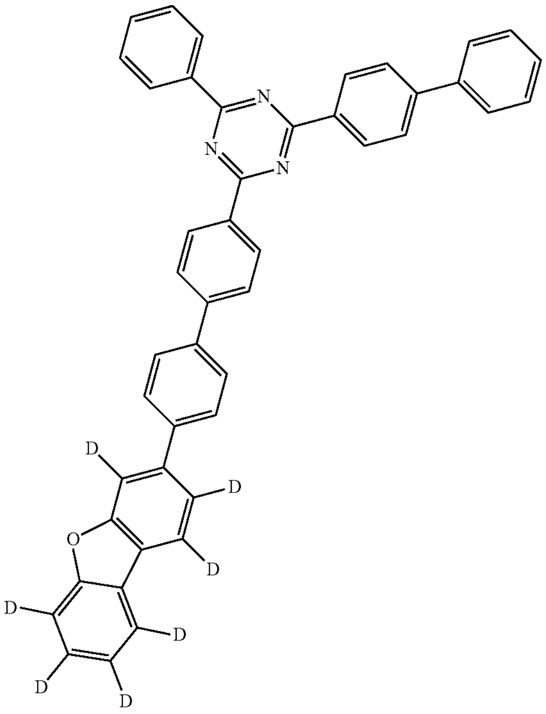
421
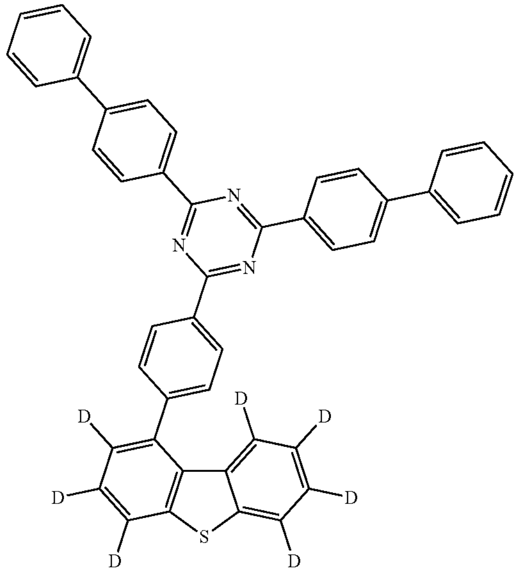
-continued
422
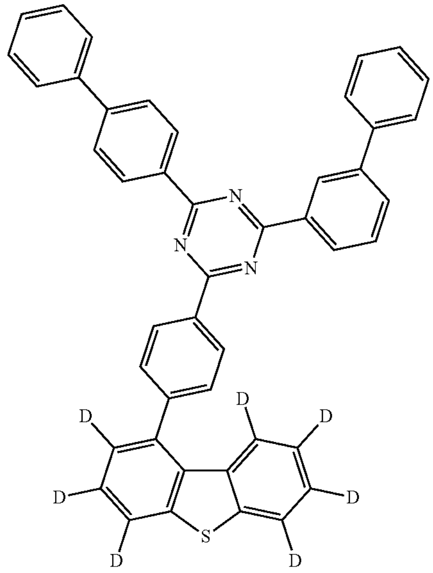
423
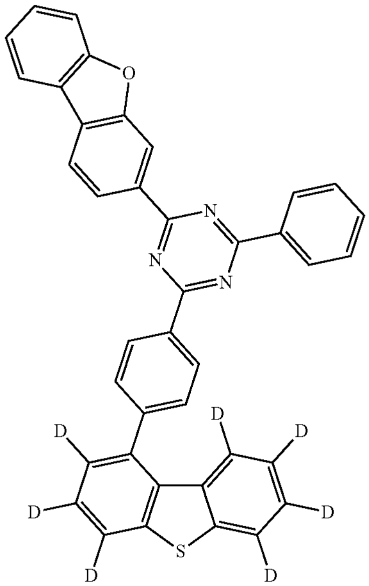

-continued
424
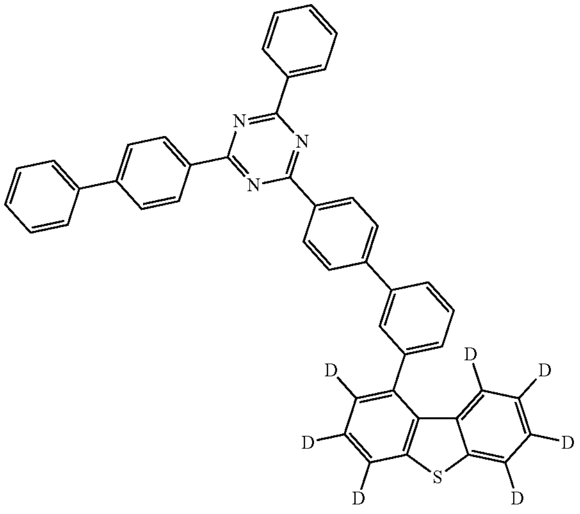
425
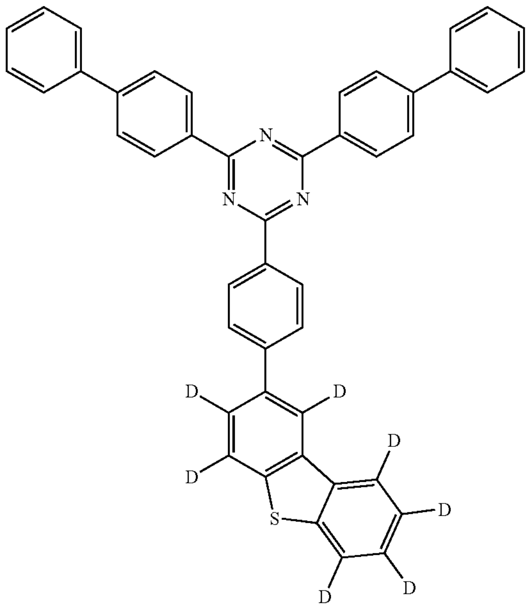
-continued
426
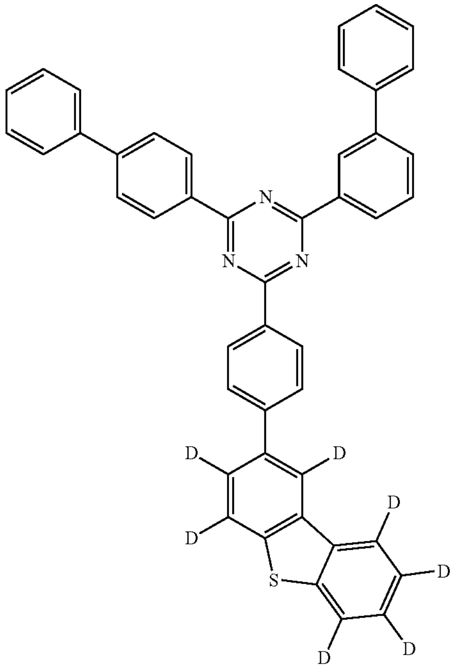
427
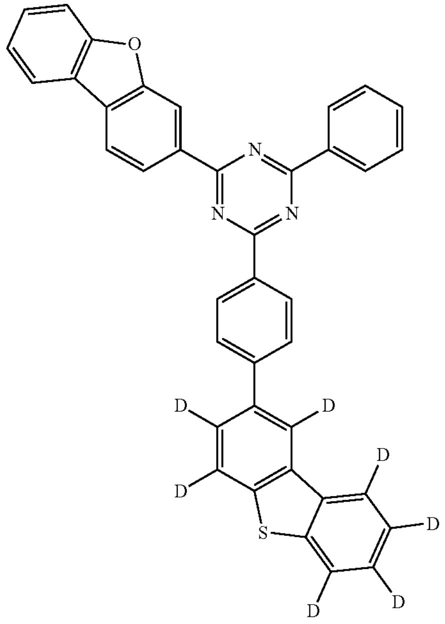

-continued
428
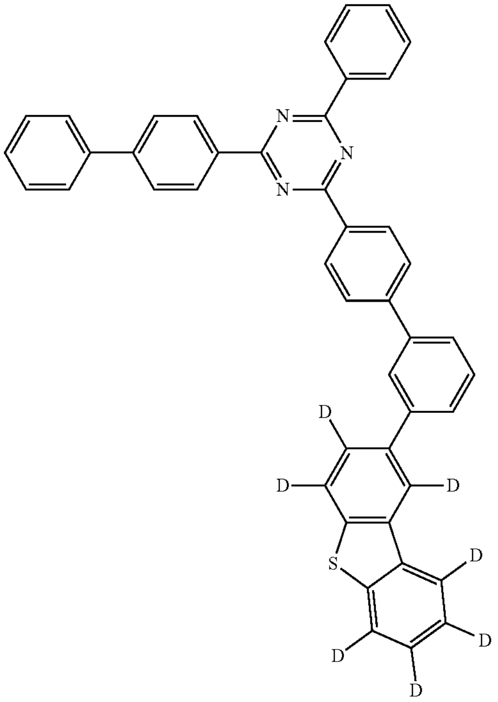
429
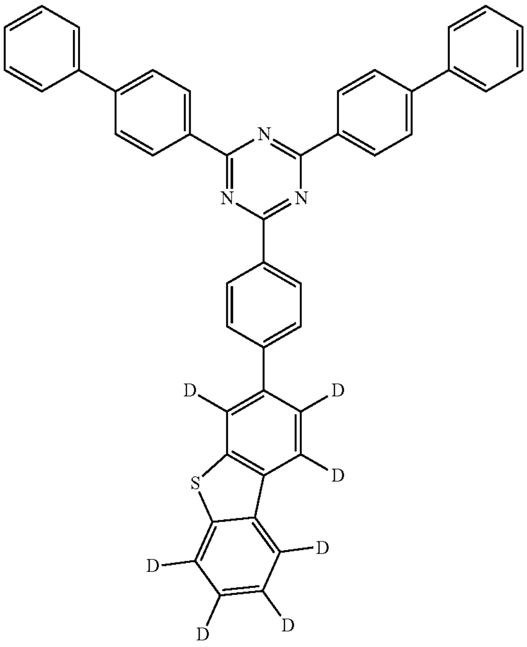
-continued
430
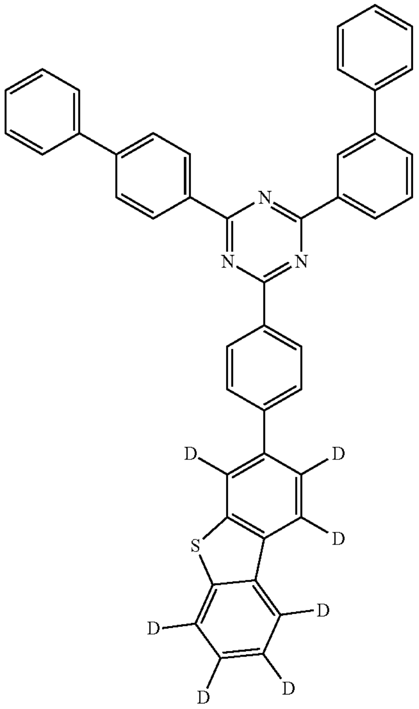
430
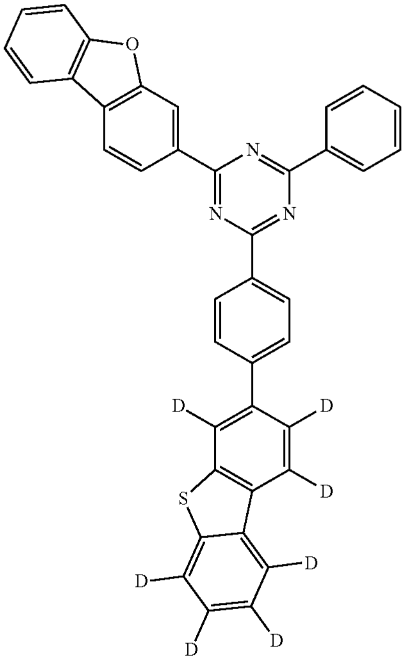

-continued
432
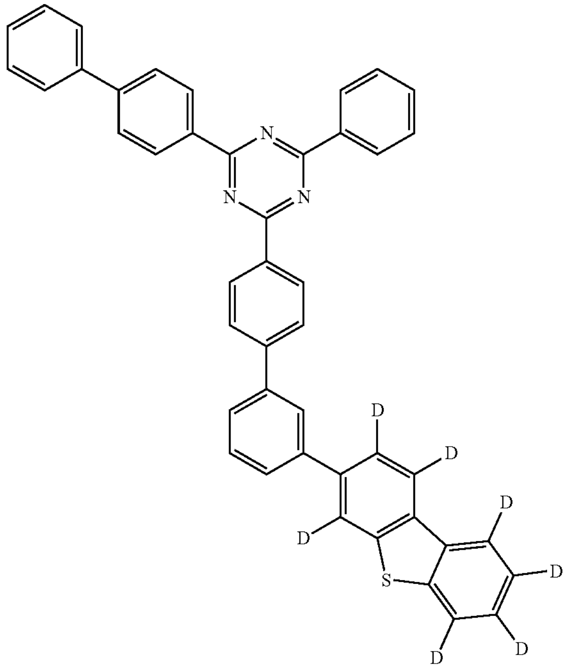
433
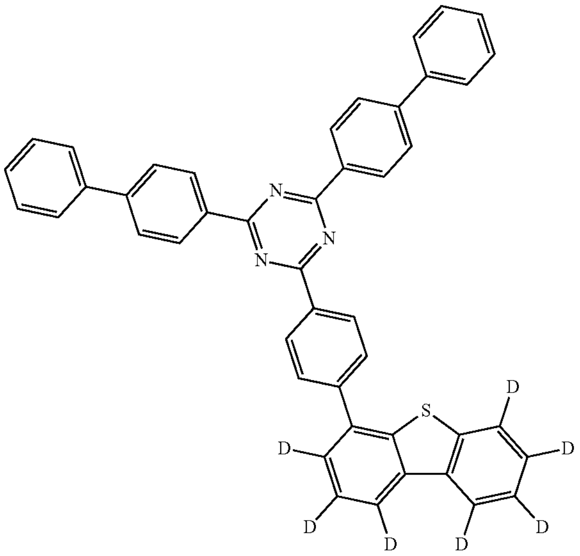
-continued
434
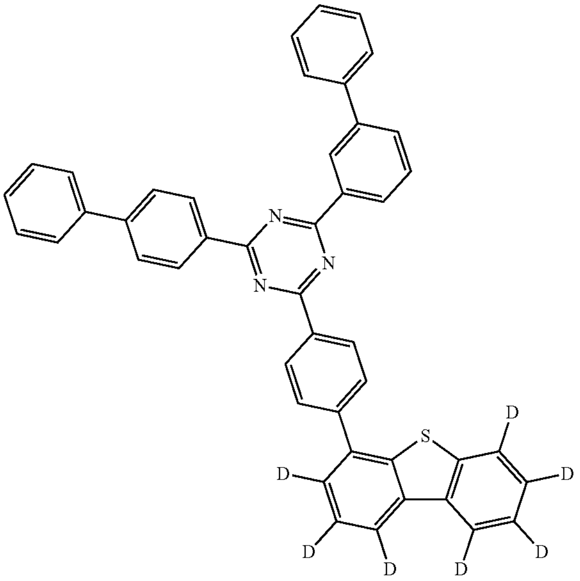
435
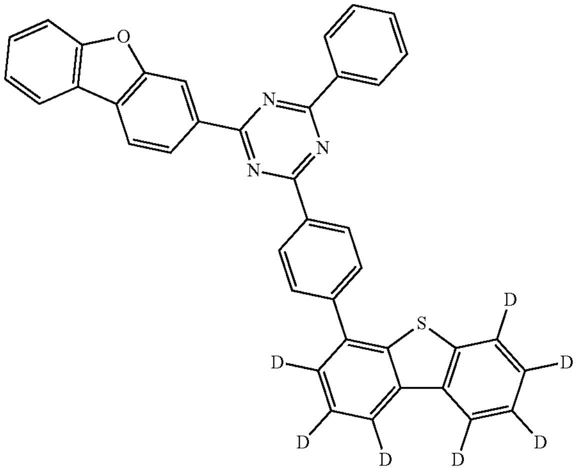

-continued
436
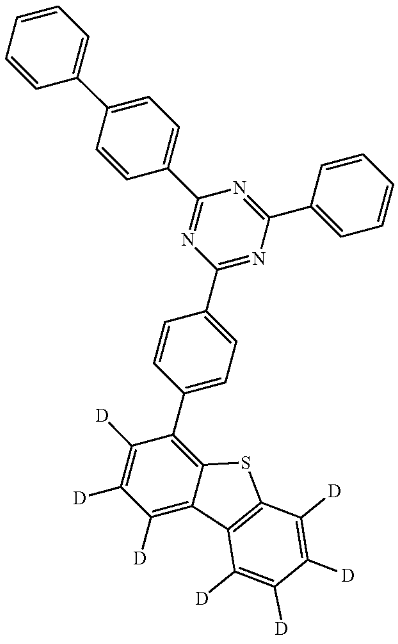
437
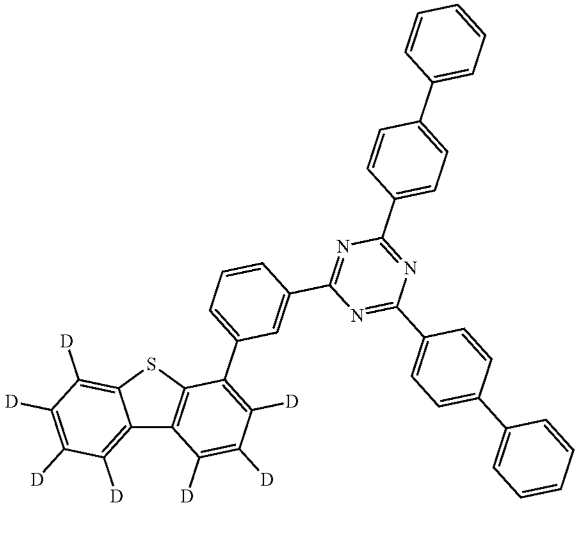
-continued
438
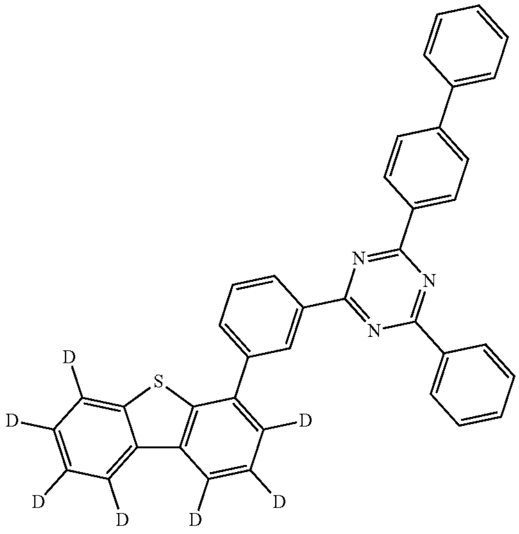
439
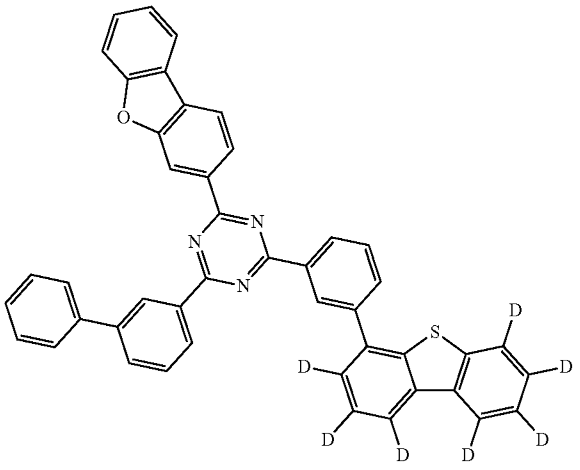
440
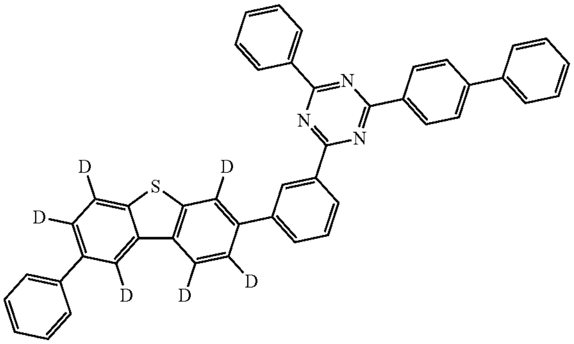

-continued
441
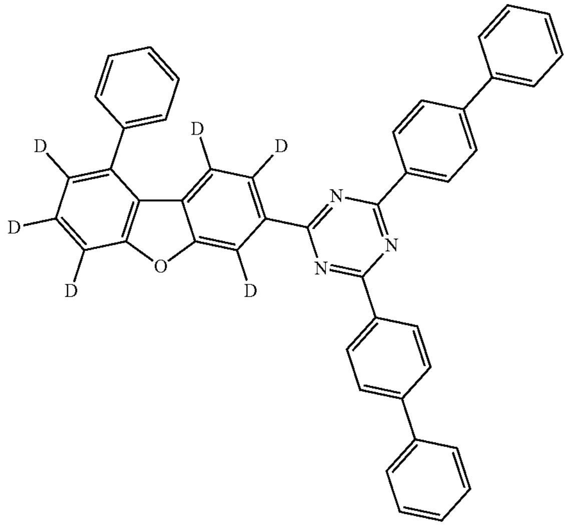
442
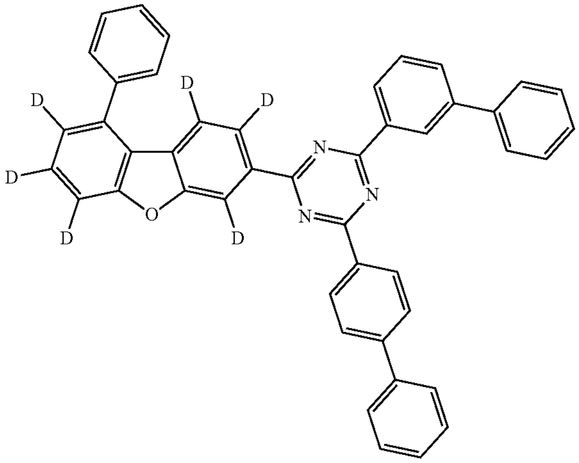
443
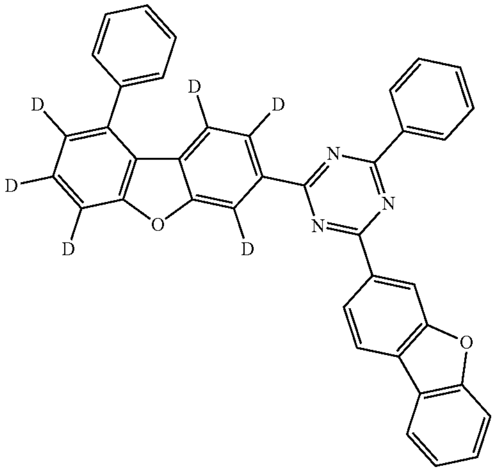
-continued
444
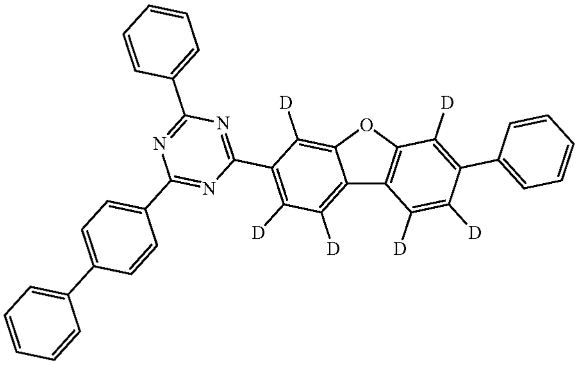
445
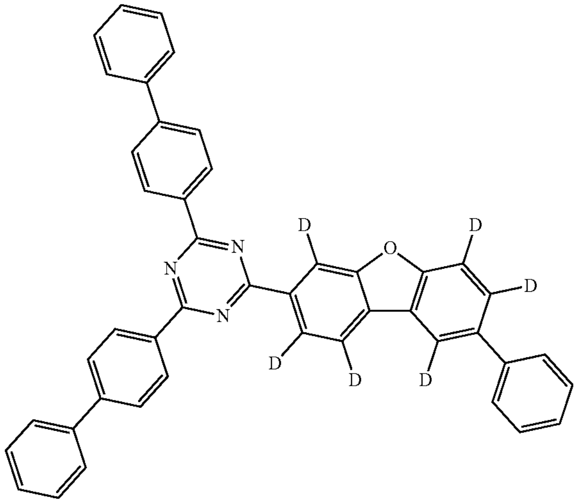
446
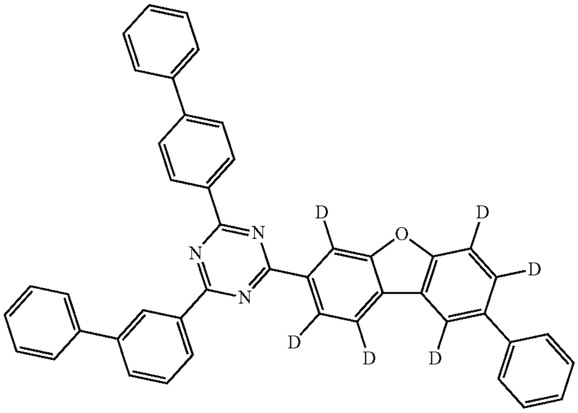

-continued
447
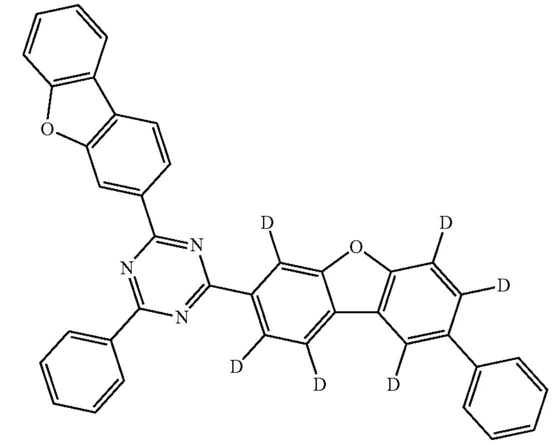
448
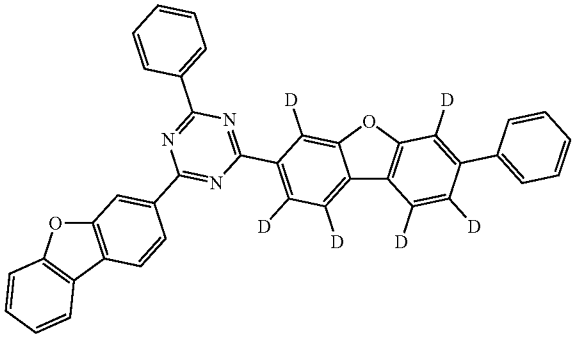
449
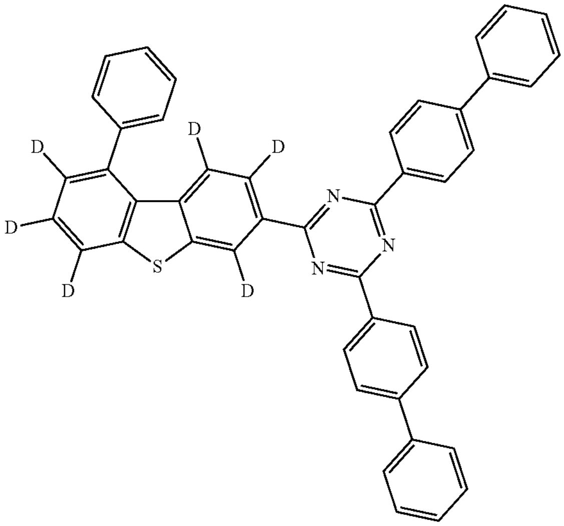
-continued
450
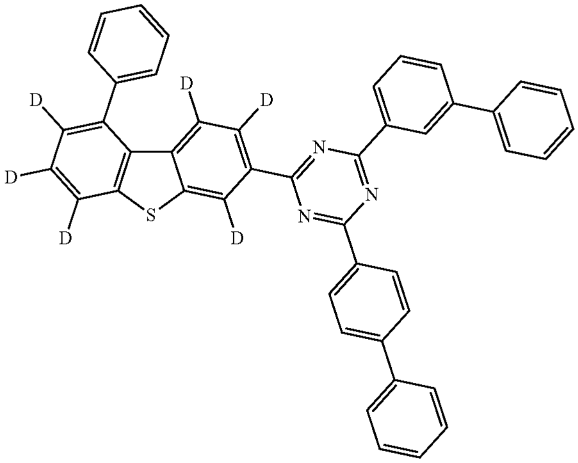
451
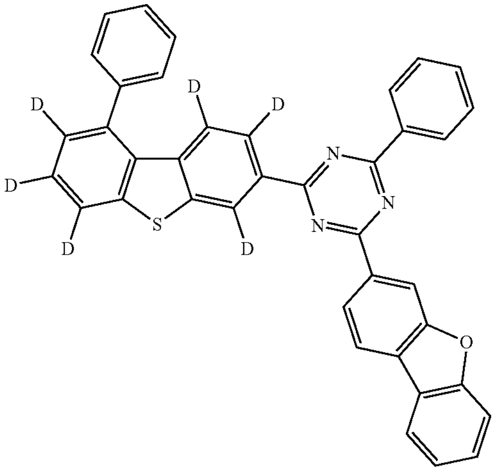
452
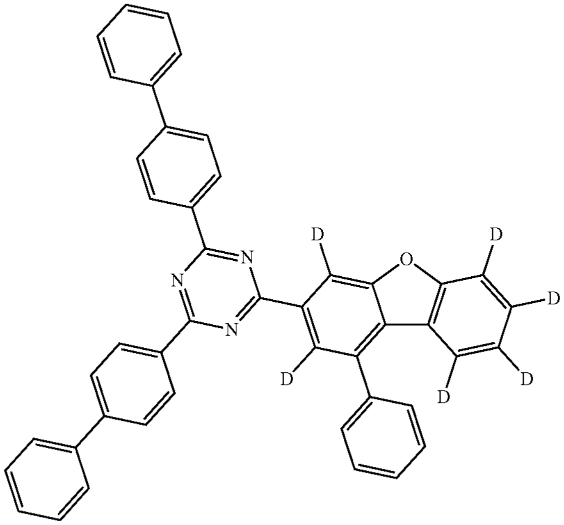

-continued
453
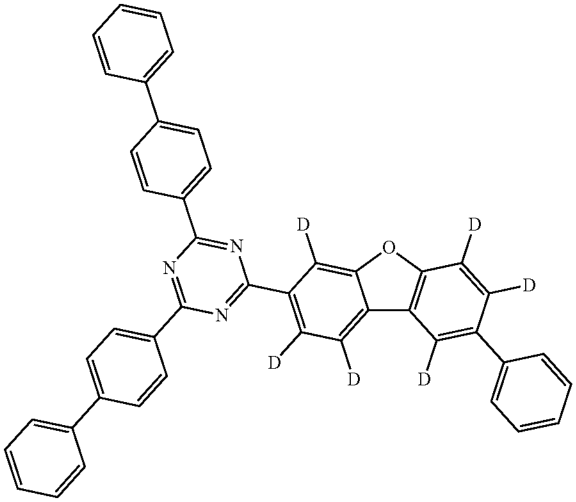
454
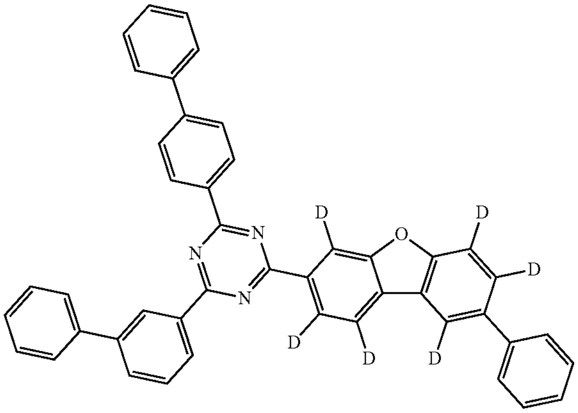
455
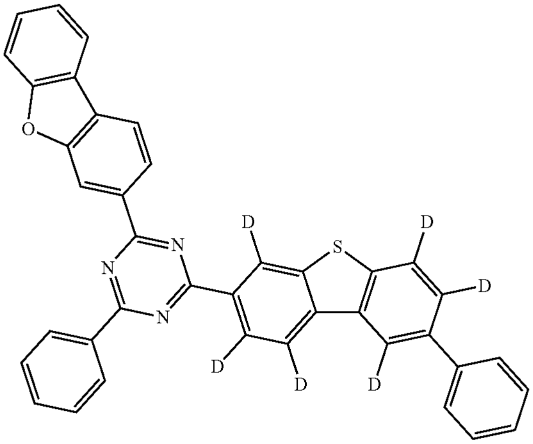
-continued
456
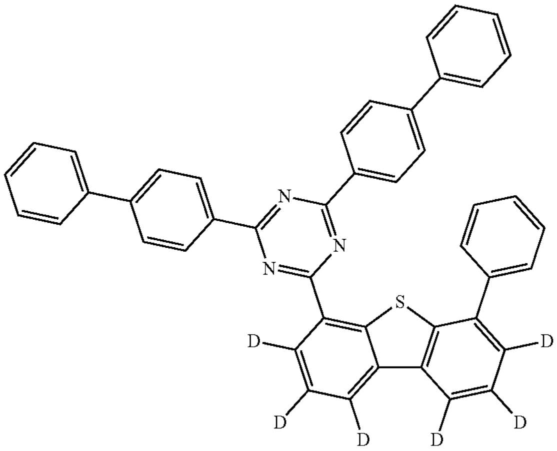
457
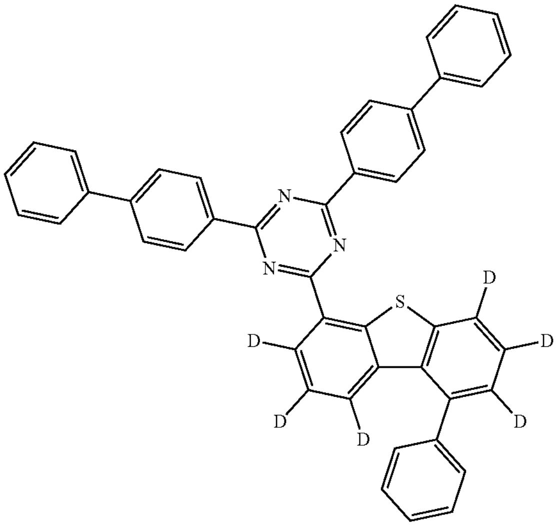
458
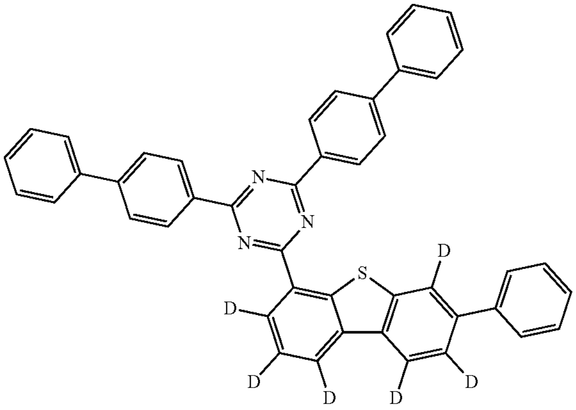

-continued
459
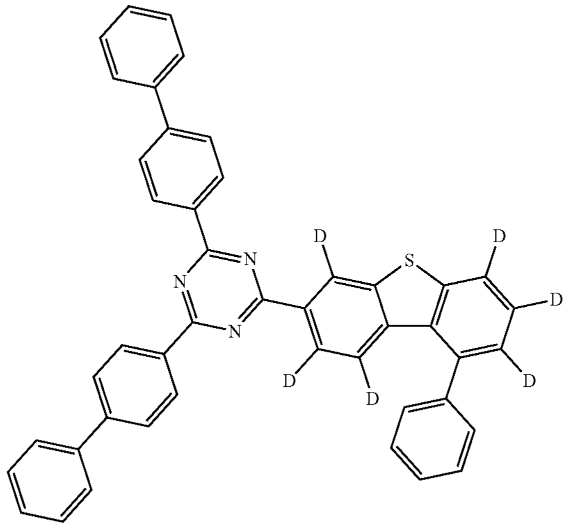
460
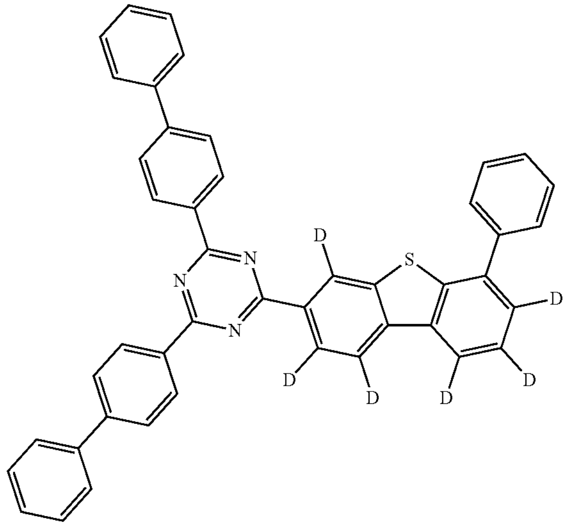
461
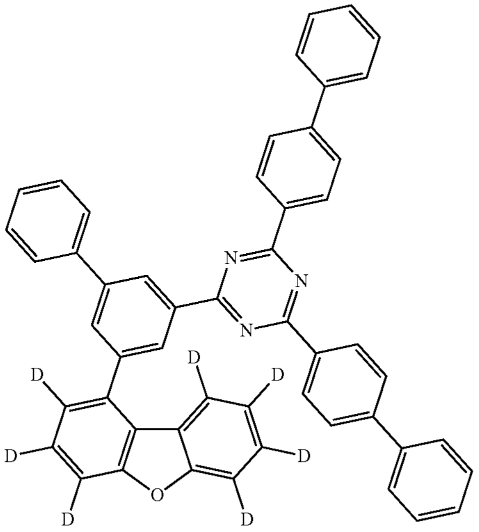
-continued
462
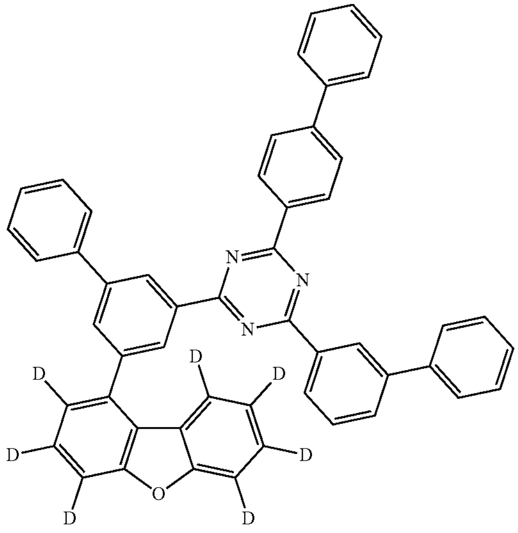
463
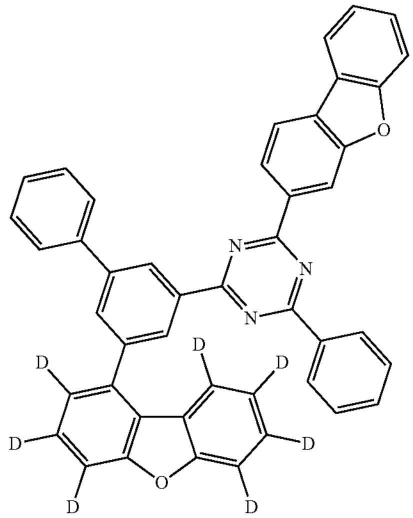
464
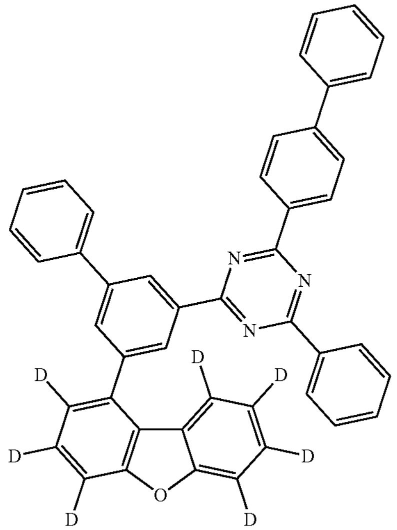

-continued
465
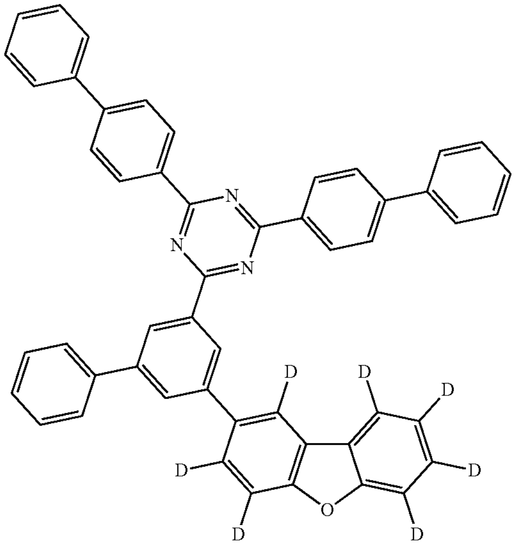
466
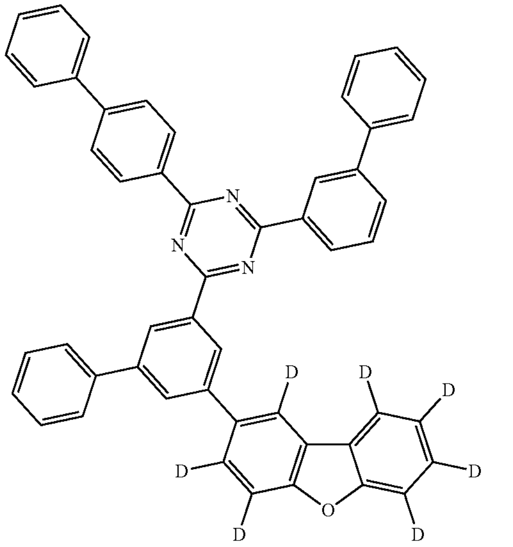
467
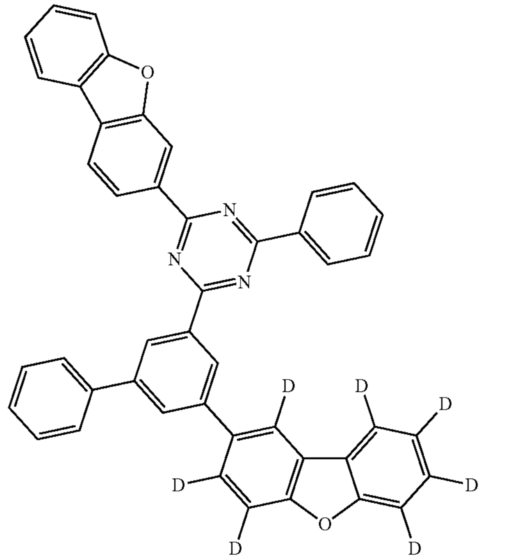
-continued
468
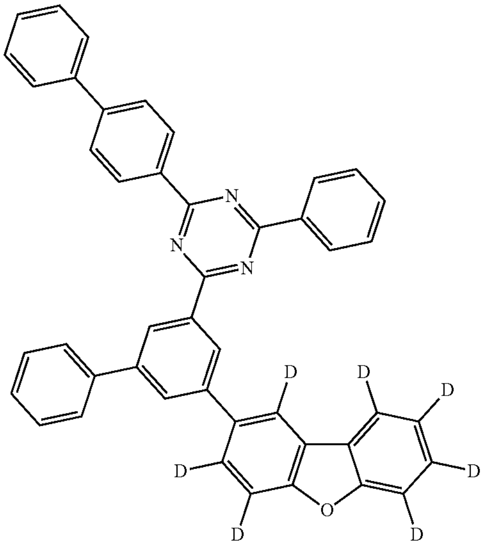
469
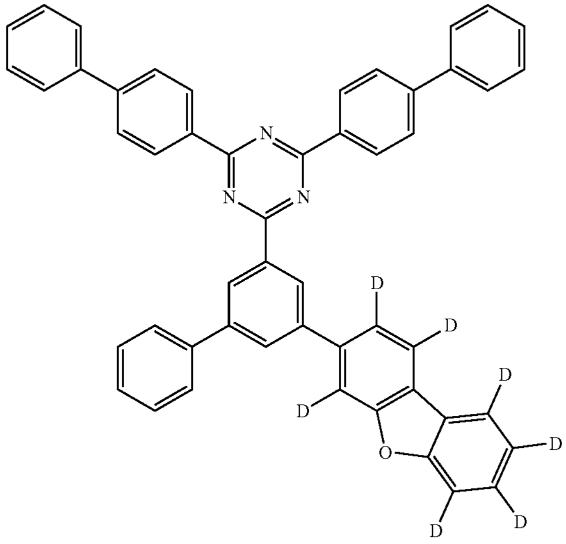

-continued
470
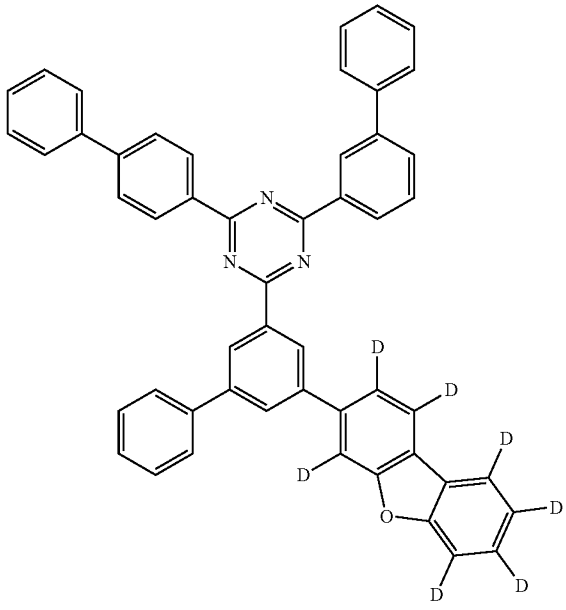
471
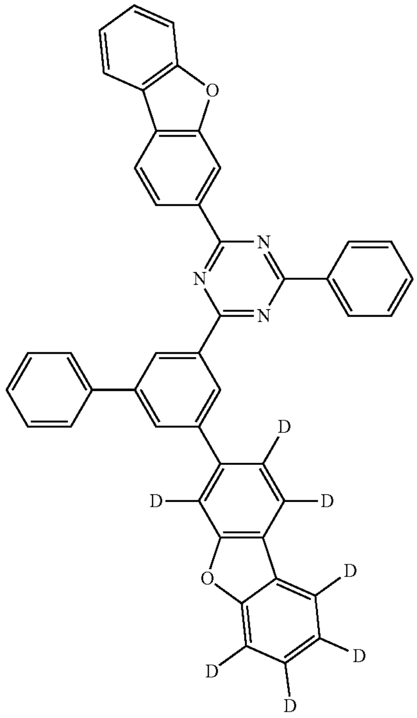
-continued
472
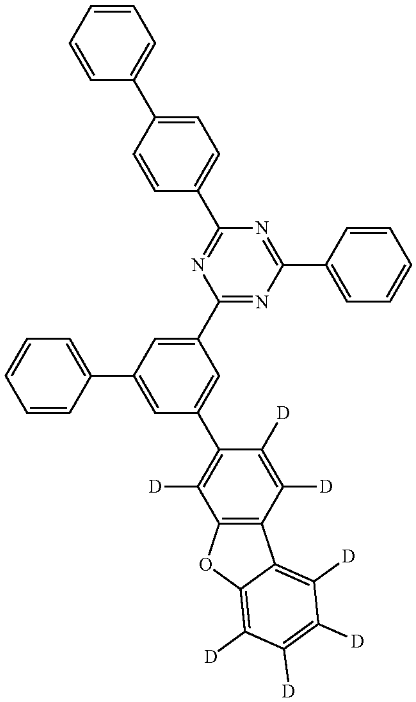
473
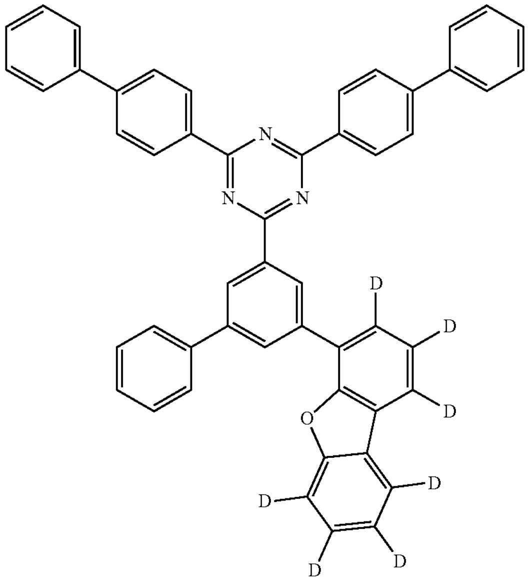

-continued
474
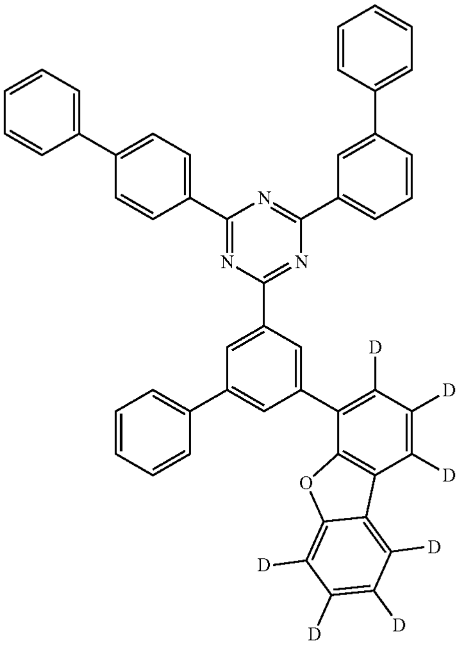
475
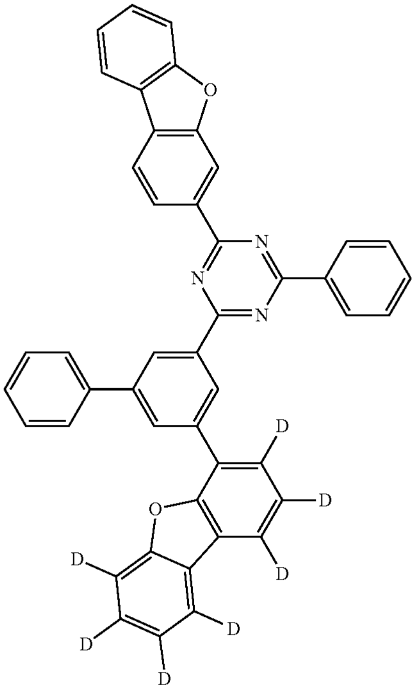
-continued
476
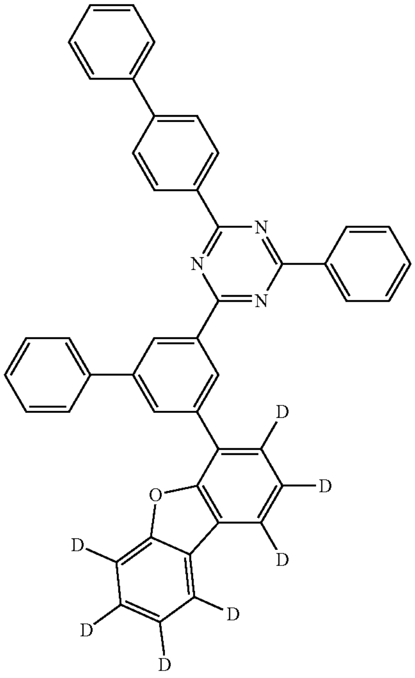
477
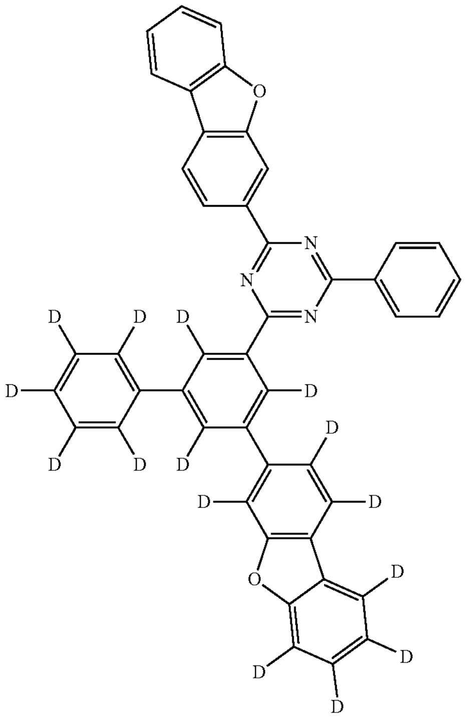

-continued
478
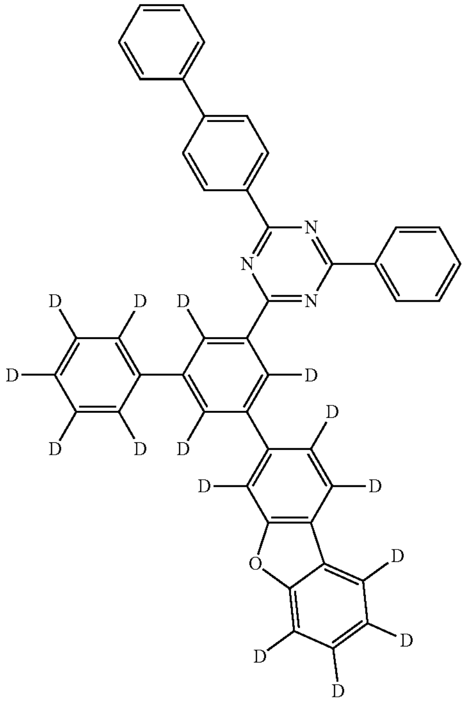
479
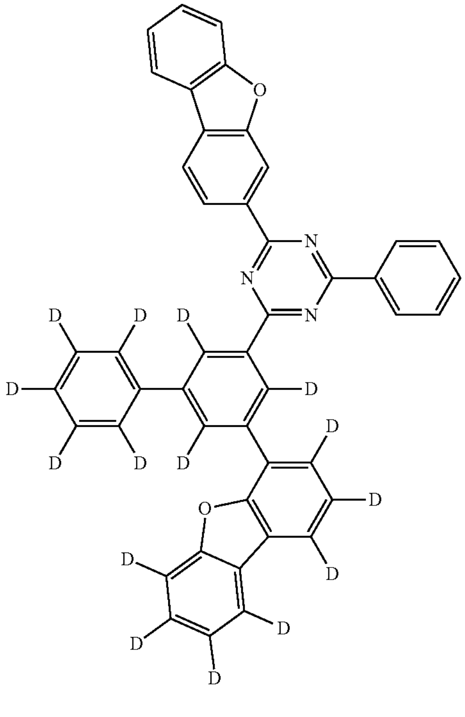
-continued
480
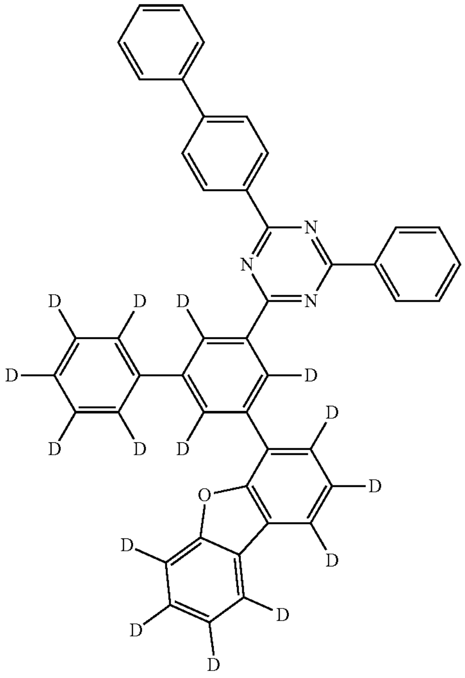
481
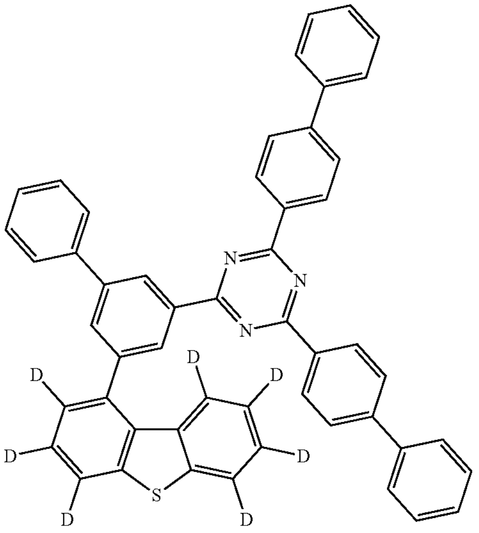

-continued
482
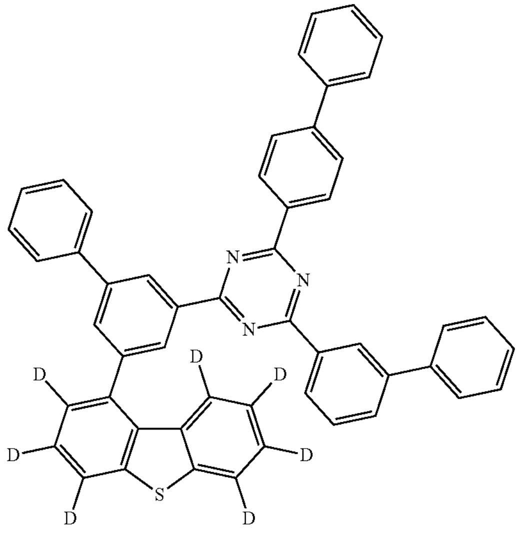
483
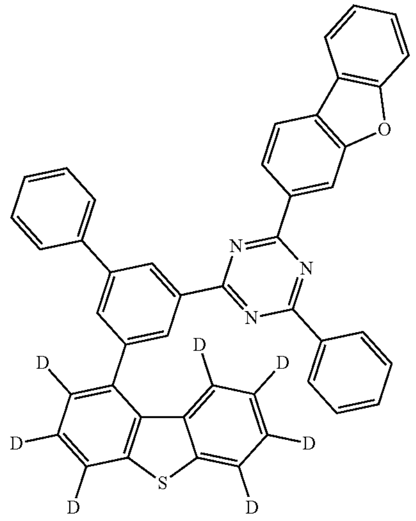
484
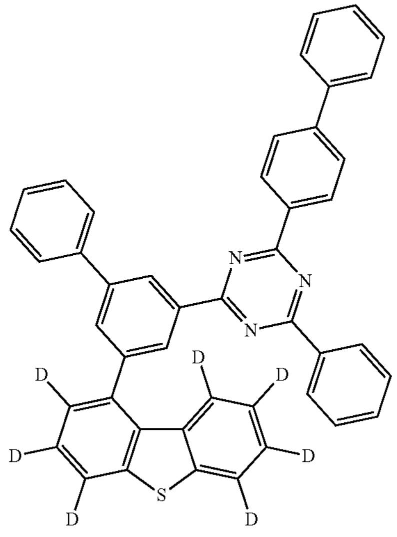
-continued
485
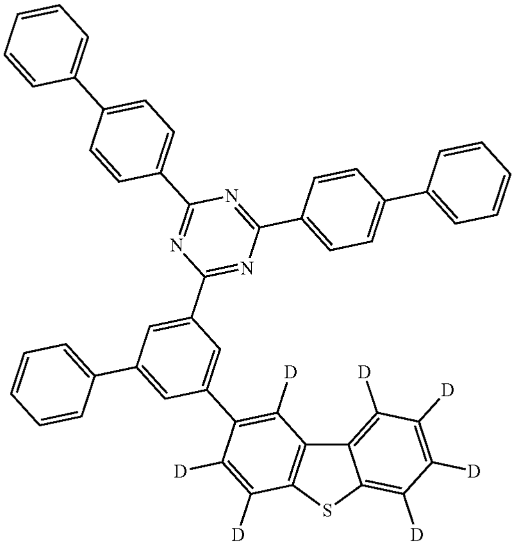
486
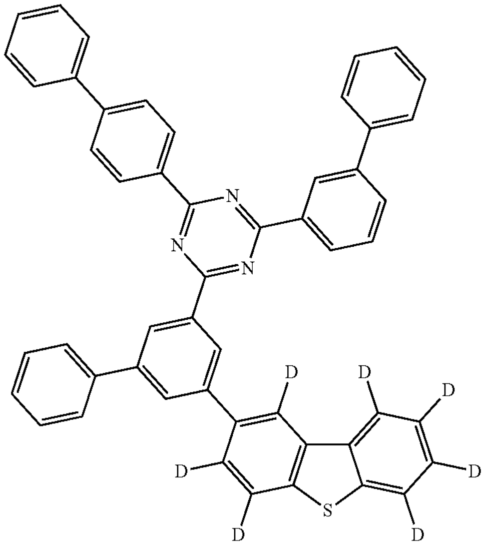
487
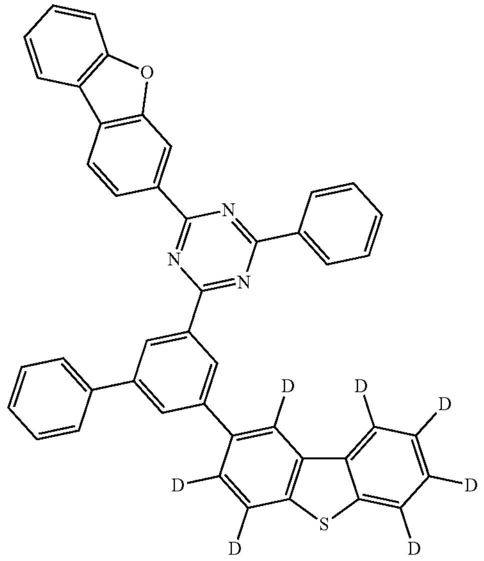

-continued
488
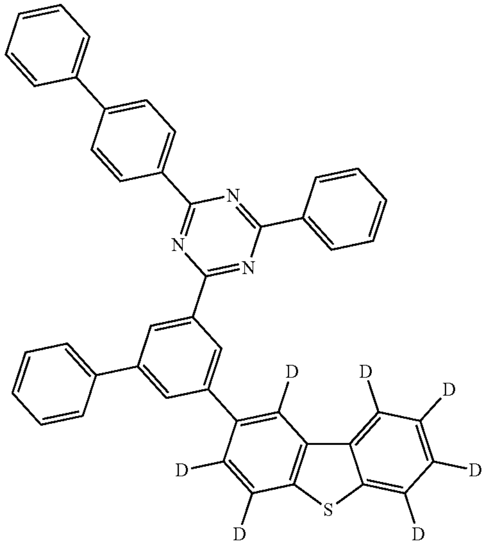
489
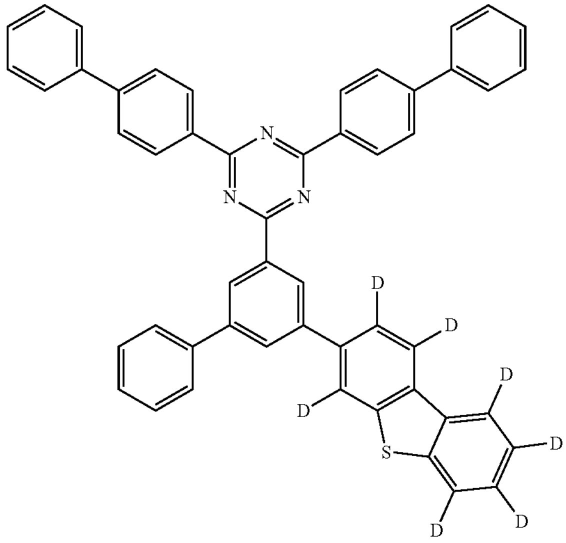
-continued
490
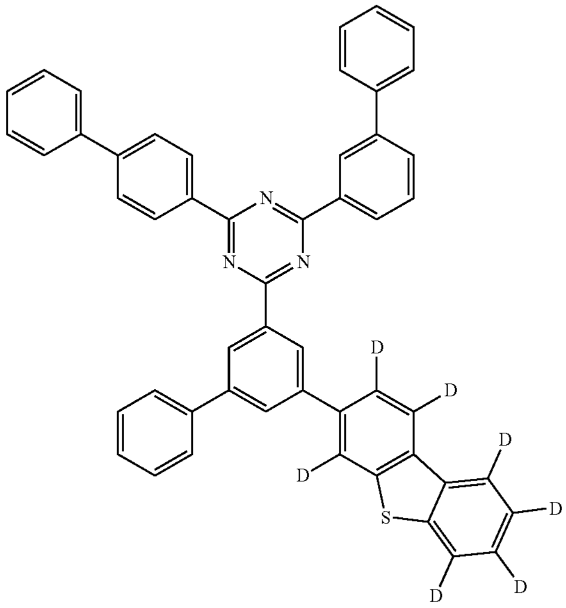
491
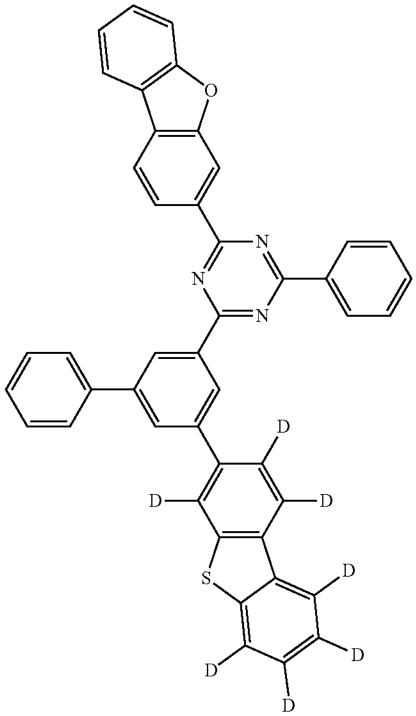

-continued
492
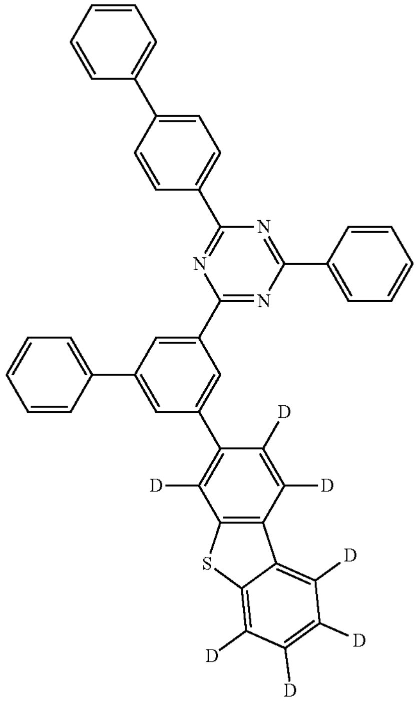
493
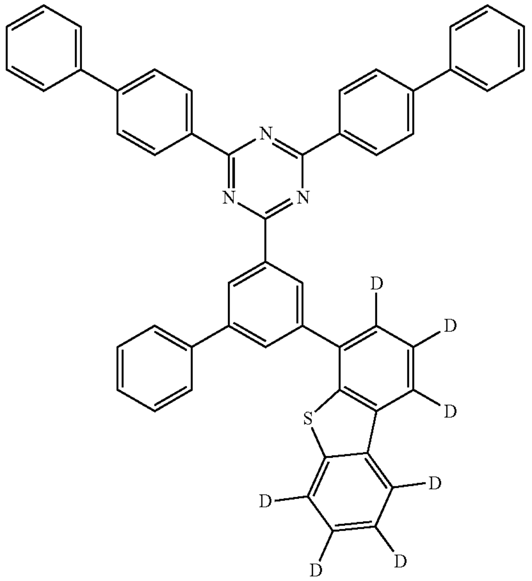
-continued
494
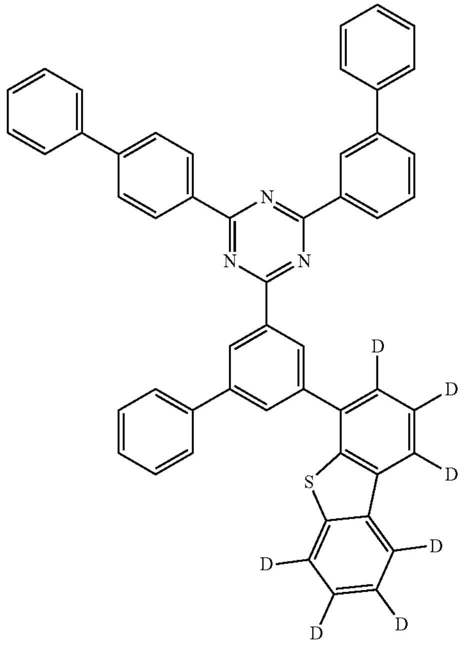
495
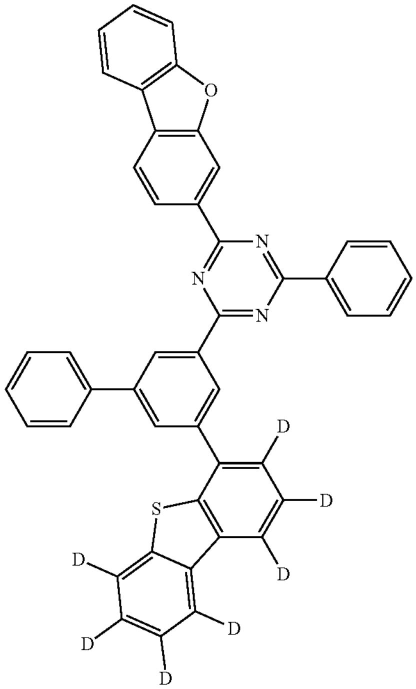

-continued
496
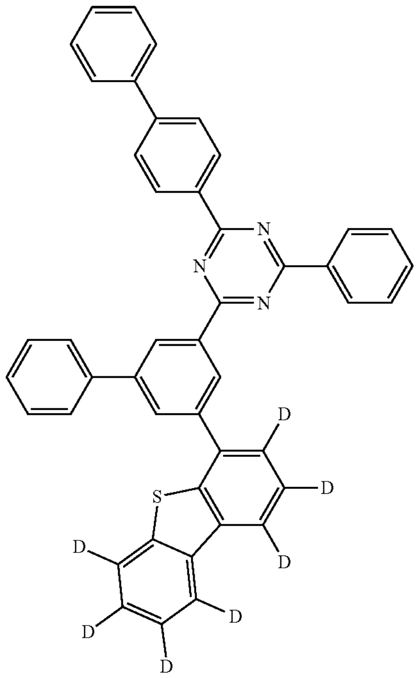
497
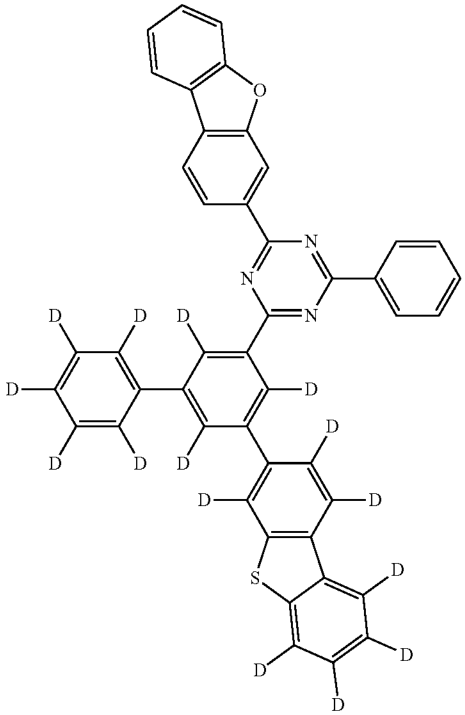
-continued
498
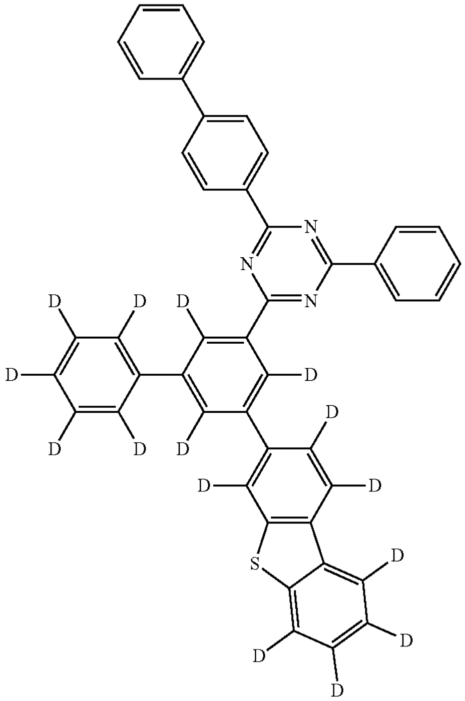
499
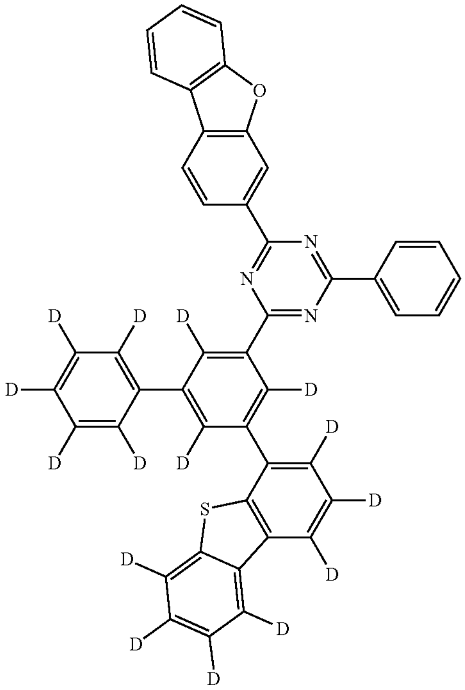

-continued

500

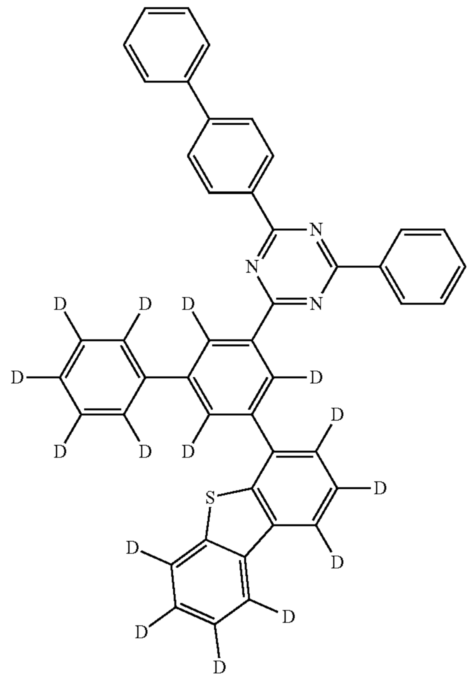

501

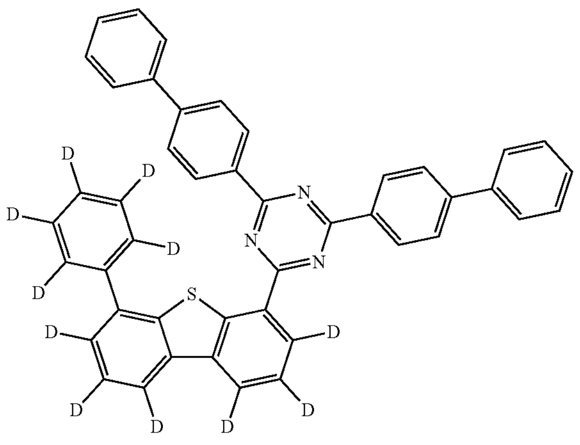

In addition, by introducing various substituents to the structure of Chemical Formula 1, compounds having unique properties of the introduced substituents may be synthesized. For example, by introducing substituents normally used as hole injection layer materials, hole transfer layer materials, light emitting layer materials, electron transfer layer materials and charge generation layer materials used for manufacturing an organic light emitting device to the core structure, materials satisfying conditions required for each organic material layer may be synthesized.

In addition, by introducing various substituents to the structure of Chemical Formula 1, the energy band gap may be finely controlled, and meanwhile, properties at interfaces between organic materials are enhanced, and material applications may become diverse.

Meanwhile, the compound has a high glass transition temperature (Tg), and has excellent thermal stability. Such an increase in the thermal stability becomes an important factor providing driving stability to a device.

In addition, one embodiment of the present application provides an organic light emitting device comprising a first electrode; a second electrode provided opposite to the first electrode; and one or more organic material layers provided between the first electrode and the second electrode, wherein one or more layers of the organic material layers comprise the heterocyclic compound represented by Chemical Formula 1.

In one embodiment of the present application, the first electrode may be an anode, and the second electrode may be a cathode.

In another embodiment, the first electrode may be a cathode, and the second electrode may be an anode.

In one embodiment of the present application, the organic light emitting device may be a blue organic light emitting device, and the heterocyclic compound according to Chemical Formula 1 may be used as a material of the blue organic light emitting device.

In one embodiment of the present application, the organic light emitting device may be a green organic light emitting device, and the heterocyclic compound represented by Chemical Formula 1 may be used as a material of the green organic light emitting device.

In one embodiment of the present application, the organic light emitting device may be a red organic light emitting device, and the heterocyclic compound represented by Chemical Formula 1 may be used as a material of the red organic light emitting device.

In one embodiment of the present application, the organic light emitting device may be a blue organic light emitting device, and the heterocyclic compound according to Chemical Formula 1 may be used as a light emitting layer material of the blue organic light emitting device.

In one embodiment of the present application, the organic light emitting device may be a green organic light emitting device, and the heterocyclic compound represented by Chemical Formula 1 may be used as a light emitting layer material of the green organic light emitting device.

In one embodiment of the present application, the organic light emitting device may be a red organic light emitting device, and the heterocyclic compound represented by Chemical Formula 1 may be used as a light emitting layer material of the red organic light emitting device.

Specific details on the heterocyclic compound represented by Chemical Formula 1 are the same as the descriptions provided above.

The organic light emitting device of the present disclosure may be manufactured using common organic light emitting device manufacturing methods and materials except that one or more organic material layers are formed using the heterocyclic compound described above.

The heterocyclic compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present disclosure may be formed in a single layer structure, or may also be formed in a multilayer structure in which two or more organic material layers are laminated. For example, the organic light emitting device according to one embodiment of the present disclosure may have a structure comprising a hole injection layer, a hole transfer layer, a light emitting layer, an electron transfer layer, an electron injection layer and the like as the organic material layer. However, the structure of the organic light emitting device is not limited thereto, and may comprise a smaller number of organic material layers.

In the organic light emitting device of the present disclosure, the organic material layer comprises a light emitting layer, and the light emitting layer may comprise the heterocyclic compound of Chemical Formula 1.

In the organic light emitting device of the present disclosure, the organic material layer comprises a light emitting layer, and the light emitting layer may comprise the heterocyclic compound of Chemical Formula 1 as a light emitting layer host.

In the organic light emitting device provided in one embodiment of the present application, the organic material layer comprising the heterocyclic compound represented by Chemical Formula 1 further comprises a heterocyclic compound represented by the following Chemical Formula 2.

[Chemical Formula 2]

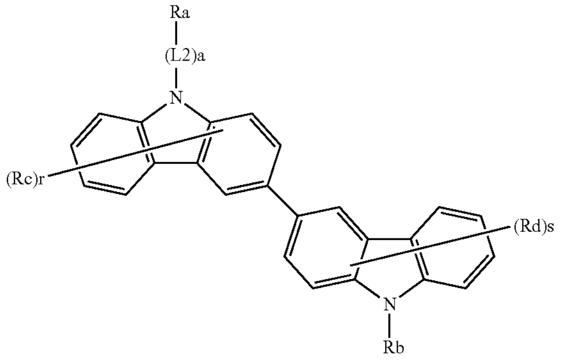

In Chemical Formula 2,

Rc and Rd are the same as or different from each other, and each independently selected from the group consisting of hydrogen; deuterium; halogen; a cyano group; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; —SiRR'R"; —P(=O)RR'; and —NRR', or two or more groups adjacent to each other bond to each other to form a substituted or unsubstituted aromatic hydrocarbon ring or a substituted or unsubstituted heteroring, L2 is a direct bond; a substituted or unsubstituted C6 to C60 arylene group; or a substituted or unsubstituted C2 to C60 heteroarylene group, Ra and Rb are the same as or different from each other, and each independently —CN; —SiRR'R"; a substituted or unsubstituted C6 to C60 aryl group; or a substituted or unsubstituted C2 to C60 heteroaryl group, R, R' and R" are the same as or different from each other, and each independently hydrogen; deuterium; a substituted or unsubstituted C1 to C60 alkyl group; or a substituted or unsubstituted C6 to C60 aryl group, a is an integer of 0 to 4, r and s are an integer of 0 to 7, and when a, s and r are 2 or greater, substituents in the parentheses are the same as or different from each other.

In one embodiment of the present application, L2 may be a direct bond; a substituted or unsubstituted C6 to C60 arylene group; or a substituted or unsubstituted C2 to C60 heteroarylene group.

In another embodiment, L2 may be a direct bond; a substituted or unsubstituted C6 to C40 arylene group; or a substituted or unsubstituted C2 to C40 heteroarylene group.

In another embodiment, L2 may be a direct bond; a C6 to C40 arylene group; or a C2 to C40 heteroarylene group.

In another embodiment, L2 may be a direct bond; a substituted or unsubstituted phenylene group; a substituted or unsubstituted biphenylene group; or a substituted or unsubstituted divalent dibenzofuran group.

In another embodiment, L2 may be a direct bond; a phenylene group; a biphenylene group; or a divalent dibenzofuran group.

In one embodiment of the present application, L2 may be substituted with deuterium.

In one embodiment of the present application, Ra and Rb are the same as or different from each other, and may be each independently —CN; SiRR'R"; a substituted or unsubstituted C6 to C60 aryl group; or a substituted or unsubstituted C2 to C60 heteroaryl group.

In another embodiment, Ra may be —CN; SiRR'R"; a substituted or unsubstituted C6 to C60 aryl group; or a substituted or unsubstituted C2 to C60 heteroaryl group.

In another embodiment, Ra may be —CN; SiRR'R"; a C6 to C40 aryl group unsubstituted or substituted with a C1 to C40 alkyl group or a C6 to C40 aryl group; or a C2 to C60 heteroaryl group unsubstituted or substituted with a C6 to C40 aryl group.

In another embodiment, Ra may be —CN; SiRR'R"; a phenyl group; a biphenyl group; a terphenyl group; a dimethylfluorenyl group; a diphenylfluorenyl group; a spirobifluorenyl group; or a dibenzofuran group unsubstituted or substituted with a phenyl group.

In another embodiment, Rb may be a substituted or unsubstituted C6 to C60 aryl group; or a substituted or unsubstituted C2 to C60 heteroaryl group.

In another embodiment, Rb may be a C6 to C60 aryl group unsubstituted or substituted with a C1 to C40 alkyl group, —CN, SiRR'R" or a C6 to C40 aryl group.

In another embodiment, Rb may be a C6 to C40 aryl group unsubstituted or substituted with a C1 to C40 alkyl group, —CN, SiRR'R" or a C6 to C40 aryl group.

In another embodiment, Rb may be a phenyl group unsubstituted or substituted with —CN or SiRR'R"; a biphenyl group unsubstituted or substituted with a phenyl group; a terphenyl group; or a dimethylfluorenyl group.

In one embodiment of the present application, Ra and Rb may be substituted with deuterium.

In one embodiment of the present application, -(L2)a-Ra and Rb of Chemical Formula 2 may be different from each other.

In one embodiment of the present application, -(L2)a-Ra and Rb of Chemical Formula 2 may be the same as each other.

In another embodiment, R, R' and R" may be a phenyl group.

In one embodiment of the present application, Chemical Formula 2 may have a deuterium content of greater than or equal to 0% and less than or equal to 100%.

In another embodiment, Chemical Formula 2 may have a deuterium content of greater than or equal to 10% and less than or equal to 100%.

In another embodiment, Chemical Formula 2 may have a deuterium content of 0%, 100%, or 10% to 80%.

In one embodiment of the present application, Rc and Rd are the same as or different from each other, and each independently selected from the group consisting of hydrogen; deuterium; halogen; a cyano group; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; —SiRR'R"; —P(═O)RR'; and —NRR', or two or more groups adjacent to each other may bond to each other to form a substituted or unsubstituted aromatic hydrocarbon ring or a substituted or unsubstituted heteroring.

In another embodiment, Rc and Rd are the same as or different from each other, and may be each independently selected from the group consisting of hydrogen; deuterium; a substituted or unsubstituted C1 to C60 alkyl group; a substituted or unsubstituted C6 to C60 aryl group; a substituted or unsubstituted C2 to C60 heteroaryl group; SiRR'R"; —P(═O)RR'; and —NRR'.

In another embodiment, Rc and Rd are the same as or different from each other, and may be each independently selected from the group consisting of hydrogen; deuterium; a substituted or unsubstituted C1 to C40 alkyl group; a substituted or unsubstituted C6 to C40 aryl group; a substituted or unsubstituted C2 to C40 heteroaryl group; SiRR'R"; —P(═O)RR'; and —NRR'.

In another embodiment, Rc and Rd are the same as or different from each other, and may be each independently selected from the group consisting of hydrogen; deuterium; a C1 to C40 alkyl group; a C6 to C40 aryl group; a C2 to C40 heteroaryl group; —SiRR'R"; —P(═O)RR'; and —NRR'.

In another embodiment, Rc and Rd are the same as or different from each other, and may be each independently selected from the group consisting of hydrogen; deuterium; a C1 to C20 alkyl group; a C6 to C20 aryl group; a C2 to C20 heteroaryl group; —SiRR'R"; —P(═O)RR'; and —NRR'.

In another embodiment, Rc and Rd are the same as or different from each other, and may be each independently hydrogen; or deuterium.

In one embodiment of the present application, r is 7, and Rc may be hydrogen.

In one embodiment of the present application, r is 7, and Rc may be deuterium.

In one embodiment of the present application, r is 7, and Rc may be hydrogen; or deuterium.

In one embodiment of the present application, s is 7, and Rd may be hydrogen.

In one embodiment of the present application, s is 7, and Rd may be deuterium.

In one embodiment of the present application, s is 7, and Rd may be hydrogen; or deuterium.

Effects of more superior efficiency and lifetime are obtained when comprising the compound of Chemical Formula 1 and the compound of Chemical Formula 2 at the same time in the organic material layer of the organic light emitting device. Such results may lead to a forecast that an exciplex phenomenon occurs when comprising the two compounds at the same time.

The exciplex phenomenon is a phenomenon of releasing energy having sizes of a donor (p-host) HOMO level and an acceptor (n-host) LUMO level due to electron exchanges between two molecules. When a donor (p-host) having a favorable hole transfer ability and an acceptor (n-host) having a favorable electron transfer ability are used as a host of a light emitting layer, holes are injected to the p-host and electrons are injected to the n-host, and therefore, a driving voltage may be lowered, which resultantly helps with enhancement in the lifetime.

In one embodiment of the present application, the heterocyclic compound of Chemical Formula 2 may be represented by any one of the following compounds.

2-1

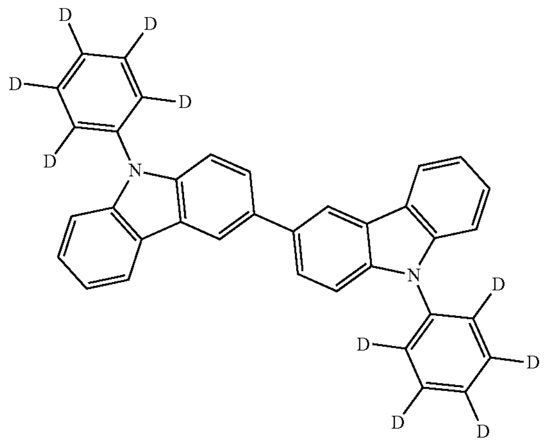

2-2

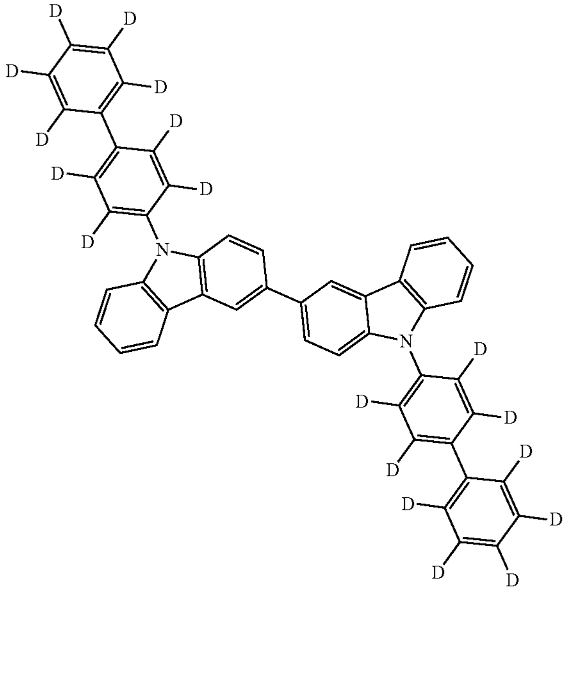

-continued
2-3
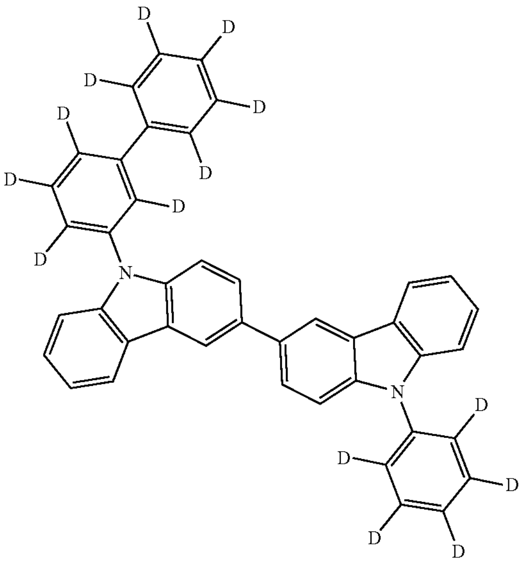
2-4
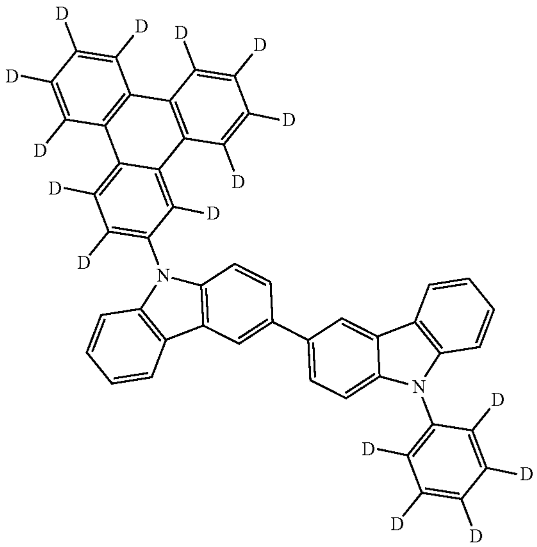
2-5
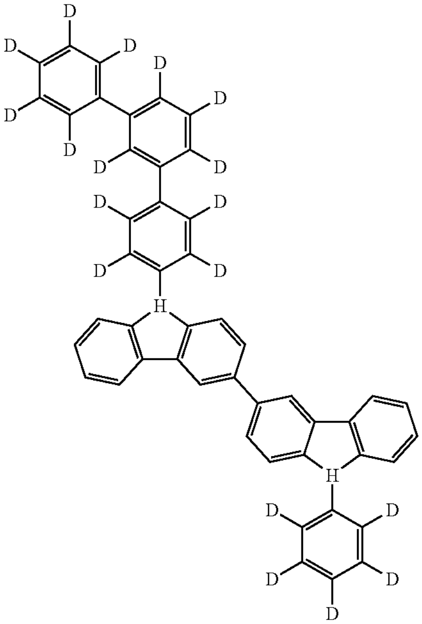
2-6
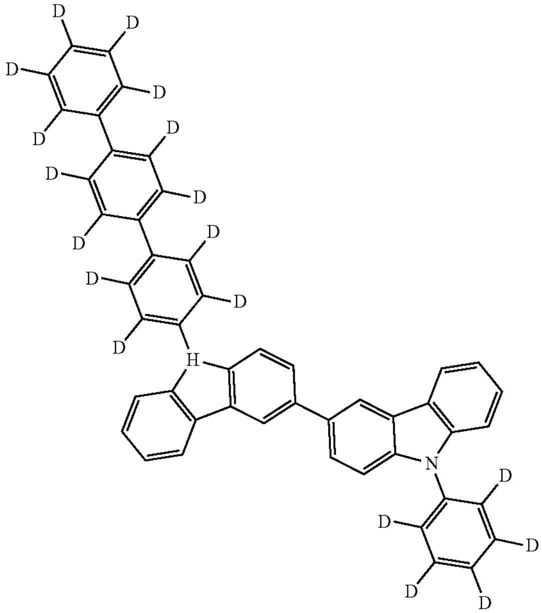

-continued
2-7
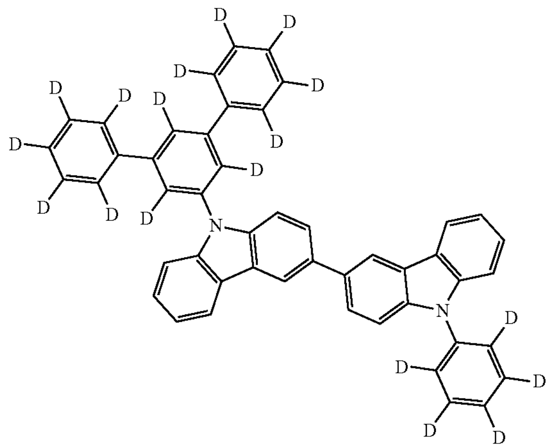
2-8
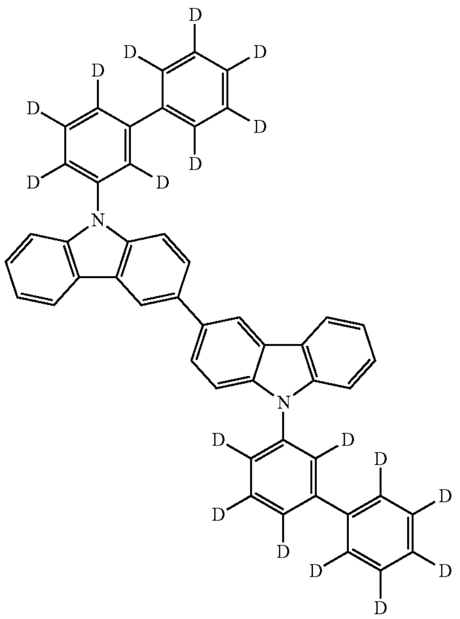
2-9
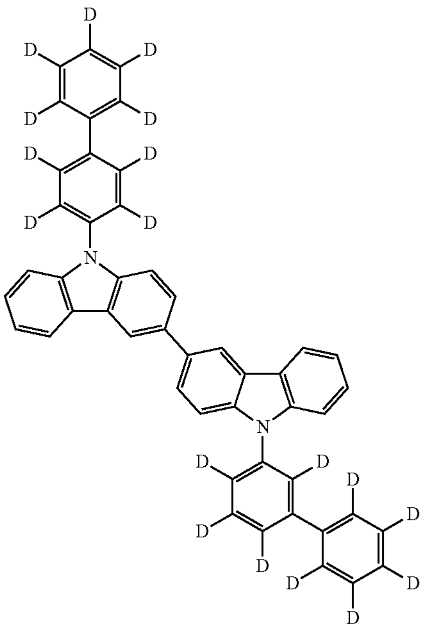
2-10
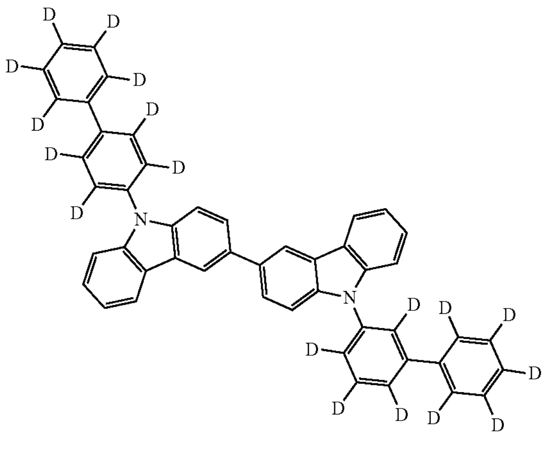

-continued
2-11
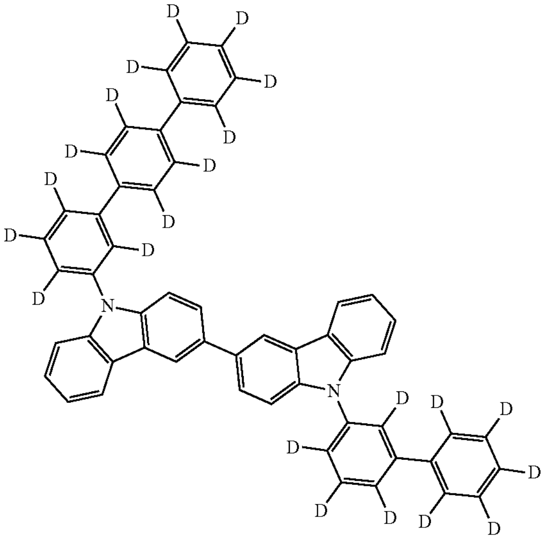
2-12
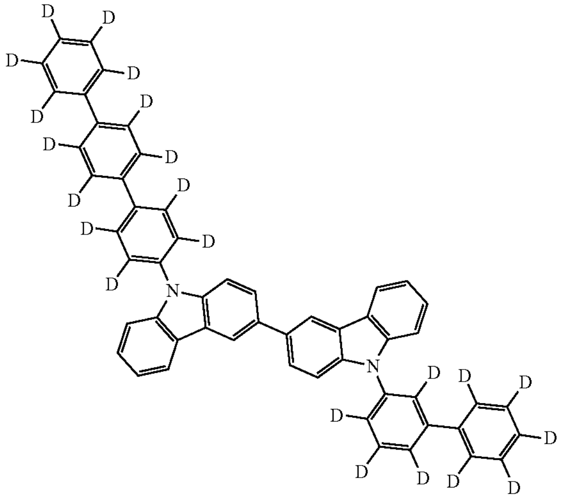
2-13
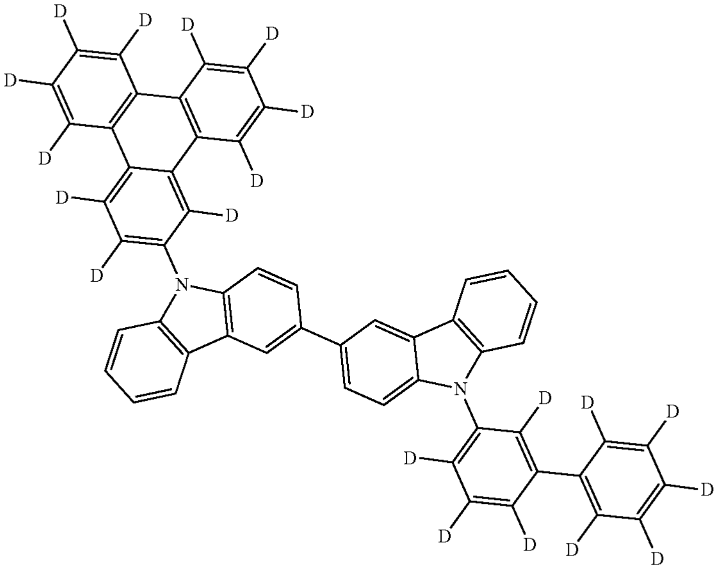

-continued
2-14
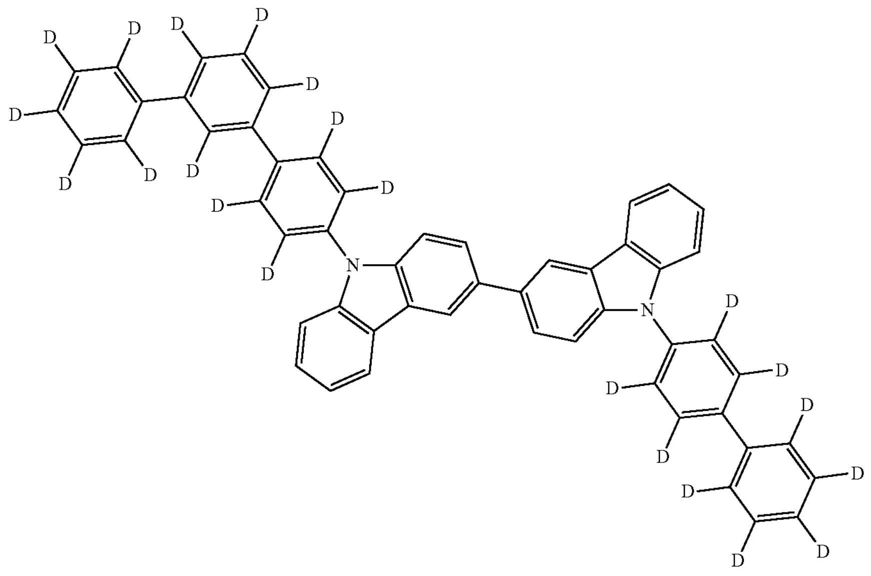
2-15
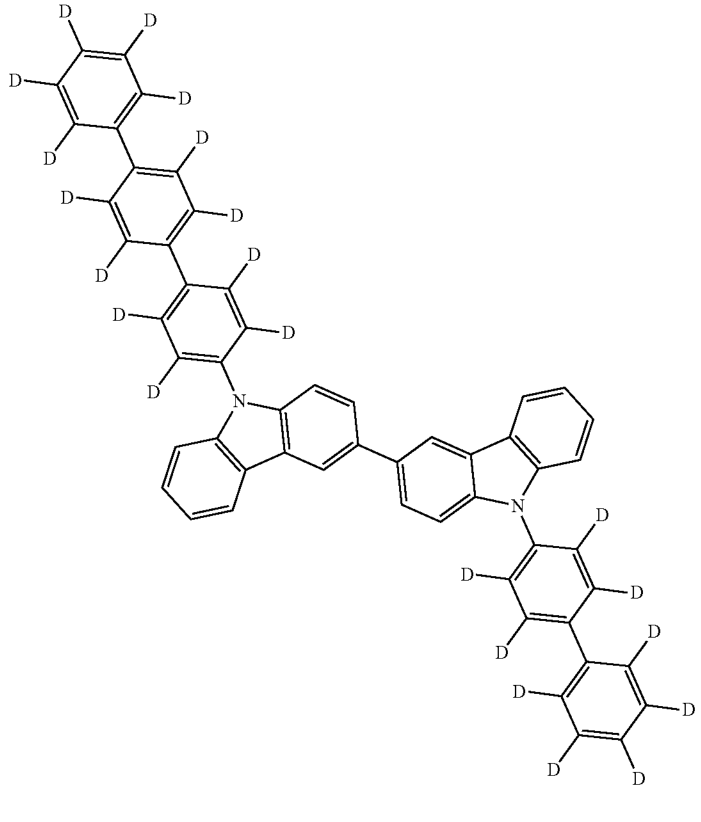

-continued
2-16
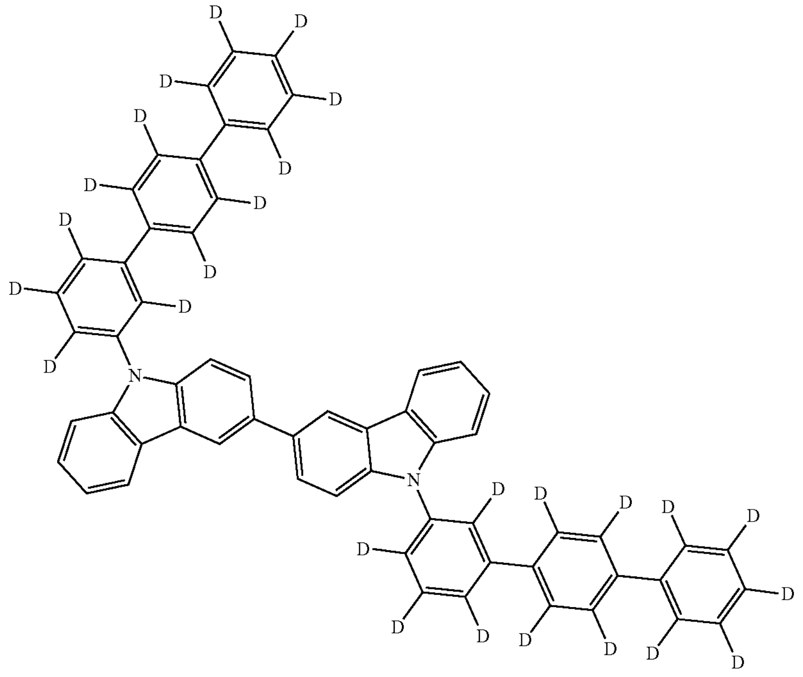
2-17
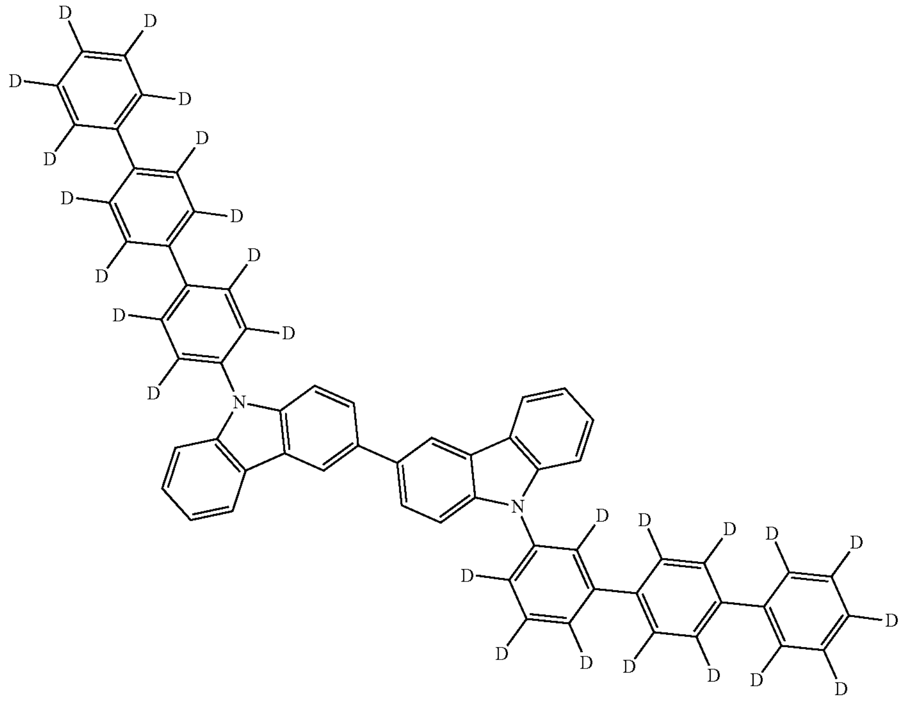

-continued
2-18
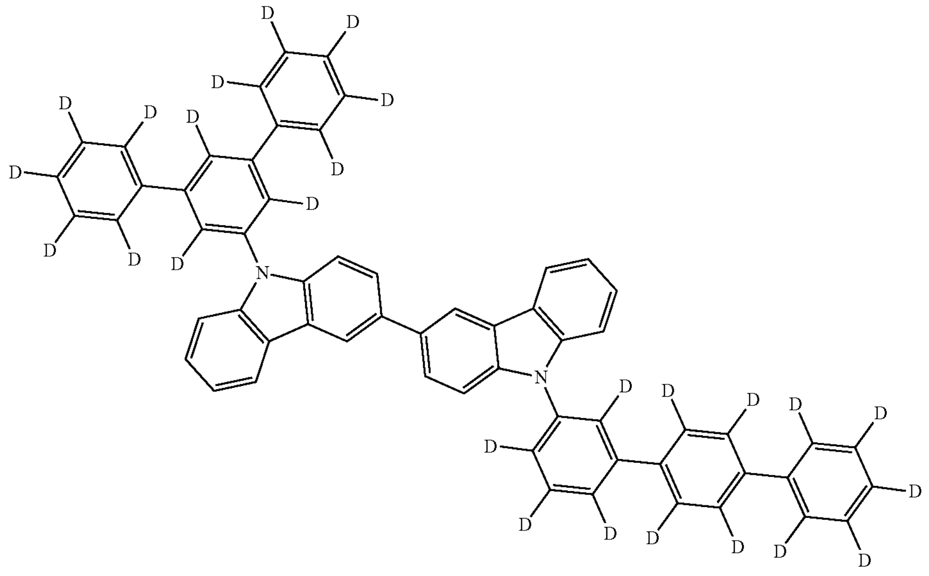
2-19
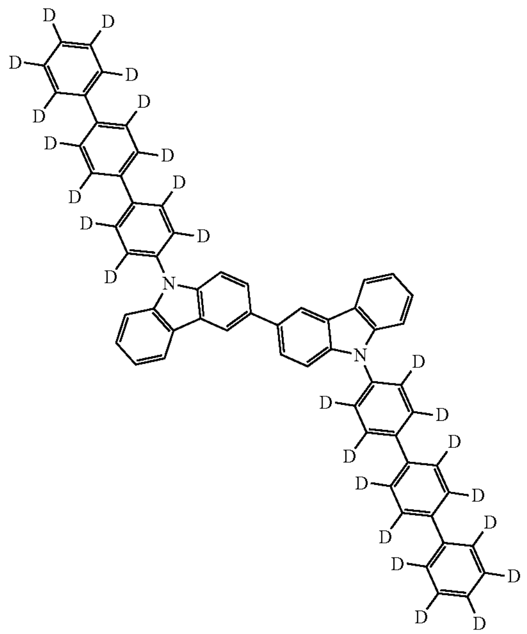
2-20
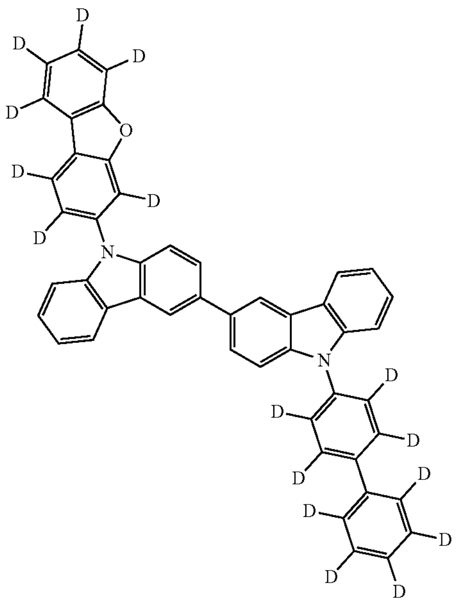

-continued
2-21
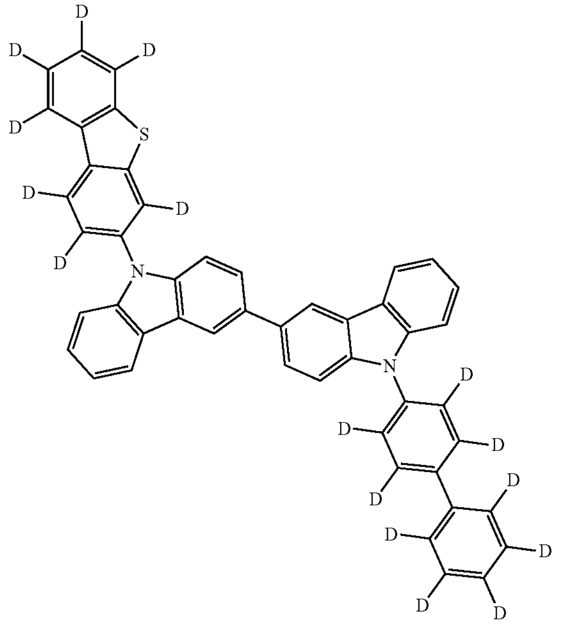
2-22
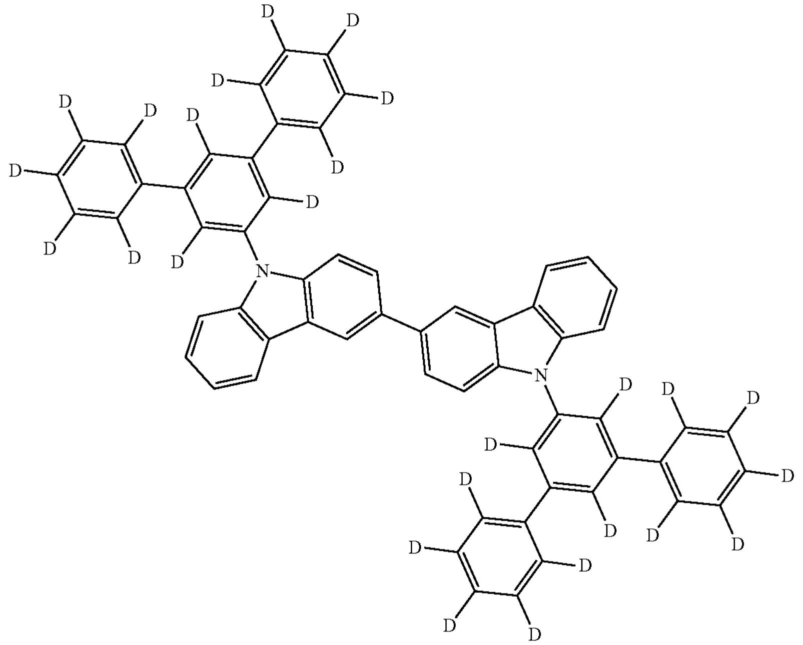

-continued
2-23
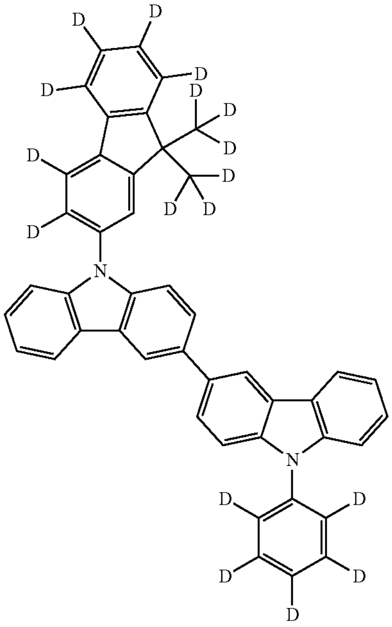
2-24
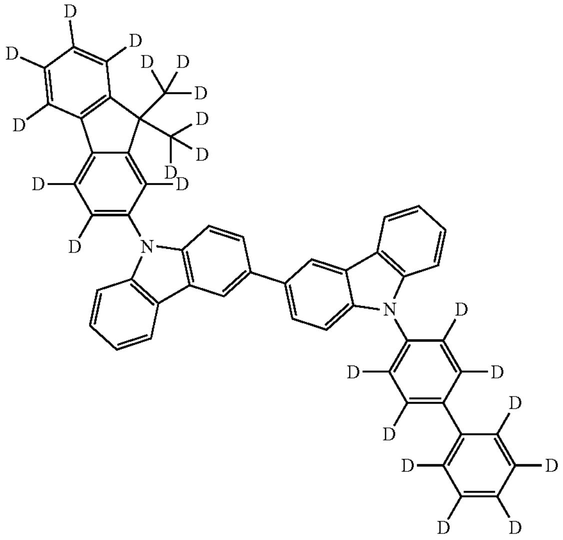
2-25
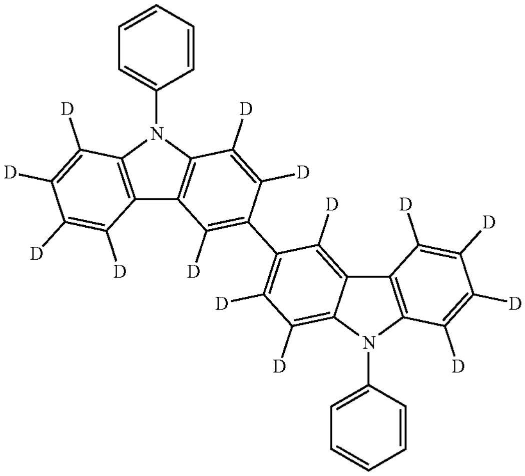
2-26
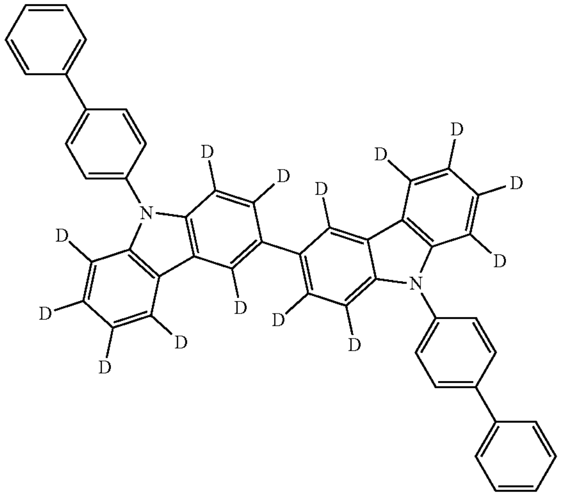

-continued
2-27
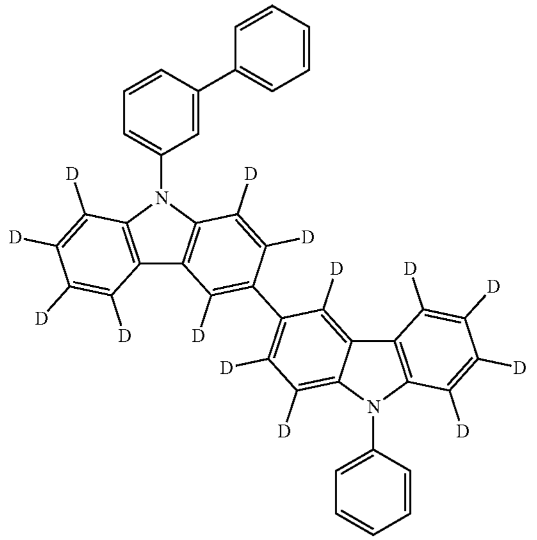
2-28
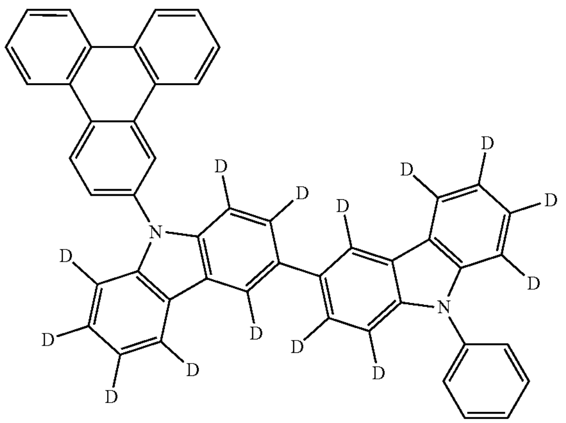
2-29
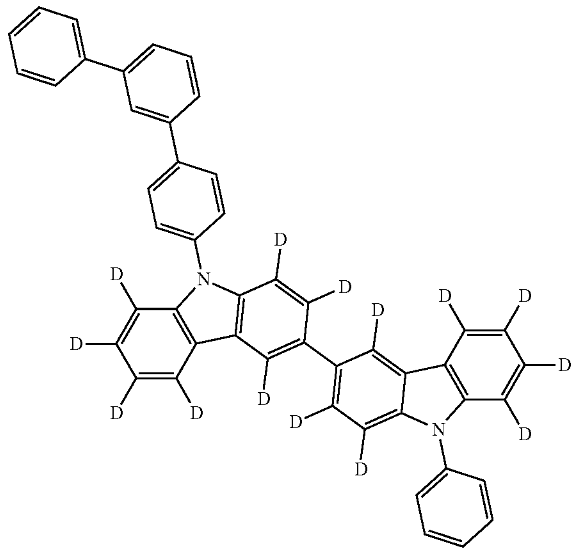
2-30
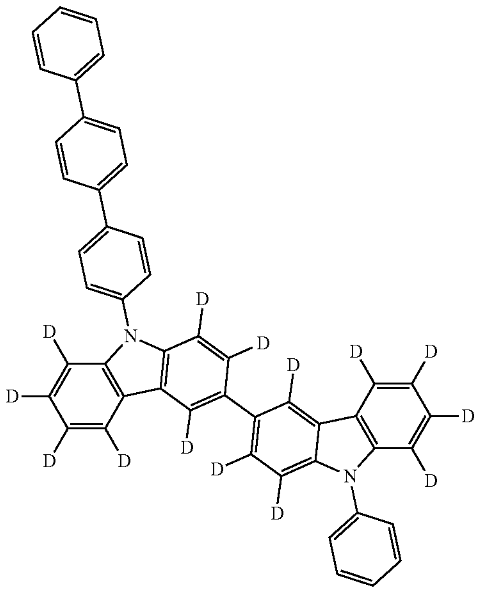

-continued
2-31
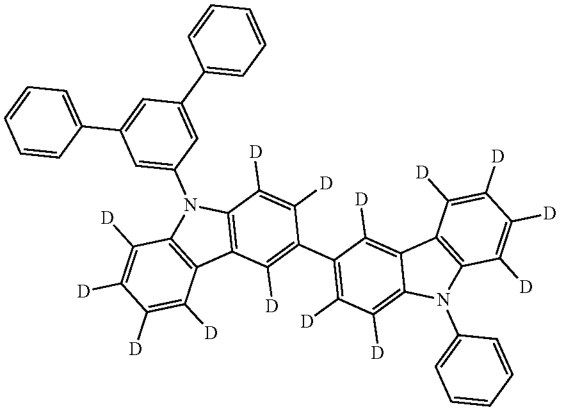
2-32
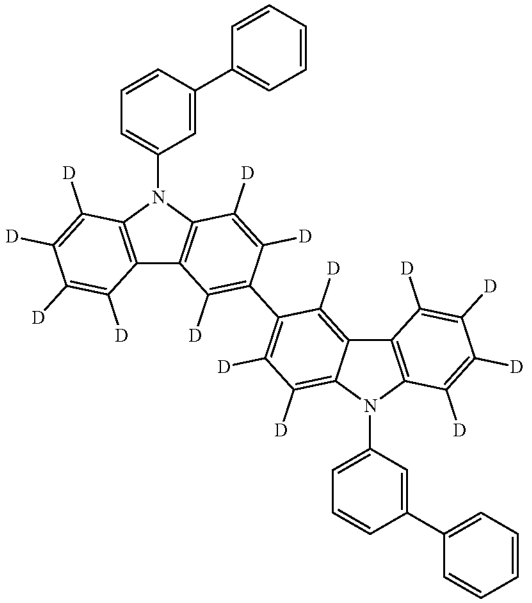
2-33
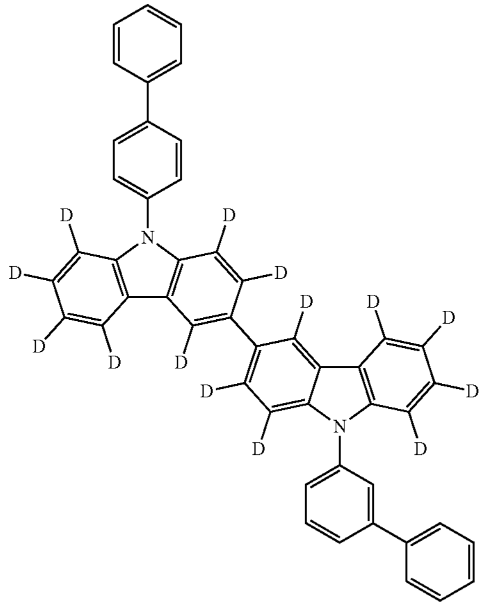
2-34
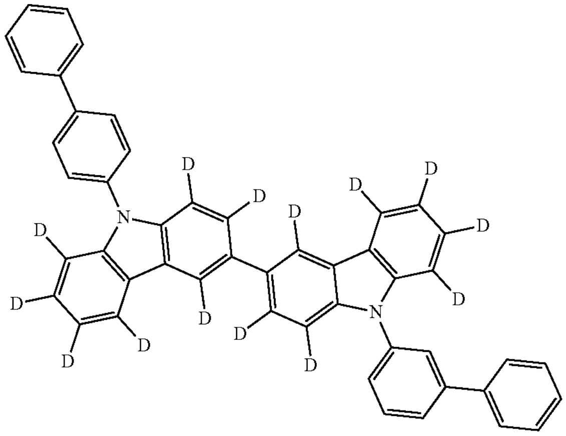

-continued
2-35
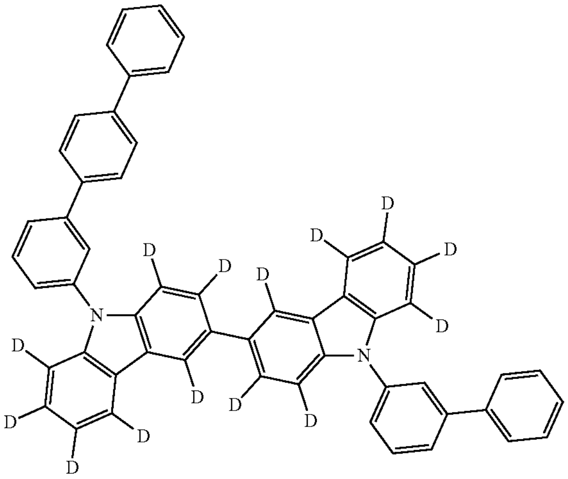
2-36
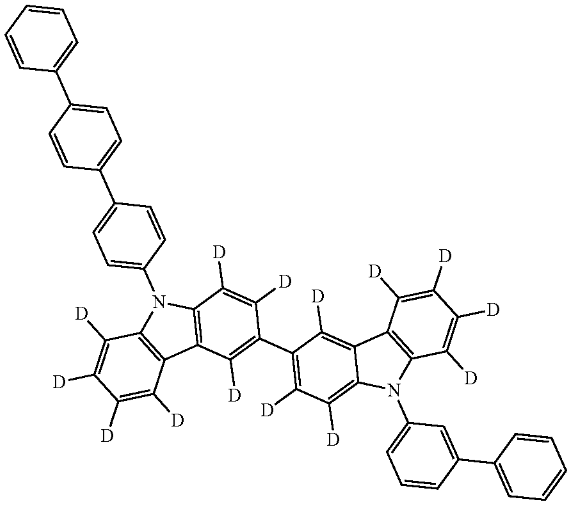
2-37
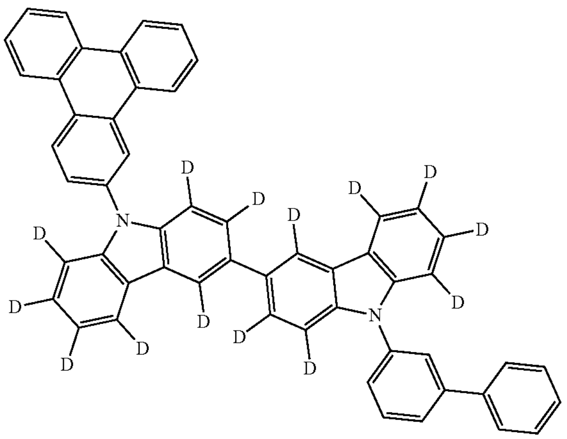
2-38
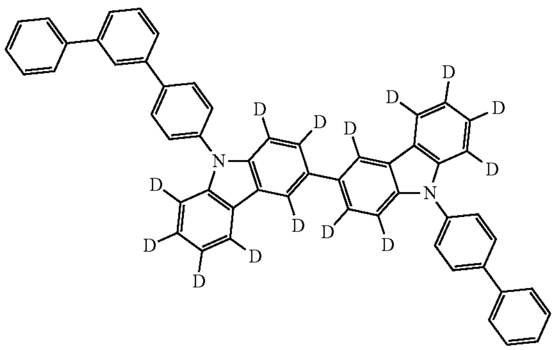
2-39
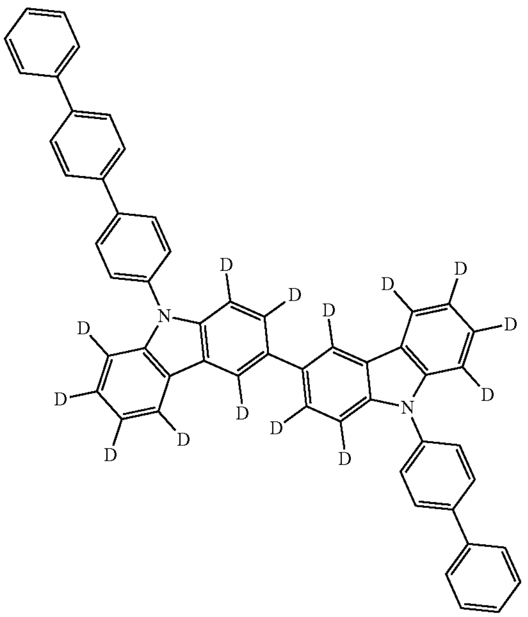
2-40
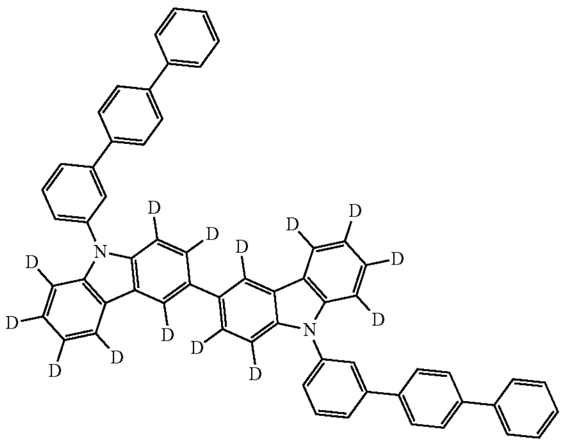

-continued
2-41
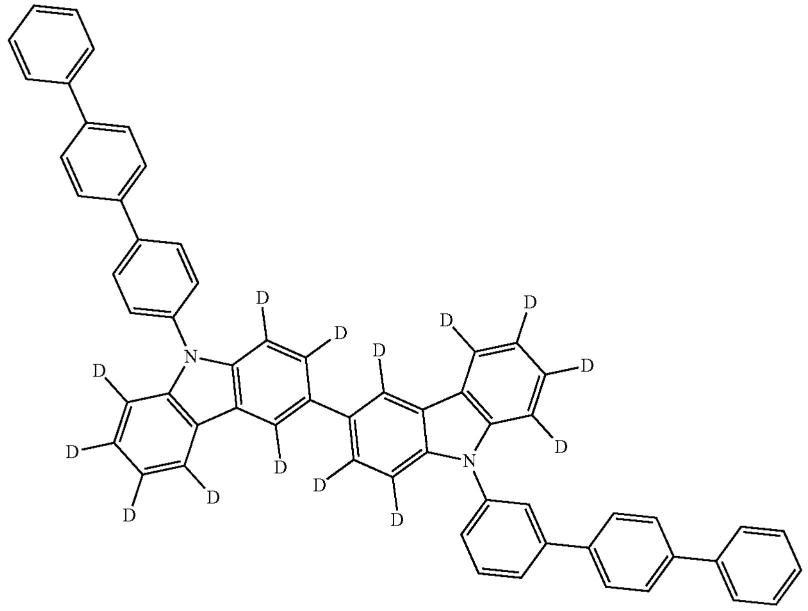
2-42
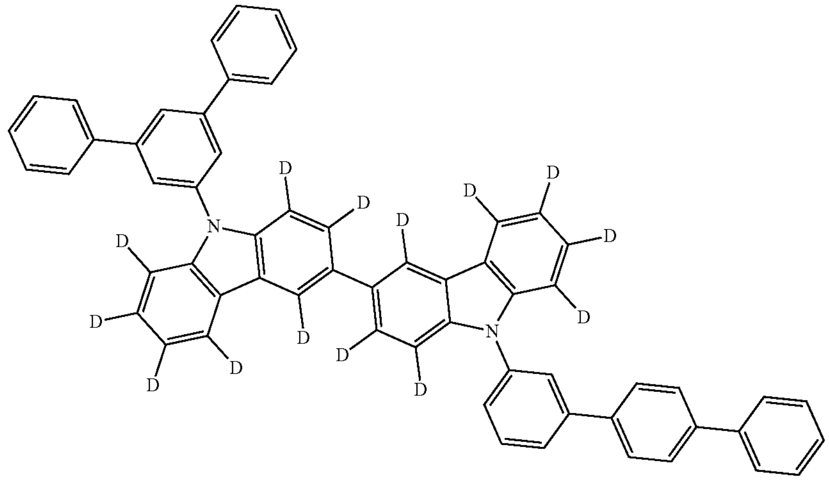

-continued
2-43
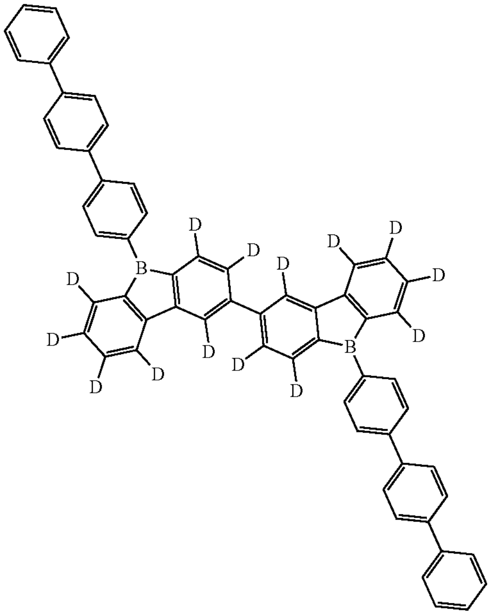
2-44
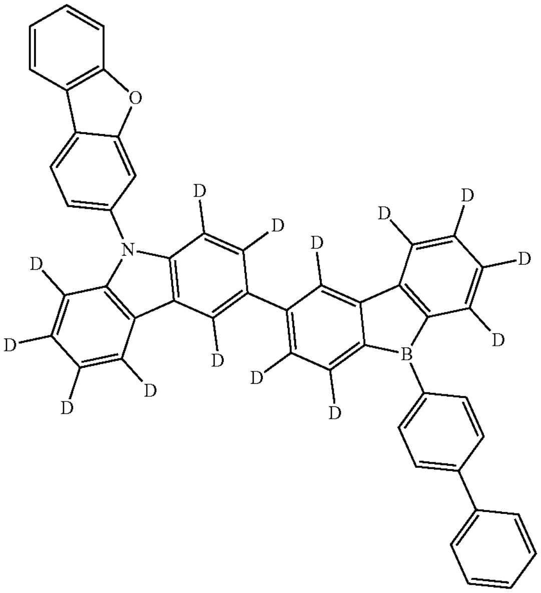
2-45
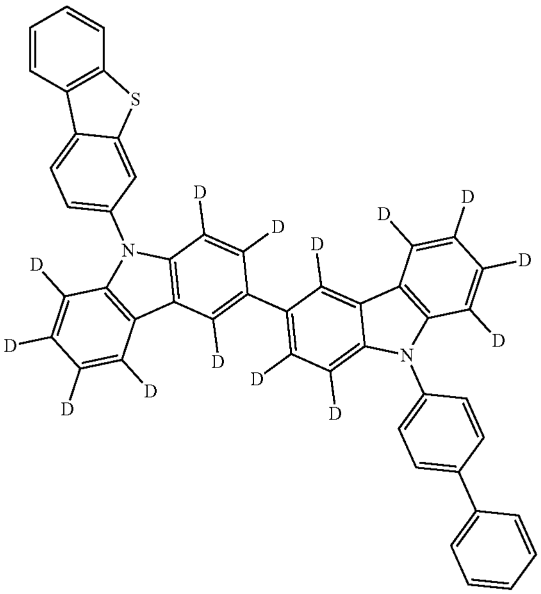
2-46
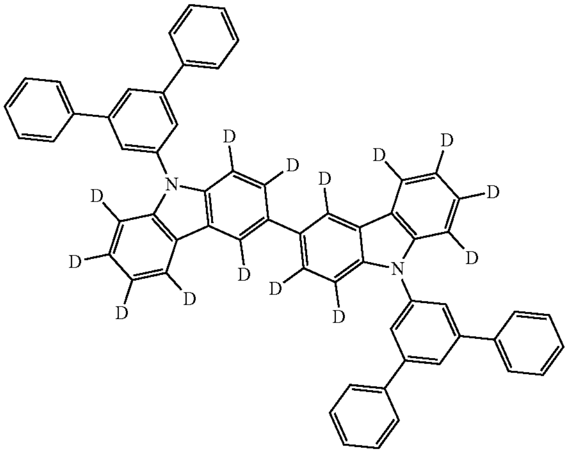

-continued
2-47
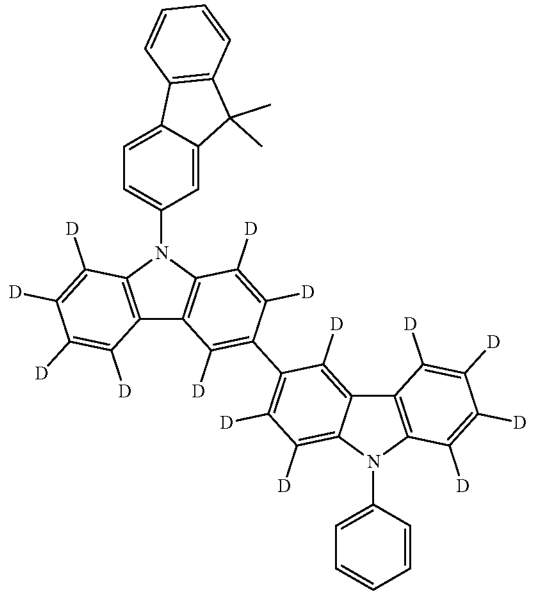
2-48
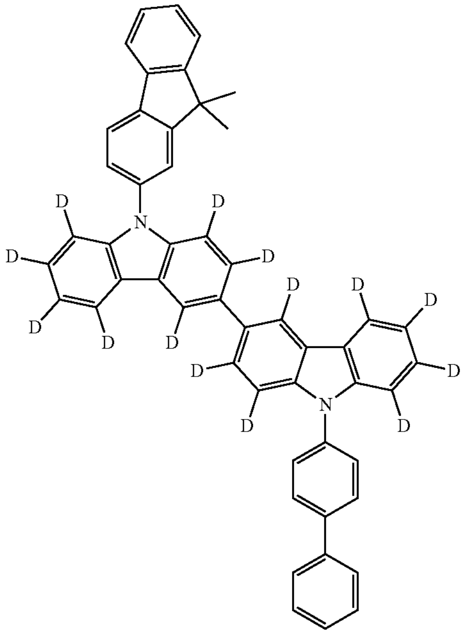
2-49
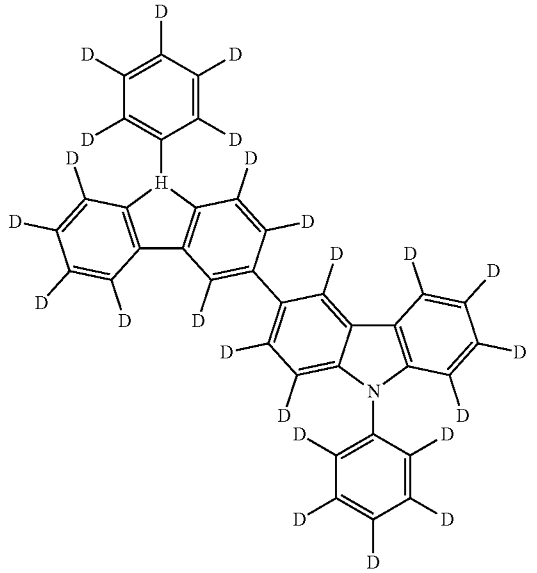
2-50
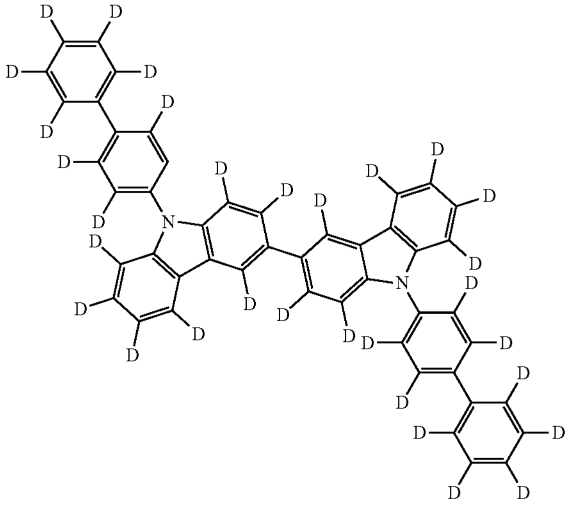

-continued
2-51
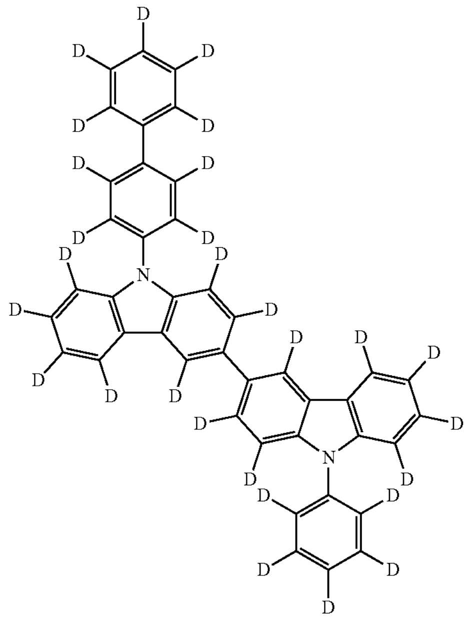
2-52
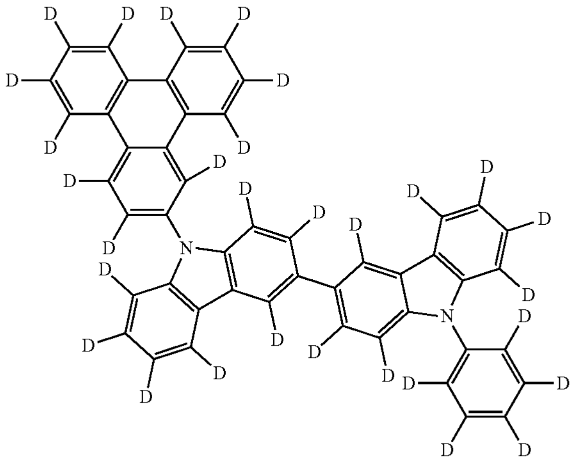
2-53
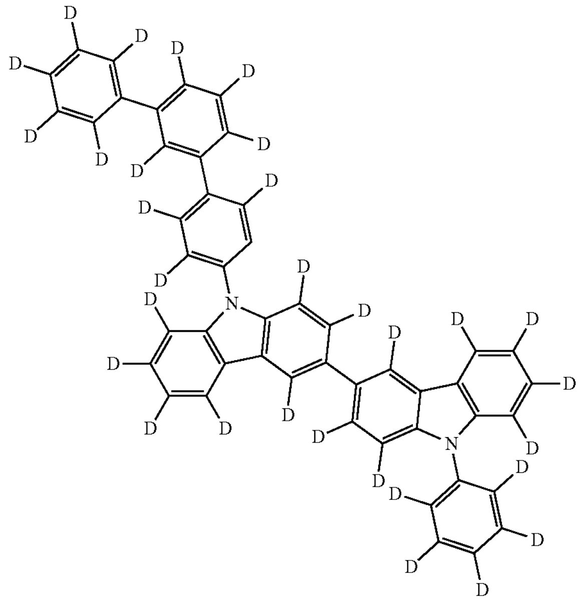
2-54
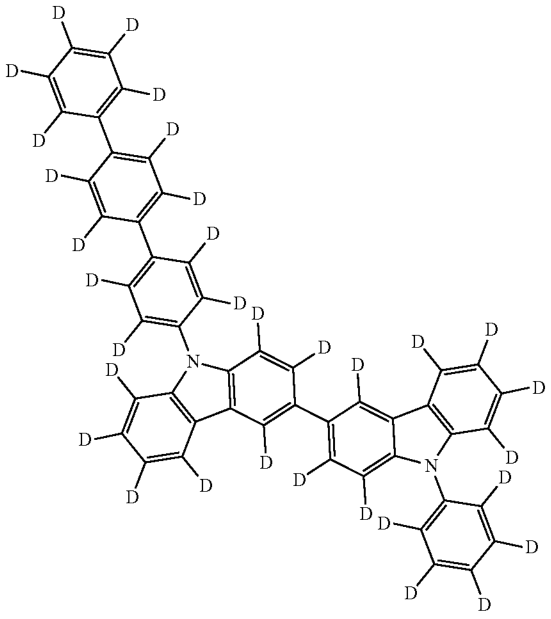

-continued
2-55
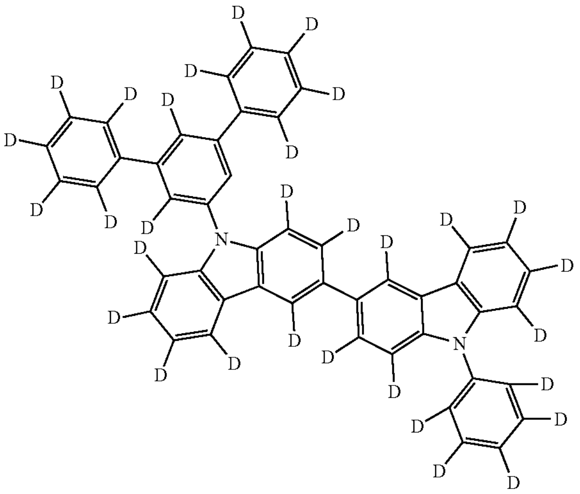
2-56
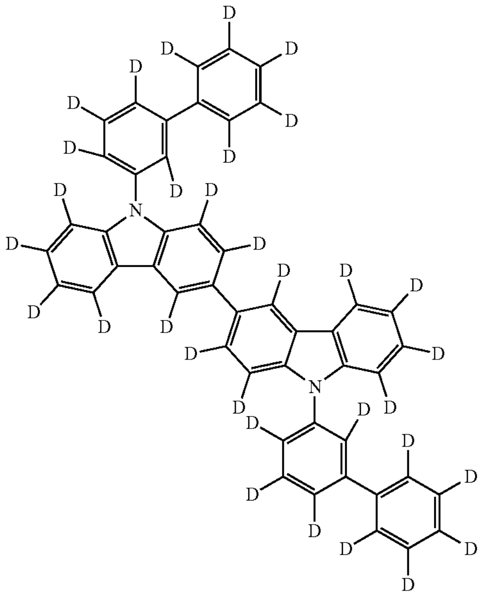
2-57
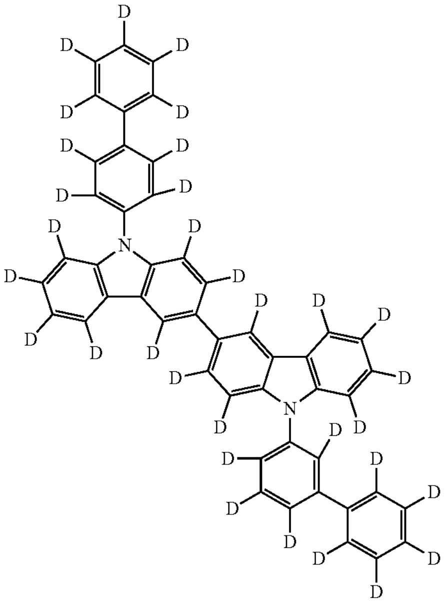
2-58
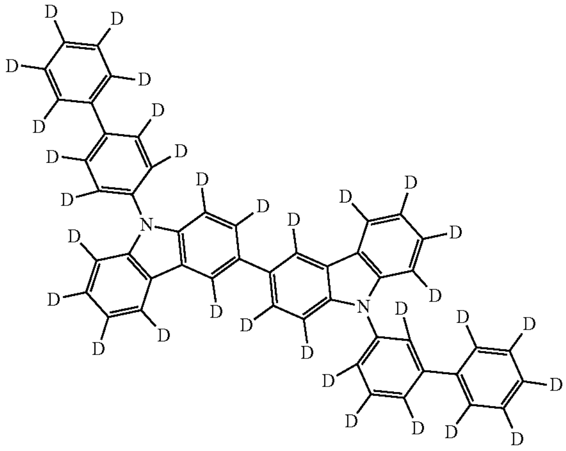

-continued
2-59
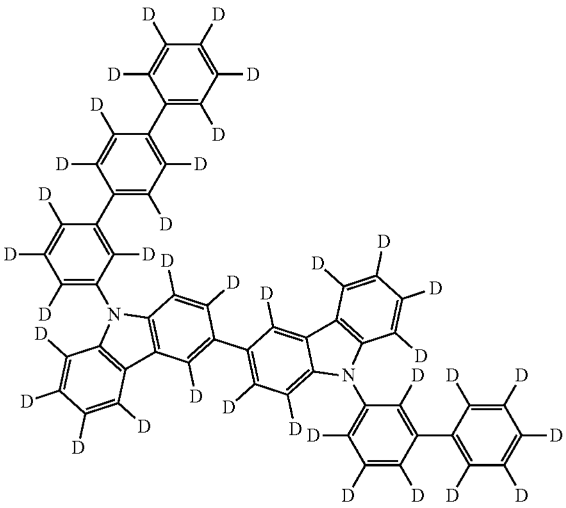
2-60
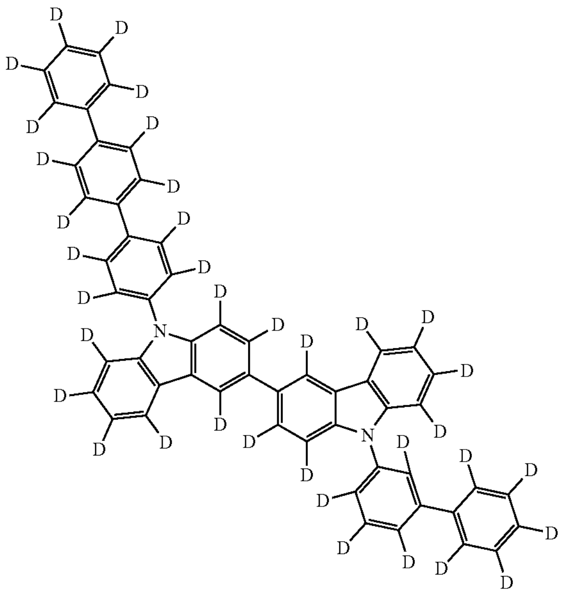
2-61
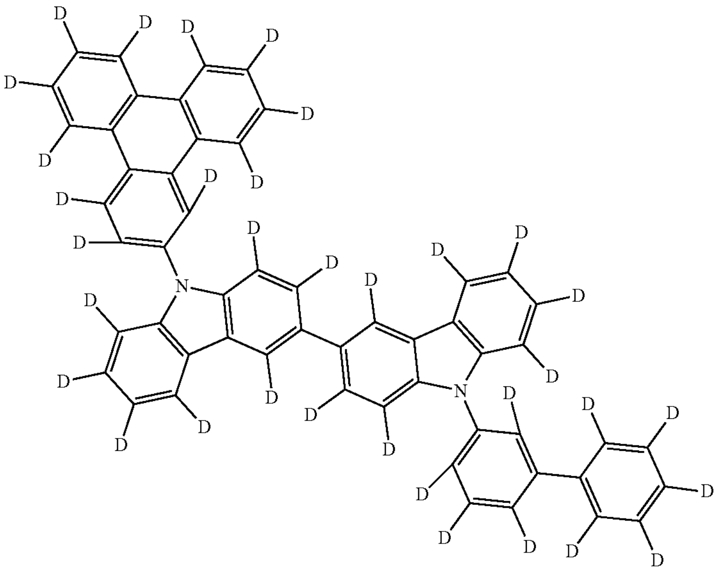

-continued
2-62
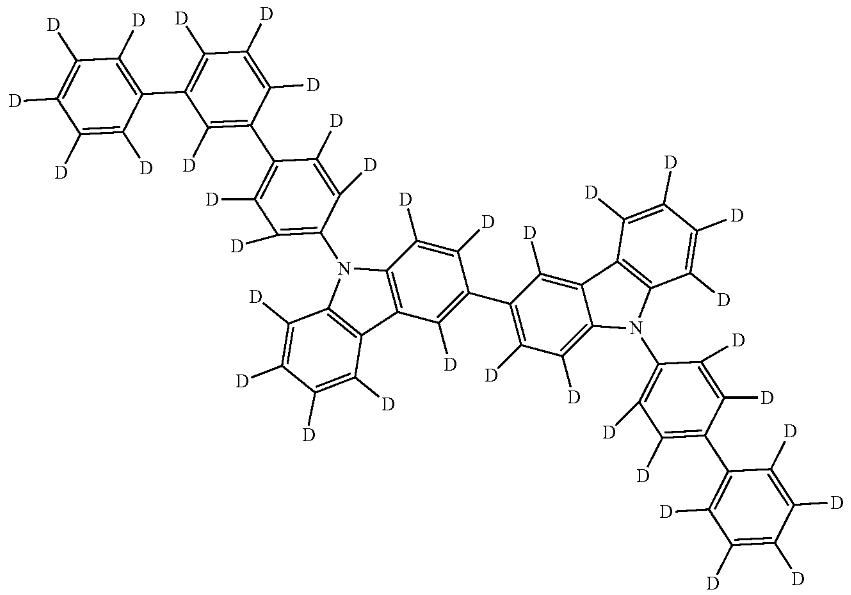
2-63
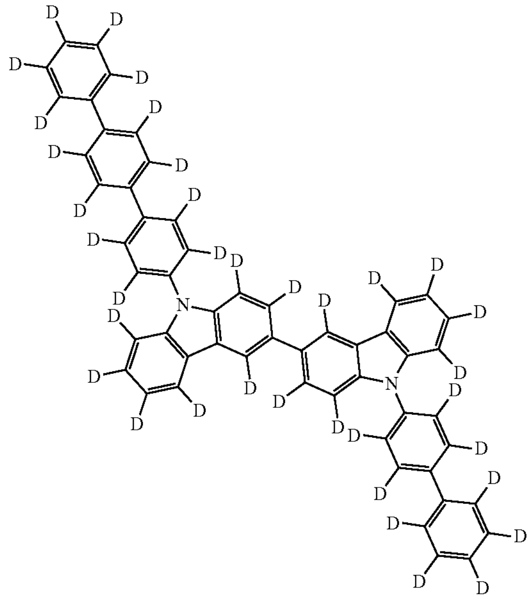

-continued
2-64
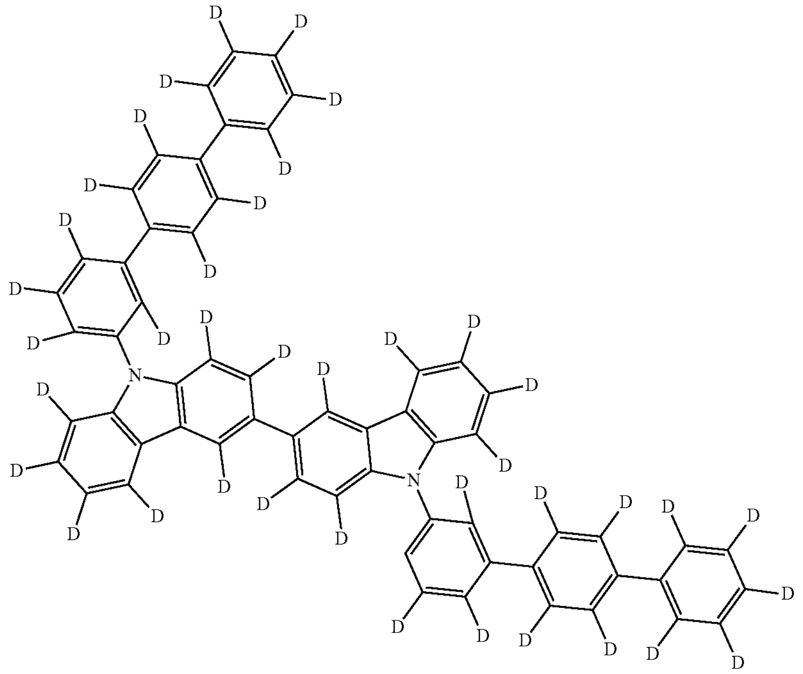
2-65
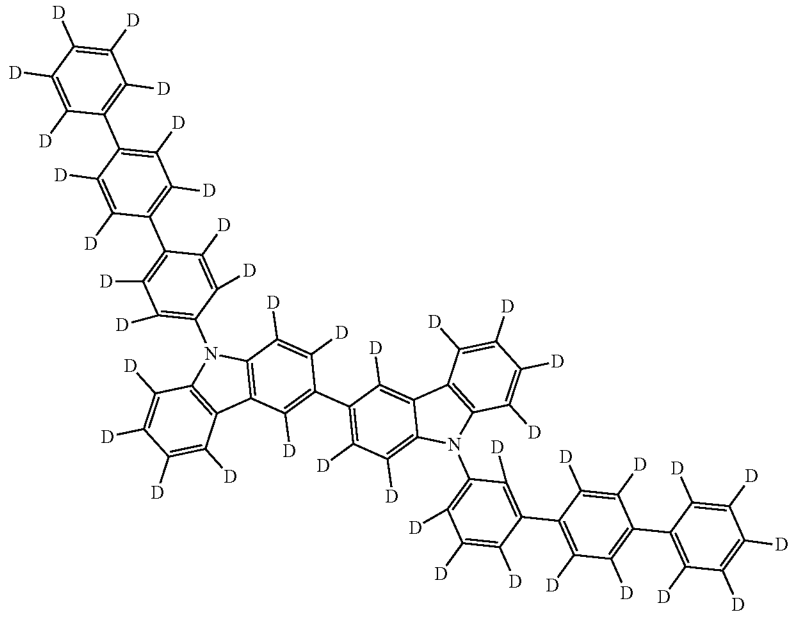

-continued
2-66
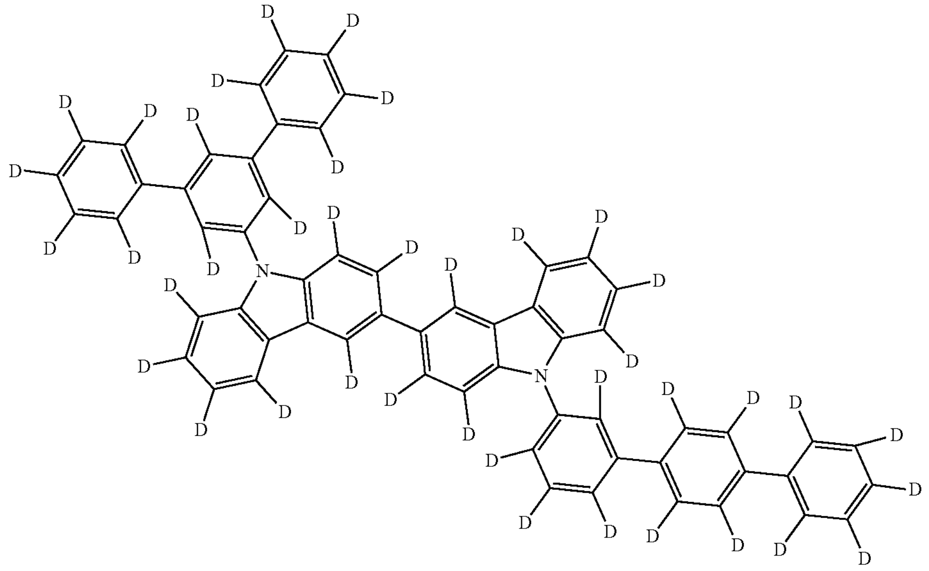
2-67
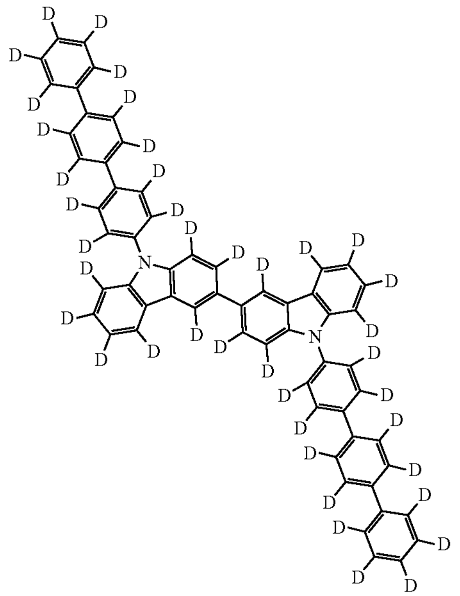
2-68
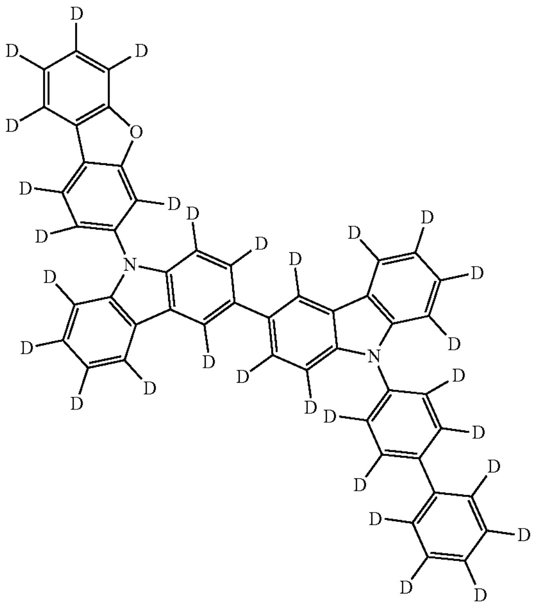

-continued
2-69
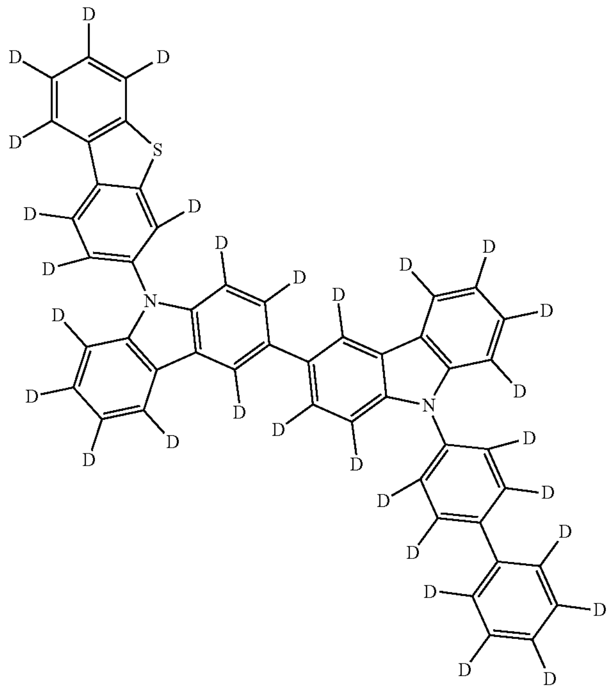
2-70
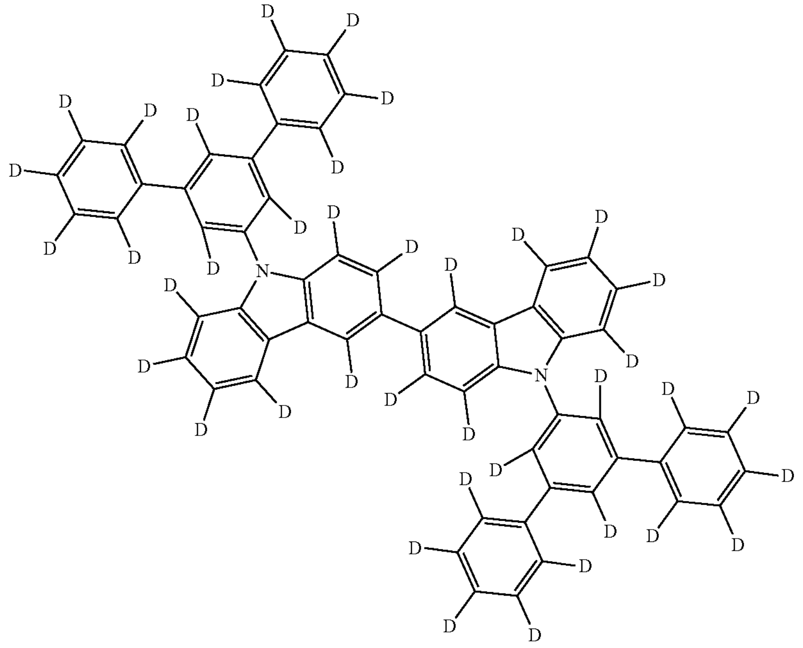

-continued
2-71
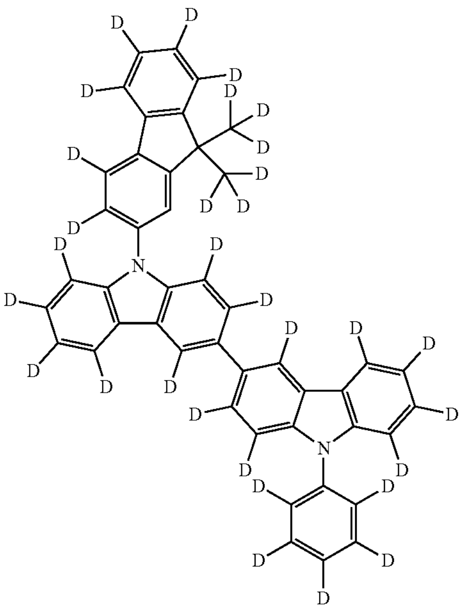
2-72
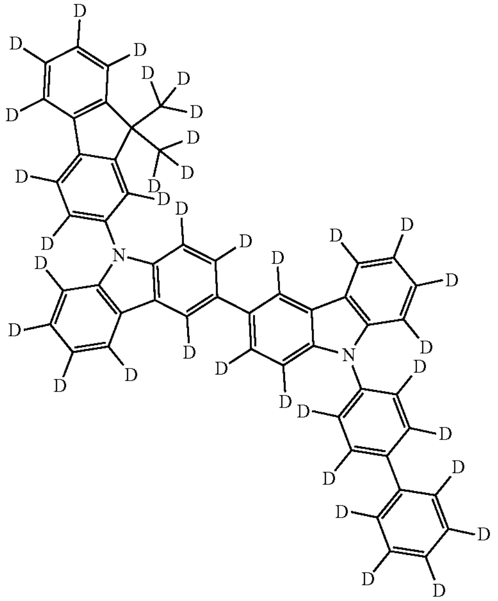
2-73
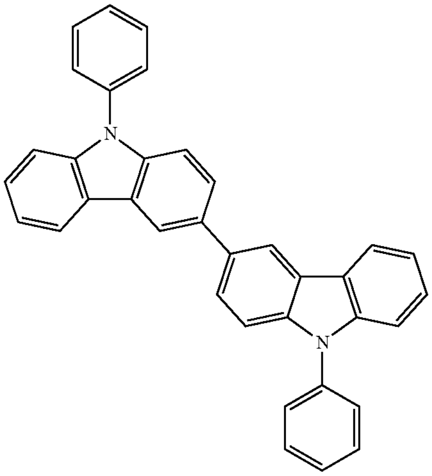
2-74
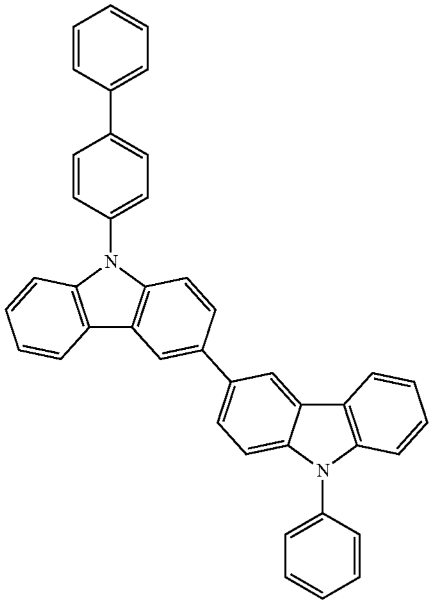

-continued
2-75
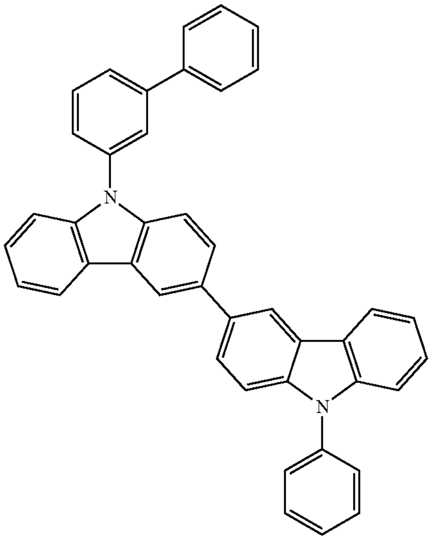
2-76
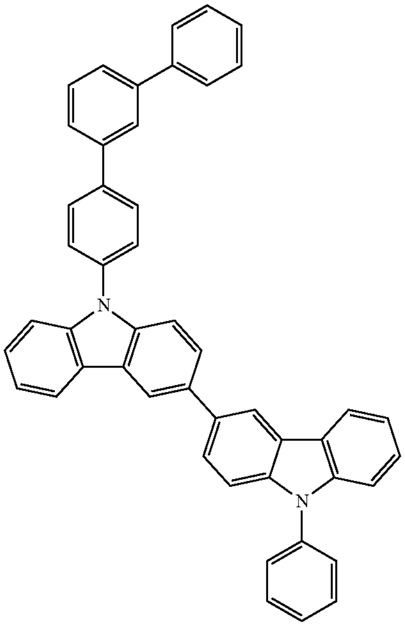
2-77
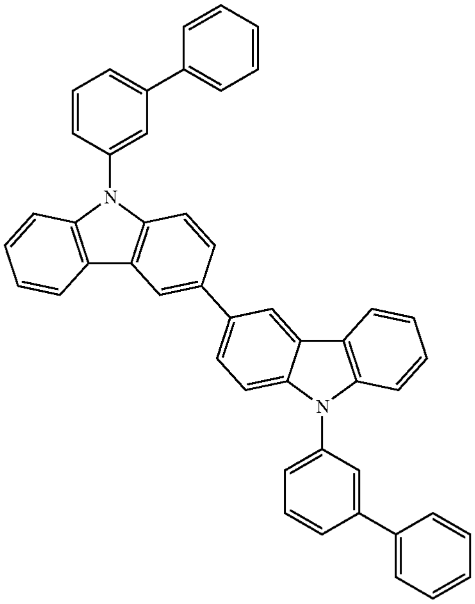
2-78
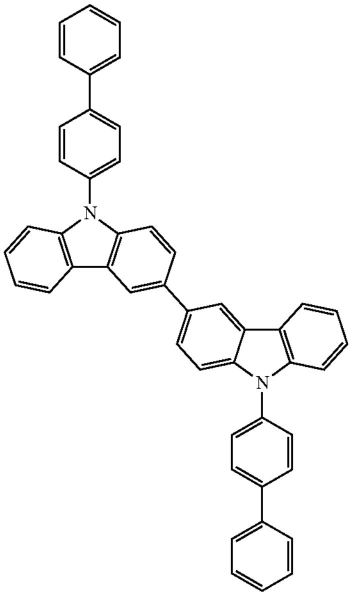

-continued 2-79

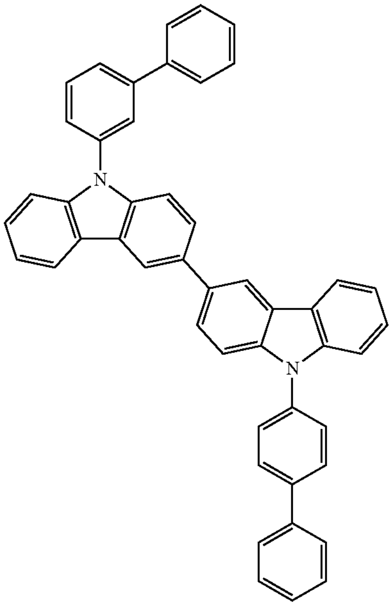

2-80

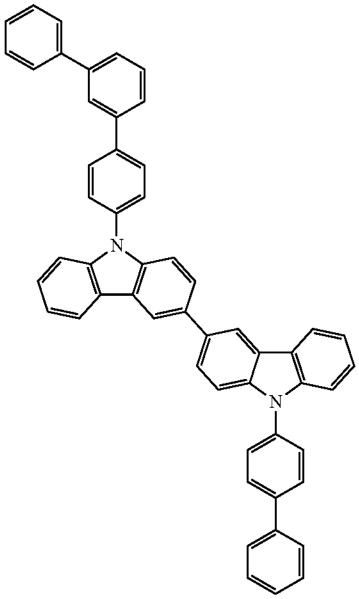

In addition, another embodiment of the present application provides a composition for an organic material layer of an organic light emitting device, the composition comprising the heterocyclic compound represented by Chemical Formula 1 and the heterocyclic compound represented by Chemical Formula 2.

Specific descriptions on the heterocyclic compound represented by Chemical Formula 1 and the heterocyclic compound represented by Chemical Formula 2 are the same as the descriptions provided above.

In the composition, the heterocyclic compound represented by Chemical Formula 1: the heterocyclic compound represented by Chemical Formula 2 may have a weight ratio of 1:10 to 10:1, 1:8 to 8:1, 1:5 to 5:1 or 1:2 to 2:1, however, the weight ratio is not limited thereto.

The composition may be used when forming an organic material of an organic light emitting device, and may be more preferably used when forming a host of a light emitting layer.

The composition has a form in which two or more compounds are simply mixed, and materials in a powder state may be mixed before forming the organic material layer of the organic light emitting device, or compounds in a liquid state may be mixed at a proper temperature or higher. The composition is in a solid state below the melting point of each material, and may be maintained in a liquid state when adjusting a temperature.

The composition may further comprise materials known in the art such as solvents and additives.

The organic light emitting device according to one embodiment of the present application may be manufactured using common organic light emitting device manufacturing methods and materials except that one or more organic material layers are formed using the heterocyclic compound represented by Chemical Formula 1 and the heterocyclic compound represented by Chemical Formula 2 described above.

The compound represented by Chemical Formula 1 and the heterocyclic compound represented by Chemical Formula 2 may be formed into an organic material layer using a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present disclosure may be formed in a single layer structure, or may also be formed in a multilayer structure in which two or more organic material layers are laminated. For example, the organic light emitting device of the present disclosure may have a structure comprising a hole injection layer, a hole transfer layer, a light emitting layer, an electron transfer layer, an electron injection layer and the like as the organic material layer. However, the structure of the organic light emitting device is not limited thereto, and may comprise a smaller number of organic material layers.

In one embodiment of the present application, the organic light emitting device may be a blue organic light emitting device, and the heterocyclic compound according to Chemical Formula 1 and the heterocyclic compound according to Chemical Formula 2 may be used as a material of the blue organic light emitting device.

In one embodiment of the present application, the organic light emitting device may be a green organic light emitting device, and the compound represented by Chemical Formula 1 and the heterocyclic compound represented by Chemical Formula 2 may be used as a material of the green organic light emitting device.

In one embodiment of the present application, the organic light emitting device may be a red organic light emitting device, and the compound represented by Chemical Formula 1 and the heterocyclic compound represented by Chemical Formula 2 may be used as a material of the red organic light emitting device.

The organic light emitting device of the present disclosure may further comprise one, two or more layers selected from the group consisting of a light emitting layer, a hole injection layer, a hole transfer layer, an electron injection layer, an electron transfer layer, an electron blocking layer and a hole blocking layer.

In the organic light emitting device provided in one embodiment of the present application, the organic material layer comprises at least one of a hole blocking layer, an electron injection layer and an electron transfer layer, and the at least one of the hole blocking layer, the electron injection layer and the electron transfer layer comprises the heterocyclic compound represented by Chemical Formula 1 and the heterocyclic compound represented by Chemical Formula 2.

In the organic light emitting device provided in one embodiment of the present application, the organic material layer comprises a light emitting layer, and the light emitting layer comprises the heterocyclic compound represented by Chemical Formula 1 and the heterocyclic compound represented by Chemical Formula 2.

In the organic light emitting device provided in one embodiment of the present application, the organic material layer comprises a light emitting layer, the light emitting layer comprises a host material, and the host material comprises the heterocyclic compound represented by Chemical Formula 1 and the heterocyclic compound represented by Chemical Formula 2.

FIG. 1 to FIG. 3 illustrate a lamination order of electrodes and organic material layers of an organic light emitting device according to one embodiment of the present application. However, the scope of the present application is not limited to these diagrams, and structures of organic light emitting devices known in the art may also be used in the present application.

FIG. 1 illustrates an organic light emitting device in which an anode (200), an organic material layer (300) and a cathode (400) are consecutively laminated on a substrate (100). However, the structure is not limited to such a structure, and as illustrated in FIG. 2, an organic light emitting device in which a cathode, an organic material layer and an anode are consecutively laminated on a substrate may also be obtained.

FIG. 3 illustrates a case of the organic material layer being a multilayer. The organic light emitting device according to FIG. 3 comprises a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, layers other than the light emitting layer may not be included, and other necessary functional layers may be further added.

One embodiment of the present application provides a method for manufacturing an organic light emitting device, the method comprising preparing a substrate; forming a first electrode on the substrate; forming one or more organic material layers on the first electrode; and forming a second electrode on the organic material layer, wherein the foaming of organic material layers comprises forming one or more organic material layers using the composition for an organic material layer according to one embodiment of the present application.

In the method for manufacturing an organic light emitting device provided in one embodiment of the present application, the forming of organic material layers is forming the heterocyclic compound of Chemical Formula 1 and the heterocyclic compound of Chemical Formula 2 using a thermal vacuum deposition method after pre-mixing.

The pre-mixing means first mixing the heterocyclic compound of Chemical Formula 1 and the heterocyclic compound of Chemical Formula 2 in one source of supply before depositing on the organic material layer.

The pre-mixed material may be referred to as the composition for an organic material layer according to one embodiment of the present application.

In the organic light emitting device according to one embodiment of the present application, materials other than the heterocyclic compound of Chemical Formula 1 and the heterocyclic compound of Chemical Formula 2 are illustrated below, however, these are for illustrative purposes only and not for limiting the scope of the present application, and may be replaced by materials known in the art.

As the anode material, materials having relatively large work function may be used, and transparent conductive oxides, metals, conductive polymers or the like may be used. Specific examples of the anode material comprise metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, and the like, but are not limited thereto.

As the cathode material, materials having relatively small work function may be used, and metals, metal oxides, conductive polymers or the like may be used. Specific examples of the cathode material comprise metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri[phenyl(m-tolyl)amino]triphenylamine (m-MTDATA) or 1,3,5-tris[4-(3-methylphenylphenylamino) phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrenesulfonate), polyaniline/camphor sulfonic acid or polyaniline/poly(4-styrene-sulfonate) that are conductive polymers having solubility, and the like, may be used.

As the hole transfer material, pyrazoline derivatives, arylamine-based derivatives, stilbene derivatives, triphenyldiamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. Herein, two or more light emitting materials may be used by being deposited as individual sources of supply or by being pre-mixed and deposited as one source of supply. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involving in light emission together may also be used.

When mixing light emitting material hosts, same series hosts may be mixed, or different series hosts may be mixed. For example, any two or more types of materials among n-type host materials or p-type host materials may be selected and used as a host material of a light emitting layer.

The organic light emitting device according to one embodiment of the present application may be a top-emission type, a bottom-emission type or a dual-emission type depending on the materials used.

The heterocyclic compound according to one embodiment of the present application may also be used in an organic electronic device comprising an organic solar cell, an organic photo conductor, an organic transistor and the like under a similar principle used in the organic light emitting device.

Hereinafter, the present specification will be described in more detail with reference to examples, however, these are for illustrative purposes only, and the scope of the present application is not limited thereto.

Preparation Example

<Preparation Example 1> Preparation of Compound 3

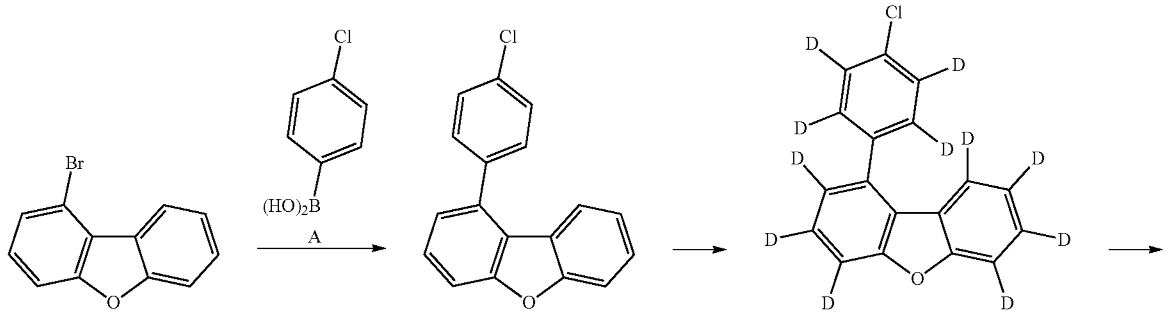

3-P4 3-P3 3-P2

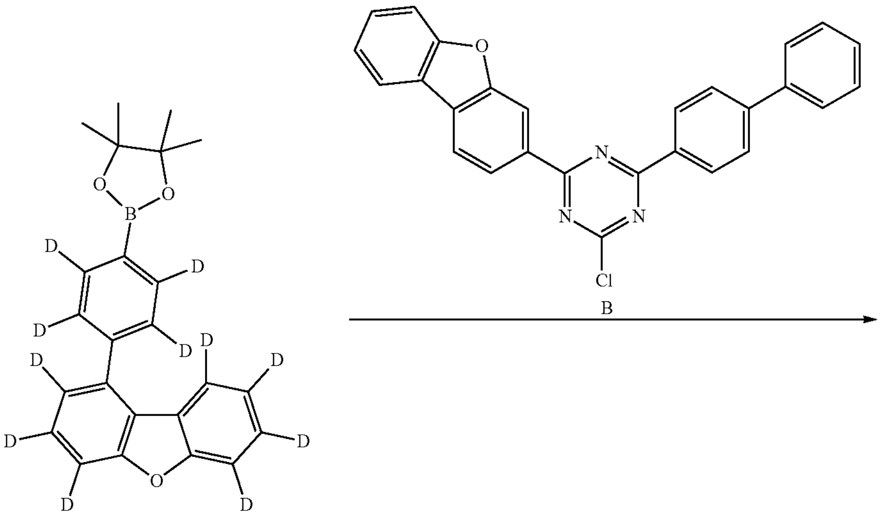

3-P1

-continued

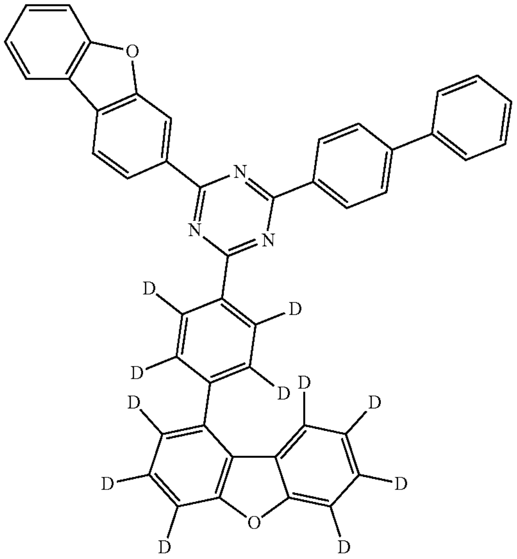

3

1) Preparation of Compound 3-P3

Compound 3-P4 (20 g, 80.94 mmol) and (4-chlorophenyl) boronic acid (12.66 g, 80.94 mmol) were dissolved in 1,4-dioxane (200 mL) and distilled water (40 mL), and after introducing $Pd(PPh_3)_4$ (4.67 g, 4.047 mmol) and $K_2CO_3$ (28 g, 202.35 mmol) thereto, the mixture was stirred for 16 hours under reflux. After the reaction was completed, ethyl acetate was introduced to the reaction solution for dissolution. The result was extracted with distilled water, and after drying the organic layer with anhydrous $MgSO_4$, the solvent was removed using a rotary evaporator. After that, the result was purified by column chromatography using dichloromethane and hexane as a developing solvent to obtain Compound 3-P3 (15.8 g, yield 70%).

2) Preparation of Compound 3-P2

*Compounds and reaction conditions are as shown in the following Table 1 and Table 2.

TABLE 1

| Example | Compound (g, Equivalent) | Solvent (g) | Catalyst (mol %) | Temperature/Time (° C., d) | Condition | Obtained Amount, Yield |
|---|---|---|---|---|---|---|
| 1 | 3-P3 (1 g, 1 eq.) | $D_2O$ (100 g) | Pt/C (10 mol %) | 150° C., 4 d | Round Flask Under Ar Bag | NO reaction |
| 2 | 3-P3 (1 g, 1 eq.) | $D_2O$, i-PrOH, cyclohexane (100 g, 50 g, 50 g) | Pt/C, Pd/C (10 mol %) | 150° C., 4 d | Round Flask Under Ar Bag | NO reaction |
| 3 | 3-P3 (1 g, 1 eq.) | $D_2O$, i-PrOH, cyclohexane (100 g, 50 g, 50 g) | Pt/C, Pd/C (10 mol %) | 200° C., 2 d | Sealed Tube | NO reaction |
| 4 | 3-P3 (1 g, 1 eq.) | $D_2O$, i-PrOH, cyclohexane (100 g, 50 g, 50 g) | Pt/C, Pd/C (10 mol %) | 150° C., 4 d | Sealed Tube | NO reaction |

TABLE 2

| Example | Compound (g, Equivalent) | Solvent (g, Equivalent) | Acid (g, Equivalent) | Time/ Temperature | Obtained Amount, Yield |
|---|---|---|---|---|---|
| 5 | 3-P3 (1 g, 1 eq.) | Benzene-D6 (100 g, 279.8 eq.) | CF3SO3H (34 g, 50.6 eq.) | 50° C., 1 h | 0.68 g, 66% |
| 6 | 3-P3 (1 g, 1 eq.) | Benzene-D6 (100 g, 279.8 eq.) | CF3SO3H (34 g, 50.6 eq.) | rt., 5 h | 0.5 g, 48% |
| 7 | 3-P3 (1 g, 1 eq.) | Benzene-D6 (100 g, 279.8 eq.) | CF3SO3H (17 g, 25 eq.) | 50° C., 1 h | 0.65 g, 62% |

TABLE 2-continued

| Example | Compound (g, Equivalent) | Solvent (g, Equivalent) | Acid (g, Equivalent) | Time/ Temperature | Obtained Amount, Yield |
|---|---|---|---|---|---|
| 8 | 3-P3 (1 g, 1 eq.) | Benzene-D6 (50 g, 139.9 eq.) | CF3SO3H (17 g, 25 eq.) | 50° C., 1 h | 0.65 g, 61% |
| 9 | 3-P3 (1 g, 1 eq.) | Benzene-D6 (50 g, 139.9 eq.) | CF3SO3H (13.6 g, 20.2 eq.) | 50° C., 1 h | 0.7 g, 68% |
| 10 | 3-P3 (1 g, 1 eq.) | DMSO-D6 (50 g, 139.9 eq.) | CF3SO3H (13.6 g, 20.2 eq.) | 50° C., 1 h | 0.5 g, 48% |
| 11 | 3-P3 (1 g, 1 eq.). | DMF-D6 (50 g, 139.9 eq.) | CF3SO3H (13.6 g, 20.2 eq.) | 50° C., 1 h | 0.5 g, 48% |
| 12 | 3-P3 (1 g, 1 eq.). | Benzene-D6 (50 g, 139.9 eq.) | CF3SO3D (13.6 g, 20.2 eq.) | 50° C., 1 h | 0.55 g, 53% |

Compound 3-P2 was synthesized under the reaction condition of Example 9 having the highest yield in Table 1 and Table 2.

Compound 3-P3 (15.8 g, 56.66 mmol) was dissolved in benzene-d6 (790 g) and $CF_3SO_3H$ (214.9 g), and stirred for 1 hour at 50° C. After the reaction was completed, the result was quenched with $Na_2CO_3$ in $D_2O$. After the quenching, ethyl acetate was introduced to the mixture solution for dissolution, and after the organic layer was separated and dried with anhydrous $MgSO_4$, the solvent was removed using a rotary evaporator. After that, the result was purified by column chromatography using dichloromethane and hexane as a developing solvent to obtain Compound 3-P2 (11.2 g, yield 68%).

3) Preparation of Compound 3-P1

Compound 3-P2 (11.2 g, 38.64 mmol) and 4,4,4',4',5,5,5',5'-octamethyl-2,2'-bi(1,3,2-dioxaborolane) (14.72 g, 57.97 mmol) were dissolved in 1,4-dioxane (120 mL), and after introducing $Pd_2(dba)_3$ (1.77 g, 1.93 mmol), potassium acetate (11.36 g, 115.94 mmol) and Sphos (1.58 g, 3.86 mmol) thereto, the mixture was stirred for 16 hours under reflux. After the reaction was completed, ethyl acetate was introduced to the reaction solution for dissolution. The result was extracted with distilled water, and after drying the organic layer with anhydrous $MgSO_4$, the solvent was removed using a rotary evaporator. After that, the result was purified by column chromatography using dichloromethane and hexane as a developing solvent to obtain Compound 3-P1 (11.8 g, yield=80%).

4) Preparation of Compound 3

Compound 3-P1 (11.8 g, 30.91 mmol) and 2-([1,1'-biphenyl]-4-yl)-4-chloro-6-(dibenzo[b,d]furan-3-yl)-1,3,5-triazine (13.41 g, 30.91 mmol) were dissolved in 1,4-dioxane (125 mL) and distilled water (25 mL), and after introducing $Pd(PPh_3)_4$ (1.78 g, 1.54 mmol) and $K_2CO_3$ (10.68 g, 77.29 mmol) thereto, the mixture was stirred for 6 hours under reflux. After the reaction was completed, dichloromethane was introduced to the reaction solution for dissolution. The result was extracted with distilled water, and after drying the organic layer with anhydrous $MgSO_4$, the solvent was removed using a rotary evaporator. After that, the result was purified by column chromatography using dichloromethane and hexane as a developing solvent to obtain Compound 3 (14.12 g, yield=70%).

Target compounds of the following Table 3 were synthesized in the same manner as in Preparation Example 1 except that Intermediate 1 of the following Table 3 was used instead of Compound 3-P4, Intermediate 2 of the following Table 3 was used instead of Compound A, and Intermediate 3 of the following Table 3 was used instead of Compound B.

TABLE 3

| Compound No. | Intermediate 1 | Intermediate 2 | Intermediate 3 |
|---|---|---|---|
| 6 | 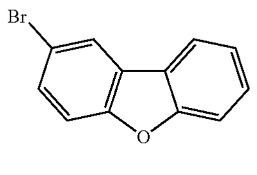 [SMILES: Brc1ccc2oc3ccccc3c2c1] | 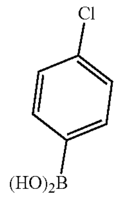 | 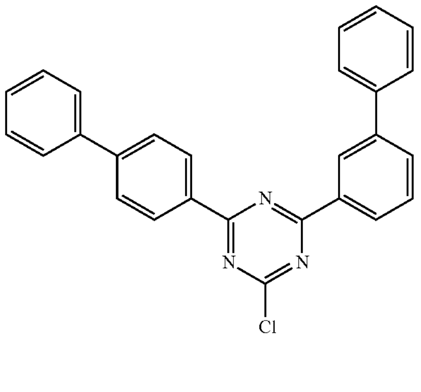 [SMILES: Clc1nc(-c2ccc(-c3ccccc3)cc2)nc(-c2cccc(-c3ccccc3)c2)n1] |

TABLE 3-continued
| | | |
|---|---|---|
| 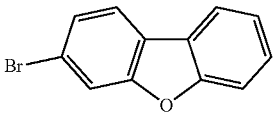 [SMILES: Brc1ccc2c(c1)oc1ccccc12] | 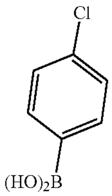 | 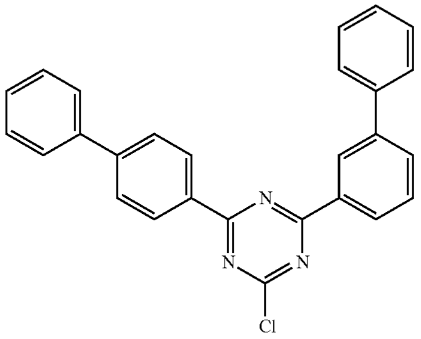 [SMILES: Clc1nc(-c2ccc(-c3ccccc3)cc2)nc(-c2cccc(-c3ccccc3)c2)n1] |
| 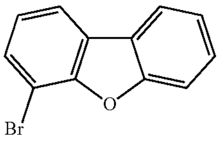 [SMILES: Brc1cccc2c1oc1ccccc12] | 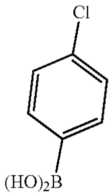 | 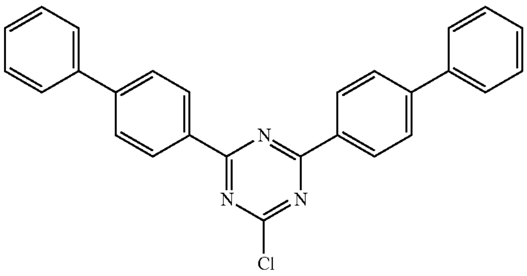 [SMILES: Clc1nc(-c2ccc(-c3ccccc3)cc2)nc(-c2ccc(-c3ccccc3)cc2)n1] |
| 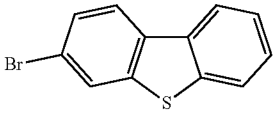 [SMILES: Brc1ccc2c(c1)sc1ccccc12] | 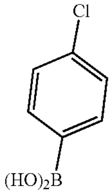 | 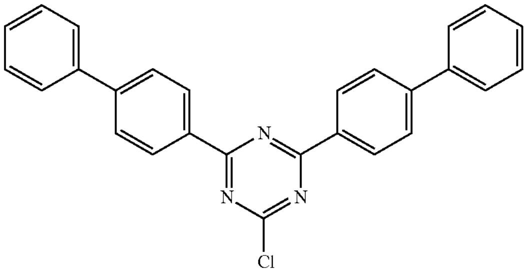 [SMILES: Clc1nc(-c2ccc(-c3ccccc3)cc2)nc(-c2ccc(-c3ccccc3)cc2)n1] |
| 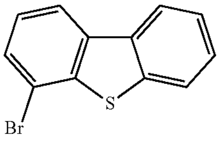 [SMILES: Brc1cccc2c1sc1ccccc12] | 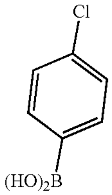 | 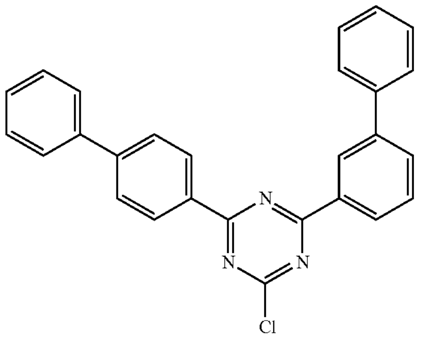 [SMILES: Clc1nc(-c2ccc(-c3ccccc3)cc2)nc(-c2cccc(-c3ccccc3)c2)n1] |
| 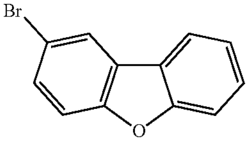 [SMILES: Brc1ccc2oc3ccccc3c2c1] | 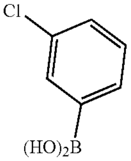 | 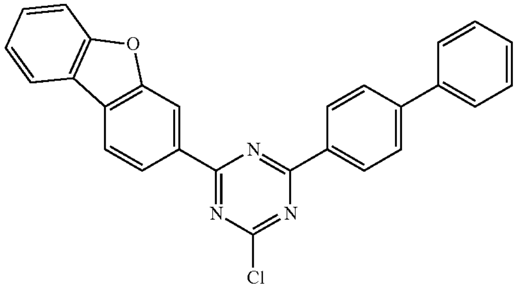 [SMILES: Clc1nc(-c2ccc(-c3ccccc3)cc2)nc(-c2ccc3c(c2)oc2ccccc23)n1] |

TABLE 3-continued
| | | | |
|---|---|---|---|
| 41 | 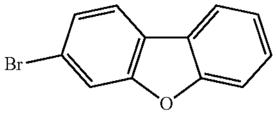 [SMILES: Brc1ccc2c(c1)oc1ccccc12] | 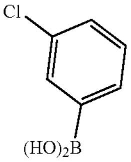 | 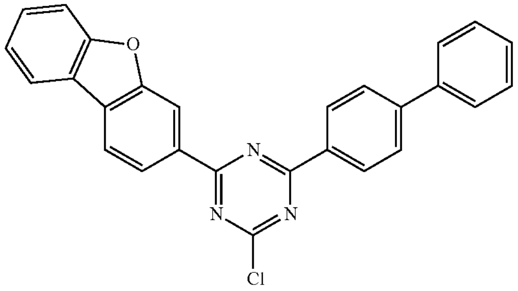 [SMILES: Clc1nc(-c2ccc(-c3ccccc3)cc2)nc(-c2ccc3c(c2)oc2ccccc23)n1] |
| 58 | 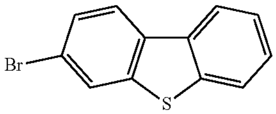 [SMILES: Brc1ccc2c(c1)sc1ccccc12] | 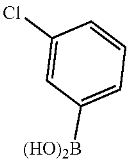 | 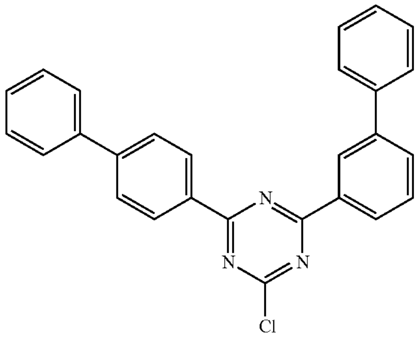 [SMILES: Clc1nc(-c2ccc(-c3ccccc3)cc2)nc(-c2cccc(-c3ccccc3)c2)n1] |
| 61 | 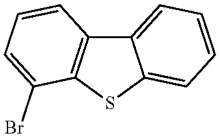 [SMILES: Brc1cccc2c1sc1ccccc12] | 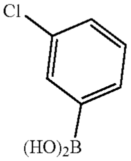 | 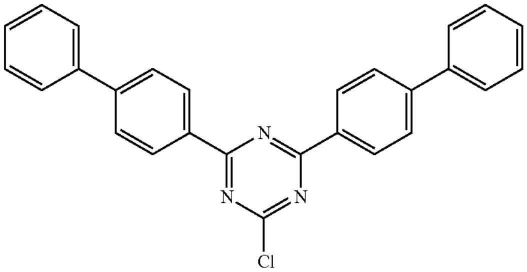 [SMILES: Clc1nc(-c2ccc(-c3ccccc3)cc2)nc(-c2ccc(-c3ccccc3)cc2)n1] |
| 62 | 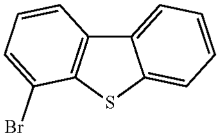 [SMILES: Brc1cccc2c1sc1ccccc12] | 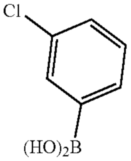 | 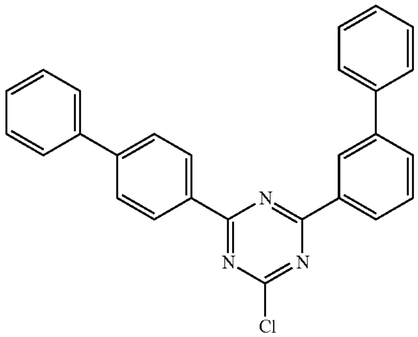 [SMILES: Clc1nc(-c2ccc(-c3ccccc3)cc2)nc(-c2cccc(-c3ccccc3)c2)n1] |
| 64 | 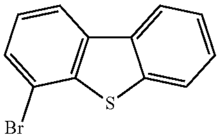 [SMILES: Brc1cccc2c1sc1ccccc12] | 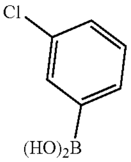 | 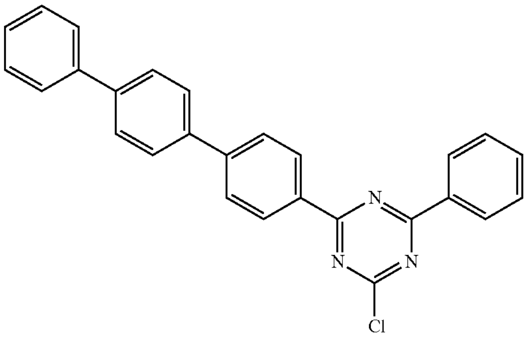 [SMILES: Clc1nc(-c2ccccc2)nc(-c2ccc(-c3ccc(-c4ccccc4)cc3)cc2)n1] |

TABLE 3-continued
| | | | |
|---|---|---|---|
| 65 | 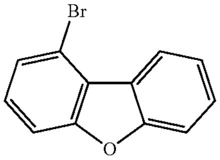 | 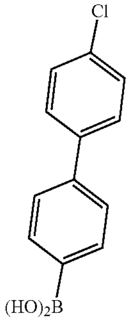 [SMILES: OB(O)c1ccc(-c2ccc(Cl)cc2)cc1] | 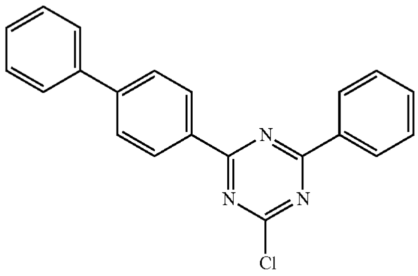 [SMILES: Clc1nc(-c2ccccc2)nc(-c2ccc(-c3ccccc3)cc2)n1] |
| 74 | 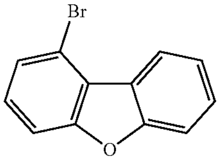 [SMILES: Brc1cccc2oc3ccccc3c12] | 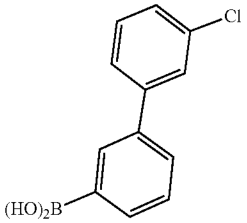 [SMILES: OB(O)c1cccc(-c2cccc(Cl)c2)c1] | 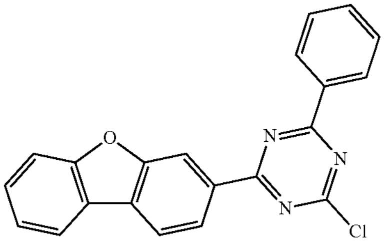 [SMILES: Clc1nc(-c2ccccc2)nc(-c2ccc3c(c2)oc2ccccc23)n1] |
| 97 | 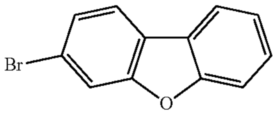 | 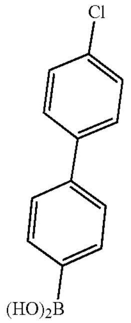 [SMILES: OB(O)c1ccc(-c2ccc(Cl)cc2)cc1] | 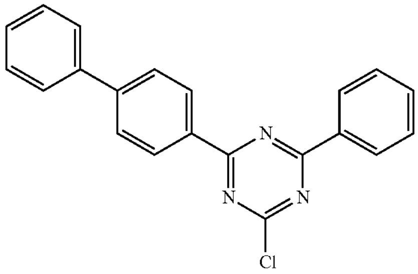 [SMILES: Clc1nc(-c2ccccc2)nc(-c2ccc(-c3ccccc3)cc2)n1] |
| 115 | 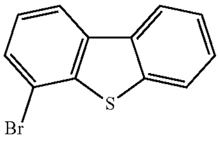 | 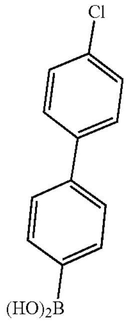 [SMILES: OB(O)c1ccc(-c2ccc(Cl)cc2)cc1] | 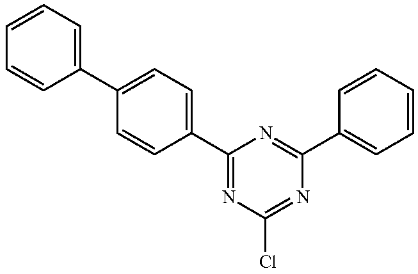 [SMILES: Clc1nc(-c2ccccc2)nc(-c2ccc(-c3ccccc3)cc2)n1] |
| 123 | 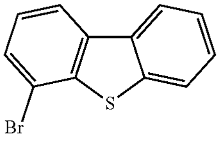 | 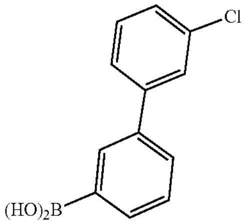 [SMILES: OB(O)c1cccc(-c2cccc(Cl)c2)c1] | 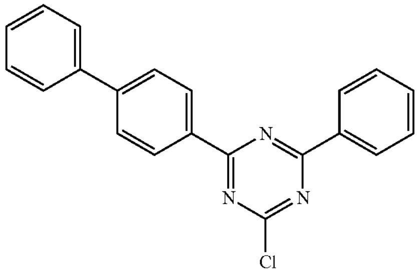 [SMILES: Clc1nc(-c2ccccc2)nc(-c2ccc(-c3ccccc3)cc2)n1] |

TABLE 3-continued
| | | | |
|---|---|---|---|
| 124 | 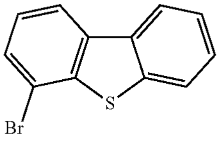 | 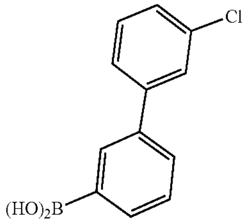 [SMILES: OB(O)c1cccc(-c2cccc(Cl)c2)c1] | 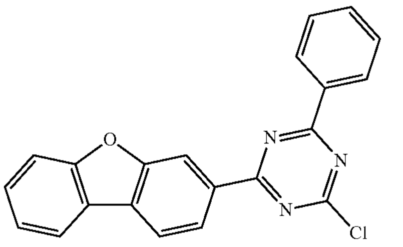 [SMILES: Clc1nc(-c2ccccc2)nc(-c2ccc3c(c2)oc2ccccc23)n1] |
| 127 | 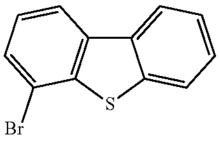 [SMILES: Brc1cccc2c1sc1ccccc12] | 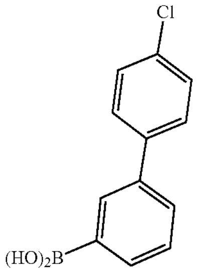 [SMILES: OB(O)c1cccc(-c2ccc(Cl)cc2)c1] | 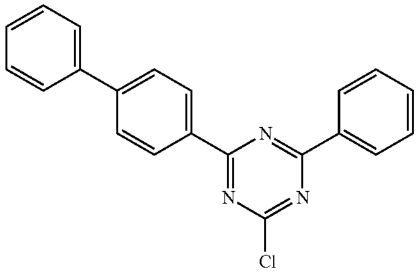 [SMILES: Clc1nc(-c2ccccc2)nc(-c2ccc(-c3ccccc3)cc2)n1] |
| 129 | 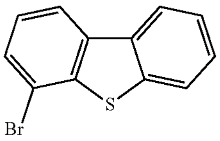 | 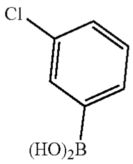 | 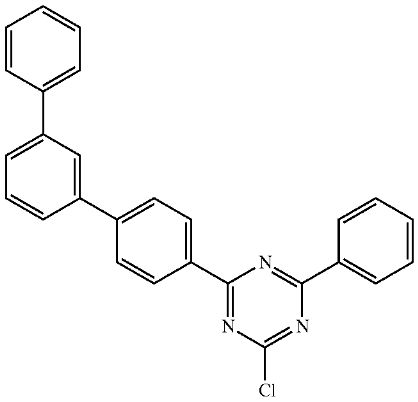 [SMILES: Clc1nc(-c2ccccc2)nc(-c2ccc(-c3cccc(-c4ccccc4)c3)cc2)n1] |
| 139 | 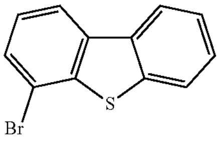 | 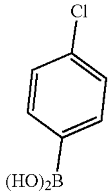 | 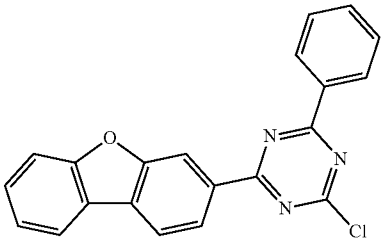 [SMILES: Clc1nc(-c2ccccc2)nc(-c2ccc3c(c2)oc2ccccc23)n1] |
| 9 | 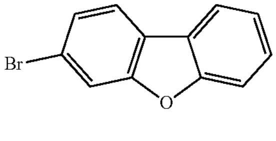 | 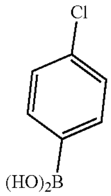 | 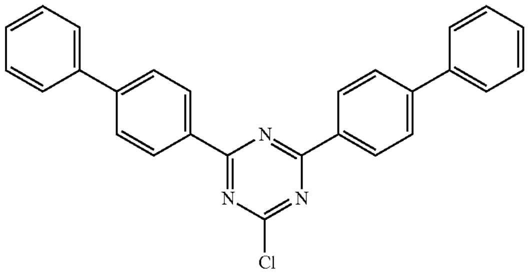 [SMILES: Clc1nc(-c2ccc(-c3ccccc3)cc2)nc(-c2ccc(-c3ccccc3)cc2)n1] |

TABLE 3-continued
| | | | |
|---|---|---|---|
| 12 | 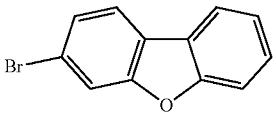 | 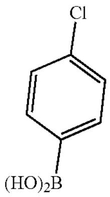 | 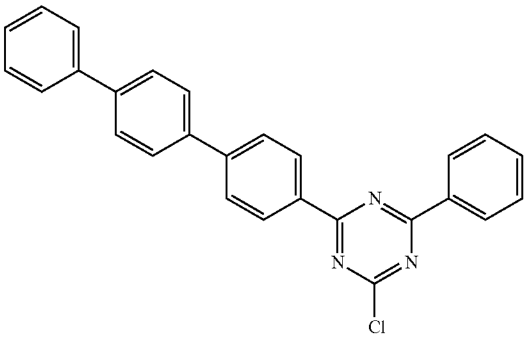 [SMILES: Clc1nc(-c2ccccc2)nc(-c2ccc(-c3ccc(-c4ccccc4)cc3)cc2)n1] |
| 17 | 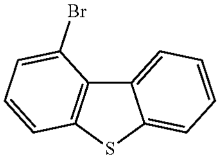 [SMILES: Brc1cccc2sc3ccccc3c12] | 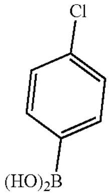 | 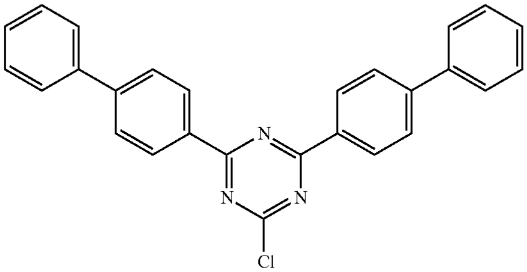 [SMILES: Clc1nc(-c2ccc(-c3ccccc3)cc2)nc(-c2ccc(-c3ccccc3)cc2)n1] |
| 26 | 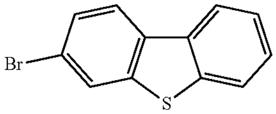 | 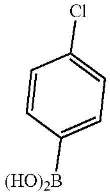 | 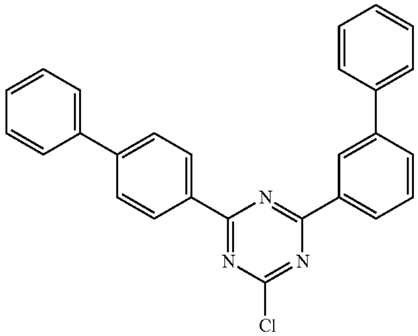 [SMILES: Clc1nc(-c2ccc(-c3ccccc3)cc2)nc(-c2cccc(-c3ccccc3)c2)n1] |
| 29 | 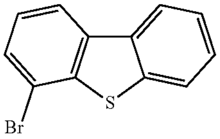 [SMILES: Brc1cccc2c1sc1ccccc12] | 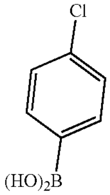 | 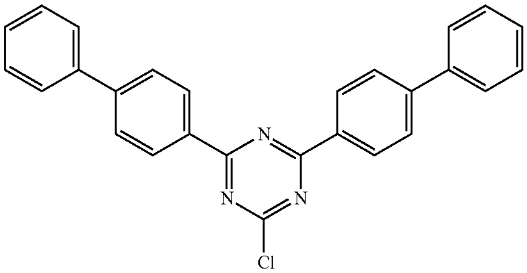 [SMILES: Clc1nc(-c2ccc(-c3ccccc3)cc2)nc(-c2ccc(-c3ccccc3)cc2)n1] |
| 57 | 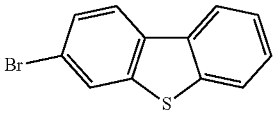 | 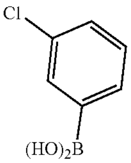 | 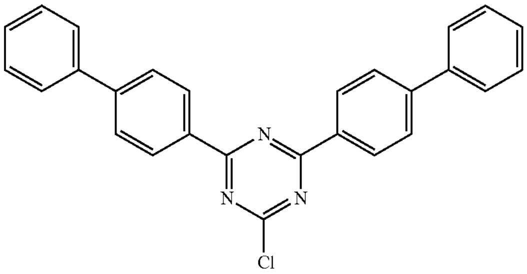 [SMILES: Clc1nc(-c2ccc(-c3ccccc3)cc2)nc(-c2ccc(-c3ccccc3)cc2)n1] |

TABLE 3-continued
| | | | |
|---|---|---|---|
| 68 | 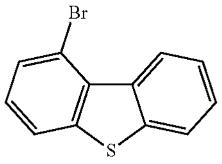 [SMILES: Brc1cccc2sc3ccccc3c12] | 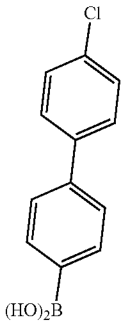 [SMILES: OB(O)c1ccc(-c2ccc(Cl)cc2)cc1] | 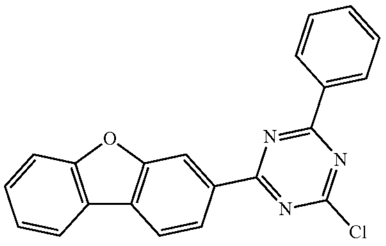 [SMILES: Clc1nc(-c2ccccc2)nc(-c2ccc3c(c2)oc2ccccc23)n1] |
| 114 | 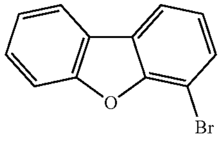 [SMILES: Brc1cccc2c1oc1ccccc12] | 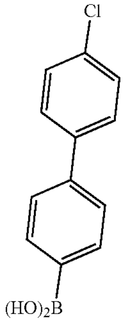 [SMILES: OB(O)c1ccc(-c2ccc(Cl)cc2)cc1] | 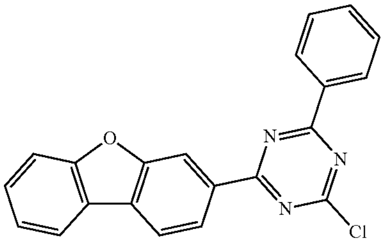 [SMILES: Clc1nc(-c2ccccc2)nc(-c2ccc3c(c2)oc2ccccc23)n1] |
| 118 | 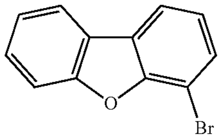 [SMILES: Brc1cccc2c1oc1ccccc12] | 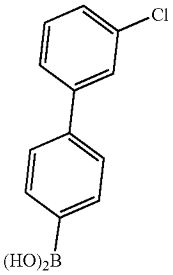 [SMILES: OB(O)c1ccc(-c2cccc(Cl)c2)cc1] | 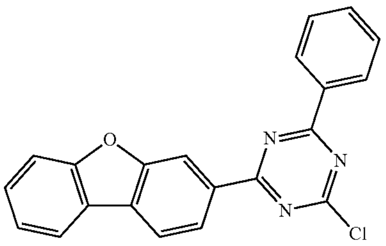 [SMILES: Clc1nc(-c2ccccc2)nc(-c2ccc3c(c2)oc2ccccc23)n1] |
| 119 | 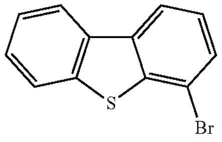 [SMILES: Brc1cccc2c1sc1ccccc12] | 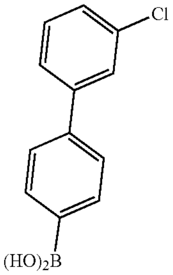 [SMILES: OB(O)c1ccc(-c2cccc(Cl)c2)cc1] | 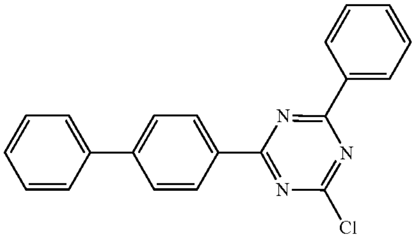 [SMILES: Clc1nc(-c2ccccc2)nc(-c2ccc(-c3ccccc3)cc2)n1] |
| 140 | 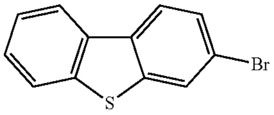 [SMILES: Brc1ccc2c(c1)sc1ccccc12] | 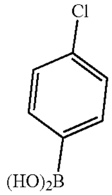 | 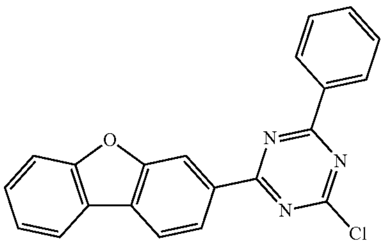 [SMILES: Clc1nc(-c2ccccc2)nc(-c2ccc3c(c2)oc2ccccc23)n1] |

TABLE 3-continued
| Compound No. | Target Compound | Yield |
|---|---|---|
| 6 | 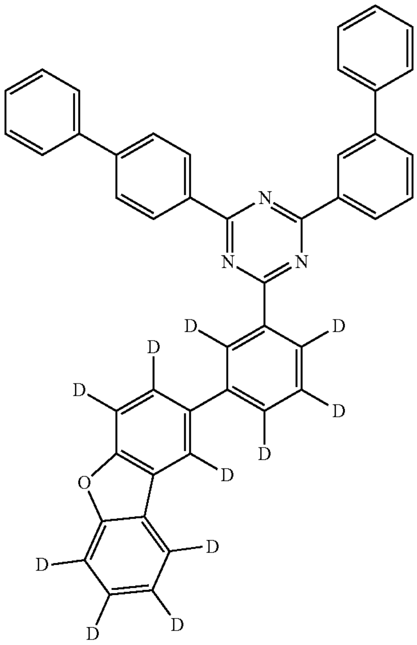 [SMILES: [2H]c1c([2H])c(-c2nc(-c3ccc(-c4ccccc4)cc3)nc(-c3cccc(-c4ccccc4)c3)n2)c([2H])c(-c2c([2H])c([2H])c3oc4c([2H])c([2H])c([2H])c([2H])c4c3c2[2H])c1[2H]] | 69% |
| 10 | 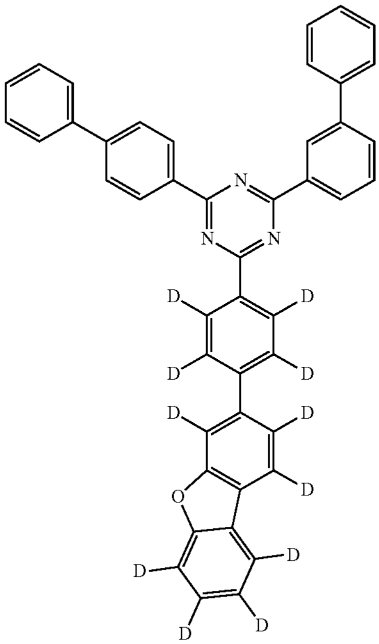 | 68% |

TABLE 3-continued
| | | |
|---|---|---|
| 13 | 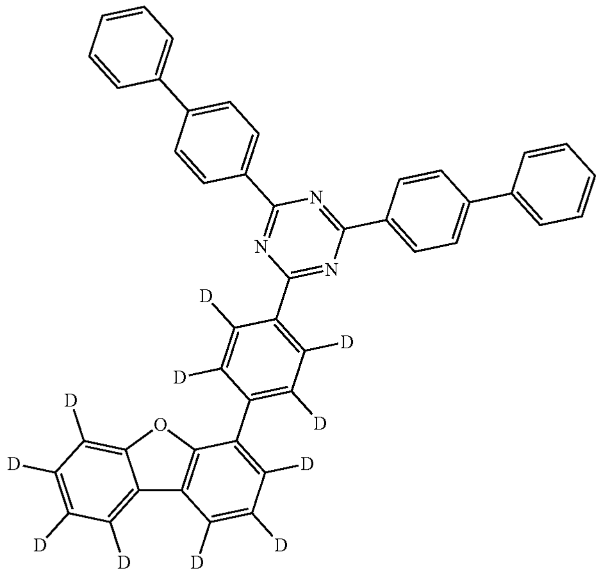 [SMILES: [2H]c1c([2H])c(-c2c([2H])c([2H])c([2H])c3c2oc2c([2H])c([2H])c([2H])c([2H])c23)c([2H])c([2H])c1-c1nc(-c2ccc(-c3ccccc3)cc2)nc(-c2ccc(-c3ccccc3)cc2)n1] | 66% |
| 25 | 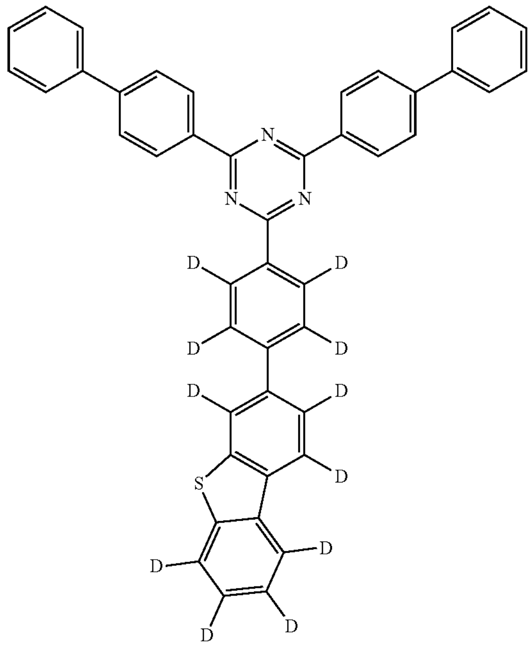 | 67% |

TABLE 3-continued
| | | |
|---|---|---|
| 30 | 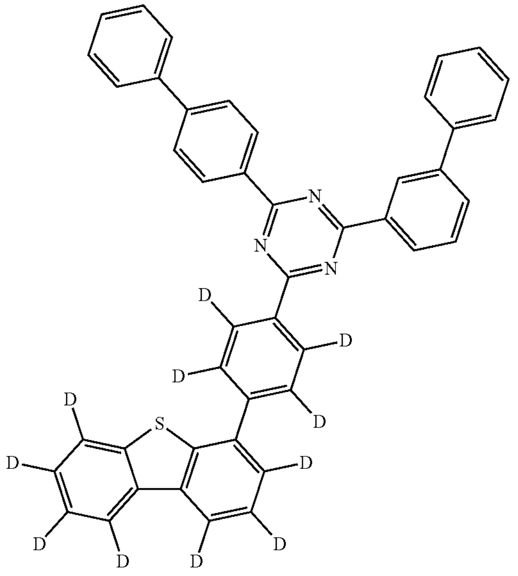 [SMILES: [2H]c1c([2H])c(-c2c([2H])c([2H])c([2H])c3c2sc2c([2H])c([2H])c([2H])c([2H])c23)c([2H])c([2H])c1-c1nc(-c2ccc(-c3ccccc3)cc2)nc(-c2cccc(-c3ccccc3)c2)n1] | 70% |
| 35 | 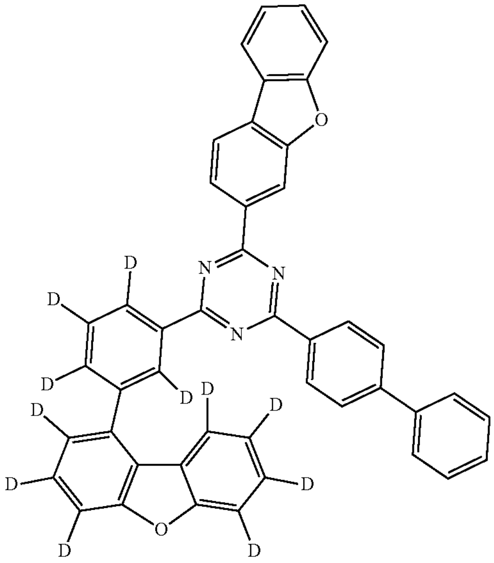 [SMILES: [2H]c1c([2H])c(-c2nc(-c3ccc(-c4ccccc4)cc3)nc(-c3ccc4c(c3)oc3ccccc34)n2)c([2H])c(-c2c([2H])c([2H])c([2H])c3oc4c([2H])c([2H])c([2H])c([2H])c4c23)c1[2H]] | 69% |

TABLE 3-continued
| | | |
|---|---|---|
| 41 | 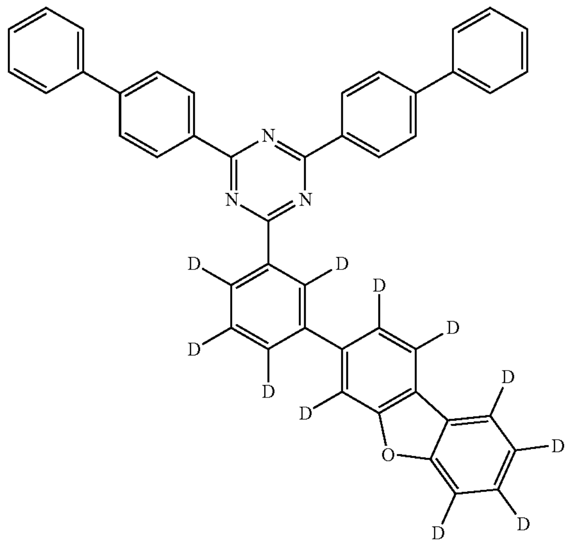 [SMILES: [2H]c1c([2H])c(-c2nc(-c3ccc(-c4ccccc4)cc3)nc(-c3ccc(-c4ccccc4)cc3)n2)c([2H])c(-c2c([2H])c([2H])c3c(oc4c([2H])c([2H])c([2H])c([2H])c43)c2[2H])c1[2H]] | 68% |
| 58 | 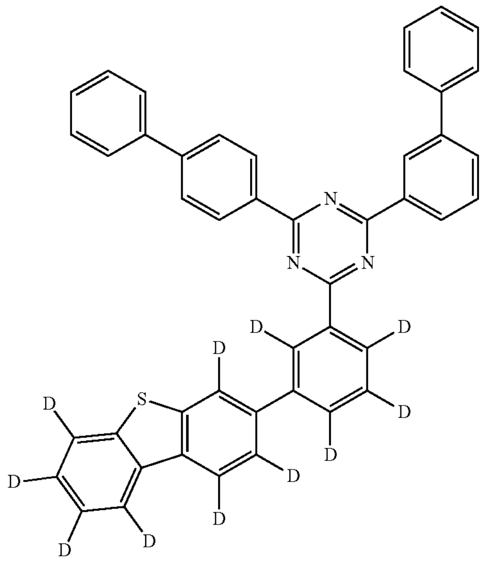 [SMILES: [2H]c1c([2H])c(-c2nc(-c3ccc(-c4ccccc4)cc3)nc(-c3cccc(-c4ccccc4)c3)n2)c([2H])c(-c2c([2H])c([2H])c3c(sc4c([2H])c([2H])c([2H])c([2H])c43)c2[2H])c1[2H]] | 66% |

TABLE 3-continued
| | | |
|---|---|---|
| 61 | 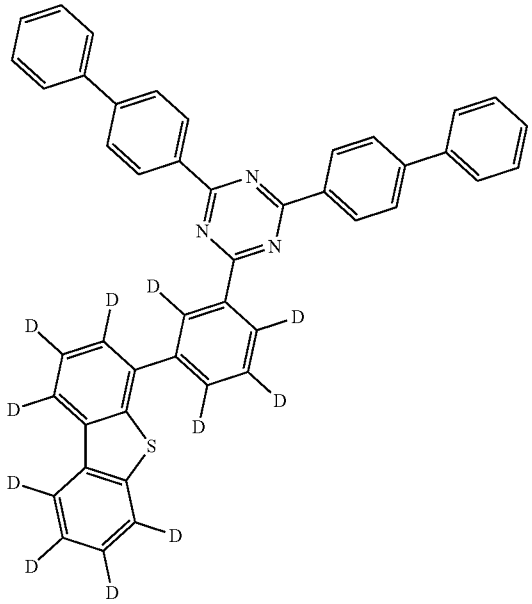 [SMILES: [2H]c1c([2H])c(-c2nc(-c3ccc(-c4ccccc4)cc3)nc(-c3ccc(-c4ccccc4)cc3)n2)c([2H])c(-c2c([2H])c([2H])c([2H])c3c2sc2c([2H])c([2H])c([2H])c([2H])c23)c1[2H]] | 67% |
| 62 | 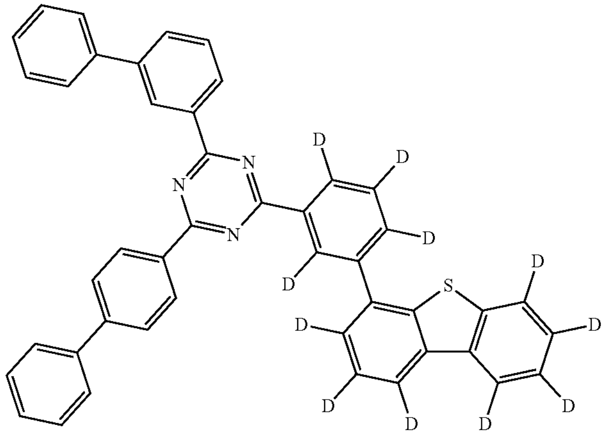 [SMILES: [2H]c1c([2H])c(-c2nc(-c3ccc(-c4ccccc4)cc3)nc(-c3cccc(-c4ccccc4)c3)n2)c([2H])c(-c2c([2H])c([2H])c([2H])c3c2sc2c([2H])c([2H])c([2H])c([2H])c23)c1[2H]] | 70% |
| 64 | 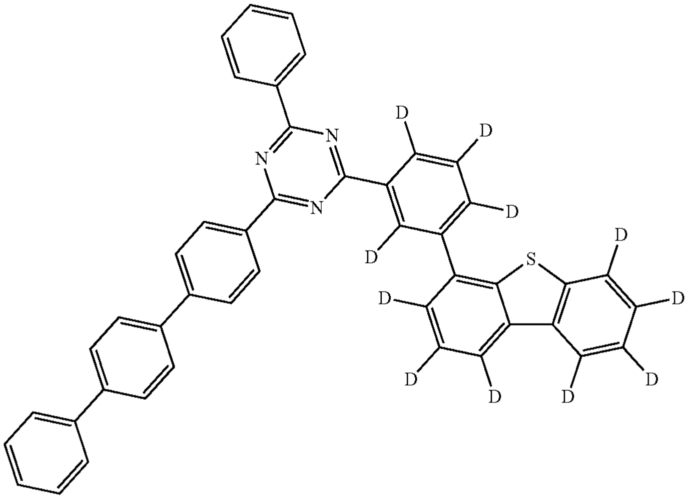 [SMILES: [2H]c1c([2H])c(-c2nc(-c3ccccc3)nc(-c3ccc(-c4ccc(-c5ccccc5)cc4)cc3)n2)c([2H])c(-c2c([2H])c([2H])c([2H])c3c2sc2c([2H])c([2H])c([2H])c([2H])c23)c1[2H]] | 69% |

TABLE 3-continued
| | | |
|---|---|---|
| 65 | 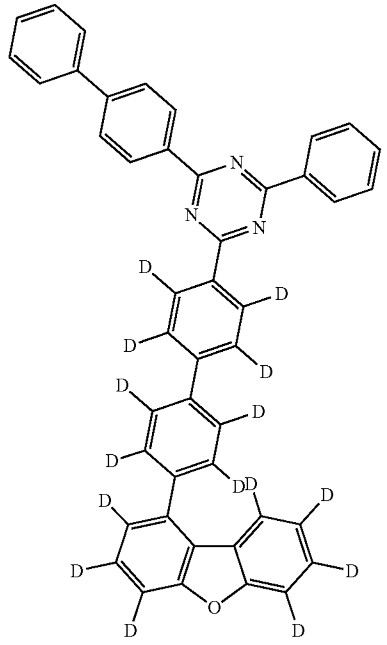 [SMILES: [2H]c1c([2H])c(-c2c([2H])c([2H])c(-c3c([2H])c([2H])c([2H])c4oc5c([2H])c([2H])c([2H])c([2H])c5c34)c([2H])c2[2H])c([2H])c([2H])c1-c1nc(-c2ccccc2)nc(-c2ccc(-c3ccccc3)cc2)n1] | 68% |
| 74 | 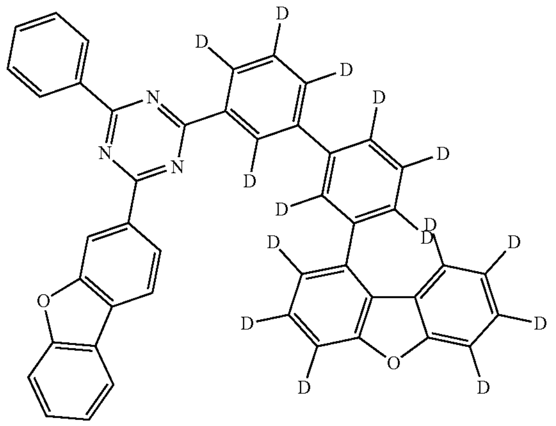 [SMILES: [2H]c1c([2H])c(-c2nc(-c3ccccc3)nc(-c3ccc4c(c3)oc3ccccc34)n2)c([2H])c(-c2c([2H])c([2H])c([2H])c(-c3c([2H])c([2H])c([2H])c4oc5c([2H])c([2H])c([2H])c([2H])c5c34)c2[2H])c1[2H]] | 66% |

TABLE 3-continued
| | | |
|---|---|---|
| 97 | 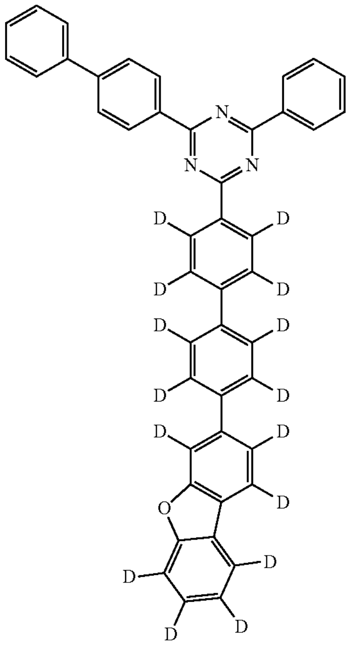 [SMILES: [2H]c1c([2H])c(-c2c([2H])c([2H])c(-c3c([2H])c([2H])c4c(oc5c([2H])c([2H])c([2H])c([2H])c54)c3[2H])c([2H])c2[2H])c([2H])c([2H])c1-c1nc(-c2ccccc2)nc(-c2ccc(-c3ccccc3)cc2)n1] | 67% |
| 115 | 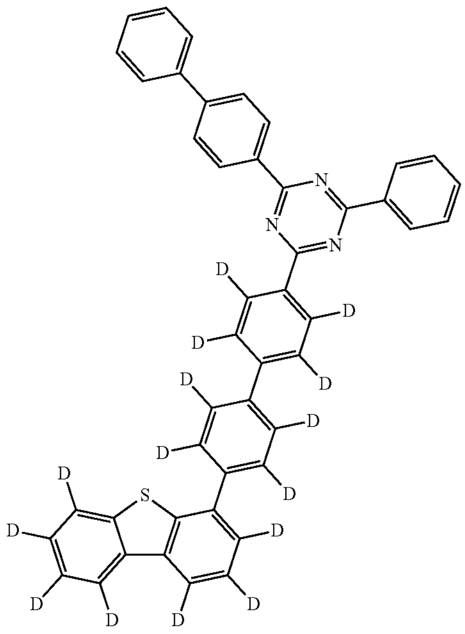 [SMILES: [2H]c1c([2H])c(-c2c([2H])c([2H])c(-c3c([2H])c([2H])c([2H])c4c3sc3c([2H])c([2H])c([2H])c([2H])c34)c([2H])c2[2H])c([2H])c([2H])c1-c1nc(-c2ccccc2)nc(-c2ccc(-c3ccccc3)cc2)n1] | 70% |

TABLE 3-continued
| | | |
|---|---|---|
| 123 | 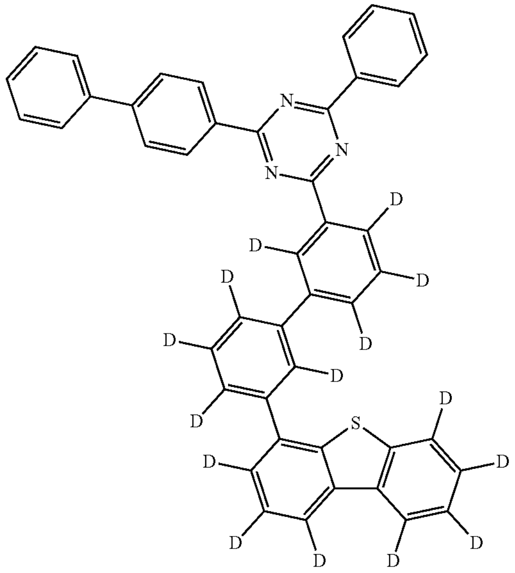 [SMILES: [2H]c1c([2H])c(-c2nc(-c3ccccc3)nc(-c3ccc(-c4ccccc4)cc3)n2)c([2H])c(-c2c([2H])c([2H])c([2H])c(-c3c([2H])c([2H])c([2H])c4c3sc3c([2H])c([2H])c([2H])c([2H])c34)c2[2H])c1[2H]] | 69% |
| 124 | 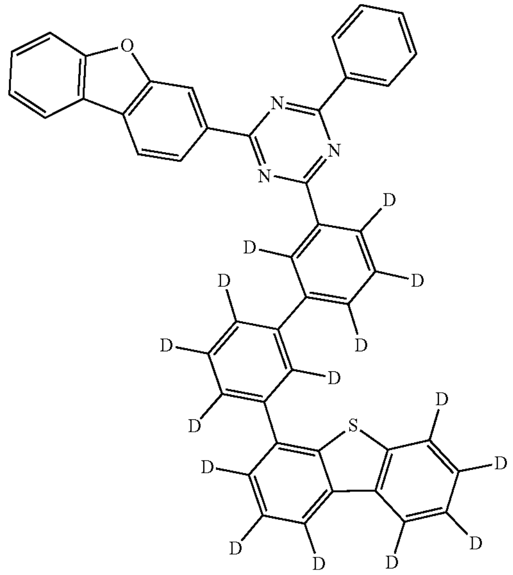 [SMILES: [2H]c1c([2H])c(-c2nc(-c3ccccc3)nc(-c3ccc4c(c3)oc3ccccc34)n2)c([2H])c(-c2c([2H])c([2H])c([2H])c(-c3c([2H])c([2H])c([2H])c4c3sc3c([2H])c([2H])c([2H])c([2H])c34)c2[2H])c1[2H]] | 68% |

TABLE 3-continued
| | | |
|---|---|---|
| 127 | 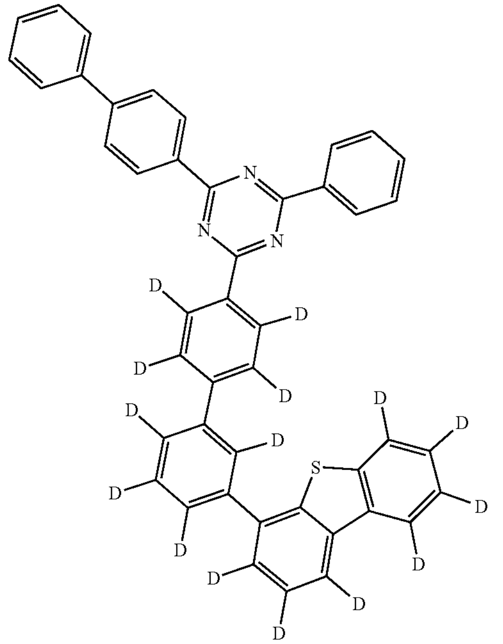 [SMILES: [2H]c1c([2H])c(-c2c([2H])c([2H])c(-c3nc(-c4ccccc4)nc(-c4ccc(-c5ccccc5)cc4)n3)c([2H])c2[2H])c([2H])c(-c2c([2H])c([2H])c([2H])c3c2sc2c([2H])c([2H])c([2H])c([2H])c23)c1[2H]] | 66% |
| 129 | 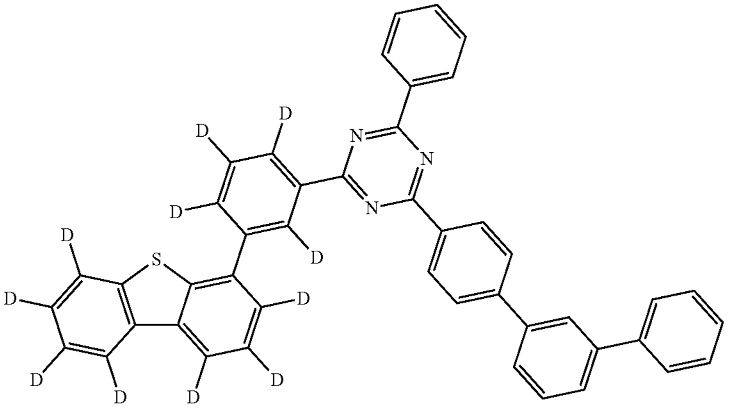 [SMILES: [2H]c1c([2H])c(-c2nc(-c3ccccc3)nc(-c3ccc(-c4cccc(-c5ccccc5)c4)cc3)n2)c([2H])c(-c2c([2H])c([2H])c([2H])c3c2sc2c([2H])c([2H])c([2H])c([2H])c23)c1[2H]] | 67% |
| 139 | 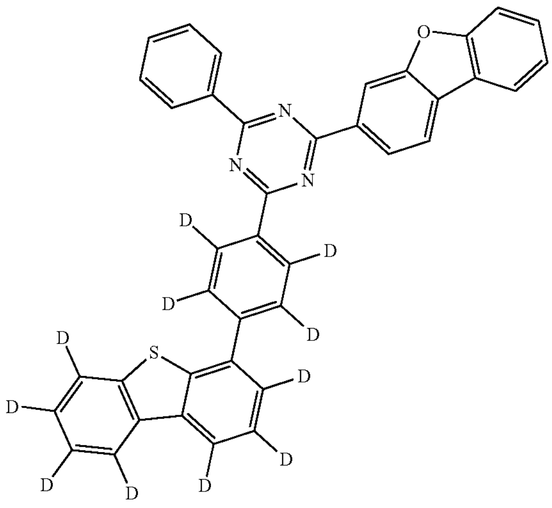 [SMILES: [2H]c1c([2H])c(-c2c([2H])c([2H])c([2H])c3c2sc2c([2H])c([2H])c([2H])c([2H])c23)c([2H])c([2H])c1-c1nc(-c2ccccc2)nc(-c2ccc3c(c2)oc2ccccc23)n1] | 70% |

TABLE 3-continued
| | | |
|---|---|---|
| 9 | 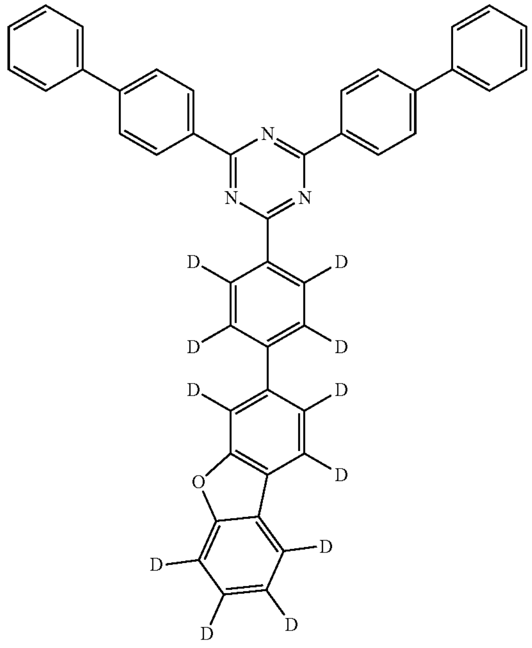 [SMILES: [2H]c1c([2H])c(-c2c([2H])c([2H])c3c(oc4c([2H])c([2H])c([2H])c([2H])c43)c2[2H])c([2H])c([2H])c1-c1nc(-c2ccc(-c3ccccc3)cc2)nc(-c2ccc(-c3ccccc3)cc2)n1] | 66% |
| 12 | 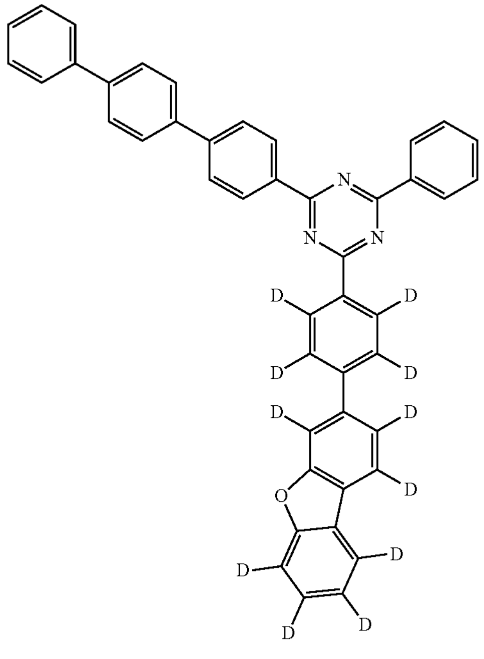 [SMILES: [2H]c1c([2H])c(-c2c([2H])c([2H])c3c(oc4c([2H])c([2H])c([2H])c([2H])c43)c2[2H])c([2H])c([2H])c1-c1nc(-c2ccccc2)nc(-c2ccc(-c3ccc(-c4ccccc4)cc3)cc2)n1] | 67% |

TABLE 3-continued
| | | |
|---|---|---|
| 17 | 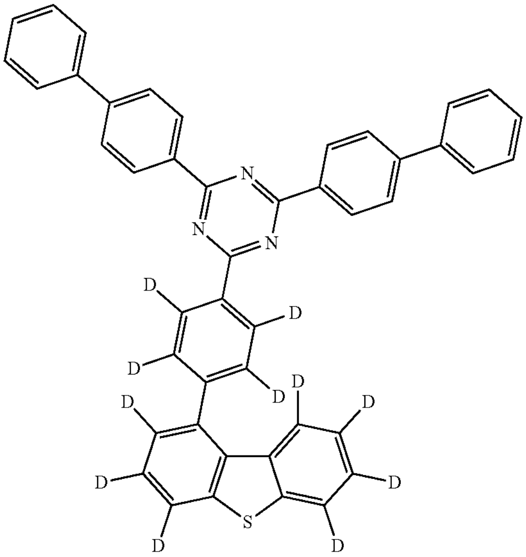 [SMILES: [2H]c1c([2H])c(-c2c([2H])c([2H])c([2H])c3sc4c([2H])c([2H])c([2H])c([2H])c4c23)c([2H])c([2H])c1-c1nc(-c2ccc(-c3ccccc3)cc2)nc(-c2ccc(-c3ccccc3)cc2)n1] | 70% |
| 26 | 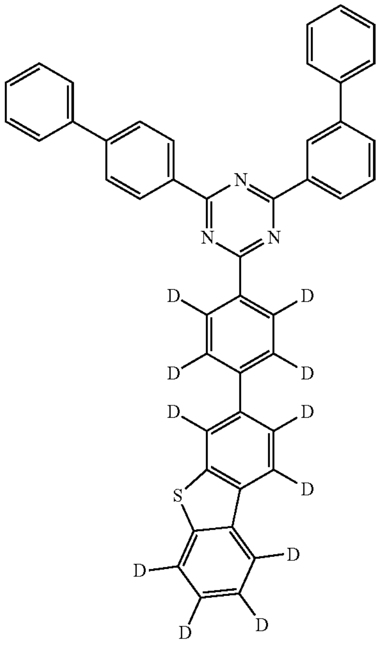 [SMILES: [2H]c1c([2H])c(-c2c([2H])c([2H])c3c(sc4c([2H])c([2H])c([2H])c([2H])c43)c2[2H])c([2H])c([2H])c1-c1nc(-c2ccc(-c3ccccc3)cc2)nc(-c2cccc(-c3ccccc3)c2)n1] | 69% |

TABLE 3-continued
| | | |
|---|---|---|
| 29 | 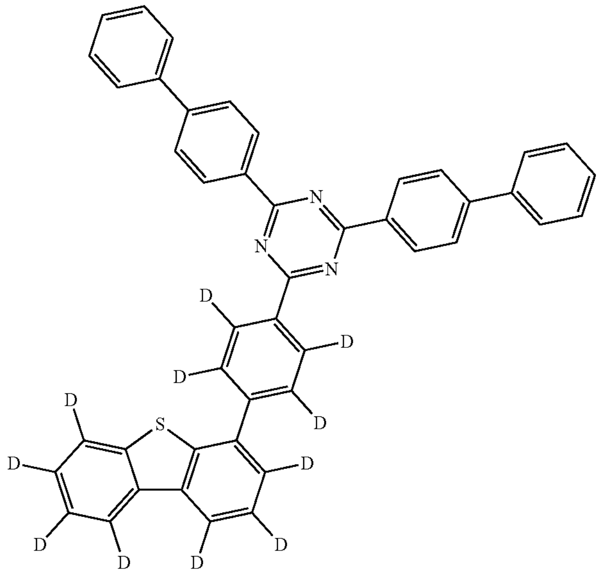 [SMILES: [2H]c1c([2H])c(-c2c([2H])c([2H])c([2H])c3c2sc2c([2H])c([2H])c([2H])c([2H])c23)c([2H])c([2H])c1-c1nc(-c2ccc(-c3ccccc3)cc2)nc(-c2ccc(-c3ccccc3)cc2)n1] | 66% |
| 57 | 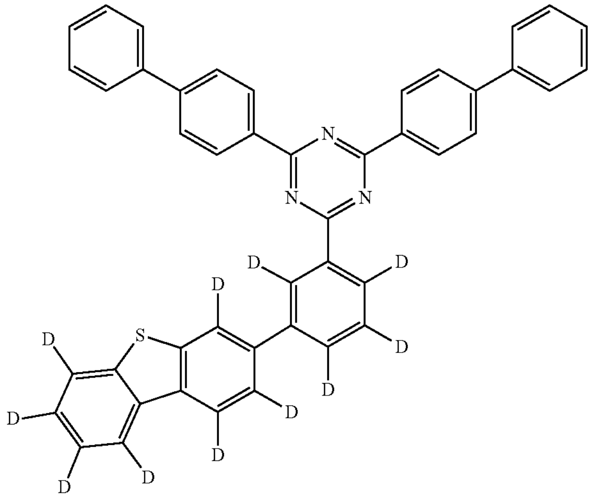 [SMILES: [2H]c1c([2H])c(-c2nc(-c3ccc(-c4ccccc4)cc3)nc(-c3ccc(-c4ccccc4)cc3)n2)c([2H])c(-c2c([2H])c([2H])c3c(sc4c([2H])c([2H])c([2H])c([2H])c43)c2[2H])c1[2H]] | 67% |

TABLE 3-continued
| | | |
|---|---|---|
| 68 | 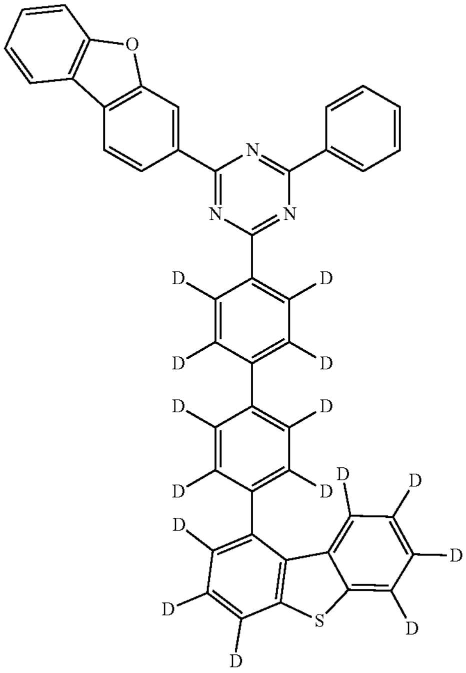 [SMILES: [2H]c1c([2H])c(-c2c([2H])c([2H])c(-c3c([2H])c([2H])c([2H])c4sc5c([2H])c([2H])c([2H])c([2H])c5c34)c([2H])c2[2H])c([2H])c([2H])c1-c1nc(-c2ccccc2)nc(-c2ccc3c(c2)oc2ccccc23)n1] | 70% |
| 114 | 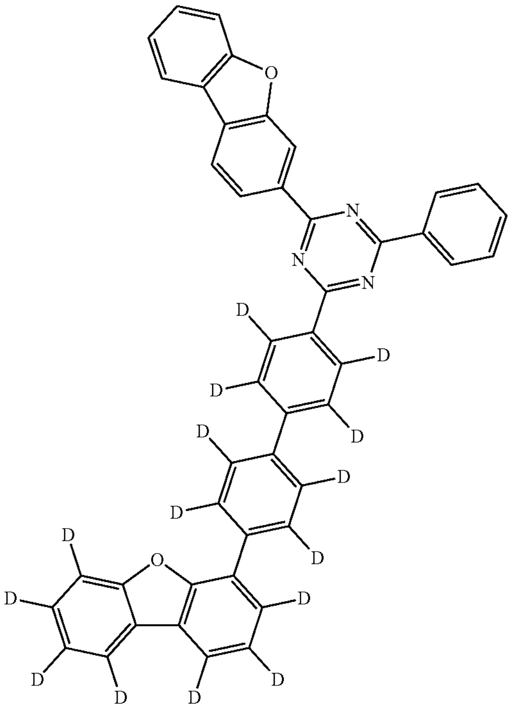 [SMILES: [2H]c1c([2H])c(-c2c([2H])c([2H])c(-c3c([2H])c([2H])c([2H])c4c3oc3c([2H])c([2H])c([2H])c([2H])c34)c([2H])c2[2H])c([2H])c([2H])c1-c1nc(-c2ccccc2)nc(-c2ccc3c(c2)oc2ccccc23)n1] | 69% |

TABLE 3-continued
118
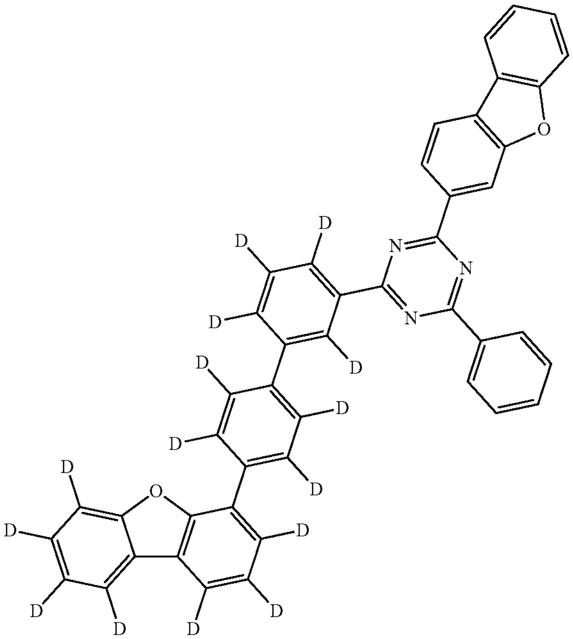 [SMILES: [2H]c1c([2H])c(-c2nc(-c3ccccc3)nc(-c3ccc4c(c3)oc3ccccc34)n2)c([2H])c(-c2c([2H])c([2H])c(-c3c([2H])c([2H])c([2H])c4c3oc3c([2H])c([2H])c([2H])c([2H])c34)c([2H])c2[2H])c1[2H]]
66%
119
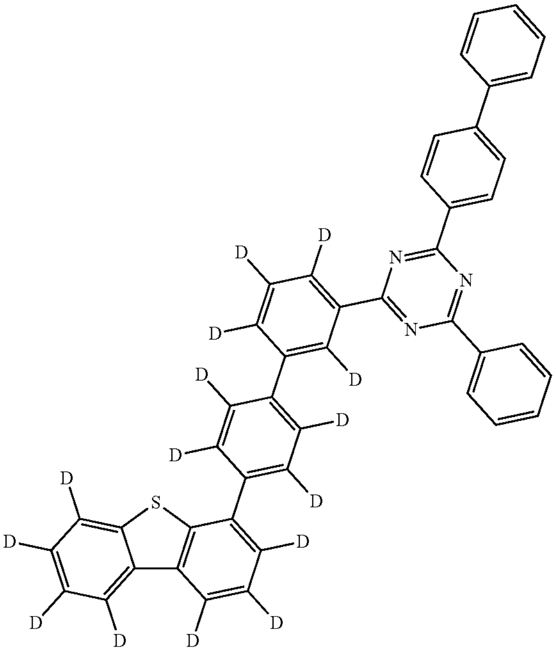 [SMILES: [2H]c1c([2H])c(-c2nc(-c3ccccc3)nc(-c3ccc(-c4ccccc4)cc3)n2)c([2H])c(-c2c([2H])c([2H])c(-c3c([2H])c([2H])c([2H])c4c3sc3c([2H])c([2H])c([2H])c([2H])c34)c([2H])c2[2H])c1[2H]]
67%

TABLE 3-continued
| | | |
|---|---|---|
| 140 | 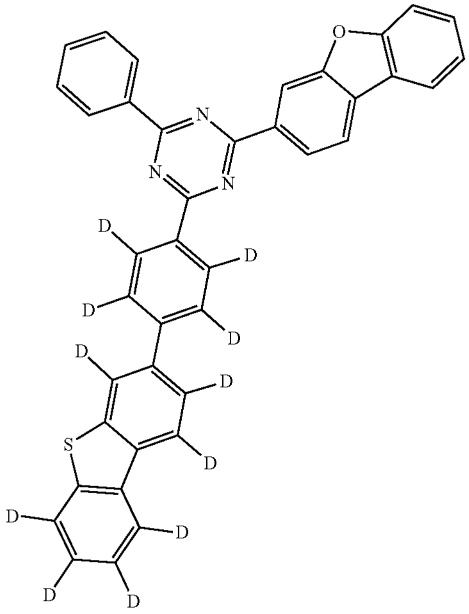 [SMILES: [2H]c1c([2H])c(-c2c([2H])c([2H])c3c(sc4c([2H])c([2H])c([2H])c([2H])c43)c2[2H])c([2H])c([2H])c1-c1nc(-c2ccccc2)nc(-c2ccc3c(c2)oc2ccccc23)n1] | 70% |
Preparation Example
<Preparation Example 2> Preparation of Compound 141
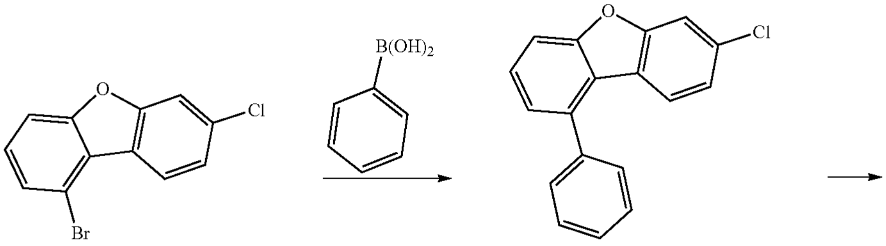
141-P6 141-P5
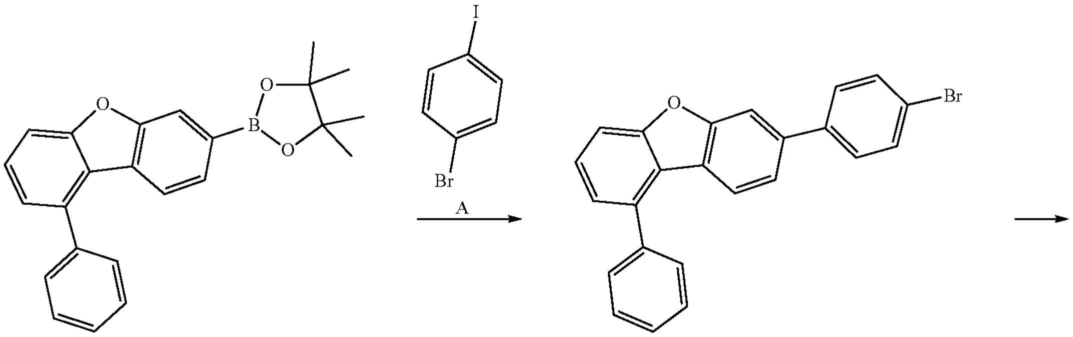
141-P4 141-P3

-continued
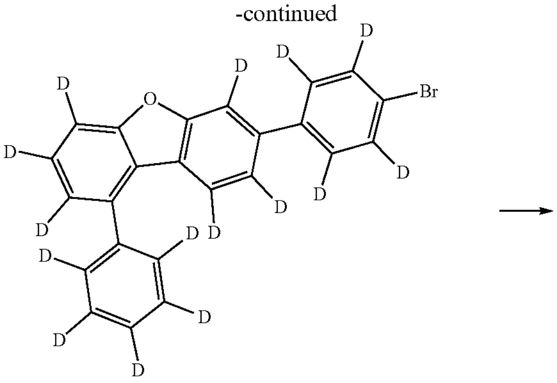
141-P2
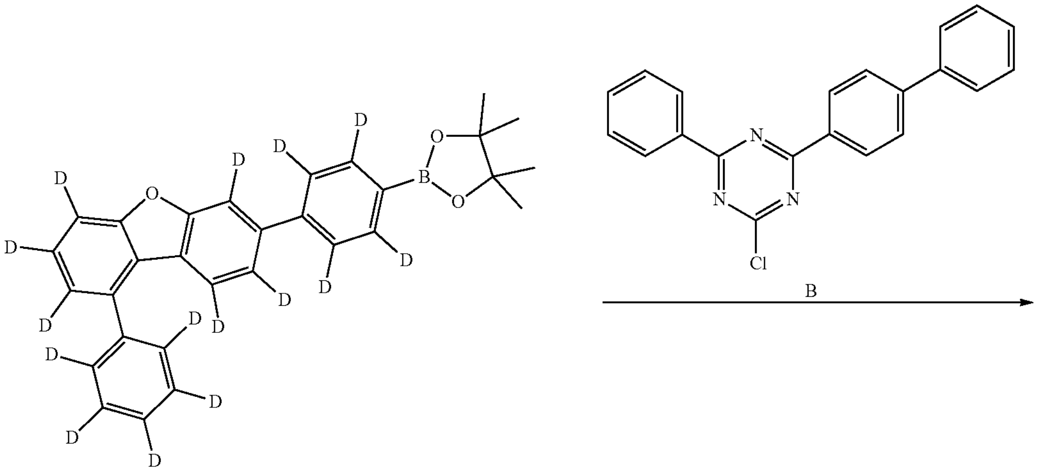
141-P1
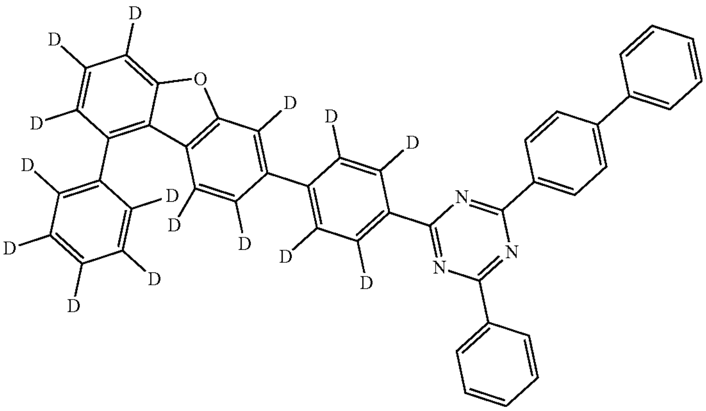
141

1) Preparation of Compound 141-P5

Compound 141-P6 (22.79 g, 80.94 mmol) and phenylboronic acid (9.8 g, 80.94 mmol) were dissolved in 1,4-dioxane (250 mL) and distilled water (50 mL), and after introducing $Pd(PPh_3)_4$ (4.67 g, 4.047 mmol) and $K_2CO_3$ (28 g, 202.35 mmol) thereto, the mixture was stirred for 16 hours under reflux. After the reaction was completed, ethyl acetate was introduced to the reaction solution for dissolution. The result was extracted with distilled water, and after drying the organic layer with anhydrous $MgSO_4$, the solvent was removed using a rotary evaporator. After that, the result was purified by column chromatography using dichloromethane and hexane as a developing solvent to obtain Compound 141-P5 (16.9 g, yield 75%).

2) Preparation of Compound 141-P4

Compound 141-P5 (16.9 g, 60.70 mmol) and 4,4,4',4',5,5,5',5'-octamethyl-2,2'-bi(1,3,2-dioxaborolane) (23.12 g, 91.05 mmol) were dissolved in 1,4-dioxane (170 mL), and after introducing $Pd_2(dba)_3$ (2.78 g, 3.03 mmol), potassium acetate (14.87 g, 151.75 mmol) and S phos (2.50 g, 6.07 mmol) thereto, the mixture was stirred for 16 hours under reflux. After the reaction was completed, ethyl acetate was introduced to the reaction solution for dissolution. The result was extracted with distilled water, and after drying the organic layer with anhydrous $MgSO_4$, the solvent was removed using a rotary evaporator. After that, the result was purified by column chromatography using dichloromethane and hexane as a developing solvent to obtain Compound 141-P4 (17.98 g, yield=80%).

3) Preparation of Compound 141-P3

Compound 141-P4 (17.98 g, 48.56 mmol) and 1-bromo-4-iodobenzene (17.86 g, 63.13 mmol) were dissolved in 1,4-dioxane (220 mL) and distilled water (45 mL), and after introducing $Pd(PPh_3)_4$ (2.80 g, 2.43 mmol) and $K_2CO_3$ (16.78 g, 121.4 mmol) thereto, the mixture was stirred for 16 hours under reflux. After the reaction was completed, ethyl acetate was introduced to the reaction solution for dissolution. The result was extracted with distilled water, and after drying the organic layer with anhydrous $MgSO_4$, the solvent was removed using a rotary evaporator. After that, the result was purified by column chromatography using dichloromethane and hexane as a developing solvent to obtain Compound 141-P3 (13.57 g, yield 70%).

4) Preparation of Compound 141-P2

Compound 141-P3 (13.57 g, 33.99 mmol) was dissolved in benzene-d6 (678.5 g) and $CF_3SO_3H$ (184.5 g), and stirred for 1 hour at 50° C. After the reaction was completed, the result was quenched with $Na_2CO_3$ in $D_2O$. After the quenching, ethyl acetate was introduced to the mixture solution for dissolution, and after the organic layer was separated and dried with anhydrous $MgSO_4$, the solvent was removed using a rotary evaporator. After that, the result was purified by column chromatography using dichloromethane and hexane as a developing solvent to obtain Compound 141-P2 (9.58 g, yield 68%).

5) Preparation of Compound 141-P1

Compound 141-P2 (9.58 g, 23.11 mmol) and 4,4,4',4',5,5,5',5'-octamethyl-2,2'-bi(1,3,2-dioxaborolane) (8.80 g, 34.67 mmol) were dissolved in 1,4-dioxane (100 mL), and after introducing $Pd(dppf)Cl_2$ (0.85 g, 1.16 mmol) and potassium acetate (6.8 g, 69.33 mmol) thereto, the mixture was stirred for 6 hours under reflux. After the reaction was completed, ethyl acetate was introduced to the reaction solution for dissolution. The result was extracted with distilled water, and after drying the organic layer with anhydrous $MgSO_4$, the solvent was removed using a rotary evaporator. After that, the result was purified by column chromatography using dichloromethane and hexane as a developing solvent to obtain Compound 141-P1 (8.53 g, yield=80%).

6) Preparation of Compound 141

Compound 141-P1 (8.3 g, 18.49 mmol) and 2-([1,1'-biphenyl]-4-yl)-4-chloro-6-phenyl-1,3,5-triazine (6.36 g, 18.49 mmol) were dissolved in 1,4-dioxane (100 mL) and distilled water (20 mL), and after introducing $Pd(PPh_3)_4$ (1.07 g, 0.93 mmol) and $K_2CO_3$ (6.39 g, 46.23 mmol) thereto, the mixture was stirred for 4 hours under reflux. After the reaction was completed, dichloromethane was introduced to the reaction solution for dissolution. The result was extracted with distilled water, and after drying the organic layer with anhydrous $MgSO_4$, the solvent was removed using a rotary evaporator. After that, the result was purified by column chromatography using dichloromethane and hexane as a developing solvent to obtain Compound 141 (8.32 g, yield=70%).

Target compounds of the following Table 4 were synthesized in the same manner as in Preparation Example 2 except that Intermediate 1 of the following Table 4 was used instead of Compound 141-P6, and Intermediate 2 of the following Table 4 was used instead of Compound A.

TABLE 4

| Compound No. | Intermediate 1 | Intermediate 2 | Target Compound | Yield |
|---|---|---|---|---|
| 149 | 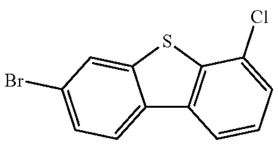 [SMILES: Clc1cccc2c1sc1cc(Br)ccc12] | 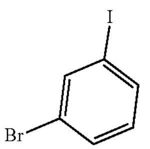 | 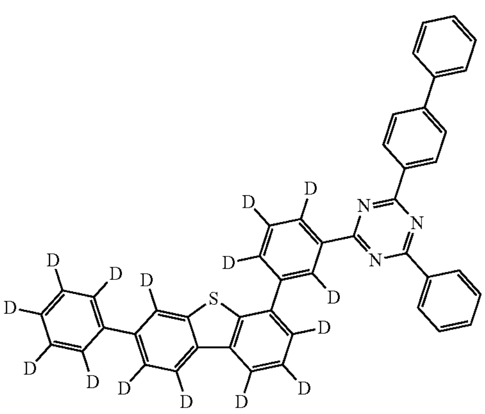 [SMILES: [2H]c1c([2H])c([2H])c(-c2c([2H])c([2H])c3c(sc4c(-c5c([2H])c([2H])c([2H])c(-c6nc(-c7ccccc7)nc(-c7ccc(-c8ccccc8)cc7)n6)c5[2H])c([2H])c([2H])c([2H])c43)c2[2H])c([2H])c1[2H]] | 70% |

TABLE 4-continued
| Compound No. | Intermediate 1 | Intermediate 2 | Target Compound | Yield |
|---|---|---|---|---|
| 150 | 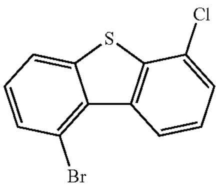 [SMILES: Clc1cccc2c1sc1cccc(Br)c12] | 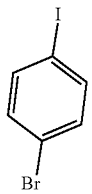 | 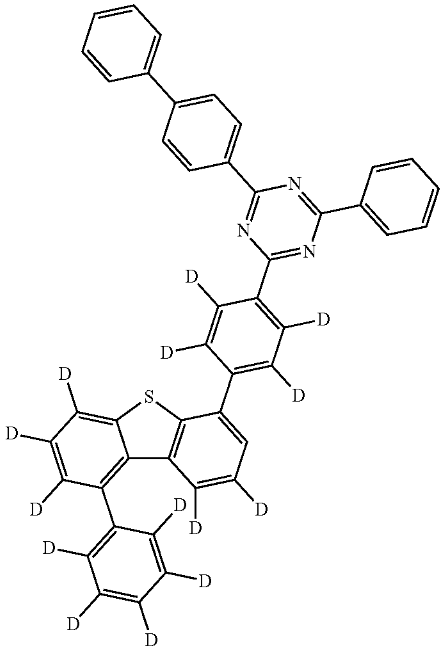 [SMILES: [2H]c1cc(-c2c([2H])c([2H])c(-c3nc(-c4ccccc4)nc(-c4ccc(-c5ccccc5)cc4)n3)c([2H])c2[2H])c2sc3c([2H])c([2H])c([2H])c(-c4c([2H])c([2H])c([2H])c([2H])c4[2H])c3c2c1[2H]] | 69% |
| 160 | 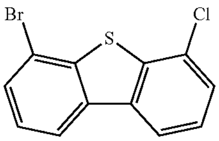 [SMILES: Clc1cccc2c1sc1c(Br)cccc12] | 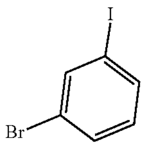 | 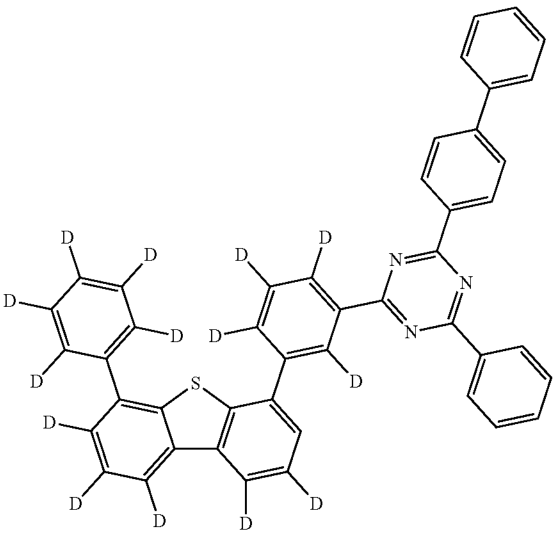 [SMILES: [2H]c1cc(-c2c([2H])c([2H])c([2H])c(-c3nc(-c4ccccc4)nc(-c4ccc(-c5ccccc5)cc4)n3)c2[2H])c2sc3c(-c4c([2H])c([2H])c([2H])c([2H])c4[2H])c([2H])c([2H])c([2H])c3c2c1[2H]] | 68% |

Preparation Example
<Preparation Example 3> Preparation of Compound 181
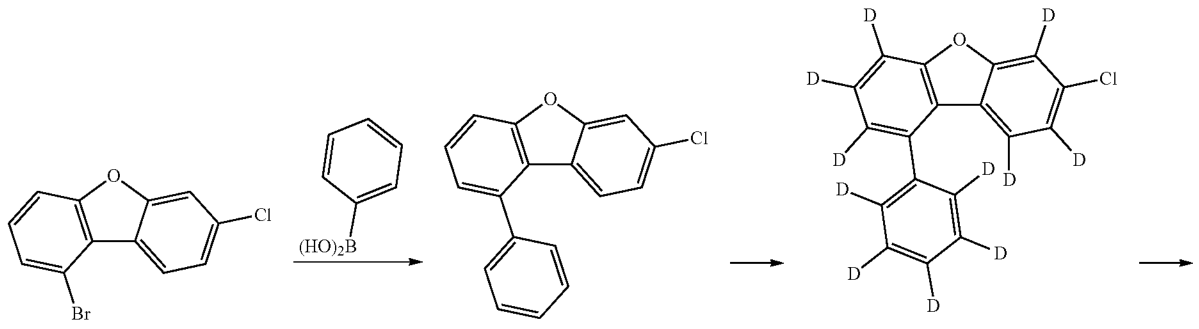
181-P4 181-P3 181-P2
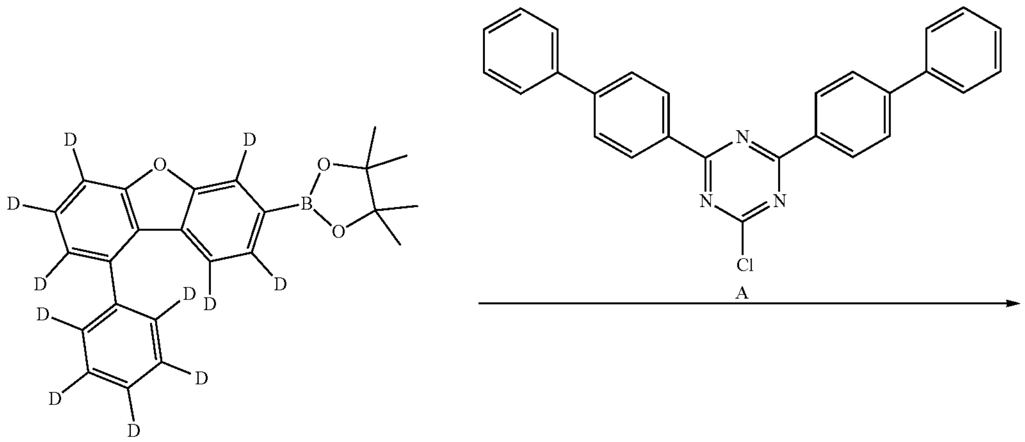
181-P1
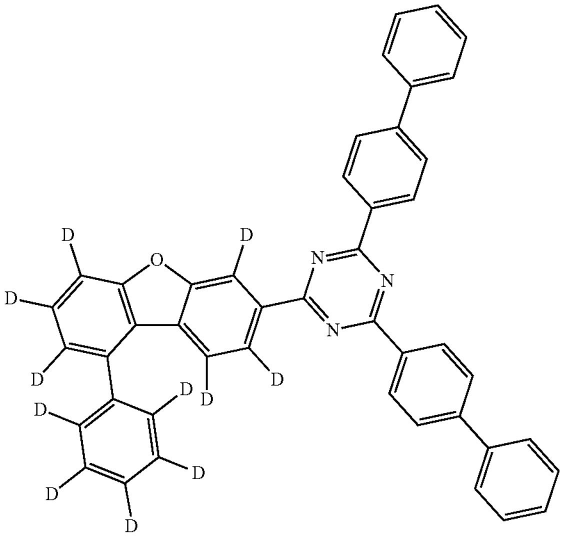
181

1) Preparation of Compound 181-P3

Compound 181-P4 (22.79 g, 80.94 mmol) and phenylboronic acid (9.8 g, 80.94 mmol) were dissolved in 1,4-dioxane (250 mL) and distilled water (50 mL), and after introducing $Pd(PPh_3)_4$ (4.67 g, 4.047 mmol) and $K_2CO_3$ (28 g, 202.35 mmol) thereto, the mixture was stirred for 16 hours under reflux. After the reaction was completed, ethyl acetate was introduced to the reaction solution for dissolution. The result was extracted with distilled water, and after drying the organic layer with anhydrous $MgSO_4$, the solvent was removed using a rotary evaporator. After that, the result was purified by column chromatography using dichloromethane and hexane as a developing solvent to obtain Compound 181-P3 (16.9 g, yield 75%).

2) Preparation of Compound 181-P2

Compound 3-P3 (16.9 g, 60.70 mmol) was dissolved in benzene-d6 (845 g) and $CF_3SO_3H$ (230 g), and stirred for 1 hour at 50° C. After the reaction was completed, the result was quenched with $Na_2CO_3$ in $D_2O$. After the quenching, ethyl acetate was introduced to the mixture solution for dissolution, and after the organic layer was separated and dried with anhydrous $MgSO_4$, the solvent was removed using a rotary evaporator. After that, the result was purified by column chromatography using dichloromethane and hexane as a developing solvent to obtain Compound 181-P2 (11.96 g, yield 68%).

3) Preparation of Compound 181-P1

Compound 181-P2 (11.96 g, 41.28 mmol) and 4,4,4',4',5,5,5',5'-octamethyl-2,2'-bi(1,3,2-dioxaborolane) (15.72 g, 61.92 mmol) were dissolved in 1,4-dioxane (120 mL), and after introducing $Pd_2(dba)_3$ (1.89 g, 2.06 mmol), potassium acetate (12.14 g, 123.84 mmol) and S phos (1.69 g, 4.12 mmol) thereto, the mixture was stirred for 16 hours under reflux. After the reaction was completed, ethyl acetate was introduced to the reaction solution for dissolution. The result was extracted with distilled water, and after drying the organic layer with anhydrous $MgSO_4$, the solvent was removed using a rotary evaporator. After that, the result was purified by column chromatography using dichloromethane and hexane as a developing solvent to obtain Compound 181-P1 (12.6 g, yield=80%).

4) Preparation of Compound 181

Compound 181-P1 (12.6 g, 33.02 mmol) and 2,4-di([1,1'-biphenyl]-4-yl)-6-chloro-1,3,5-triazine (13.87 g, 30.91 mmol) were dissolved in 1,4-dioxane (125 mL) and distilled water (25 mL), and after introducing $Pd(PPh_3)_4$ (1.91 g, 1.65 mmol) and $K_2CO_3$ (11.41 g, 82.55 mmol) thereto, the mixture was stirred for 5 hours under reflux. After the reaction was completed, dichloromethane was introduced to the reaction solution for dissolution. The result was extracted with distilled water, and after drying the organic layer with anhydrous $MgSO_4$, the solvent was removed using a rotary evaporator. After that, the result was purified by column chromatography using dichloromethane and hexane as a developing solvent to obtain Compound 181 (14.76 g, yield=70%).

Target compounds of the following Table 5 were synthesized in the same manner as in Preparation Example 3 except that Intermediate 1 of the following Table 5 was used instead of Compound 181-P4, and Intermediate 2 of the following Table 5 was used instead of Compound A.

TABLE 5

| Compound No. | Intermediate 1 | Intermediate 3 | Target Compound | Yield |
|---|---|---|---|---|
| 183 | 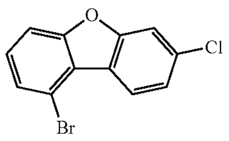 [SMILES: Clc1ccc2c(c1)oc1cccc(Br)c12] | 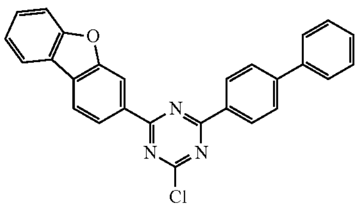 [SMILES: Clc1nc(-c2ccc(-c3ccccc3)cc2)nc(-c2ccc3c(c2)oc2ccccc23)n1] | 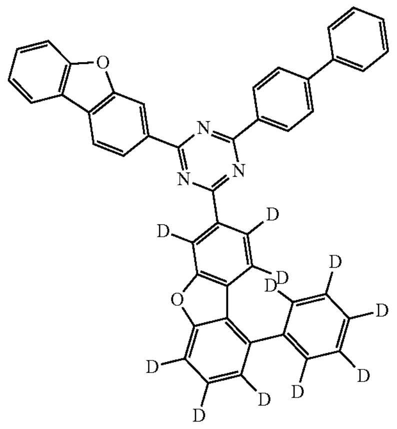 [SMILES: [2H]c1c([2H])c([2H])c(-c2c([2H])c([2H])c([2H])c3oc4c([2H])c(-c5nc(-c6ccc(-c7ccccc7)cc6)nc(-c6ccc7c(c6)oc6ccccc67)n5)c([2H])c([2H])c4c23)c([2H])c1[2H]] | 69% |

TABLE 5-continued
| Compound No. | Intermediate 1 | Intermediate 3 | Target Compound | Yield |
|---|---|---|---|---|
| 185 | 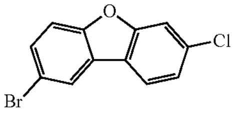 [SMILES: Clc1ccc2c(c1)oc1ccc(Br)cc12] | 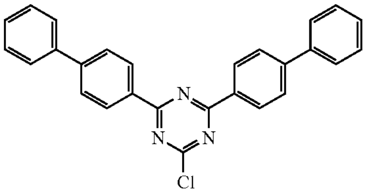 [SMILES: Clc1nc(-c2ccc(-c3ccccc3)cc2)nc(-c2ccc(-c3ccccc3)cc2)n1] | 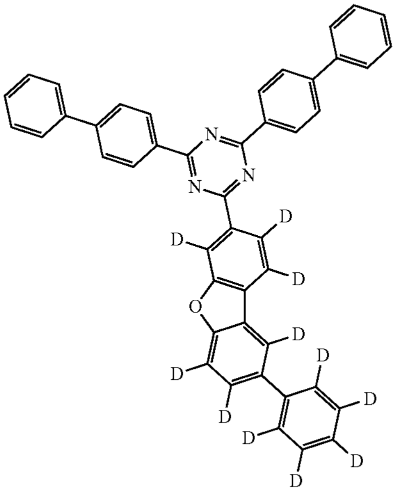 [SMILES: [2H]c1c([2H])c([2H])c(-c2c([2H])c([2H])c3oc4c([2H])c(-c5nc(-c6ccc(-c7ccccc7)cc6)nc(-c6ccc(-c7ccccc7)cc6)n5)c([2H])c([2H])c4c3c2[2H])c([2H])c1[2H]] | 68% |
| 186 | 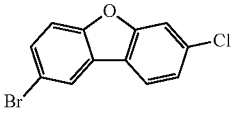 [SMILES: Clc1ccc2c(c1)oc1ccc(Br)cc12] | 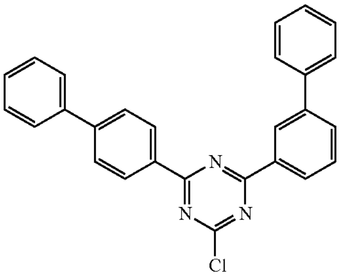 [SMILES: Clc1nc(-c2ccc(-c3ccccc3)cc2)nc(-c2cccc(-c3ccccc3)c2)n1] | 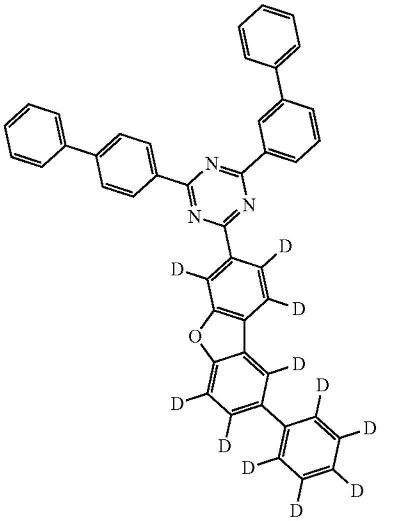 [SMILES: [2H]c1c([2H])c([2H])c(-c2c([2H])c([2H])c3oc4c([2H])c(-c5nc(-c6ccc(-c7ccccc7)cc6)nc(-c6cccc(-c7ccccc7)c6)n5)c([2H])c([2H])c4c3c2[2H])c([2H])c1[2H]] | 70% |
| 189 | 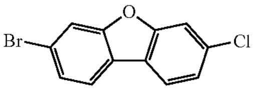 [SMILES: Clc1ccc2c(c1)oc1cc(Br)ccc12] | 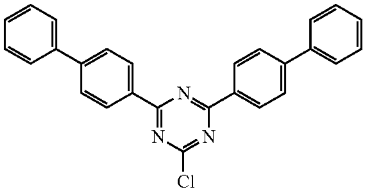 [SMILES: Clc1nc(-c2ccc(-c3ccccc3)cc2)nc(-c2ccc(-c3ccccc3)cc2)n1] | 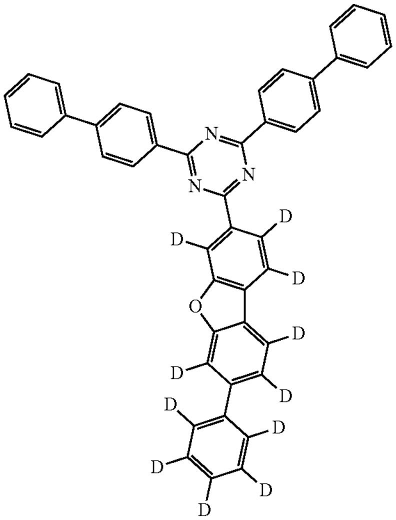 [SMILES: [2H]c1c([2H])c([2H])c(-c2c([2H])c([2H])c3c(oc4c([2H])c(-c5nc(-c6ccc(-c7ccccc7)cc6)nc(-c6ccc(-c7ccccc7)cc6)n5)c([2H])c([2H])c43)c2[2H])c([2H])c1[2H]] | 67% |

TABLE 5-continued
| Compound No. | Intermediate 1 | Intermediate 3 | Target Compound | Yield |
|---|---|---|---|---|
| 197 | 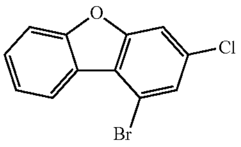 [SMILES: Clc1cc(Br)c2c(c1)oc1ccccc12] | 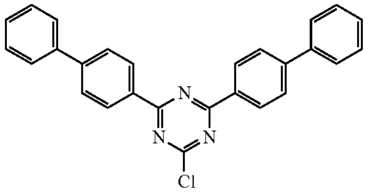 [SMILES: Clc1nc(-c2ccc(-c3ccccc3)cc2)nc(-c2ccc(-c3ccccc3)cc2)n1] | 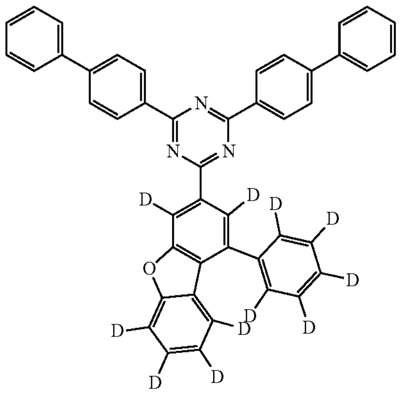 [SMILES: [2H]c1c([2H])c([2H])c(-c2c([2H])c(-c3nc(-c4ccc(-c5ccccc5)cc4)nc(-c4ccc(-c5ccccc5)cc4)n3)c([2H])c3oc4c([2H])c([2H])c([2H])c([2H])c4c23)c([2H])c1[2H]] | 66% |
| 261 | 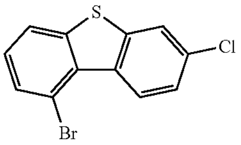 [SMILES: Clc1ccc2c(c1)sc1cccc(Br)c12] | 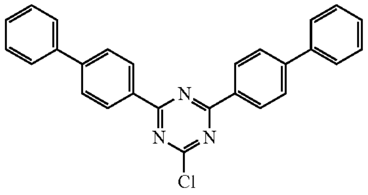 [SMILES: Clc1nc(-c2ccc(-c3ccccc3)cc2)nc(-c2ccc(-c3ccccc3)cc2)n1] | 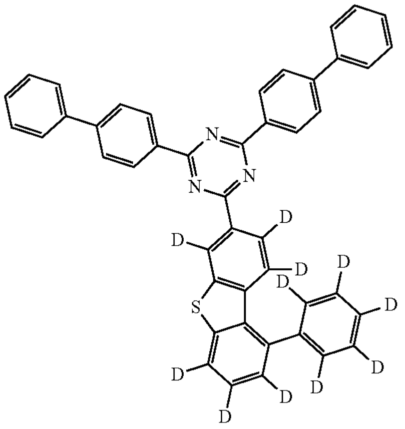 [SMILES: [2H]c1c([2H])c([2H])c(-c2c([2H])c([2H])c([2H])c3sc4c([2H])c(-c5nc(-c6ccc(-c7ccccc7)cc6)nc(-c6ccc(-c7ccccc7)cc6)n5)c([2H])c([2H])c4c23)c([2H])c1[2H]] | 69% |
| 263 | 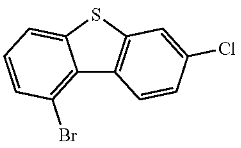 [SMILES: Clc1ccc2c(c1)sc1cccc(Br)c12] | 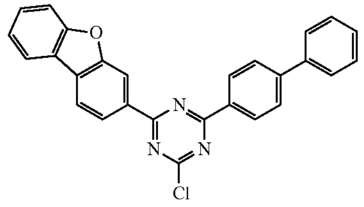 [SMILES: Clc1nc(-c2ccc(-c3ccccc3)cc2)nc(-c2ccc3c(c2)oc2ccccc23)n1] | 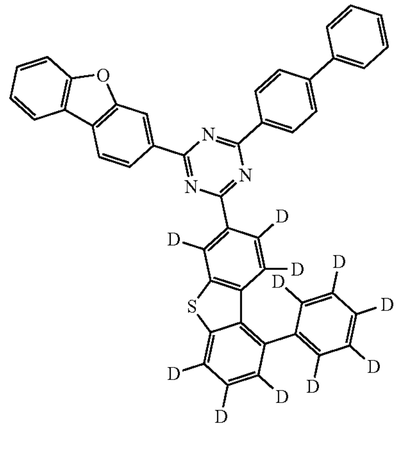 [SMILES: [2H]c1c([2H])c([2H])c(-c2c([2H])c([2H])c([2H])c3sc4c([2H])c(-c5nc(-c6ccc(-c7ccccc7)cc6)nc(-c6ccc7c(c6)oc6ccccc67)n5)c([2H])c([2H])c4c23)c([2H])c1[2H]] | 68% |

TABLE 5-continued
| Compound No. | Intermediate 1 | Intermediate 3 | Target Compound | Yield |
|---|---|---|---|---|
| 274 | 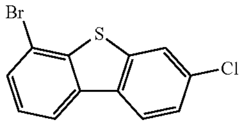 [SMILES: Clc1ccc2c(c1)sc1c(Br)cccc12] | 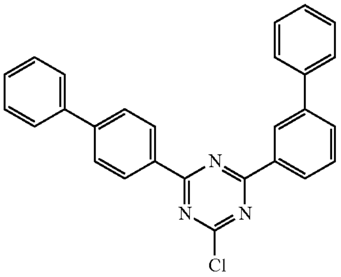 [SMILES: Clc1nc(-c2ccc(-c3ccccc3)cc2)nc(-c2cccc(-c3ccccc3)c2)n1] | 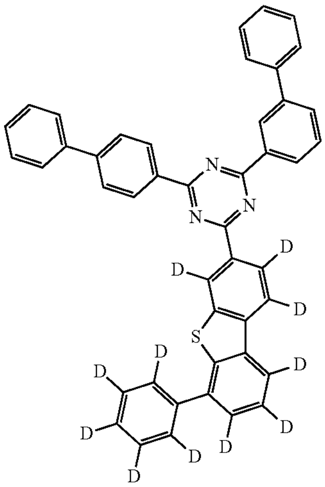 [SMILES: [2H]c1c([2H])c([2H])c(-c2c([2H])c([2H])c([2H])c3c2sc2c([2H])c(-c4nc(-c5ccc(-c6ccccc6)cc5)nc(-c5cccc(-c6ccccc6)c5)n4)c([2H])c([2H])c23)c([2H])c1[2H]] | 70% |
| 325 | 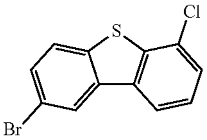 [SMILES: Clc1cccc2c1sc1ccc(Br)cc12] | 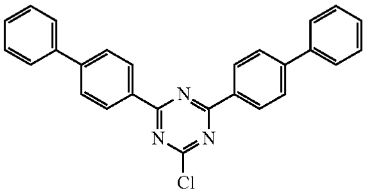 [SMILES: Clc1nc(-c2ccc(-c3ccccc3)cc2)nc(-c2ccc(-c3ccccc3)cc2)n1] | 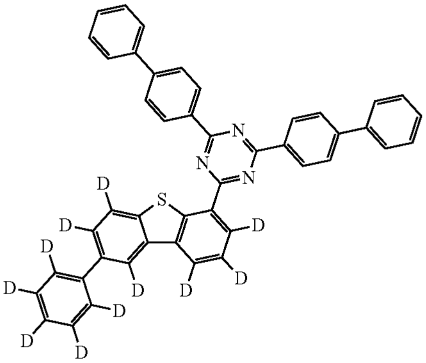 [SMILES: [2H]c1c([2H])c([2H])c(-c2c([2H])c([2H])c3sc4c(-c5nc(-c6ccc(-c7ccccc7)cc6)nc(-c6ccc(-c7ccccc7)cc6)n5)c([2H])c([2H])c([2H])c4c3c2[2H])c([2H])c1[2H]] | 67% |
| 187 | 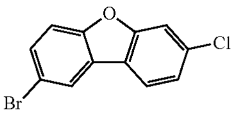 [SMILES: Clc1ccc2c(c1)oc1ccc(Br)cc12] | 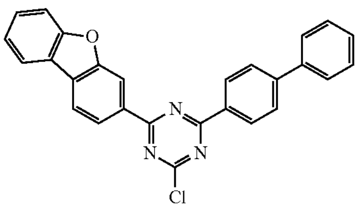 [SMILES: Clc1nc(-c2ccc(-c3ccccc3)cc2)nc(-c2ccc3c(c2)oc2ccccc23)n1] | 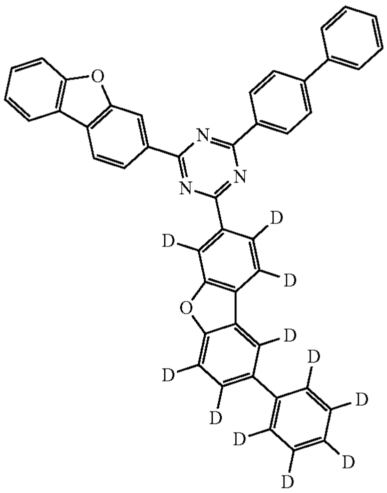 [SMILES: [2H]c1c([2H])c([2H])c(-c2c([2H])c([2H])c3oc4c([2H])c(-c5nc(-c6ccc(-c7ccccc7)cc6)nc(-c6ccc7c(c6)oc6ccccc67)n5)c([2H])c([2H])c4c3c2[2H])c([2H])c1[2H]] | 66% |

TABLE 5-continued
| Compound No. | Intermediate 1 | Intermediate 3 | Target Compound | Yield |
|---|---|---|---|---|
| 193 | 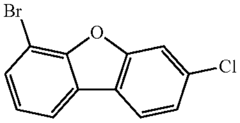 [SMILES: Clc1ccc2c(c1)oc1c(Br)cccc12] | 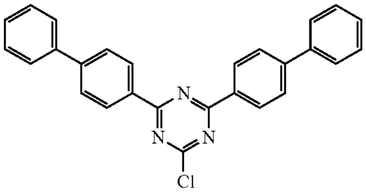 [SMILES: Clc1nc(-c2ccc(-c3ccccc3)cc2)nc(-c2ccc(-c3ccccc3)cc2)n1] | 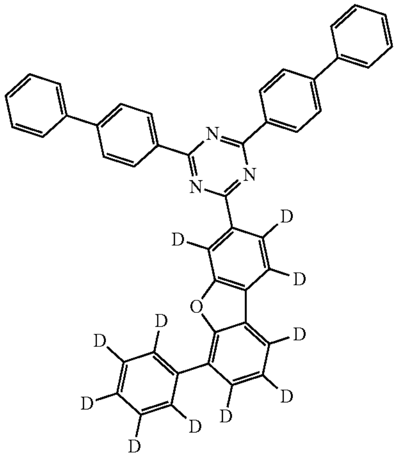 [SMILES: [2H]c1c([2H])c([2H])c(-c2c([2H])c([2H])c([2H])c3c2oc2c([2H])c(-c4nc(-c5ccc(-c6ccccc6)cc5)nc(-c5ccc(-c6ccccc6)cc5)n4)c([2H])c([2H])c23)c([2H])c1[2H]] | 69% |
| 199 | 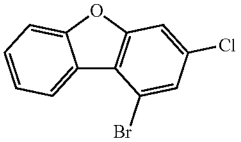 [SMILES: Clc1cc(Br)c2c(c1)oc1ccccc12] | 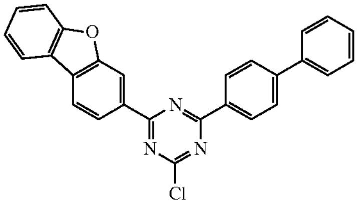 [SMILES: Clc1nc(-c2ccc(-c3ccccc3)cc2)nc(-c2ccc3c(c2)oc2ccccc23)n1] | 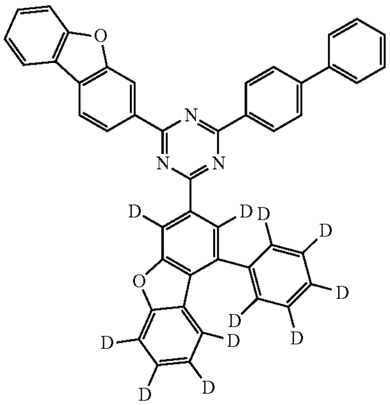 [SMILES: [2H]c1c([2H])c([2H])c(-c2c([2H])c(-c3nc(-c4ccc(-c5ccccc5)cc4)nc(-c4ccc5c(c4)oc4ccccc45)n3)c([2H])c3oc4c([2H])c([2H])c([2H])c([2H])c4c23)c([2H])c1[2H]] | 68% |
| 253 | 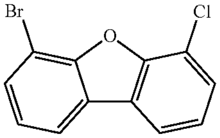 [SMILES: Clc1cccc2c1oc1c(Br)cccc12] | 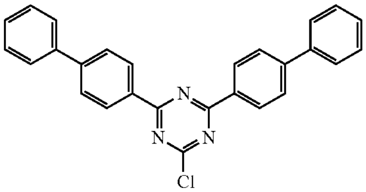 [SMILES: Clc1nc(-c2ccc(-c3ccccc3)cc2)nc(-c2ccc(-c3ccccc3)cc2)n1] | 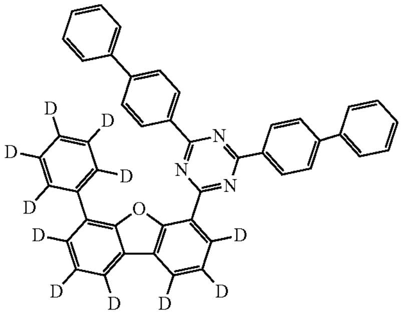 [SMILES: [2H]c1c([2H])c([2H])c(-c2c([2H])c([2H])c([2H])c3c2oc2c(-c4nc(-c5ccc(-c6ccccc6)cc5)nc(-c5ccc(-c6ccccc6)cc5)n4)c([2H])c([2H])c([2H])c23)c([2H])c1[2H]] | 70% |
| 255 | 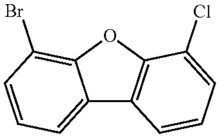 [SMILES: Clc1cccc2c1oc1c(Br)cccc12] | 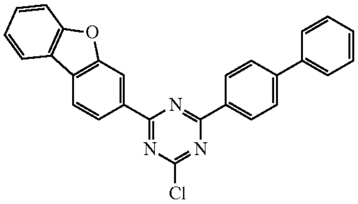 [SMILES: Clc1nc(-c2ccc(-c3ccccc3)cc2)nc(-c2ccc3c(c2)oc2ccccc23)n1] | 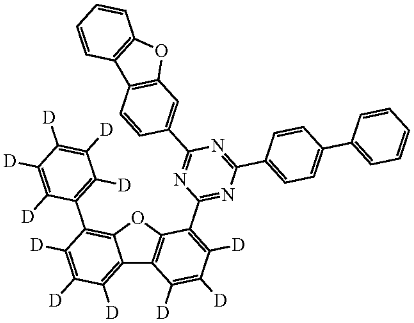 [SMILES: [2H]c1c([2H])c([2H])c(-c2c([2H])c([2H])c([2H])c3c2oc2c(-c4nc(-c5ccc(-c6ccccc6)cc5)nc(-c5ccc6c(c5)oc5ccccc56)n4)c([2H])c([2H])c([2H])c23)c([2H])c1[2H]] | 67% |

TABLE 5-continued
| Compound No. | Intermediate 1 | Intermediate 3 | Target Compound | Yield |
|---|---|---|---|---|
| 501 | 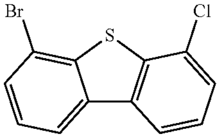 [SMILES: Clc1cccc2c1sc1c(Br)cccc12] | 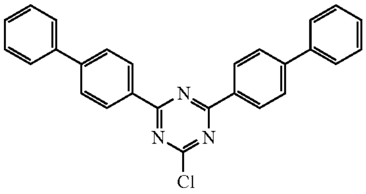 [SMILES: Clc1nc(-c2ccc(-c3ccccc3)cc2)nc(-c2ccc(-c3ccccc3)cc2)n1] | 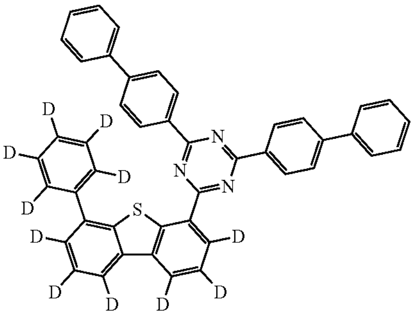 [SMILES: [2H]c1c([2H])c([2H])c(-c2c([2H])c([2H])c([2H])c3c2sc2c(-c4nc(-c5ccc(-c6ccccc6)cc5)nc(-c5ccc(-c6ccccc6)cc5)n4)c([2H])c([2H])c([2H])c23)c([2H])c1[2H]] | 66% |
[Preparation Example 4] Preparation of Compound 2-79
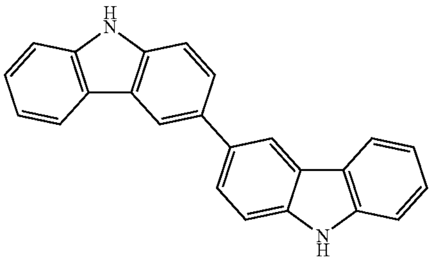
+
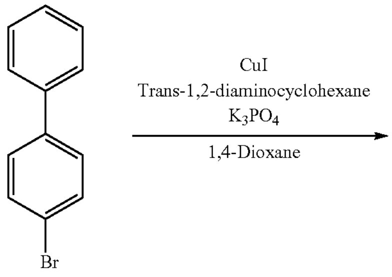
[E]
-continued
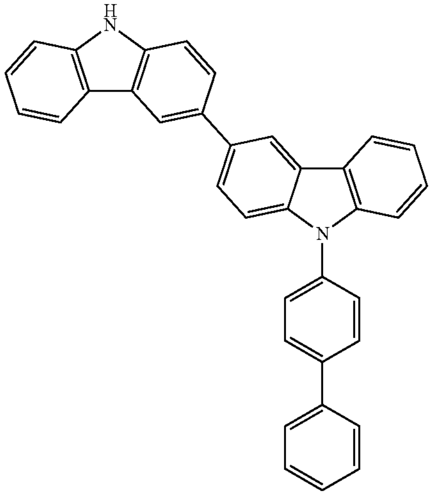
2-79-1
+
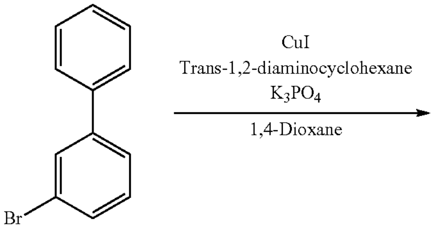
[E']

-continued

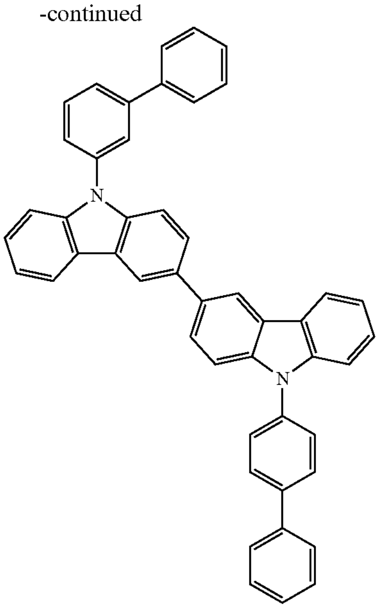

2-79

4-1) Preparation of Intermediate 2-79-1

In a one-neck round bottom flask, 9H,9'H-3,3'-bicarbazole (10 g, 0.030 mol), 4-bromo-1,1'-biphenyl [E] (7.26 g, 0.030 mol), CuI (0.57 g, 0.003 mol), trans-1,2-diaminocyclohexane (0.34 g, 0.003 mol) and $K_3PO_4$ (12.74 g, 0.06 mol) were dissolved in 1,4-dioxane (100 mL), and refluxed for 8 hours at 125° C. After the reaction was completed, the result was extracted by introducing distilled water and DCM thereto at room temperature, and after drying the organic layer with $MgSO_4$, the solvent was removed using a rotary evaporator. The reaction material was purified by column chromatography (DCM:hexane=1:3), and recrystallized with methanol to obtain Intermediate 2-79-1 (13.92 g, yield 94%).

4-2) Preparation of Compound 2-79

In a one-neck round bottom flask, Intermediate 2-2-1 (13.92 g, 0.028 mol), 3-bromo-1,1'-biphenyl [E'] (6.83 g, 0.028 mol), CuI (0.53 g, 0.0028 mol), trans-1,2-diaminocyclohexane (0.32 g, 0.0028 mol) and $K_3PO_4$ (11.89 g, 0.056 mol) were dissolved in 1,4-dioxane (140 mL), and refluxed for 8 hours at 125° C. After the reaction was completed, the result was extracted by introducing distilled water and DCM thereto at room temperature, and after drying the organic layer with $MgSO_4$, the solvent was removed using a rotary evaporator. The reaction material was purified by column chromatography (DCM:hexane=1:3), and recrystallized with methanol to obtain target Compound 2-79 (16.14 g, yield 88%).

When Compound E and Compound E' are the same, Compound E may be introduced in 2 equivalents in Preparation Example 4 to directly synthesize the target compound. In other words, when Compound E and Compound E' are the same, Preparation Example 4-2 may be skipped.

The following target Compound G1 was synthesized in the same manner as in Preparation Example 4 except that Compounds E1 and E'1 of the following Table 6 were used instead of 4-bromo-1,1'-biphenyl [E] and 4-bromo-1,1'-biphenyl [E'].

TABLE 6

| Compound | Compound E1 | Compound E' 1 | Compound G1 | Yield |
|---|---|---|---|---|
| 2-76 | 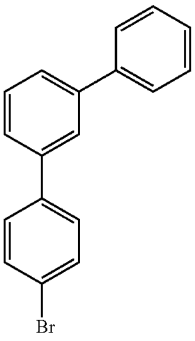 [SMILES: Brc1ccc(-c2cccc(-c3ccccc3)c2)cc1] | 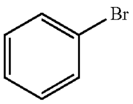 | 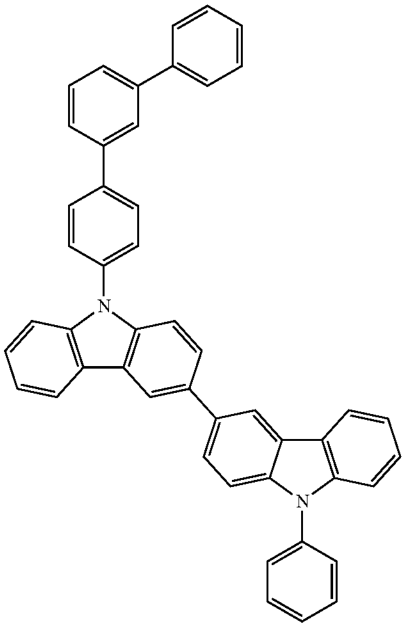 [SMILES: c1ccc(-c2cccc(-c3ccc(-n4c5ccccc5c5cc(-c6ccc7c(c6)c6ccccc6n7-c6ccccc6)ccc54)cc3)c2)cc1] | 72% |

TABLE 6-continued
| Compound | Compound E1 | Compound E' 1 | Compound G1 | Yield |
|---|---|---|---|---|
| 2-77 | 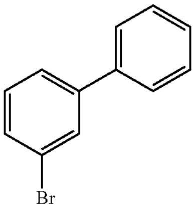 [SMILES: Brc1cccc(-c2ccccc2)c1] | 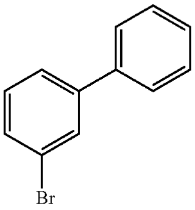 [SMILES: Brc1cccc(-c2ccccc2)c1] | 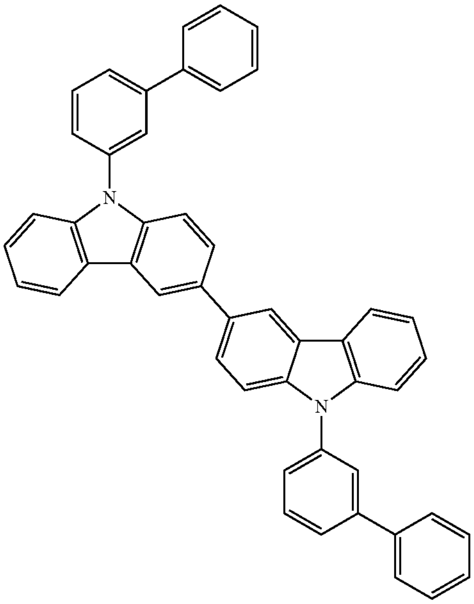 [SMILES: c1ccc(-c2cccc(-n3c4ccccc4c4cc(-c5ccc6c(c5)c5ccccc5n6-c5cccc(-c6ccccc6)c5)ccc43)c2)cc1] | 83% |
| 2-78 | 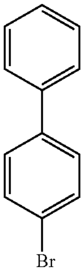 | 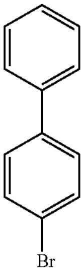 [SMILES: Brc1ccc(-c2ccccc2)cc1] | 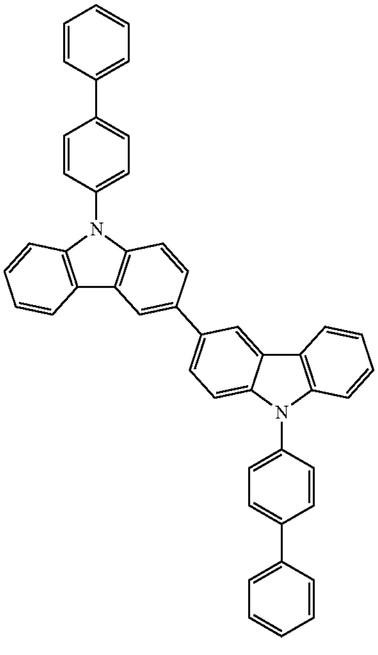 [SMILES: c1ccc(-c2ccc(-n3c4ccccc4c4cc(-c5ccc6c(c5)c5ccccc5n6-c5ccc(-c6ccccc6)cc5)ccc43)cc2)cc1] | 88% |

TABLE 6-continued
| Compound | Compound E1 | Compound E' 1 | Compound G1 | Yield |
|---|---|---|---|---|
| 2-74 | 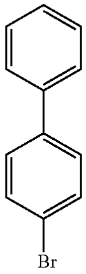 | 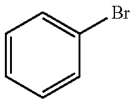 | 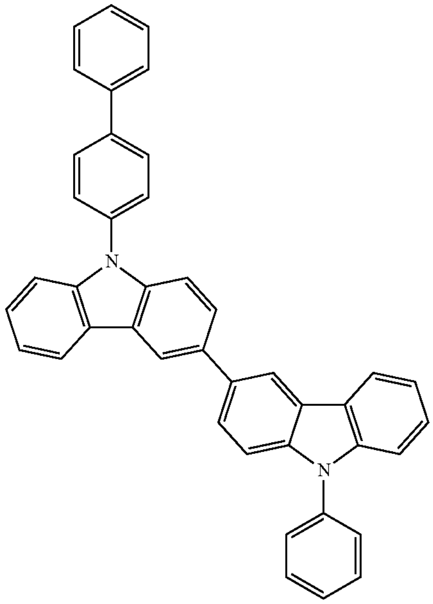 [SMILES: c1ccc(-c2ccc(-n3c4ccccc4c4cc(-c5ccc6c(c5)c5ccccc5n6-c5ccccc5)ccc43)cc2)cc1] | 73% |
[Preparation Example 5] Preparation of Compound 2-57
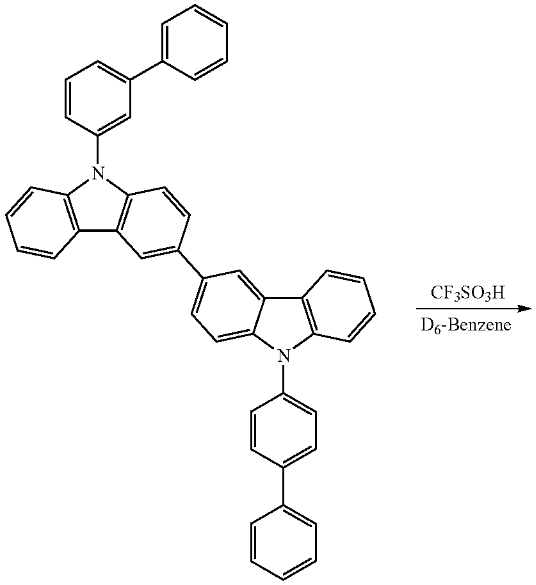
2-79
-continued
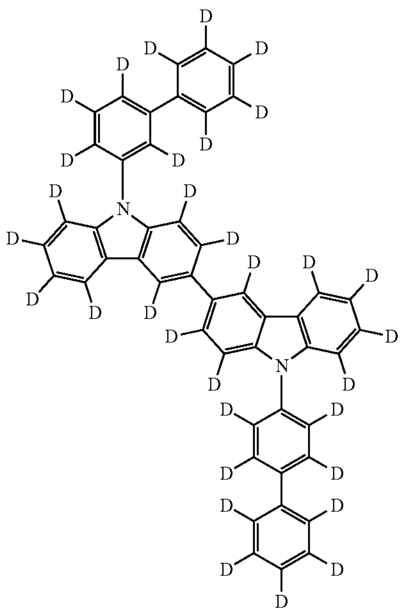
2-57

1) Preparation of Compound 2-57

In a one-neck round bottom flask, a mixture of Intermediate 2-79 (12.17 g, 0.017 mol), triflic acid (51.5 g) and $D_6$-benzene (608.5 mL) was stirred for 1 hour at 50° C. After the reaction was completed, the result was quenched with $Na_2CO_3$ in $D_2O$. After the quenching, DCM was introduced to the mixture solution for dissolution, and after the organic layer was separated and dried with anhydrous $MgSO_4$, the solvent was removed using a rotary evaporator. After that, the result was purified by column chromatography using dichloromethane and hexane as a developing solvent to obtain target Compound 2-57 (8.01 g, yield 70%).

The following target Compound G2 was synthesized in the same manner as in Preparation Example 5 except that Compound E3 of the following Table 7 was used instead of Compound 2-79.

TABLE 7

| Compound | Compound E3 | Compound G3 | Yield |
|---|---|---|---|
| 2-51 | 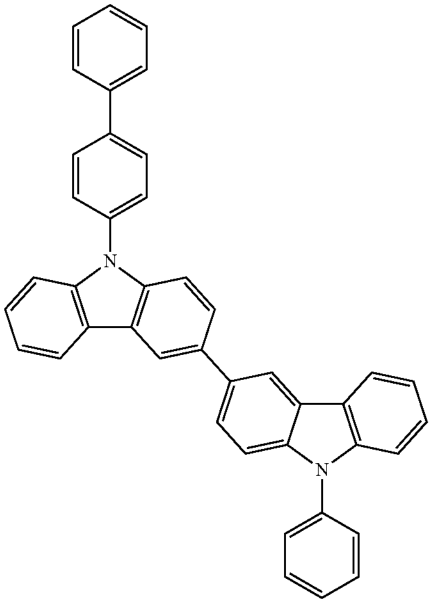 [SMILES: c1ccc(-c2ccc(-n3c4ccccc4c4cc(-c5ccc6c(c5)c5ccccc5n6-c5ccccc5)ccc43)cc2)cc1] | 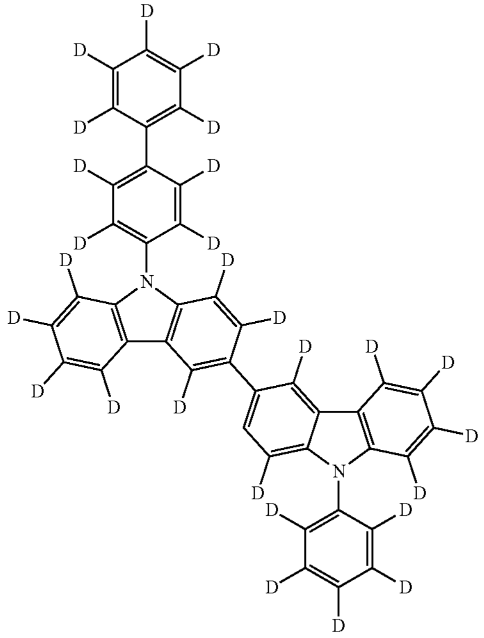 [SMILES: [2H]c1c([2H])c([2H])c(-c2c([2H])c([2H])c(-n3c4c([2H])c([2H])c([2H])c([2H])c4c4c([2H])c(-c5cc([2H])c6c(c5[2H])c5c([2H])c([2H])c([2H])c([2H])c5n6-c5c([2H])c([2H])c([2H])c([2H])c5[2H])c([2H])c([2H])c43)c([2H])c2[2H])c([2H])c1[2H]] | 68% |
| 2-53 | 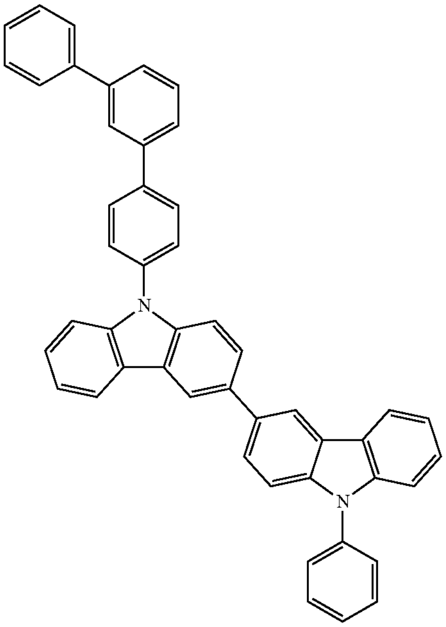 [SMILES: c1ccc(-c2cccc(-c3ccc(-n4c5ccccc5c5cc(-c6ccc7c(c6)c6ccccc6n7-c6ccccc6)ccc54)cc3)c2)cc1] | 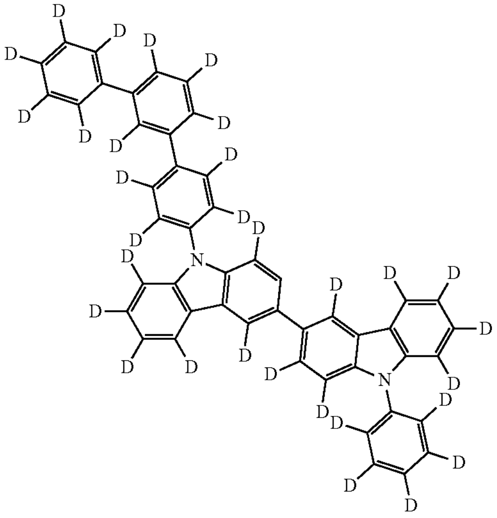 [SMILES: [2H]c1c([2H])c([2H])c(-c2c([2H])c([2H])c([2H])c(-c3c([2H])c([2H])c(-n4c5c([2H])cc(-c6c([2H])c([2H])c7c(c6[2H])c6c([2H])c([2H])c([2H])c([2H])c6n7-c6c([2H])c([2H])c([2H])c([2H])c6[2H])c([2H])c5c5c([2H])c([2H])c([2H])c([2H])c54)c([2H])c3[2H])c2[2H])c([2H])c1[2H]] | 70% |

TABLE 7-continued

| Compound | Compound E3 | Compound G3 | Yield |
|---|---|---|---|
| 2-56 | 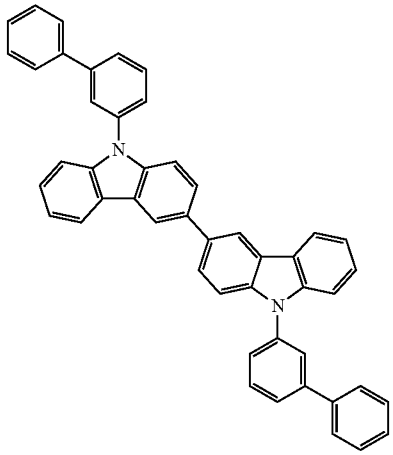 [SMILES: c1ccc(-c2cccc(-n3c4ccccc4c4cc(-c5ccc6c(c5)c5ccccc5n6-c5cccc(-c6ccccc6)c5)ccc43)c2)cc1] | 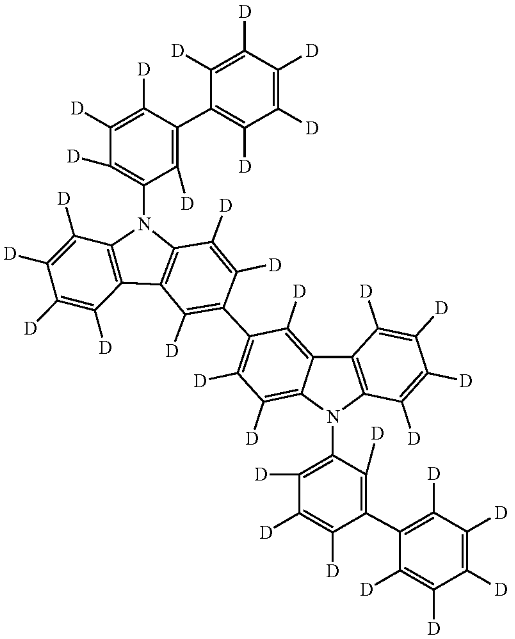 [SMILES: [2H]c1c([2H])c([2H])c(-c2c([2H])c([2H])c([2H])c(-n3c4c([2H])c([2H])c([2H])c([2H])c4c4c([2H])c(-c5c([2H])c([2H])c6c(c5[2H])c5c([2H])c([2H])c([2H])c([2H])c5n6-c5c([2H])c([2H])c([2H])c(-c6c([2H])c([2H])c([2H])c([2H])c6[2H])c5[2H])c([2H])c([2H])c43)c2[2H])c([2H])c1[2H]] | 69% |
| 2-50 | 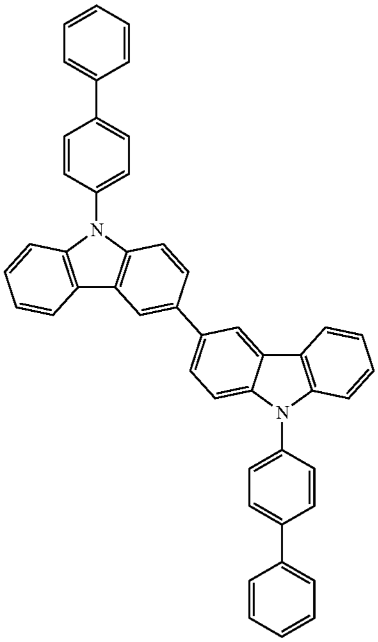 [SMILES: c1ccc(-c2ccc(-n3c4ccccc4c4cc(-c5ccc6c(c5)c5ccccc5n6-c5ccc(-c6ccccc6)cc5)ccc43)cc2)cc1] | 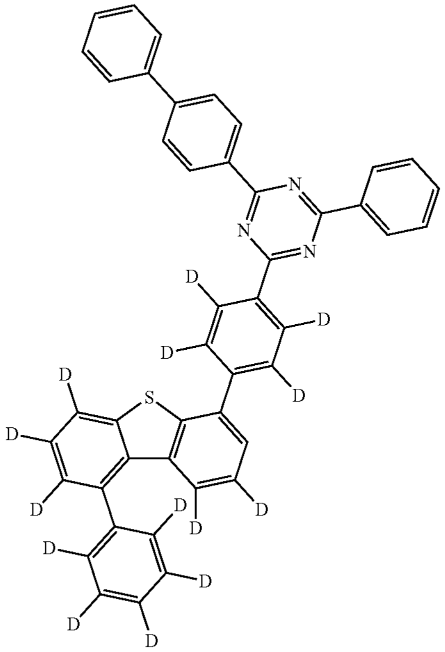 [SMILES: [2H]c1cc(-c2c([2H])c([2H])c(-c3nc(-c4ccccc4)nc(-c4ccc(-c5ccccc5)cc4)n3)c([2H])c2[2H])c2sc3c([2H])c([2H])c([2H])c(-c4c([2H])c([2H])c([2H])c([2H])c4[2H])c3c2c1[2H]] | 68% |

Compounds other than the compounds described in Preparation Examples 1 to 5 and Table 1 to Table 7 were also prepared in the same manner as in the methods described in the preparation examples described above, and the synthesis results are shown in the following Table 8 and Table 9. The following Table 8 shows measurement values of $^1$H NMR ($CDCl_3$, 400 MHz), and the following Table 9 shows measurement values of FD-mass spectrometry (FD-Mass: field desorption mass spectrometry).

TABLE 8

| Compound | $^{1}$H NMR ($CDCl_3$, 300 MHz) |
|---|---|
| 3 | δ = 8.03-7.96 (4H, m), 7.82-7.75 (4H, m), 7.54-7.25 (8H, m) |
| 6 | δ = 8.38 (1H, d), 7.96-7.94 (3H, m), 7.75-7.73 (5H, m), 7.61 (1H, d), 7.49-7.41 (6H, m), 7.25 (2H, d) |
| 10 | δ = 8.38 (1H, d), 7.96-7.94 (3H, m), 7.75-7.73 (5H, m), 7.61 (1H, d), 7.49-7.41 (6H, m), 7.25 (2H, d) |
| 13 | δ = 7.96 (4H, d), 7.75 (4H, d), 7.49-7.41 (6H, m), 7.25 (4H, d) |
| 25 | δ = 7.96 (4H, d), 7.75 (4H, d), 7.49-7.41 (6H, m), 7.25 (4H, d) |
| 30 | δ = 8.38 (1H, d), 7.96-7.94 (3H, m), 7.75-7.73 (5H, m), 7.61 (1H, d), 7.49-7.41 (6H, m), 7.25 (2H, d) |
| 35 | δ = 8.03-7.96 (4H, m), 7.82-7.75 (4H, m), 7.54-7.25 (8H, m) |
| 41 | δ = 7.96 (4H, d), 7.75 (4H, d), 7.49-7.41 (6H, m), 7.25 (4H, d) |
| 58 | δ = 8.38 (1H, d), 7.96-7.94 (3H, m), 7.75-7.73 (5H, m), 7.61 (1H, d), 7.49-7.41 (6H, m), 7.25 (2H, d) |
| 61 | δ = 7.96 (4H, d), 7.75 (4H, d), 7.49-7.41 (6H, m), 7.25 (4H, d) |
| 62 | δ = 8.38 (1H, d), 7.96-7.94 (3H, m), 7.75-7.73 (5H, m), 7.61 (1H, d), 7.49-7.41 (6H, m), 7.25 (2H, d) |
| 64 | δ = 8.36 (2H, d), 7.96 (2H, d), 7.75 (2H, d), 7.50-7.41 (6H, m), 7.25 (6H, m) |
| 65 | δ = 8.36 (2H, d), 7.96 (2H, d), 7.75 (2H, d), 7.50-7.41 (6H, m), 7.25 (2H, d) |
| 74 | δ = 8.36 (2H, d), 8.03-7.98 (2H, m), 7.82-7.76 (2H, m), 7.54-7.50 (4H, m), 7.39-7.31 (2H, m) |
| 97 | δ = 8.36 (2H, d), 7.96 (2H, d), 7.75 (2H, d), 7.50-7.41 (6H, m), 7.25 (2H, d) |
| 115 | δ = 8.36 (2H, d), 7.96 (2H, d), 7.75 (2H, d), 7.50-7.41 (6H, m), 7.25 (2H, d) |
| 123 | δ = 8.36 (2H, d), 7.96 (2H, d), 7.75 (2H, d), 7.50-7.41 (6H, m), 7.25 (2H, d) |
| 124 | δ = 8.36 (2H, d), 8.03-7.98 (2H, m), 7.82-7.76 (2H, m), 7.54-7.50 (4H, m), 7.39-7.31 (2H, m) |
| 127 | δ = 8.36 (2H, d), 7.96 (2H, d), 7.75 (2H, d), 7.50-7.41 (6H, m), 7.25 (2H, d) |
| 129 | δ = 8.36 (2H, d), 7.96-7.94 (3H, m), 7.75-7.73 (3H, m), 7.61(2H, d), 7.50-7.41 (6H, m), 7.25 (2H, d) |
| 139 | δ = 8.36 (2H, d), 8.03-7.98 (2H, m), 7.82-7.76 (2H, m), 7.54-7.50 (4H, m), 7.39-7.31 (2H, m) |
| 141 | δ = 8.36 (2H, d), 7.96 (2H, d), 7.75 (2H, d), 7.50-7.41 (6H, m), 7.25 (2H, d) |
| 150 | δ = 8.36 (2H, d), 7.96 (2H, d), 7.75 (2H, d), 7.50-7.41 (6H, m), 7.25 (2H, d) |
| 160 | δ = 8.36 (2H, d), 7.96 (2H, d), 7.75 (2H, d), 7.50-7.41 (6H, m), 7.25 (2H, d) |
| 181 | δ = 7.96 (4H, d), 7.75 (4H, d), 7.49-7.41 (6H, m), 7.25 (4H, d) |
| 183 | δ = 8.03-7.96 (4H, m), 7.82-7.75 (4H, m), 7.54-7.25 (8H, m) |
| 185 | δ = 7.96 (4H, d), 7.75 (4H, d), 7.49-7.41 (6H, m), 7.25 (4H, d) |
| 186 | δ = 8.38 (1H, d), 7.96-7.94 (3H, m), 7.75-7.73 (5H, m), 7.61 (1H, d), 7.49-7.41 (6H, m), 7.25 (2H, d) |
| 189 | δ = 7.96 (4H, d), 7.75 (4H, d), 7.49-7.41 (6H, m), 7.25 (4H, d) |
| 197 | δ = 7.96 (4H, d), 7.75 (4H, d), 7.49-7.41 (6H, m), 7.25 (4H, d) |
| 261 | δ = 7.96 (4H, d), 7.75 (4H, d), 7.49-7.41 (6H, m), 7.25 (4H, d) |
| 263 | δ = 8.03-7.96 (4H, m), 7.82-7.75 (4H, m), 7.54-7.25 (8H, m) |
| 274 | δ = 8.38 (1H, d), 7.96-7.94 (3H, m), 7.75-7.73 (5H, m), 7.61 (1H, d), 7.49-7.41 (6H, m), 7.25 (2H, d) |
| 325 | δ = 7.96 (4H, d), 7.75 (4H, d), 7.49-7.41 (6H, m), 7.25 (4H, d) |
| 9 | δ = 7.96 (4H, d), 7.75 (4H, d), 7.49-7.41 (6H, m), 7.25 (4H, d) |
| 12 | δ = 8.36 (2H, d), 7.96 (2H, d), 7.75 (2H, d), 7.50-7.41 (6H, m), 7.25 (6H, m) |
| 17 | δ = 7.96 (4H, d), 7.75 (4H, d), 7.49-7.41 (6H, m), 7.25 (4H, d) |
| 26 | δ = 8.38 (1H, d), 7.96-7.94 (3H, m), 7.75-7.73 (5H, m), 7.61 (1H, d), 7.49-7.41 (6H, m), 7.25 (2H, d) |
| 29 | δ = 7.96 (4H, d), 7.75 (4H, d), 7.49-7.41 (6H, m), 7.25 (4H, d) |
| 57 | δ = 7.96 (4H, d), 7.75 (4H, d), 7.49-7.41 (6H, m), 7.25 (4H, d) |
| 68 | δ = 8.36 (2H, d), 8.03-7.98 (2H, m), 7.82-7.76 (2H, m), 7.54-7.50 (4H, m), 7.39-7.31 (2H, m) |
| 114 | δ = 8.36 (2H, d), 8.03-7.98 (2H, m), 7.82-7.76 (2H, m), 7.54-7.50 (4H, m), 7.39-7.31 (2H, m) |
| 118 | δ = 8.36 (2H, d), 8.03-7.98 (2H, m), 7.82-7.76 (2H, m), 7.54-7.50 (4H, m), 7.39-7.31 (2H, m) |
| 119 | δ = 8.36 (2H, d), 7.96 (2H, d), 7.75 (2H, d), 7.50-7.41 (6H, m), 7.25 (2H, d) |
| 140 | δ = 8.36 (2H, d), 8.03-7.98 (2H, m), 7.82-7.76 (2H, m), 7.54-7.50 (4H, m), 7.39-7.31 (2H, m) |
| 149 | δ = 8.36 (2H, d), 7.96 (2H, d), 7.75 (2H, d), 7.50-7.41 (6H, m), 7.25 (2H, d) |
| 187 | δ = 8.03-7.96 (4H, m), 7.82-7.75 (4H, m), 7.54-7.25 (8H, m) |
| 193 | δ = 7.96 (4H, d), 7.75 (4H, d), 7.49-7.41 (6H, m), 7.25 (4H, d) |
| 199 | δ = 8.03-7.96 (4H, m), 7.82-7.75 (4H, m), 7.54-7.25 (8H, m) |
| 253 | δ = 7.96 (4H, d), 7.75 (4H, d), 7.49-7.41 (6H, m), 7.25 (4H, d) |

TABLE 8-continued

| Compound | $^1$H NMR ($CDCl_3$, 300 MHz) |
|---|---|
| 255 | δ = 8.03-7.96 (4H, m), 7.82-7.75 (4H, m), 7.54-7.25 (8H, m) |
| 501 | δ = 7.96 (4H, d), 7.75 (4H, d), 7.49-7.41 (6H, m), 7.25 (4H, d) |
| 2-50 | δ = No $^1$H NMR peak by deuterium content of 100% |
| 2-51 | δ = No $^1$H NMR peak by deuterium content of 100% |
| 2-53 | δ = No $^1$H NMR peak by deuterium content of 100% |
| 2-56 | δ = No $^1$H NMR peak by deuterium content of 100% |
| 2-57 | δ = No $^1$H NMR peak by deuterium content of 100% |
| 2-74 | δ = 8.55 (1H, d), 8.30 (1H, d), 8.19-8.13 (2H, m), 7.94-7.89 (8H, m), 7.77-7.75 (3H, m), 7.62-7.35 (11H, m), 7.20-7.16 (2H m) |
| 2-76 | δ = 8.55 (1H, d), 8.30 (1H, d), 8.13~8.19 (2H, m), 7.89~7.99 (9H, m), 7.73~7.77 (4H, m), 7.35~7.62 (13H, m), 7.16~7.20 (2H, m) |
| 2-77 | δ = 8.55 (1H, d), 8.30 (1H, d), 8.13~8.21 (4H, m), 7.89~7.99 (4H, m), 7.35~7.77 (20H, m), 7.16~7.20 (2H, t) |
| 2-78 | δ = 8.55 (1H, d), 8.30 (1H, d), 8.13~8.19 (2H, m), 7.89~7.99 (12H, m), 7.75~7.77 (5H, m), 7.58 (1H, d), 7.35~7.50 (8H, m), 7.16~7.20 (2H, m) |
| 2-79 | δ = 8.55 (1H, d), 8.30 (1H, d), 8.21-8.13 (3H, m), 7.99-7.89 (8H, m), 7.77-7.35 (12H, m), 7.20-7.16 (2H, m) |

TABLE 9

| Compound | FD-MS | Compound | FD-MS |
|---|---|---|---|
| 3 | m/z = 652.28($C_{45}H_{16}D_{11}N_3O_2$ = 652.80) | 6 | m/z = 638.30($C_{45}H_{18}D_{11}N_3O$ = 638.81) |
| 10 | m/z = 638.30($C_{45}H_{18}D_{11}N_3O$ = 638.81) | 13 | m/z = 638.30($C_{45}H_{18}D_{11}N_3O$ = 638.81) |
| 25 | m/z = 654.28($C_{45}H_{18}D_{11}N_3S$ = 654.88) | 30 | m/z = 654.28($C_{45}H_{18}D_{11}N_3S$ = 654.88) |
| 35 | m/z = 652.28($C_{45}H_{16}D_{11}N_3O_2$ = 652.80) | 41 | m/z = 638.30($C_{45}H_{18}D_{11}N_3O$ = 638.81) |
| 58 | m/z = 654.28($C_{45}H_{18}D_{11}N_3S$ = 654.88) | 61 | m/z = 654.28($C_{45}H_{18}D_{11}N_3S$ = 654.88) |
| 62 | m/z = 654.28($C_{45}H_{18}D_{11}N_3S$ = 654.88) | 64 | m/z = 654.28($C_{45}H_{18}D_{11}N_3S$ = 654.88) |
| 65 | m/z = 642.33($C_{45}H_{14}D_{15}N_3O$ = 642.84) | 74 | m/z = 656.30($C_{45}H_{12}D_{15}N_3O_2$ = 654.88) |
| 97 | m/z = 642.33($C_{45}H_{14}D_{15}N_3O$ = 642.84) | 115 | m/z = 658.30($C_{45}H_{14}D_{15}N_3S$ = 658.90) |
| 123 | m/z = 658.30($C_{45}H_{14}D_{15}N_3S$ = 658.90) | 124 | m/z = 672.28($C_{45}H_{12}D_{15}N_3OS$ = 672.88) |
| 127 | m/z = 658.30($C_{45}H_{14}D_{15}N_3S$ = 658.90) | 129 | m/z = 654.28($C_{45}H_{18}D_{11}N_3S$ = 654.88) |
| 139 | m/z = 592.23($C_{39}H_{12}D_{11}N_3OS$ = 592.76) | 141 | m/z = 642.33($C_{45}H_{14}D_{15}N_3O$ = 642.84) |
| 150 | m/z = 657.30($C_{45}H_{15}D_{14}N_3S$ = 657.89) | 160 | m/z = 657.30($C_{45}H_{15}D_{14}N_3S$ = 657.89) |
| 181 | m/z = 638.30($C_{45}H_{18}D_{11}N_3O$ = 638.81) | 183 | m/z = 652.28($C_{45}H_{16}D_{11}N_3O_2$ = 652.80) |
| 185 | m/z = 638.30($C_{45}H_{18}D_{11}N_3O$ = 638.81) | 186 | m/z = 638.30($C_{45}H_{18}D_{11}N_3O$ = 638.81) |
| 189 | m/z = 638.30($C_{45}H_{18}D_{11}N_3O$ = 638.81) | 197 | m/z = 638.30($C_{45}H_{18}D_{11}N_3O$ = 638.81) |
| 261 | m/z = 654.28($C_{45}H_{18}D_{11}N_3S$ = 654.88) | 263 | m/z = 668.26($C_{45}H_{16}D_{11}N_3OS$ = 668.86) |
| 274 | m/z = 654.28($C_{45}H_{18}D_{11}N_3S$ = 654.88) | 325 | m/z = 654.28($C_{45}H_{18}D_{11}N_3S$ = 654.88) |
| 9 | m/z = 638.30($C_{45}H_{18}D_{11}N_3O$ = 638.81) | 12 | m/z = 638.30($C_{45}H_{18}D_{11}N_3O$ = 638.81) |
| 17 | m/z = 654.28($C_{45}H_{18}D_{11}N_3S$ = 654.88) | 26 | m/z = 654.28($C_{45}H_{18}D_{11}N_3S$ = 654.88) |
| 29 | m/z = 654.28($C_{45}H_{18}D_{11}N_3S$ = 654.88) | 57 | m/z = 654.28($C_{45}H_{18}D_{11}N_3S$ = 654.88) |
| 68 | m/z = 672.28($C_{45}H_{12}D_{15}N_3OS$ = 672.88) | 114 | m/z = 656.30($C_{45}H_{12}D_{15}N_3O_2$ = 656.82) |
| 118 | m/z = 656.30($C_{45}H_{12}D_{15}N_3O_2$ = 656.82) | 119 | m/z = 658.30($C_{45}H_{14}D_{15}N_3S$ = 658.90) |
| 140 | m/z = 592.23($C_{39}H_{12}D_{11}N_3OS$ = 592.76) | 149 | m/z = 658.30($C_{45}H_{14}D_{15}N_3S$ = 658.90) |
| 187 | m/z = 652.28($C_{45}H_{16}D_{11}N_3O_2$ = 652.80) | 193 | m/z = 638.30($C_{45}H_{18}D_{11}N_3O$ = 638.81) |
| 199 | m/z = 652.28($C_{45}H_{16}D_{11}N_3O_2$ = 652.80) | 253 | m/z = 638.30($C_{45}H_{18}D_{11}N_3O$ = 638.81) |
| 255 | m/z = 652.28($C_{45}H_{16}D_{11}N_3O_2$ = 652.80) | 501 | m/z = 654.28($C_{45}H_{18}D_{11}N_3S$ = 654.88) |
| 2-79 | m/z = 636.80($C_{48}H_{32}N_2$ = 636.26) | 2-74 | m/z = 560.23($C_{42}H_{28}N_2$ = 560.70) |
| 2-51 | m/z = 588.87($C_{42}D_{28}N_2$ = 588.40) | 2-53 | m/z = 668.99($C_{48}D_{32}N_2$ = 668.46) |
| 2-56 | m/z = 668.99($C_{48}D_{32}N_2$ = 668.46) | 2-50 | m/z = 668.99($C_{48}D_{32}N_2$ = 668.46) |
| 2-76 | m/z = 636.80($C_{48}H_{32}N_2$ = 636.26) | 2-77 | m/z = 636.80($C_{48}H_{32}N_2$ = 636.26) |
| 2-78 | m/z = 636.80($C_{48}H_{32}N_2$ = 636.26) | 2-57 | m/z = 668.46($C_{48}D_{32}N_2$ = 668.99) |

Experimental Example 1

1) Manufacture of Organic Light Emitting Device

A glass substrate on which ITO was coated as a thin film to a thickness of 1,500 Å was cleaned with distilled water ultrasonic waves. After the cleaning with distilled water was finished, the substrate was ultrasonic cleaned with solvents such as acetone, methanol and isopropyl alcohol, then dried, and WO treatment was conducted for 5 minutes using UV in a UV cleaner. After that, the substrate was transferred to a plasma cleaner (PT), and after conducting plasma treatment under vacuum for ITO work function and residual film removal, the substrate was transferred to a thermal deposition apparatus for organic deposition.

On the transparent ITO electrode (anode), a hole injection layer 2-TNATA (4,4',4"-tris[2-naphthyl(phenyl)amino]triphenylamine) and a hole transfer layer NPB (N,N'-di(1-naphthyl)-N,N'-diphenyl-(1,1'-biphenyl)-4,4'-diamine), which are common layers, were formed.

A light emitting layer was thermal vacuum deposited thereon as follows. The light emitting layer was deposited to 360 Å using the heterocyclic compound of Chemical Formula 1 as a host and $Ir(ppy)_3$ (tris(2-phenylpyridine)iridium) as a green phosphorescent dopant, and doping $Ir(ppy)_3$ to the host by 7%. After that, BCP was deposited to 60 Å as a hole blocking layer, and $Alq_3$ was deposited to 200 Å thereon as an electron transfer layer. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å, and as a result, an organic electroluminescent device was manufactured.

In the following Table 10, a green host was used in the examples and the comparative examples except for the example separately indicated to use a red host. As a red phosphorescent dopant, $Ir(piq)_2(acac)$ was used.

Meanwhile, all the organic compounds required to manufacture the OLED were vacuum sublimation purified under $10^{-8}$ torr to $10^{-6}$ torr for each material to be used in the OLED manufacture.

[Comparative Compound]

[A]

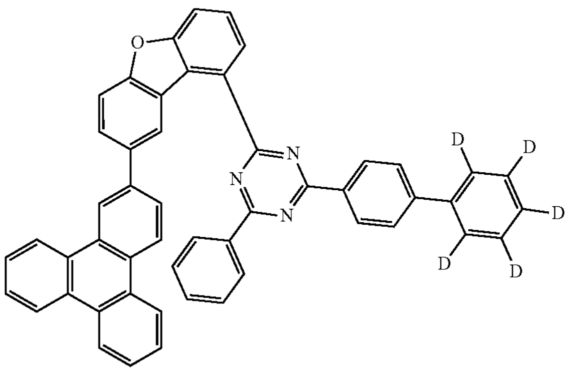

[B]

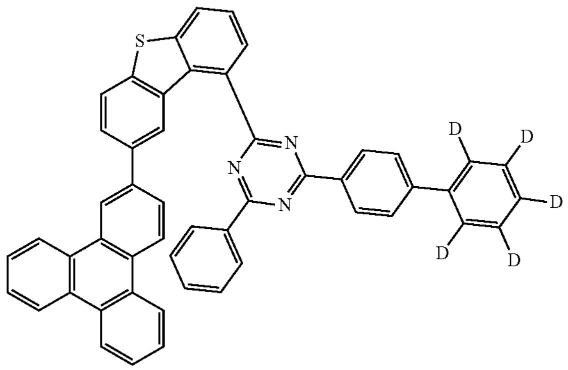

[C]

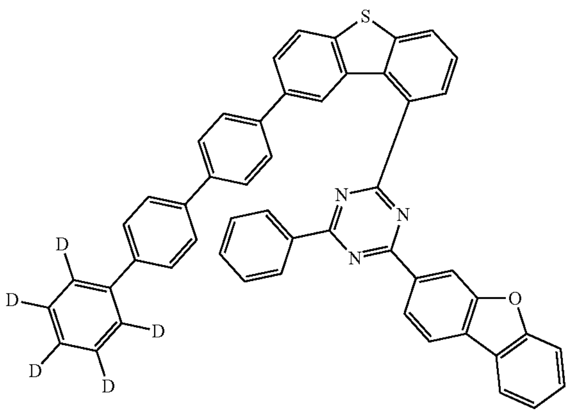

-continued

[D]

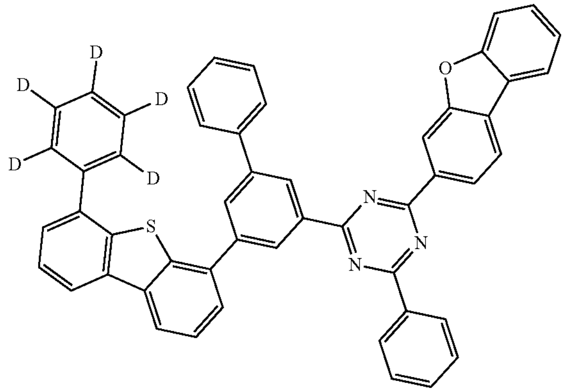

[E]

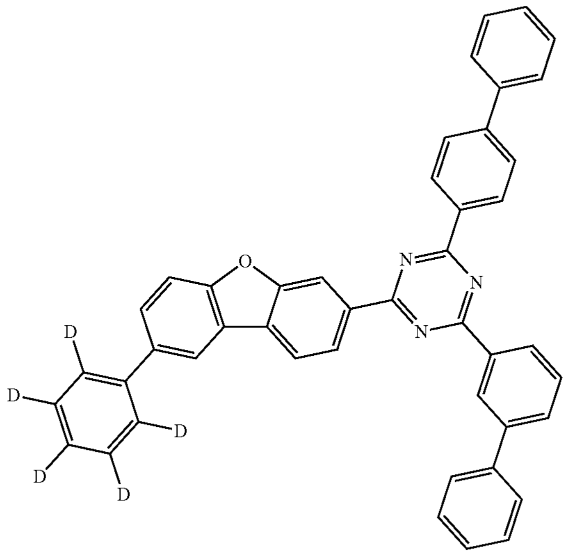

[F]

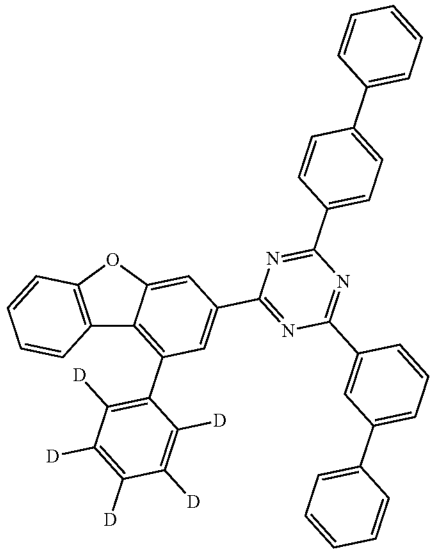

-continued
[G]
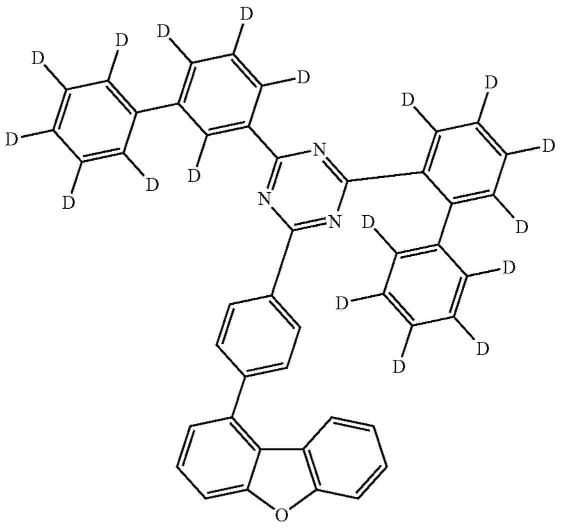
[H]
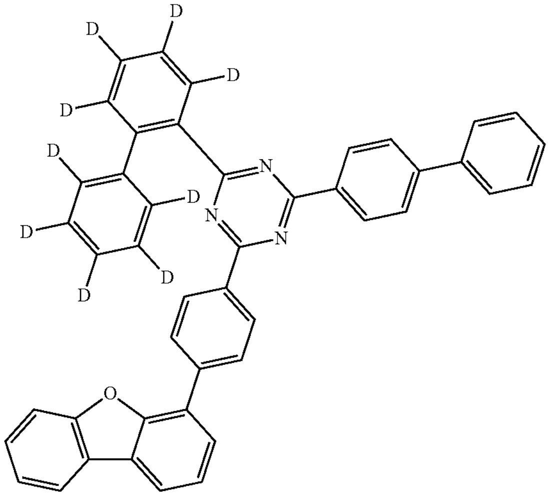
[I]
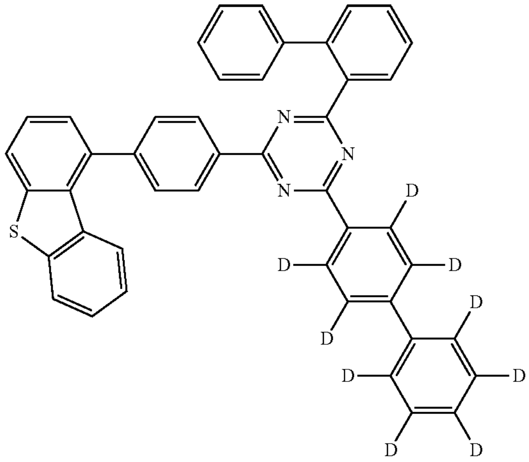
-continued
[J]
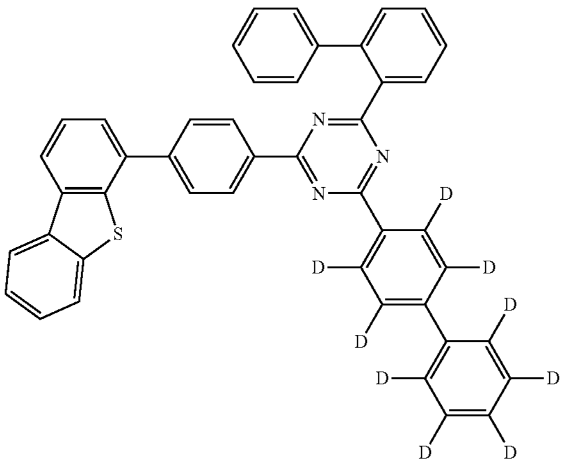
[Reference Compound]
[K]
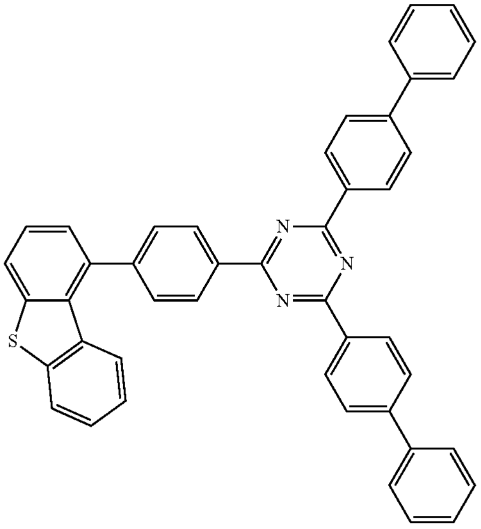

-continued

[L]

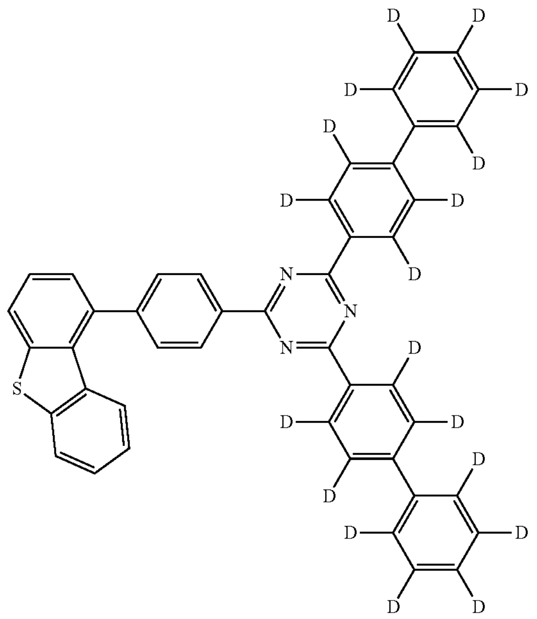

-continued

[M]

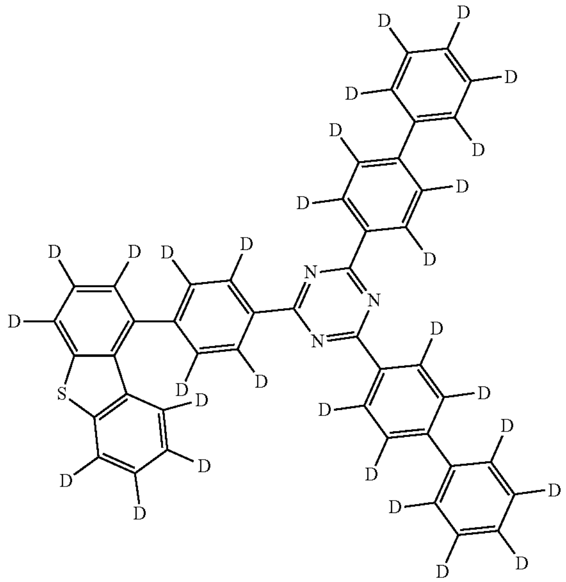

2) Driving Voltage and Light Emission Efficiency of Organic Electroluminescent Device For each of the organic electroluminescent devices manufactured as above, electroluminescent (EL) properties were measured using M7000 manufactured by McScience Inc., and with the measurement results, $T_{90}$ was measured when standard luminance was 6,000 cd/$m^2$ through a lifetime measurement system (M6000) manufactured by McScience Inc.

Results of measuring driving voltage, light emission efficiency, color coordinate (CIE) and lifetime of the organic light emitting devices manufactured according to the present disclosure are as shown in the following Table 10.

TABLE 10

| | Compound | Driving Voltage (V) | Light Emission Efficiency (cd/A) | Color Coordinate (x, y) | Lifetime ($T_{90}$) |
|---|---|---|---|---|---|
| Example 1 | 3 | 4.10 | 60.8 | (0.243, 0.714) | 102 |
| Example 2 | 6 | 4.16 | 61.3 | (0.241, 0.711) | 103 |
| Example 3 | 10 | 4.09 | 62.0 | (0.241, 0.714) | 109 |
| Example 4 | 13 | 3.99 | 62.6 | (0.241, 0.715) | 112 |
| Example 5 | 25 | 4.13 | 61.5 | (0.231, 0.712) | 107 |
| Example 6 | 30 | 4.05 | 62.0 | (0.251, 0.714) | 110 |
| Example 7 | 35 | 4.13 | 61.1 | (0.241, 0.711) | 107 |
| Example 8 | 41 | 4.01 | 61.8 | (0.251, 0.714) | 105 |
| Example 9 | 58 | 4.05 | 63.4 | (0.241, 0.714) | 106 |
| Example 10 | 61 | 4.12 | 62.9 | (0.242, 0.713) | 113 |
| Example 11 | 62 | 4.03 | 62.4 | (0.248, 0.715) | 119 |
| Example 12 | 64 | 4.09 | 61.9 | (0.251, 0.714) | 124 |
| Example 13 | 65 | 4.15 | 61.6 | (0.251, 0.714) | 120 |
| Example 14 | 74 | 4.10 | 61.3 | (0.247, 0.727) | 123 |
| Example 15 | 97 | 4.05 | 62.1 | (0.231, 0.711) | 118 |
| Example 16 | 115 | 4.04 | 62.6 | (0.246, 0.717) | 113 |
| Example 17 | 123 | 4.12 | 63.4 | (0.231, 0.711) | 110 |
| Example 18 | 124 (Red Host) | 4.15 | 60.1 | (0.671, 0.320) | 98 |
| Example 19 | 127 | 4.04 | 62.8 | (0.246, 0.717) | 105 |
| Example 20 | 129 | 4.01 | 62.1 | (0.233, 0.701) | 103 |
| Example 21 | 139 | 3.99 | 61.8 | (0.251, 0.713) | 118 |
| Example 22 | 141 | 4.05 | 62.4 | (0.254, 0.724) | 119 |
| Example 23 | 150 | 4.01 | 61.9 | (0.233, 0.703) | 121 |
| Example 24 | 160 | 4.11 | 63.4 | (0.234, 0.714) | 115 |
| Example 25 | 181 | 4.06 | 61.3 | (0.243, 0.693) | 110 |
| Example 26 | 183 | 4.02 | 61.9 | (0.251, 0.724) | 105 |

TABLE 10-continued

| | Compound | Driving Voltage (V) | Light Emission Efficiency (cd/A) | Color Coordinate (x, y) | Lifetime ($T_{90}$) |
|---|---|---|---|---|---|
| Example 27 | 185 | 4.11 | 62.4 | (0.242, 0.713) | 120 |
| Example 28 | 186 | 3.99 | 62.9 | (0.243, 0.712) | 121 |
| Example 29 | 189 | 3.94 | 61.6 | (0.242, 0.716) | 121 |
| Example 30 | 197 | 4.10 | 62.1 | (0.241, 0.713) | 119 |
| Example 31 | 261 | 4.16 | 62.6 | (0.236, 0.715) | 120 |
| Example 32 | 263 | 4.11 | 63.1 | (0.247, 0.712) | 115 |
| Example 33 | 274 | 4.05 | 63.4 | (0.243, 0.712) | 110 |
| Example 34 | 325 | 4.01 | 61.1 | (0.249, 0.711) | 108 |
| Example 35 | 9 | 4.10 | 62.1 | (0.243, 0.714) | 110 |
| Example 36 | 12 | 4.08 | 61.8 | (0.241, 0.711) | 108 |
| Example 37 | 17 | 4.07 | 63.2 | (0.238, 0.721) | 130 |
| Example 38 | 26 | 4.16 | 62.6 | (0.241, 0.715) | 111 |
| Example 39 | 29 | 4.12 | 63.4 | (0.231, 0.712) | 120 |
| Example 40 | 57 | 4.11 | 61.9 | (0.251, 0.714) | 115 |
| Example 41 | 68 | 4.09 | 62.3 | (0.241, 0.711) | 114 |
| Example 42 | 114 | 4.09 | 62.5 | (0.251, 0.714) | 117 |
| Example 43 | 118 | 4.13 | 62.7 | (0.241, 0.714) | 110 |
| Example 44 | 119 | 4.10 | 62.9 | (0.242, 0.713) | 115 |
| Example 45 | 140 | 4.12 | 61.9 | (0.249, 0.713) | 120 |
| Example 46 | 149 | 4.08 | 61.7 | (0.243, 0.712) | 121 |
| Example 47 | 187 | 4.06 | 62 | (0.242, 0.716) | 118 |
| Example 48 | 193 | 4.05 | 62.2 | (0.241, 0.713) | 113 |
| Example 49 | 199 | 4.09 | 63 | (0.236, 0.715) | 117 |
| Example 50 | 253 | 4.10 | 63.1 | (0.247, 0.712) | 115 |
| Example 51 | 255 | 4.11 | 62.8 | (0.243, 0.712) | 116 |
| Example 52 | 509 | 4.08 | 62.5 | (0.249, 0.711) | 115 |
| Comparative Example 1 | A | 4.25 | 56.8 | (0.245, 0.716) | 58 |
| Comparative Example 2 | B | 4.22 | 56.5 | (0.246, 0.715) | 58 |
| Comparative Example 3 | C | 4.20 | 56.2 | (0.244, 0.712) | 62 |
| Comparative Example 4 | D | 4.20 | 56.7 | (0.245, 0.712) | 63 |
| Comparative Example 5 | E | 4.24 | 56.6 | (0.245, 0.717) | 60 |
| Comparative Example 6 | F | 4.23 | 56.7 | (0.249, 0.713) | 61 |
| Comparative Example 7 | G | 4.43 | 54.2 | (0.243, 0.712) | 50 |
| Comparative Example 8 | H | 4.42 | 55.5 | (0.242, 0.716) | 55 |
| Comparative Example 9 | I | 4.45 | 55.4 | (0.241, 0.713) | 53 |
| Comparative Example 10 | J | 4.45 | 55.3 | (0.236, 0.715) | 54 |
| Reference Example 1 | K | 4.18 | 57.8 | (0.260, 0.708) | 63 |
| Reference Example 2 | L | 4.20 | 56.0 | (0.248, 0.716) | 57 |
| Reference Example 3 | M | 4.18 | 57.7 | (0.251, 0.713) | 83 |

From the results of Table 10, it is seen that the organic light emitting device comprising the heterocyclic compound of Chemical Formula 1 of the present disclosure is superior in all aspects of driving voltage, light emission efficiency and lifetime compared to the comparative examples.

Specifically, when examining Comparative Example 1 to Comparative Example 6, terminal phenyl is substituted with deuterium instead of hydrogen, and in the present disclosure, the heteroring is substituted with deuterium. Molecules are thermally damaged by electron migration when driving an organic light emitting device. Particularly, structures comprising dibenzofuran and dibenzothiophene are highly likely to have defects in oxygen or sulfur, a most unstable site.

In the compound of the present disclosure, the heterocyclic compound is substituted with deuterium having a larger molecular weight than hydrogen in order to prevent this phenomenon, and as a result, molecular energy is lowered by reducing changes in the vibrational frequency, which resultantly increases molecular stability. In addition, it may be identified that, since single bond dissociation energy of carbon and deuterium is higher than single bond dissociation energy of carbon and hydrogen, thermal stability of the molecule increases, and a device lifetime is improved as a result.

A host material needs to readily receive electrons and holes and readily transfer these to a dopant, and in Comparative Example 7 to Comparative Example 10, the triazine group is substituted with biphenyl bonding at an ortho position. In the ortho bonding, steric hindrance occurs between substituents, and electrons and holes are not stably received. Overall device performance is considered to decline due to structural instability caused by such steric hinderance.

Meanwhile, in the present disclosure, a biphenyl-based substituent bonds to the triazine group bonding at a para position. Since the biphenyl-based substituent is stretched lengthwise in para, steric hindrance does not occur in the molecule compared to when the biphenyl-based bonds at an ortho position, which is considered to more stably receive electrons and holes.

An OLED has excellent efficiency and lifetime as a recombination zone (RZ) locates at the center of a light emitting layer. A unipolar material that does not comprise carbazole such as a compound having triazine bonding to a heteroring has relatively faster electron migration compared to hole migration (refer to FIG. 6).

Accordingly, when checking the RZ, the RZ is formed closer to a hole transfer layer than the center of EML (refer to FIG. 5). When examining electron cloud distribution of HOMO and LUMO states in the material of Compound 17, LUMO is distributed in the triazine-based substituent and HOMO is distributed in the heteroring (refer to FIG. 4). In an organic compound molecule, holes migrate through HOMO, and electrons migrate through LUMO. A compound substituted with deuterium has higher packing density compared to a compound substituted with hydrogen. Accordingly, holes or electrons migrate faster when substituted with deuterium since the intermolecular distance is close. When a triazine-based substituent responsible for LUMO is substituted with deuterium as in Reference Example 2, electrons migrate faster, and RZ leans more toward HTL compared when not substituted with deuterium. As a result, both efficiency and lifetime were reduced. When the whole compound is substituted with deuterium as in Reference Example 3, similar efficiency was obtained as in Reference Example 1. This is interpreted as a result that both electrons and holes become faster and RZ does not change. On the other hand, the heteroring side responsible for HOMO is substituted with deuterium in Compound 17 that is the compound of the present disclosure. Accordingly, holes migrate faster compared to in Reference Example 1 not substituted with deuterium bringing RZ close to the center of EML, and efficiency and lifetime were identified to be enhanced.

In other words, it was identified that driving voltage, light emission efficiency and lifetime were significantly superior when using the heterocyclic compound of Chemical Formula 1 of the present disclosure as a host of the light emitting layer.

The experiment of identifying the recombination zone (RZ) was prepared in the same manner as the method for manufacturing an organic light emitting device as in Experimental Example 1. The difference is a doping position of the green phosphorescent dopant in the light emitting layer.

#1 of FIG. 5 had the entire light emitting layer doped with the green phosphorescent dopant, and was used as a comparative group. In #2, only the colored part (positioned close to hole transfer layer) of 120 Å of FIG. 5 was doped, and on the remaining 240 Å, only the host was deposited. In #3, only the colored part (positioned close to the center of light emitting layer) of 120 Å of FIG. 5 was doped, and on the remaining uncolored parts, only the host was deposited. In #4, only the colored part (positioned close to hole blocking layer) of 120 Å of FIG. 5 was doped, and on the remaining uncolored parts, only the host was deposited.

In Reference Compound K, RZ is positioned close to the hole transfer layer, and #2 was identified to have the best efficiency and lifetime. This also indicates the result of electron migration being relatively faster than hole migration in FIG. 5. Reference Compound L had a lower lifetime compared to Reference Compound K by the triazine-based substituent responsible for LUMO being substituted with deuterium. This is considered to be resulting from electron migration being faster than in Reference Compound K, and RZ leaning more toward the hole transfer layer. Reference Compound M had a similar result with Reference Compound K. It is interpreted as a result that, in Reference Compound M that is a compound having the entire Reference Compound K substituted with deuterium, both electrons and holes become faster, and RZ does not change. Meanwhile, in Compound 17, #3 (positioned at the center of light emitting layer) has the highest efficiency and lifetime. As described above, the heteroring side responsible for HOMO is substituted with deuterium herein. Accordingly, hole migration becomes faster compared to in Reference Compound K not substituted with deuterium, and RZ positioning close to the center of EML was identified by having balanced migrations of electrons and holes.

With a compound having relatively faster electron migration as the compound of the present disclosure, higher efficiency is expected when using an electron blocking layer by preventing electrons from coming over from the light emitting layer.

Results of the experiments of identifying the recombination zone (RZ) for Reference Compounds K, L and M, and Compound 17, and results of the experiments on the hole only device (HOD) and the electron only device (EOD) may be identified in FIG. 5 and FIG. 6.

Experimental Example 2

1) Manufacture of Organic Light Emitting Device

A glass substrate on which ITO was coated as a thin film to a thickness of 1,500 Å was cleaned with distilled water ultrasonic waves. After the cleaning with distilled water was finished, the substrate was ultrasonic cleaned with solvents such as acetone, methanol and isopropyl alcohol, then dried, and UVO treatment was conducted for 5 minutes using UV in a UV cleaner. After that, the substrate was transferred to a plasma cleaner (PT), and after conducting plasma treatment under vacuum for ITO work function and residual film removal, the substrate was transferred to a thermal deposition apparatus for organic deposition.

On the transparent ITO electrode (anode), a hole injection layer 2-TNATA (4,4',4"-tris[2-naphthyl(phenyl)amino]triphenylamine) and a hole transfer layer NPB (N,N'-di(1-naphthyl)-N,N'-diphenyl-(1,1'-biphenyl)-4,4'-diamine), which are common layers, were formed.

A light emitting layer was thermal vacuum deposited thereon as follows. As the light emitting layer, one type of the heterocyclic compound of Chemical Formula 1 and one type of the compound of Chemical Formula 2 were premixed and then deposited to 360 Å in one source of supply as a host, and $Ir(ppy)_3$, a green phosphorescent dopant, was doped and deposited by 7% of the deposited thickness of the light emitting layer. After that, BCP was deposited to 60 Å as a hole blocking layer, and $Alq_3$ was deposited to 200 Å thereon as an electron transfer layer. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å, and as a result, an organic electroluminescent device was manufactured.

In the following Table 11, a green host was used in the examples and the comparative examples except for the example separately indicated to use a red host. As a red phosphorescent dopant, $Ir(piq)_2(acac)$ was used.

Meanwhile, all the organic compounds required to manufacture the OLED were vacuum sublimation purified under $10^{-8}$ torr to $10^{-6}$ torr for each material to be used in the OLED manufacture.

For each of the organic electroluminescent devices manufactured as above, electroluminescent (EL) properties were measured using M7000 manufactured by McScience Inc., and with the measurement results, $T_{90}$ was measured when standard luminance was 6,000 cd/m$^2$ through a lifetime measurement system (M6000) manufactured by McScience Inc.

Results of measuring driving voltage, light emission efficiency, color coordinate (CIE) and lifetime of the organic light emitting devices manufactured according to the present disclosure are as shown in the following Table 11.

TABLE 11

| | Light Emitting Layer Compound | Ratio | Driving Voltage (V) | Light Emission Efficiency (cd/A) | Color Coordinate (x, y) | Litetime ($T_{90}$) |
|---|---|---|---|---|---|---|
| Example 53 | 13:2-77 | 1:1 | 3.72 | 66.2 | (0.248, 0.637) | 160 |
| Example 54 | | 1:2 | 3.78 | 65.6 | (0.269, 0.611) | 165 |
| Example 55 | | 1:3 | 3.88 | 65.0 | (0.251, 0.693) | 170 |
| Example 56 | 13:2-56 | 1:1 | 3.71 | 66.3 | (0.248, 0.637) | 300 |
| Example 57 | | 1:2 | 3.79 | 65.7 | (0.269, 0.611) | 307 |
| Example 58 | | 1:3 | 3.87 | 65.0 | (0.251, 0.693) | 313 |
| Example 59 | 30:2-79 | 1:1 | 3.78 | 66.6 | (0.245, 0.677) | 161 |
| Example 60 | | 1:2 | 3.86 | 65.7 | (0.258, 0.647) | 165 |
| Example 61 | | 1:3 | 3.94 | 64.7 | (0.266, 0.645) | 170 |
| Example 62 | 30:2-57 | 1:1 | 3.77 | 66.7 | (0.245, 0.677) | 305 |
| Example 63 | | 1:2 | 3.85 | 65.7 | (0.258, 0.647) | 310 |
| Example 64 | | 1:3 | 3.93 | 64.8 | (0.266, 0.645) | 315 |
| Example 65 | 41:2-76 | 1:1 | 3.72 | 66.3 | (0.256, 0.673) | 162 |
| Example 66 | | 1:2 | 3.82 | 65.4 | (0.237, 0.644) | 166 |
| Example 67 | | 1:3 | 3.90 | 64.5 | (0.237, 0.624) | 171 |
| Example 68 | 41:2-53 | 1:1 | 3.73 | 66.4 | (0.256, 0.673) | 304 |
| Example 69 | | 1:2 | 3.81 | 65.5 | (0.237, 0.644) | 310 |
| Example 70 | | 1:3 | 3.89 | 64.6 | (0.237, 0.624) | 316 |
| Example 71 | 61:2-78 | 1:1 | 3.84 | 67.5 | (0.245, 0.617) | 165 |
| Example 72 | | 1:2 | 3.91 | 66.6 | (0.257, 0.624) | 170 |
| Example 73 | | 1:3 | 4.01 | 65.6 | (0.259, 0.712) | 174 |
| Example 74 | 61:2-50 | 1:1 | 3.83 | 67.6 | (0.245, 0.617) | 310 |
| Example 75 | | 1:2 | 3.91 | 66.7 | (0.257, 0.624) | 315 |
| Example 76 | | 1:3 | 4.00 | 65.7 | (0.259, 0.712) | 321 |
| Example 77 | 62:2-77 | 1:1 | 3.74 | 67.2 | (0.243, 0.643) | 166 |
| Example 78 | | 1:2 | 3.83 | 66.1 | (0.261, 0.764) | 170 |
| Example 79 | | 1:3 | 3.92 | 65.3 | (0.258, 0.628) | 175 |
| Example 80 | 62:2-56 | 1:1 | 3.75 | 67.1 | (0.243, 0.643) | 311 |
| Example 81 | | 1:2 | 3.83 | 66.1 | (0.261, 0.764) | 314 |
| Example 82 | | 1:3 | 3.91 | 65.2 | (0.258, 0.628) | 320 |
| Example 83 | 115:2-79 | 1:1 | 3.77 | 67.3 | (0.254, 0.653) | 166 |
| Example 84 | | 1:2 | 3.85 | 66.3 | (0.275, 0.657) | 170 |
| Example 85 | | 1:3 | 3.94 | 65.3 | (0.264, 0.642) | 175 |
| Example 86 | 115:2-57 | 1:1 | 3.76 | 67.3 | (0.254, 0.653) | 312 |
| Example 87 | | 1:2 | 3.84 | 66.4 | (0.275, 0.657) | 317 |
| Example 88 | | 1:3 | 3.92 | 65.4 | (0.264, 0.642) | 323 |
| Example 89 | 123:2-76 | 1:1 | 3.84 | 68.1 | (0.256, 0.638) | 167 |
| Example 90 | | 1:2 | 3.92 | 67.1 | (0.251, 0.632) | 172 |
| Example 91 | | 1:3 | 4.01 | 66.2 | (0.253, 0.684) | 177 |
| Example 92 | 123:2-53 | 1:1 | 3.83 | 68.2 | (0.256, 0.638) | 315 |
| Example 93 | | 1:2 | 3.91 | 67.2 | (0.251, 0.632) | 319 |
| Example 94 | | 1:3 | 4.00 | 66.3 | (0.253, 0.684) | 324 |
| Example 95 | 127:2-78 | 1:1 | 3.76 | 67.5 | (0.235, 0.655) | 168 |
| Example 96 | | 1:2 | 3.84 | 66.6 | (0.236, 0.624) | 173 |
| Example 97 | | 1:3 | 3.92 | 65.6 | (0.255, 0.692) | 178 |
| Example 98 | 127:2-50 | 1:1 | 3.76 | 67.5 | (0.235, 0.655) | 317 |
| Example 99 | | 1:2 | 3.84 | 66.6 | (0.236, 0.624) | 322 |
| Example 100 | | 1:3 | 3.92 | 65.6 | (0.255, 0.692) | 327 |
| Example 101 | 139:2-74 | 1:1 | 3.73 | 66.8 | (0.253, 0.724) | 169 |
| Example 102 | | 1:2 | 3.81 | 65.8 | (0.242, 0.625) | 174 |
| Example 103 | | 1:3 | 3.89 | 64.9 | (0.261, 0.623) | 177 |
| Example 104 | 139:2-51 | 1:1 | 3.72 | 66.9 | (0.253, 0.724) | 318 |
| Example 105 | | 1:2 | 3.80 | 65.9 | (0.242, 0.625) | 322 |
| Example 106 | | 1:3 | 3.88 | 65.0 | (0.261, 0.623) | 326 |
| Example 107 | 17:2-78 | 1:1 | 3.72 | 67.2 | (0.253, 0.614) | 173 |
| Example 108 | | 1:2 | 3.80 | 66.3 | (0.254, 0.659) | 178 |
| Example 109 | | 1:3 | 3.88 | 65.4 | (0.255, 0.635) | 183 |
| Example 110 | 17:2-50 | 1:1 | 3.71 | 67.3 | (0.253, 0.614) | 327 |
| Example 111 | | 1:2 | 3.79 | 66.4 | (0.254, 0.659) | 333 |
| Example 112 | | 1:3 | 3.87 | 65.4 | (0.255, 0.635) | 339 |
| Example 113 | 181:2-74 | 1:1 | 3.79 | 65.8 | (0.257, 0.714) | 325 |
| Example 114 | | 1:2 | 3.86 | 65.0 | (0.249, 0.666) | 331 |
| Example 115 | | 1:3 | 3.95 | 64.0 | (0.253, 0.635) | 337 |

TABLE 11-continued

| | Light Emitting Layer Compound | Ratio | Driving Voltage (V) | Light Emission Efficiency (cd/A) | Color Coordinate (x, y) | Litetime ($T_{90}$) |
|---|---|---|---|---|---|---|
| Example 116 | 181:2-51 | 1:1 | 3.78 | 65.9 | (0.257, 0.714) | 325 |
| Example 117 | | 1:2 | 3.86 | 65.0 | (0.249, 0.666) | 331 |
| Example 118 | | 1:3 | 3.94 | 64.1 | (0.253, 0.635) | 337 |
| Example 119 | 185:2-77 | 1:1 | 3.83 | 67.2 | (0.268, 0.615) | 170 |
| Example 120 | | 1:2 | 3.91 | 66.2 | (0.253, 0.628) | 175 |
| Example 121 | | 1:3 | 3.99 | 65.3 | (0.256, 0.713) | 180 |
| Example 122 | 185:2-56 | 1:1 | 3.82 | 67.1 | (0.268, 0.615) | 322 |
| Example 123 | | 1:2 | 3.90 | 66.1 | (0.253, 0.628) | 324 |
| Example 124 | | 1:3 | 3.99 | 65.2 | (0.256, 0.713) | 326 |
| Example 125 | 186:2-76 | 1:1 | 3.72 | 67.7 | (0.243, 0.612) | 164 |
| Example 126 | | 1:2 | 3.80 | 66.8 | (0.265, 0.669) | 168 |
| Example 127 | | 1:3 | 3.88 | 65.9 | (0.255, 0.627) | 173 |
| Example 128 | 186:2-53 | 1:1 | 3.71 | 67.6 | (0.243, 0.612) | 308 |
| Example 129 | | 1:2 | 3.79 | 66.7 | (0.265, 0.669) | 314 |
| Example 130 | | 1:3 | 3.87 | 65.7 | (0.255, 0.627) | 319 |
| Example 131 | 197:2-79 | 1:1 | 3.82 | 66.9 | (0.243, 0.653) | 166 |
| Example 132 | | 1:2 | 3.91 | 65.8 | (0.247, 0.644) | 170 |
| Example 133 | | 1:3 | 3.99 | 65.0 | (0.274, 0.658) | 174 |
| Example 134 | 197:2-57 | 1:1 | 3.81 | 66.8 | (0.243, 0.653) | 317 |
| Example 135 | | 1:2 | 3.90 | 65.8 | (0.247, 0.644) | 322 |
| Example 136 | | 1:3 | 3.98 | 64.9 | (0.274, 0.658) | 328 |
| Example 137 | 261:2-77 | 1:1 | 3.87 | 67.3 | (0.263, 0.621) | 164 |
| Example 138 | | 1:2 | 3.95 | 66.4 | (0.256, 0.670) | 166 |
| Example 139 | | 1:3 | 4.04 | 65.4 | (0.245, 0.637) | 169 |
| Example 140 | 261:2-56 | 1:1 | 3.86 | 67.4 | (0.263, 0.621) | 312 |
| Example 141 | | 1:2 | 3.94 | 66.5 | (0.256, 0.670) | 316 |
| Example 142 | | 1:3 | 4.03 | 65.5 | (0.245, 0.637) | 320 |
| Example 143 | 10:2-79 | 1:1 | 3.80 | 66.7 | (0.247, 0.613) | 166 |
| Example 144 | | 1:2 | 3.89 | 65.7 | (0.255, 0.657) | 168 |
| Example 145 | | 1:3 | 3.97 | 64.8 | (0.253, 0.612) | 172 |
| Example 146 | 10:2-57 | 1:1 | 3.80 | 66.8 | (0.247, 0.613) | 320 |
| Example 147 | | 1:2 | 3.88 | 65.8 | (0.255, 0.657) | 325 |
| Example 148 | | 1:3 | 3.96 | 64.9 | (0.253, 0.612) | 330 |
| Example 149 | 25:2-76 | 1:1 | 3.84 | 66.1 | (0.258, 0.704) | 153 |
| Example 150 | | 1:2 | 3.92 | 65.2 | (0.243, 0.627) | 155 |
| Example 151 | | 1:3 | 4.01 | 64.3 | (0.263, 0.610) | 158 |
| Example 152 | 25:2-53 | 1:1 | 3.83 | 66.2 | (0.258, 0.704) | 312 |
| Example 153 | | 1:2 | 3.91 | 65.3 | (0.243, 0.627) | 316 |
| Example 154 | | 1:3 | 4.00 | 64.4 | (0.263, 0.610) | 320 |
| Example 155 | 97:2-78 | 1:1 | 3.77 | 66.8 | (0.250, 0.703) | 162 |
| Example 156 | | 1:2 | 3.85 | 65.8 | (0.243, 0.667) | 164 |
| Example 157 | | 1:3 | 3.93 | 64.9 | (0.258, 0.637) | 167 |
| Example 158 | 97:2-50 | 1:1 | 3.78 | 66.9 | (0.250, 0.703) | 312 |
| Example 159 | | 1:2 | 3.86 | 65.9 | (0.243, 0.667) | 317 |
| Example 160 | | 1:3 | 3.94 | 65.0 | (0.258, 0.637) | 321 |
| Example 161 | 124:2-78 | 1:1 | 4.10 | 65.5 | (0.672, 0.319) | 153 |
| Example 162 | (Red Host) | 1:2 | 4.15 | 65.1 | (0.670, 0.321) | 156 |
| Example 163 | | 1:3 | 4.20 | 64.8 | (0.671, 0.320) | 159 |
| Comparative Example 11 | A:2-78 | 1:1 | 4.35 | 59.1 | (0.256, 0.723) | 95 |
| Comparative Example 12 | | 1:2 | 4.37 | 58.5 | (0.243, 0.629) | 97 |
| Comparative Example 13 | | 1:3 | 4.39 | 58.2 | (0.268, 0.734) | 100 |
| Comparative Example 14 | B:2-76 | 1:1 | 4.29 | 58.6 | (0.266, 0.657) | 93 |
| Comparative Example 15 | | 1:2 | 4.32 | 58.0 | (0.268, 0.739) | 95 |
| Comparative Example 16 | | 1:3 | 4.34 | 57.7 | (0.257, 0.624) | 98 |
| Comparative Example 17 | G:2-79 | 1:1 | 4.40 | 56.9 | (0.687, 0.643) | 80 |
| Comparative Example 18 | | 1:2 | 4.43 | 56.3 | (0.267, 0.628) | 82 |
| Comparative Example 19 | | 1:3 | 4.45 | 56.1 | (0.265, 0.624) | 84 |
| Comparative Example 20 | H:2-77 | 1:1 | 4.28 | 56.4 | (0.276, 0.613) | 75 |
| Comparative Example 21 | | 1:2 | 4.30 | 55.8 | (0.259, 0.628) | 77 |
| Comparative Example 22 | | 1:3 | 4.32 | 55.6 | (0.244, 0.628) | 79 |
| Comparative Example 23 | C:2-74 | 1:1 | 4.17 | 60.2 | (0.256, 0.723) | 108 |

TABLE 11-continued

| | Light Emitting Layer Compound | Ratio | Driving Voltage (V) | Light Emission Efficiency (cd/A) | Color Coordinate (x, y) | Litetime ($T_{90}$) |
|---|---|---|---|---|---|---|
| Comparative Example 24 | | 1:2 | 4.19 | 59.6 | (0.243, 0.629) | 111 |
| Comparative Example 25 | | 1:3 | 4.21 | 59.3 | (0.268, 0.734) | 114 |
| Comparative Example 26 | E:2-76 | 1:1 | 4.20 | 60.6 | (0.256, 0.723) | 100 |
| Comparative Example 27 | | 1:2 | 4.22 | 60.0 | (0.243, 0.629) | 104 |
| Comparative Example 28 | | 1:3 | 4.24 | 59.8 | (0.268, 0.734) | 108 |

When comparing the results of Table 10 with the results of Table 11, it may be identified that driving voltage, light emission efficiency and lifetime are all improved when using the heterocyclic compound of Chemical Formula 1 and the compound of Chemical Formula 2 at the same time as a host of the light emitting layer.

Effects of more superior efficiency and lifetime are obtained when comprising the compound of Chemical Formula 1 and the compound of Chemical Formula 2 at the same time. Such results may lead to a forecast that an exciplex phenomenon occurs when comprising the two compounds at the same time.

The exciplex phenomenon is a phenomenon of releasing energy having sizes of a donor (p-host) HOMO level and an acceptor (n-host) LUMO level due to electron exchanges between two molecules. When the exciplex phenomenon occurs between two molecules, reverse intersystem crossing (RISC) occurs, and as a result, internal quantum efficiency of fluorescence may increase up to 100%. When a donor (p-host) having a favorable hole transfer ability and an acceptor (n-host) having a favorable electron transfer ability are used as a host of a light emitting layer, holes are injected to the p-host and electrons are injected to the n-host, and therefore, a driving voltage may be lowered, which resultantly helps with enhancement in the lifetime. In the present disclosure, excellent device properties were obtained when using the compound of Chemical Formula 2 performing a donor role and the compound of Chemical Formula 1 performing an acceptor role donor as a host of the light emitting layer.

Particularly, it is identified that excellent lifetime properties are obtained when substituted with deuterium. This is a result obtained from deuterium substitution as described in the results of Table 10, and implies that compound properties may vary depending on deuterium substitution even when having a similar structure.

On the other hand, it is seen that performance in terms of driving voltage, light emission efficiency and lifetime declines when the compound not included in the scope of the present disclosure (Comparative Examples 11 to 28) is used in combination with the compound of Chemical Formula 2.

In other words, it is identified that driving voltage, light emission efficiency and lifetime are significantly superior when using the heterocyclic compound of Chemical Formula 1 and the compound of Chemical Formula 2 of the present disclosure at the same time as a host of the light emitting layer.

Particularly, it is identified that excellent lifetime properties are obtained when substituted with deuterium. This is a result obtained from deuterium substitution as described in the results of Table 10, and implies that compound properties may vary depending on deuterium substitution even when having a similar structure.

On the other hand, it is seen that performance in terms of driving voltage, light emission efficiency and lifetime declines when the compound not included in the scope of the present disclosure (Comparative Examples 14 to 31) is used in combination with the compound of Chemical Formula 2.

In other words, it is identified that driving voltage, light emission efficiency and lifetime are significantly superior when using the heterocyclic compound of Chemical Formula 1 and the compound of Chemical Formula 2 of the present disclosure at the same time as a host of the light emitting layer.

The invention claimed is:

1. A heterocyclic compound represented by the following Chemical Formula 1:

[Chemical Formula 1]

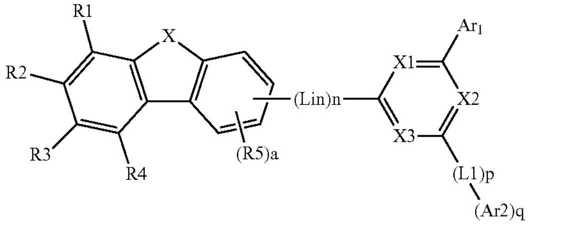

wherein, in Chemical Formula 1,

X is O; or S;

R1 to R5 are the same as or different from each other, and each independently selected from the group consisting of hydrogen; deuterium; and a phenyl group;

X1 to X3 are N; or CRe, and at least one of X1 to X3 is N;

L1 is a substituted or unsubstituted C6 to C60 arylene group; or a substituted or unsubstituted C2 to C60 heteroarylene group, wherein the heteroarylene group does not contain a nitrogen atom;

Ar1 and Ar2 are the same as or different from each other, and each independently a substituted or unsubstituted C1 to C60 alkyl group; a substituted or unsubstituted C6 to C60 aryl group; or a substituted or unsubstituted C2 to C60 heteroaryl group, wherein the heteroaryl group does not contain a nitrogen atom;

Lin is a substituted or unsubstituted C6 to C20 arylene group;

Chemical Formula 1 has a deuterium content of greater than or equal to 20% and less than or equal to 100%;

Re is hydrogen; deuterium; a substituted or unsubstituted C1 to C60 alkyl group; or a substituted or unsubstituted C6 to C60 aryl group;

a and p are an integer of 0 to 3;

q is an integer of 1 to 5;

n is an integer of 0 to 2; and when n is an integer of 2 or p, a and q are 2 or greater, substituents in the parentheses are the same as or different from each other, wherein, when

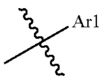

and

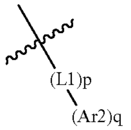

of Chemical Formula 1 are expressed as an unsubstituted biphenyl group, the biphenyl group is represented by any one of the following structural formulae:

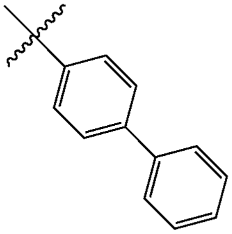

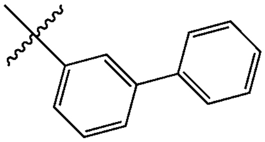

.

wherein Chemical Formula 1 is represented by a combination of the following Structural Formula A to the following Structural Formula C:

[Structural Formula A]

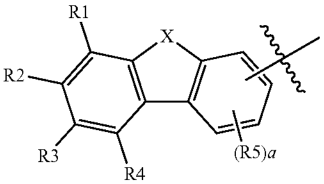

[Structural Formula B]

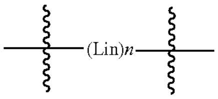

[Structural Formula C]

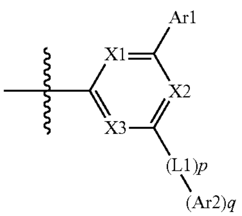

in Structural Formula A to Structural Formula C,

is a position to which Structural Formulae A to C each bond; and

Structural Formula A and Structural Formula B; or Structural Formula A has a deuterium content of 20% to 100%, Structural Formula C has a deuterium content of 10% or less, wherein when n is an integer of 0, then any one of R1 to R5 is deuterium.

2. The heterocyclic compound of claim 1, wherein Lin is represented by any one of the following structural formulae:

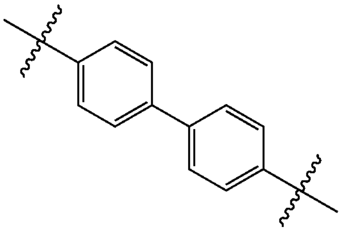

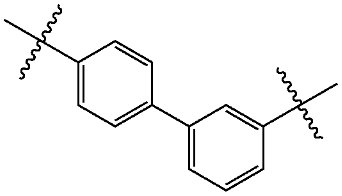

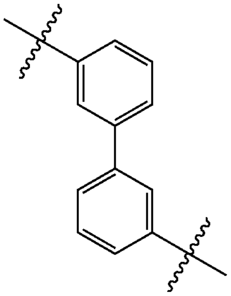

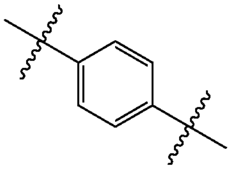

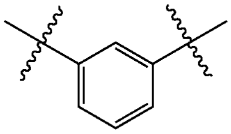

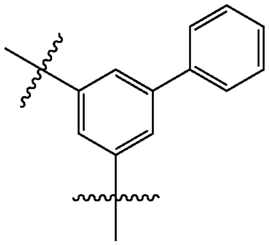

-continued
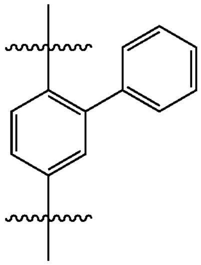
in the structural formulae,
means a position linked to the substituents of Chemical Formula 1; and
Lin is unsubstituted or substituted with deuterium.
3. The heterocyclic compound of claim 1, wherein Chemical Formula 1 is represented by any one of the following compounds:
1
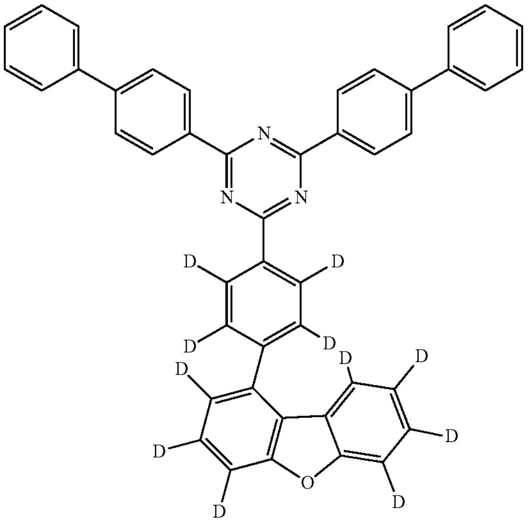
2
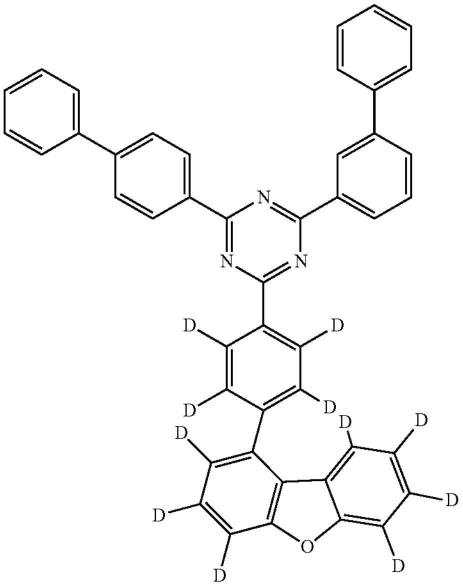
3
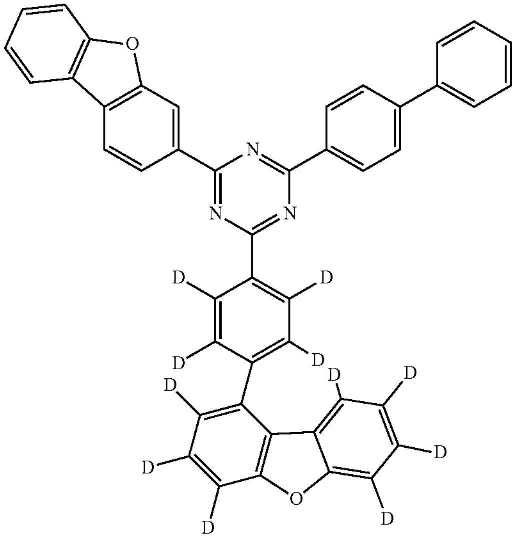
4
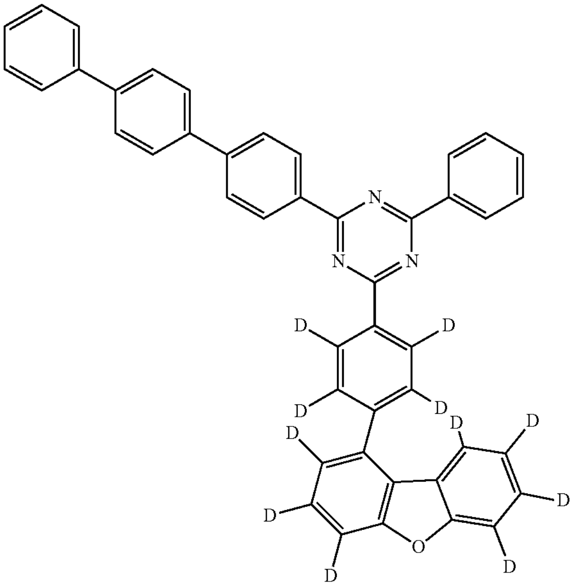

-continued
5
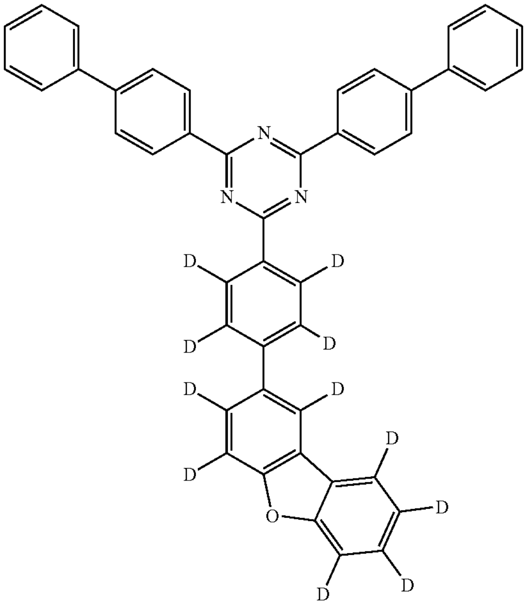
6
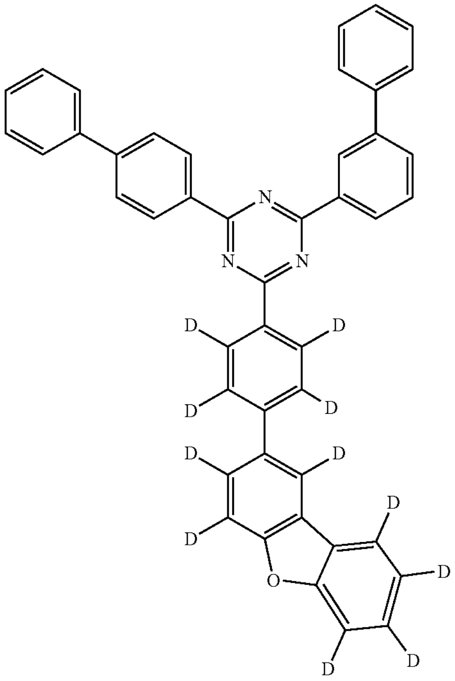
7
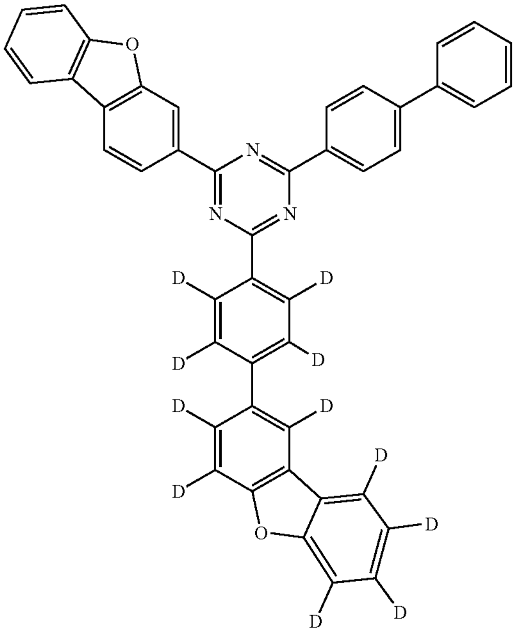
8
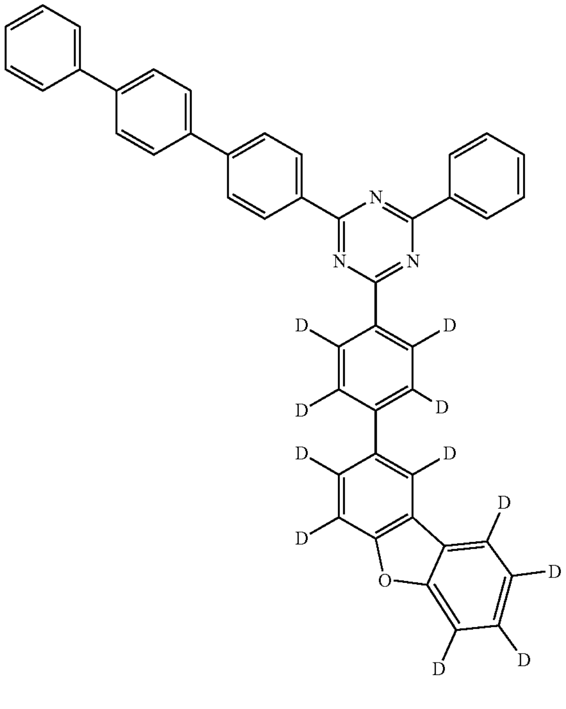

-continued
9
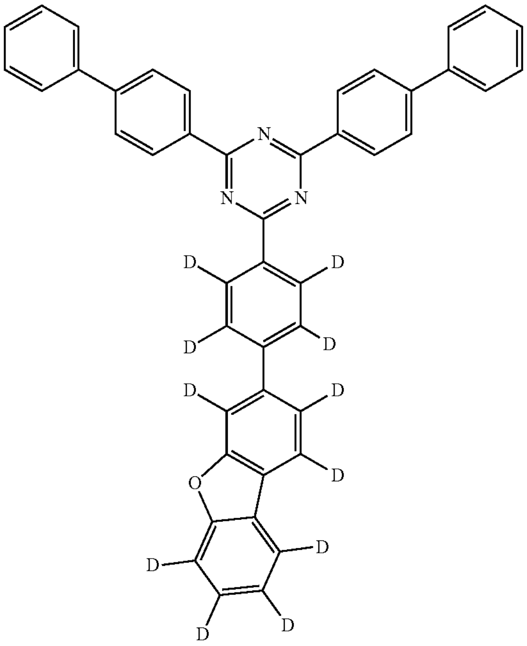
10
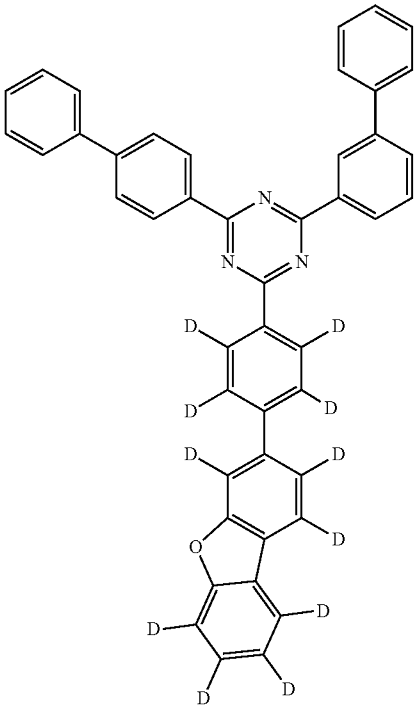
11
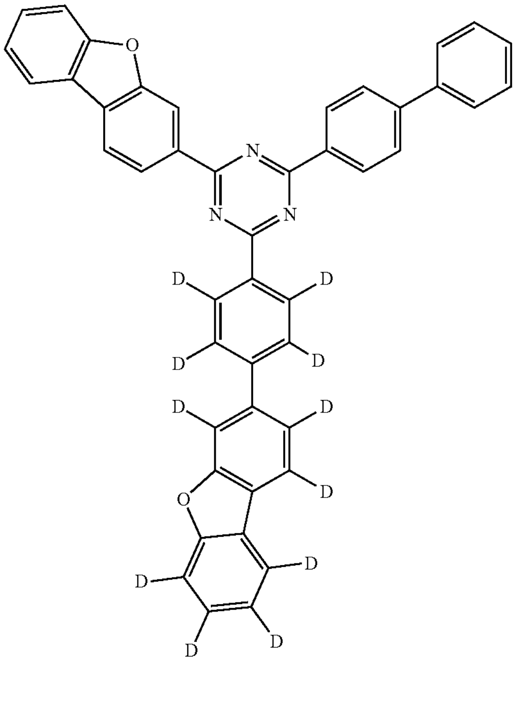
12
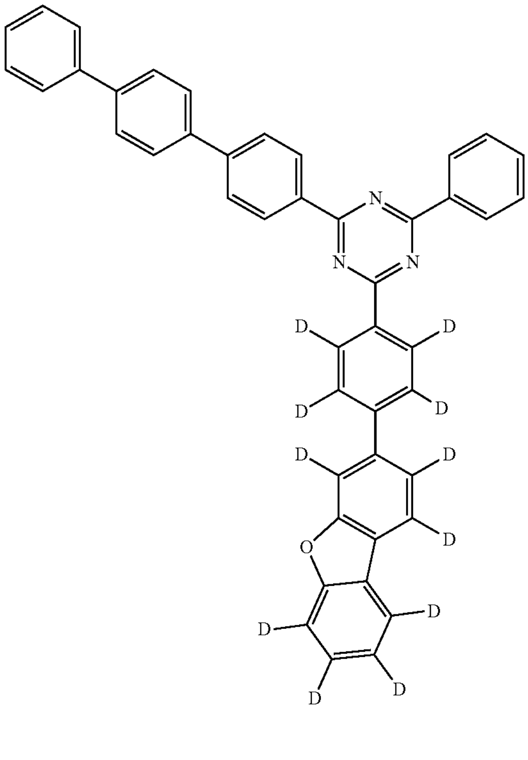

-continued
13
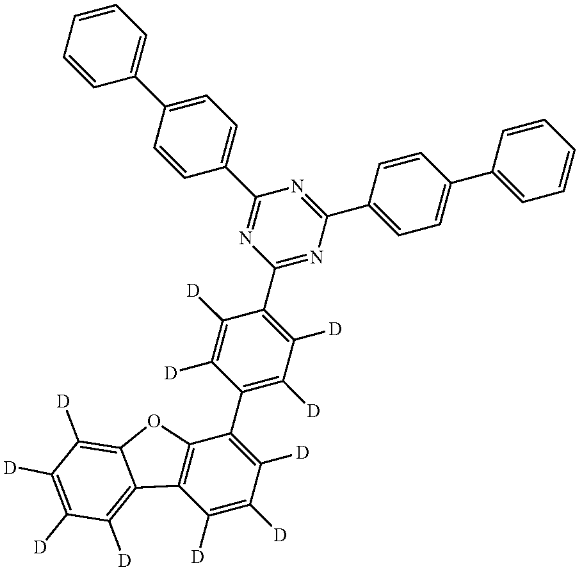
14
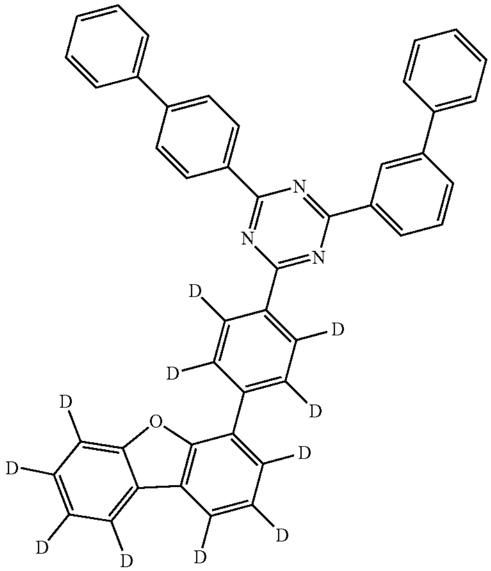
15
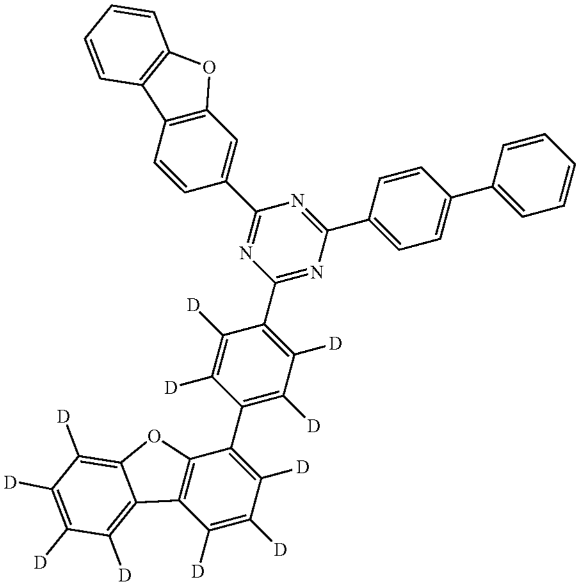
16
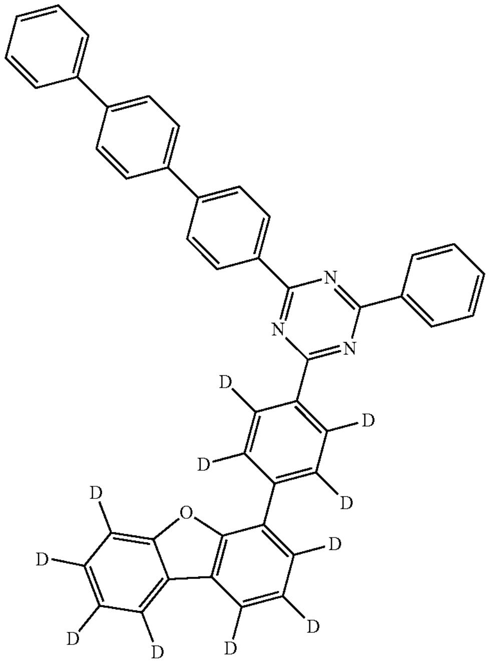

-continued
17
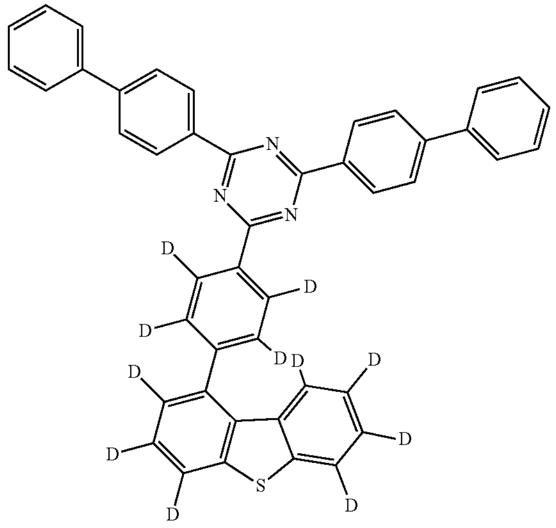
18
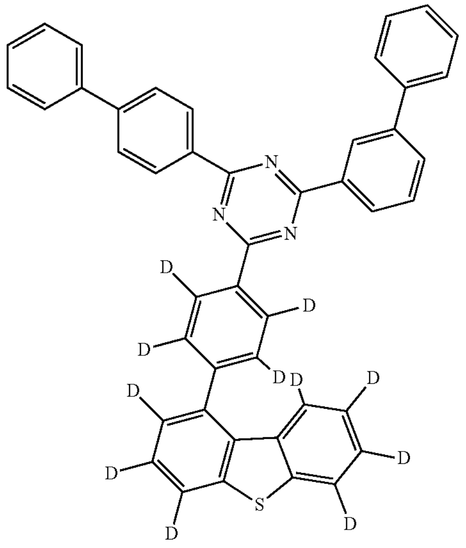
19
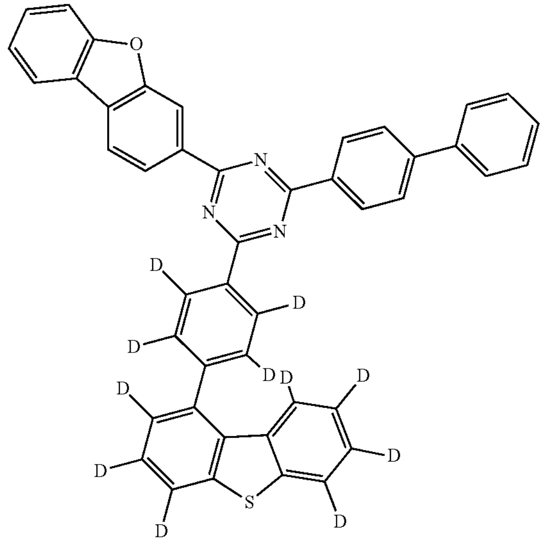
20
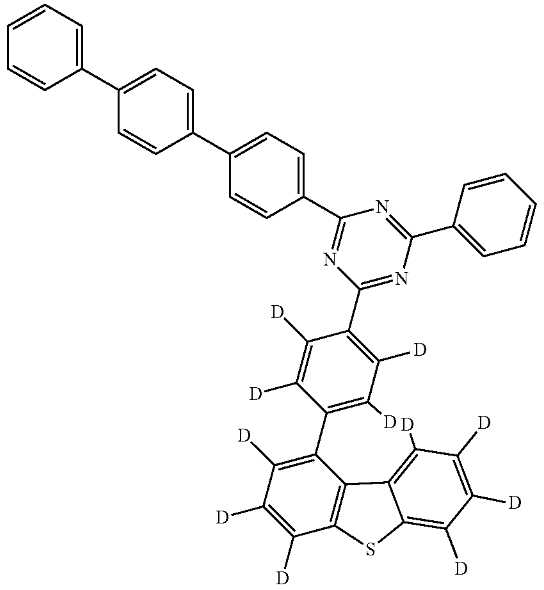
21
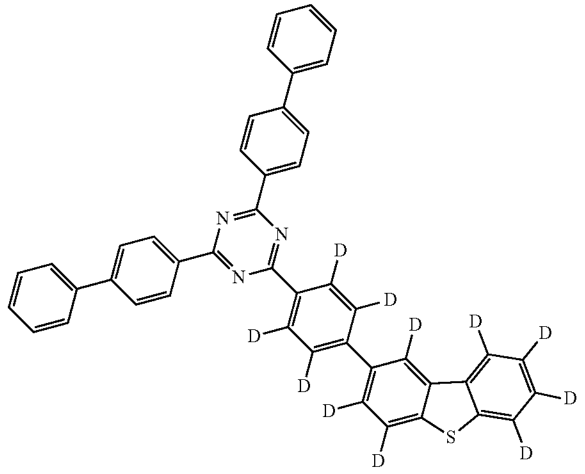
22
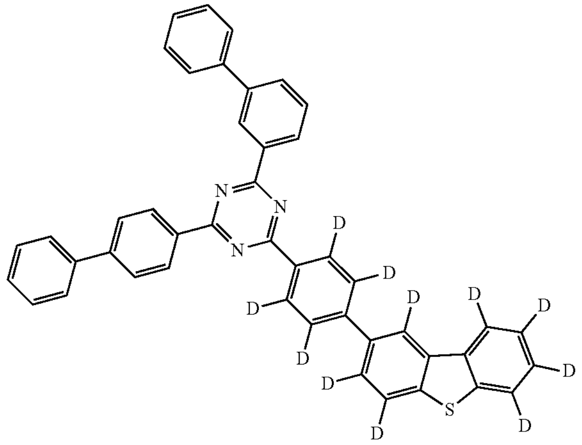

-continued
23
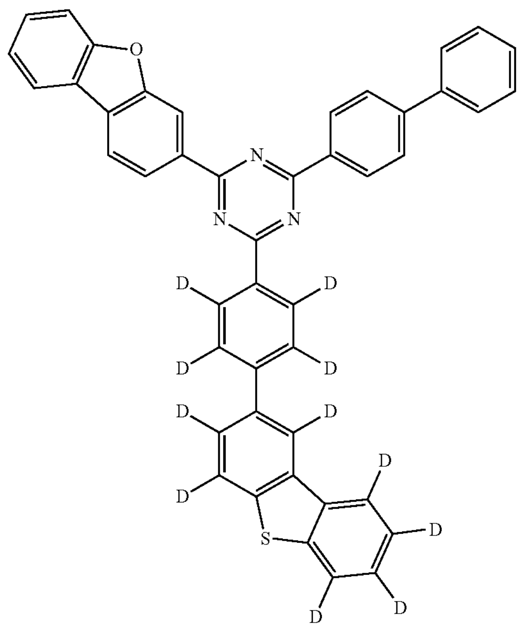
24
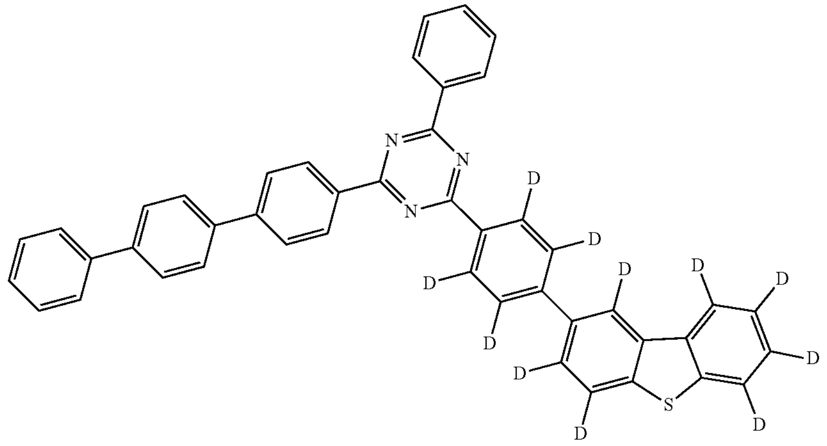

-continued
25
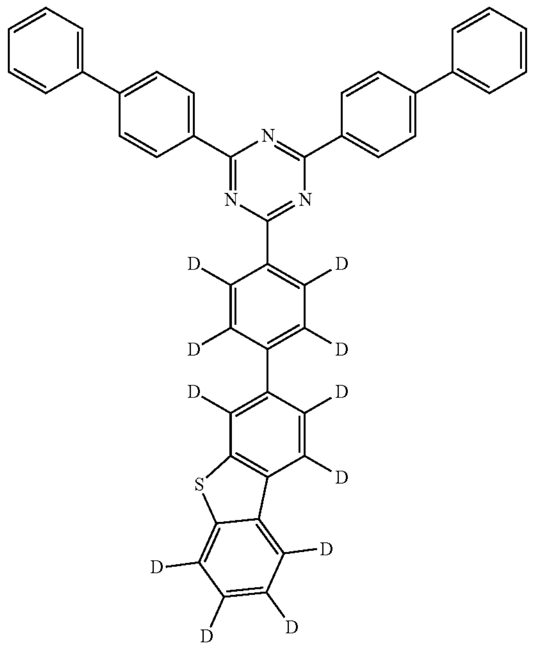
26
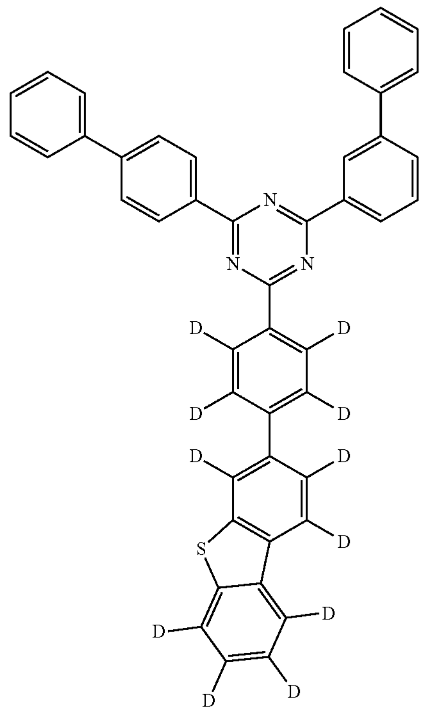
27
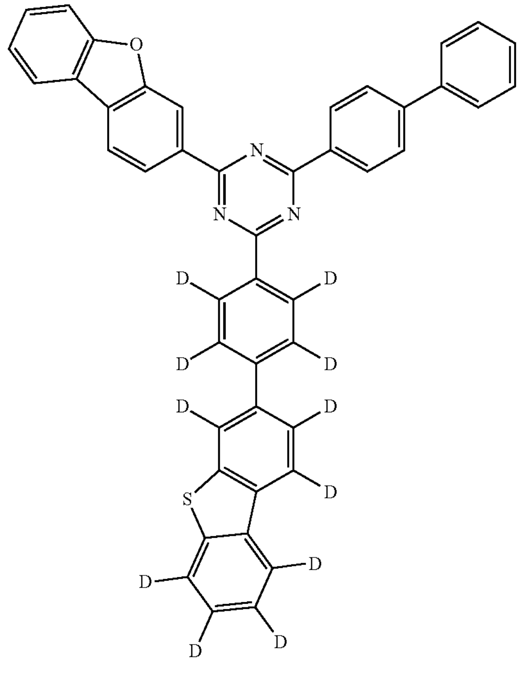
28
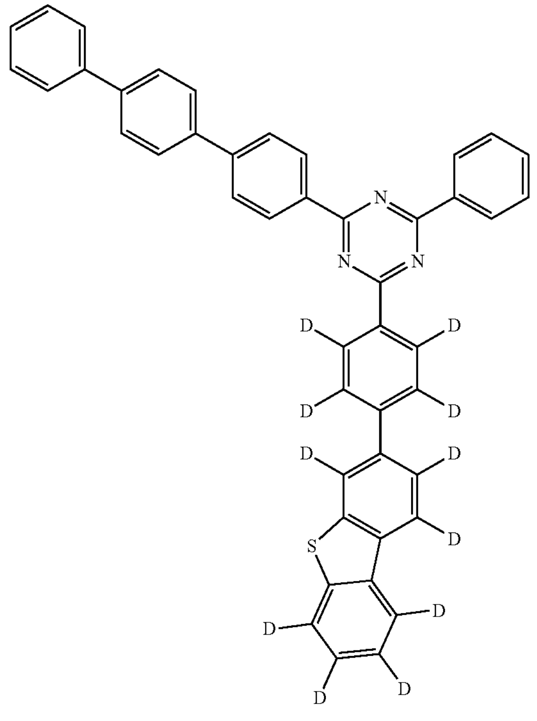

-continued
29
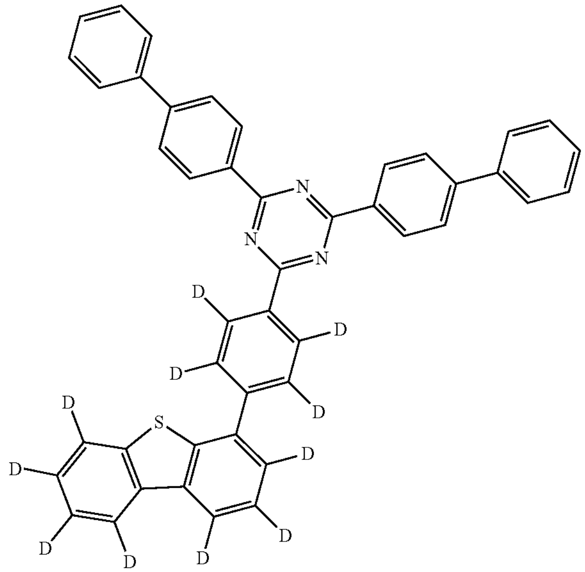
30
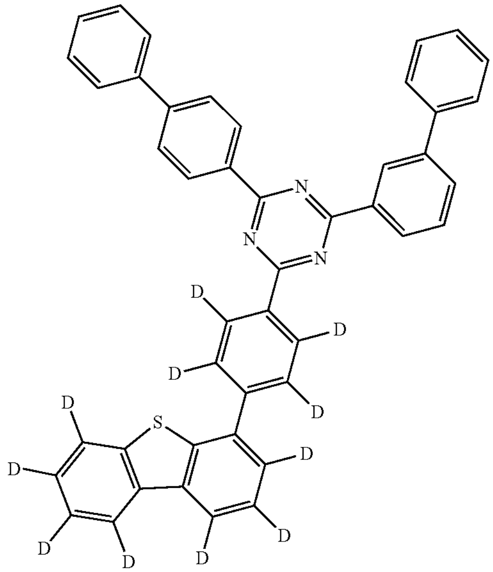
31
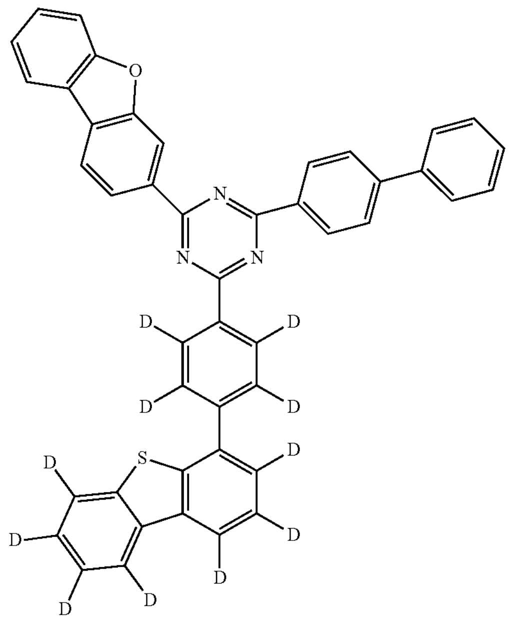
32
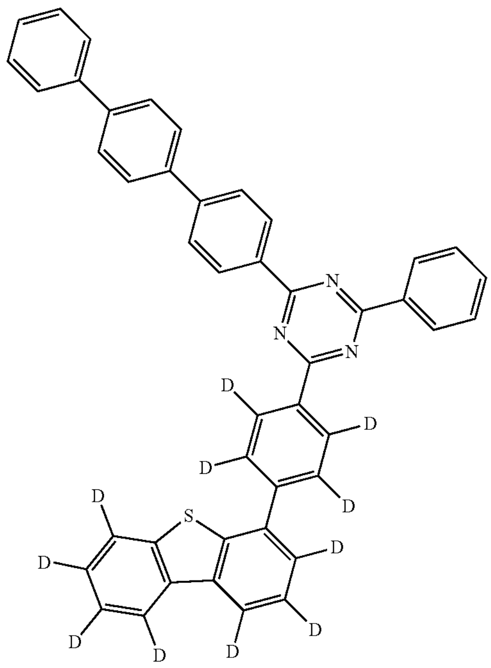

-continued
33
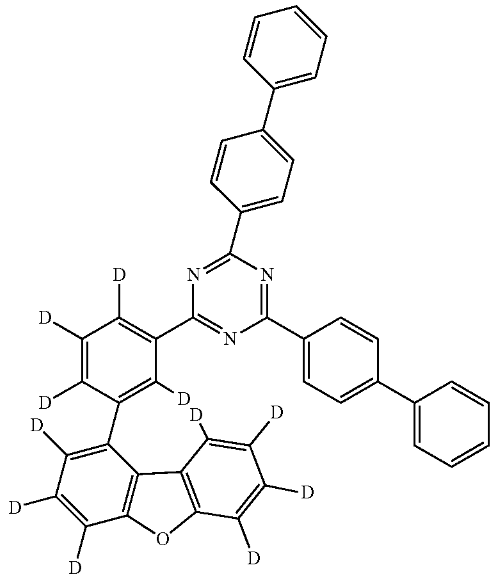
34
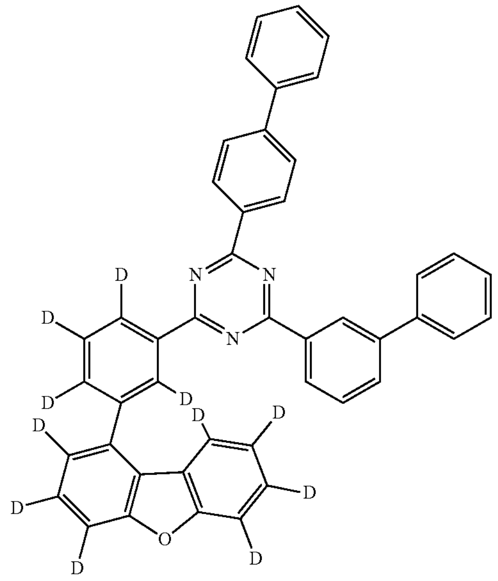
35
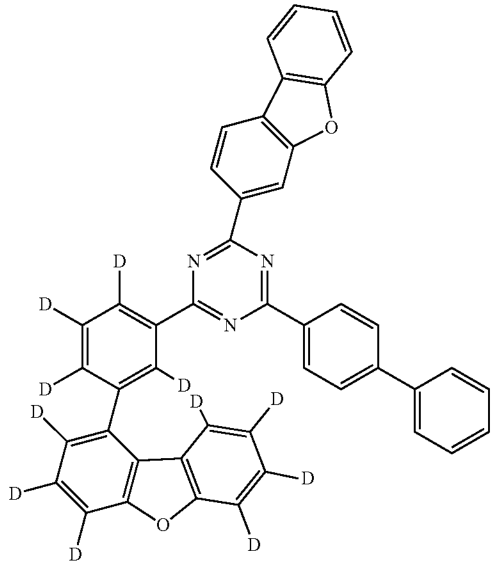
36
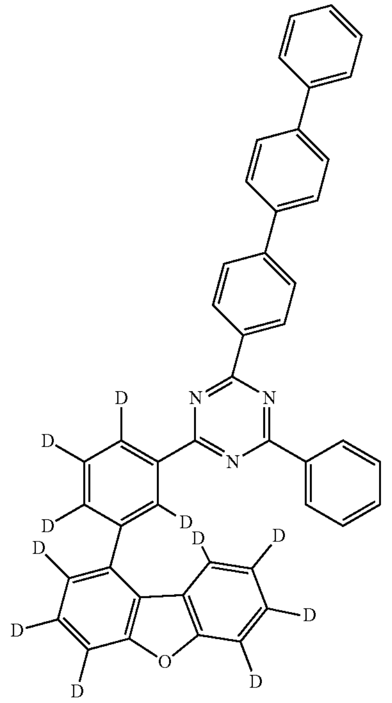

-continued
37
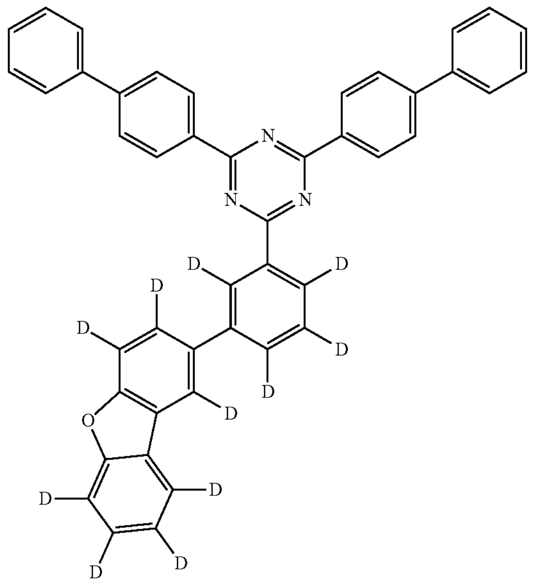
38
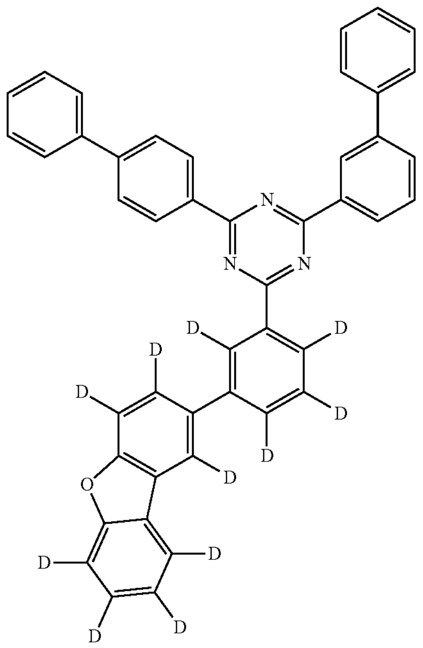
39
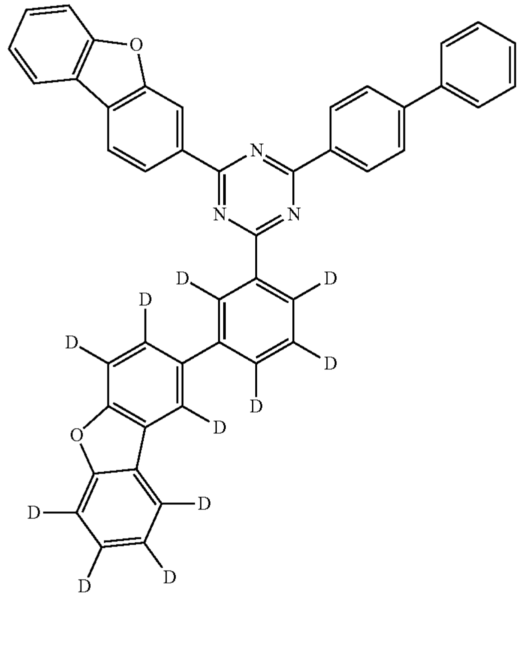
40
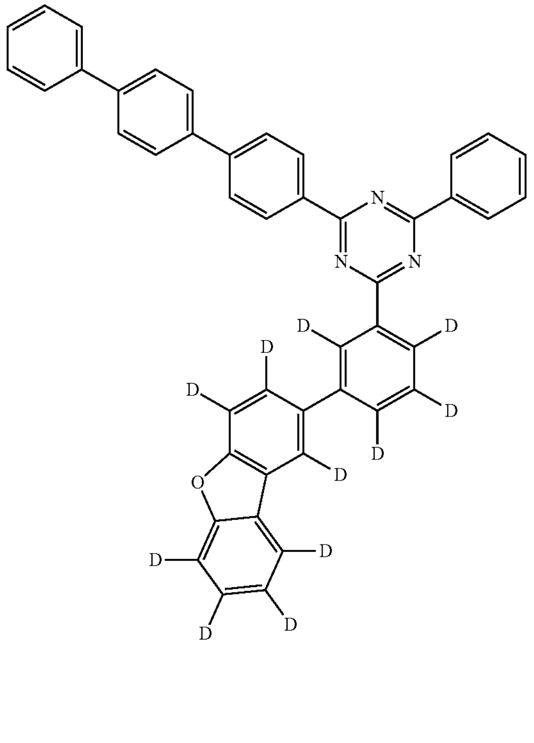

-continued
41
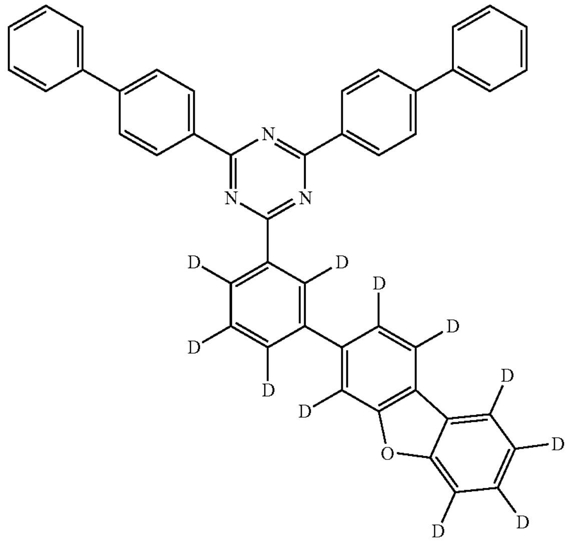
42
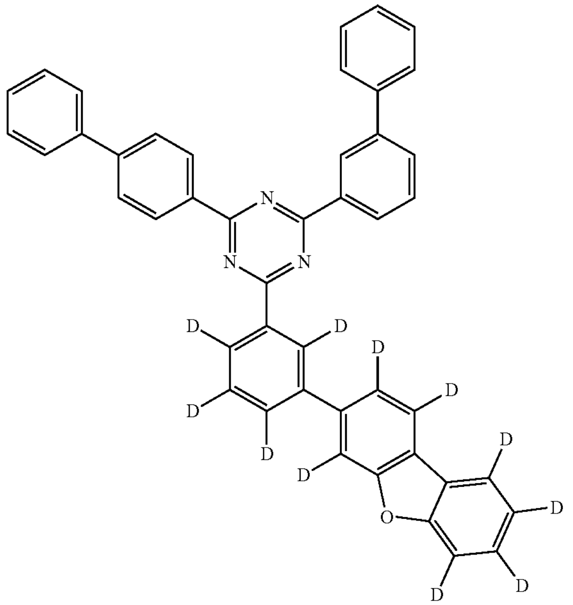
43
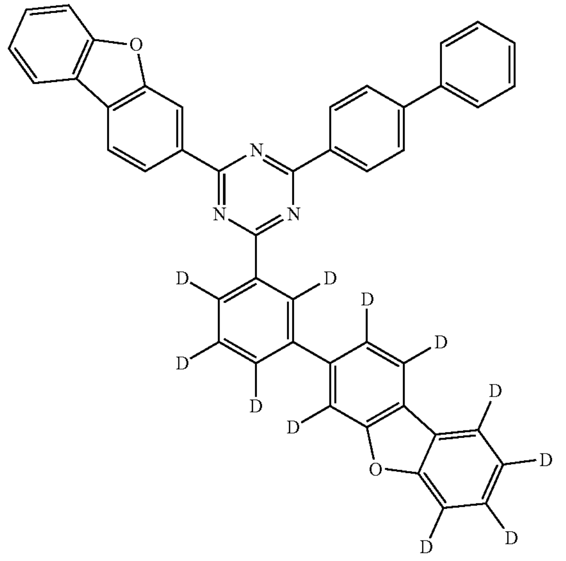
44
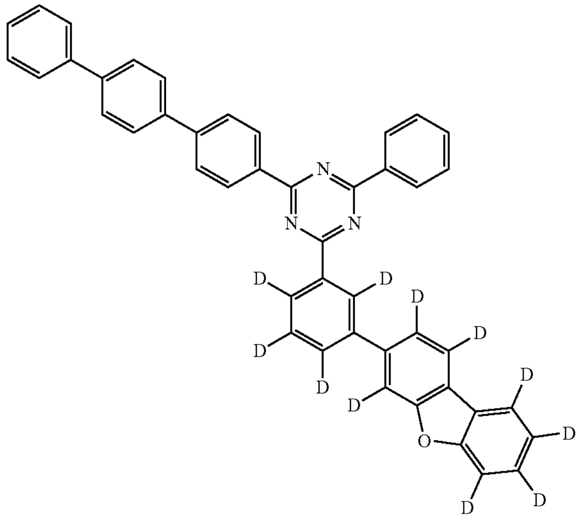

-continued
45
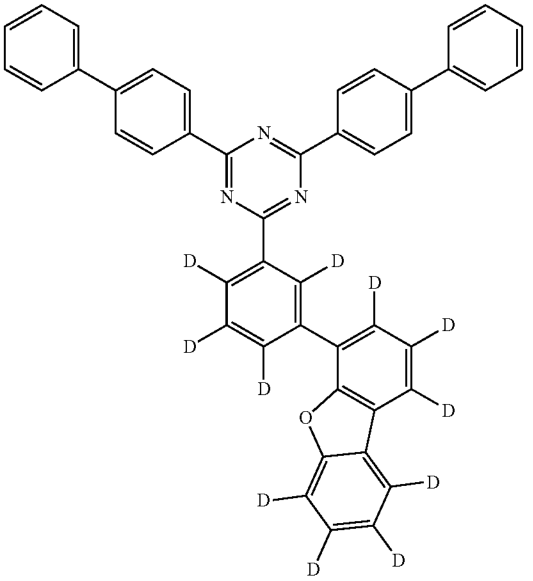
46
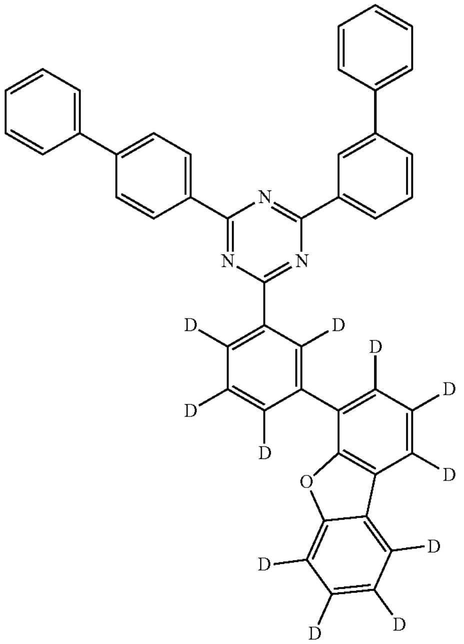
47
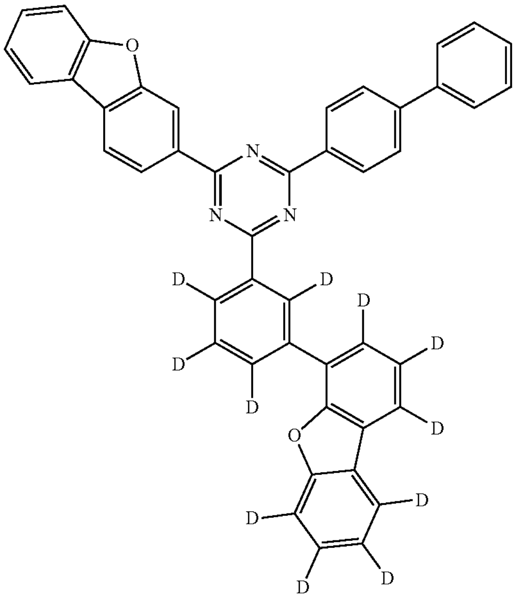
48
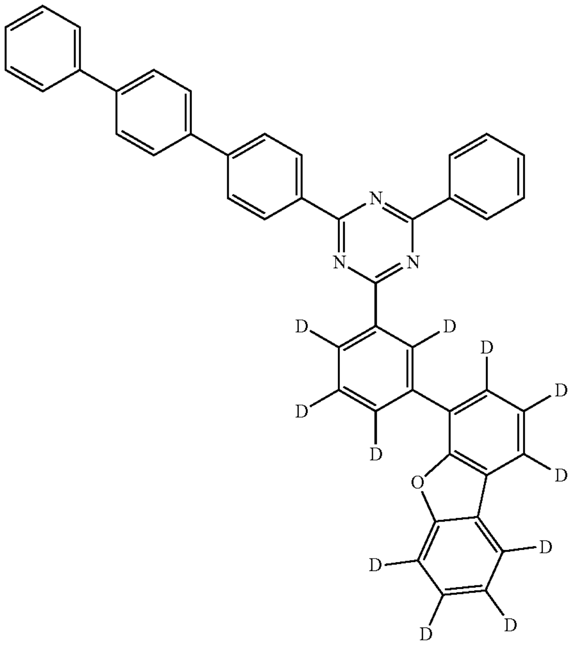

-continued
49
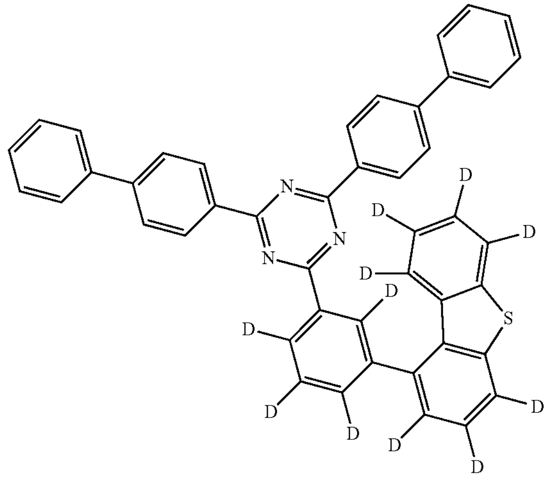
50
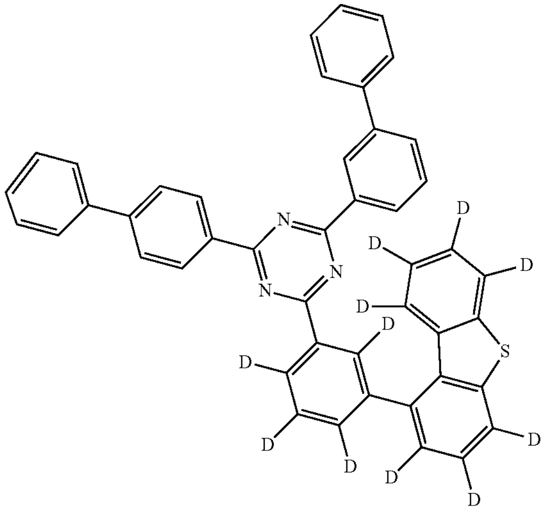
51
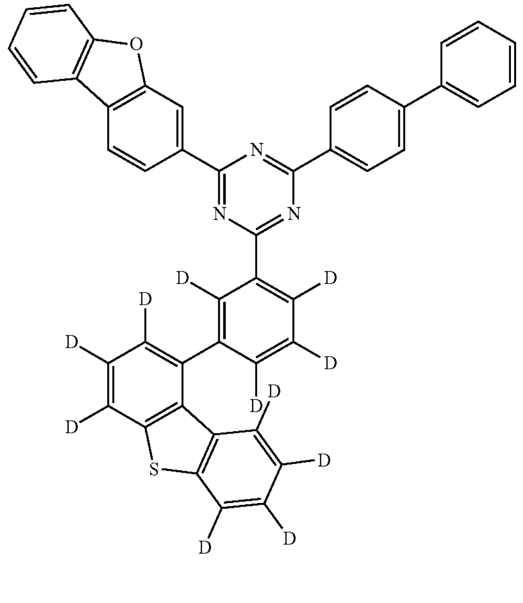
52
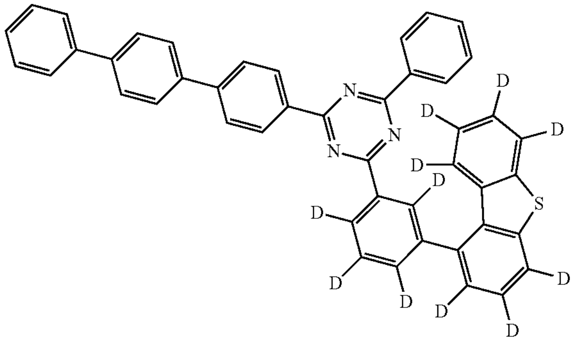

-continued
53
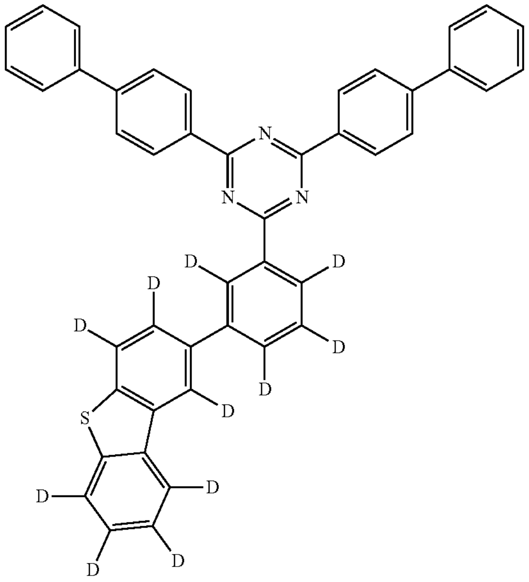
54
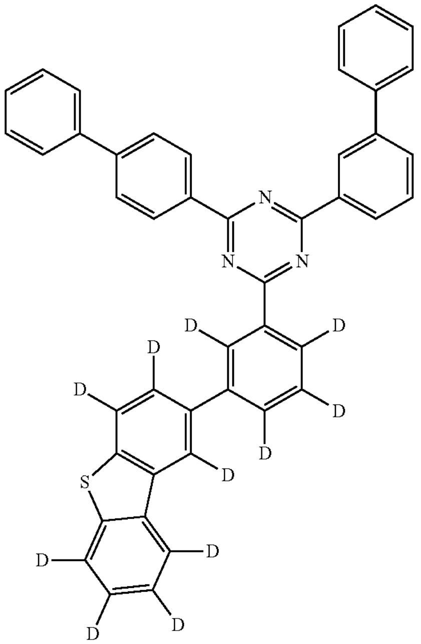
55
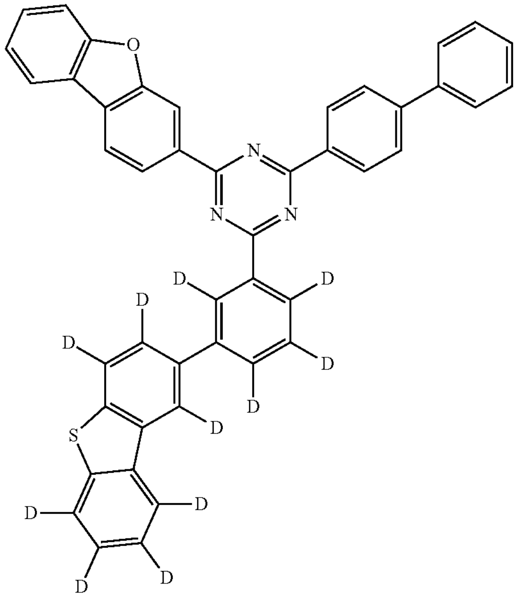
56
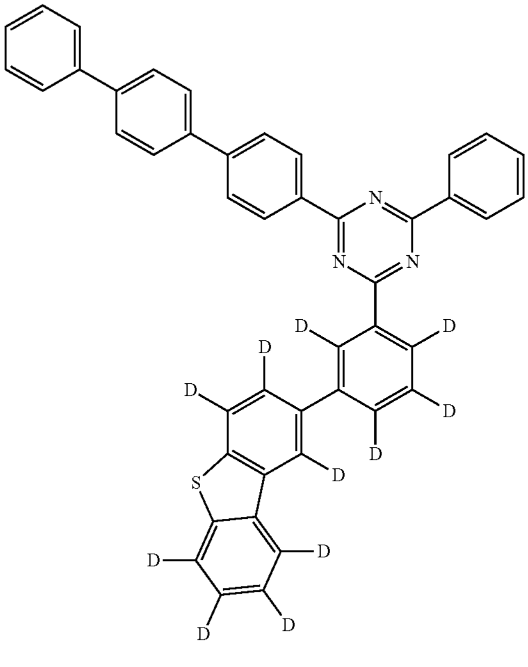

-continued
57
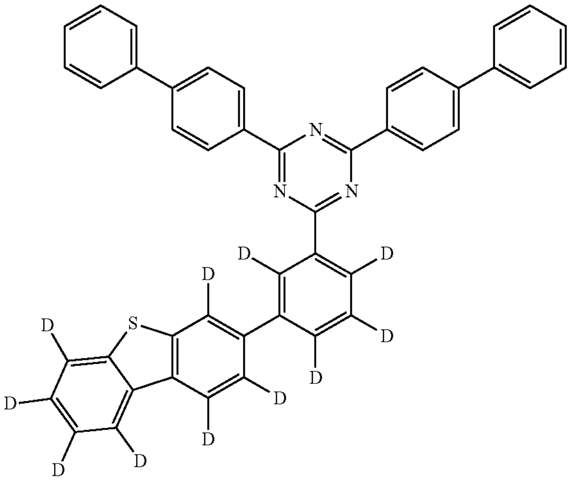
58
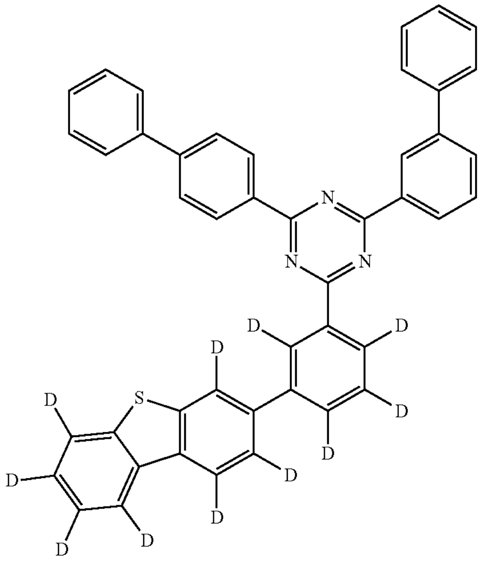
59
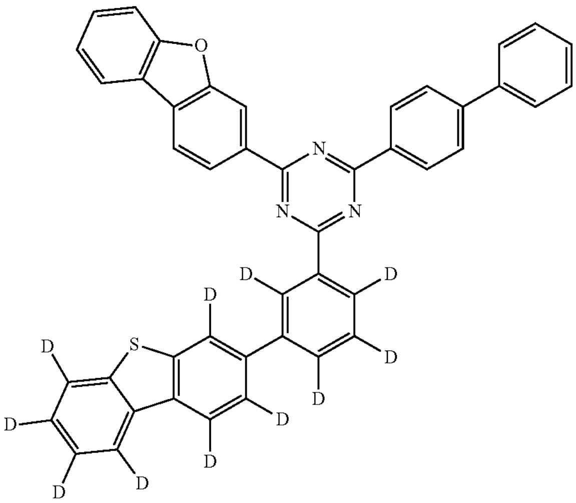
60
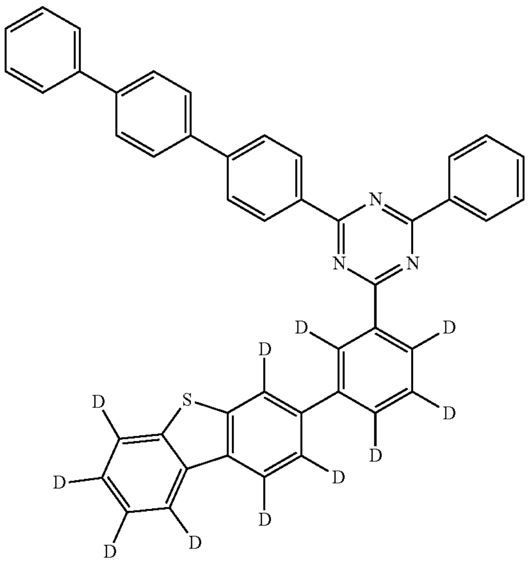

-continued
61
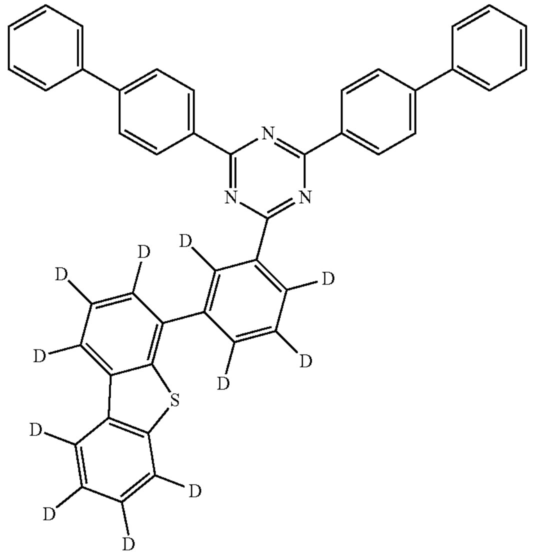
62
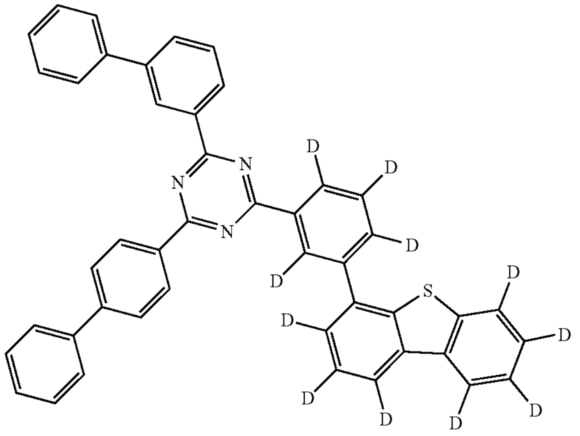
63
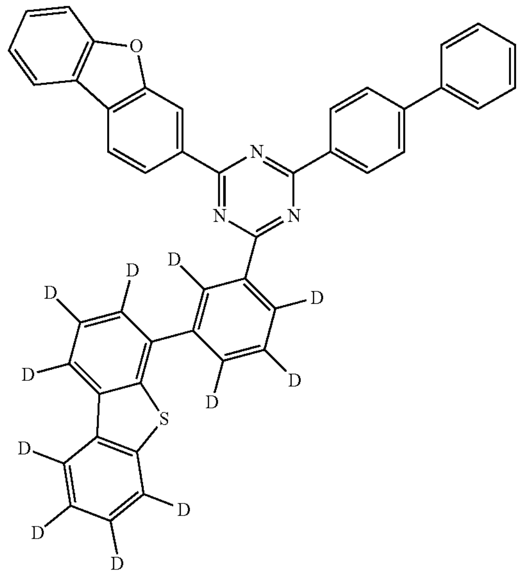
64
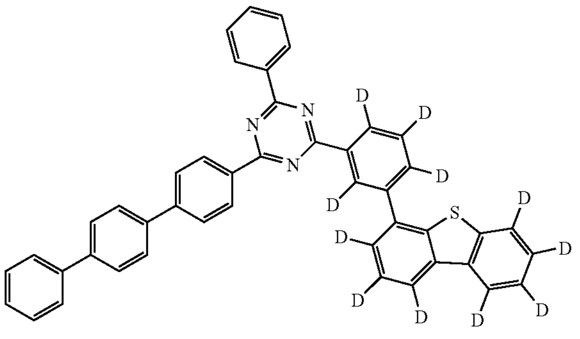

-continued
65
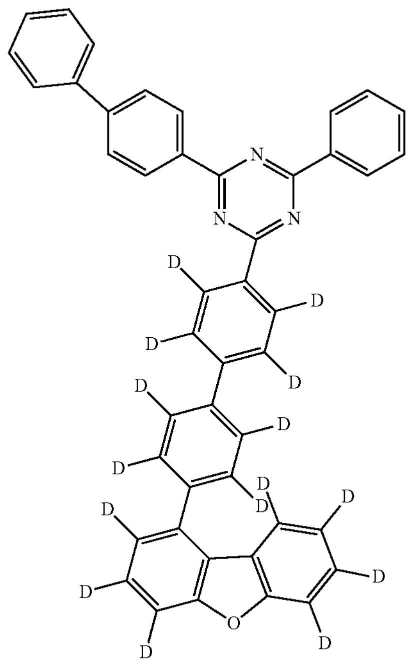
66
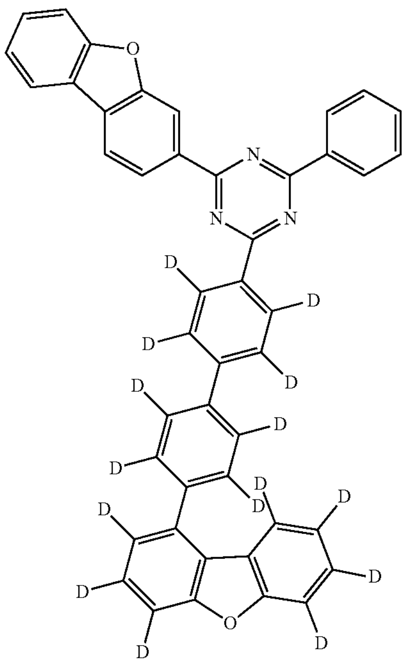
67
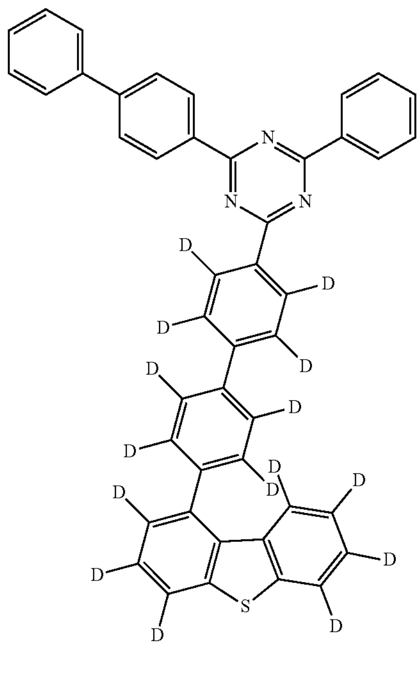
68
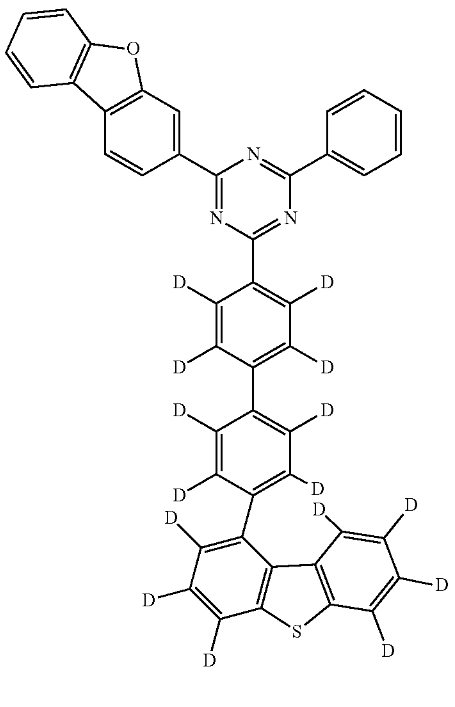

-continued
69
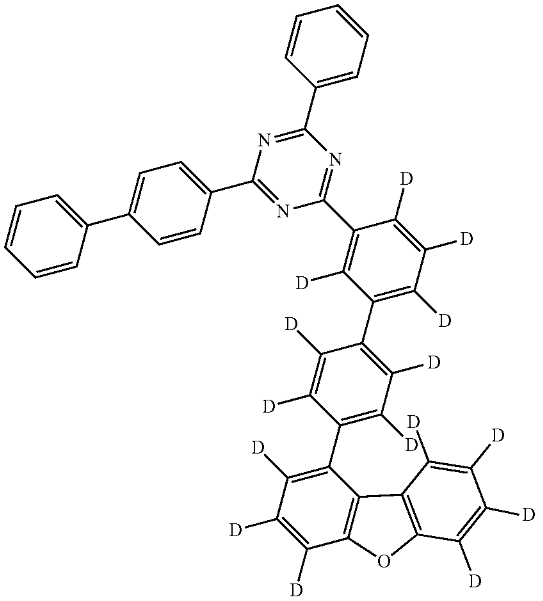
70
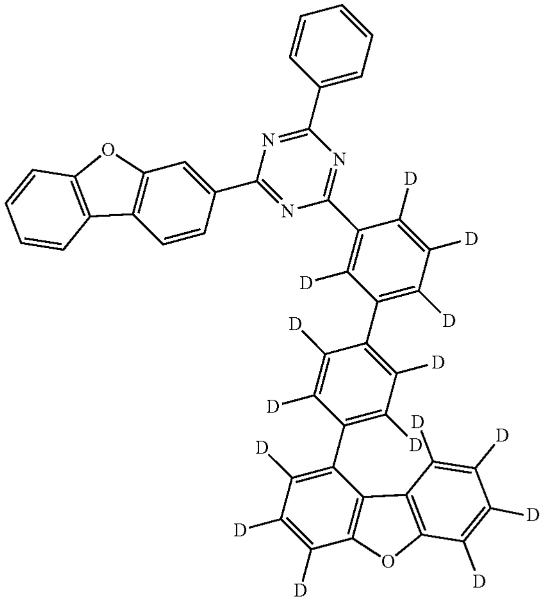
71
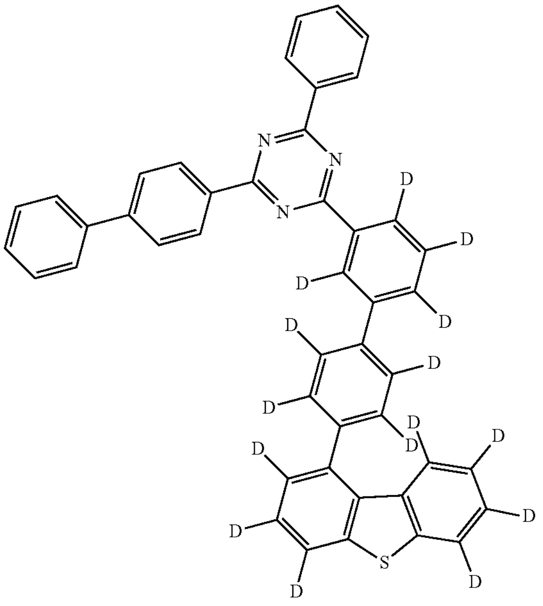
72
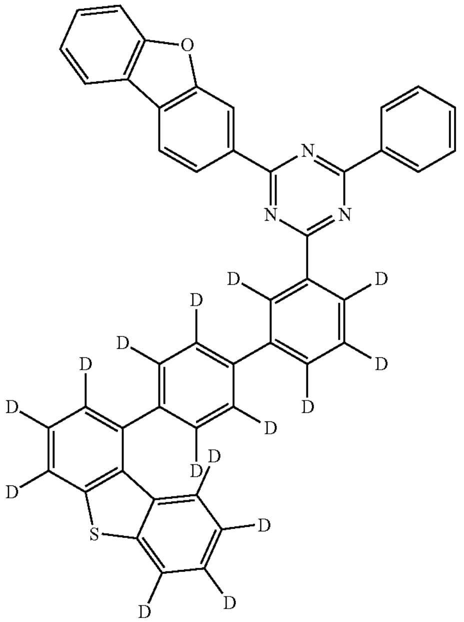

-continued
73
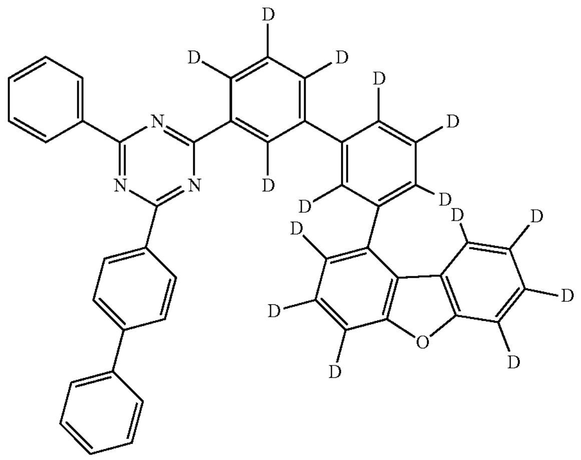
74
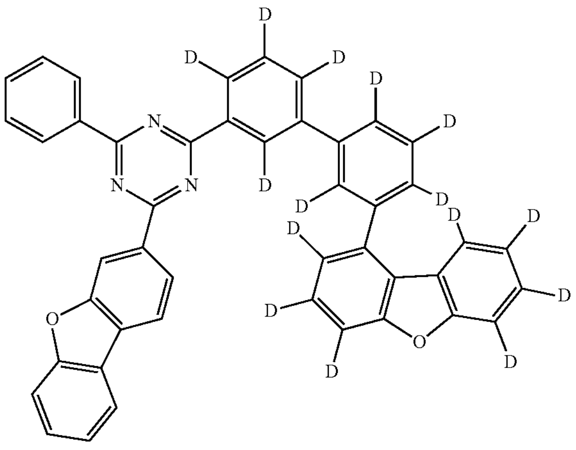
75
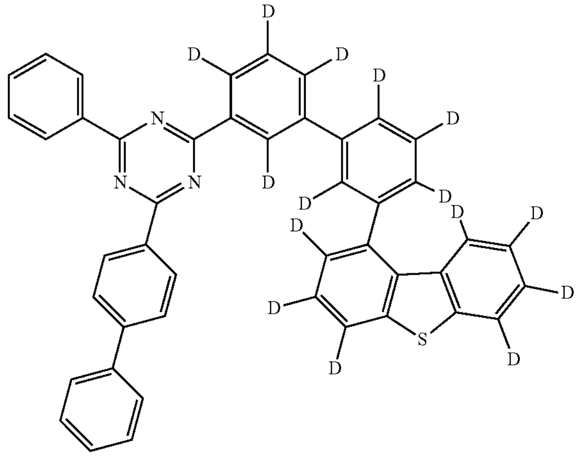
76
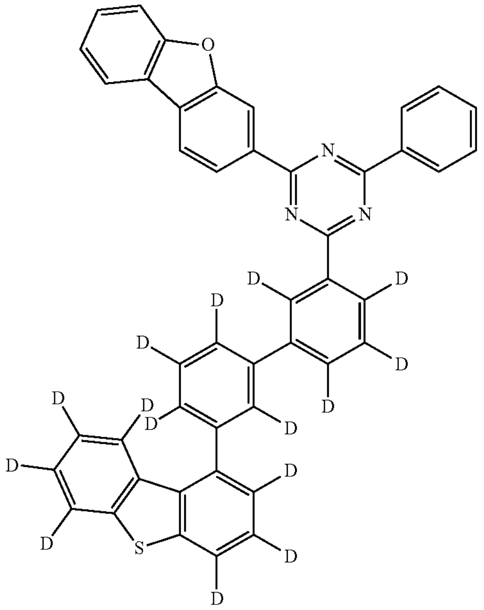
77
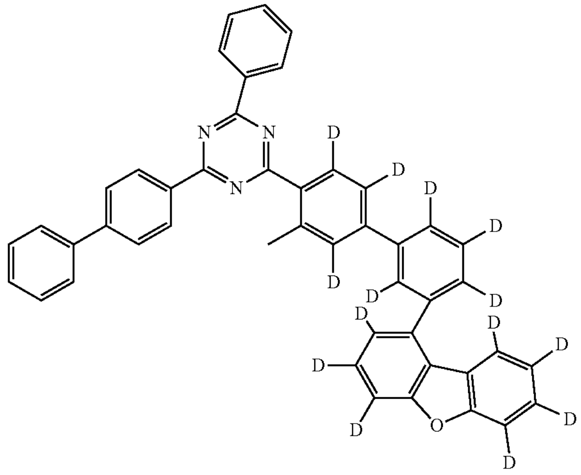
78
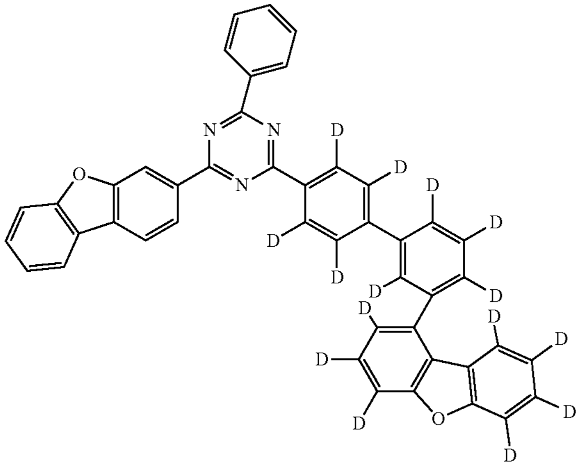

-continued
79
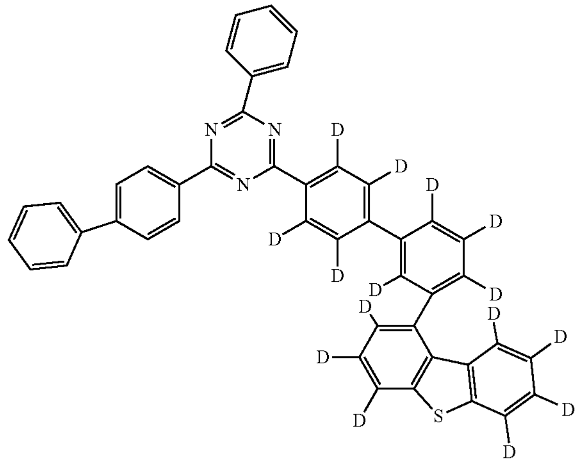
80
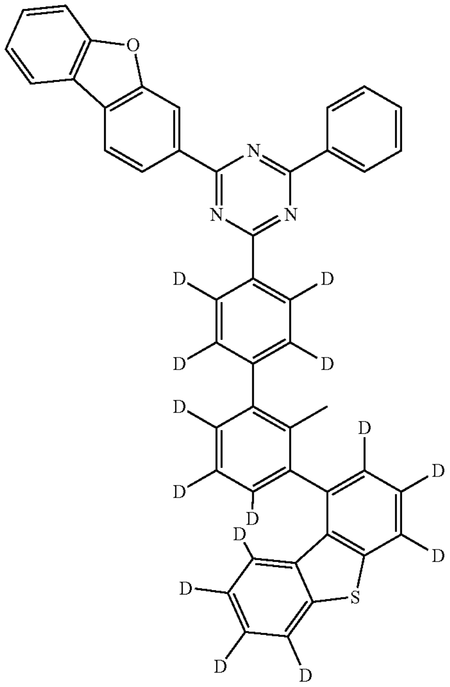
81
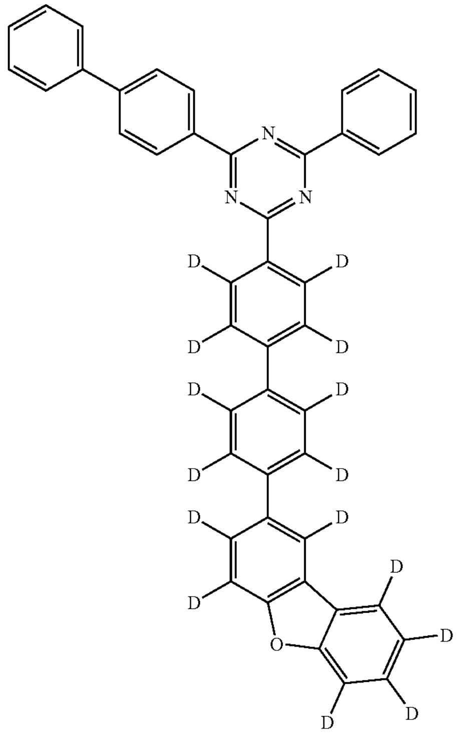
82
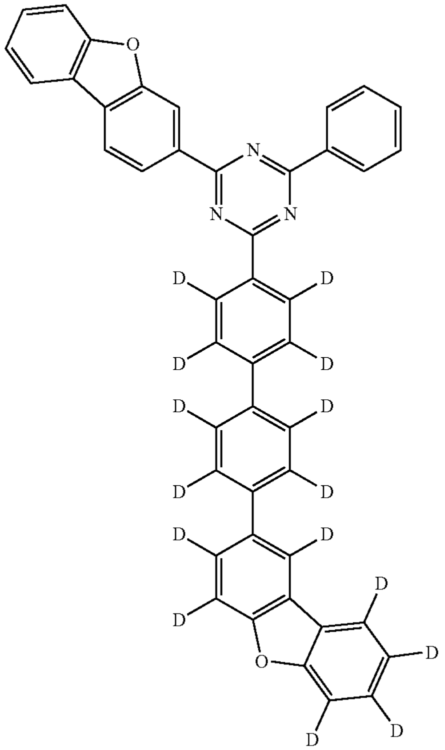

-continued
83
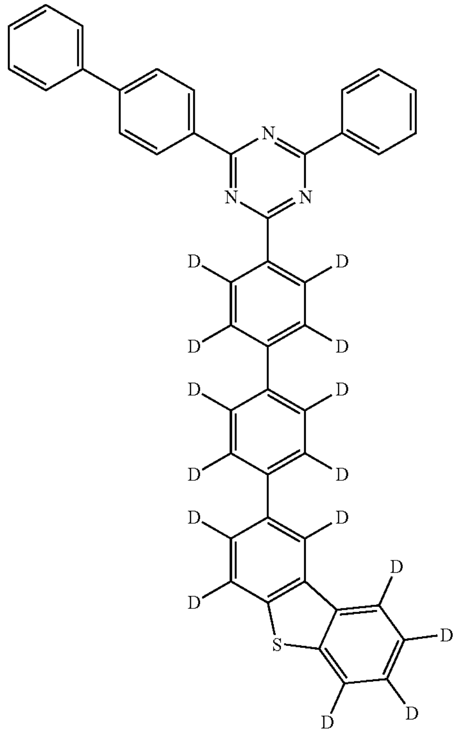
84
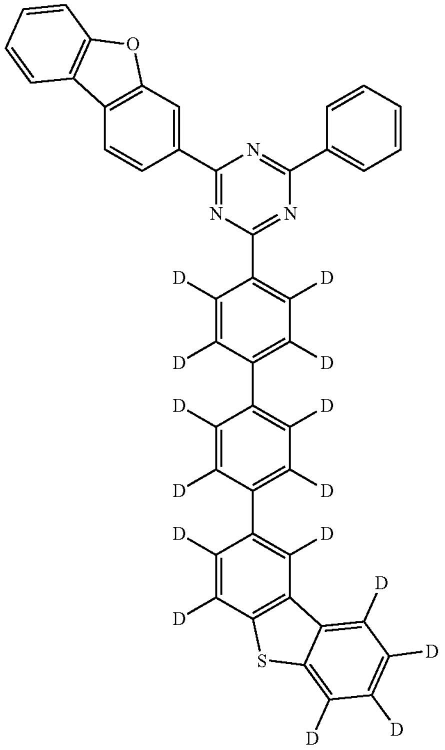
85
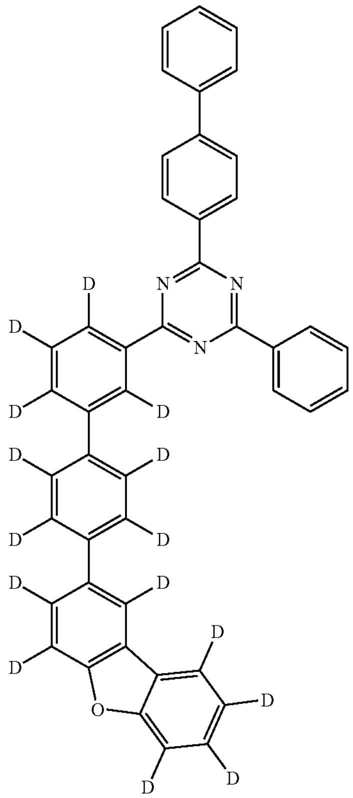
86
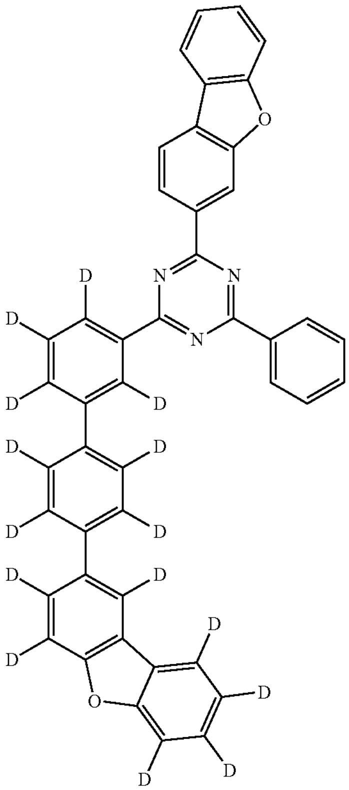

-continued
87
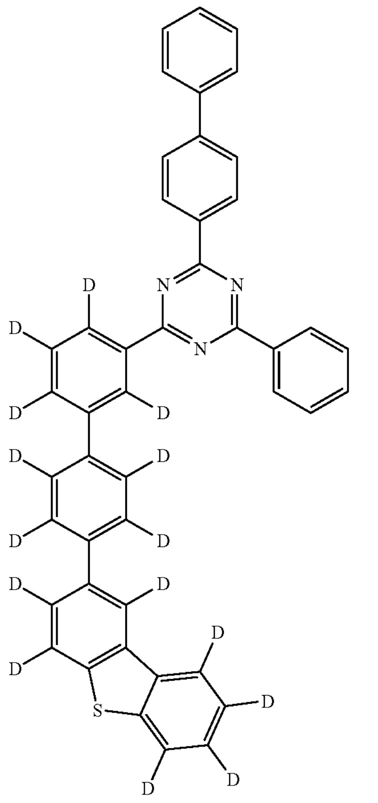
88
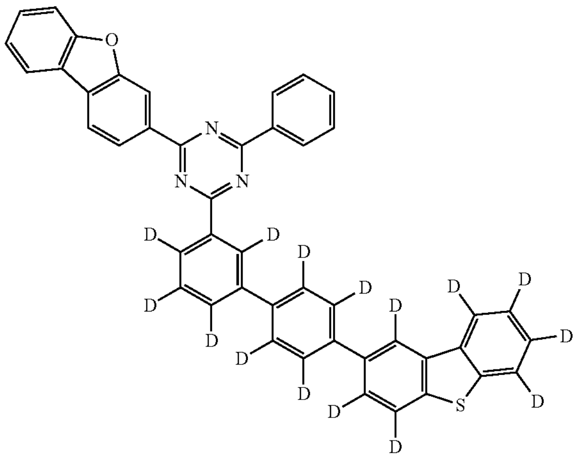
89
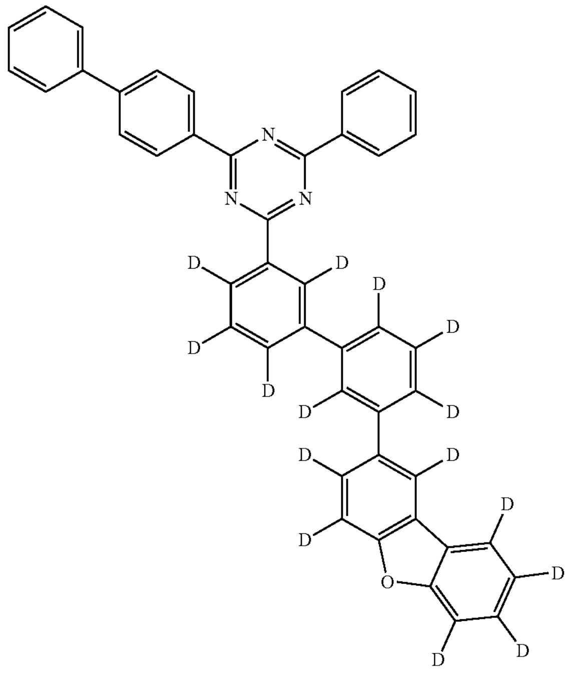
90
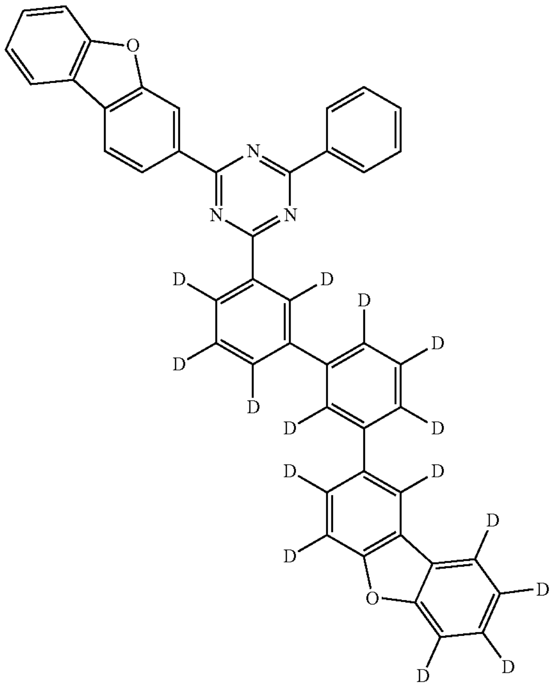

-continued
91
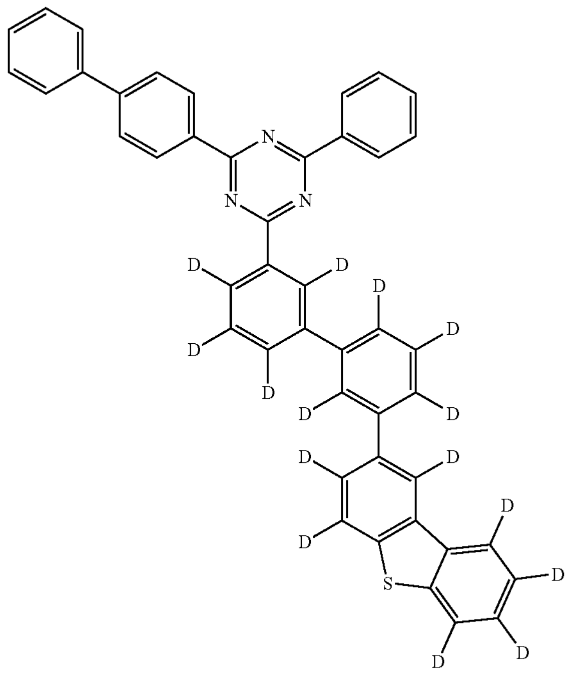
92
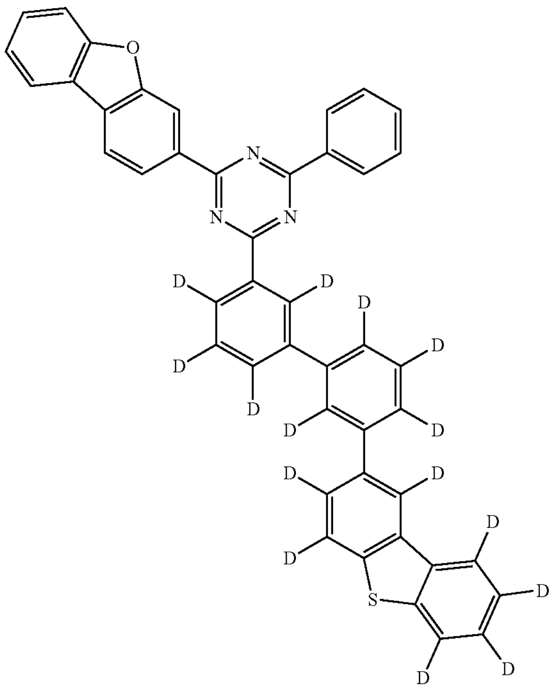
93
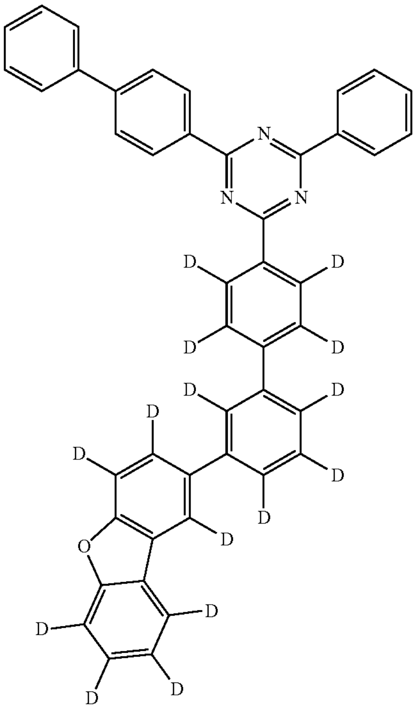
94
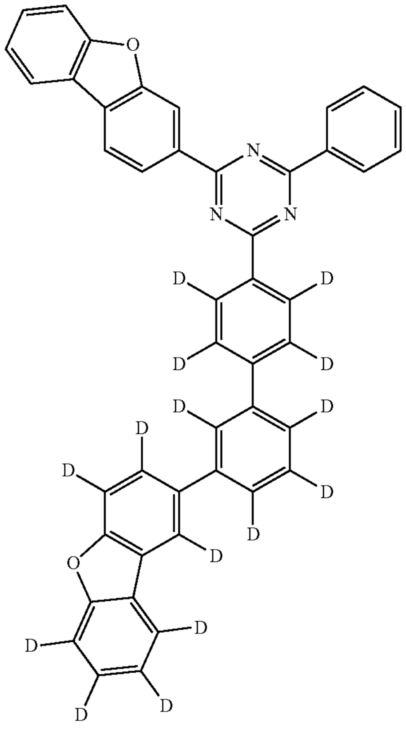

-continued
95
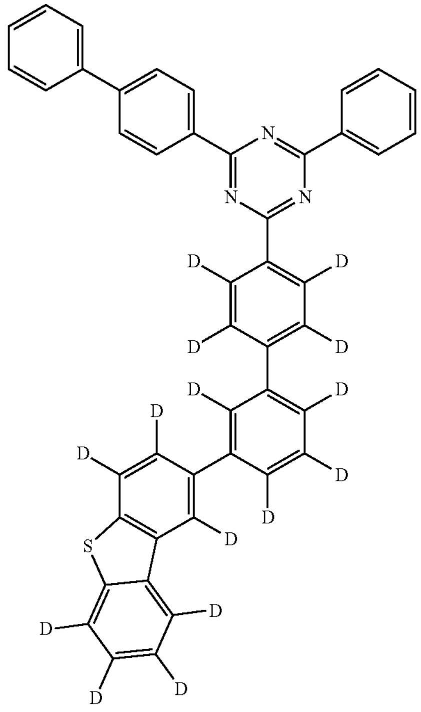
96
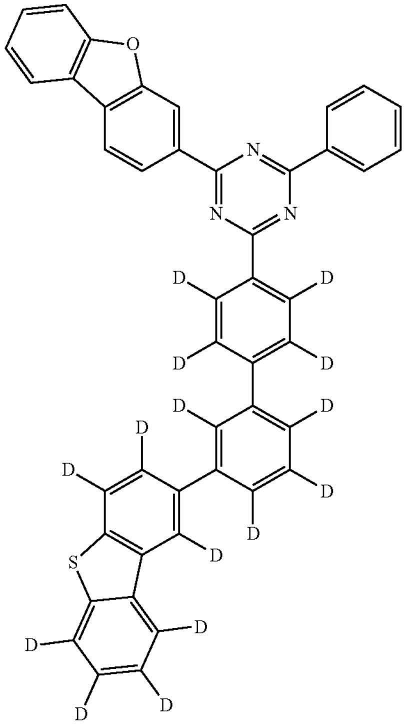
97
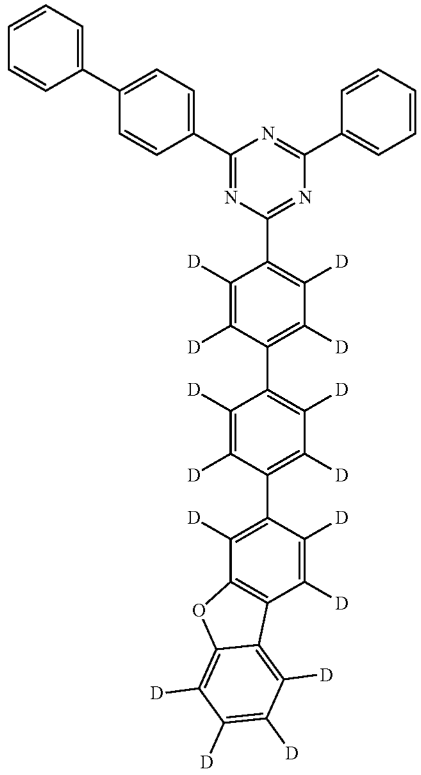
98
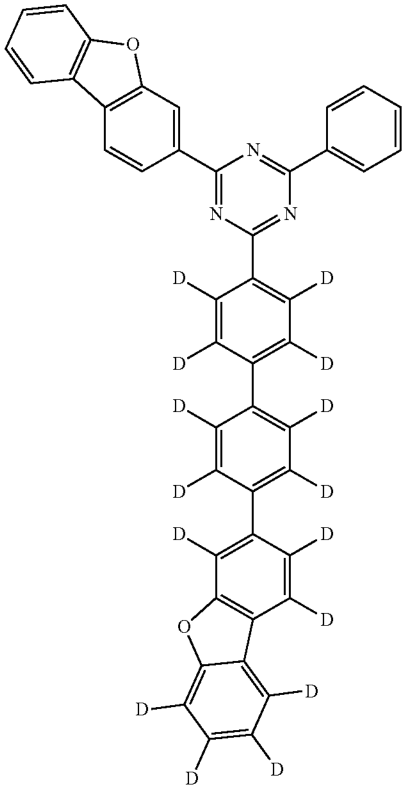

-continued
99
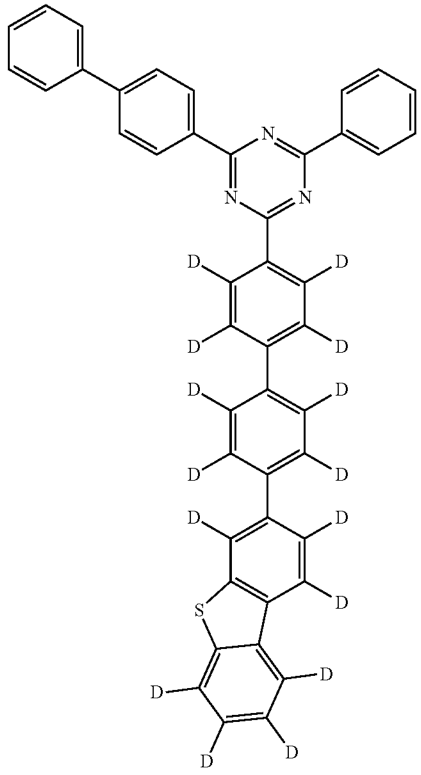
100
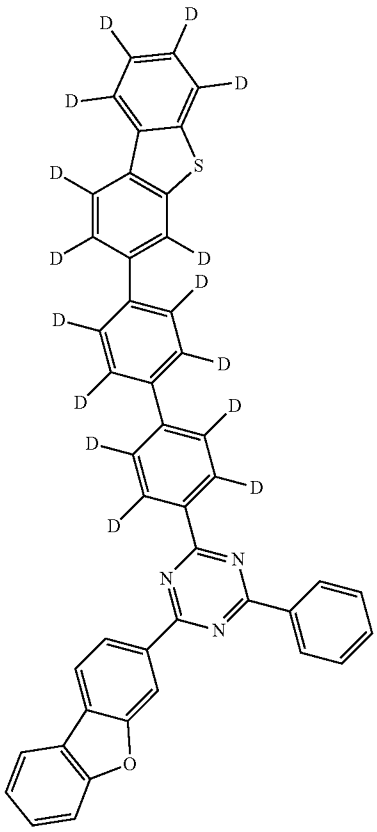
101
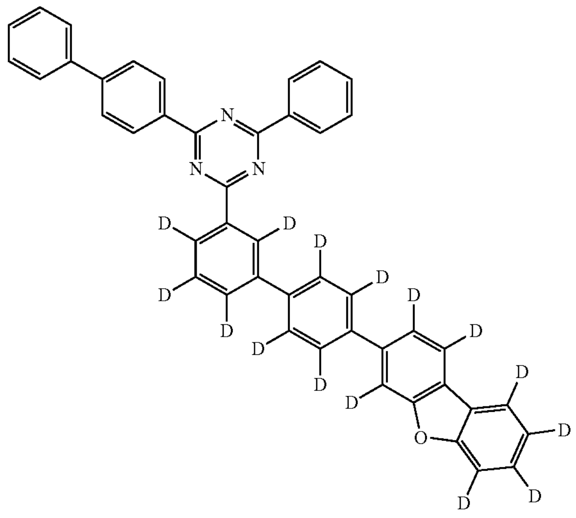
102
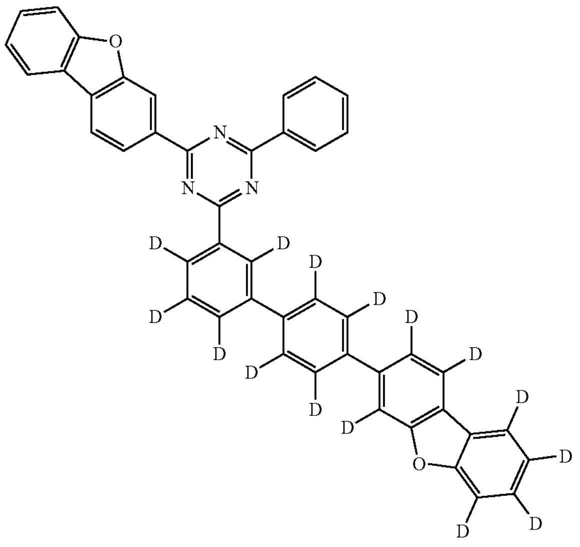

-continued
103
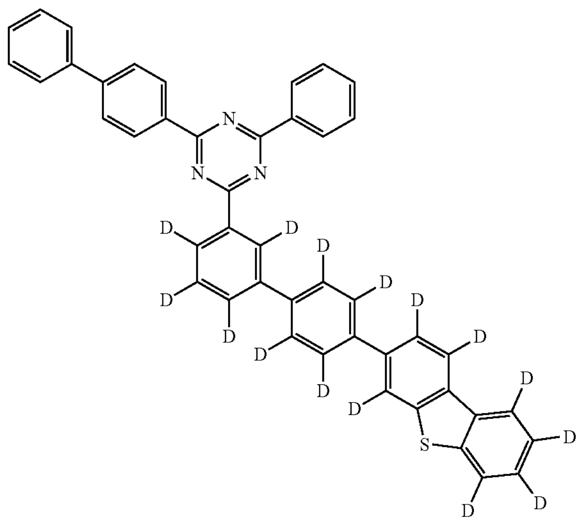
104
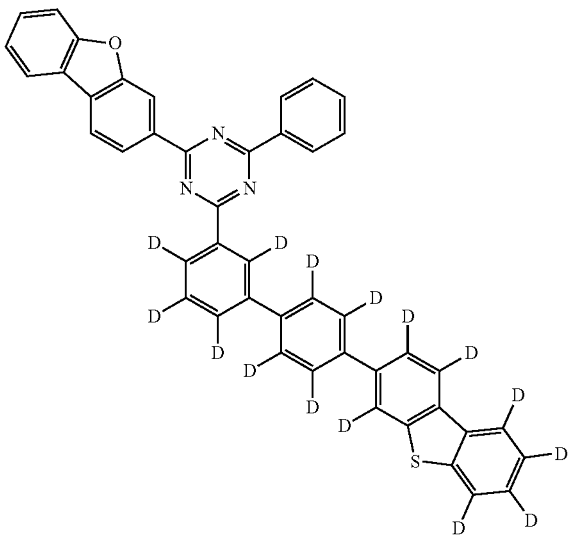
105
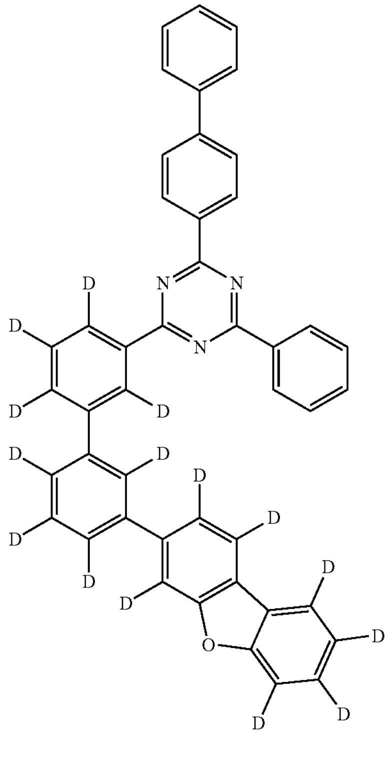
106
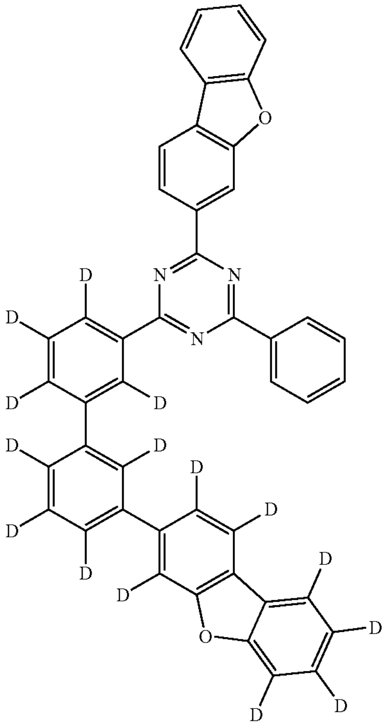

-continued
107
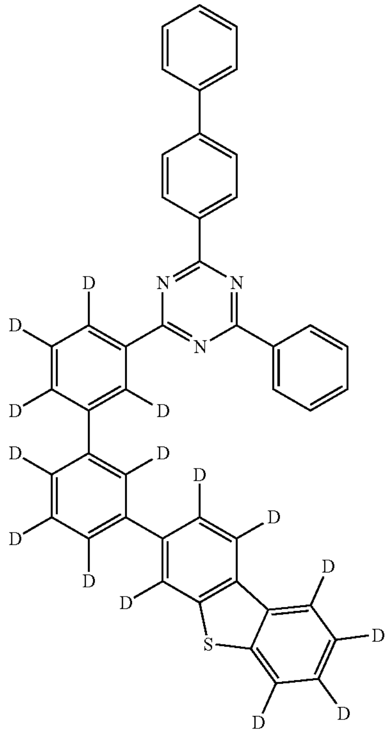
108
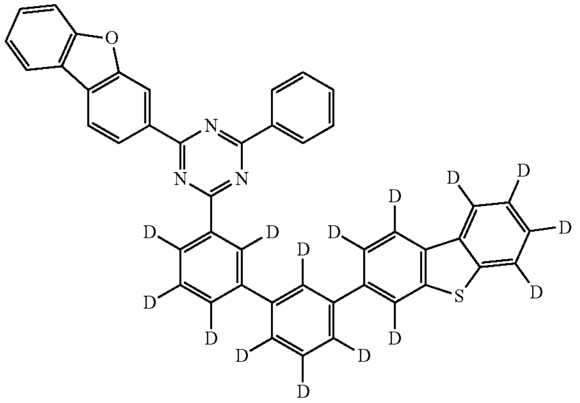
109
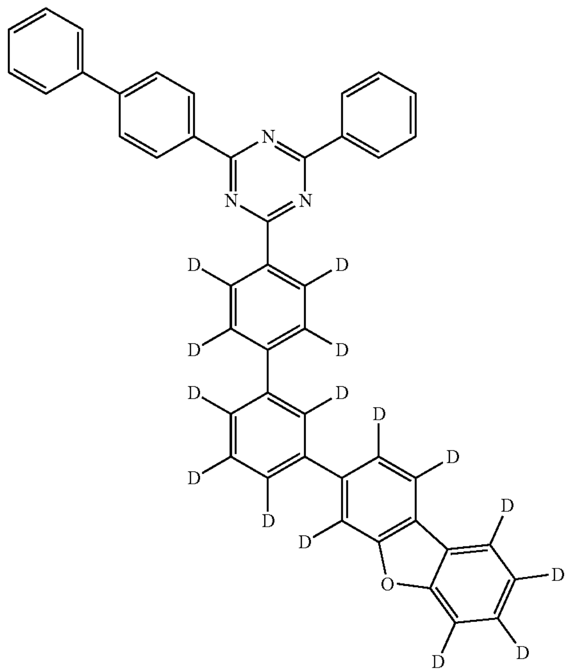
110
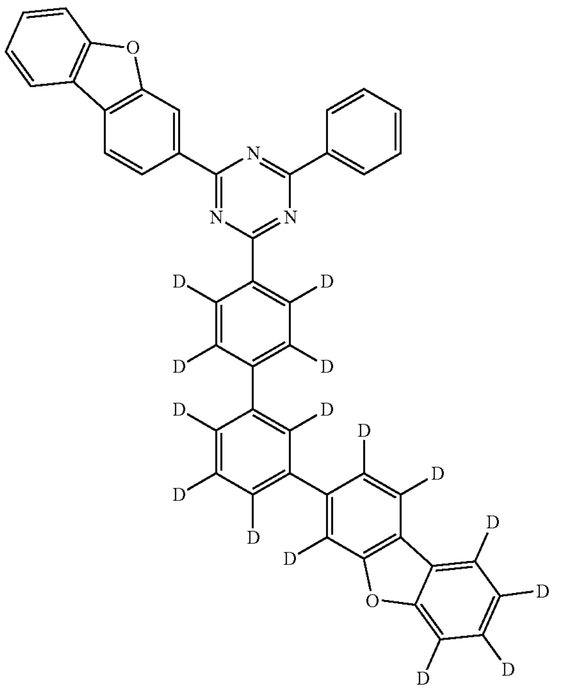

-continued
111
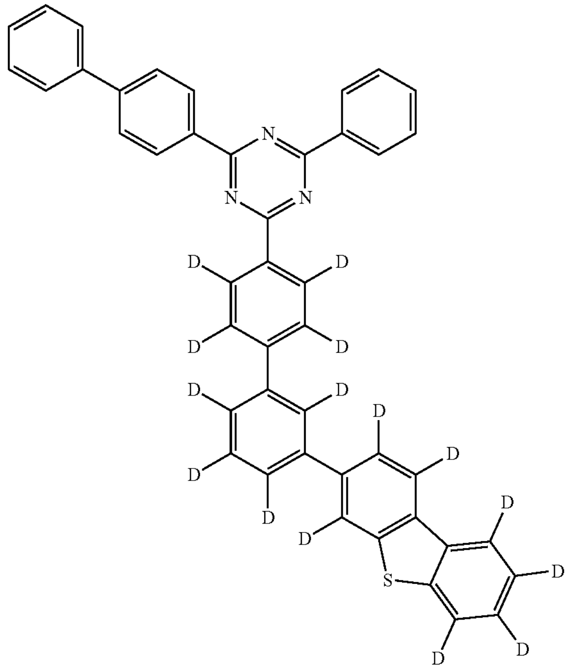
112
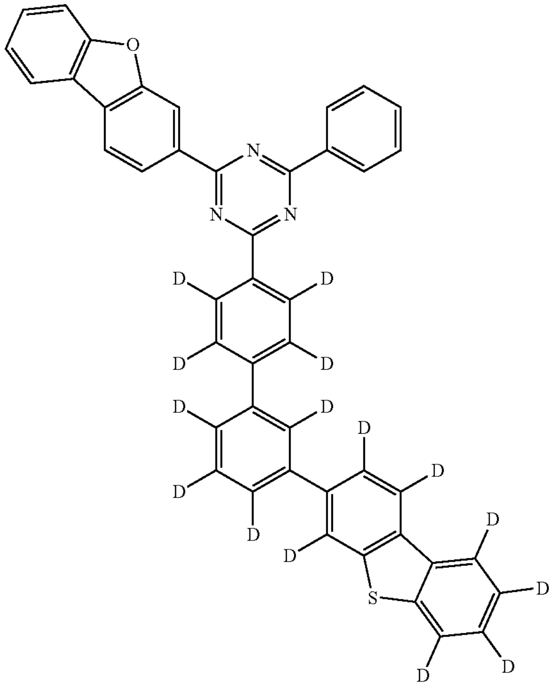
113
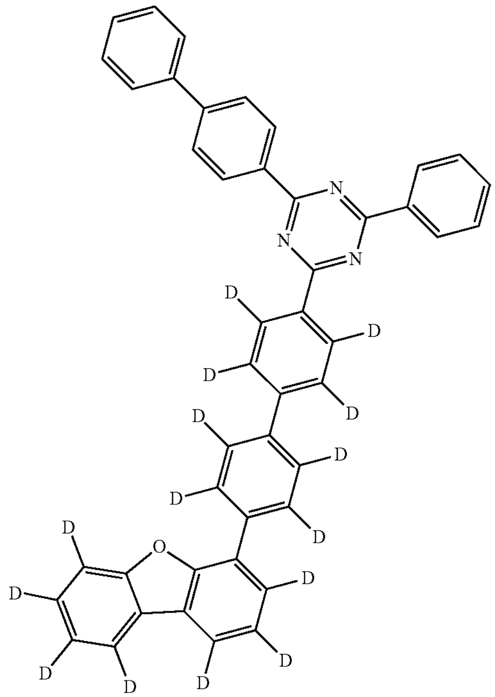
114
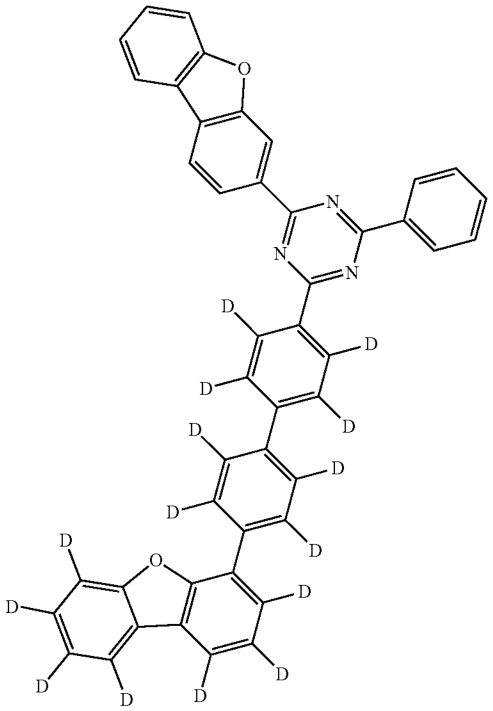

-continued
115
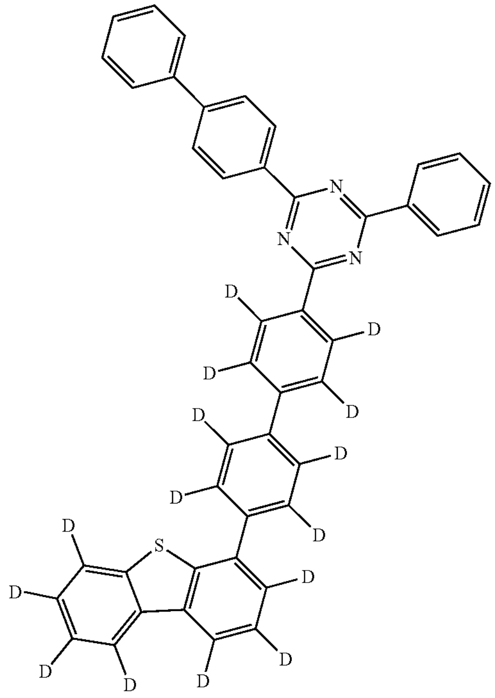
116
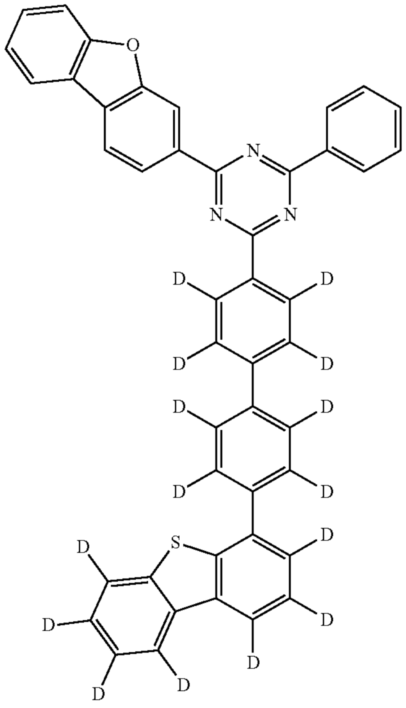
117
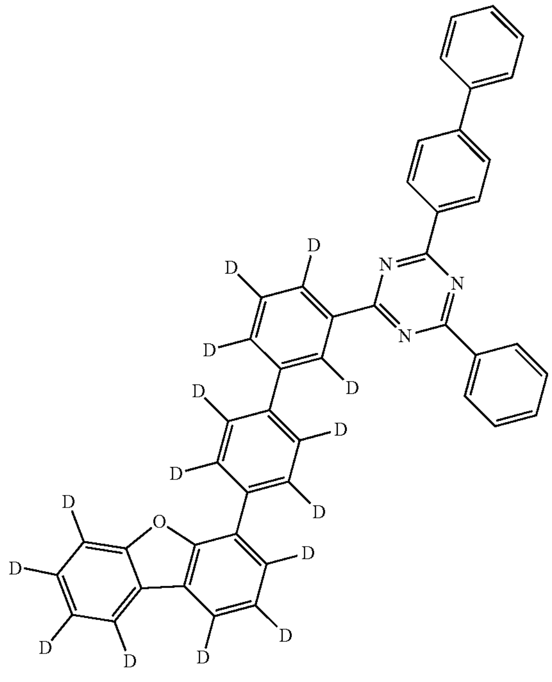
118
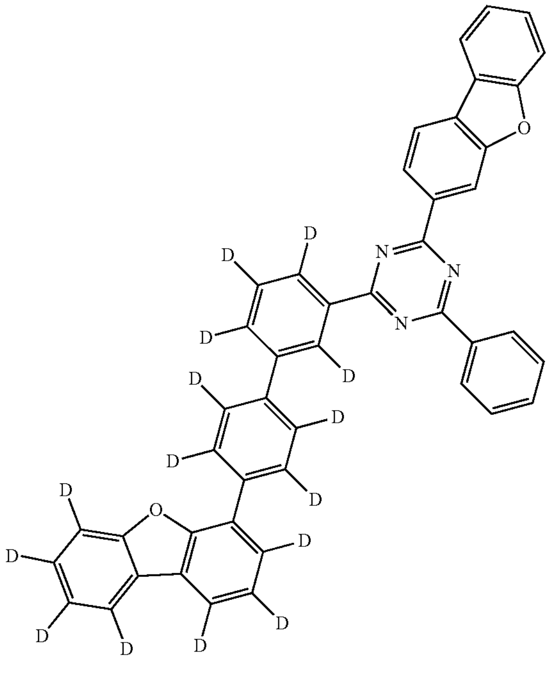

-continued
119
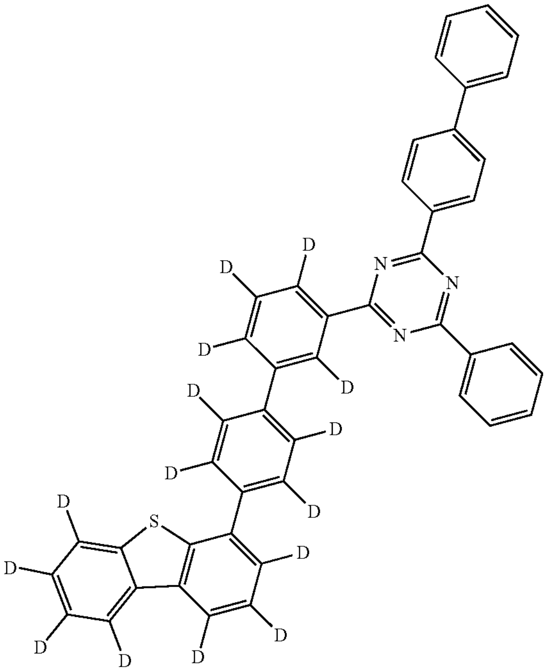
120
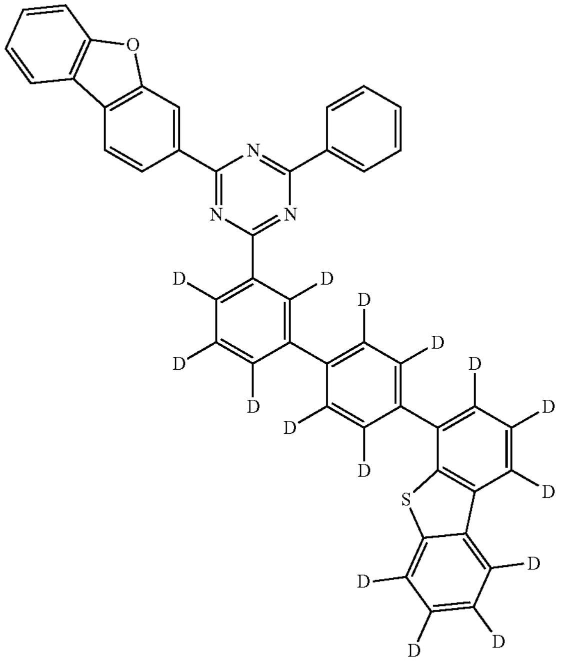
121
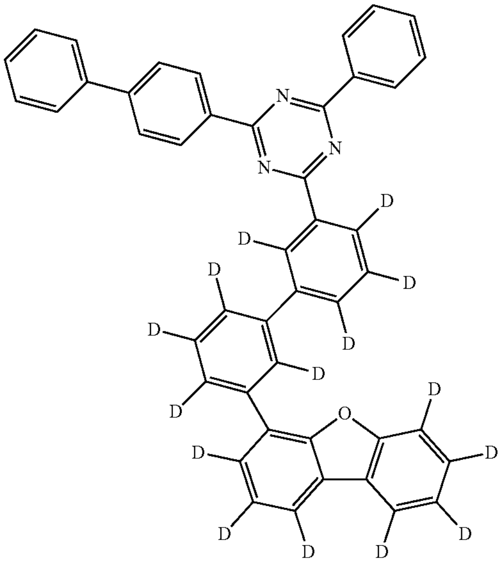
122
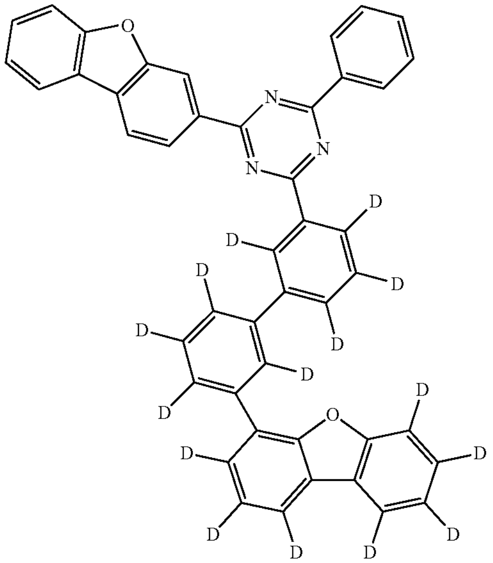

-continued
123
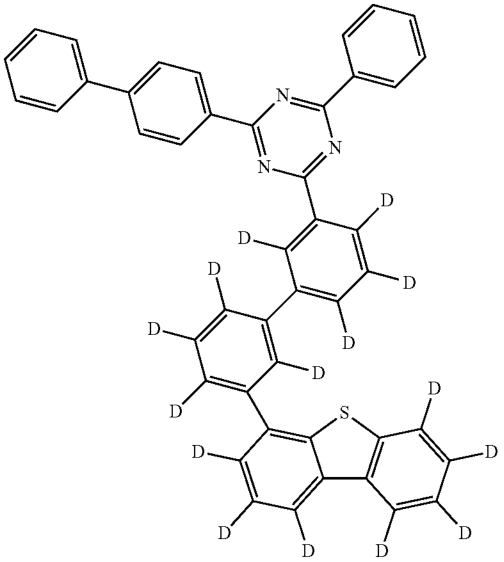
124
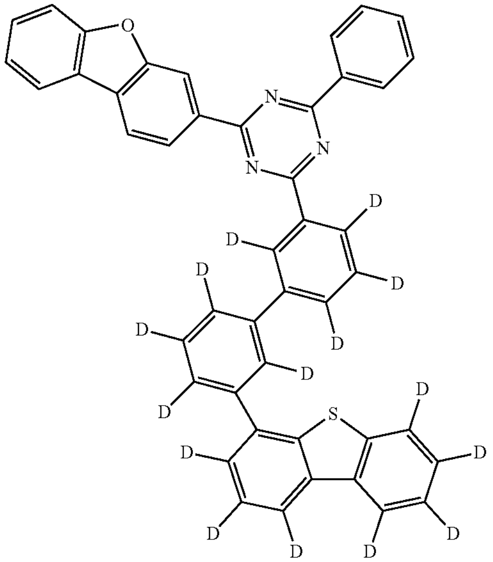
125
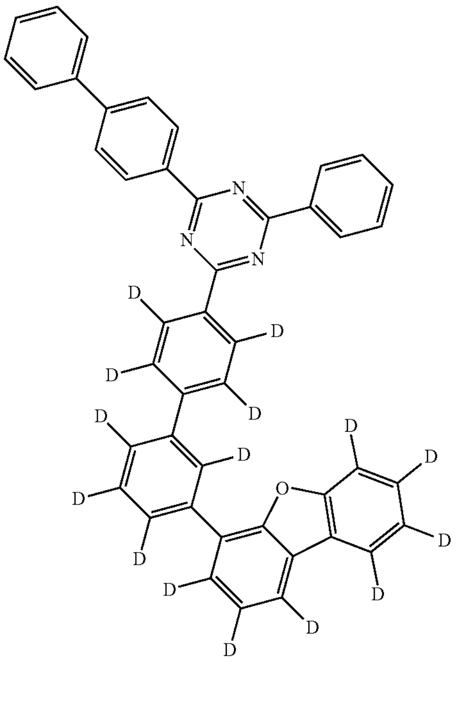
126
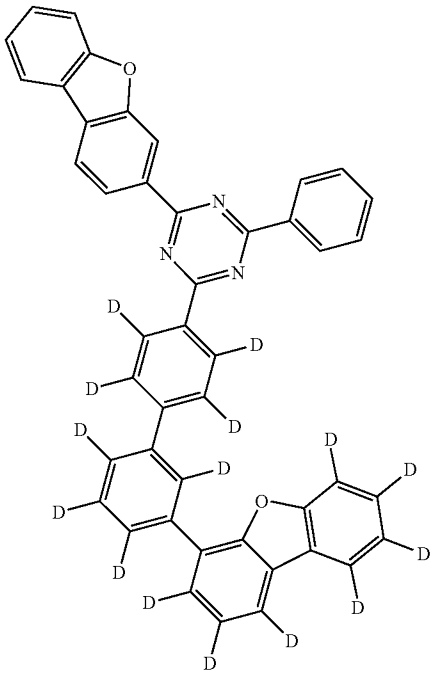

-continued
127
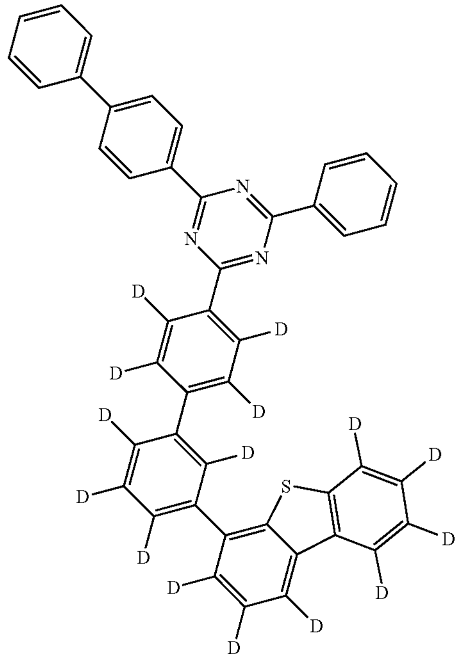
128
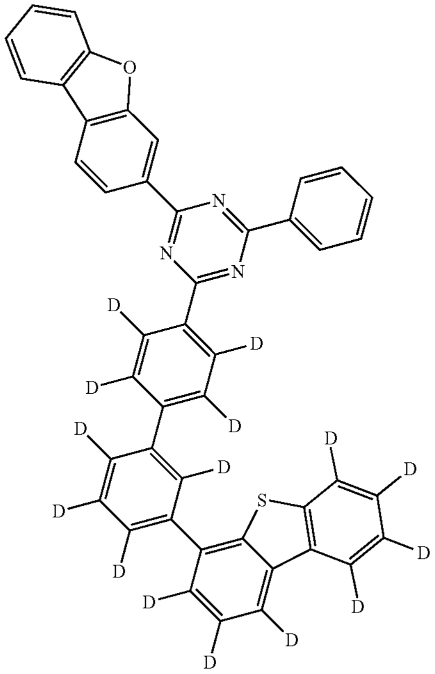
129
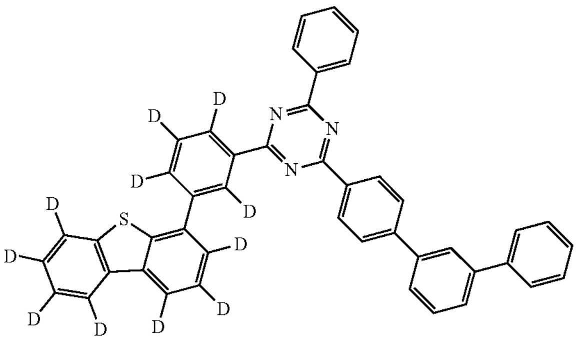
130
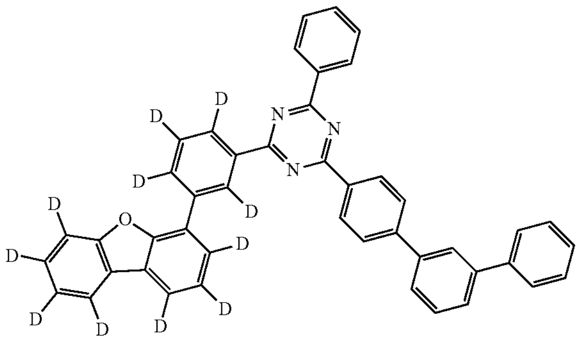
131
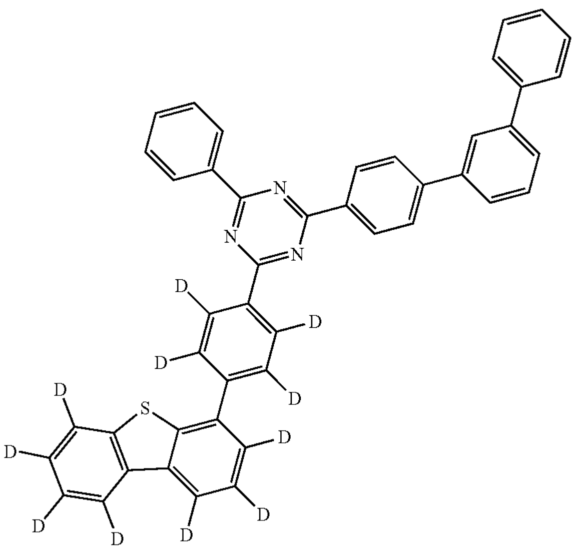
132
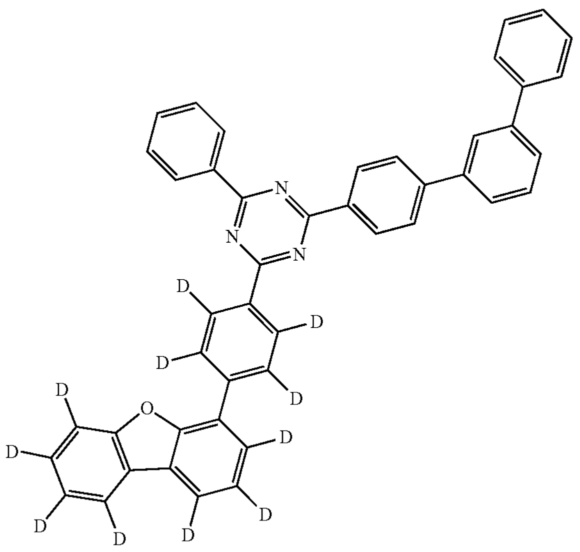

-continued
133
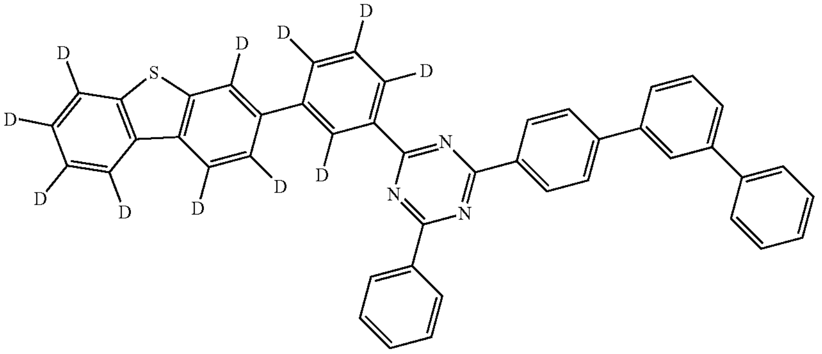
134
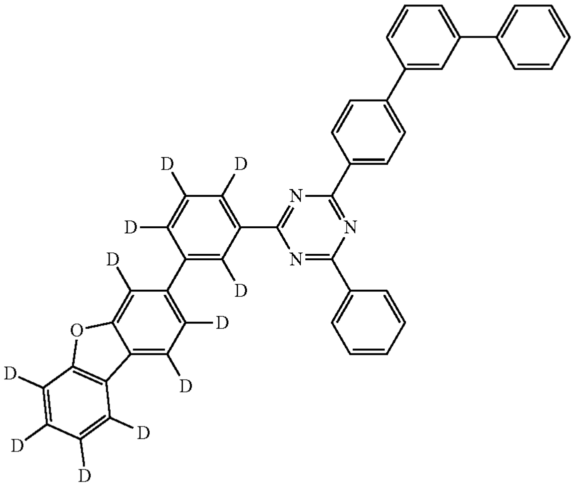
135
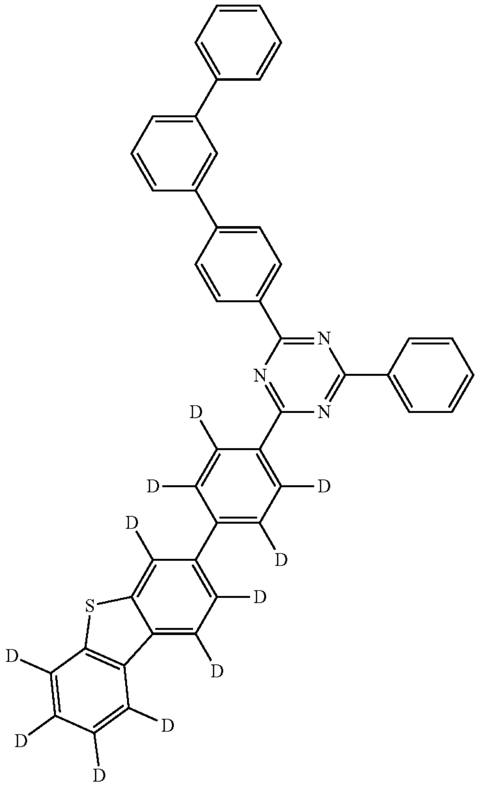

-continued
136
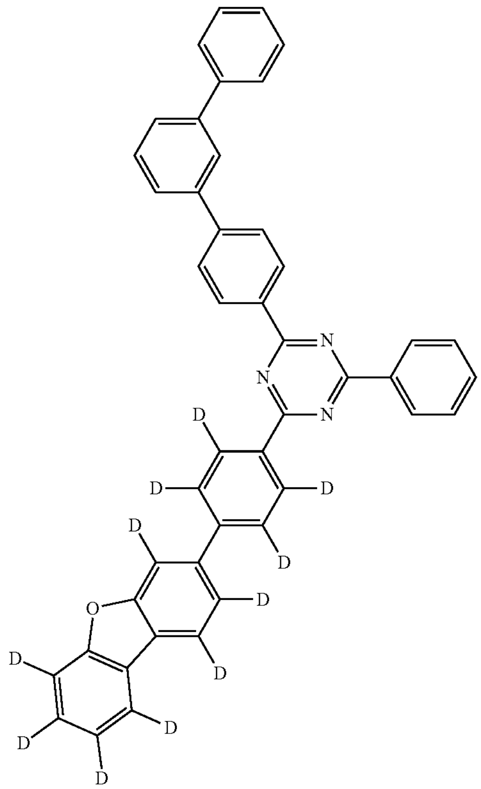
137
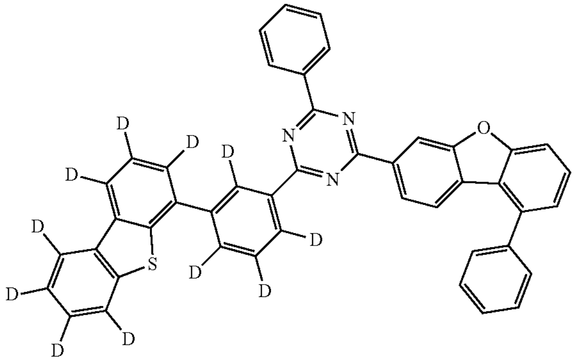
138
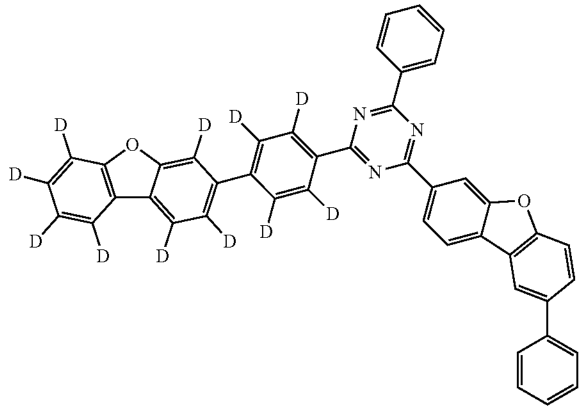
139
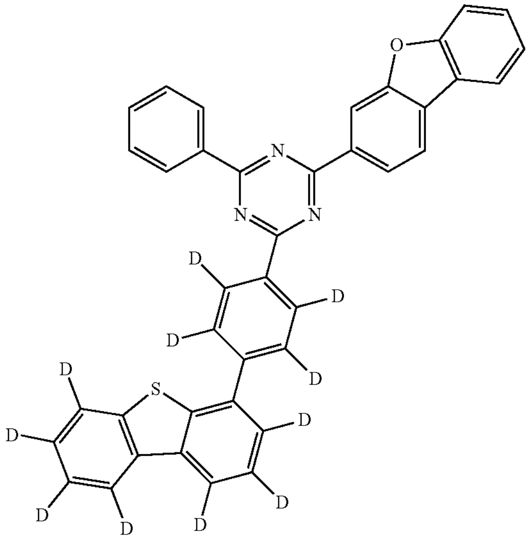

-continued
140
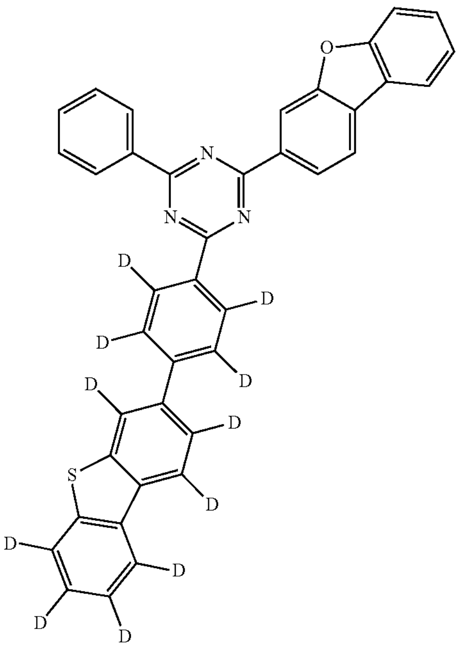
-continued
141
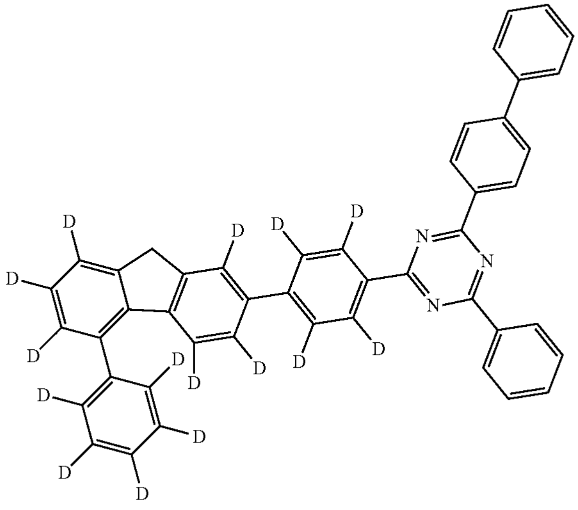
142
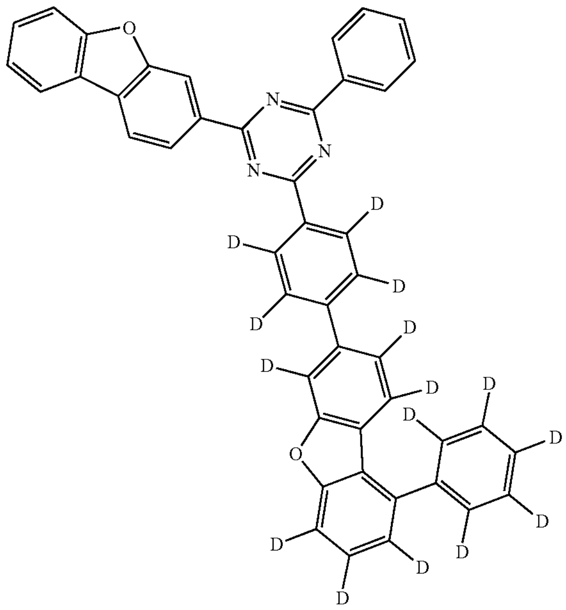

-continued
143
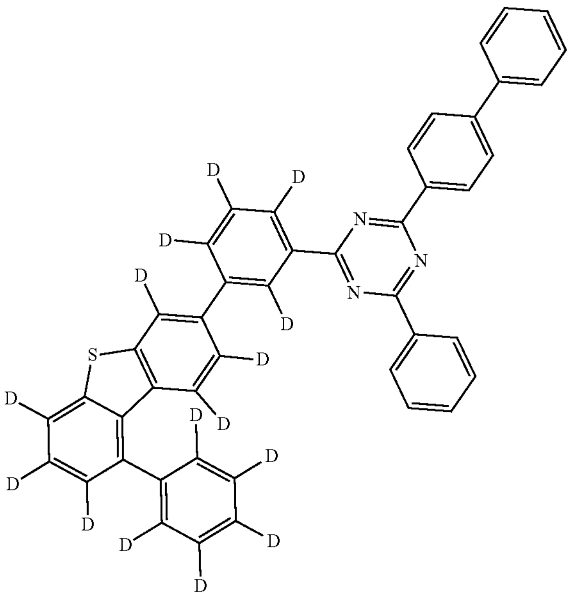
144
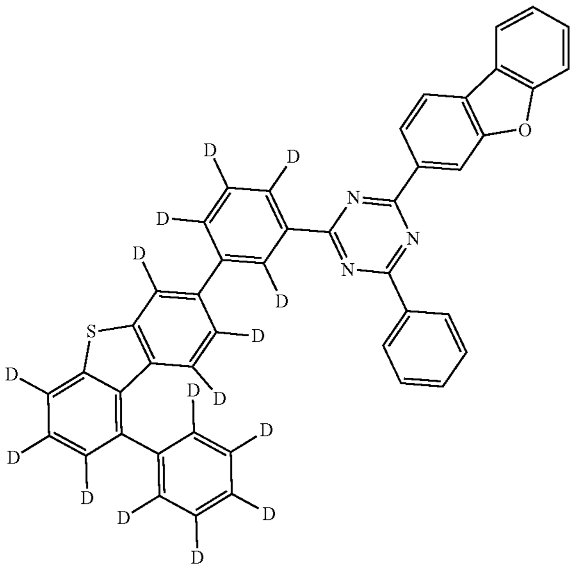
-continued
145
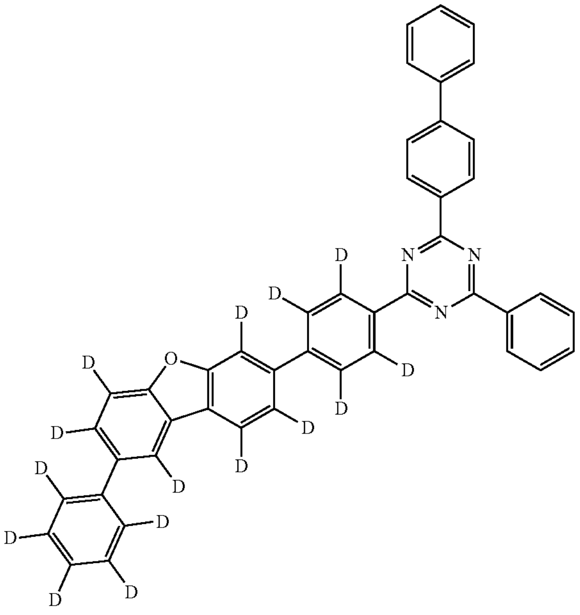
146
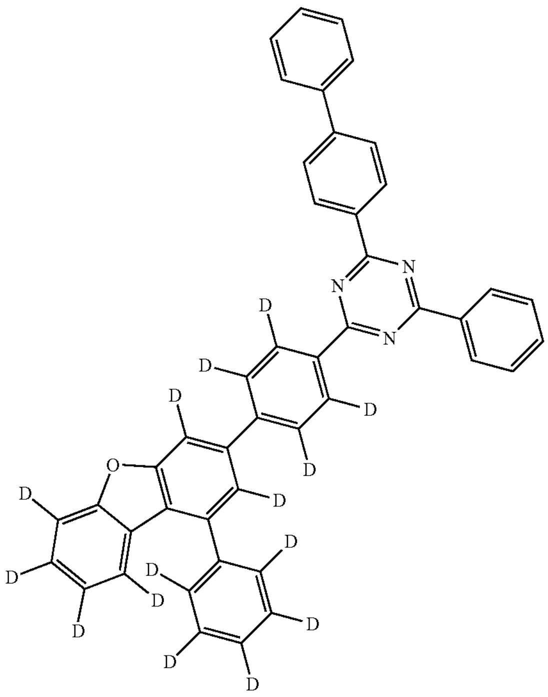

-continued
147
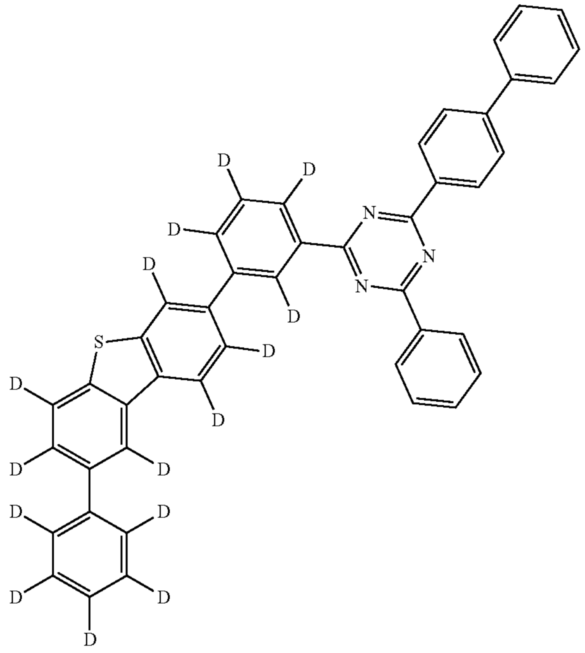
148
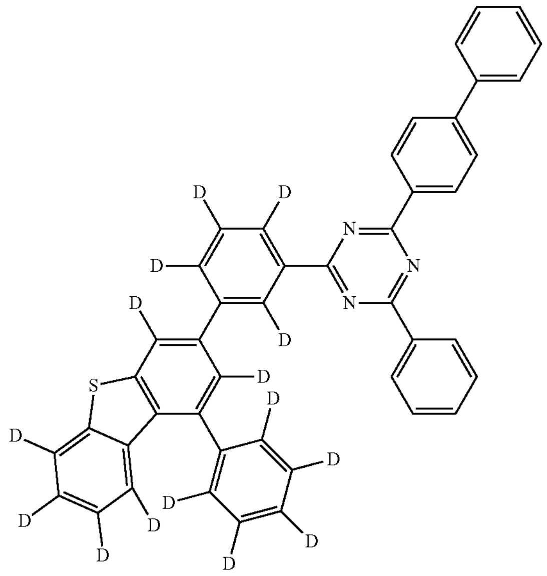
149
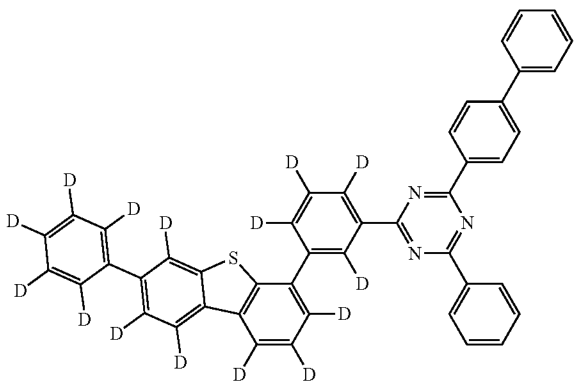
-continued
150
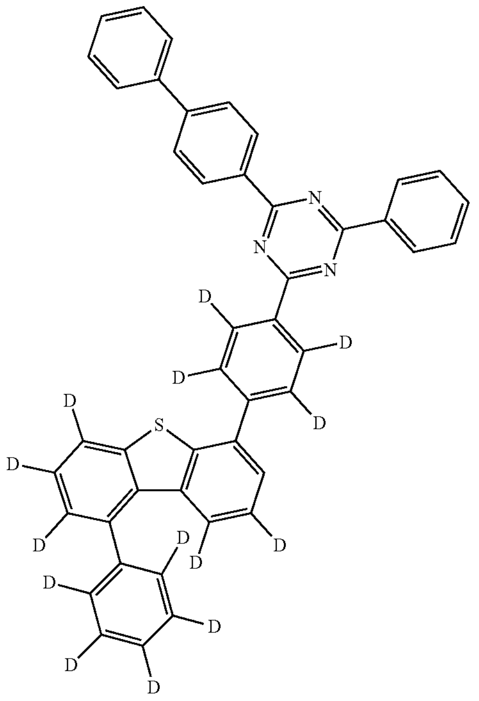
151
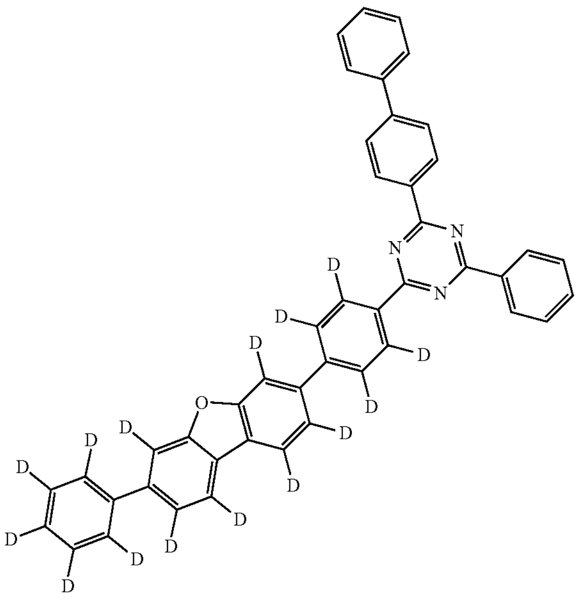

-continued
152
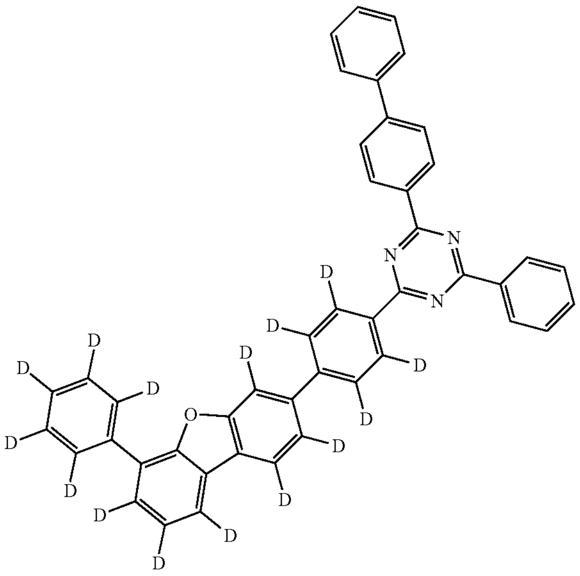
153
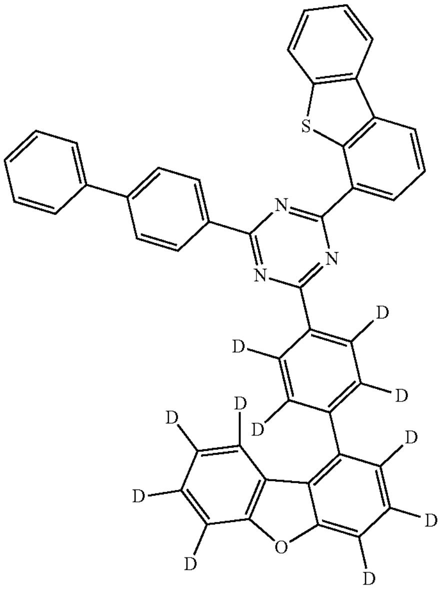
-continued
154
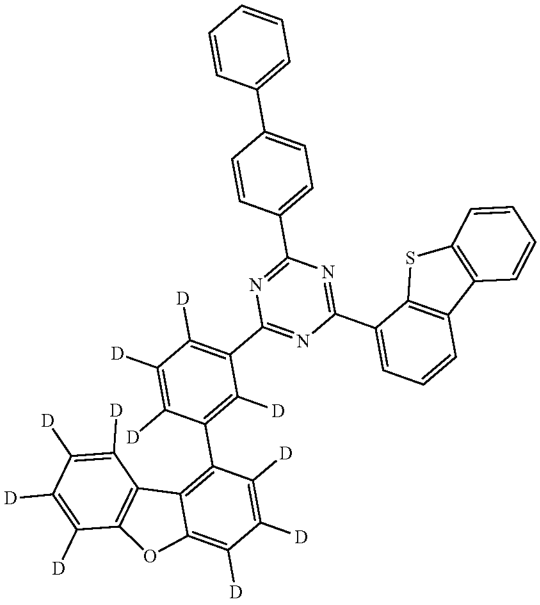
155
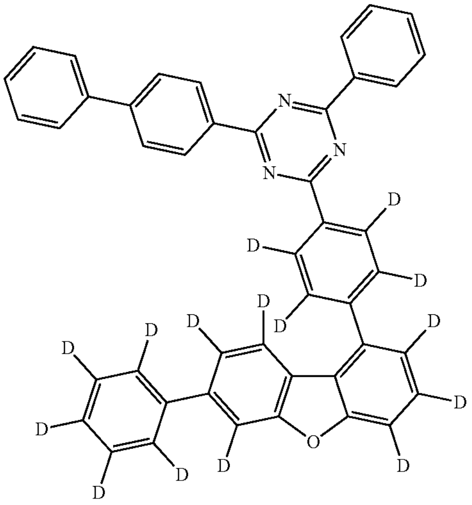
156
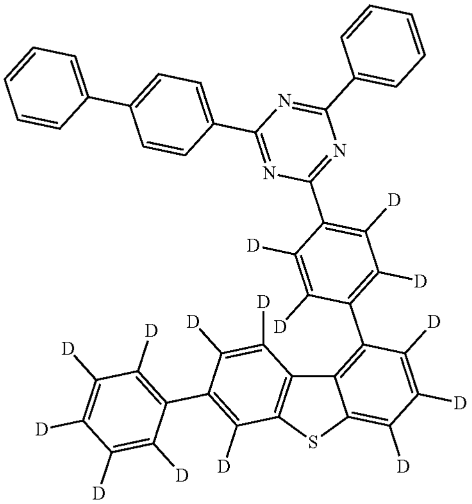

-continued
157
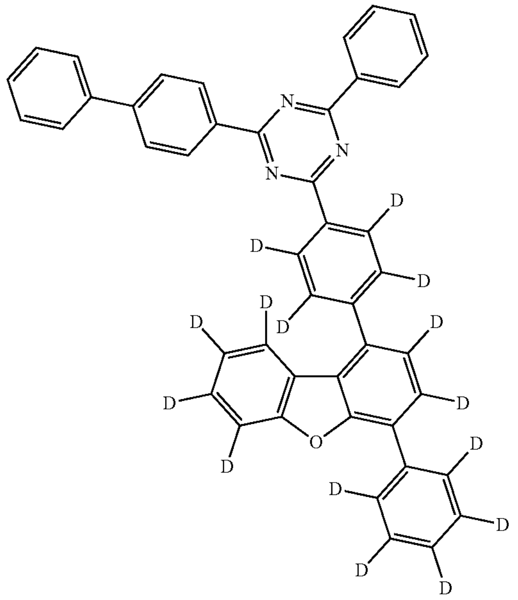
158
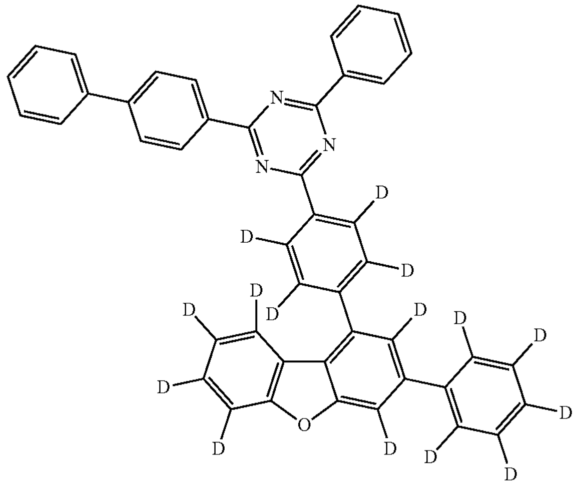
-continued
159
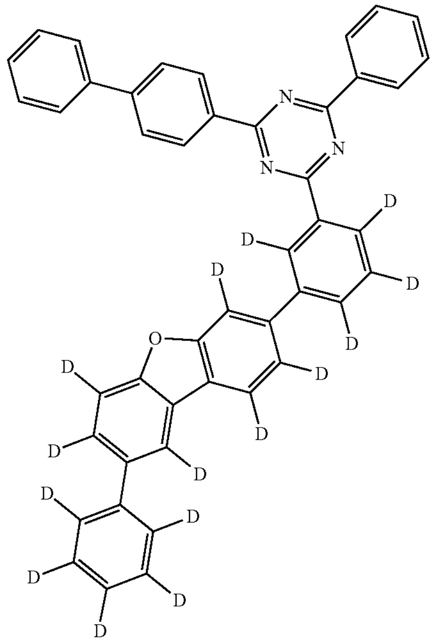
160
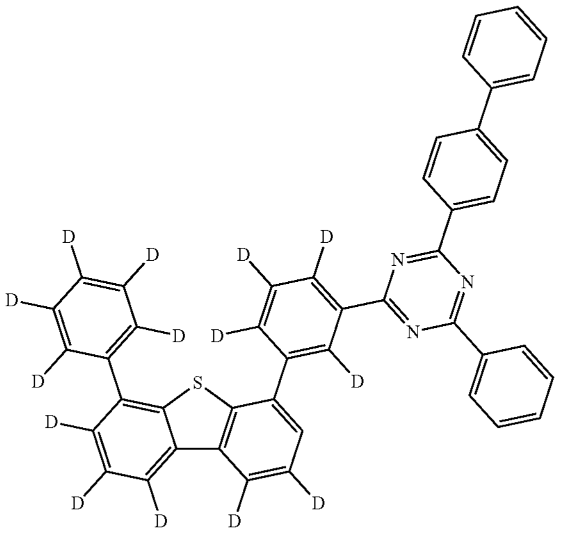
161
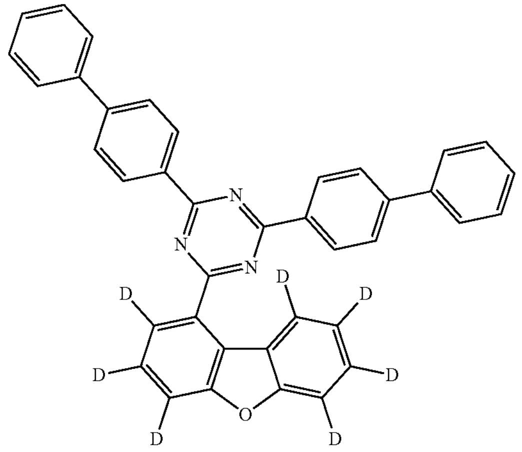

-continued
162
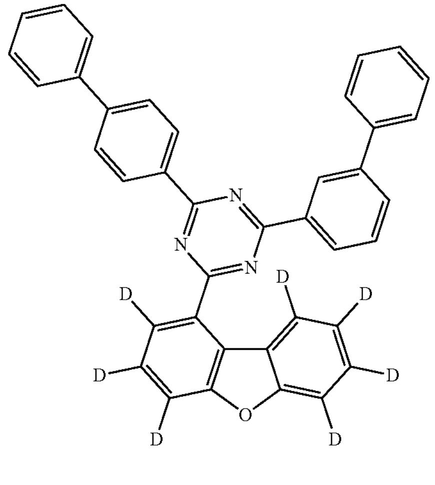
163
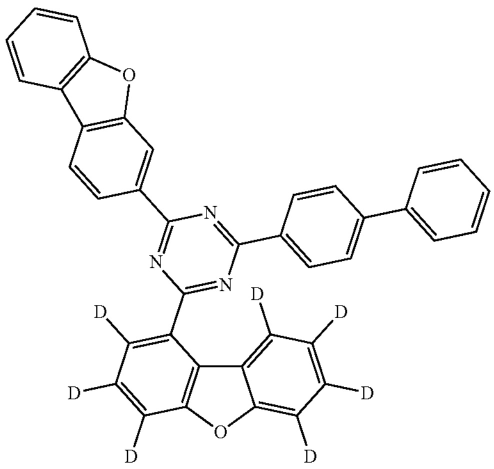
164
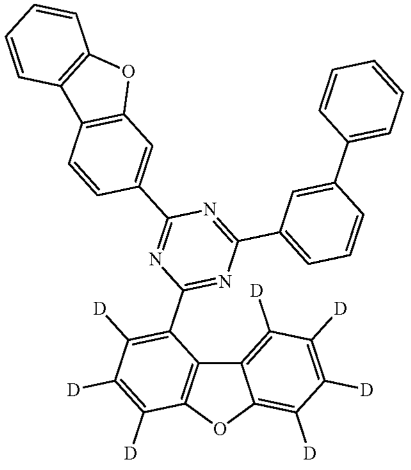
-continued
165
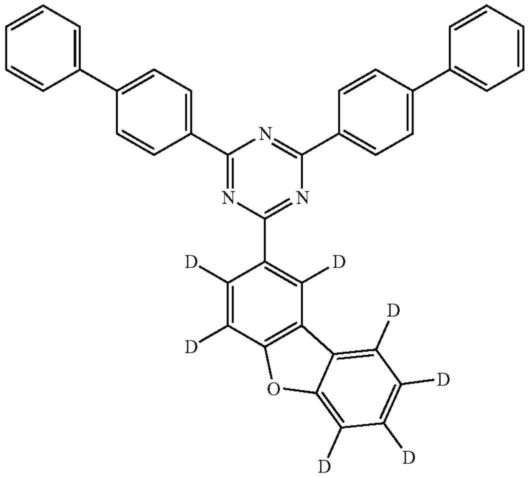
166
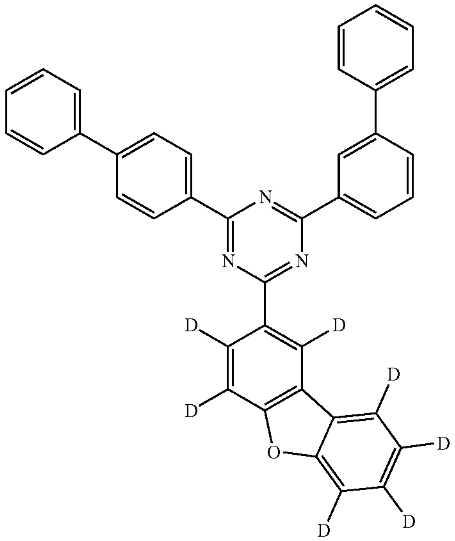
167
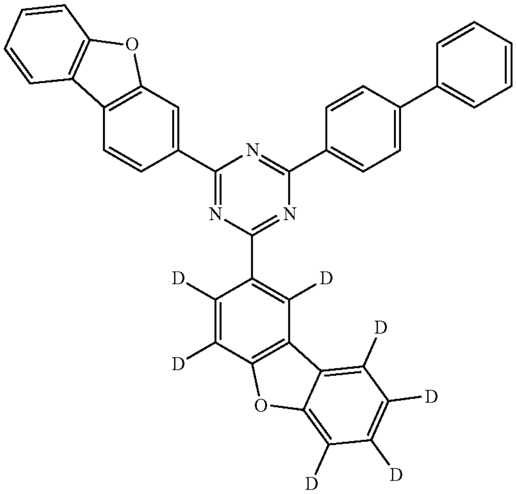

168
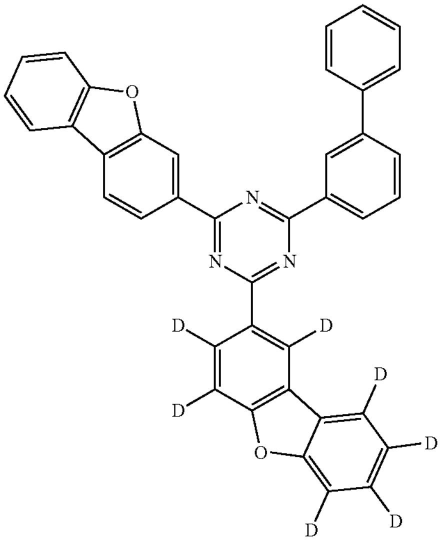
169
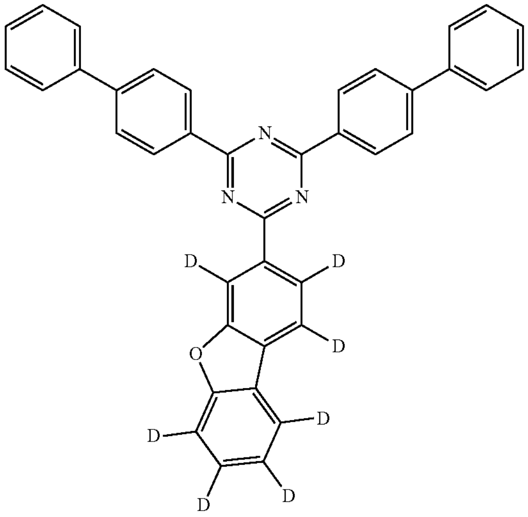
170
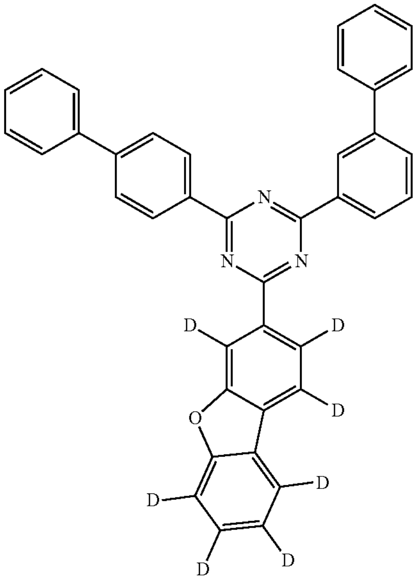
171
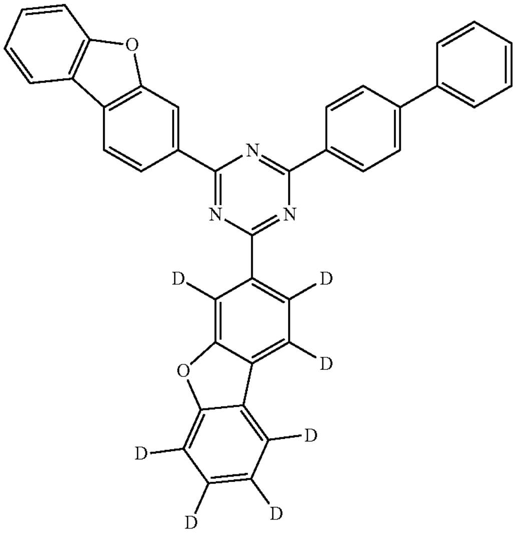
172
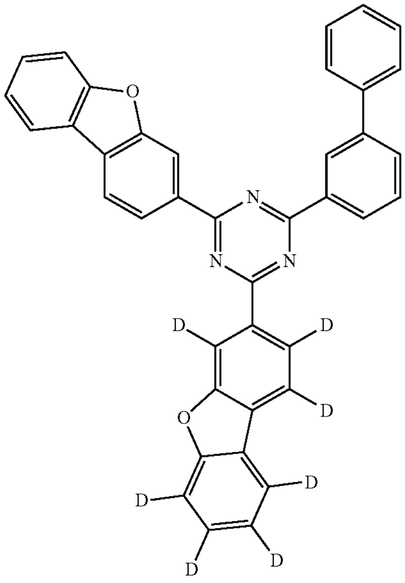
173
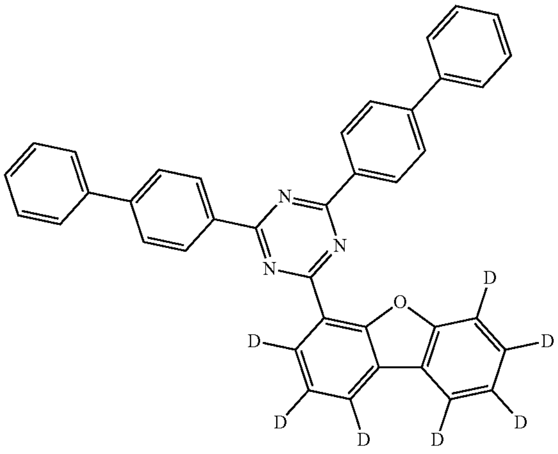

-continued
174
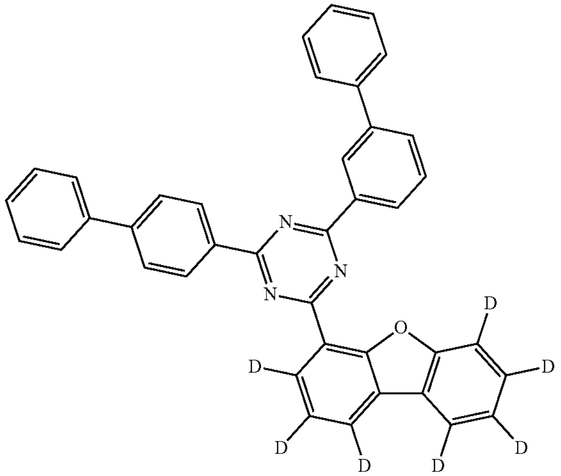
175
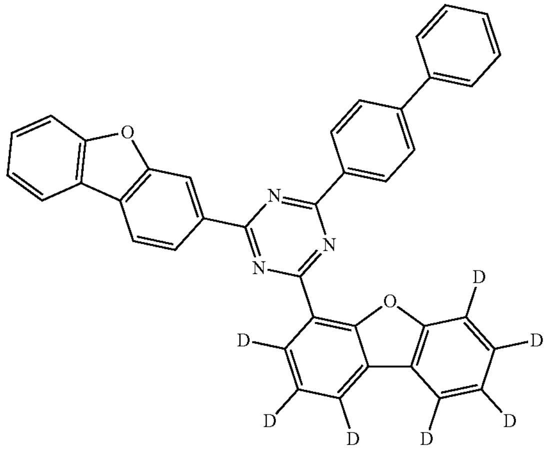
176
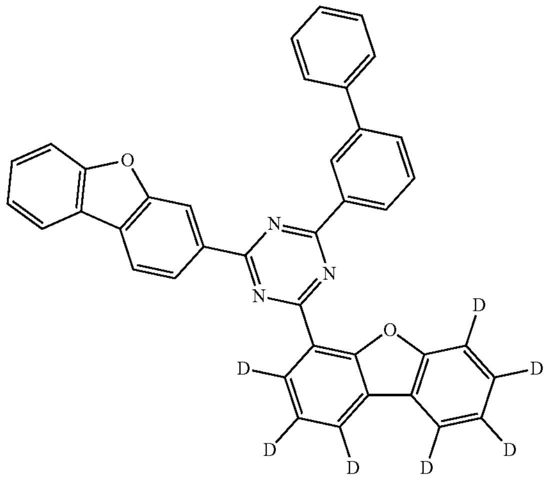
-continued
177
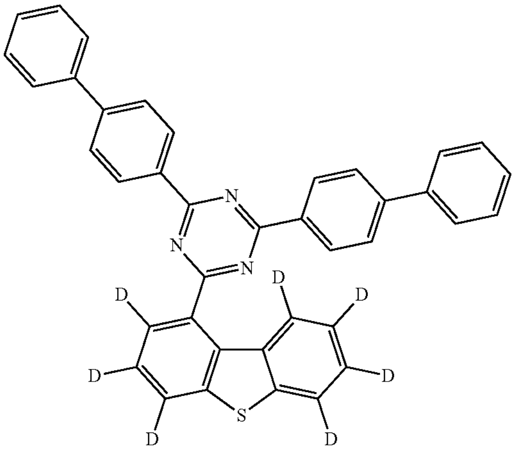
178
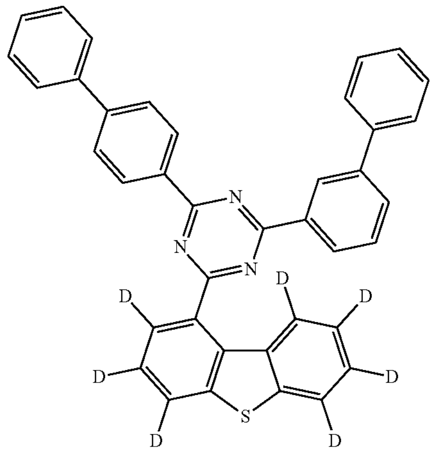
179
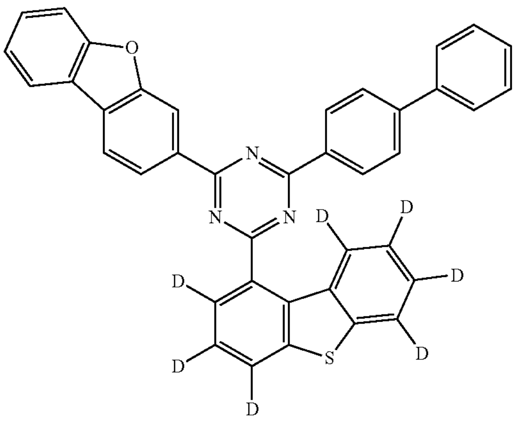

-continued
180
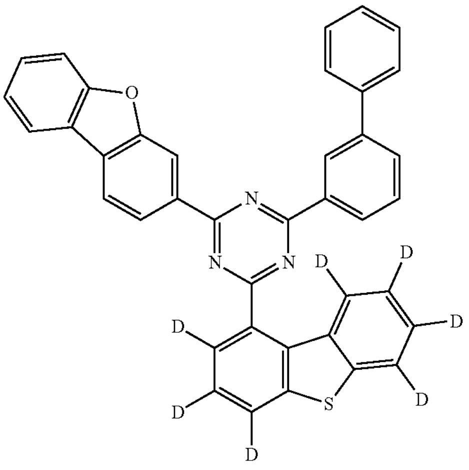
181
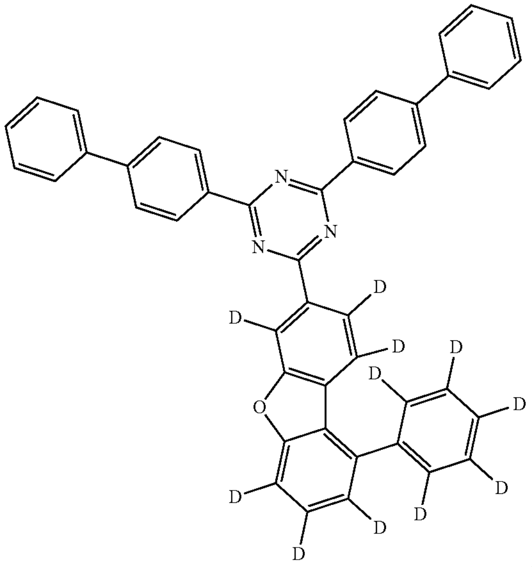
182
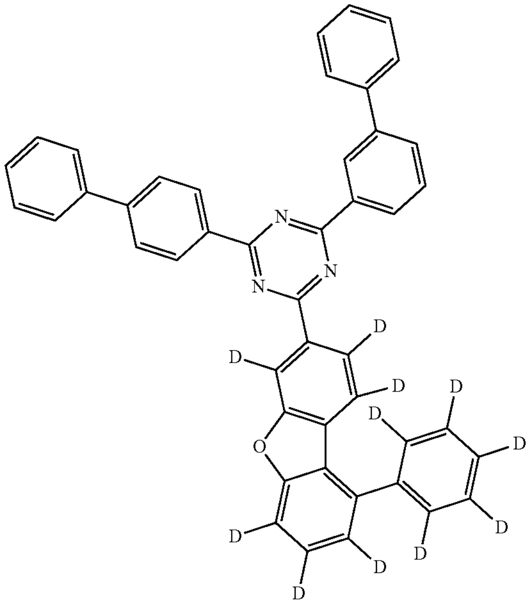
183
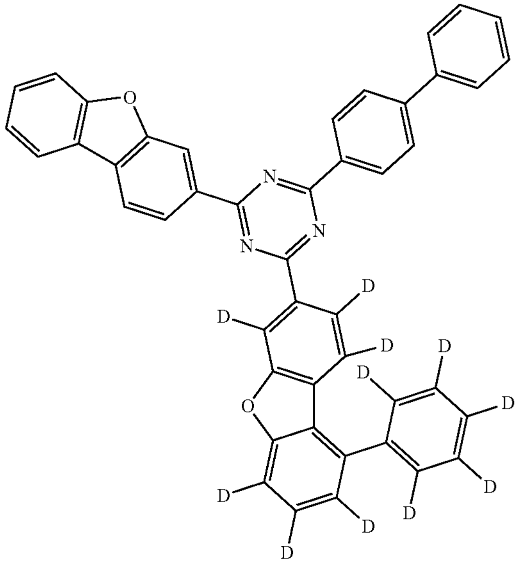
184
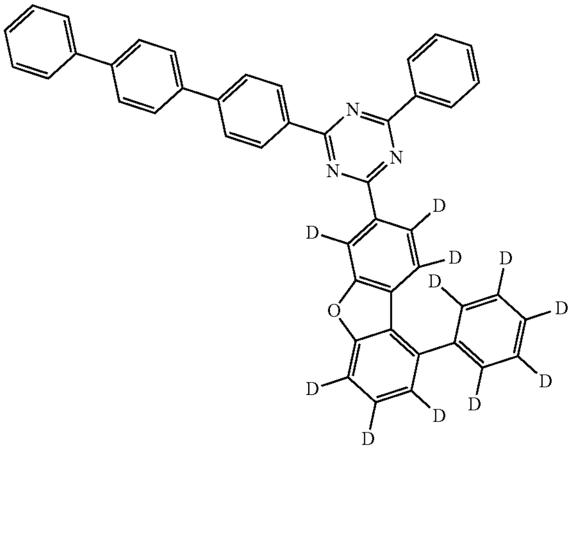

-continued
185
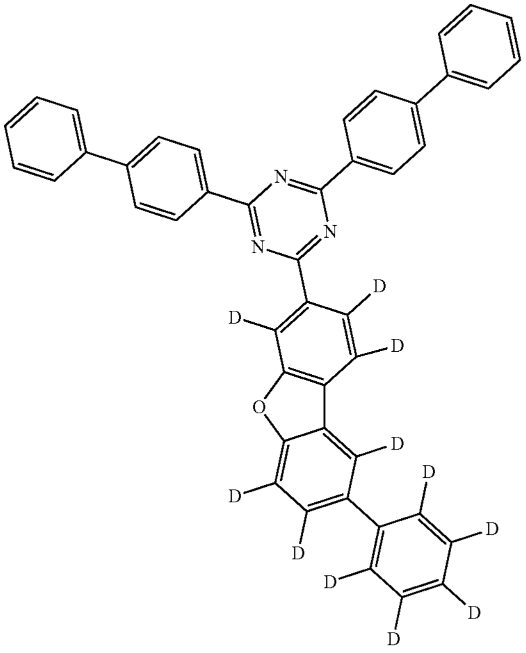
186
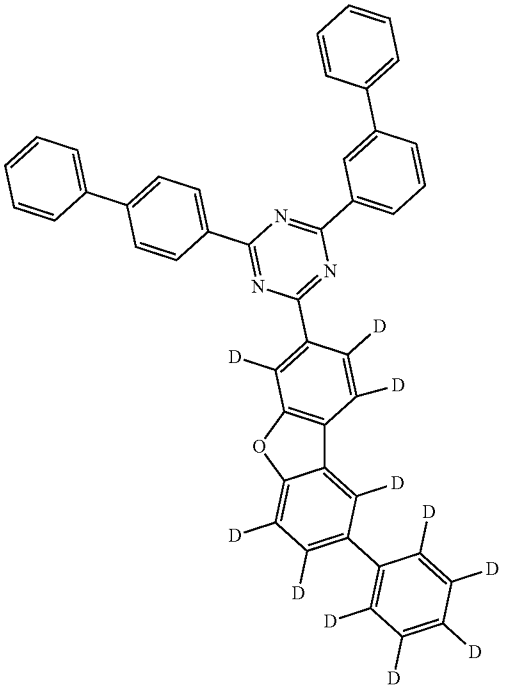
-continued
187
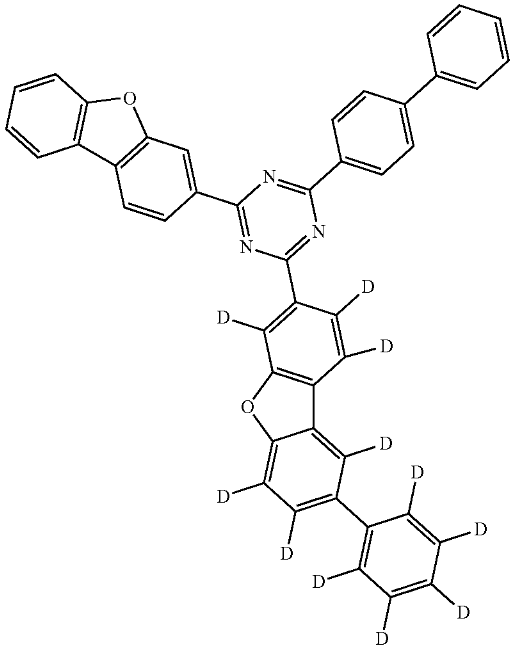
188
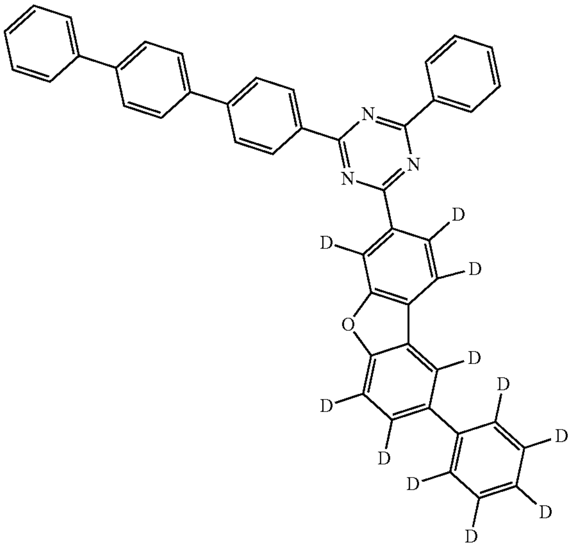

189
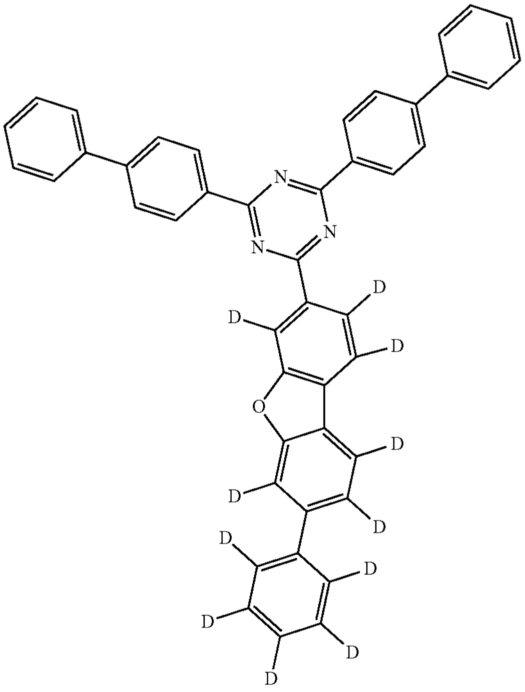
190
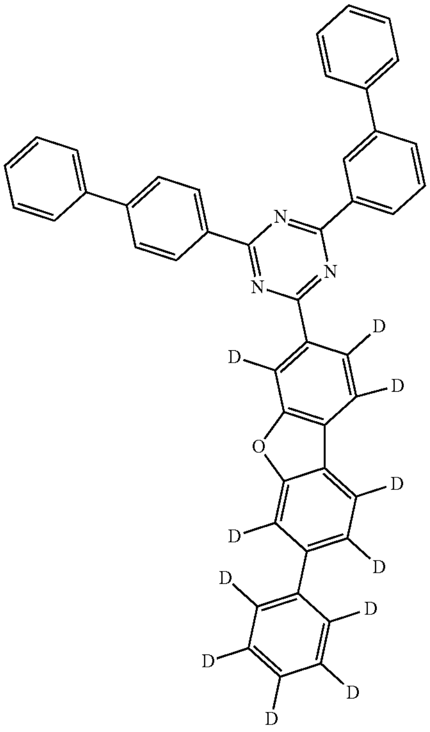
191
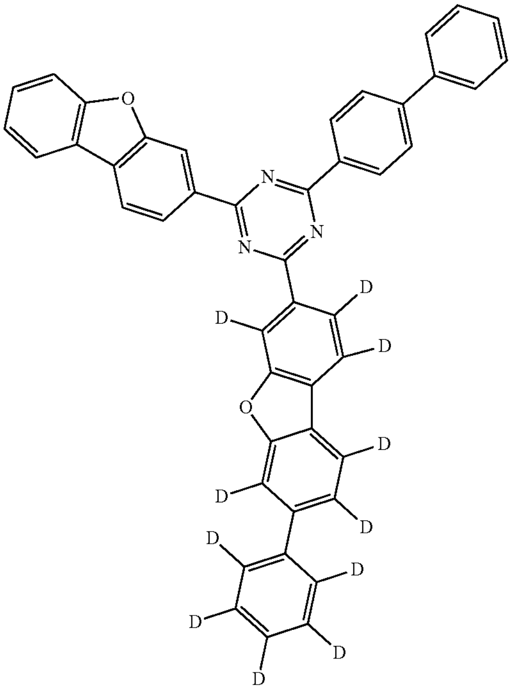
192
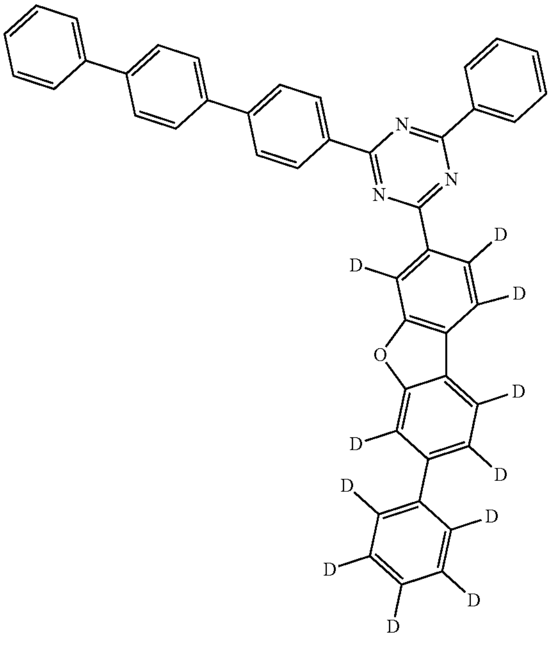

-continued
193
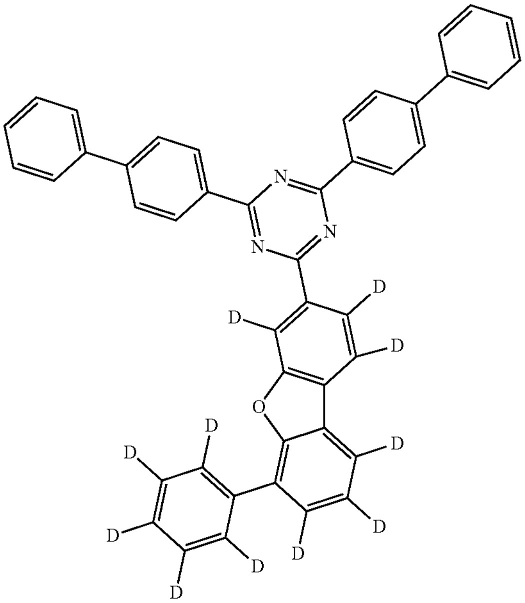
194
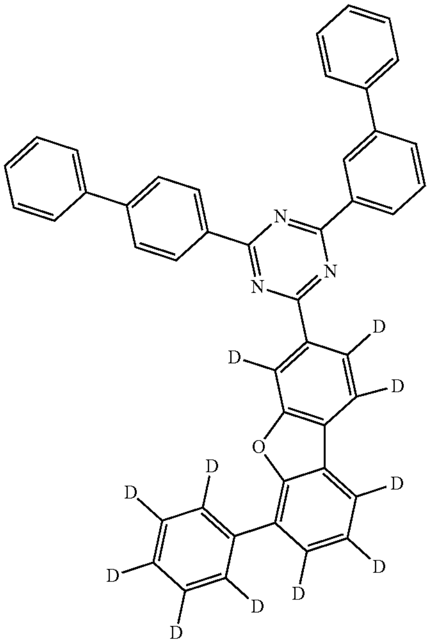
-continued
195
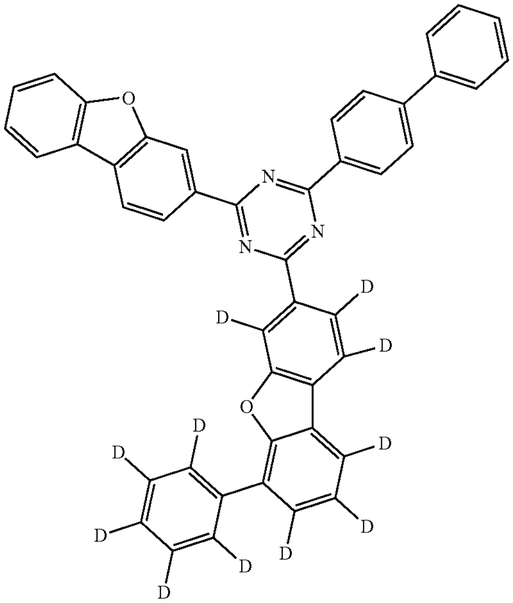
196
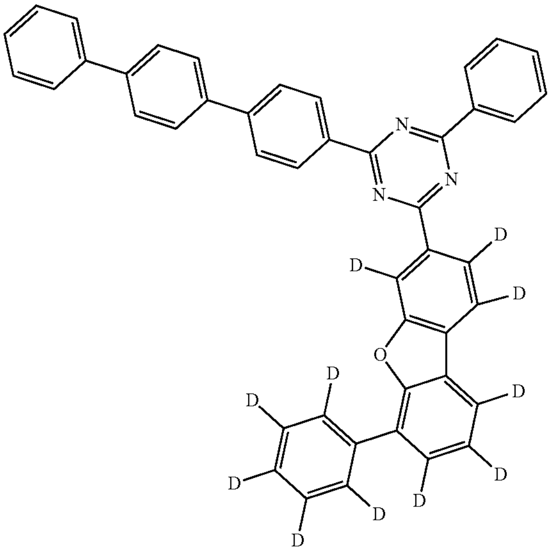

-continued
197
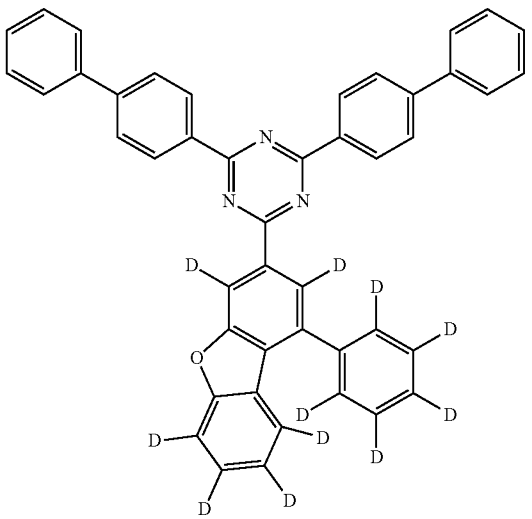
198
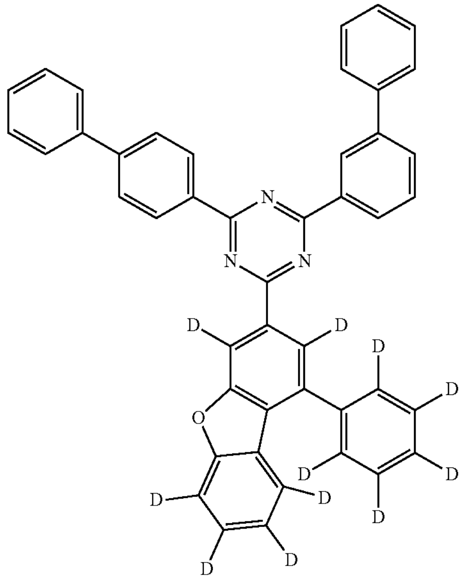
199
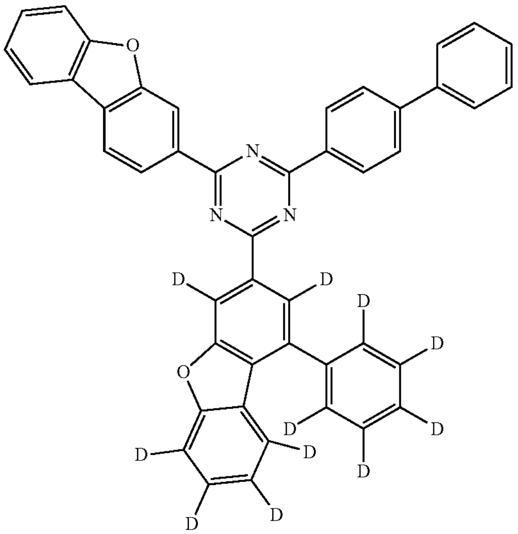
-continued
200
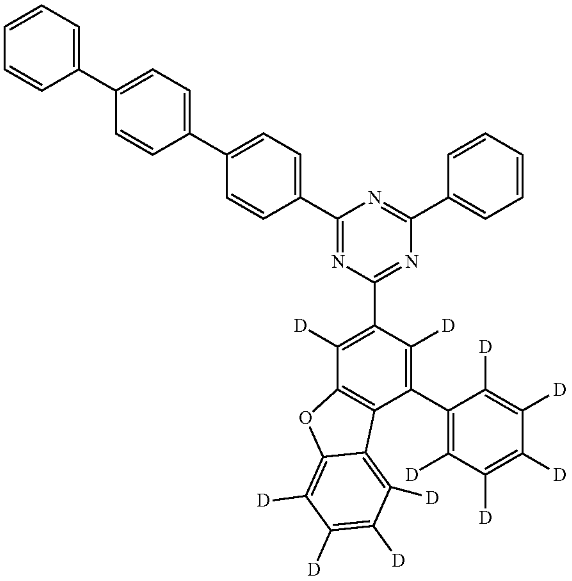
201
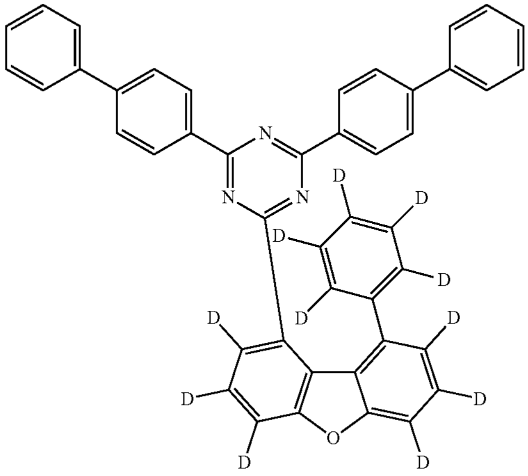
202
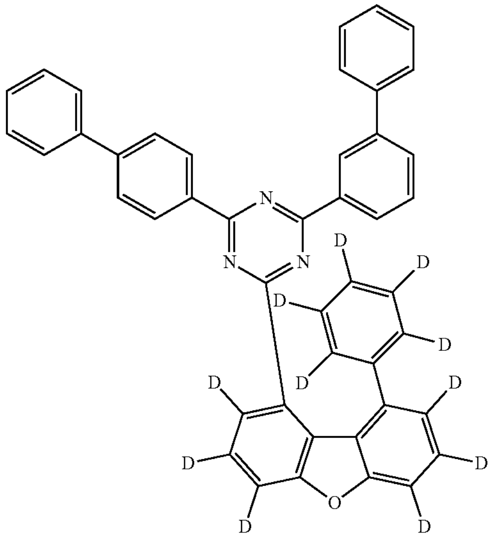

-continued
203
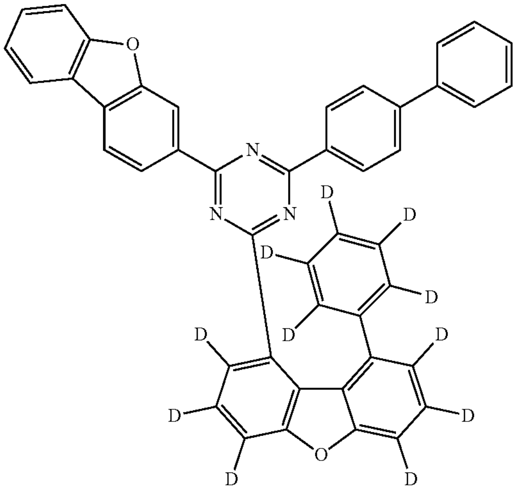
204
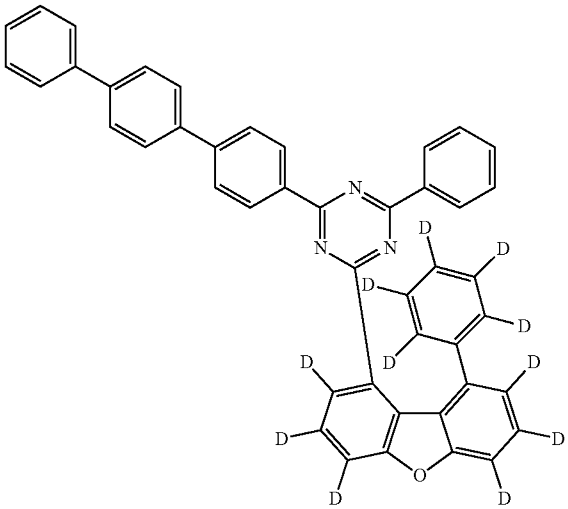
205
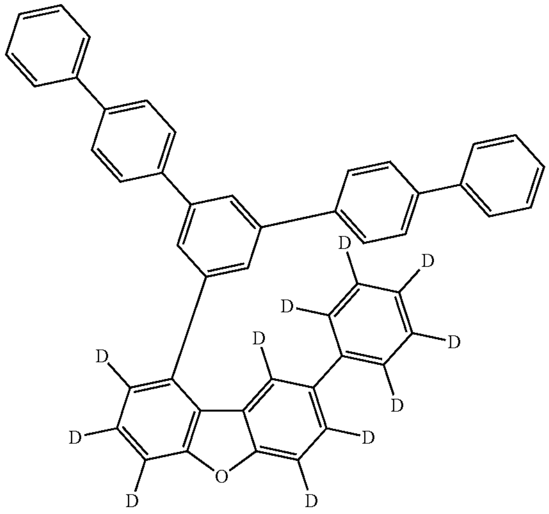
-continued
206
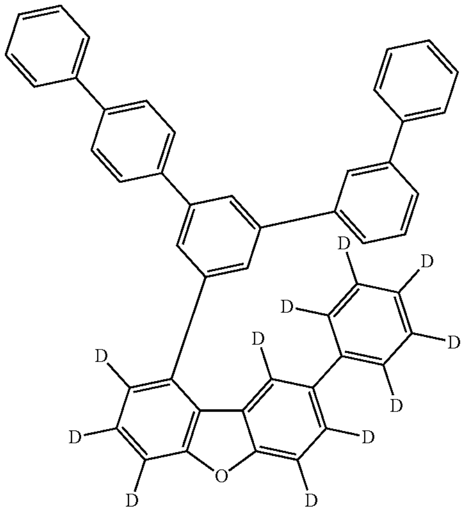
207
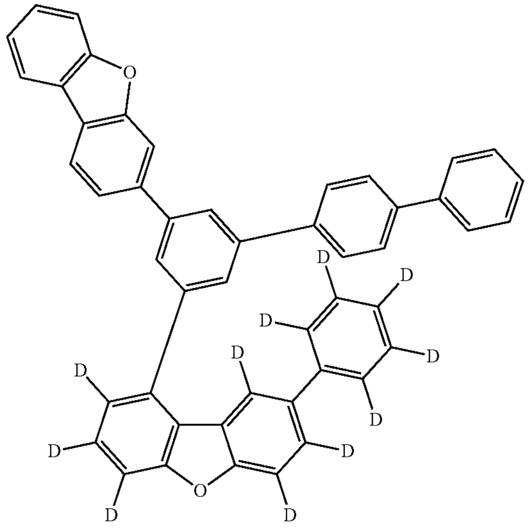

-continued
208
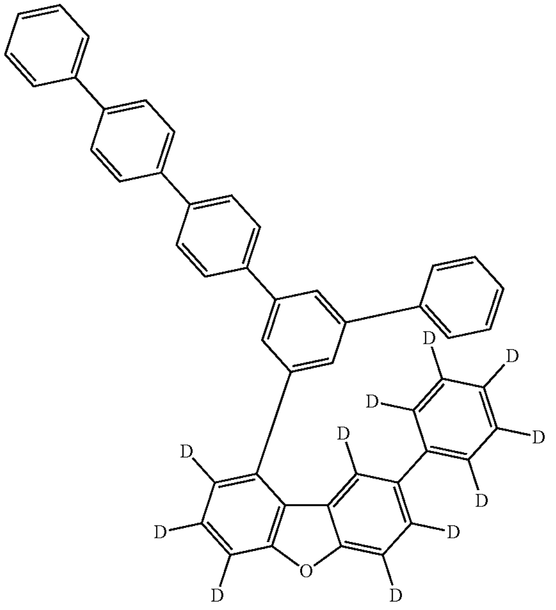
209
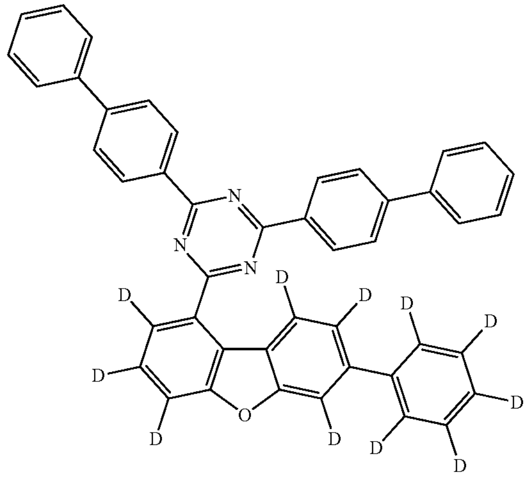
210
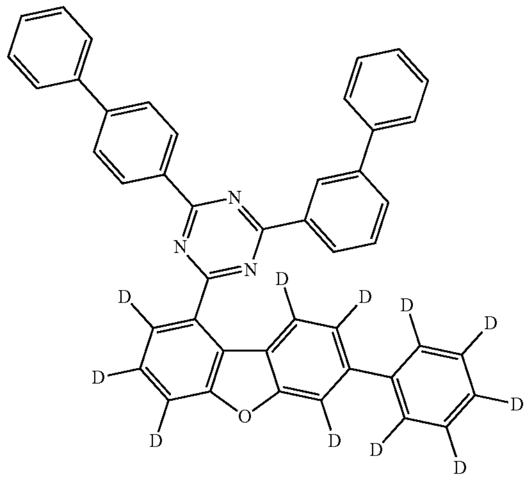
-continued
211
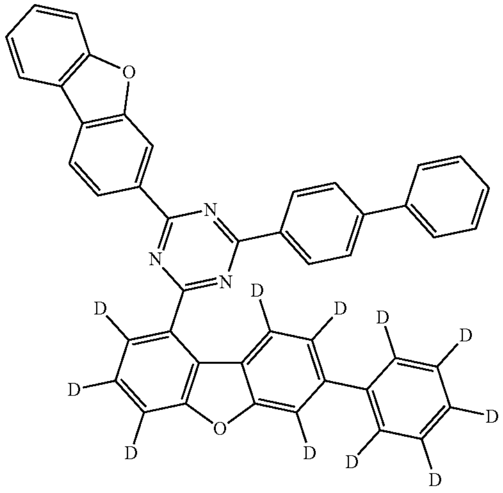
212
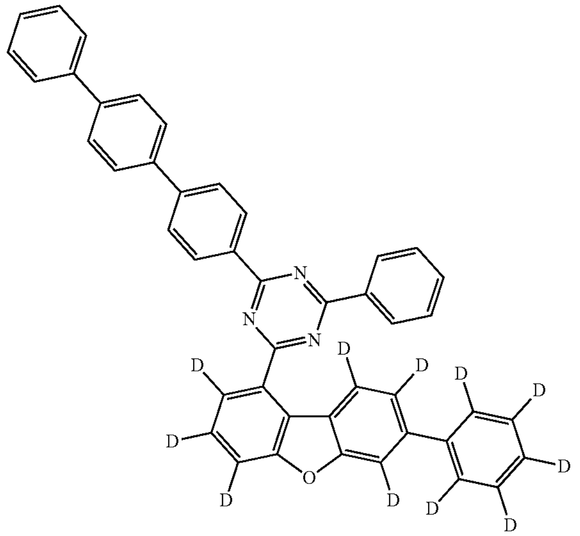
213
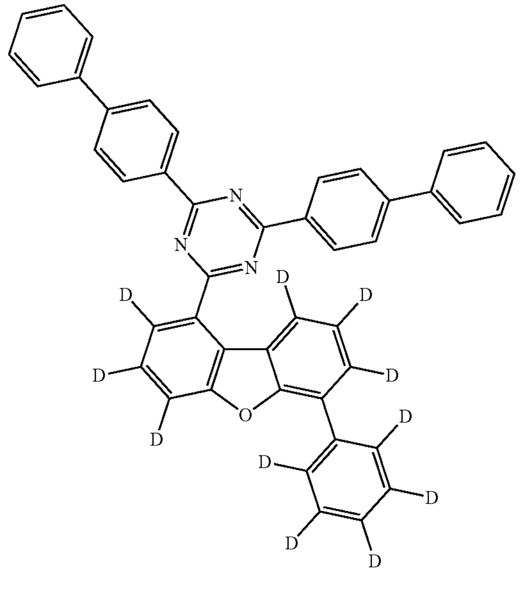

-continued
214
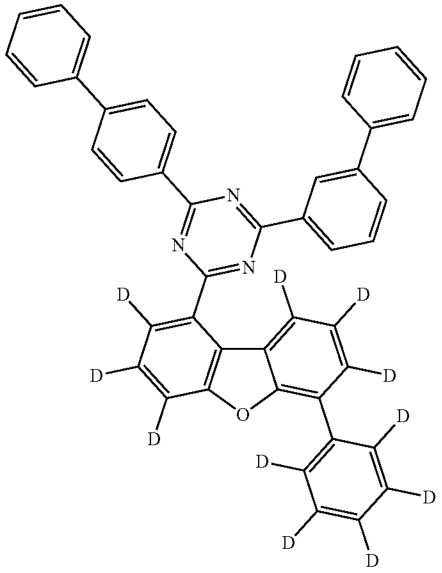
215
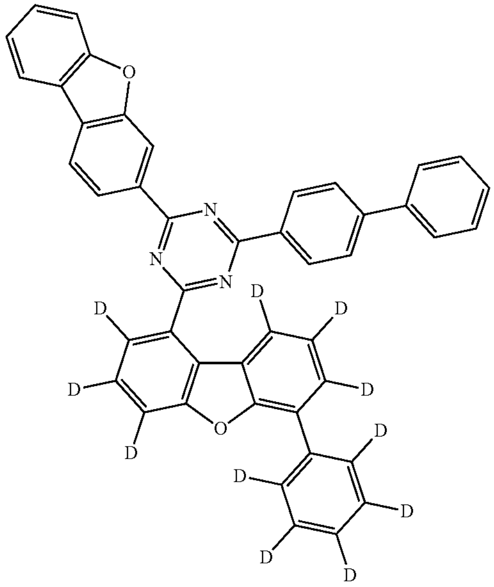
-continued
216
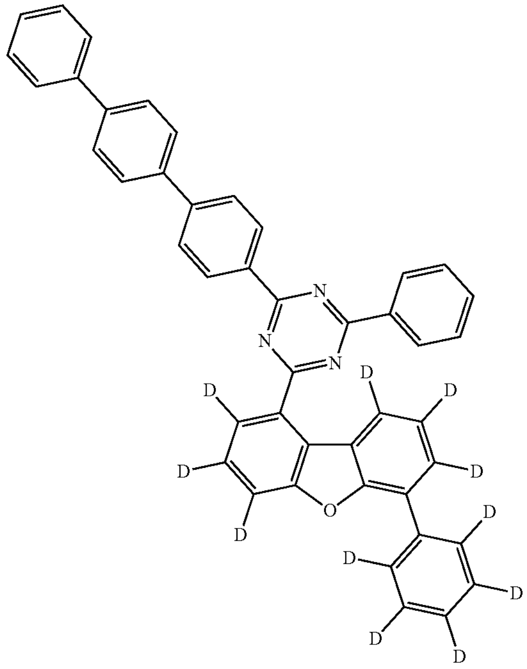
217
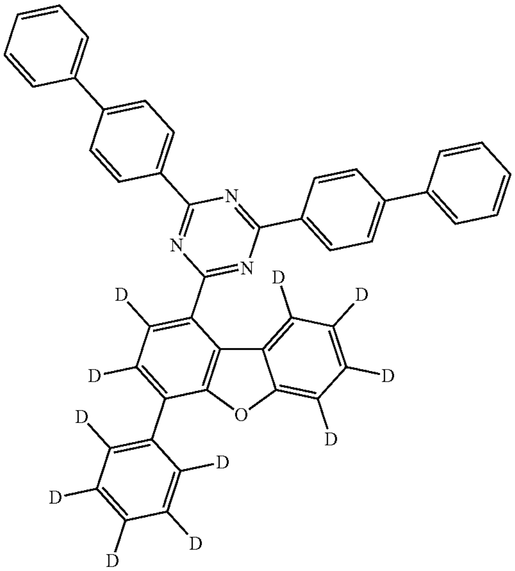

-continued
217
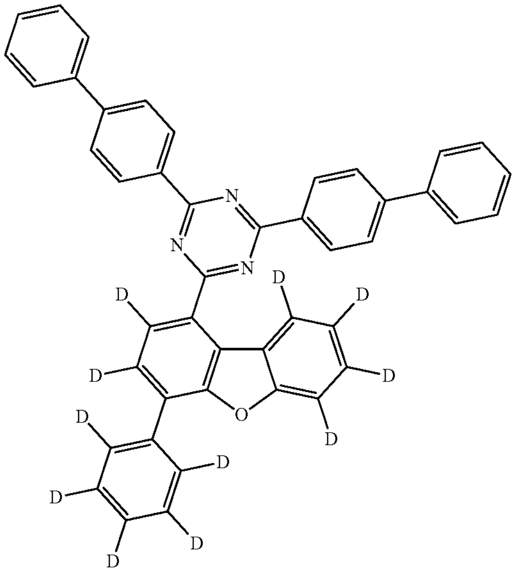
218
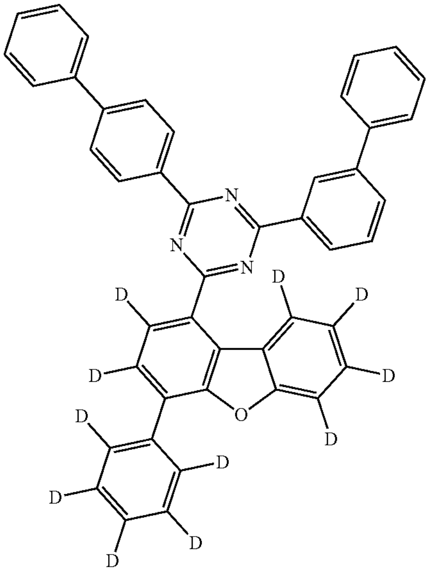
-continued
219
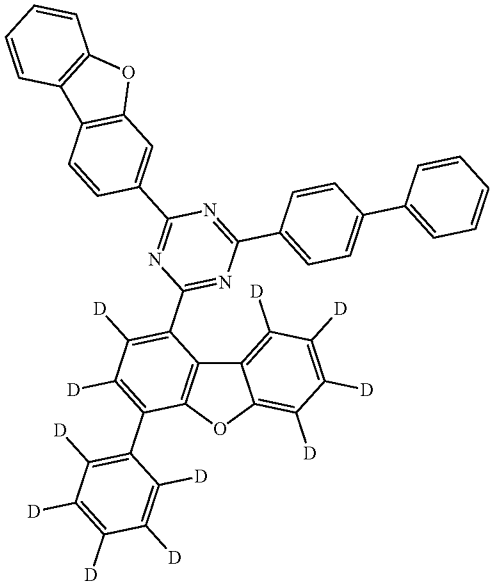
220
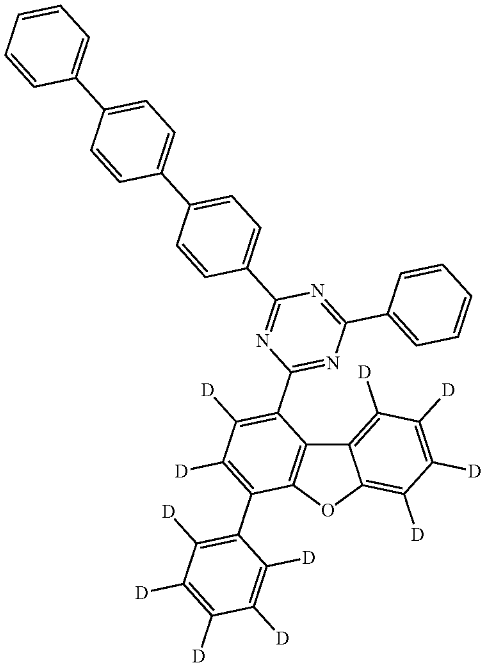

-continued
221
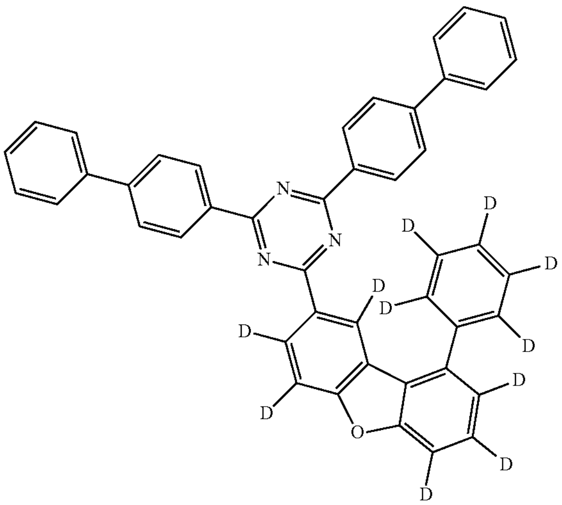
222
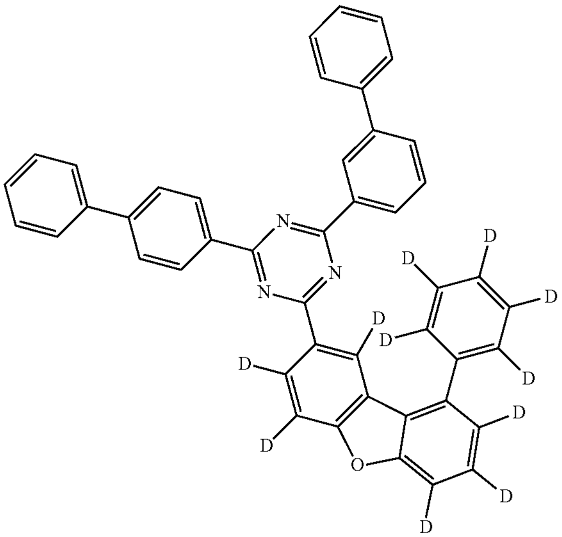
223
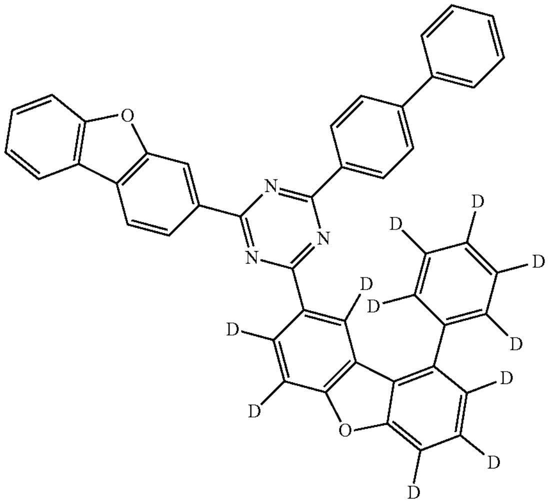
-continued
224
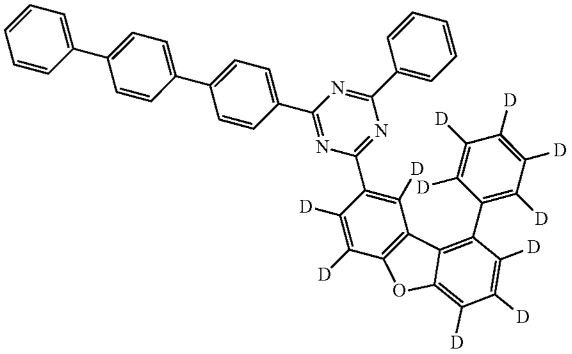
225
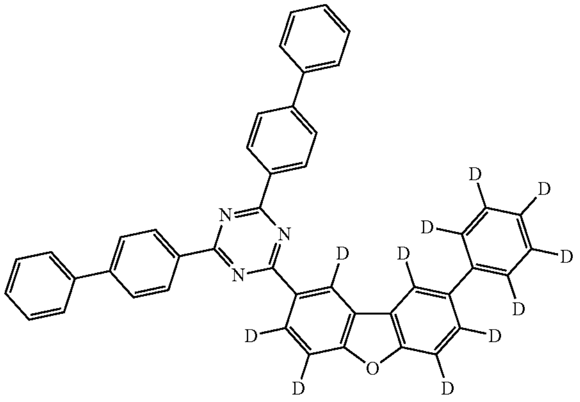
226
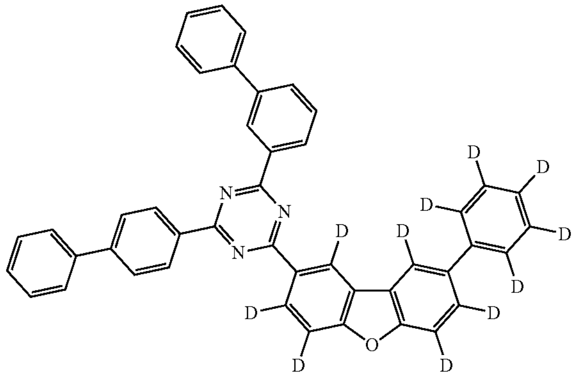
227
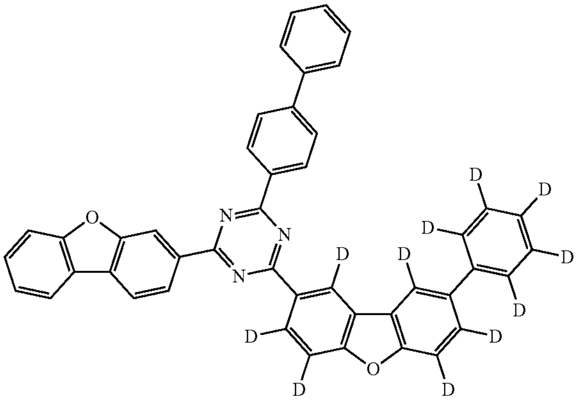

-continued
228
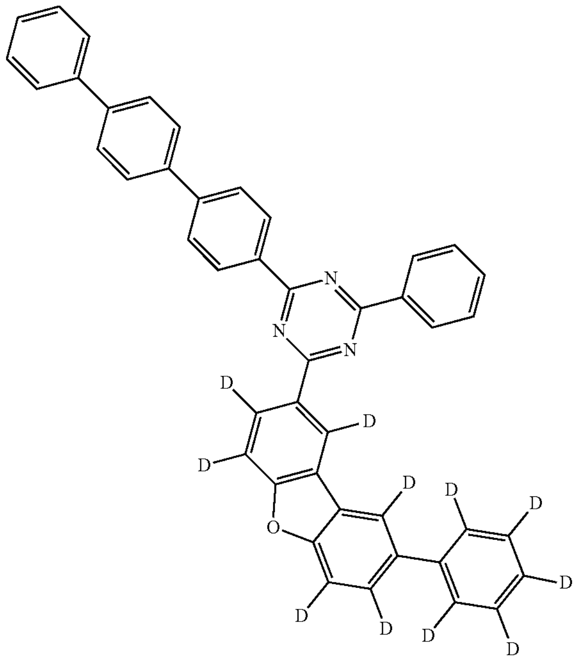
229
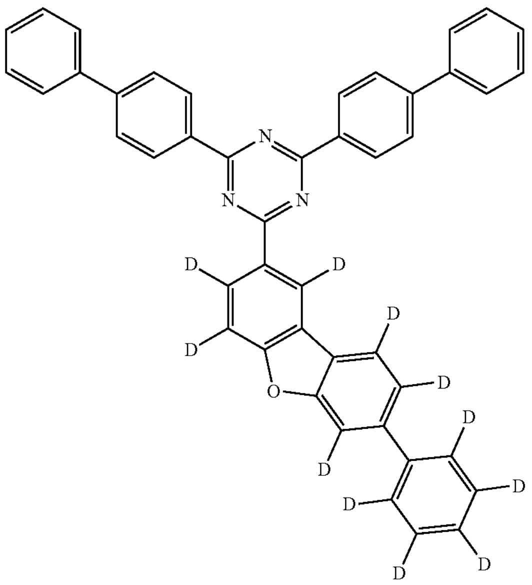
-continued
230
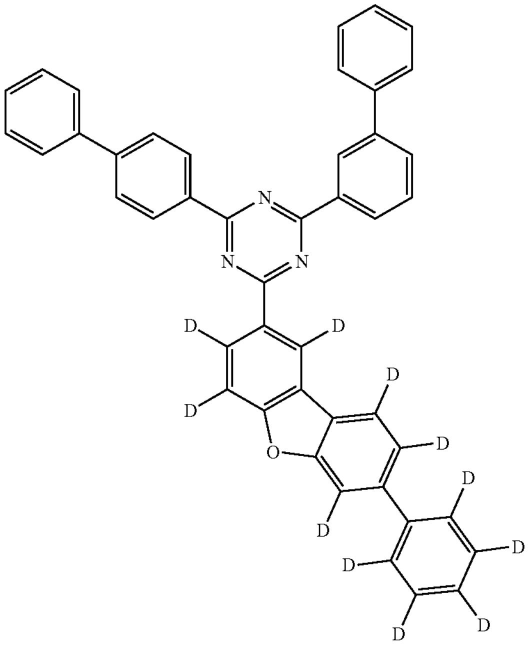
231
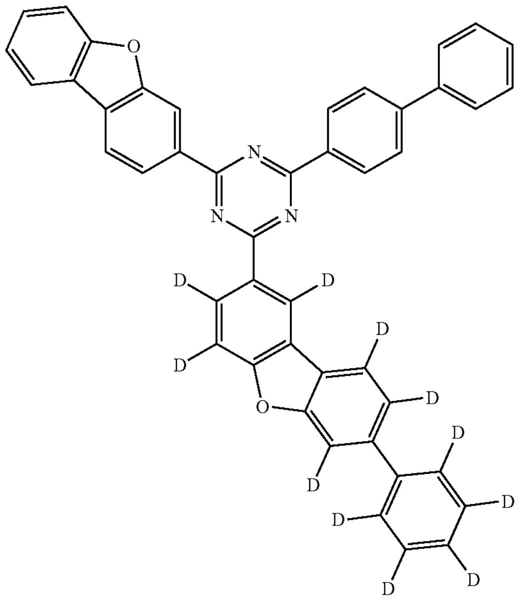

-continued
232
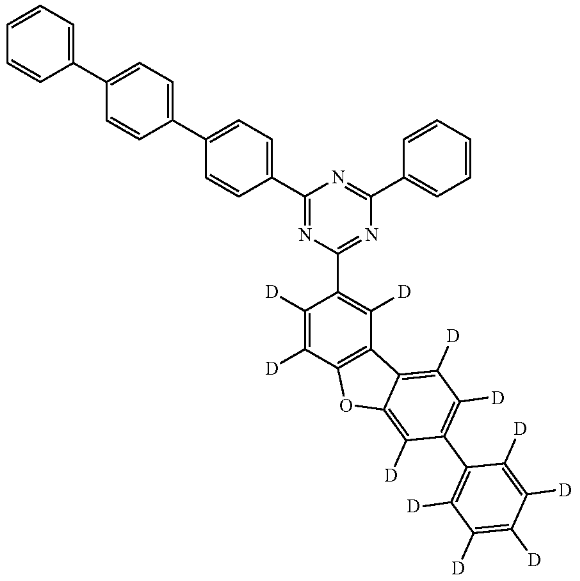
-continued
233
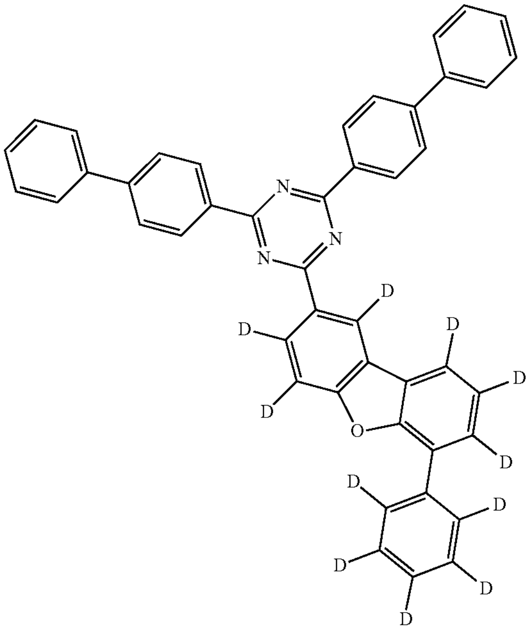
233
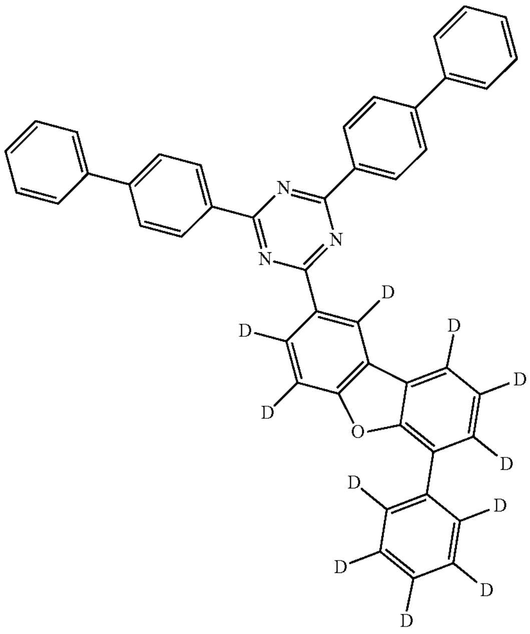
234
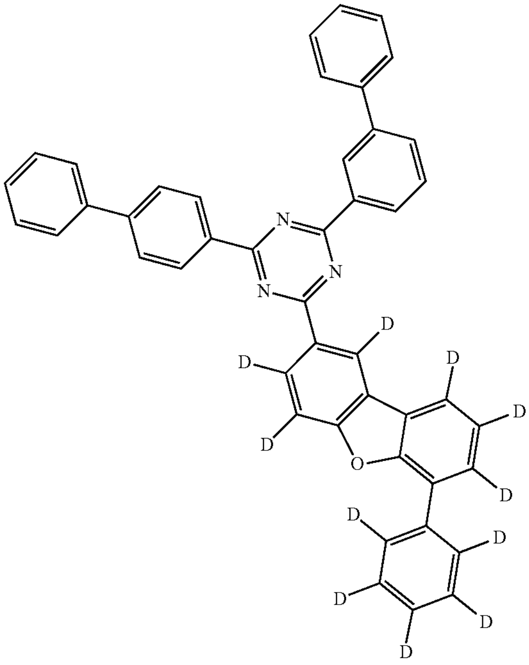

-continued
235
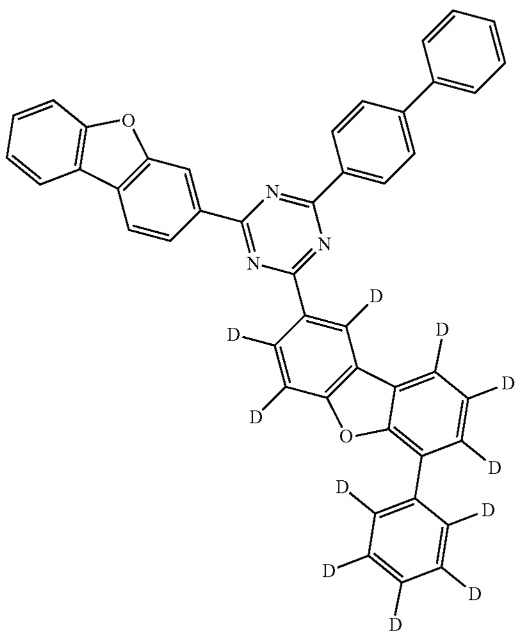
236
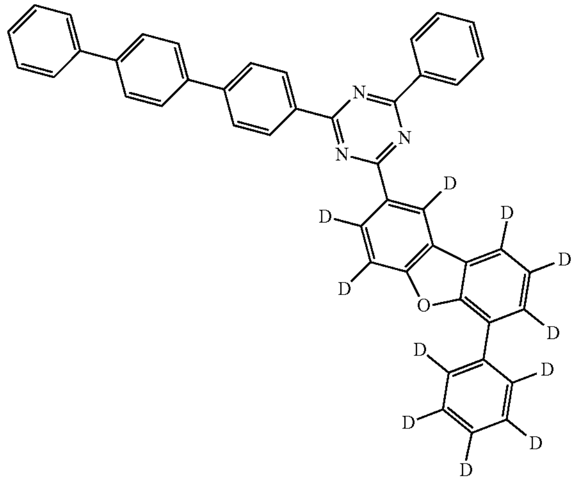
237
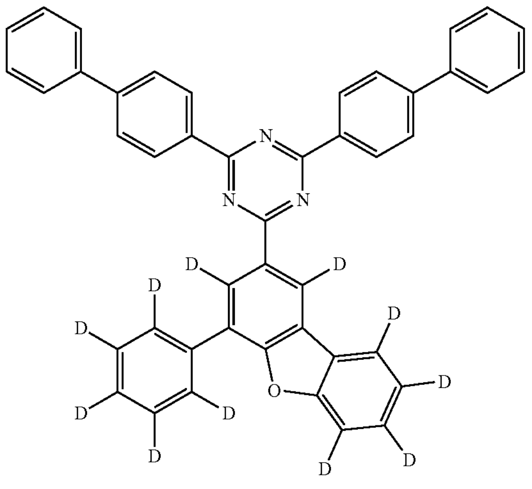
-continued
238
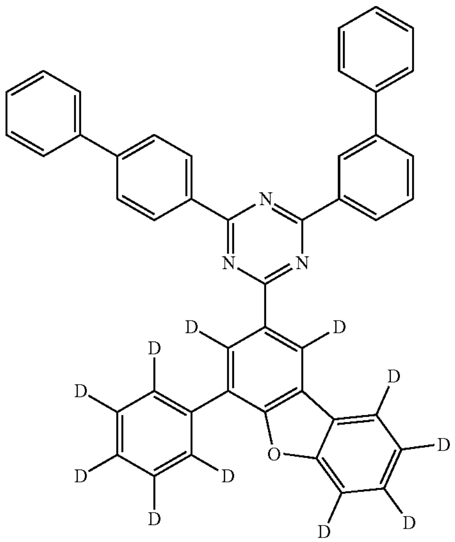
239
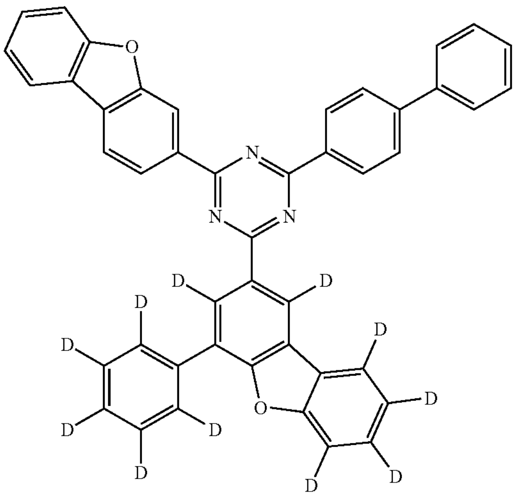
240
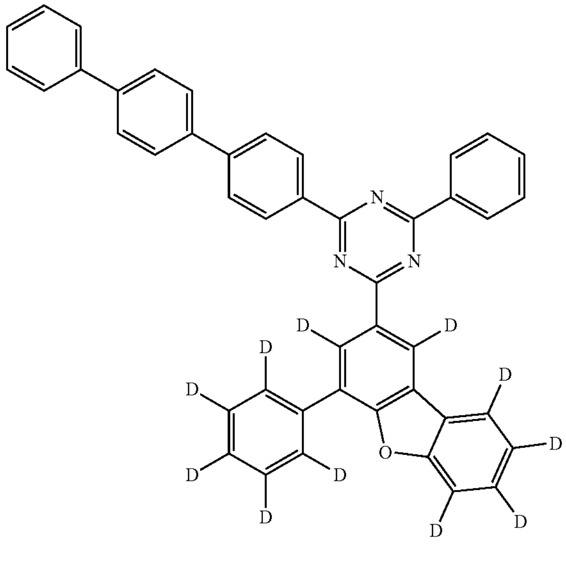

-continued
241
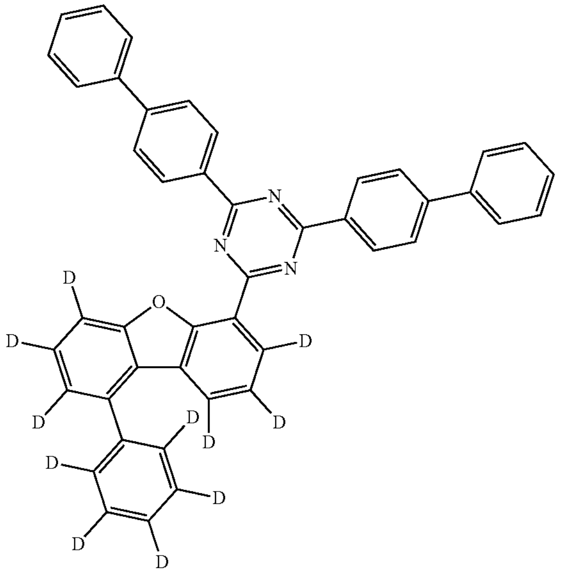
242
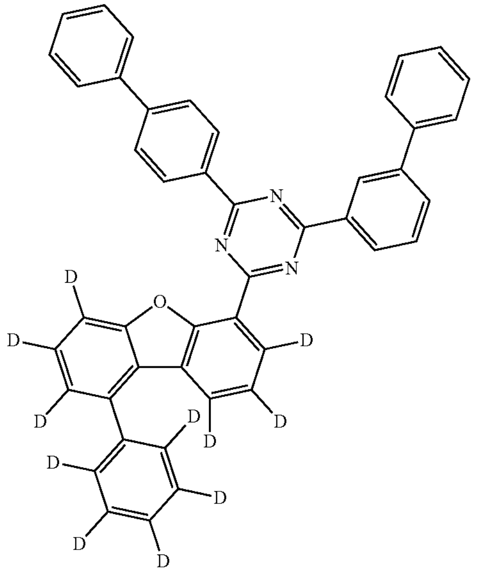
-continued
243
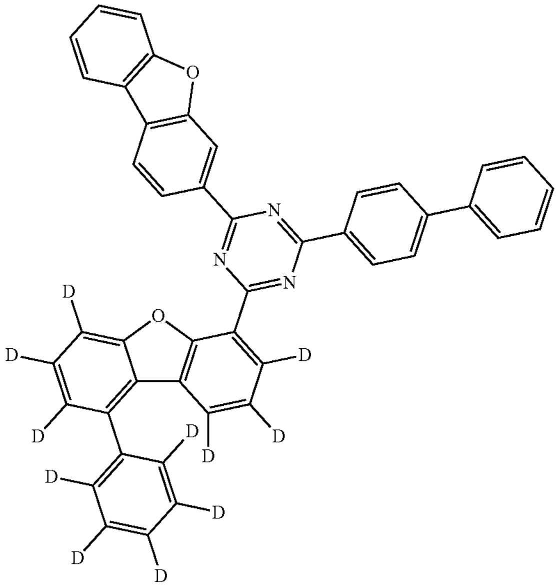
244
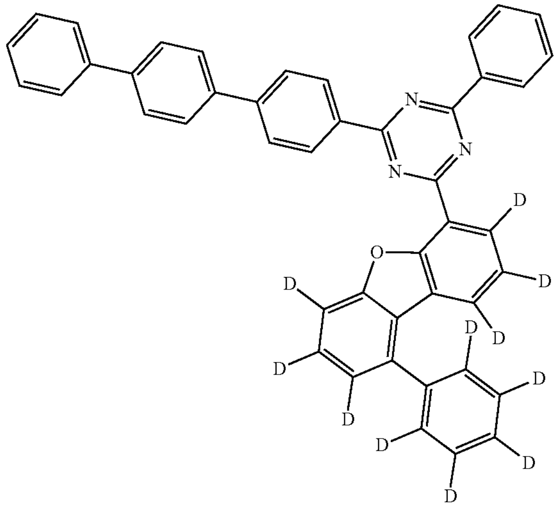
245
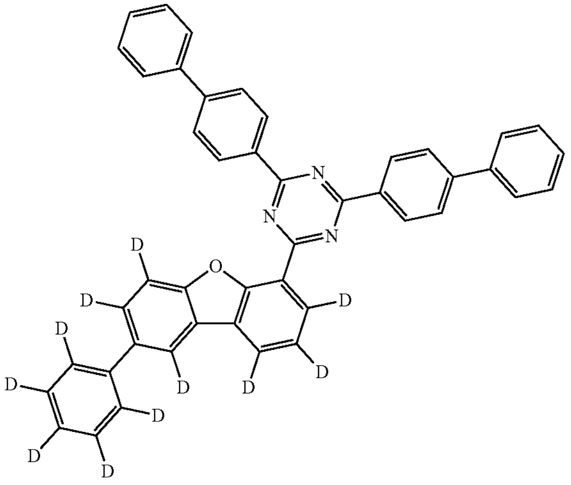

246
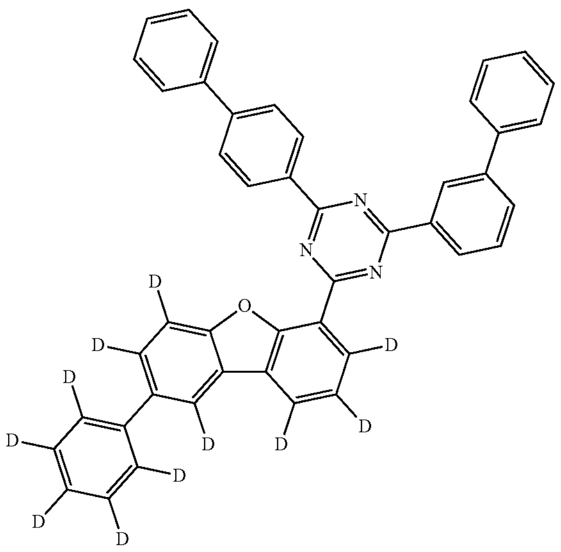
247
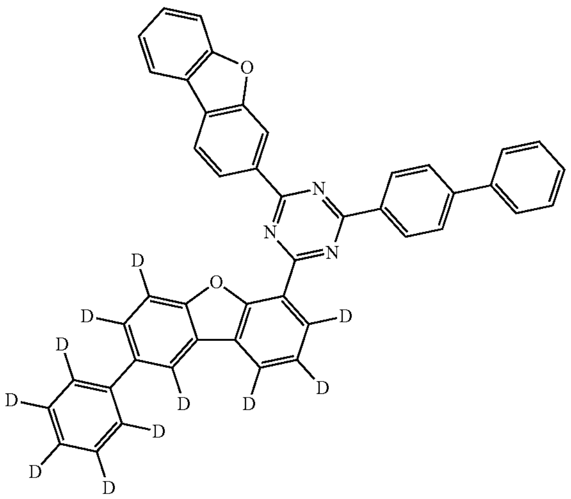
248
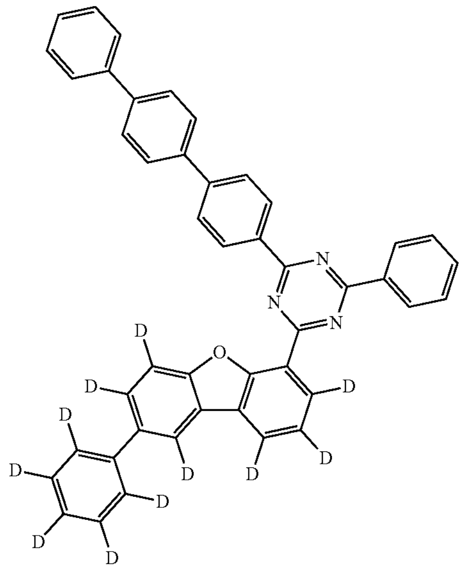
249
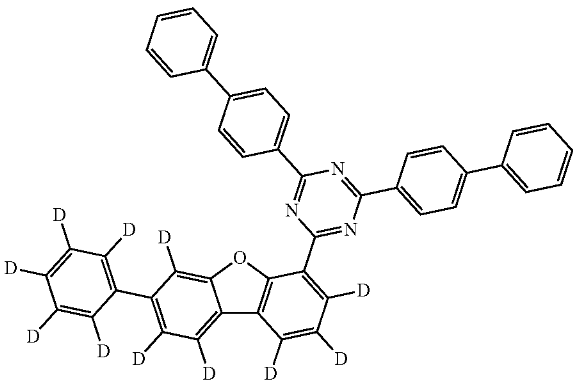
250
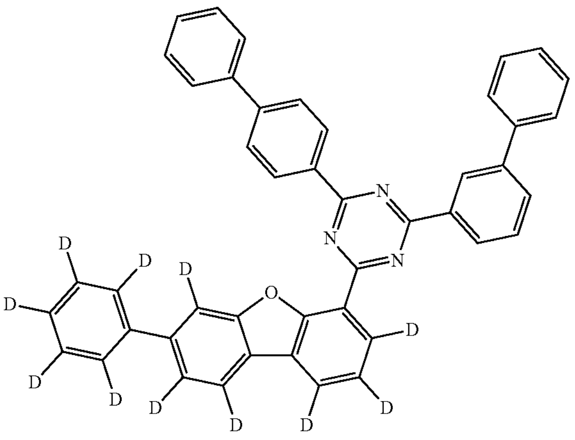
251
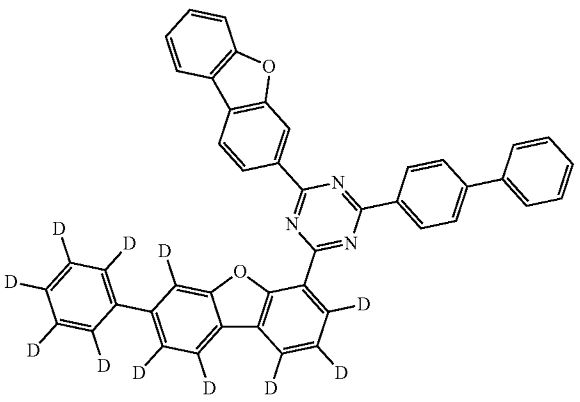

-continued
252
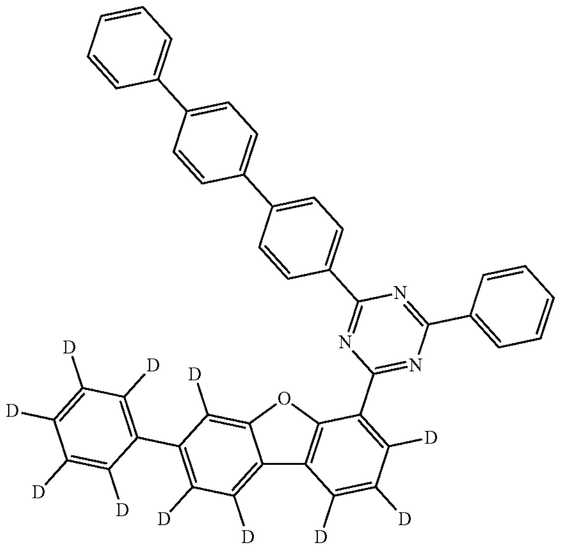
253
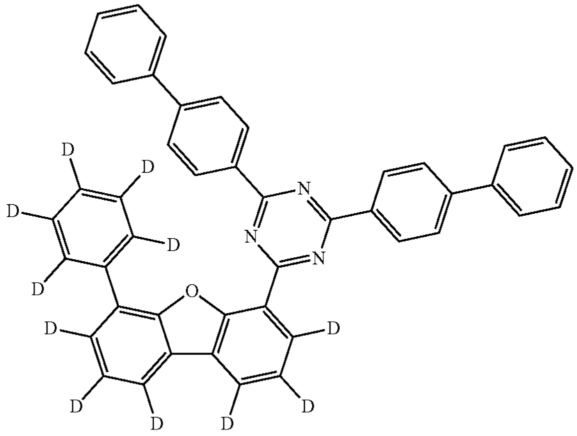
254
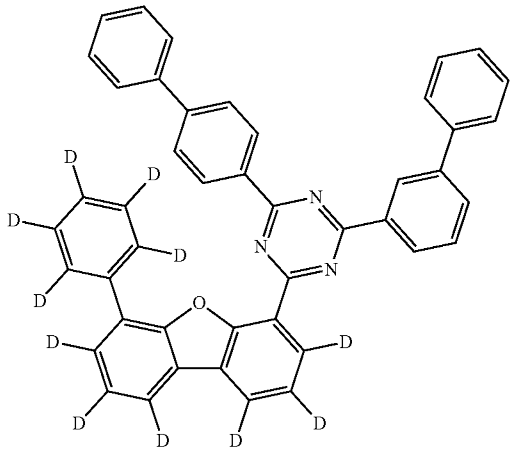
-continued
255
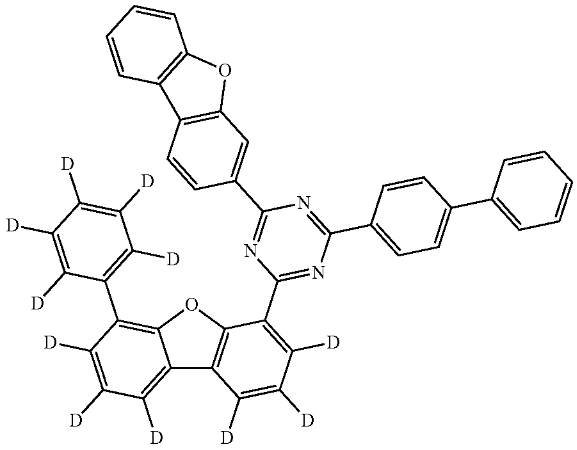
256
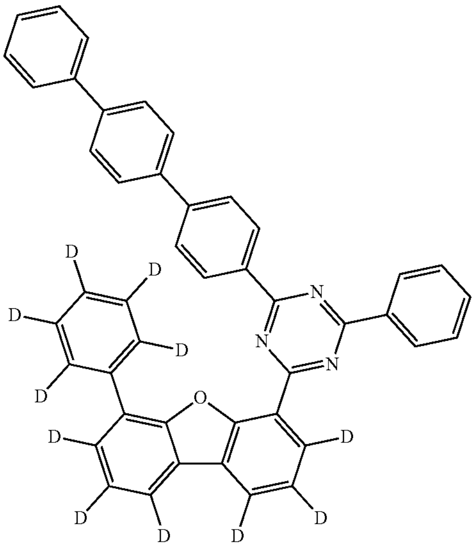
257
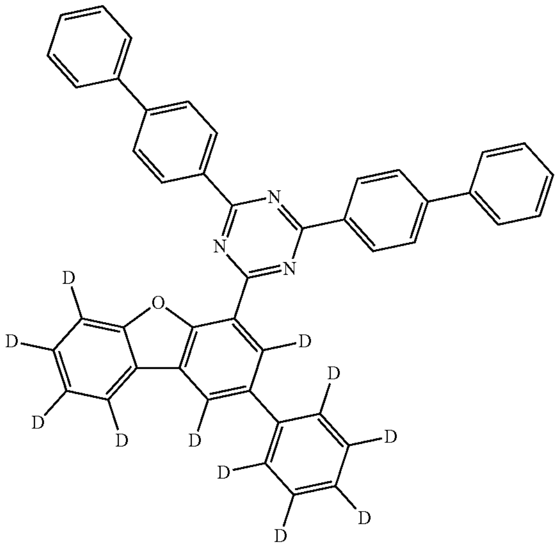

-continued
258
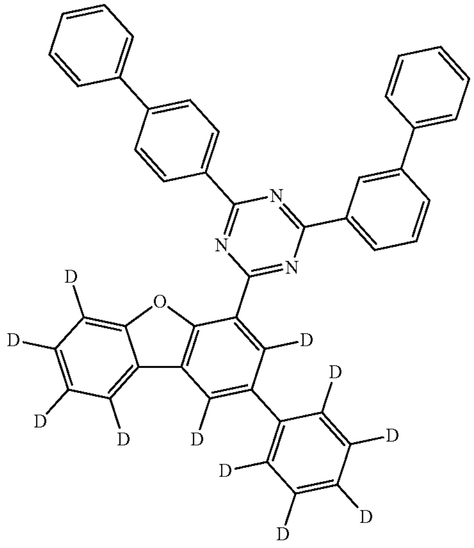
259
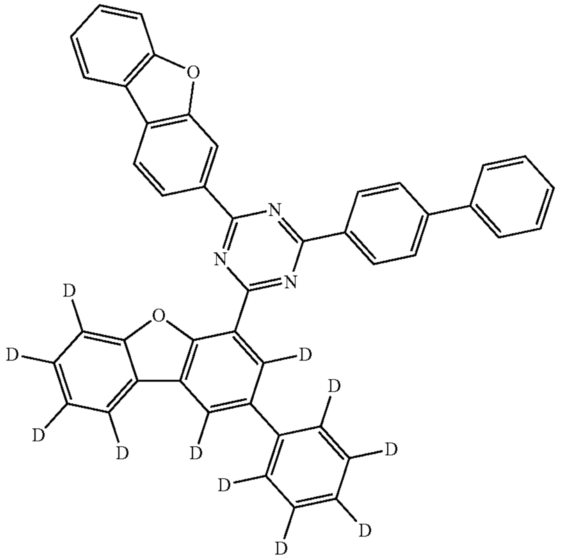
-continued
260
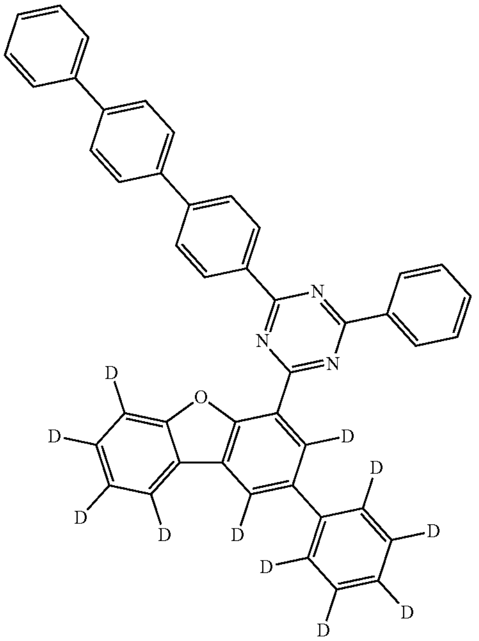
261
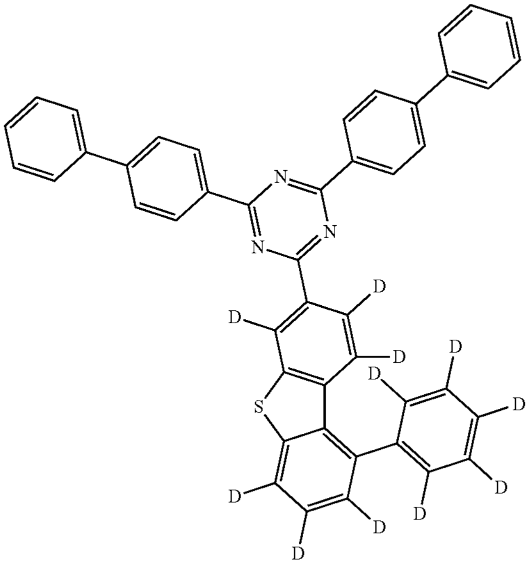

262
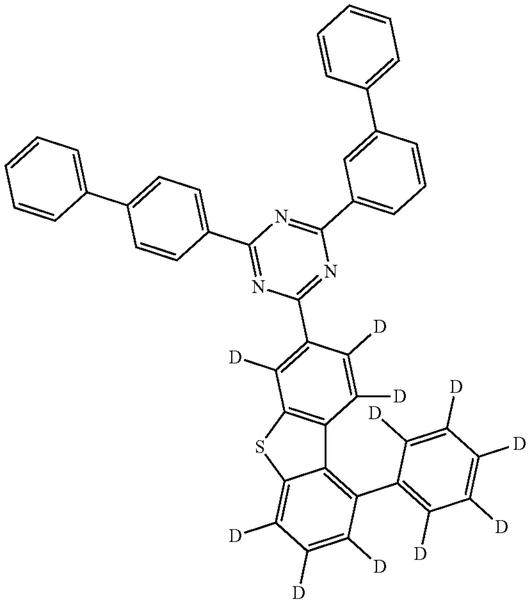
263
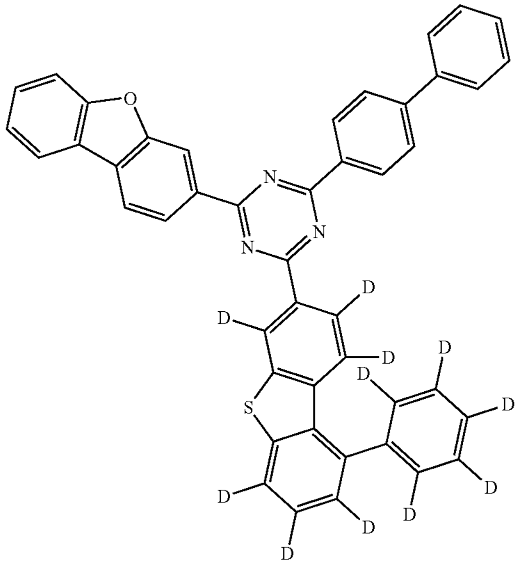
264
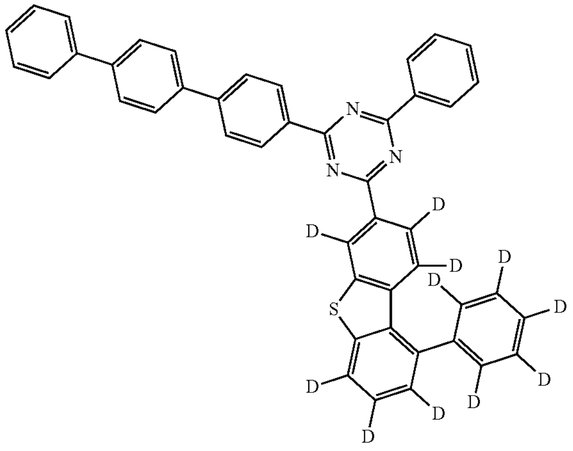
265
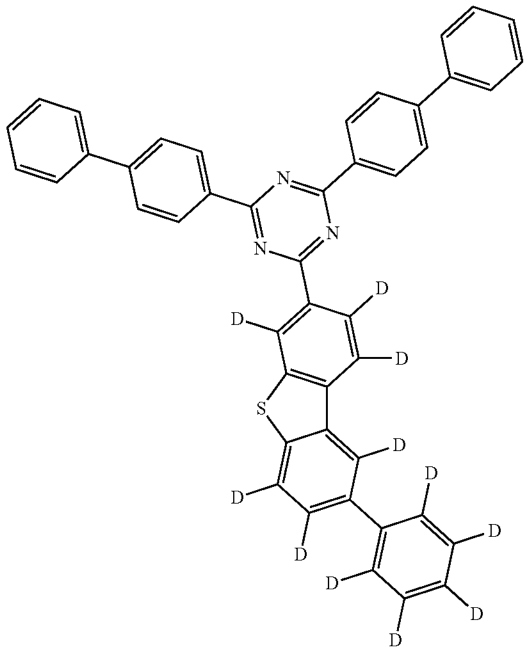

-continued
266
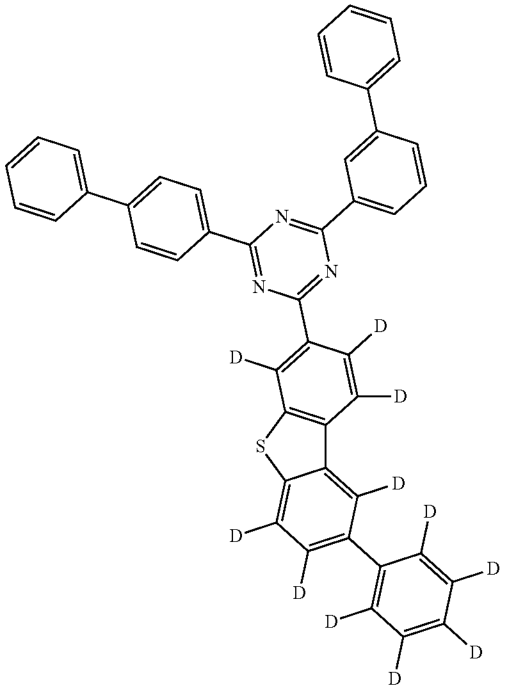
-continued
267
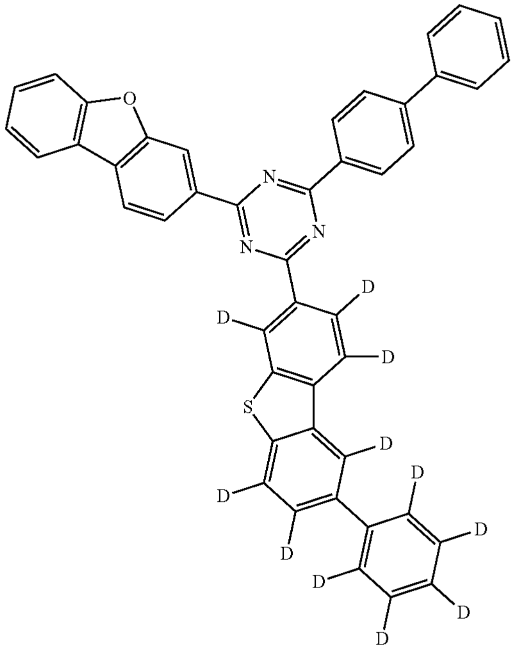
264
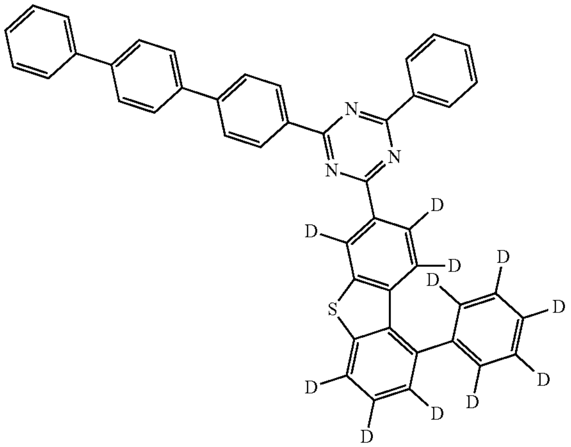
268
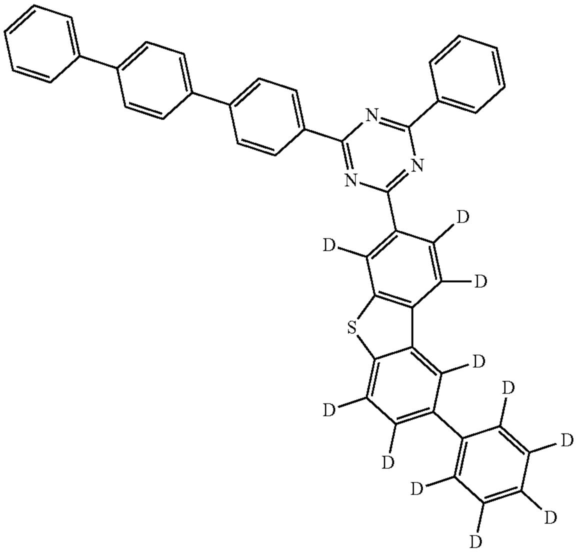

269
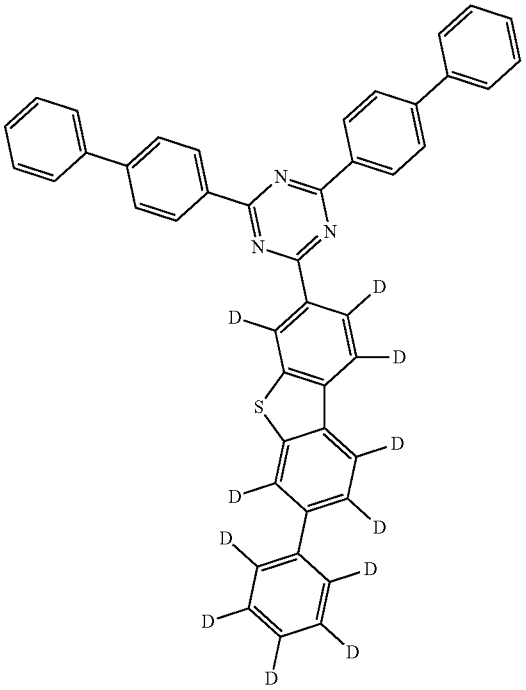
269
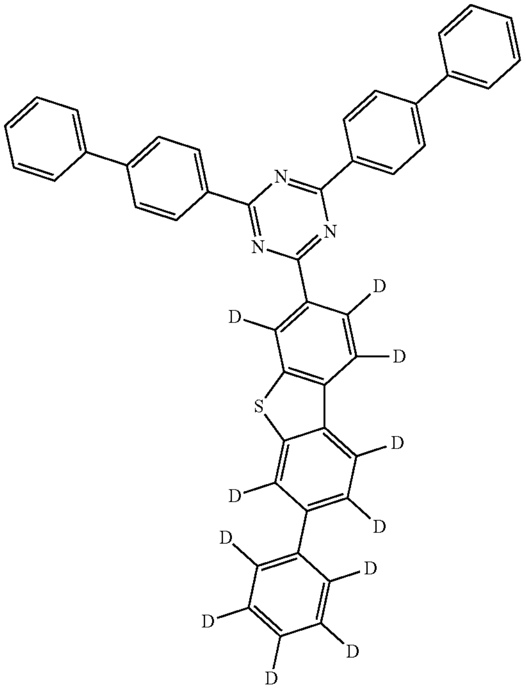
270
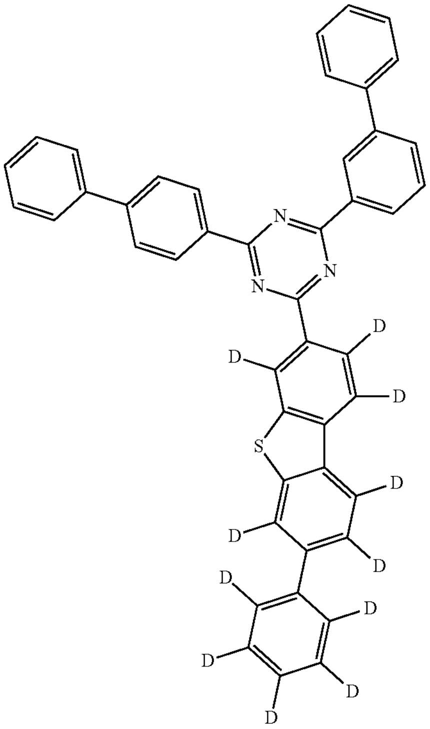
271
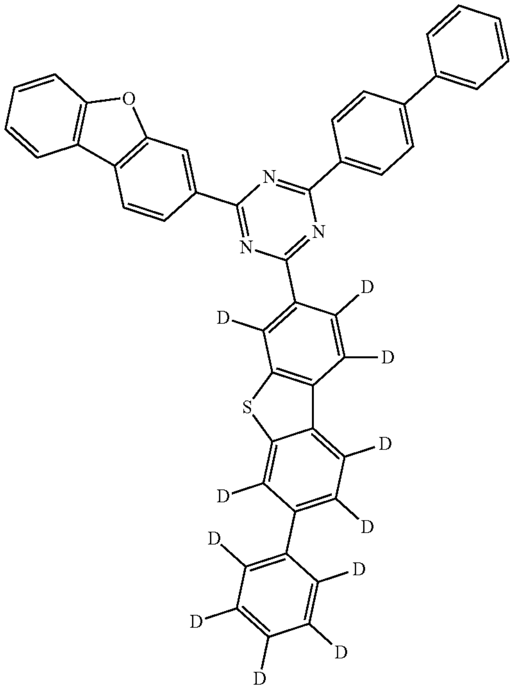

272
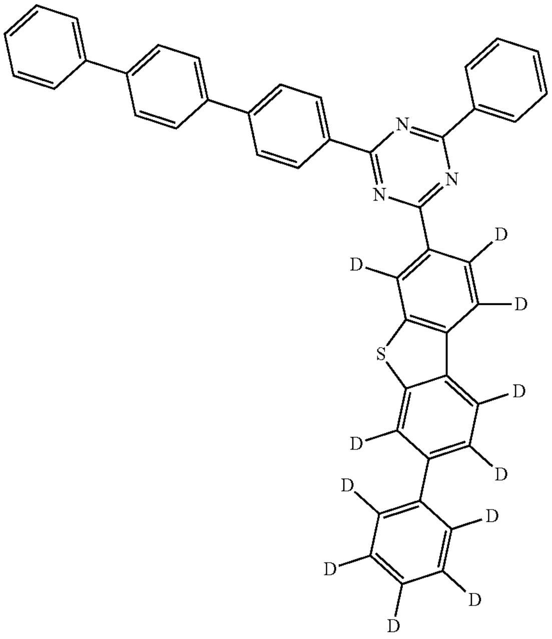
273
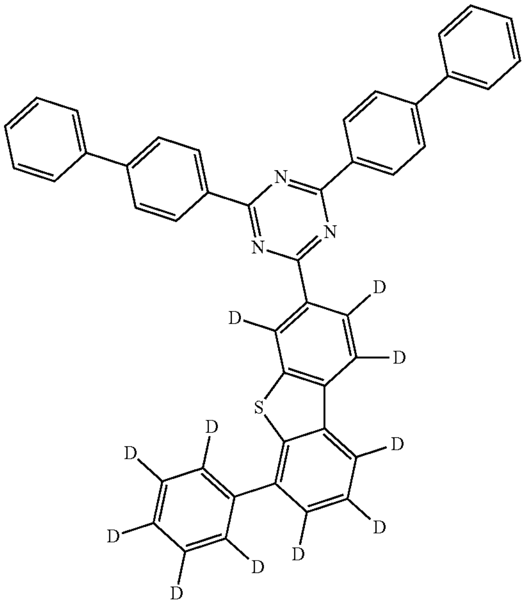
274
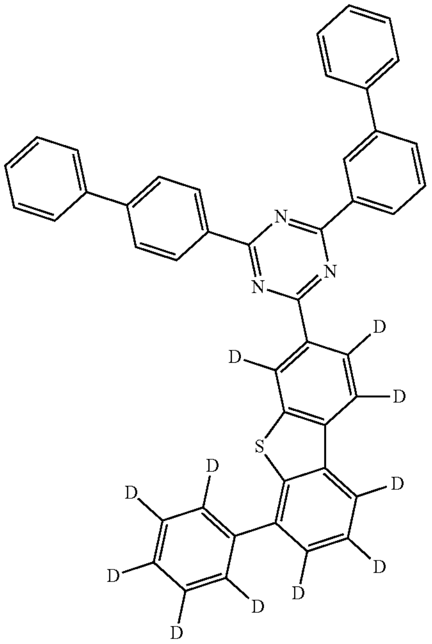
275
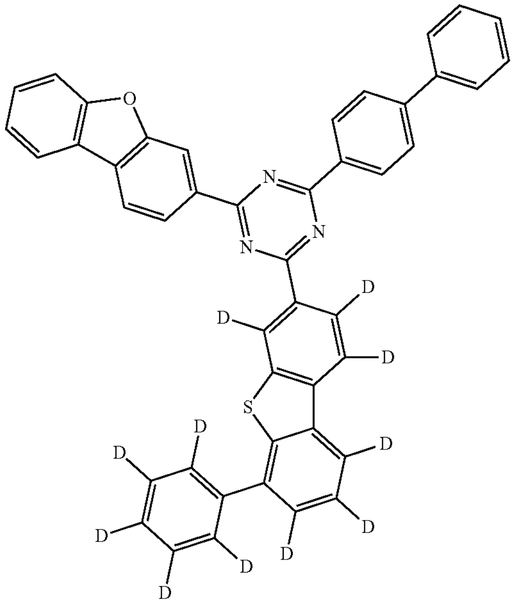

-continued
276
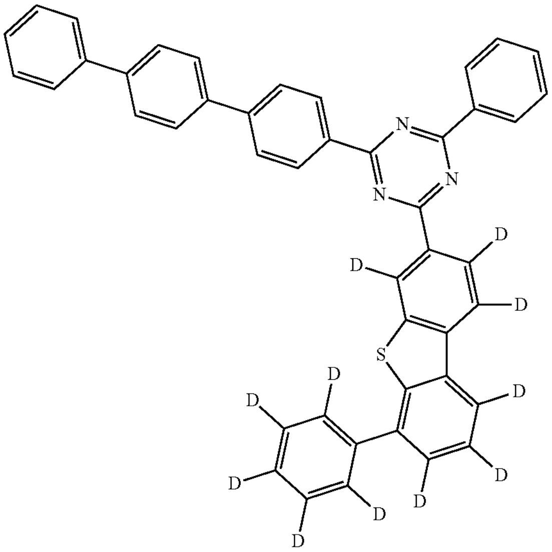
277
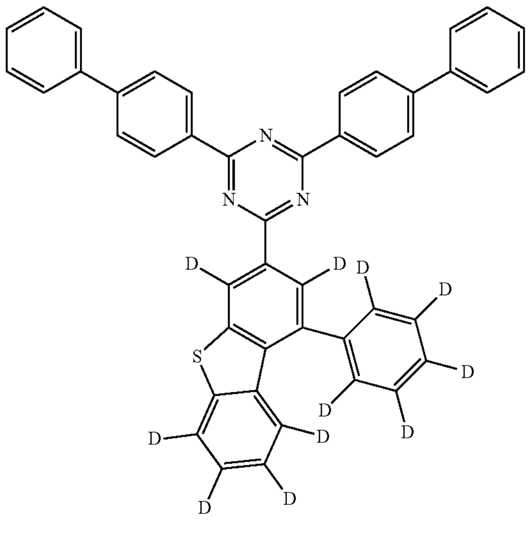
-continued
278
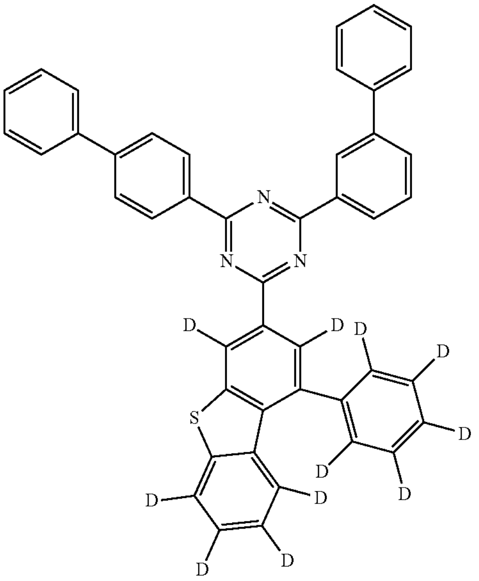
279
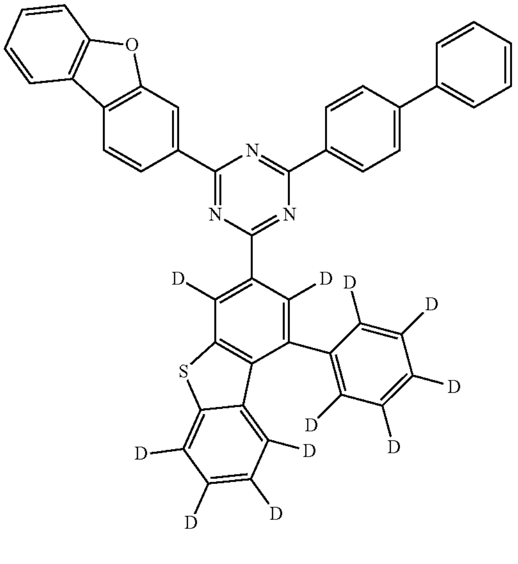

-continued
280
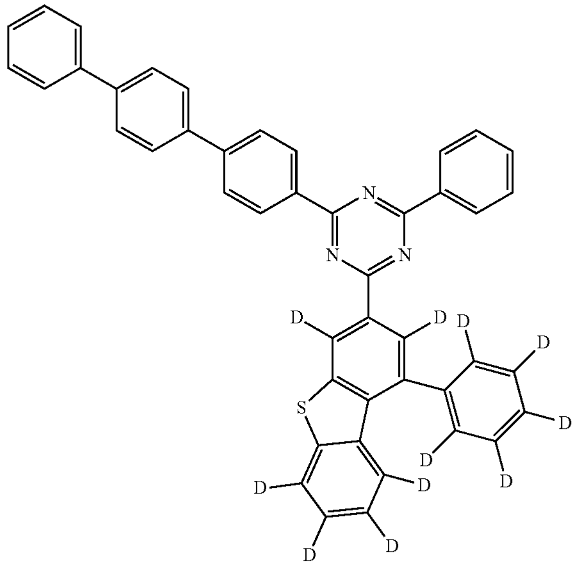
281
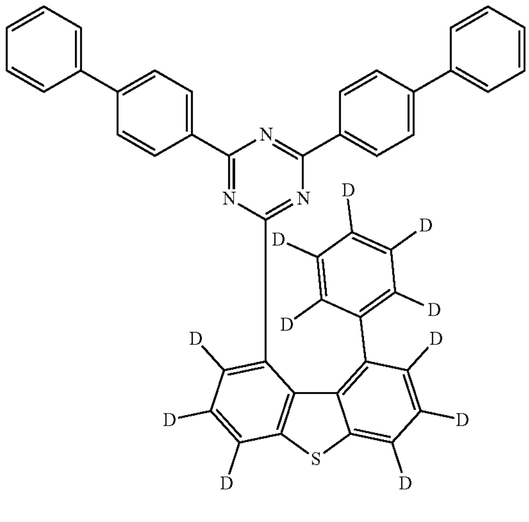
-continued
282
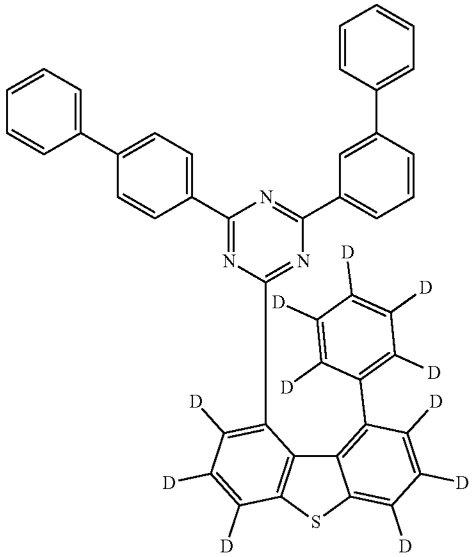
283
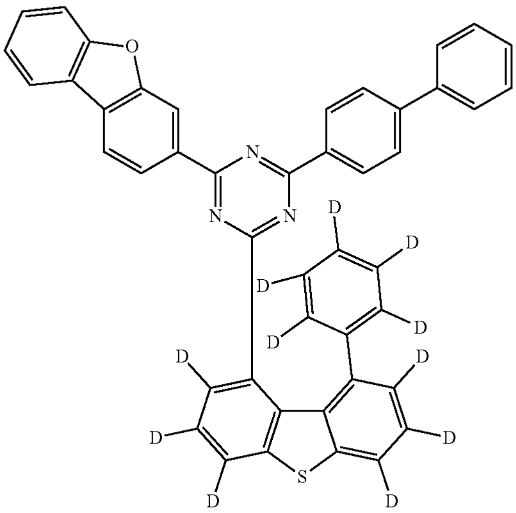
284
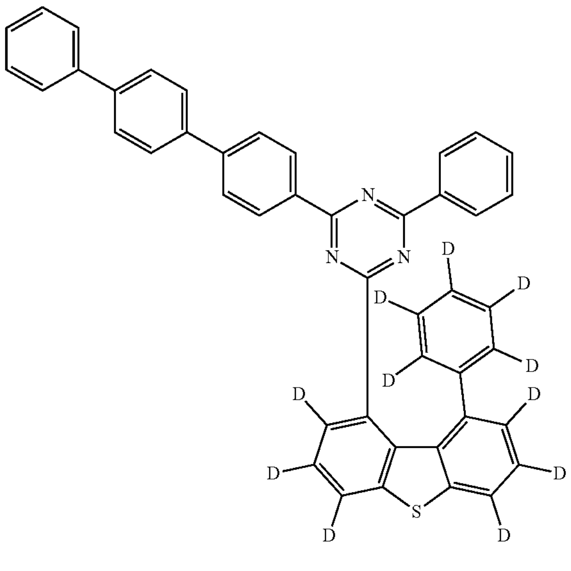

-continued
285
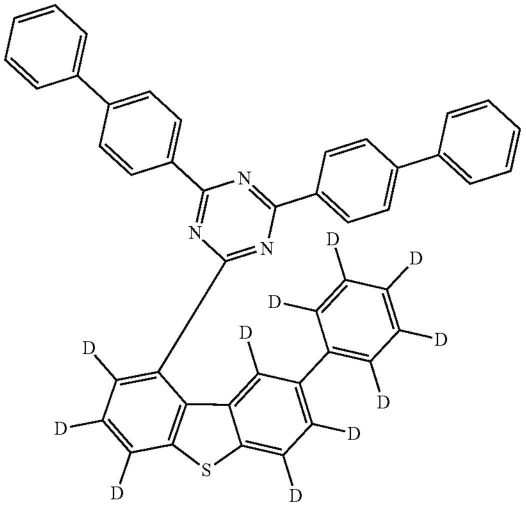
286
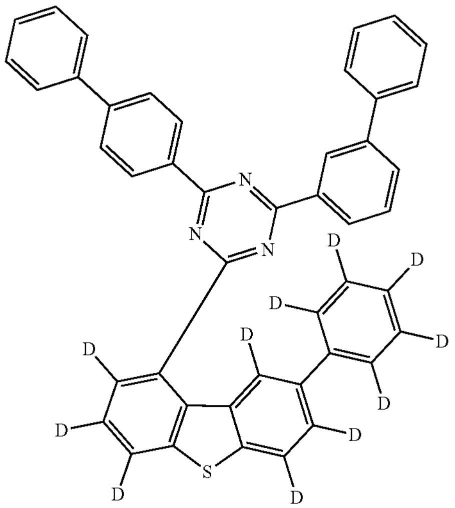
287
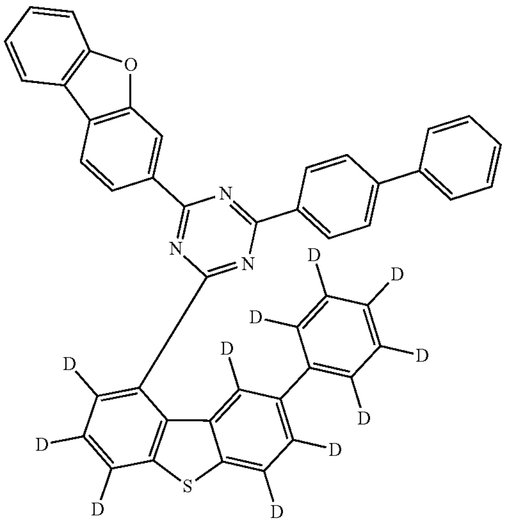
-continued
288
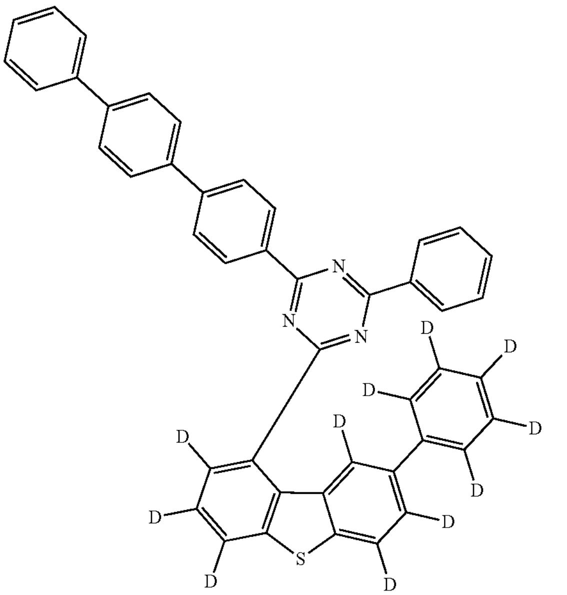
289
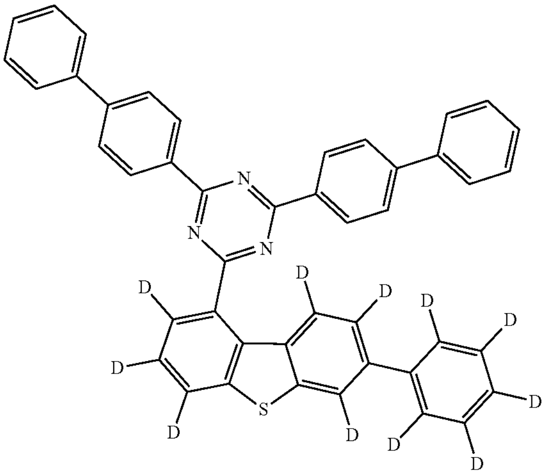
290
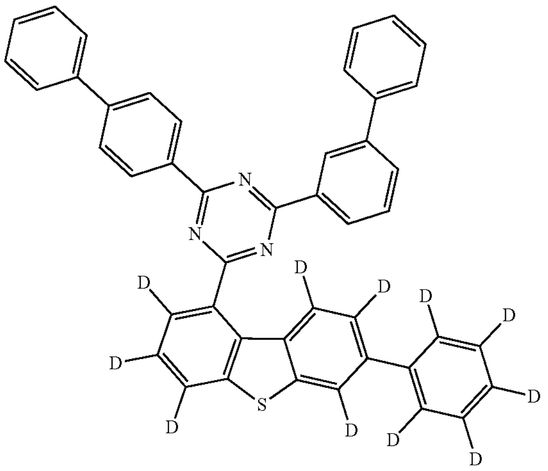

-continued
291
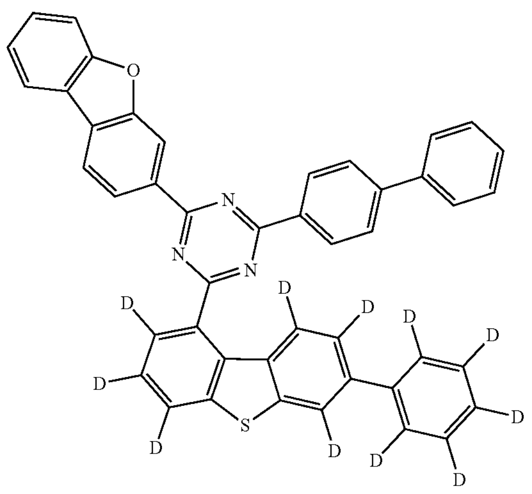
292
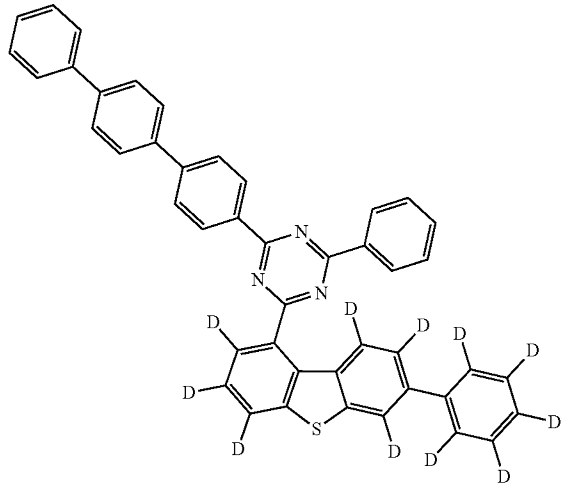
293
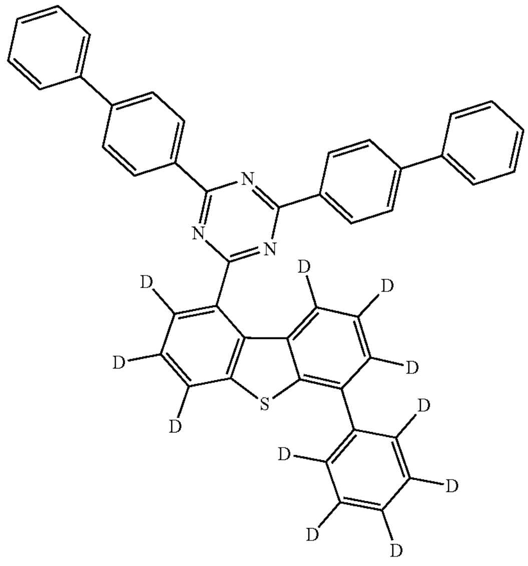
-continued
294
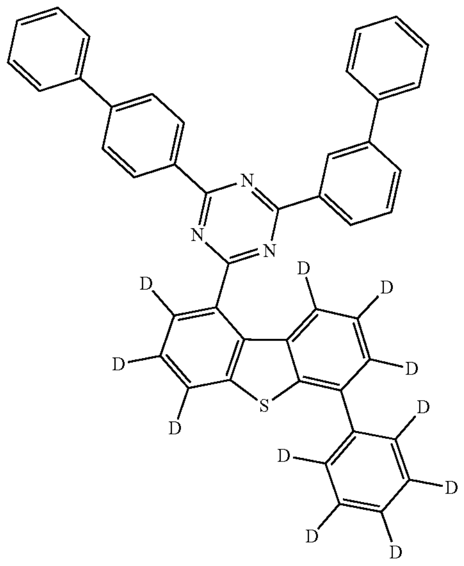
295
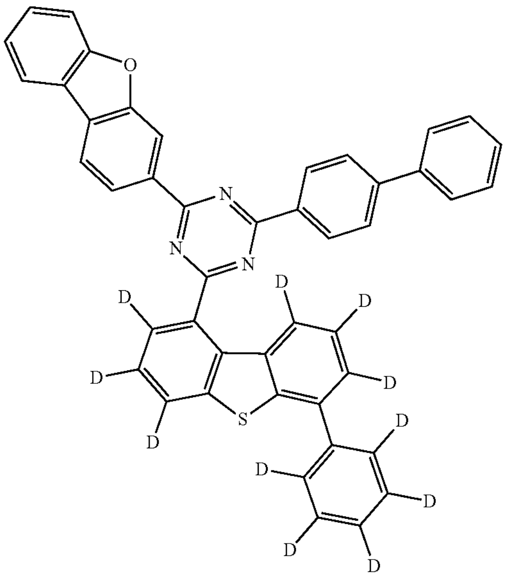

-continued
296
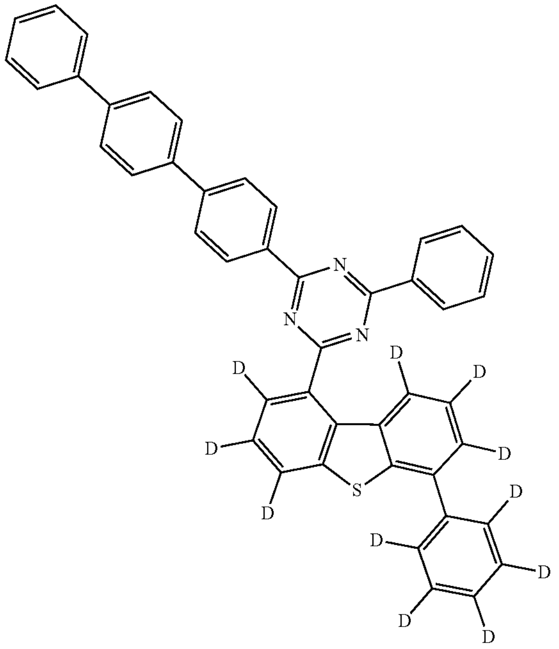
297
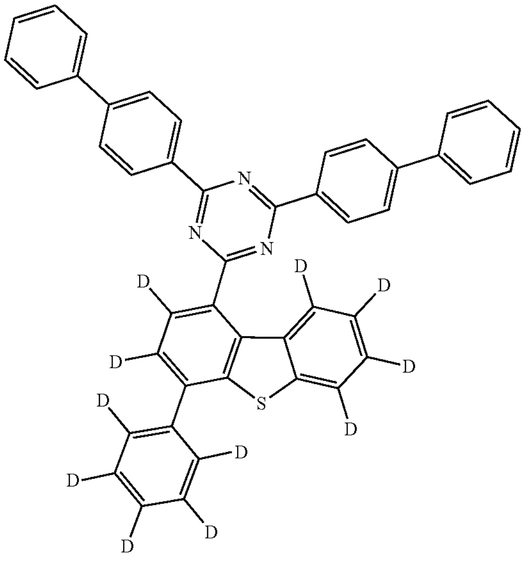
-continued
298
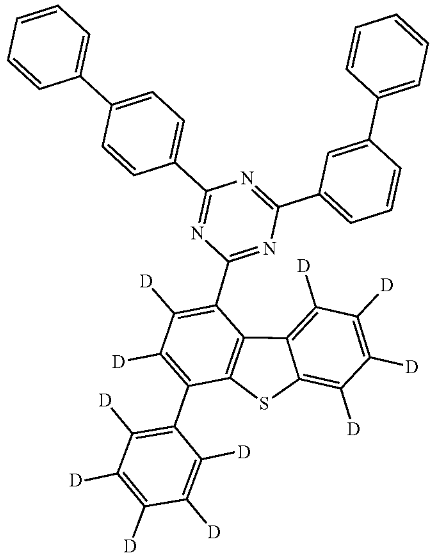
299
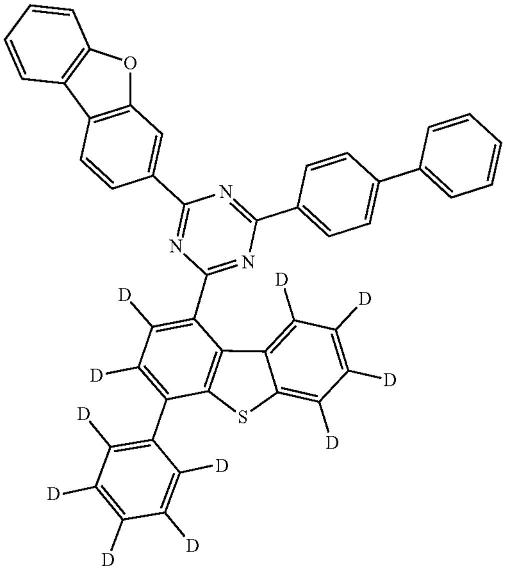

-continued
300
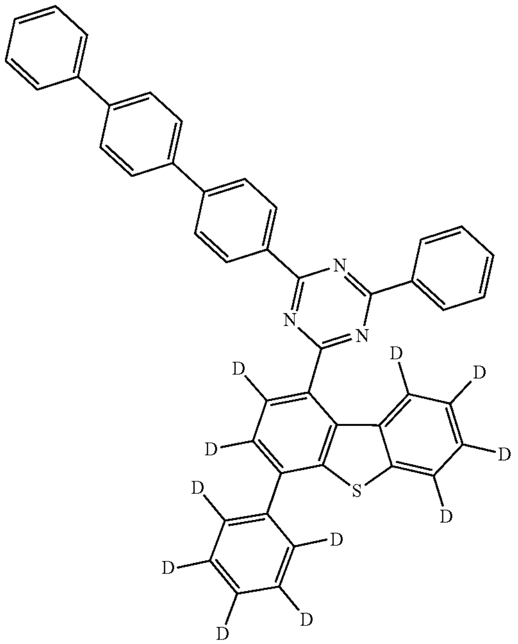
301
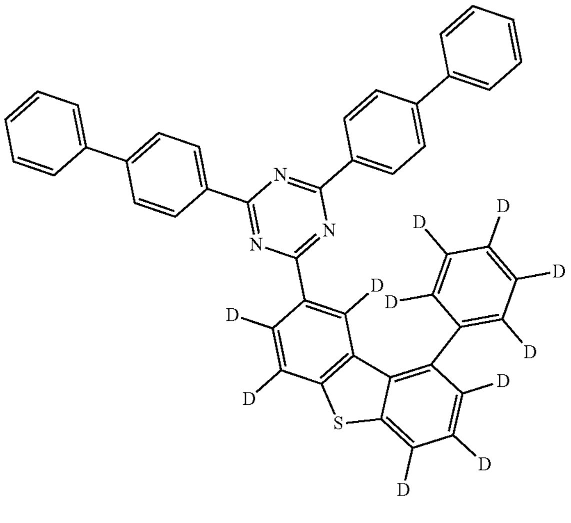
-continued
302
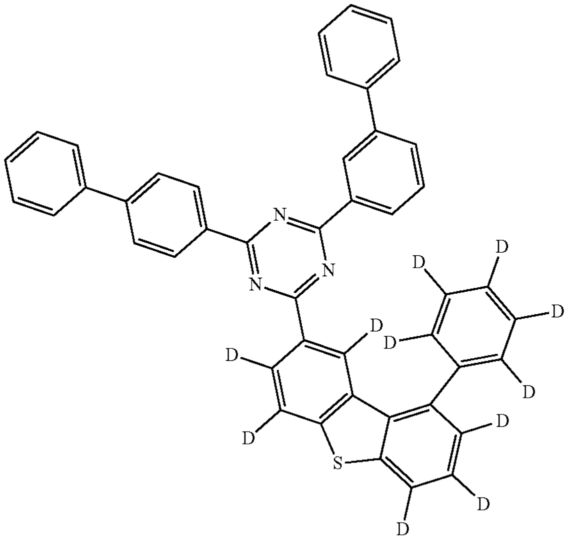
303
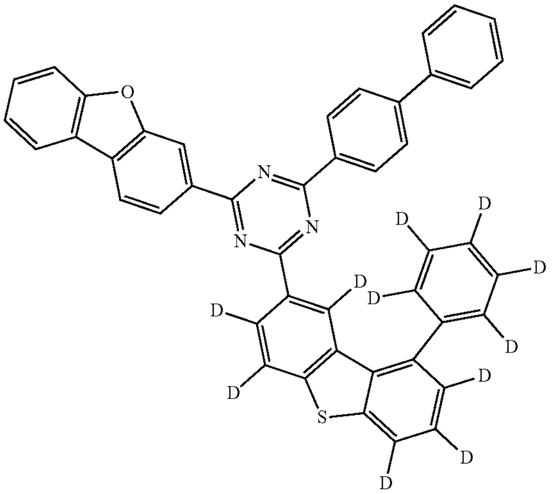
304
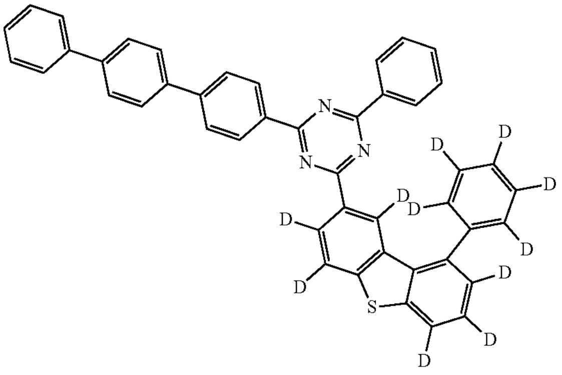

-continued
305
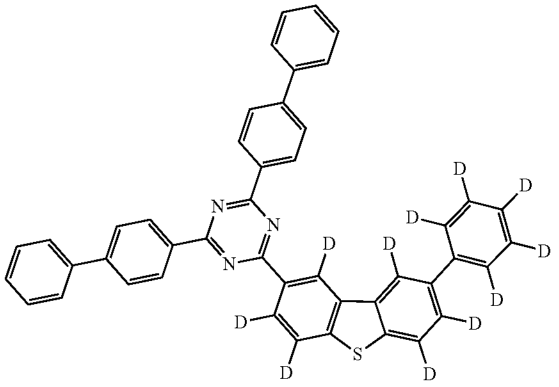
306
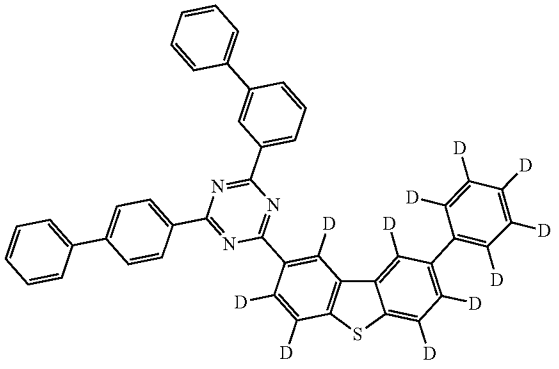
307
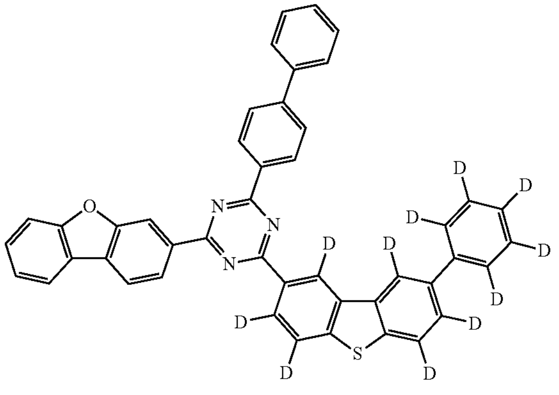
-continued
308
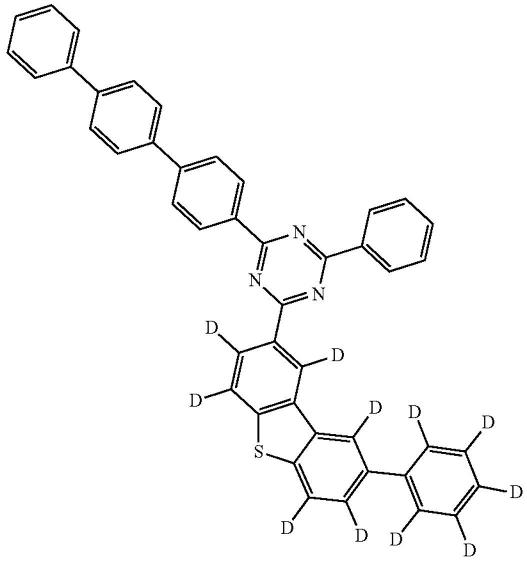
309
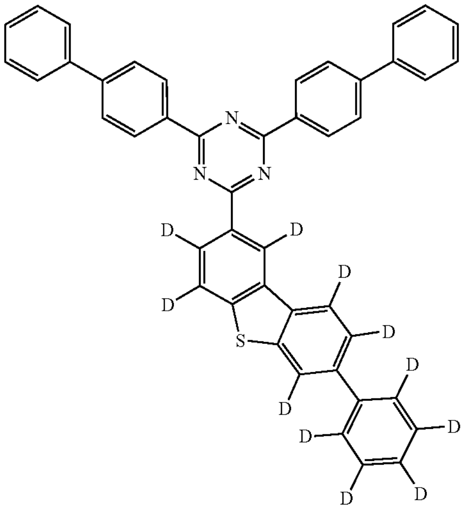
310
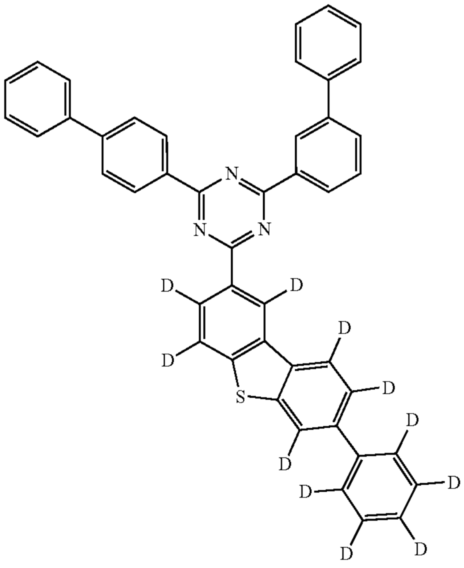

-continued
311
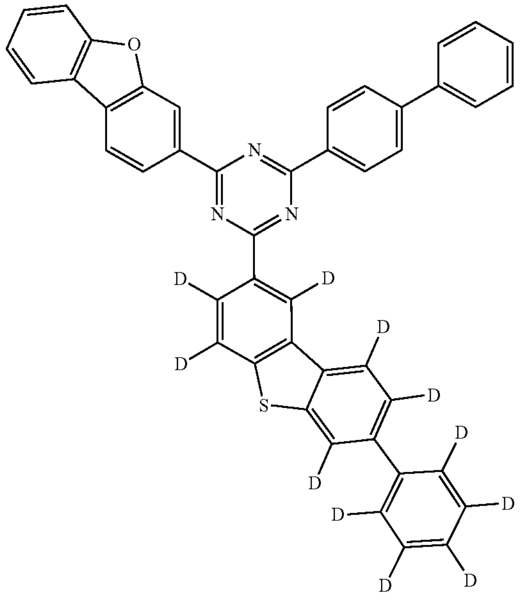
312
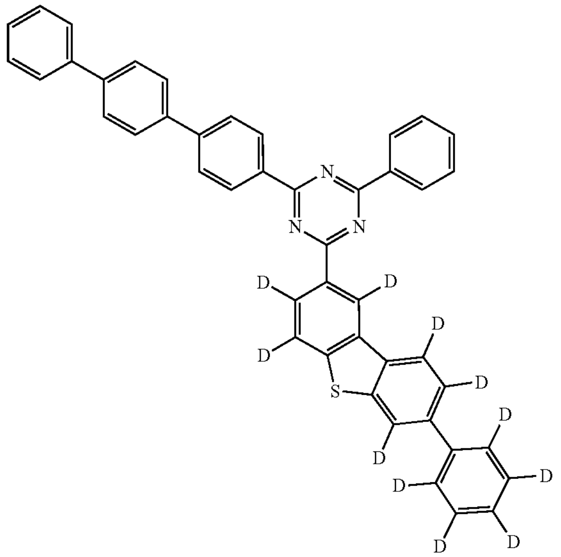
-continued
313
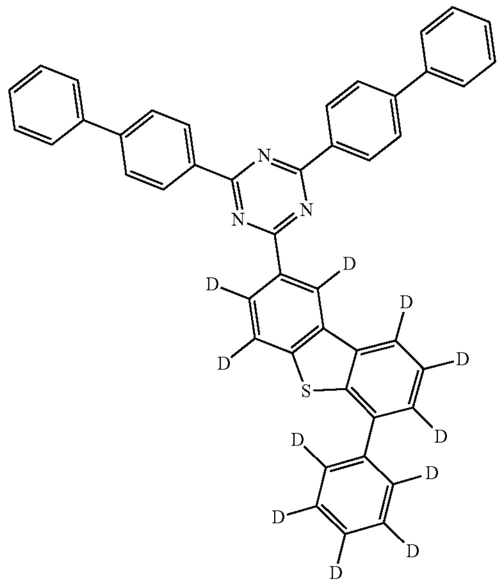
314
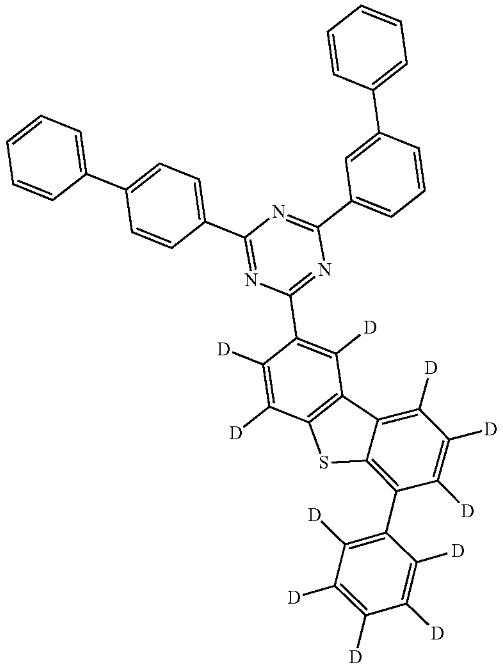

-continued
315
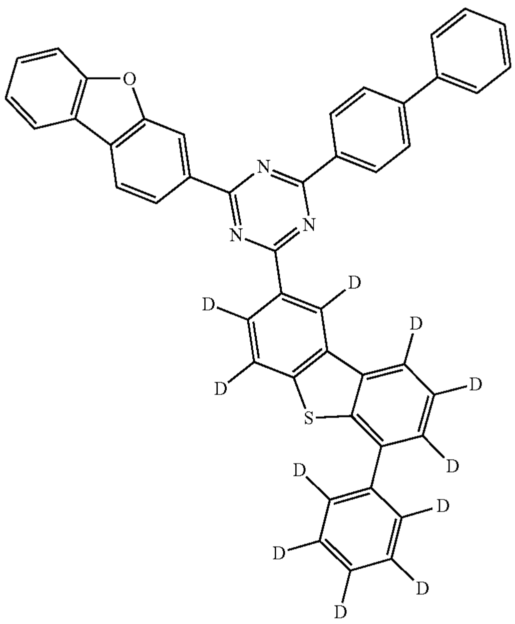
316
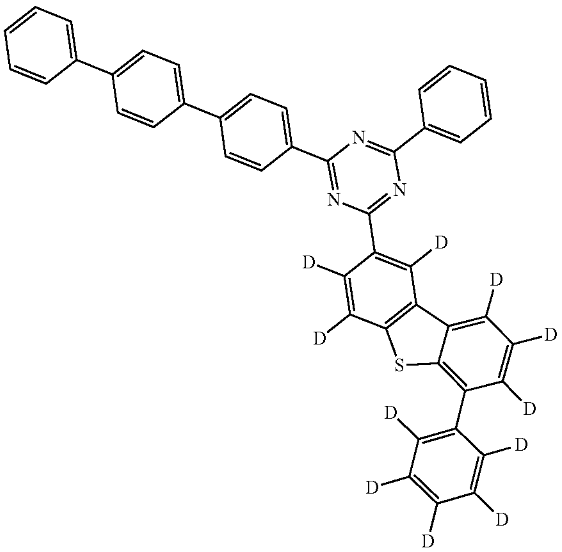
-continued
317
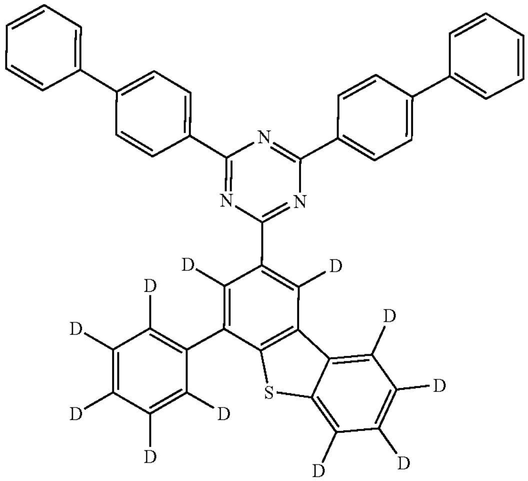
318
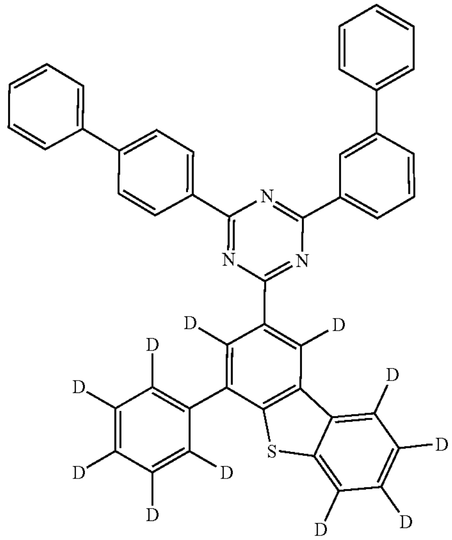
319
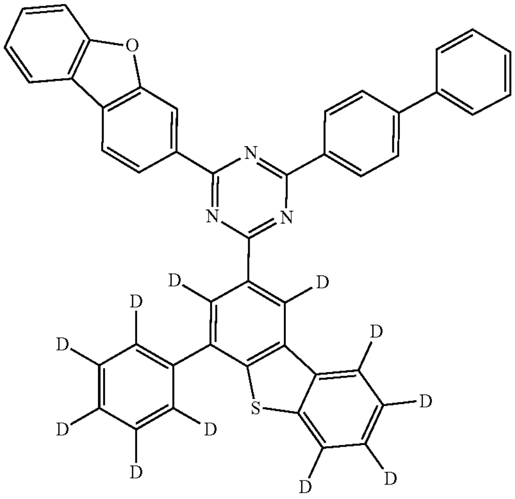

-continued
320
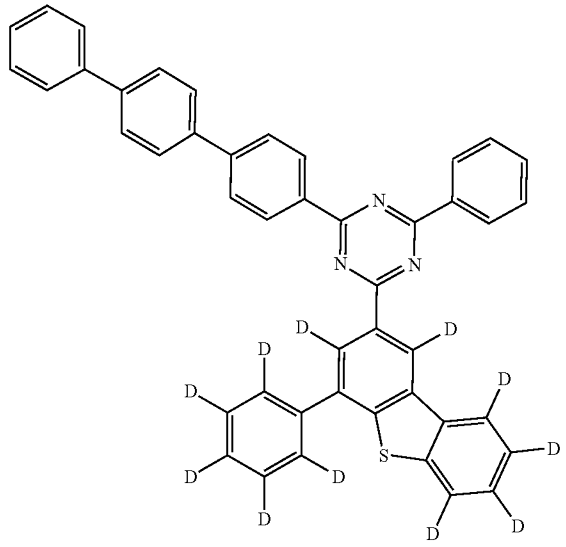
321
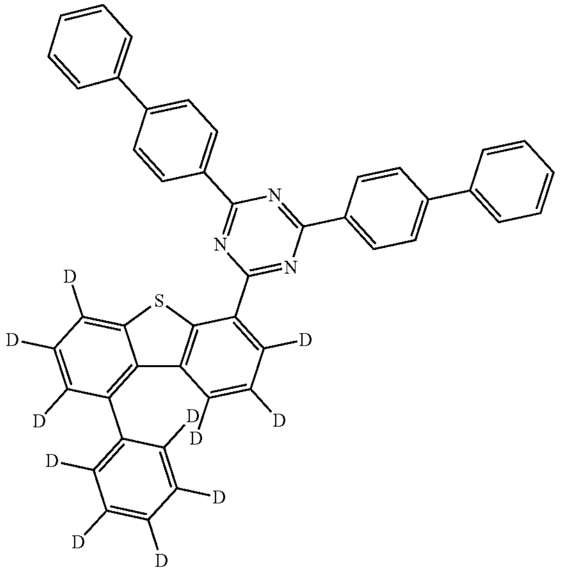
-continued
322
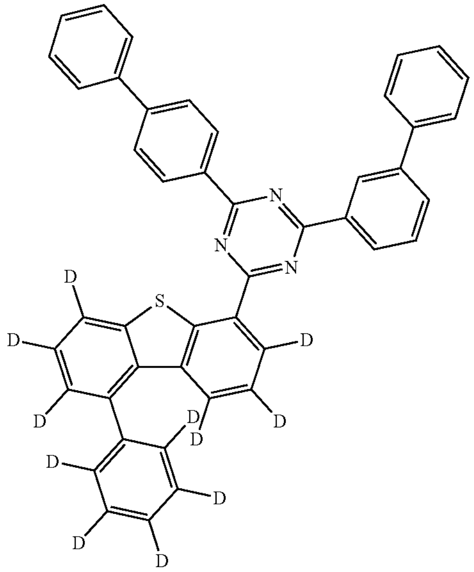
323
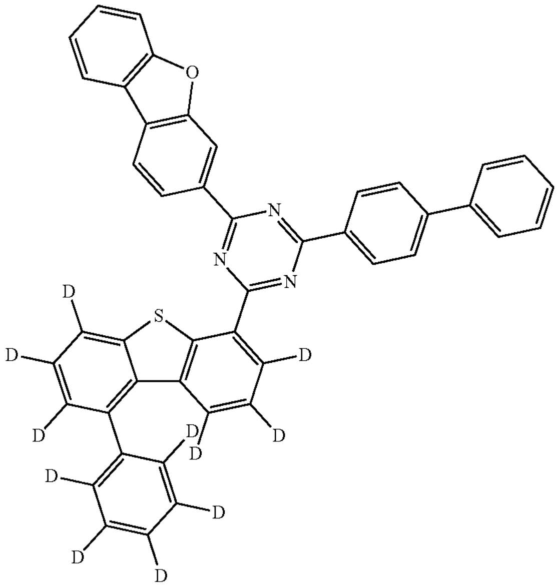

-continued
324
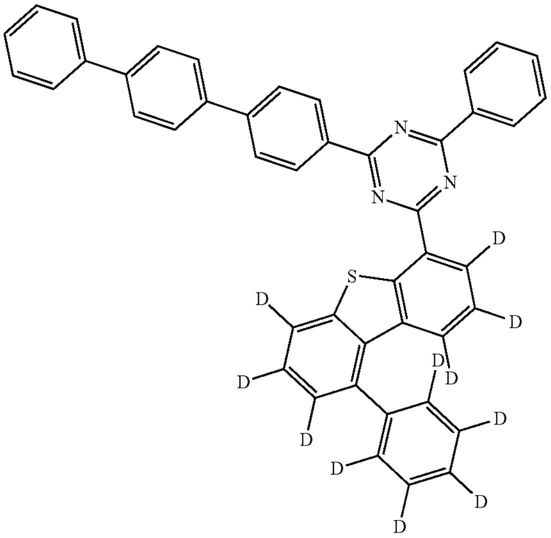
325
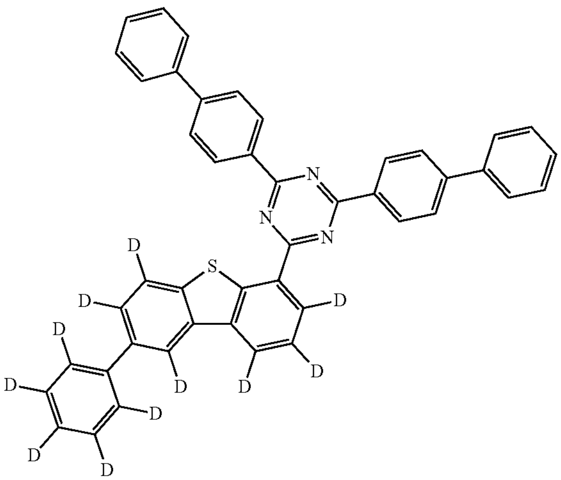
326
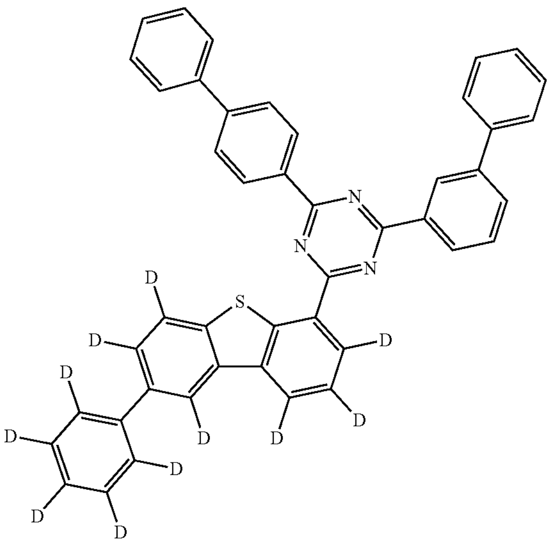
-continued
327
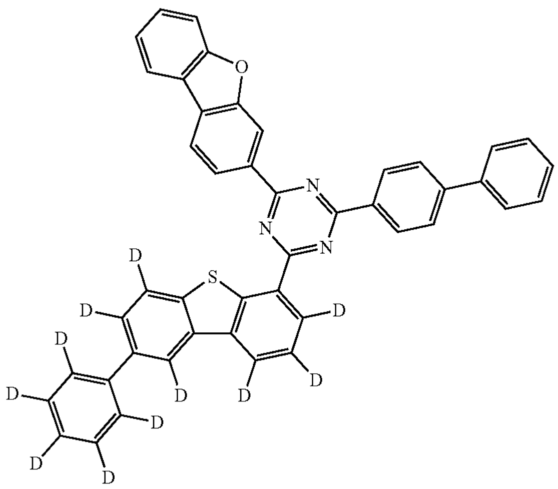
328
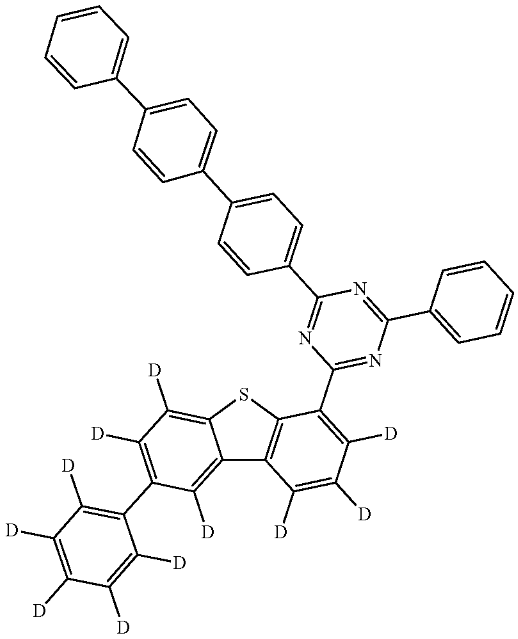
329
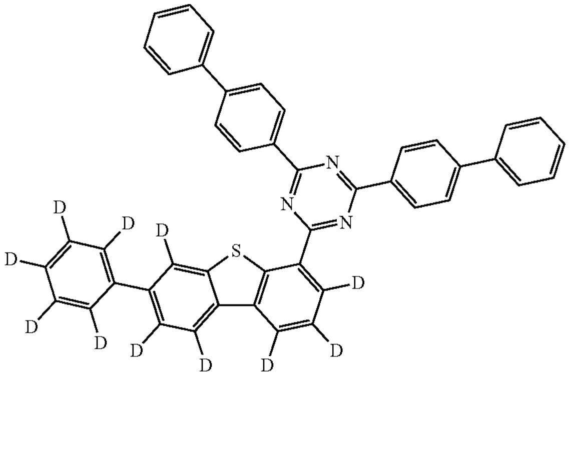

-continued
330
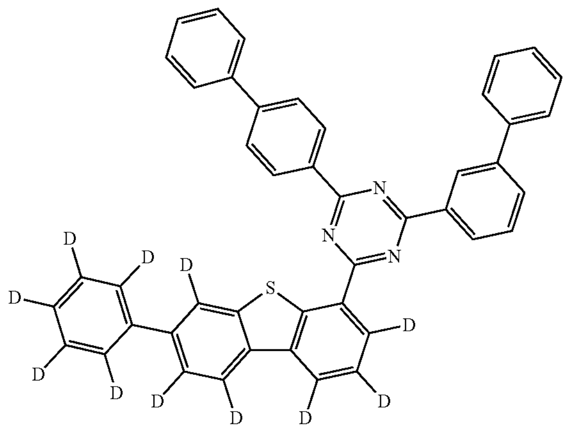
331
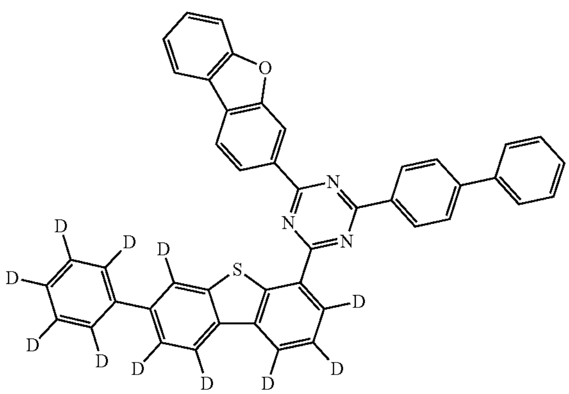
332
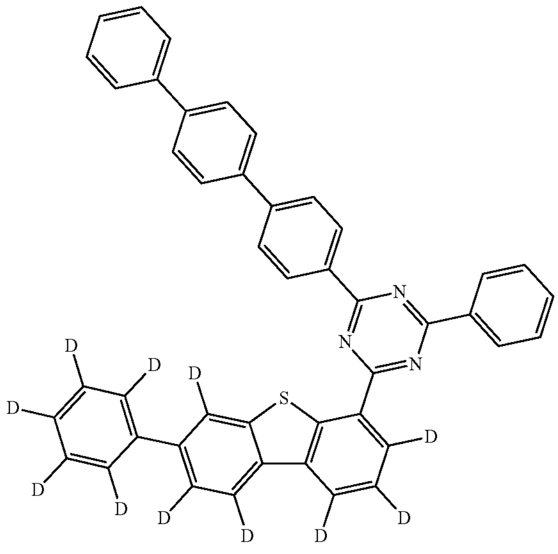
-continued
333
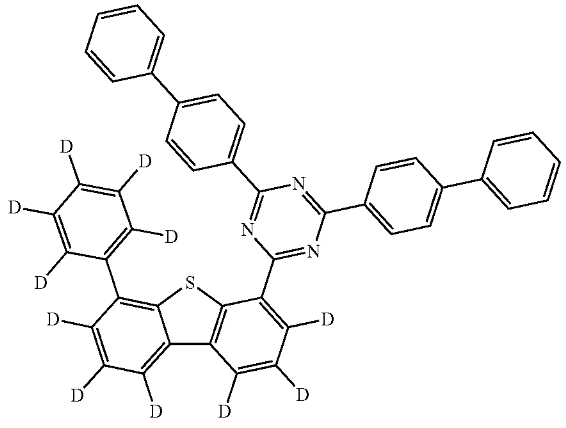
334
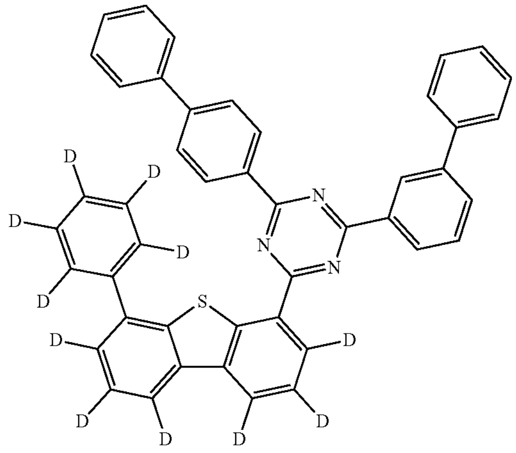
335
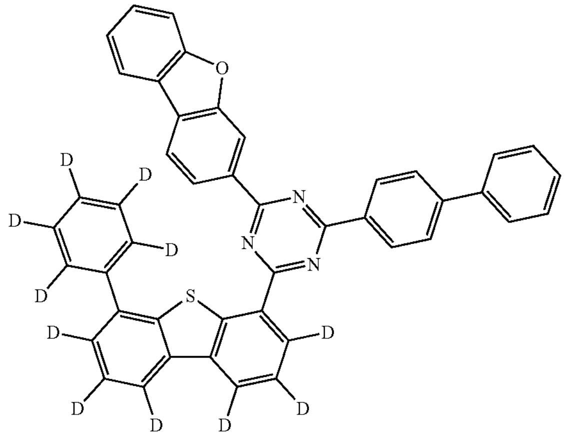

-continued
336
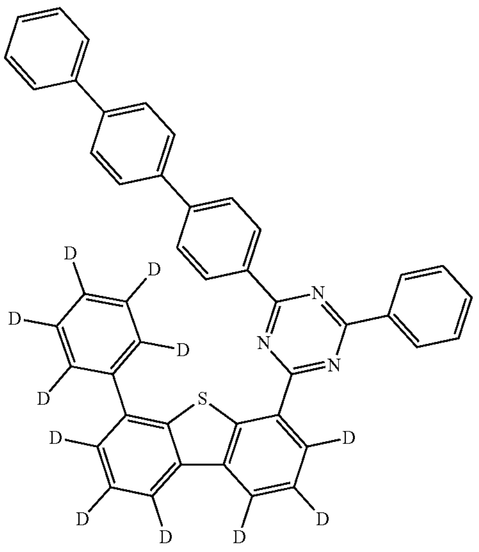
337
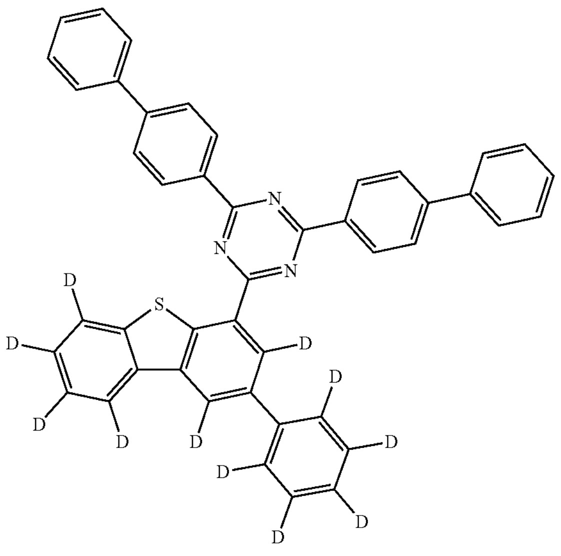
-continued
338
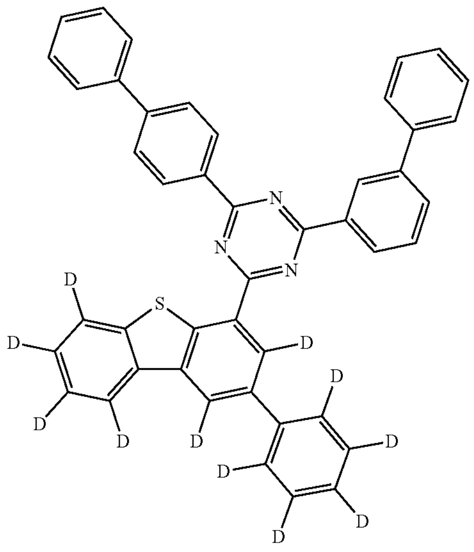
339
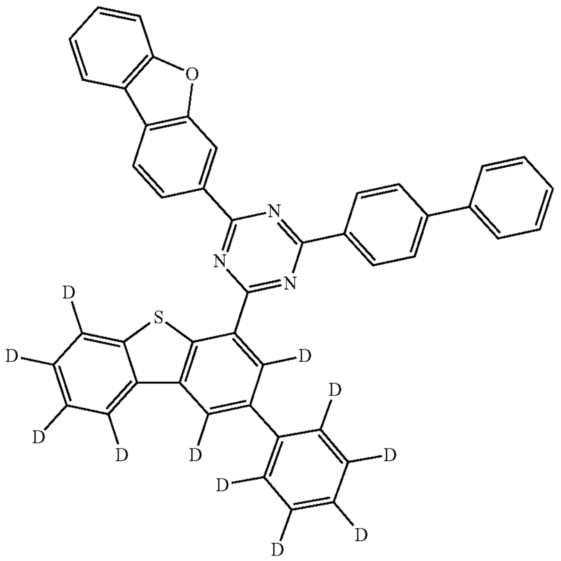

-continued
340
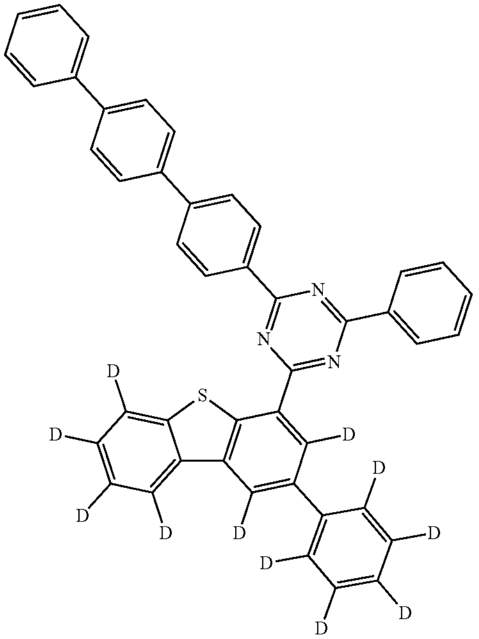
341
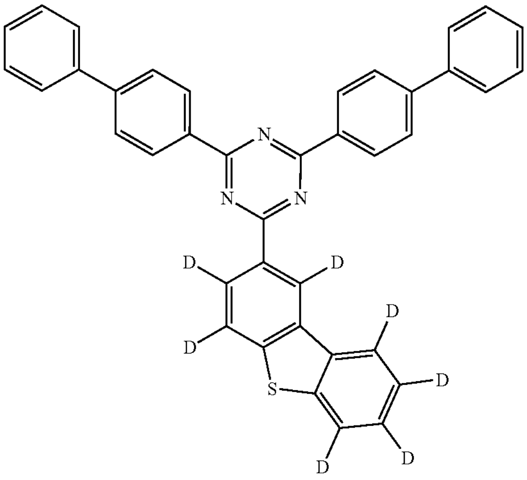
-continued
342
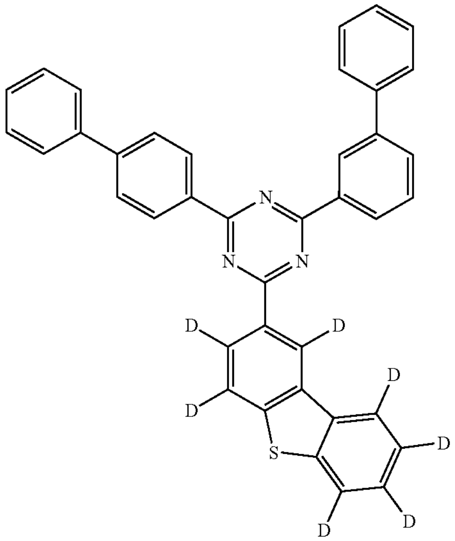
343
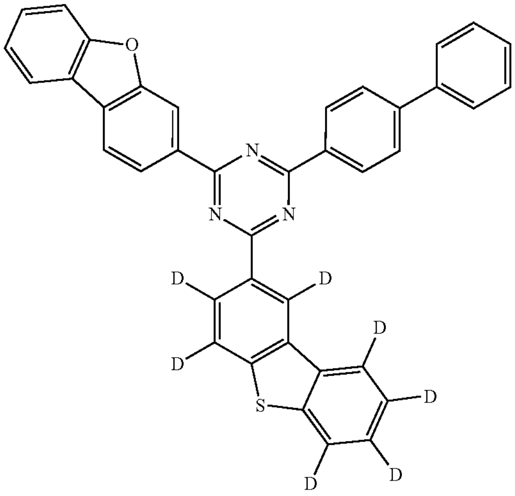
344
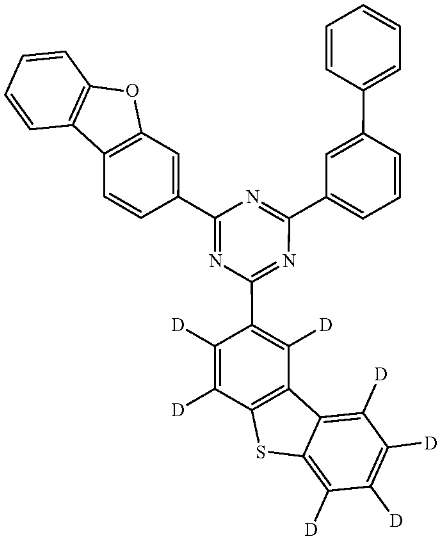

-continued
345
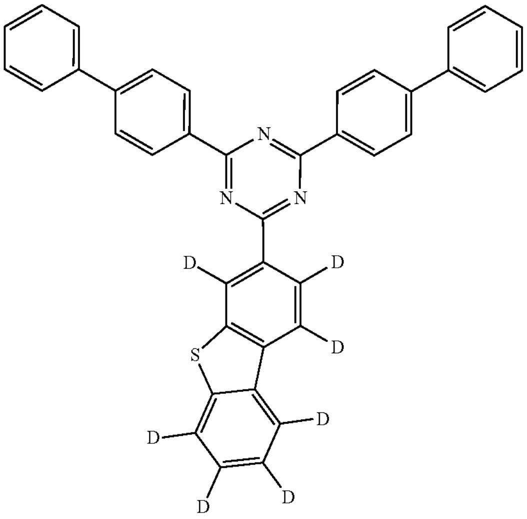
346
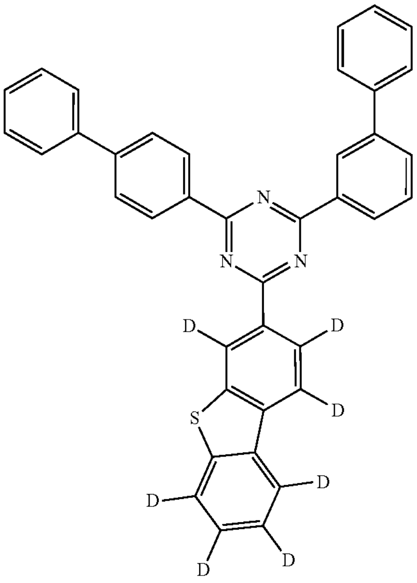
-continued
347
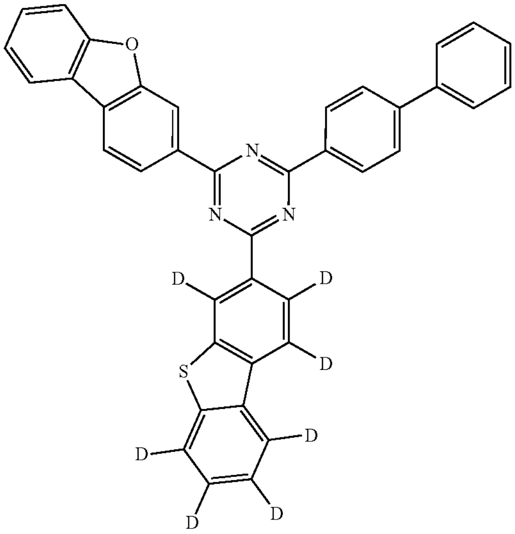
348
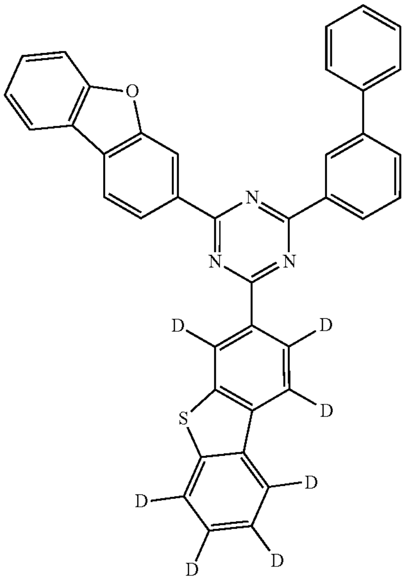
349
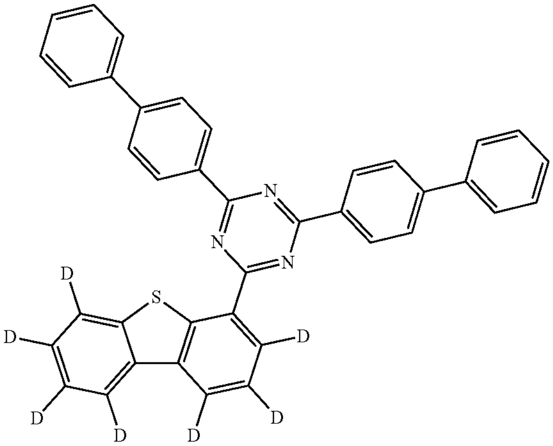

-continued
350
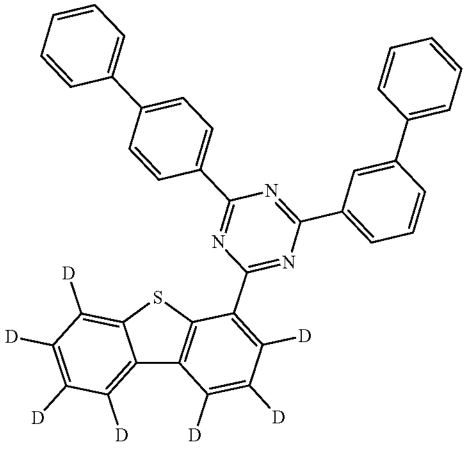
351
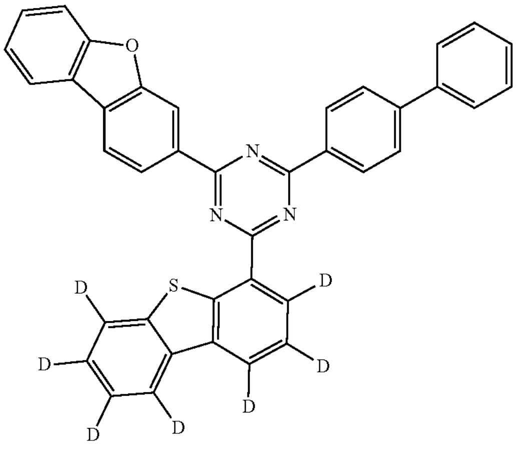
352
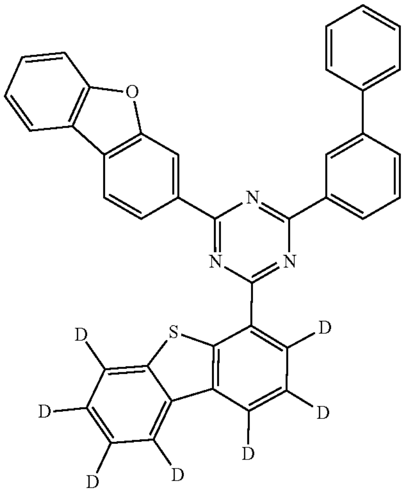
-continued
353
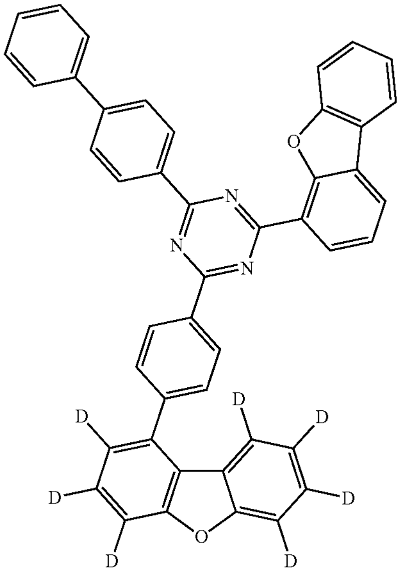
354
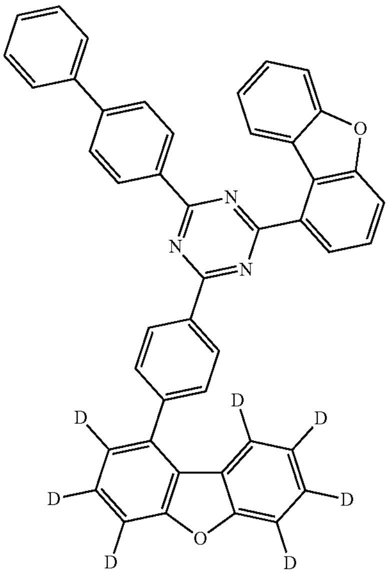

-continued
355
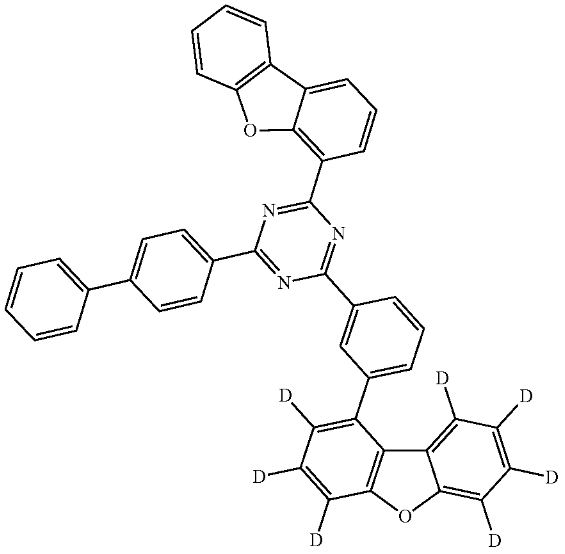
356
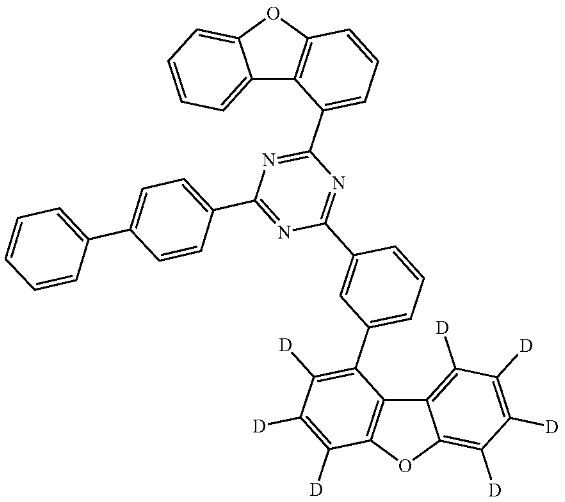
-continued
357
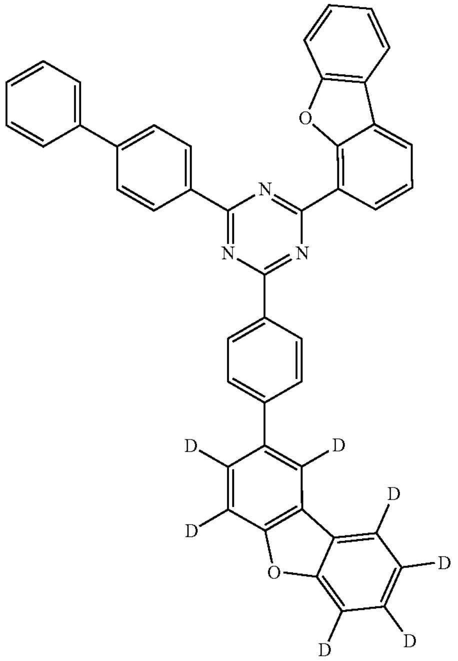
358
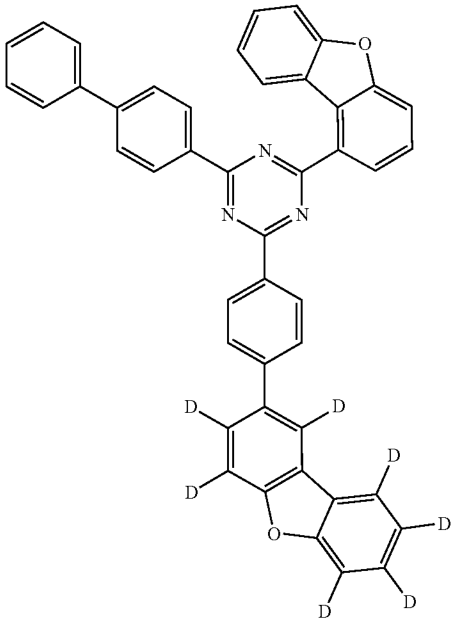

-continued
359
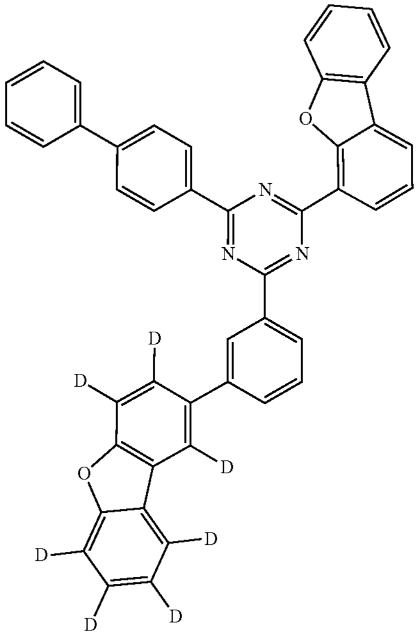
360
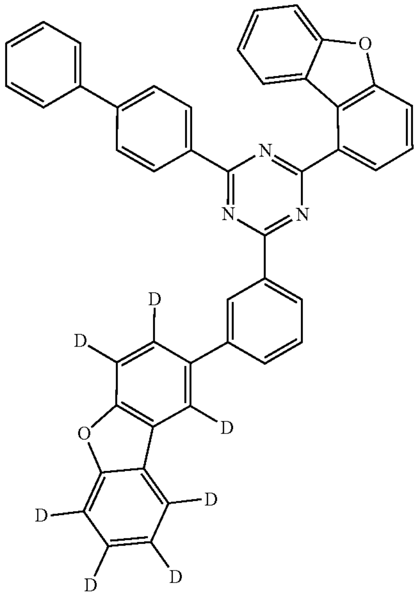
-continued
361
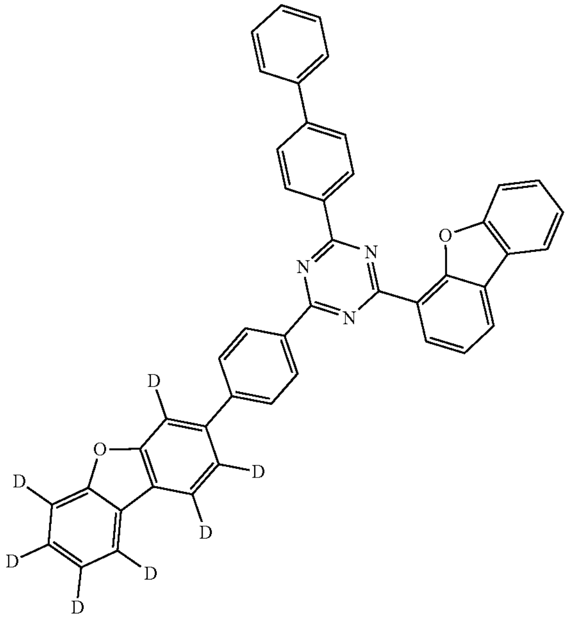
362
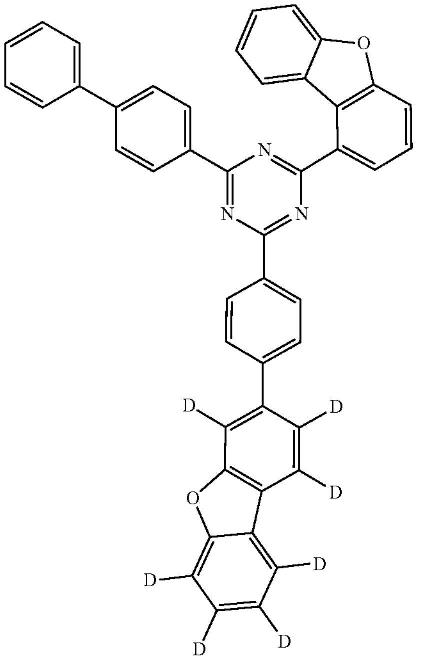

-continued
363
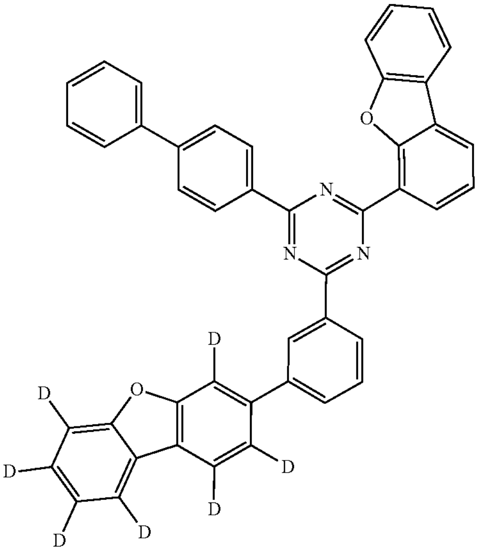
364
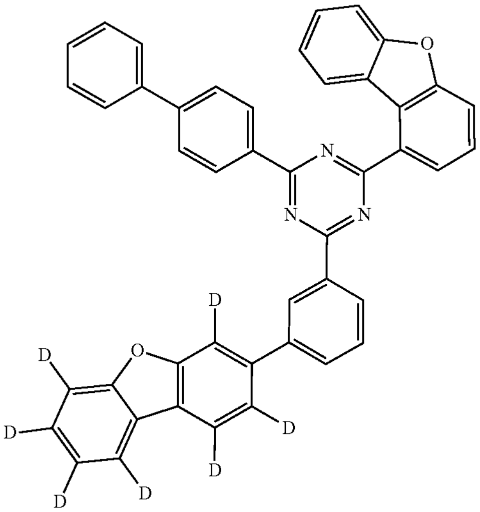
365
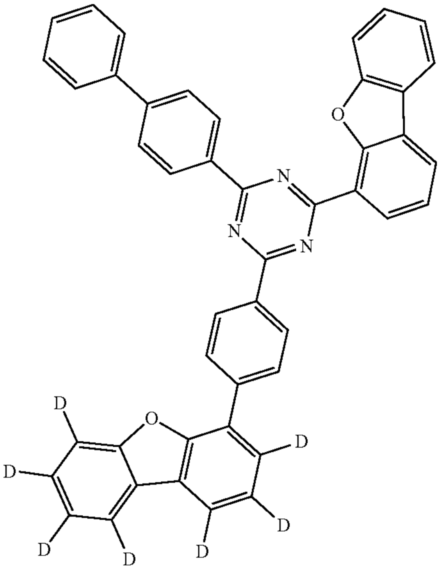
-continued
366
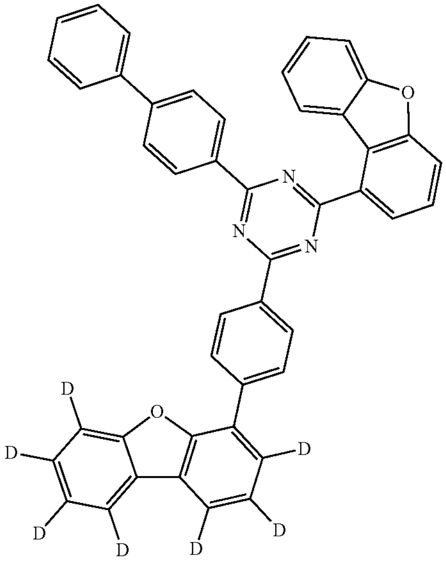
367
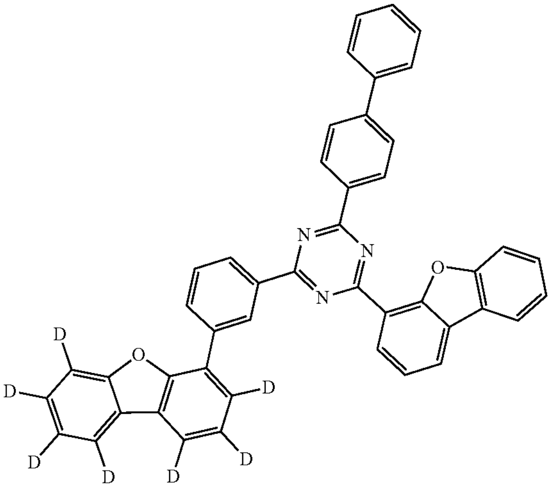
368
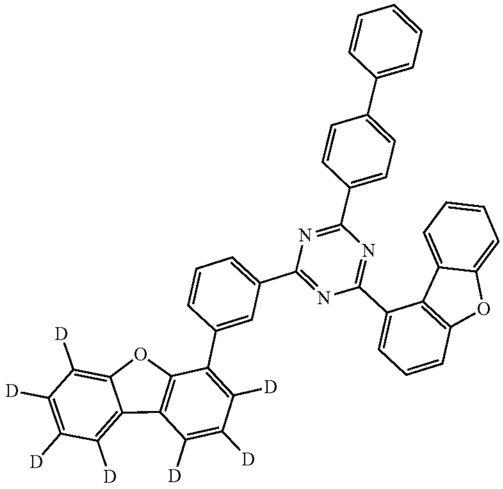

-continued
369
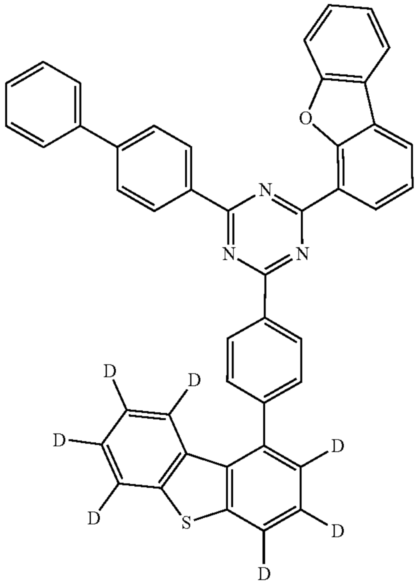
370
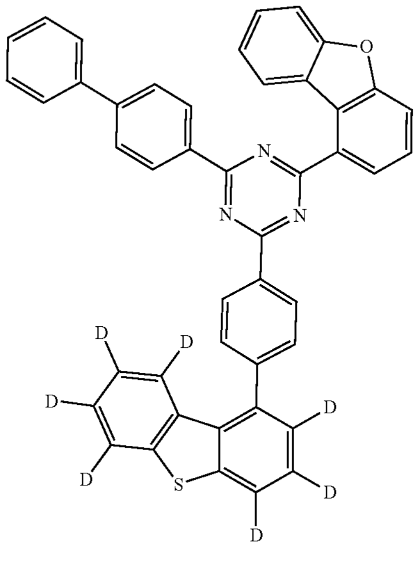
-continued
371
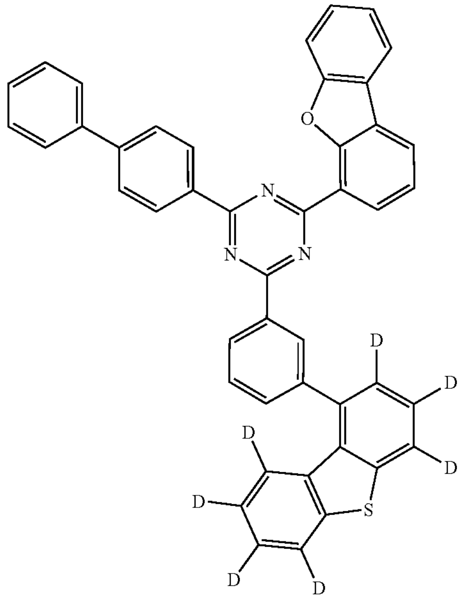
372
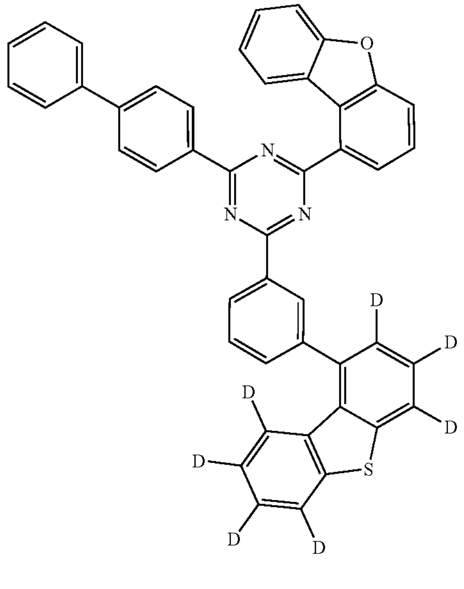

-continued
373
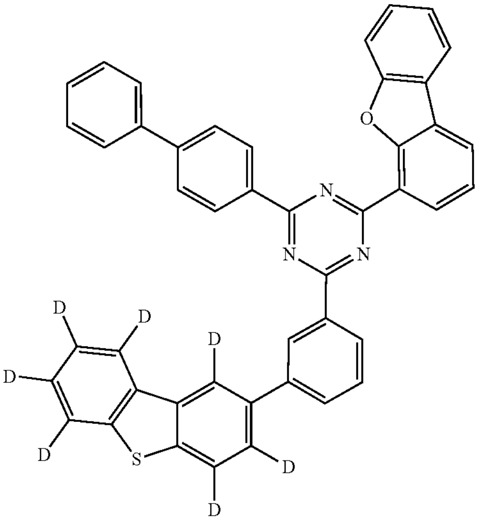
374
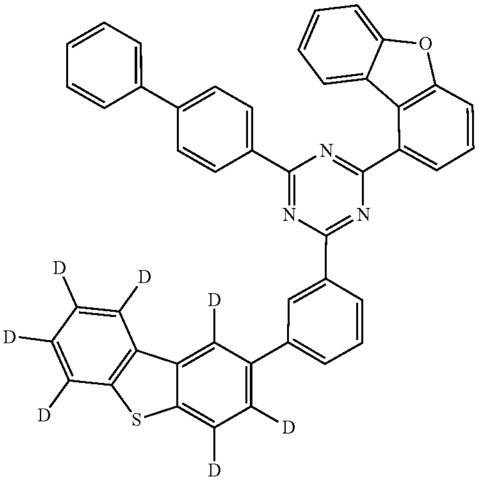
375
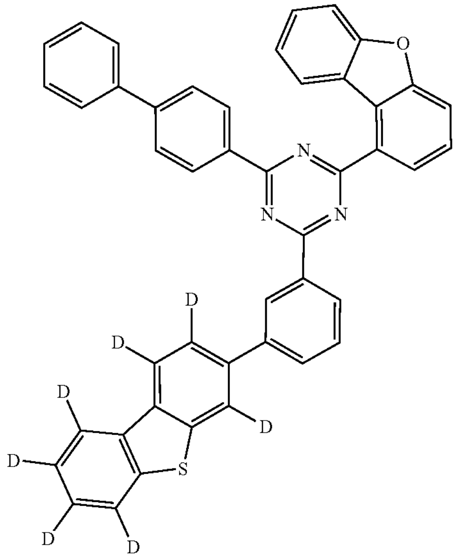
-continued
376
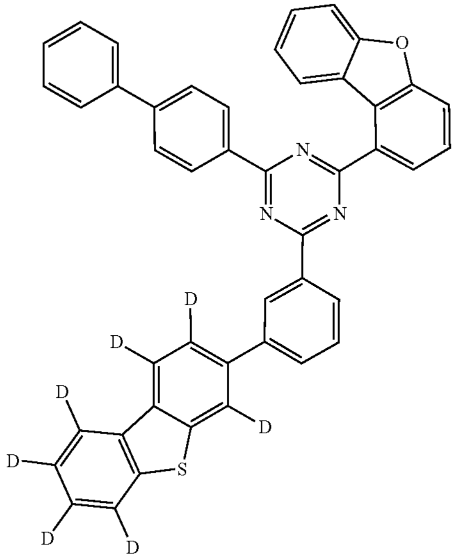
377
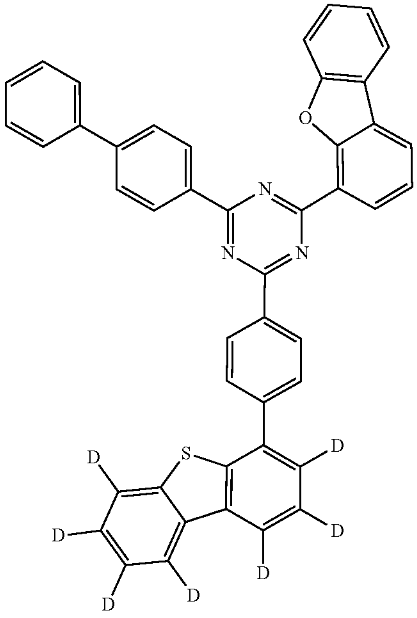

-continued
378
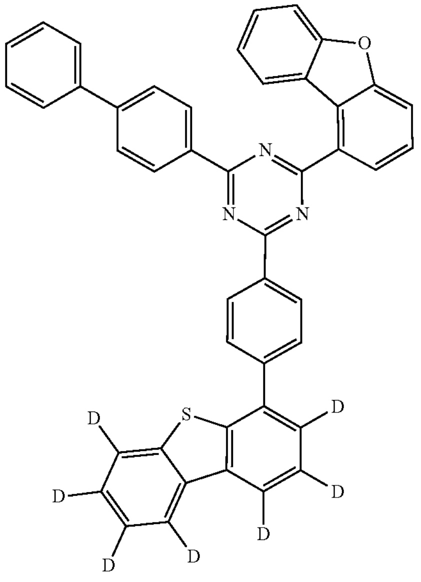
379
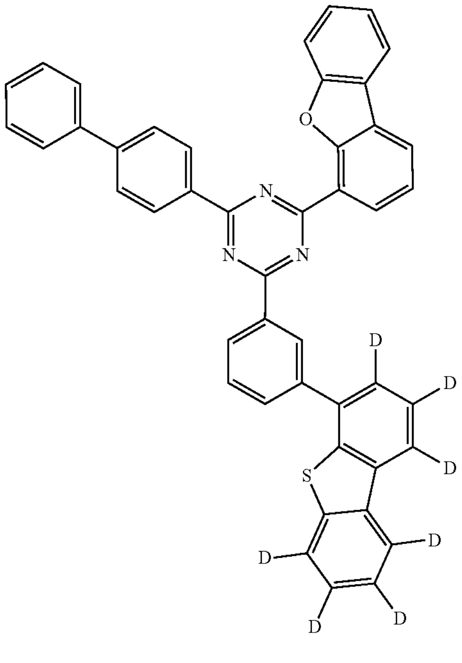
-continued
380
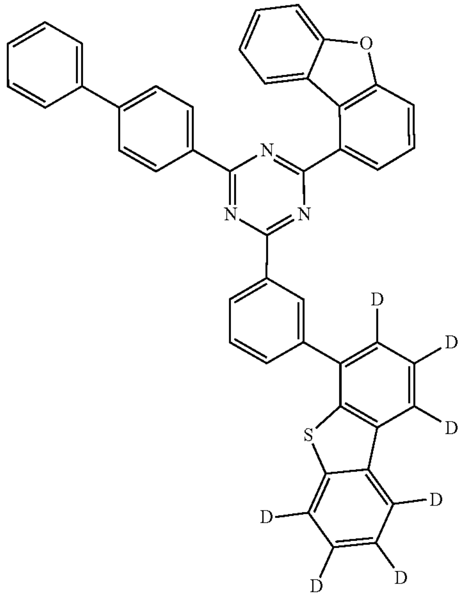
381
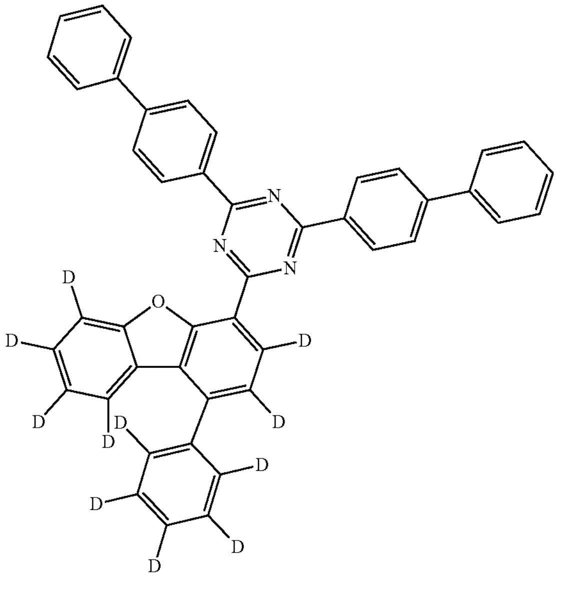

-continued
382
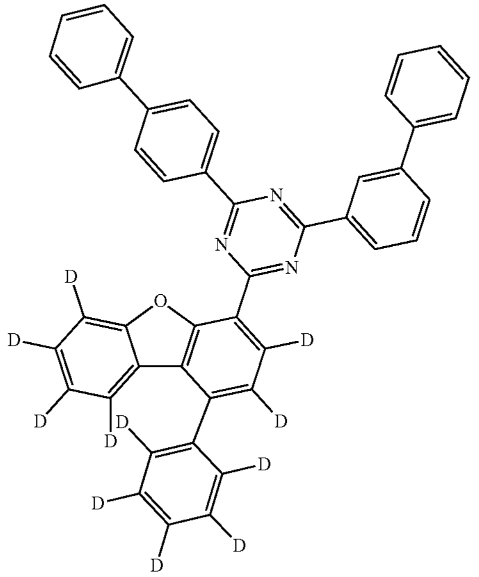
383
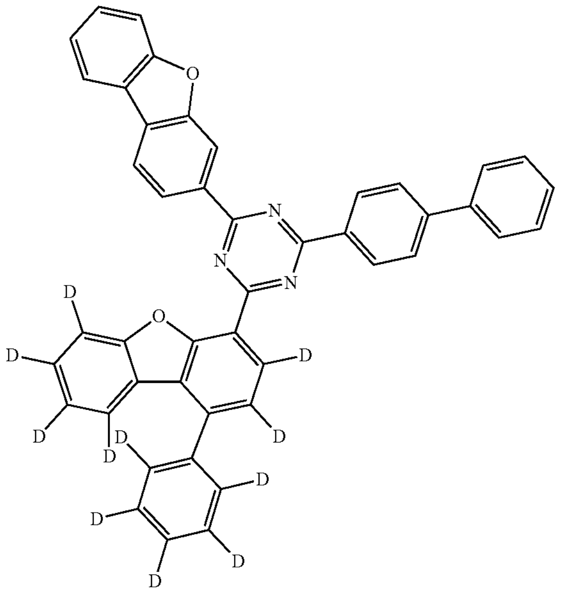
384
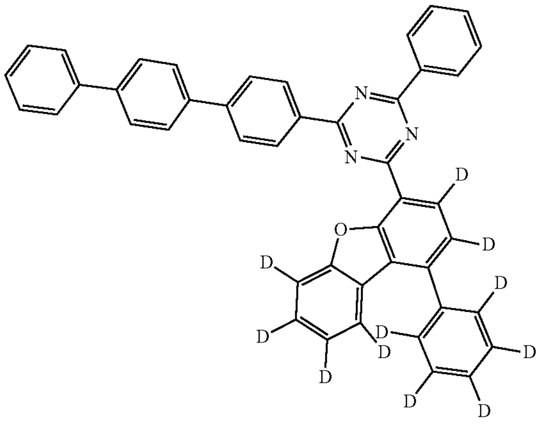
-continued
385
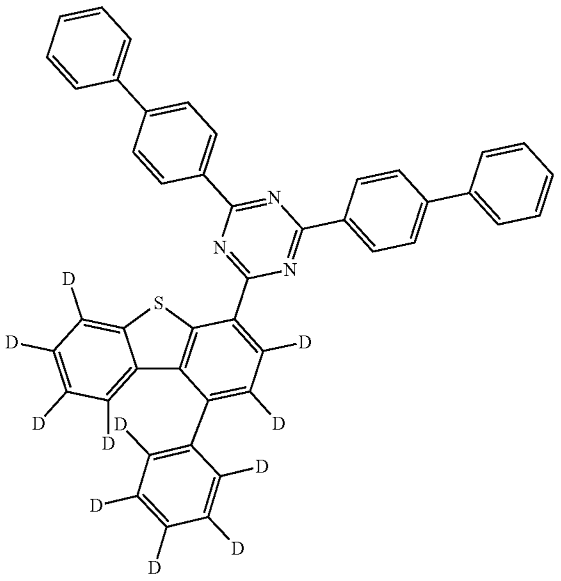
386
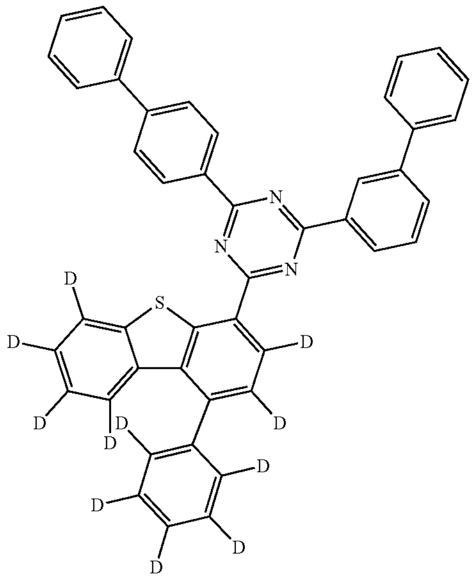

-continued
387
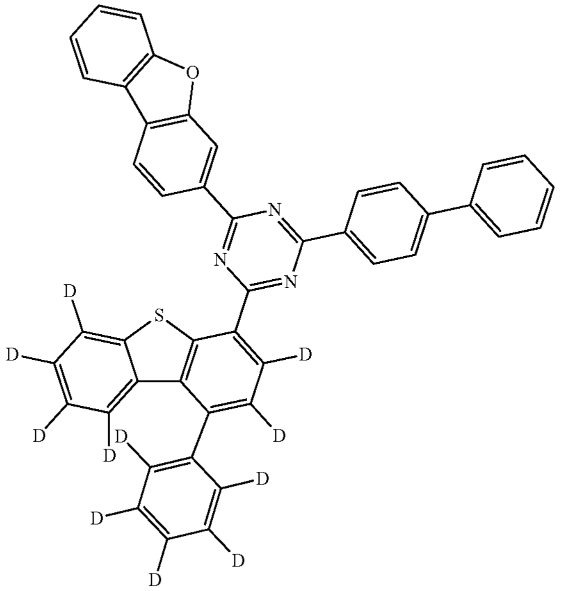
388
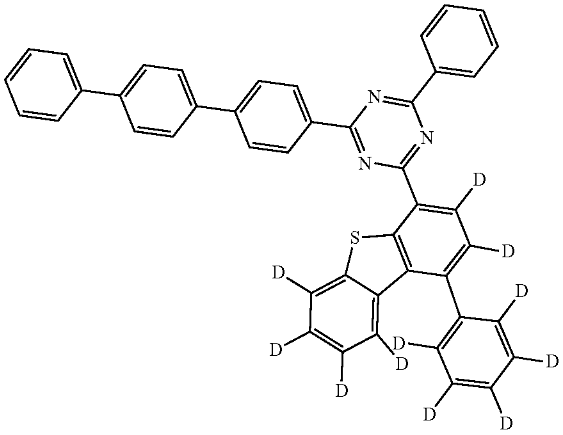
389
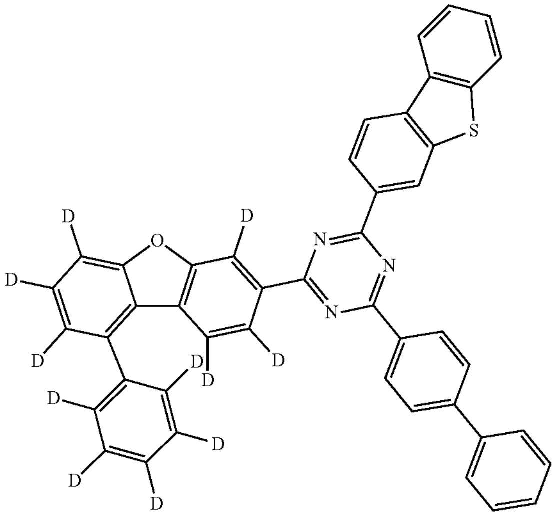
-continued
390
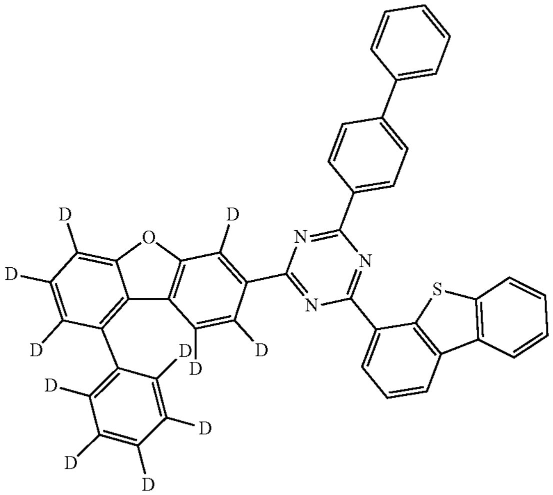
391
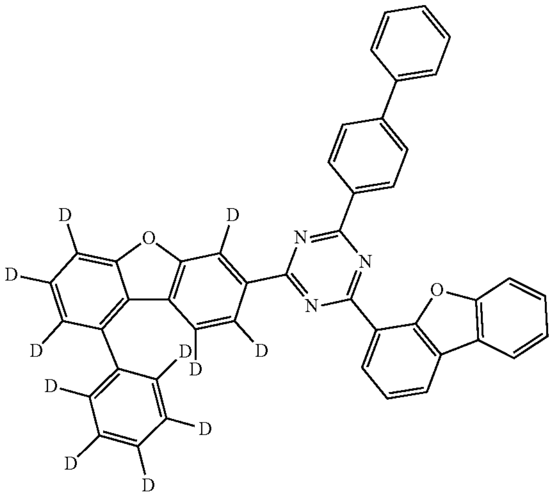
392
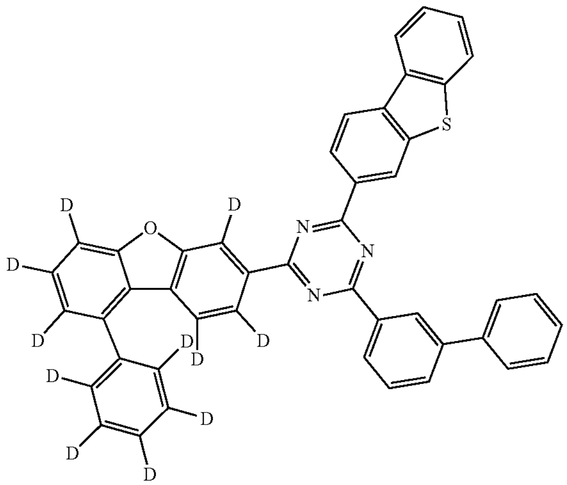

-continued
393
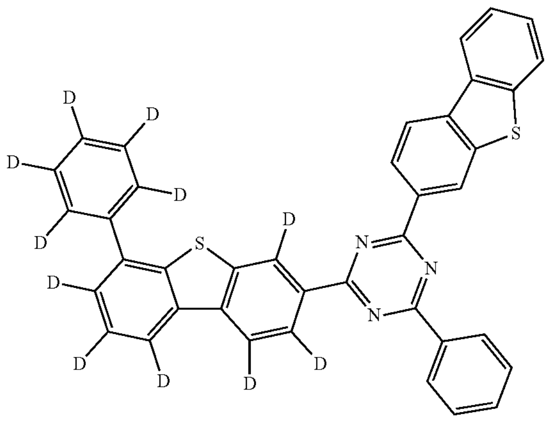
394
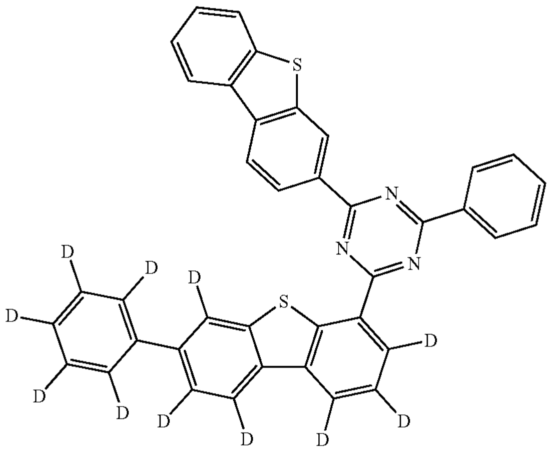
395
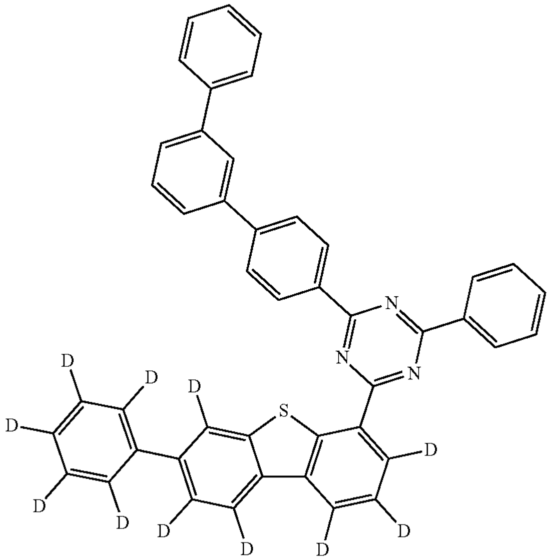
-continued
396
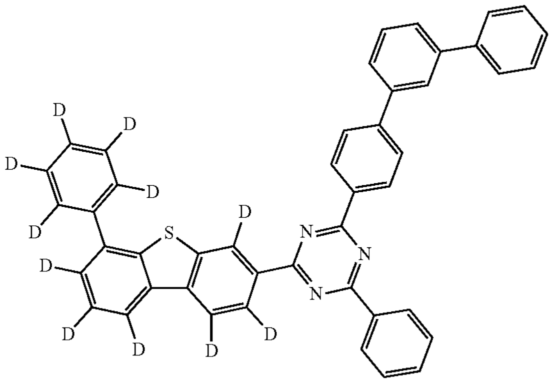
397
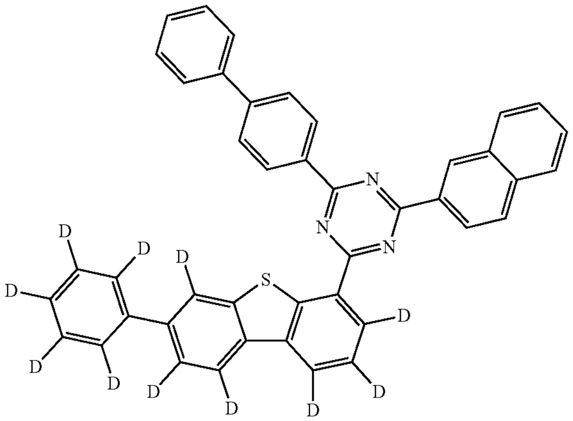
398
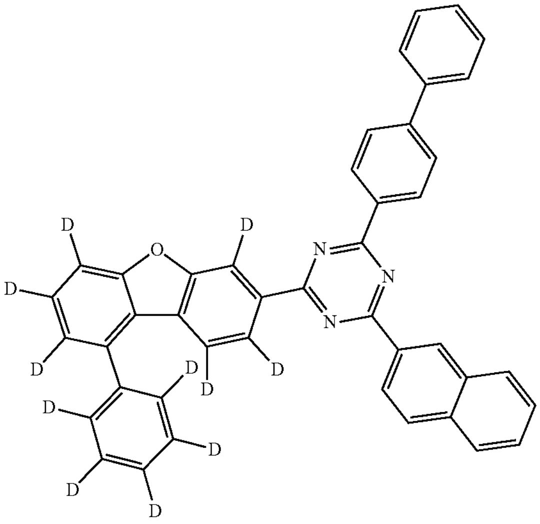

-continued
399
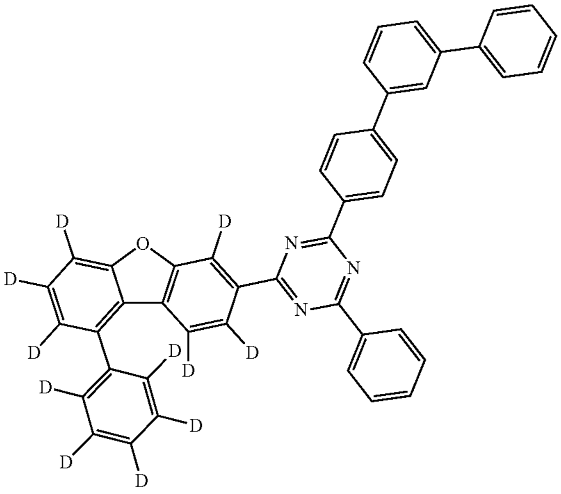
400
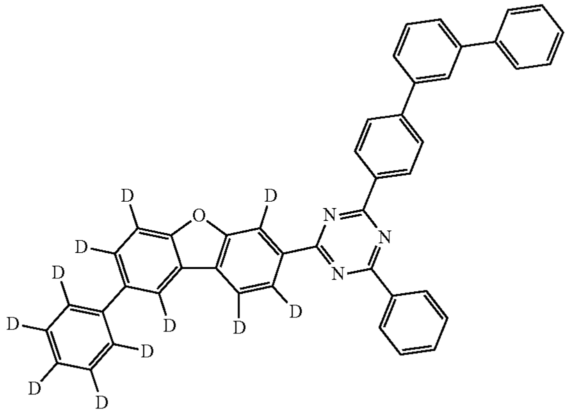
401
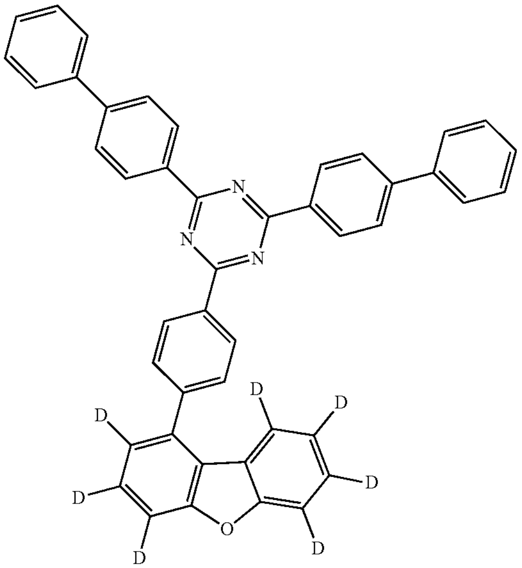
-continued
402
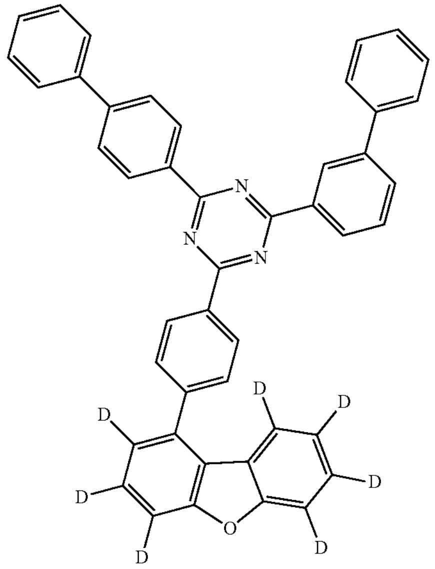
403
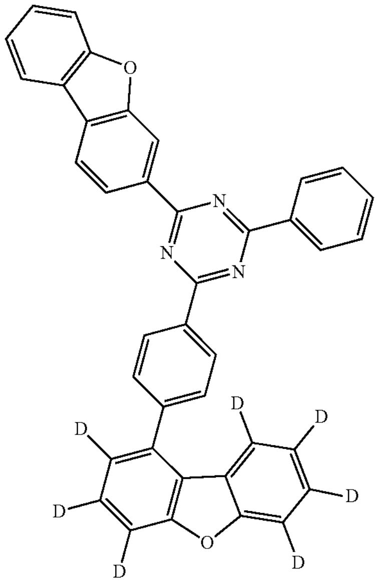
404
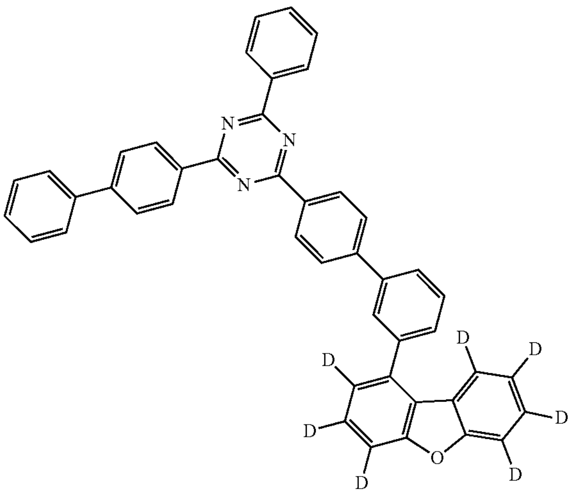

-continued
405
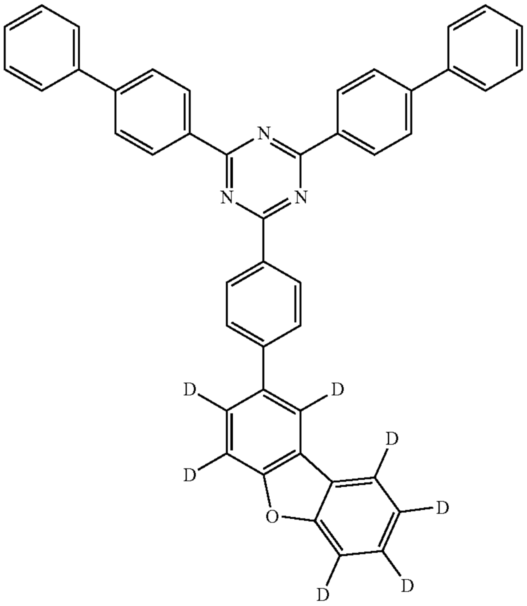
406
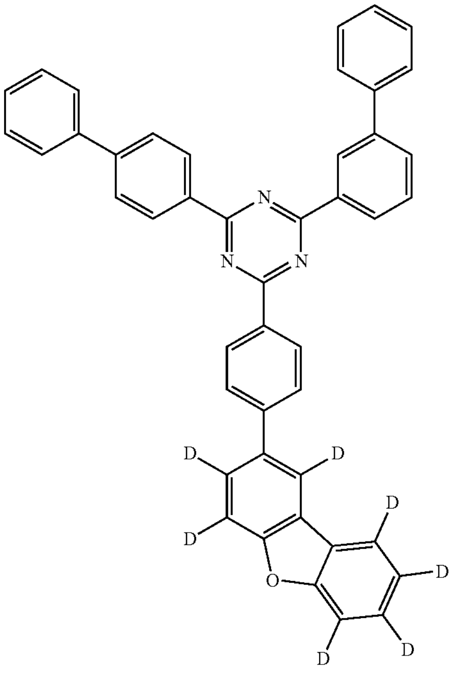
-continued
407
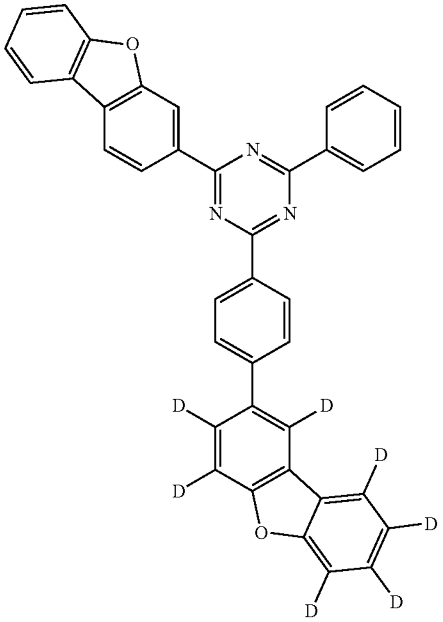
408
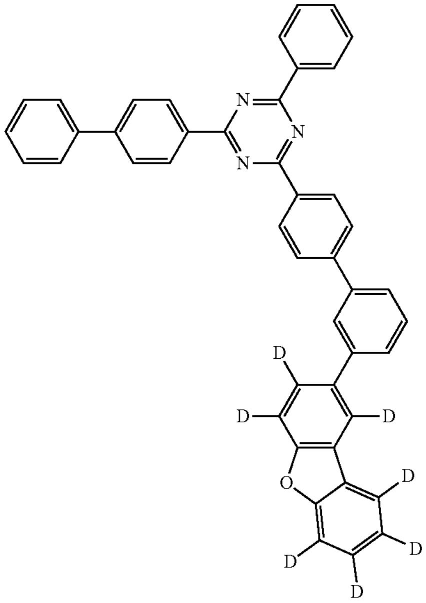

409
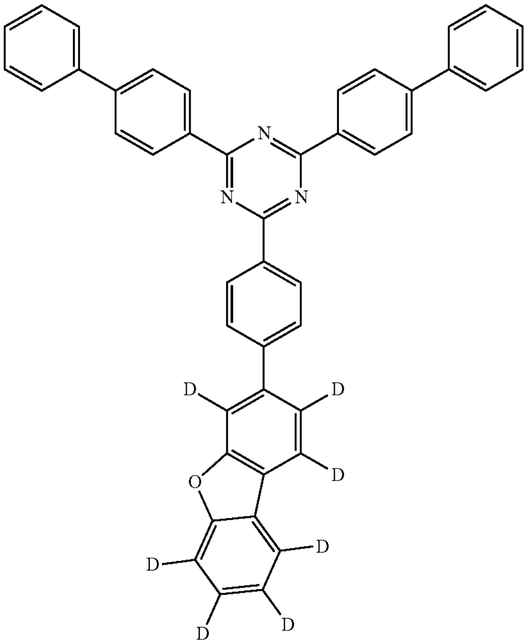
410
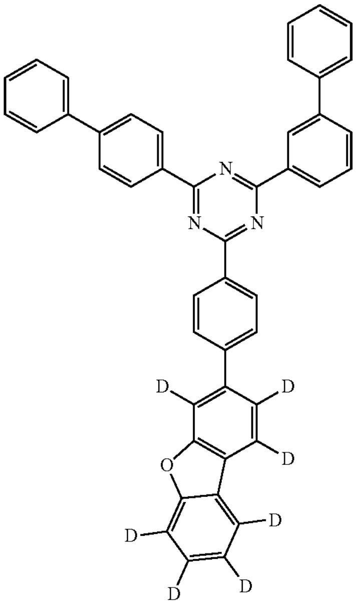
411
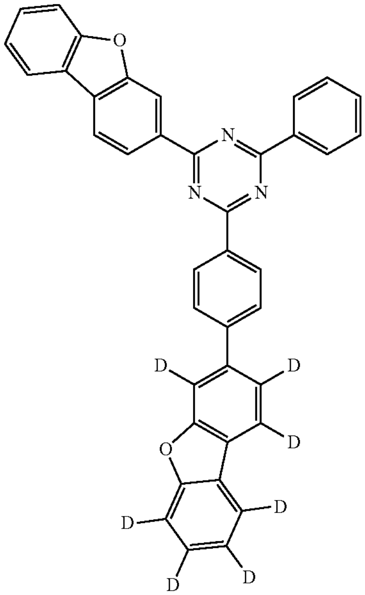
412
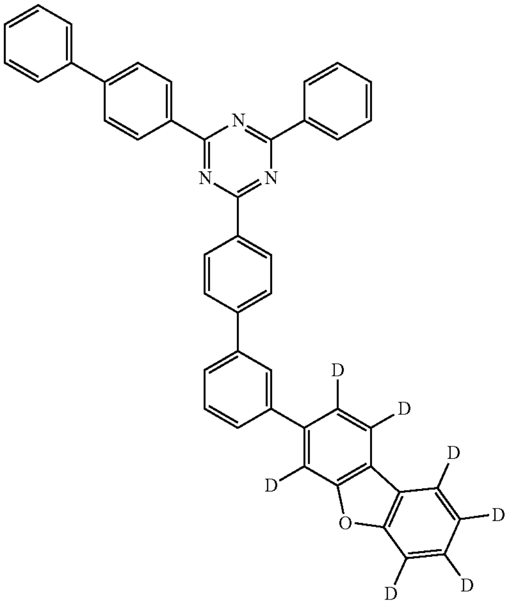

-continued
413
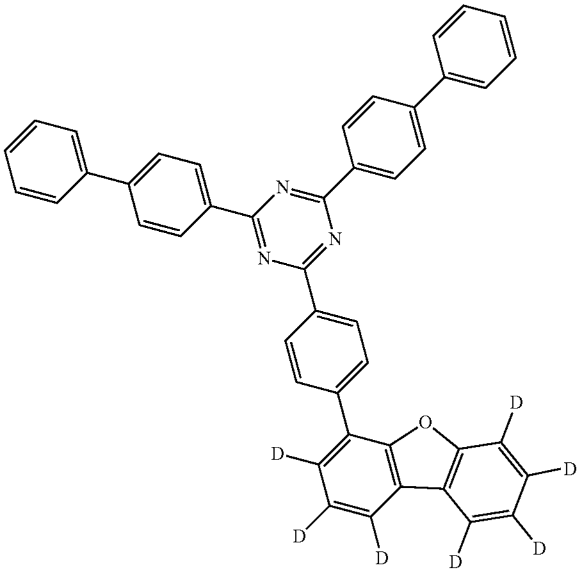
414
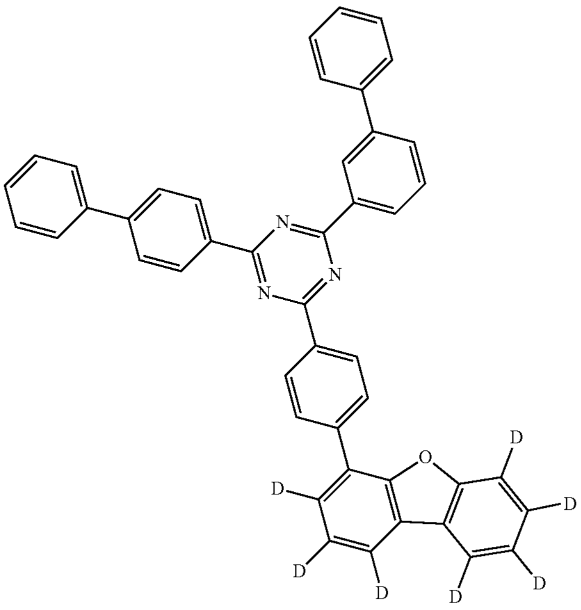
-continued
415
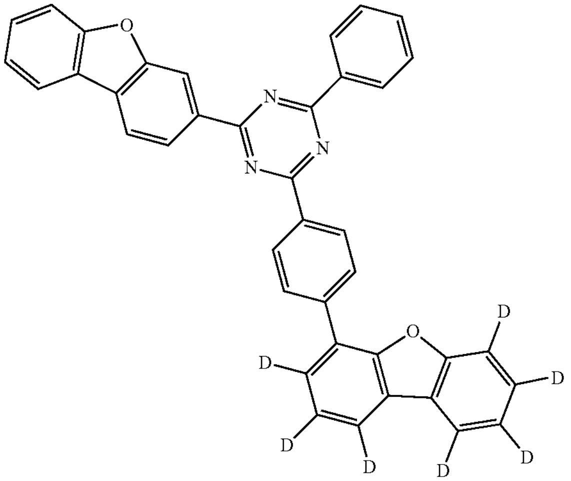
416
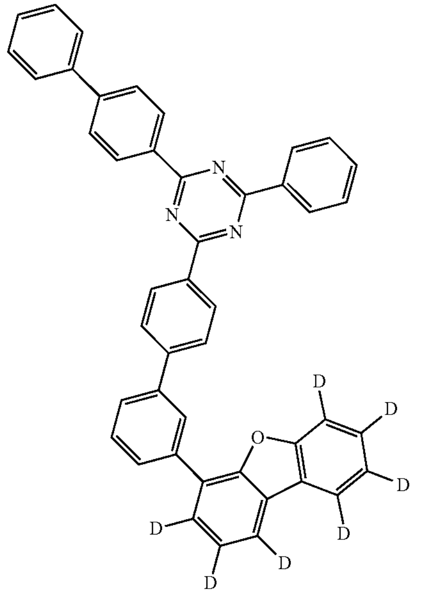
417
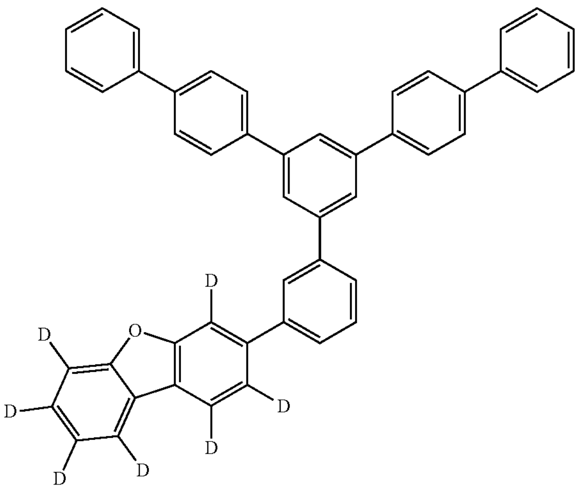

-continued
418
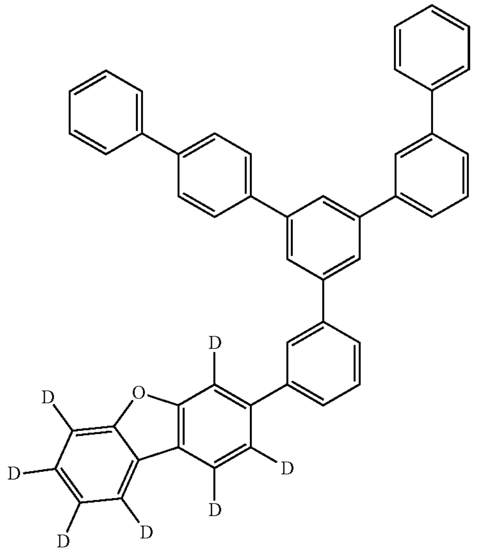
419
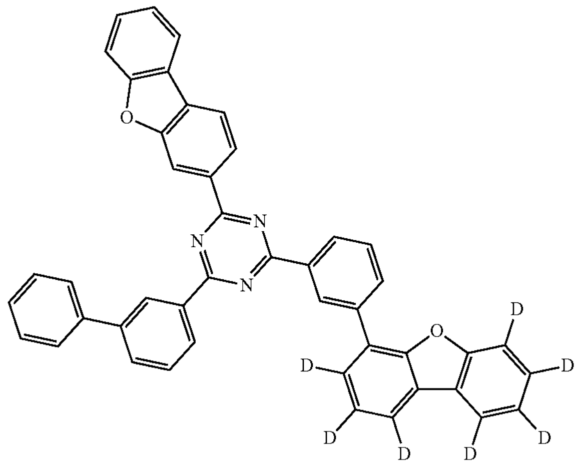
420
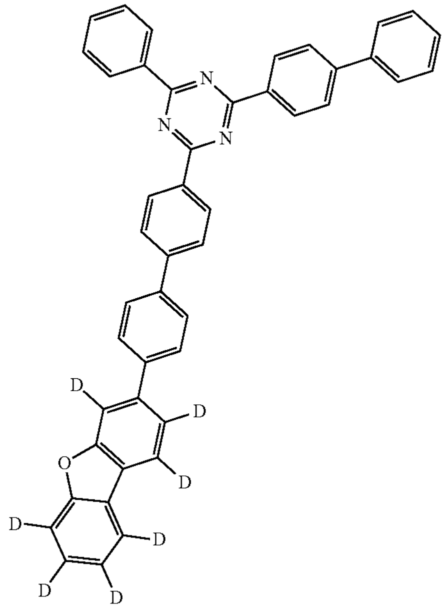
-continued
421
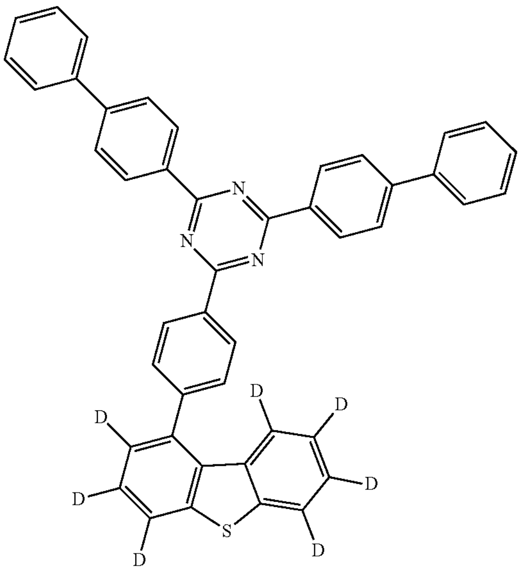
422
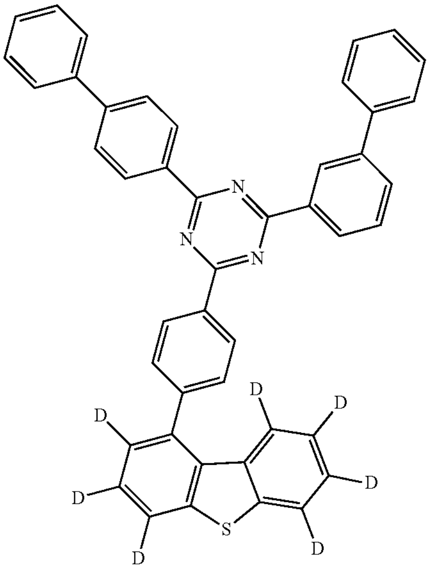

-continued
423
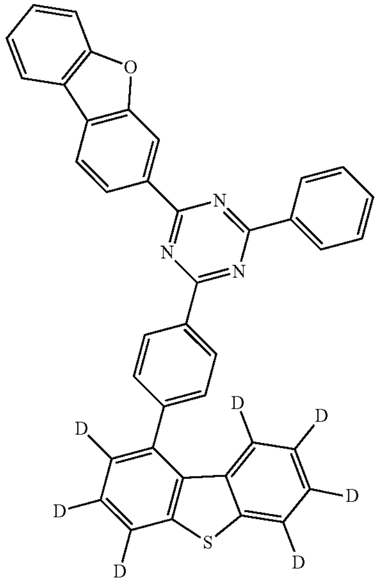
424
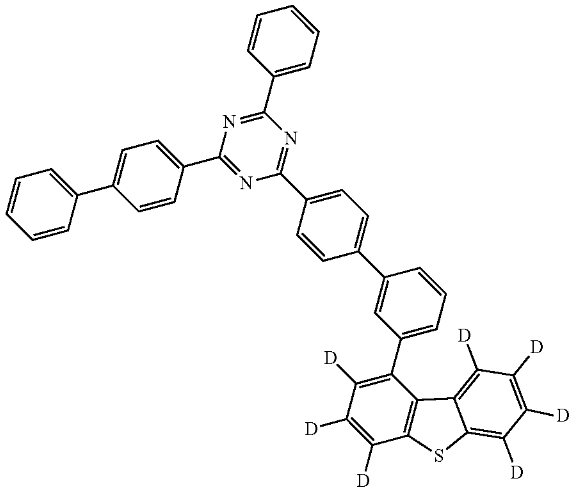
-continued
425
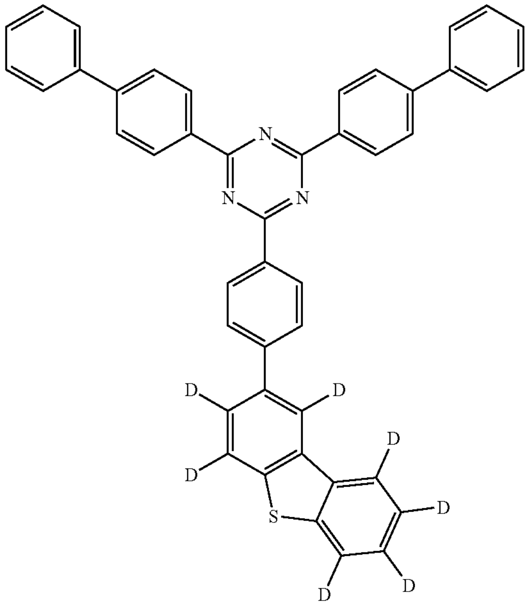
426
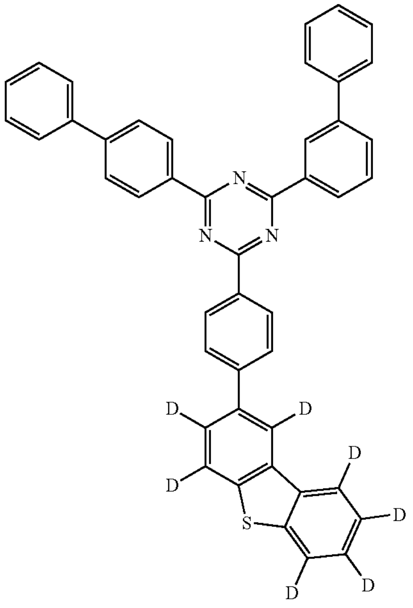

-continued
427
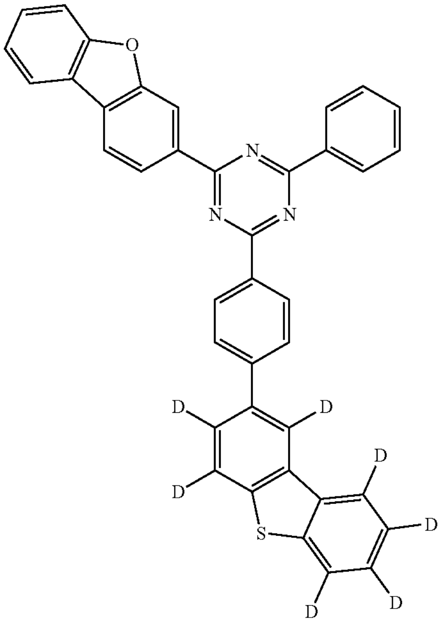
428
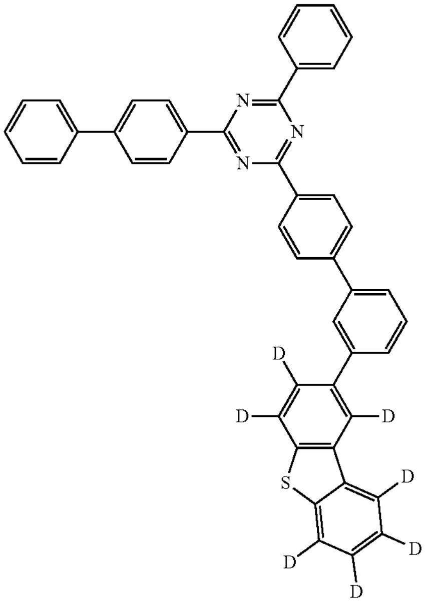
-continued
429
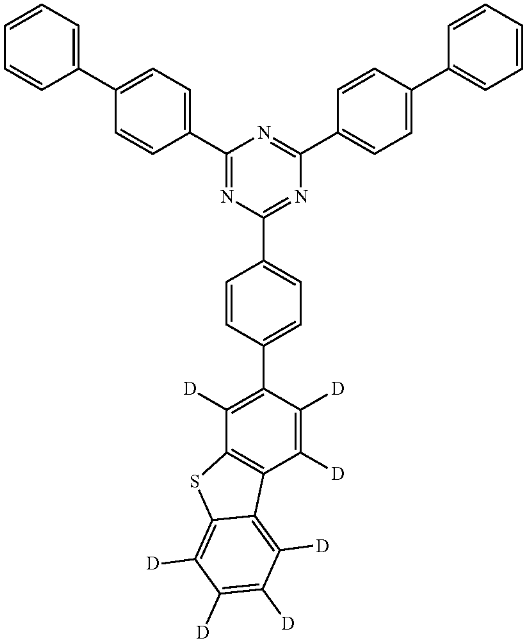
430
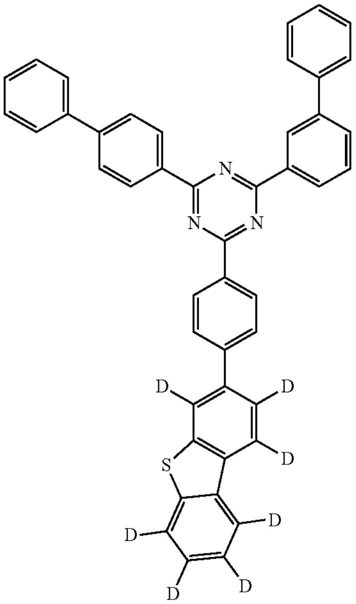

-continued
431
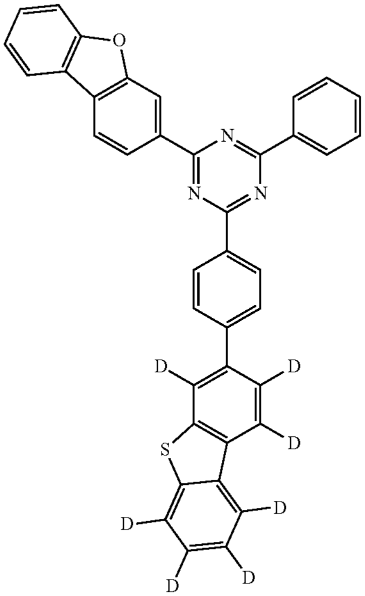
432
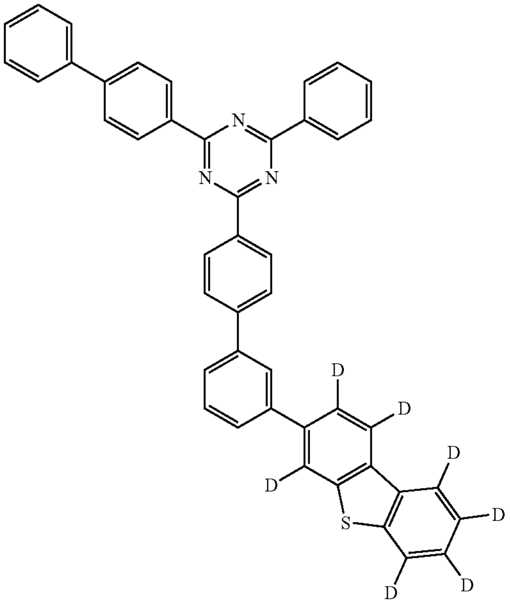
-continued
433
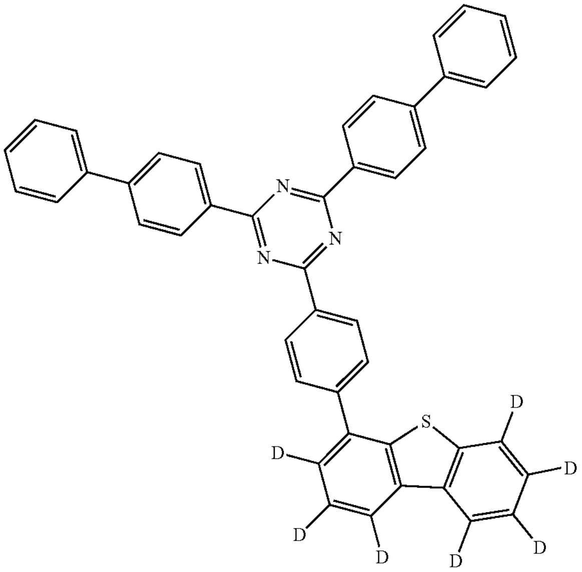
434
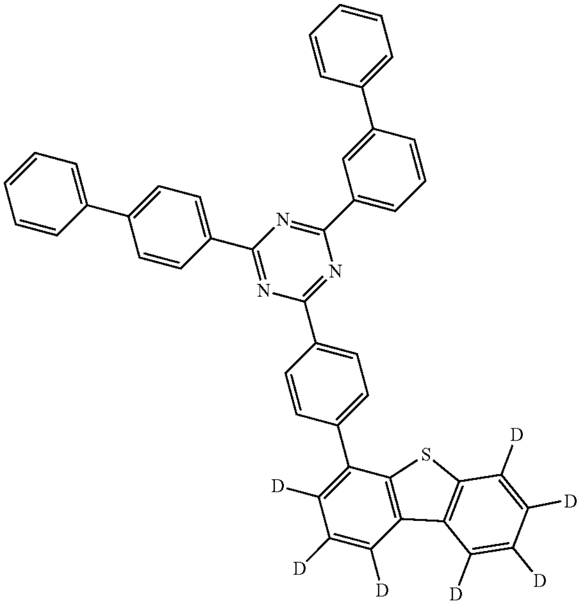

-continued
435
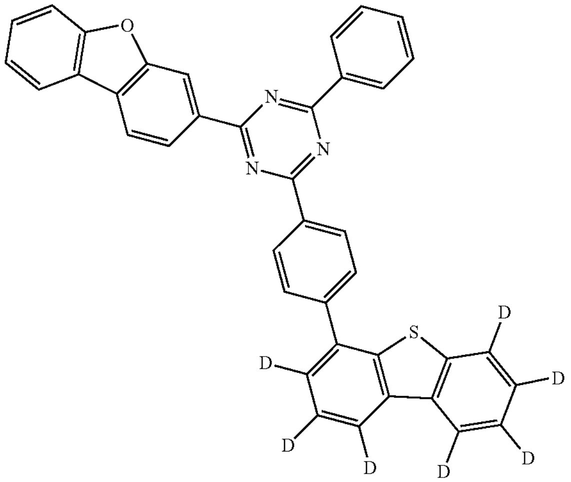
436
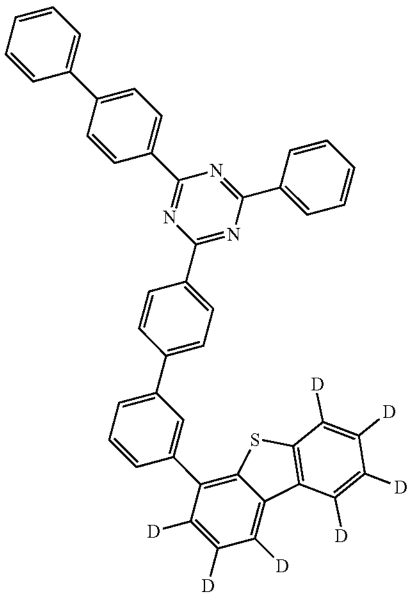
437
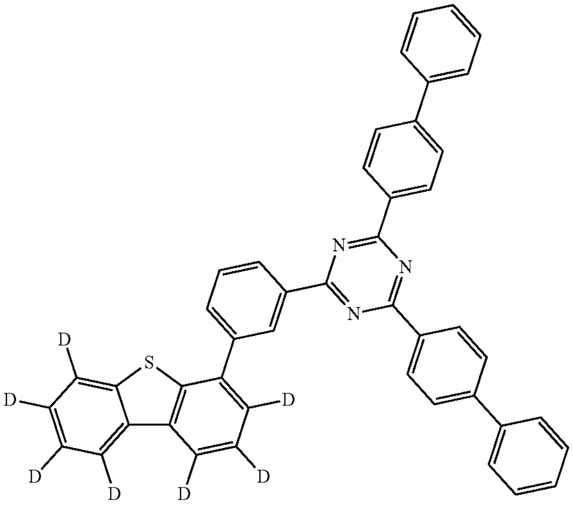
-continued
438
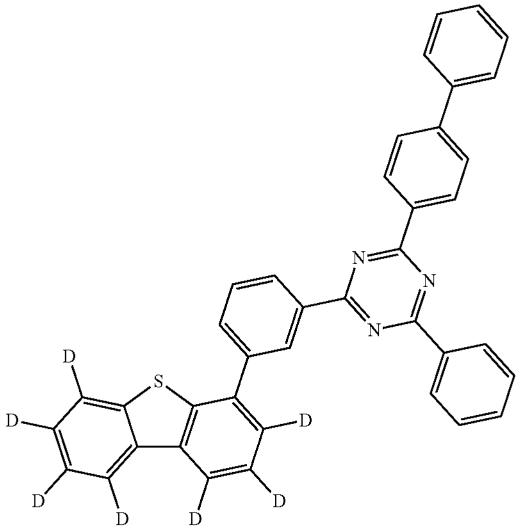
439
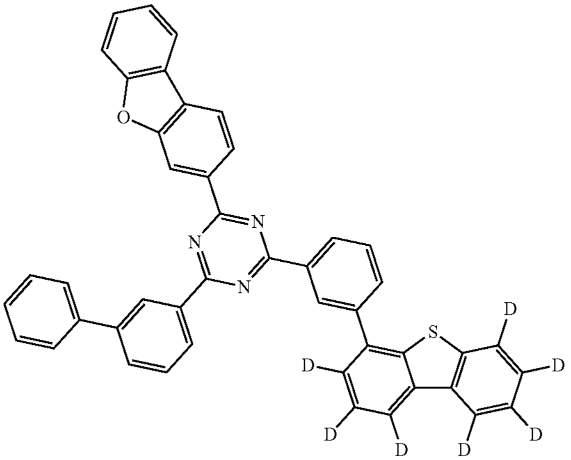
440
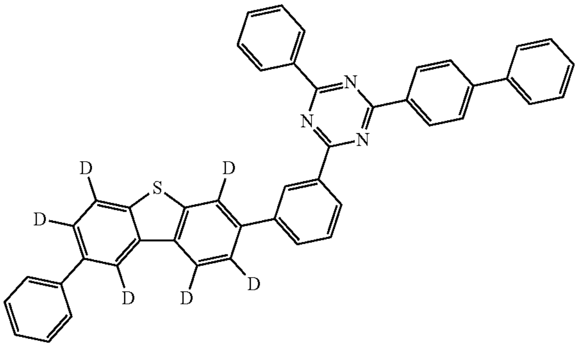

-continued
441
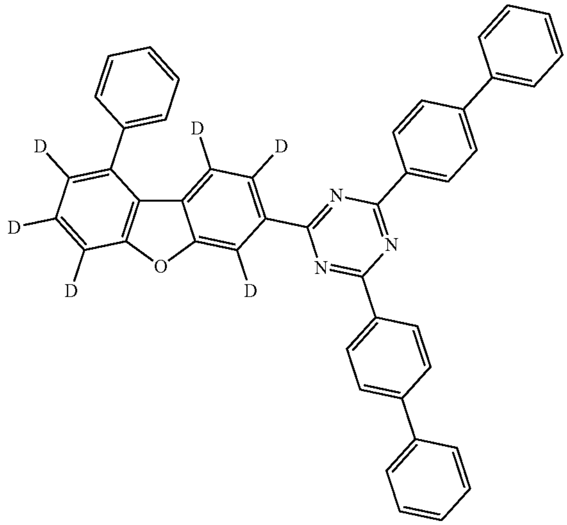
442
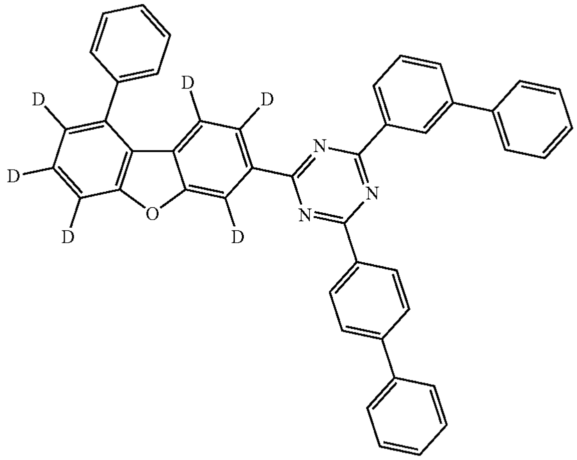
443
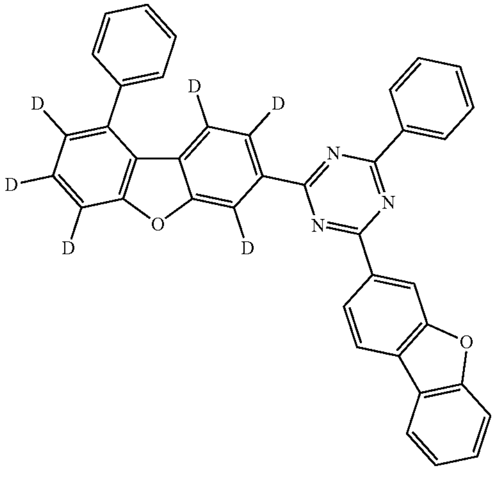
-continued
444
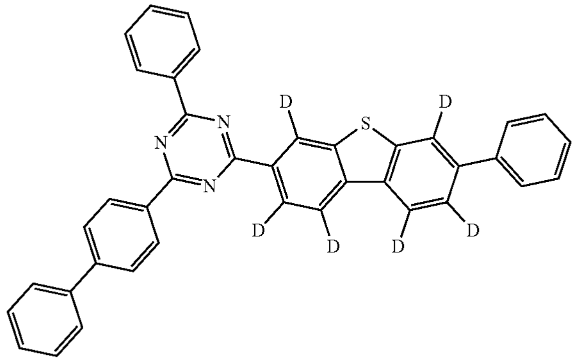
445
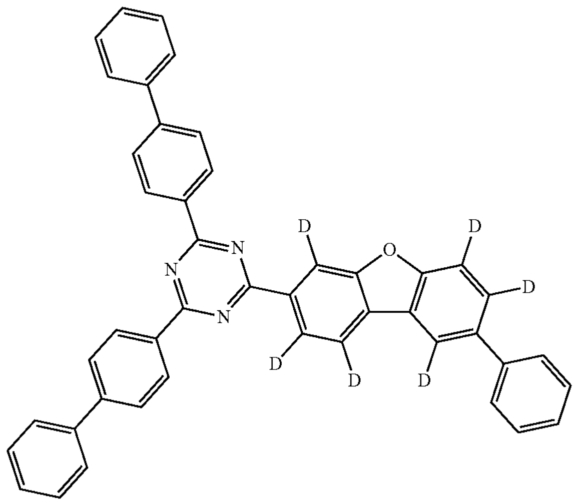
446
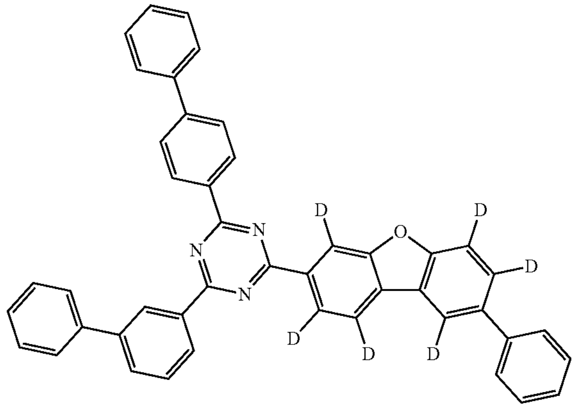

-continued
447
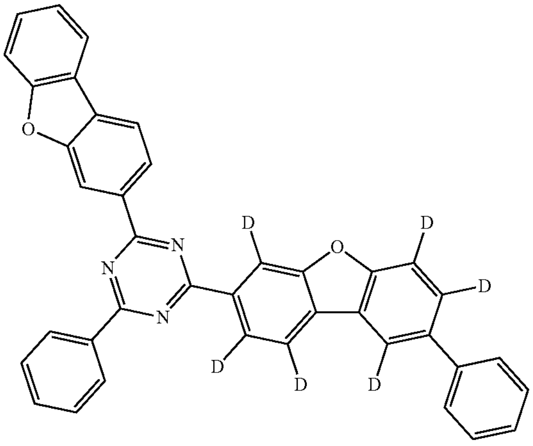
448
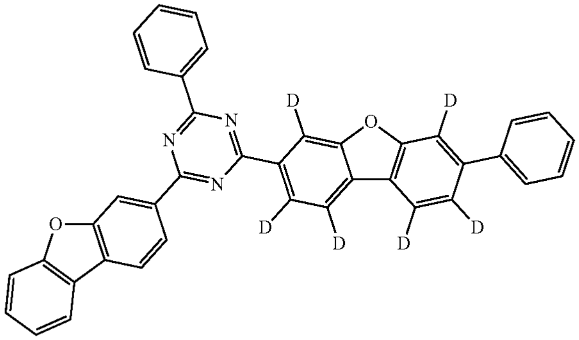
449
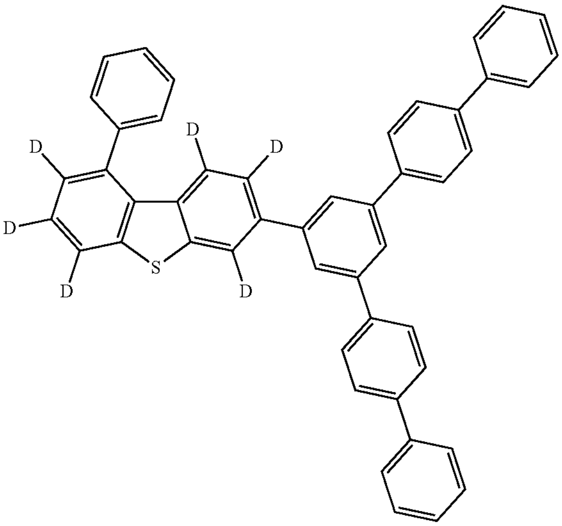
-continued
450
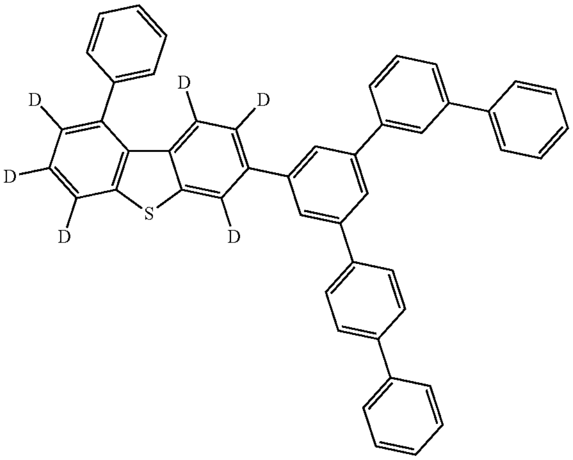
451
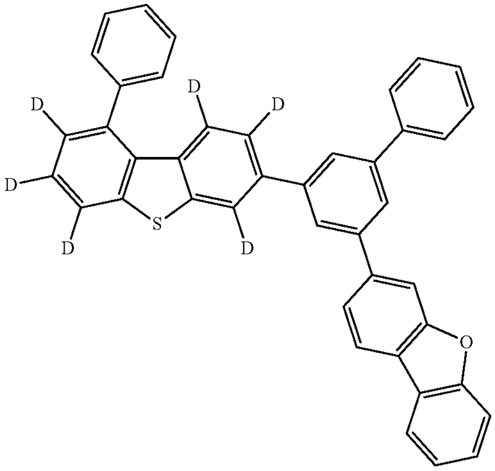
452
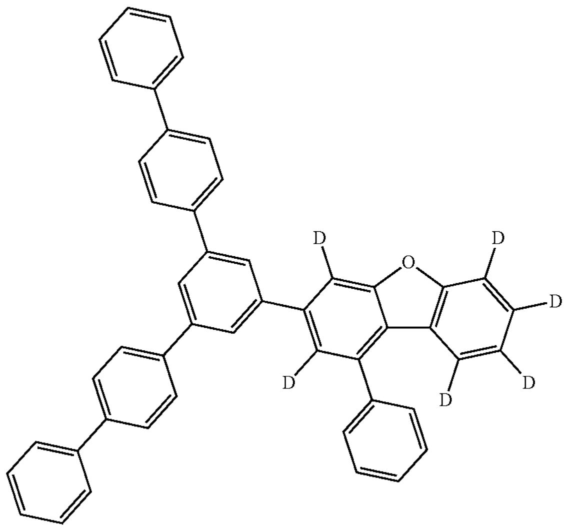

-continued
453
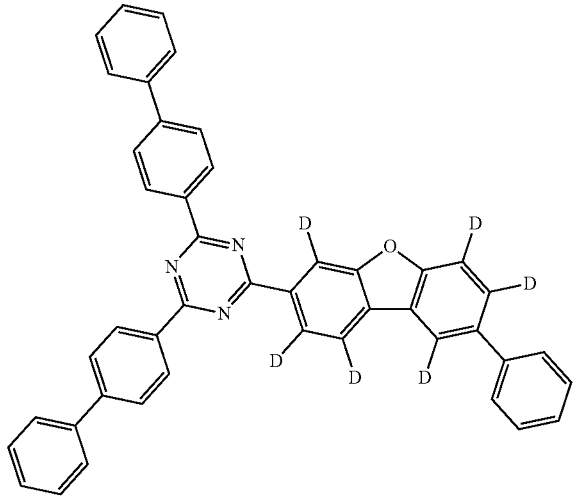
454
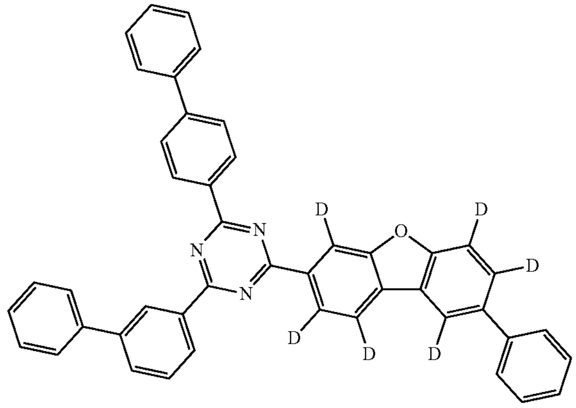
455
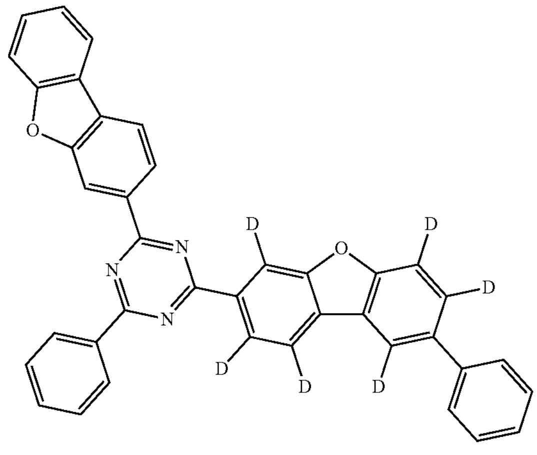
-continued
456
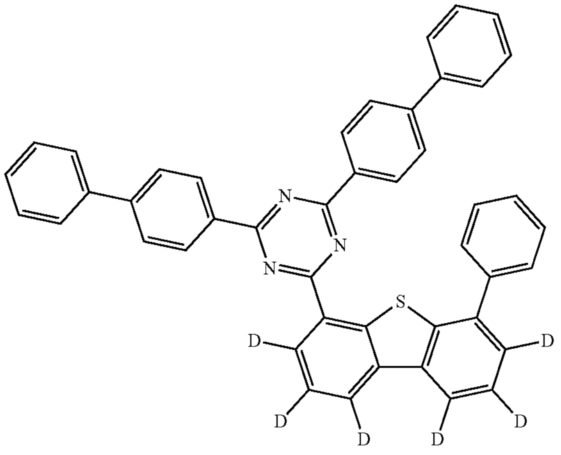
457
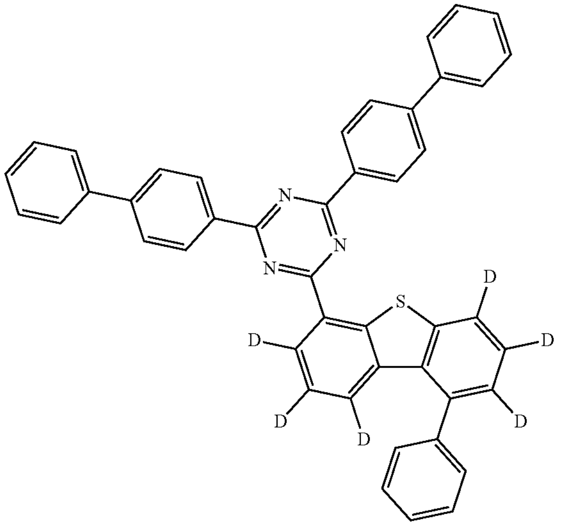
458
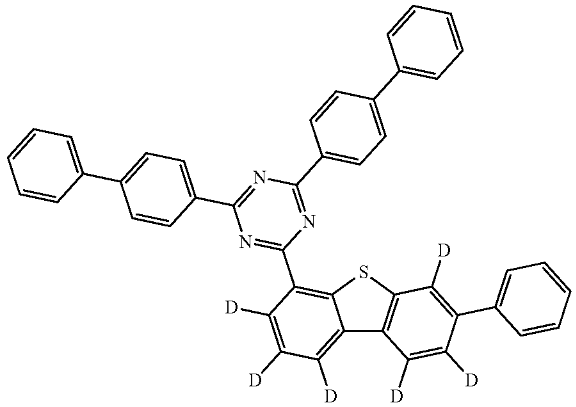

-continued
459
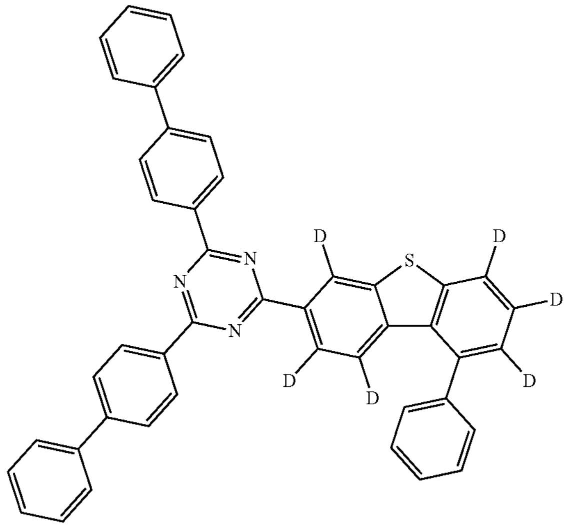
460
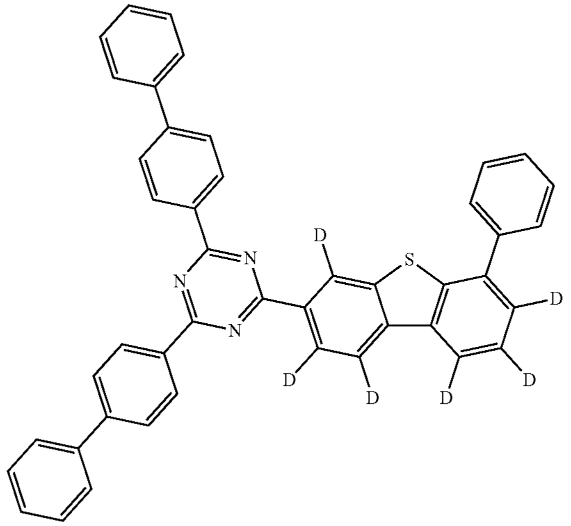
461
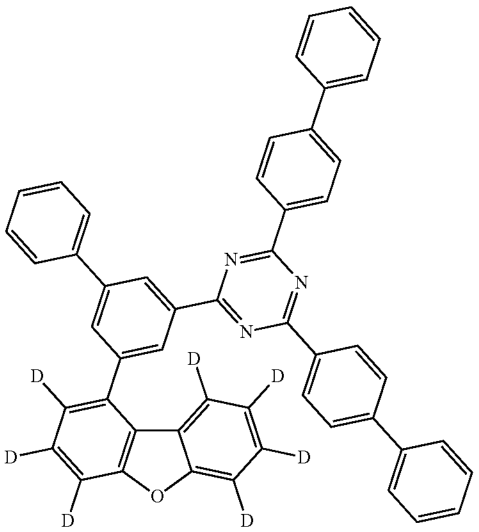
-continued
462
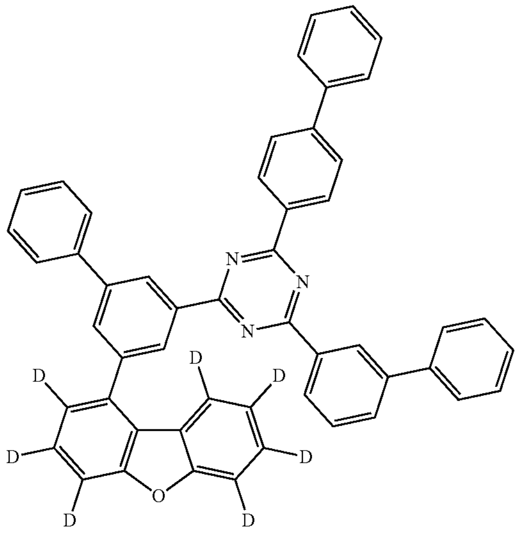
463
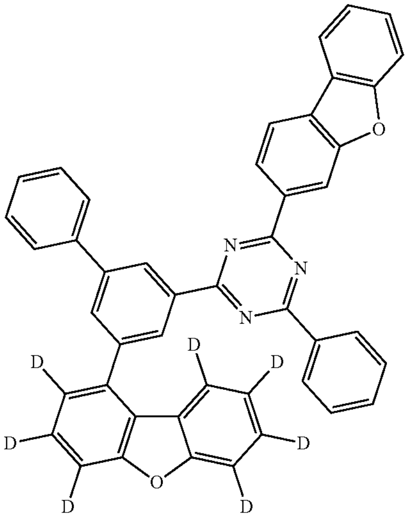
464
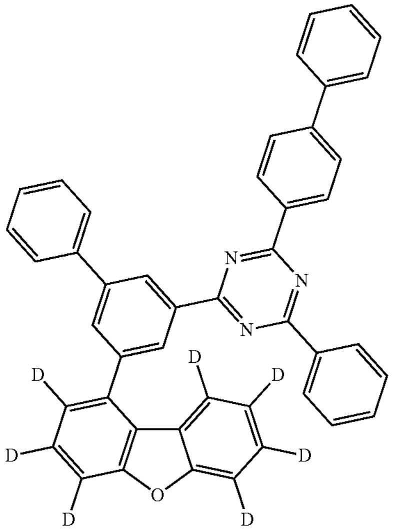

-continued
465
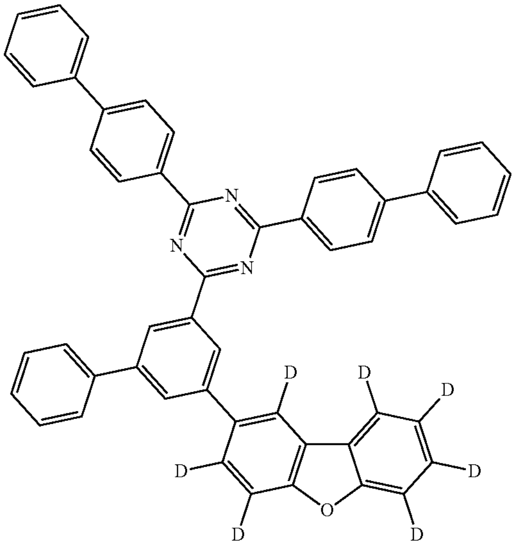
466
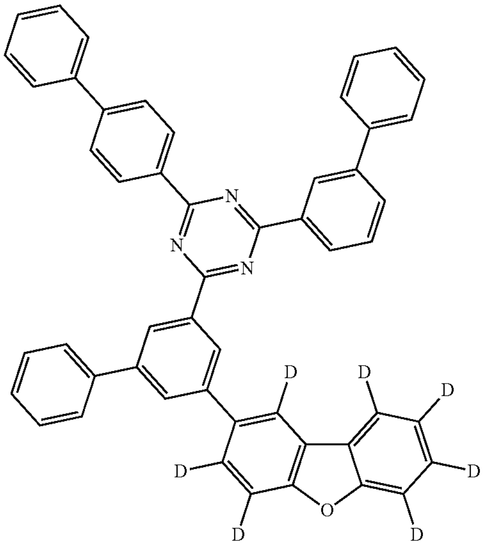
467
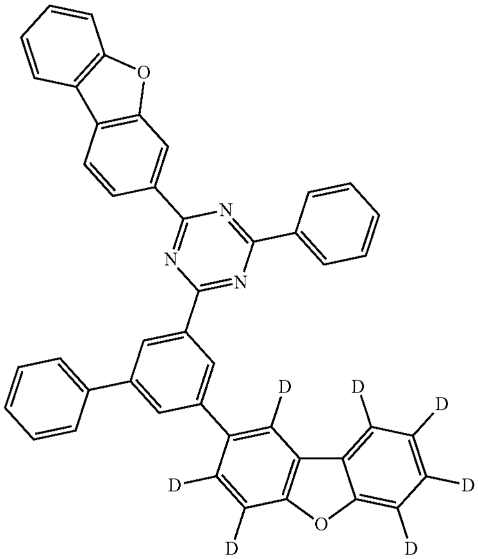
-continued
468
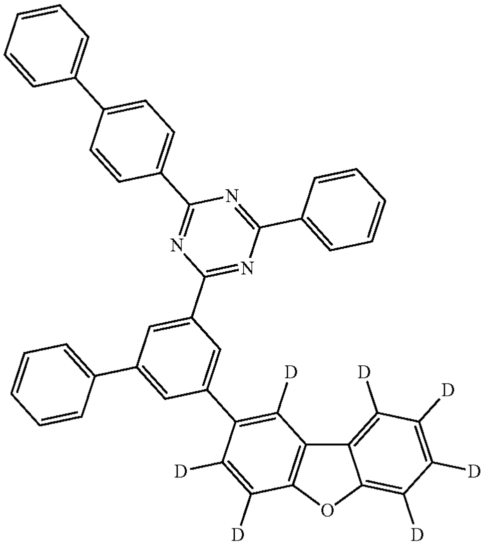
469
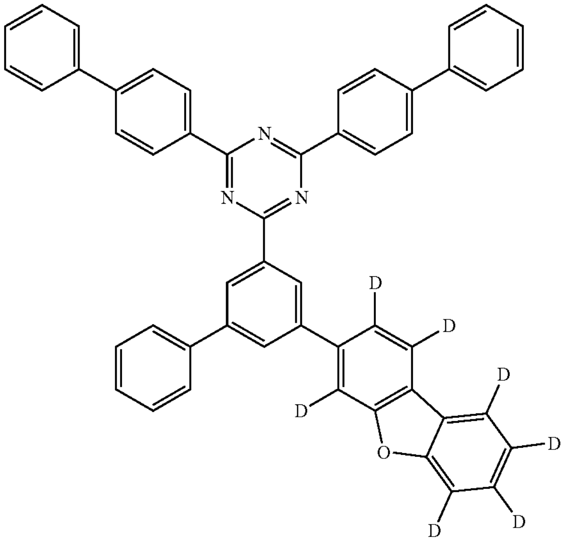

-continued
470
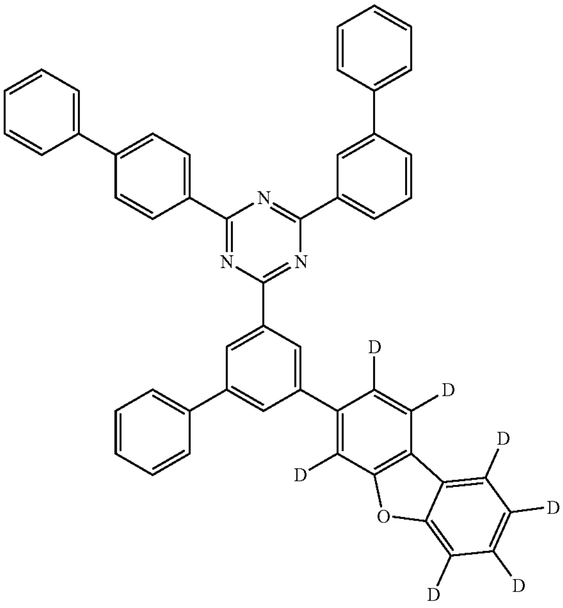
471
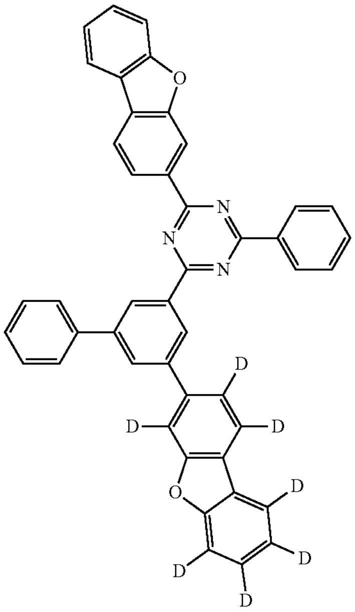
-continued
472
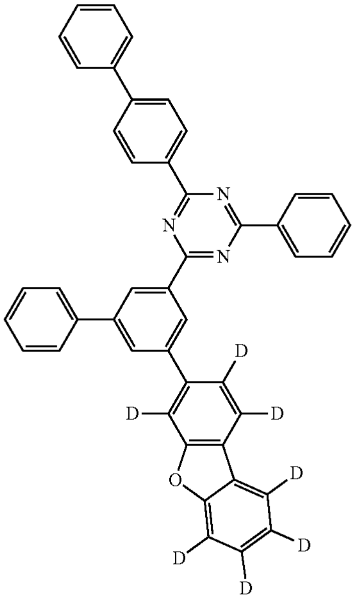
473
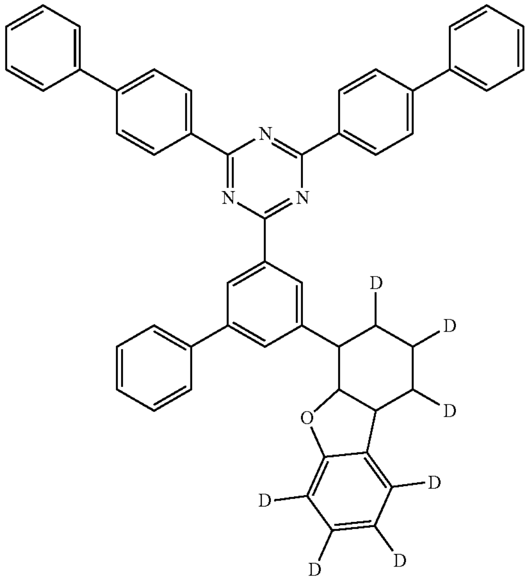

-continued
474
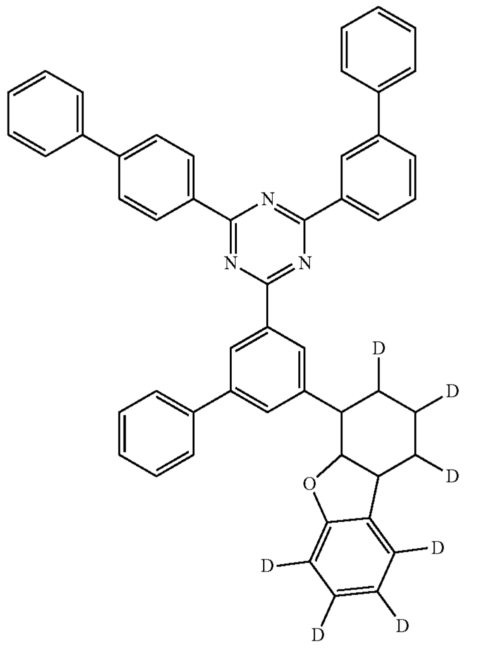
476
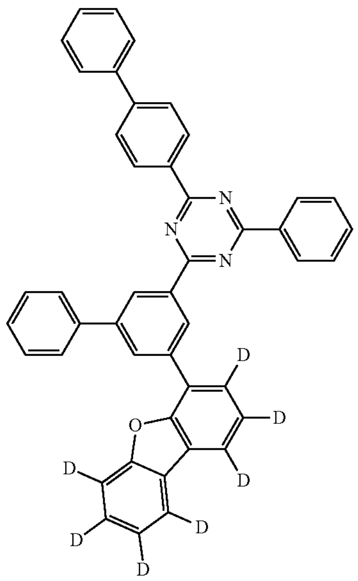
475
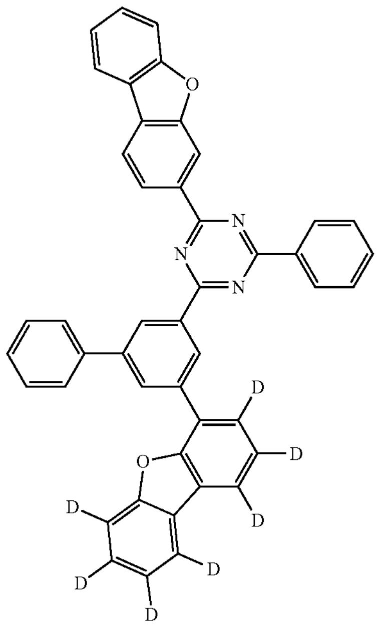
477
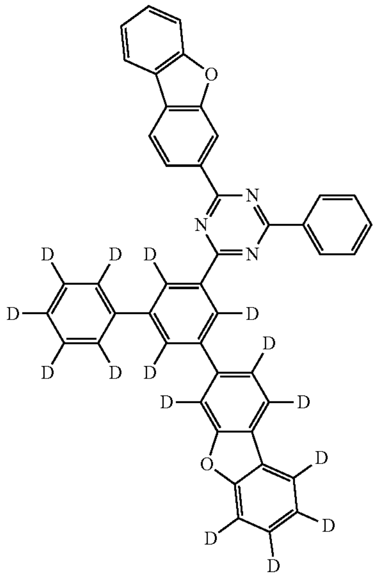

-continued
478
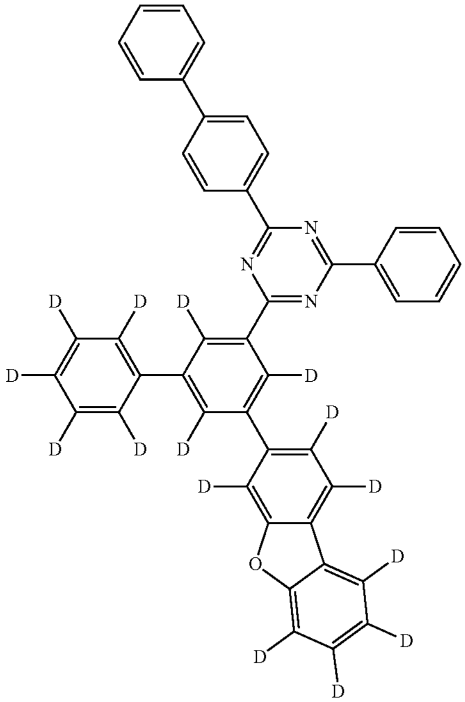
479
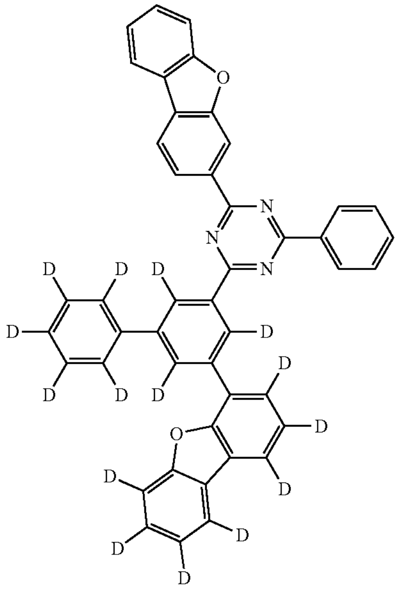
-continued
480
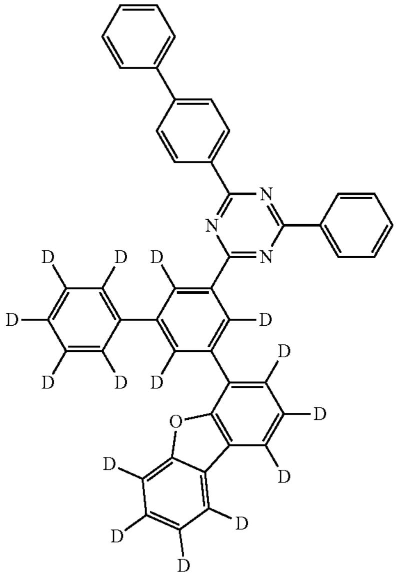
481
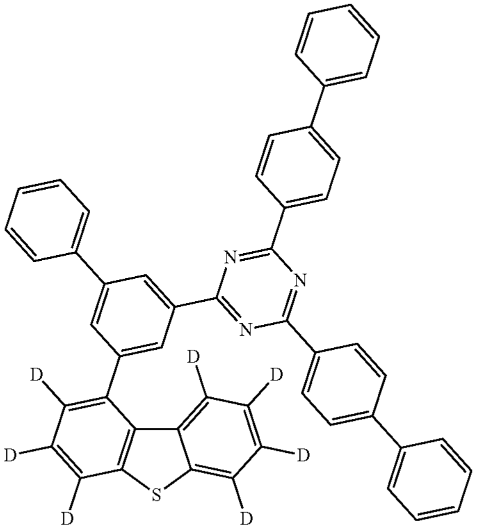
482
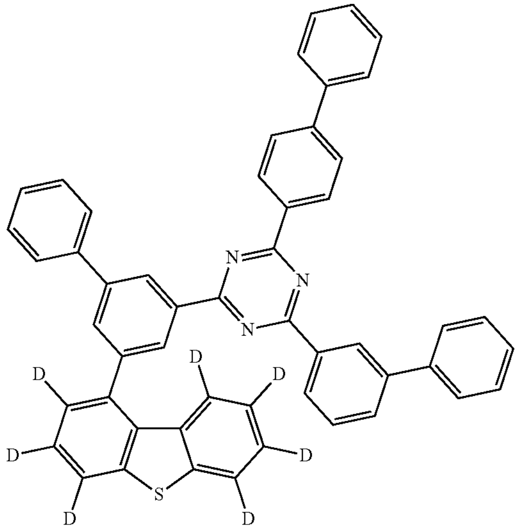

-continued
483
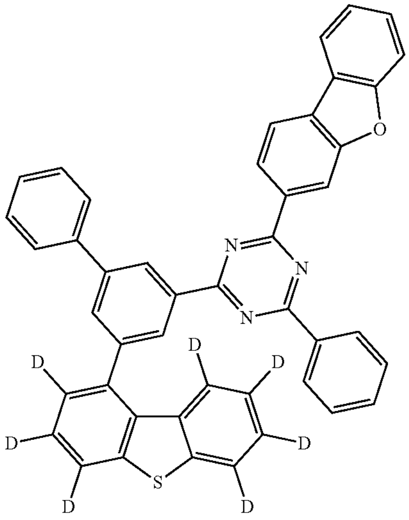
484
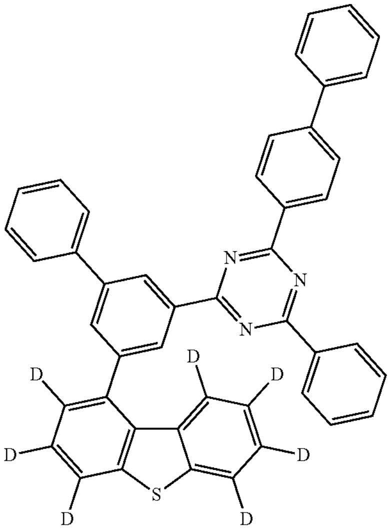
485
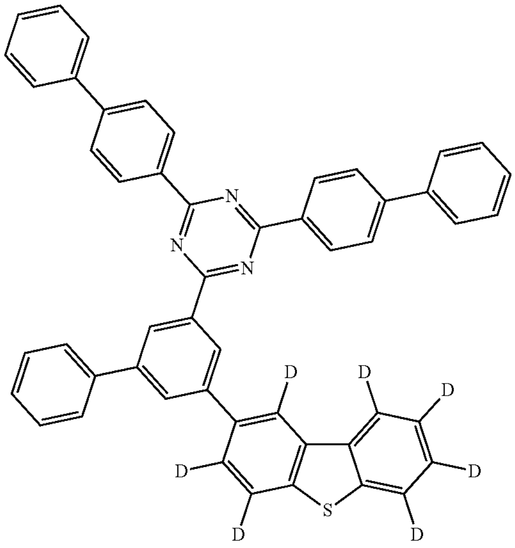
-continued
486
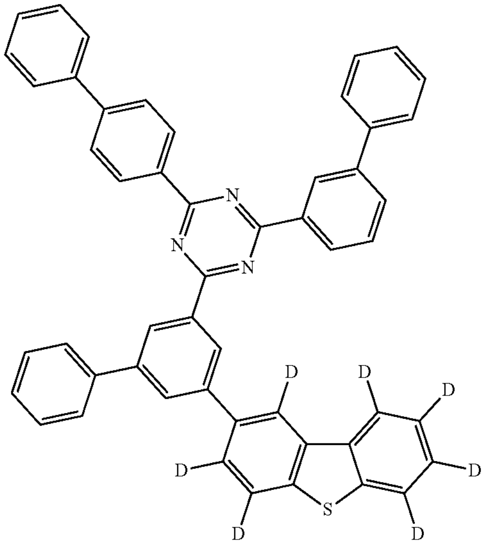
487
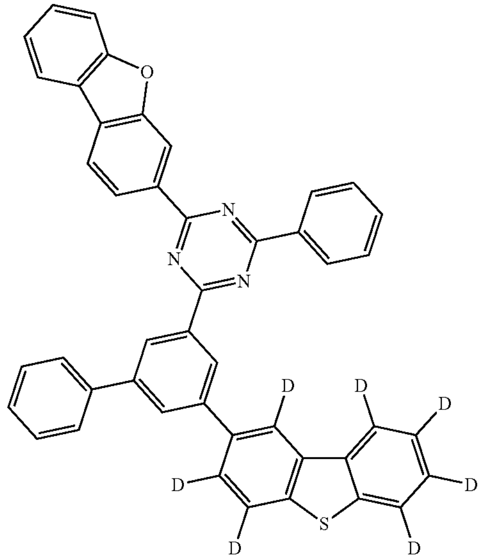
488
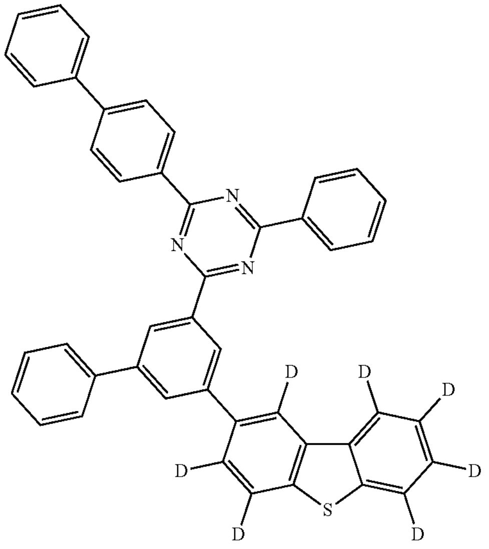

-continued
489
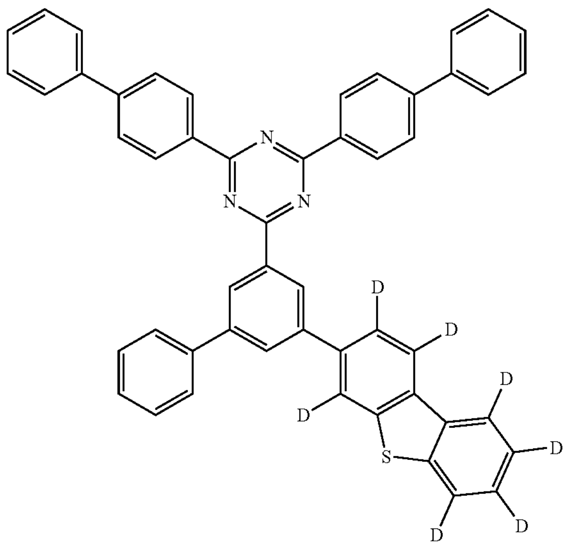
490
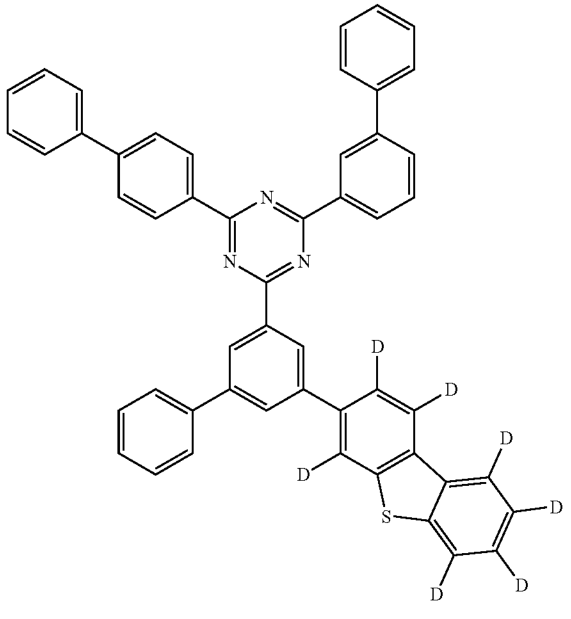
489
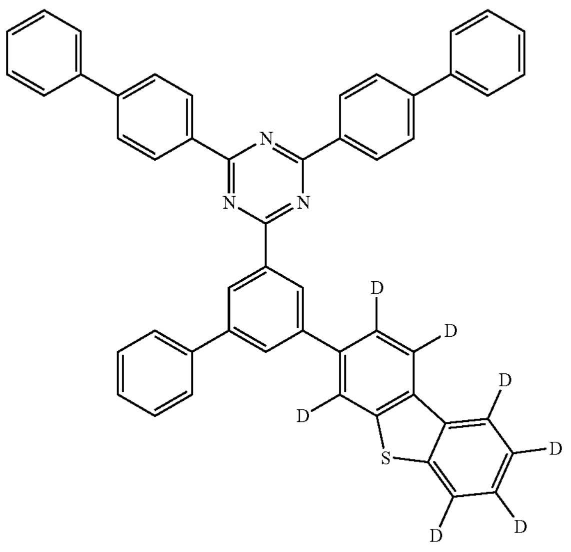
490
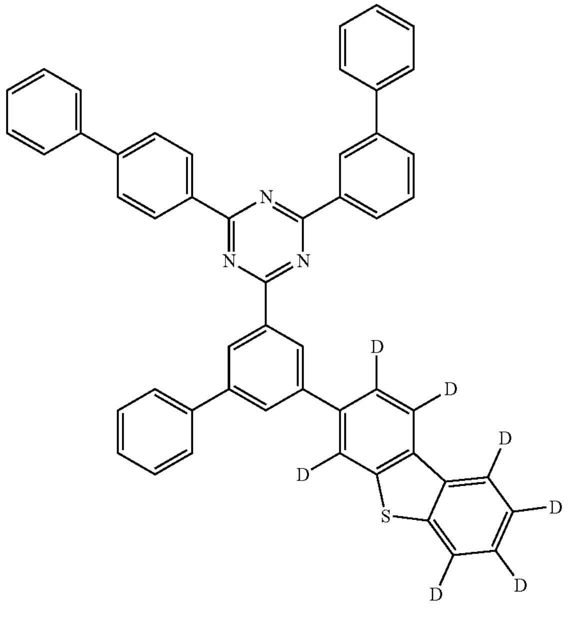

-continued
491
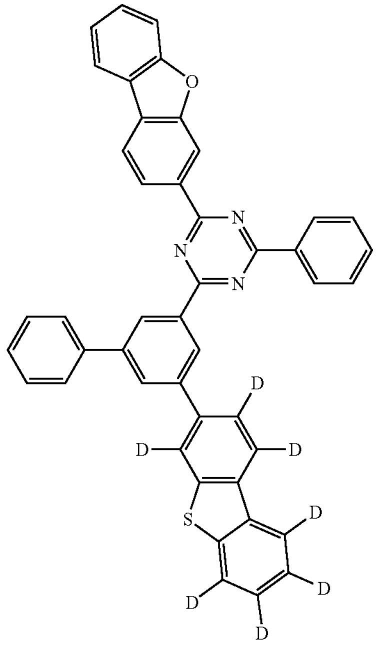
492
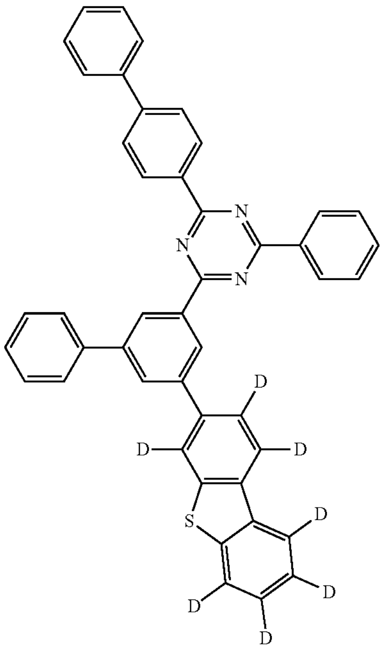
493
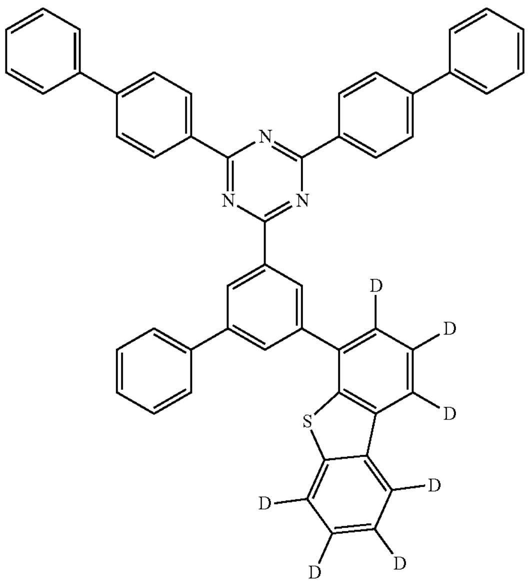
494
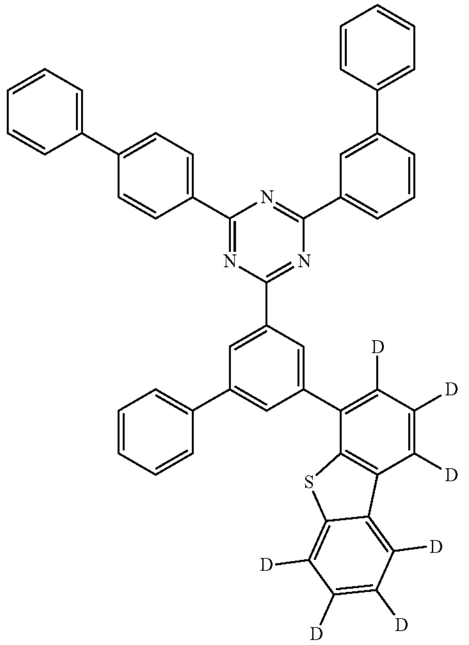

-continued
495
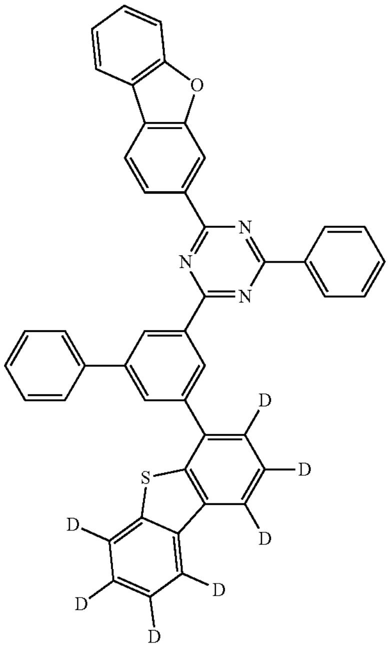
496
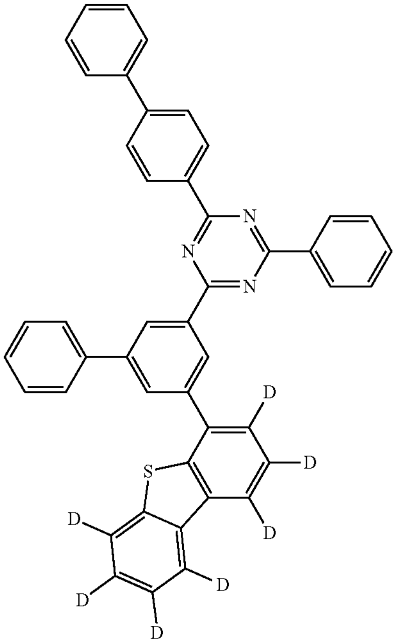
-continued
497
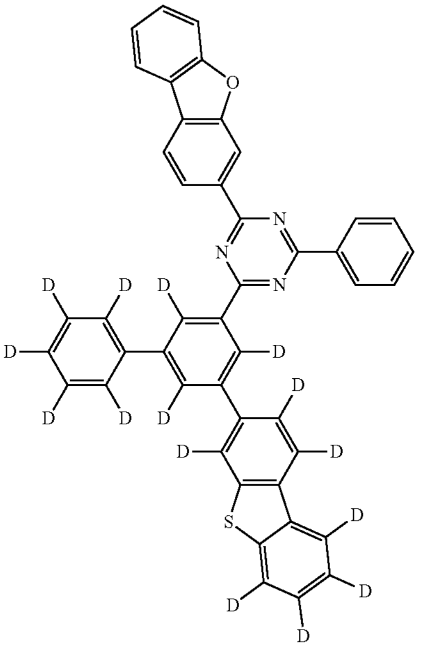
498
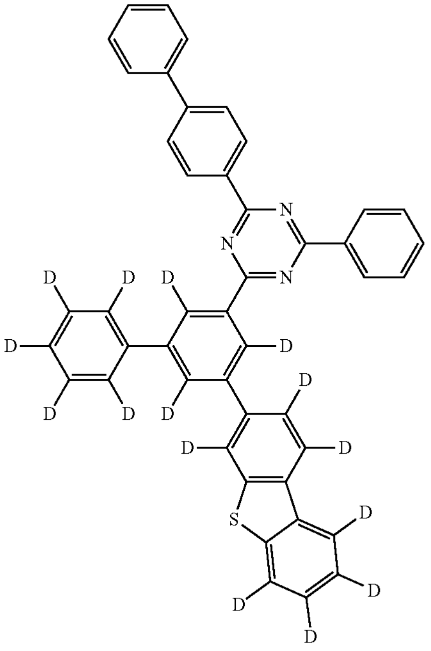

-continued

499

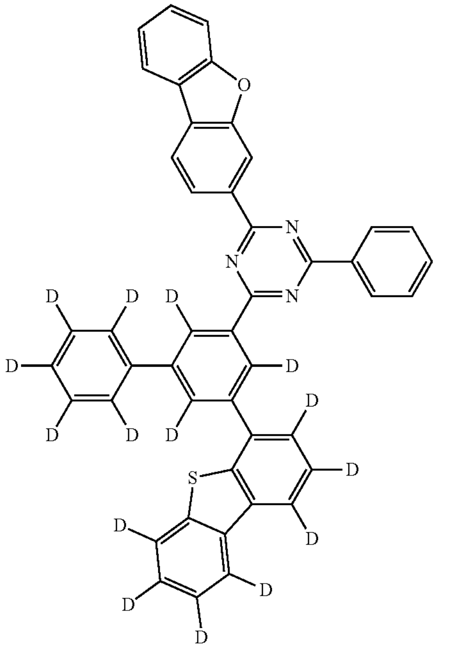

500

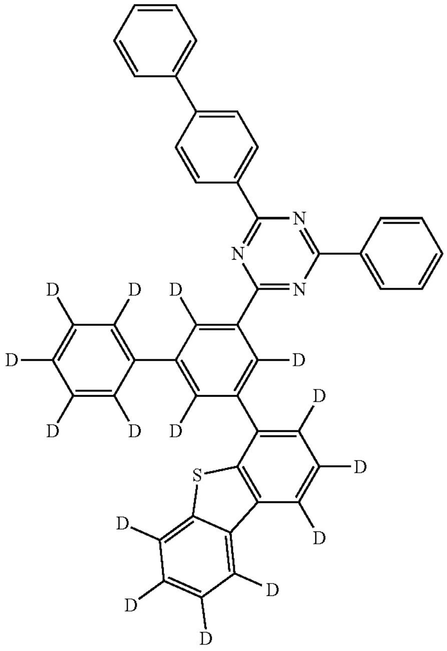

-continued

501

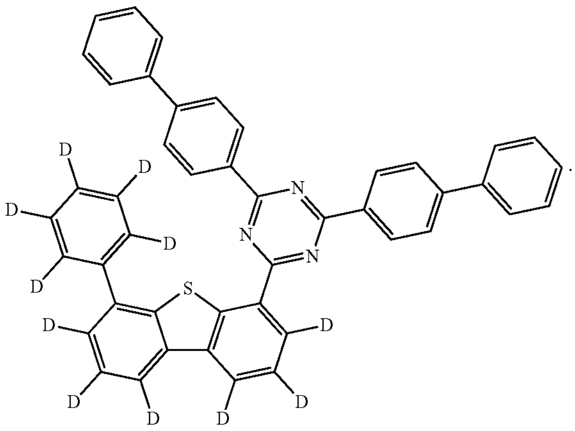

4. An organic light emitting device comprising:

a first electrode;

a second electrode provided opposite to the first electrode; and one or more organic material layers provided between the first electrode and the second electrode, wherein one or more layers of the organic material layers comprise the heterocyclic compound of claim 1.

5. The organic light emitting device of claim 4, wherein the organic material layer comprising the heterocyclic compound further comprises a heterocyclic compound represented by the following Chemical Formula 2:

[Chemical Formula 2]

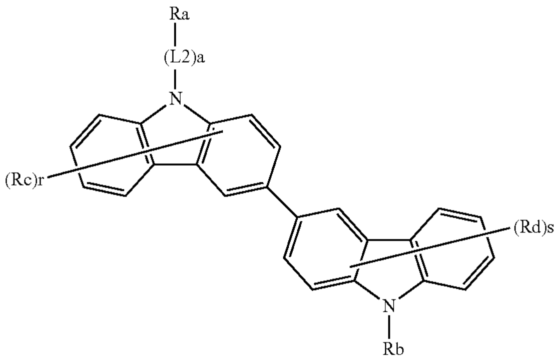

in Chemical Formula 2,

Rc and Rd are the same as or different from each other, and each independently selected from the group consisting of hydrogen; deuterium; halogen; a cyano group; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; —SiRR'R"; —P(═O)RR'; and —NRR', or two or more groups adjacent to each other bond to each other to form a substituted or unsubstituted aromatic hydrocarbon ring or a substituted or unsubstituted heteroring;

L2 is a direct bond; a substituted or unsubstituted C6 to C60 arylene group; or a substituted or unsubstituted C2 to C60 heteroarylene group;

Ra and Rb are the same as or different from each other, and each independently —CN; —SiRR'R"; a substituted or unsubstituted C6 to C60 aryl group; or a substituted or unsubstituted C2 to C60 heteroaryl group;

R, R' and R" are the same as or different from each other, and each independently hydrogen; deuterium; a substituted or unsubstituted C1 to C60 alkyl group; or a substituted or unsubstituted C6 to C60 aryl group;

a is an integer of 0 to 4;

r and s are an integer of 0 to 7; and when a, s and r are 2 or greater, substituents in the parentheses are the same as or different from each other.

6. The organic light emitting device of claim 5, wherein the heterocyclic compound represented by Chemical Formula 2 is any one selected from among the following compounds:

2-1

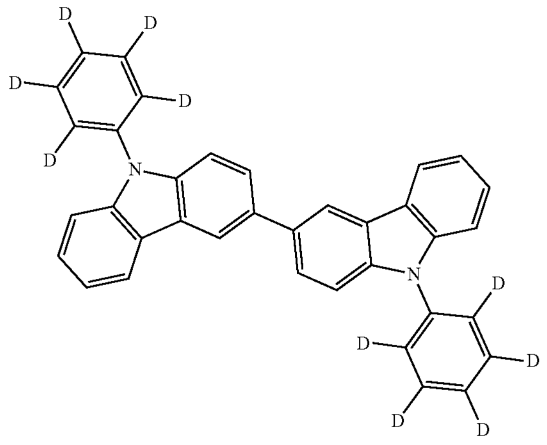

2-2

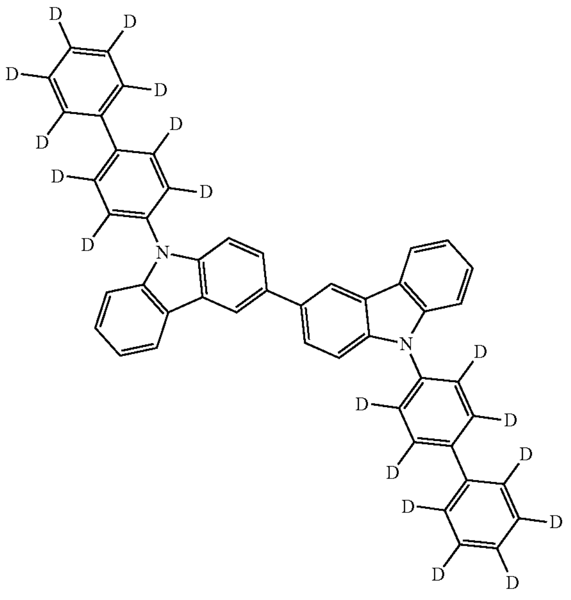

2-3

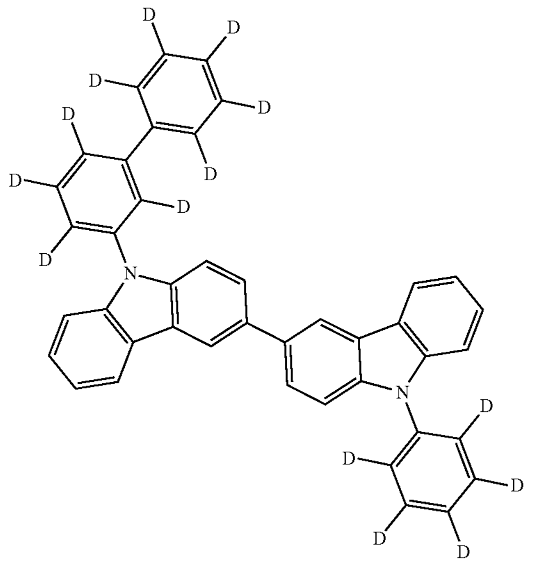

2-4

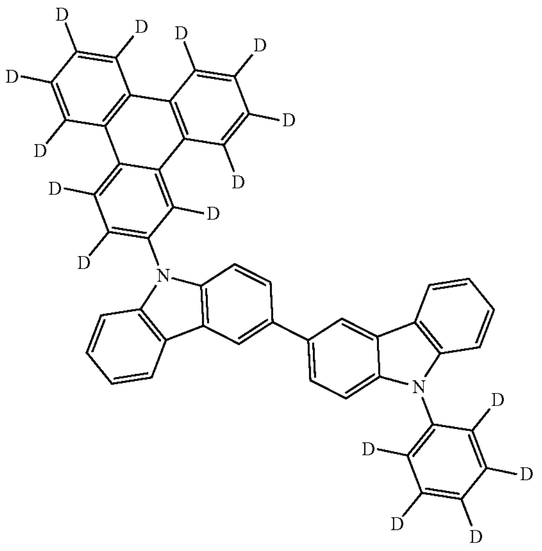

-continued
2-5
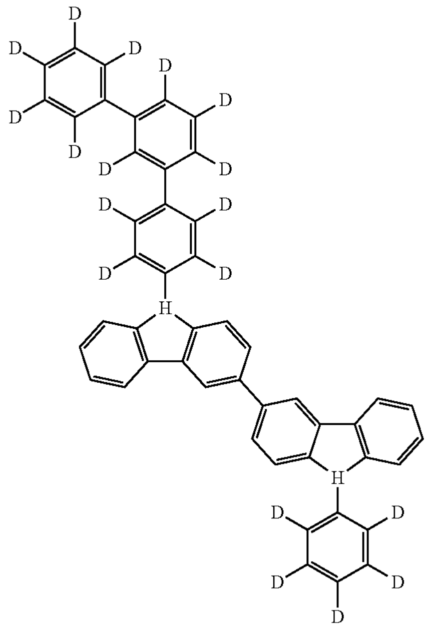
2-6
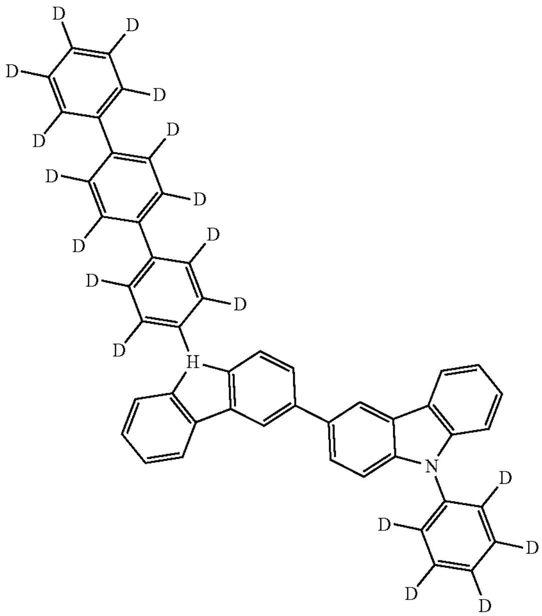
2-7
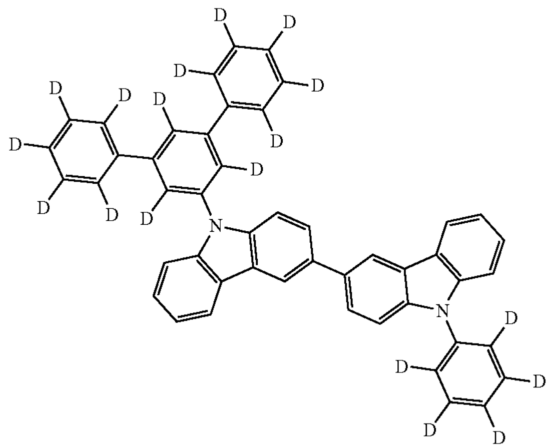
2-8
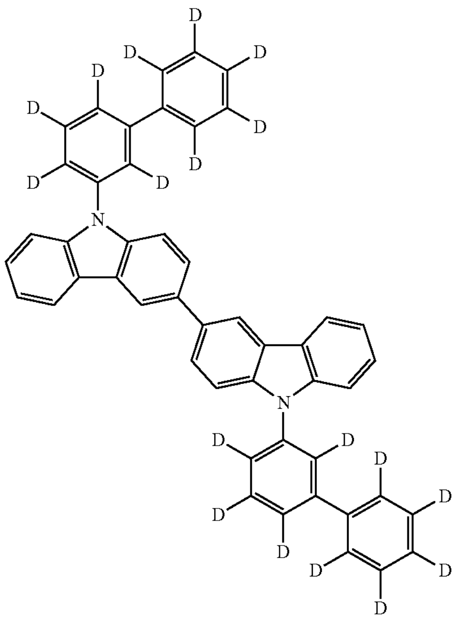

-continued
2-9
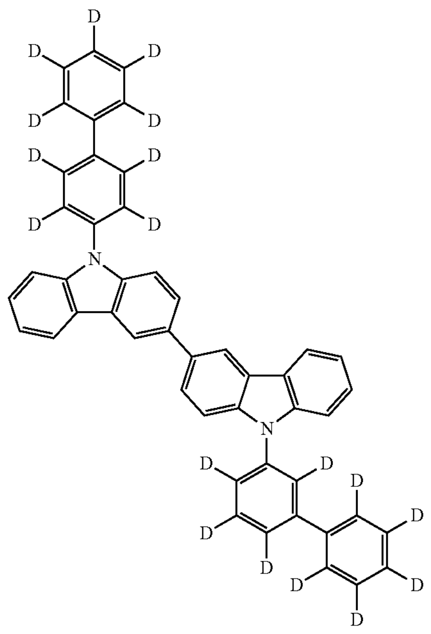
2-10
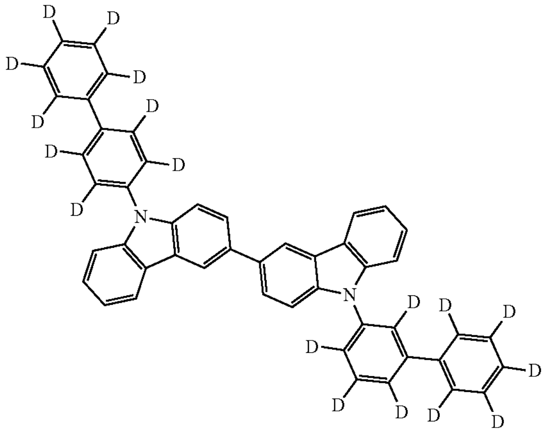
2-11
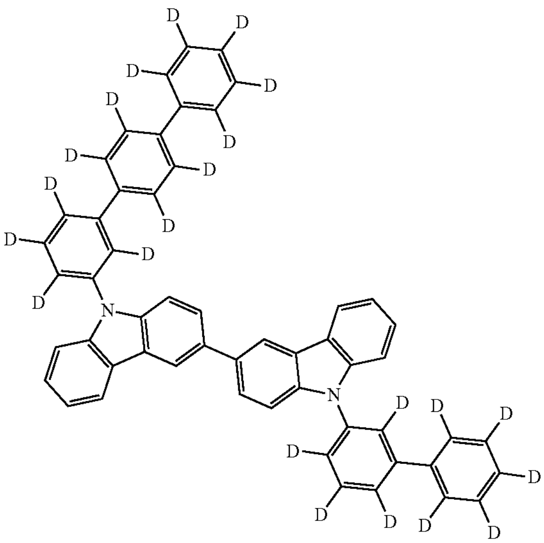
2-12
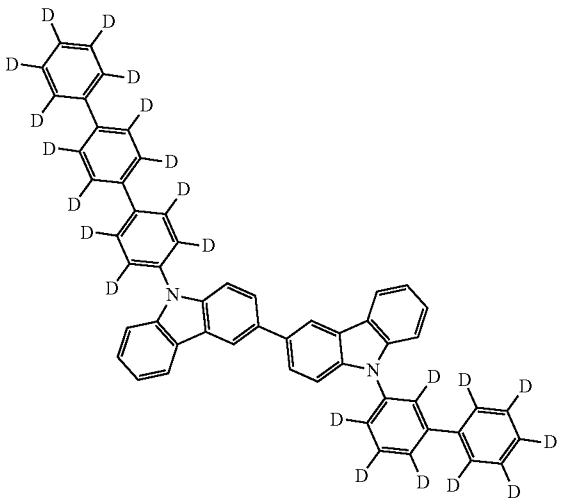

-continued
2-13
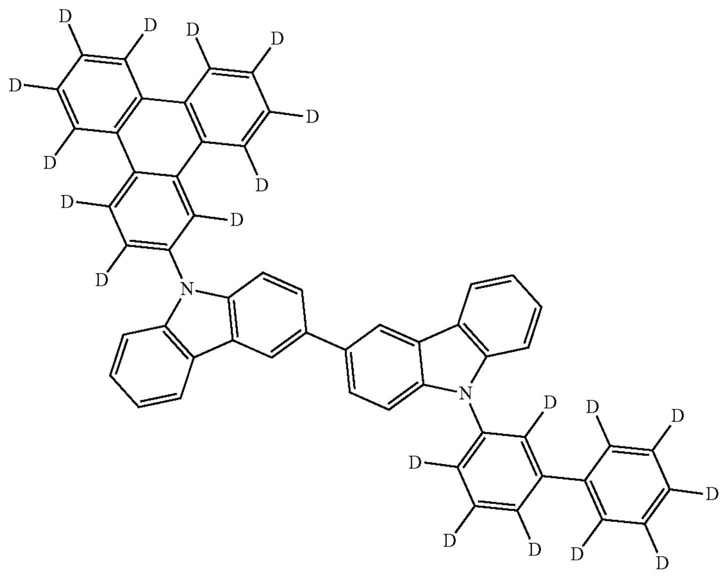
2-14
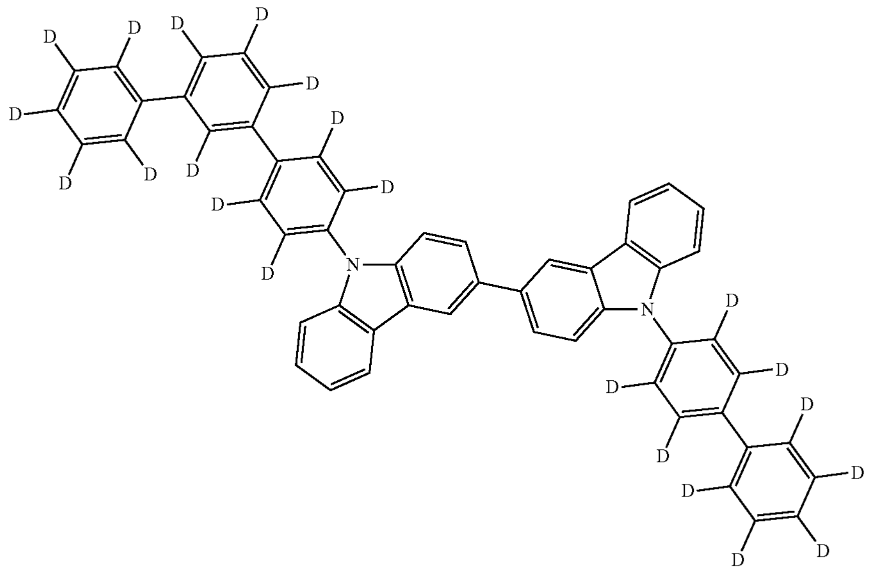

-continued
2-15
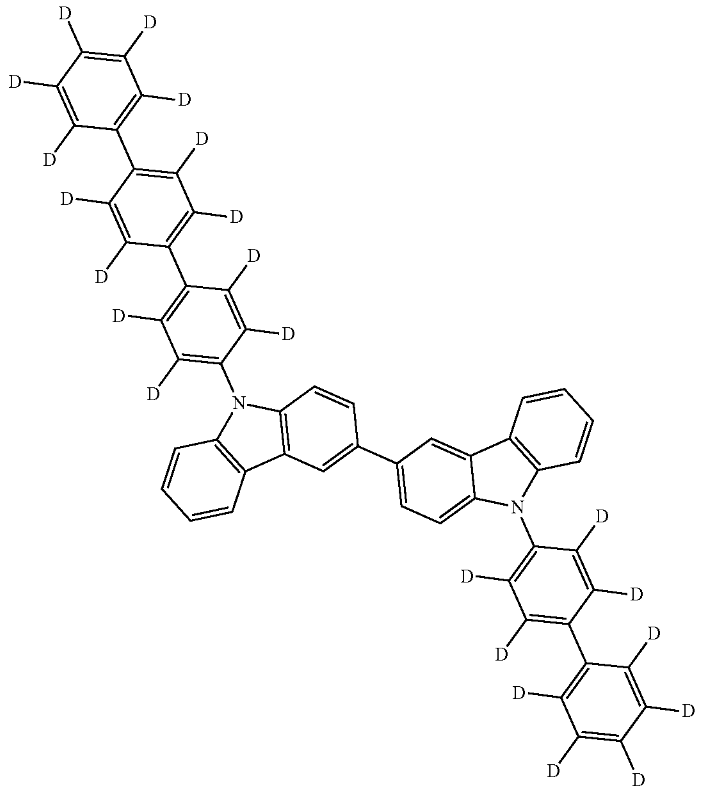
2-16
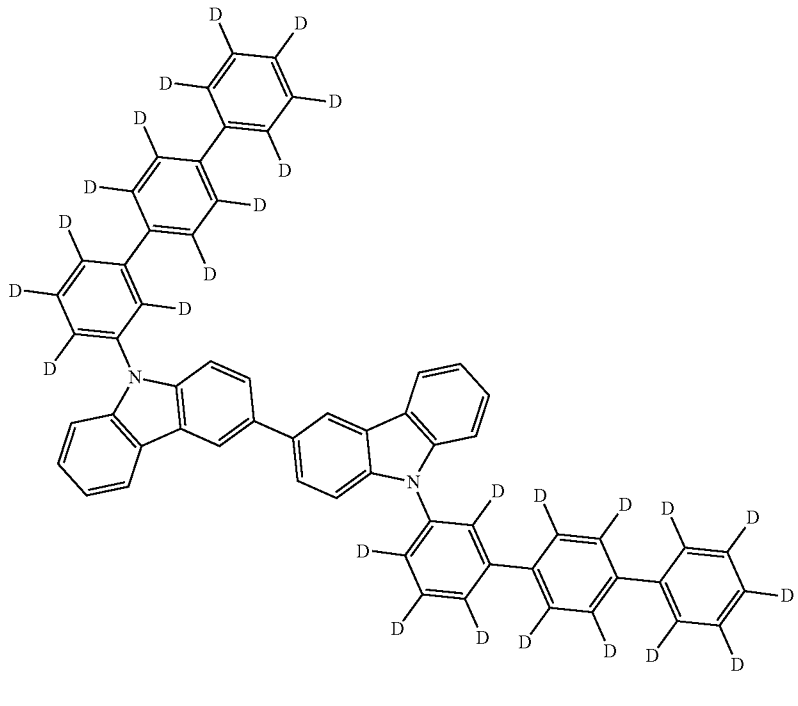

-continued
2-17
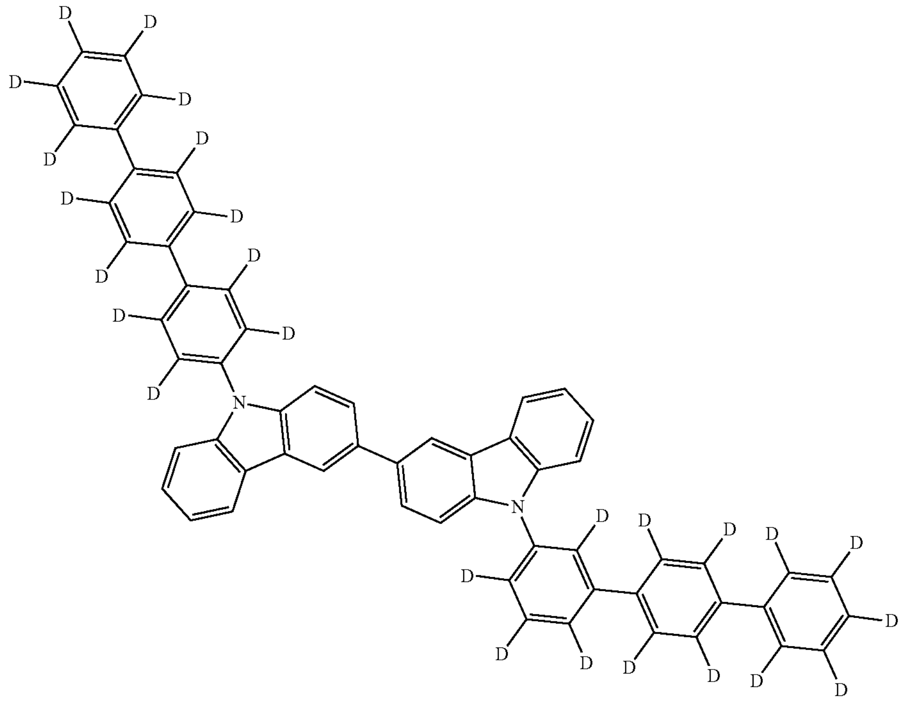
2-18
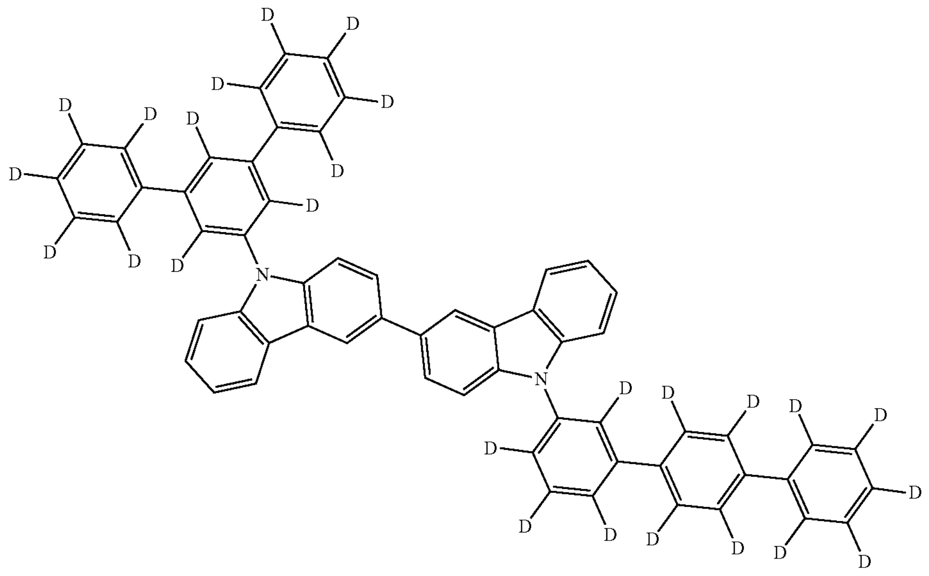

-continued
2-19
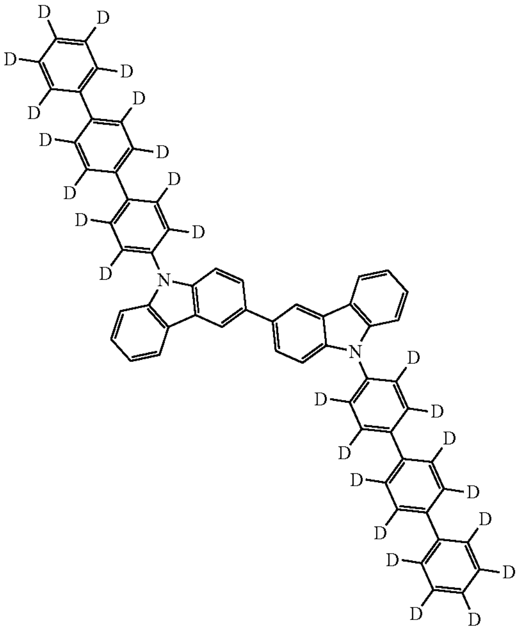
2-20
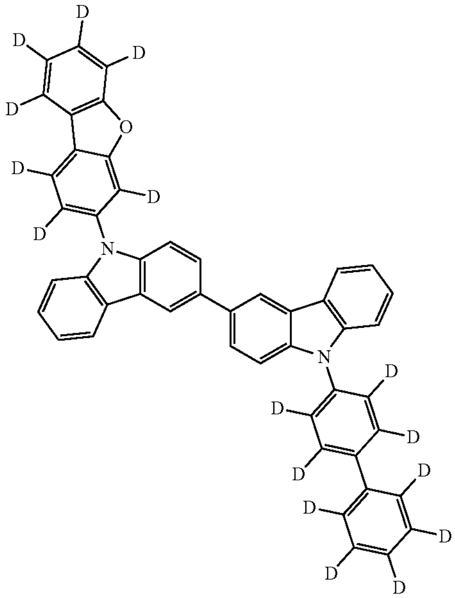
2-21
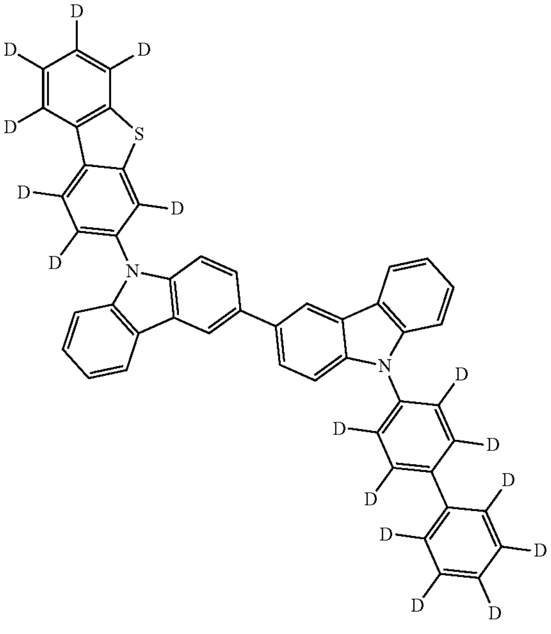

-continued
2-22
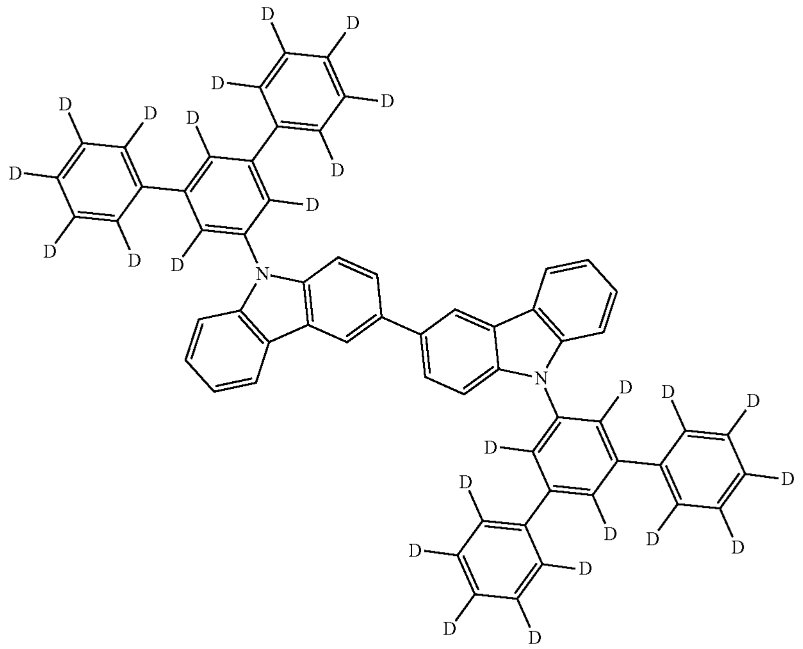
2-23
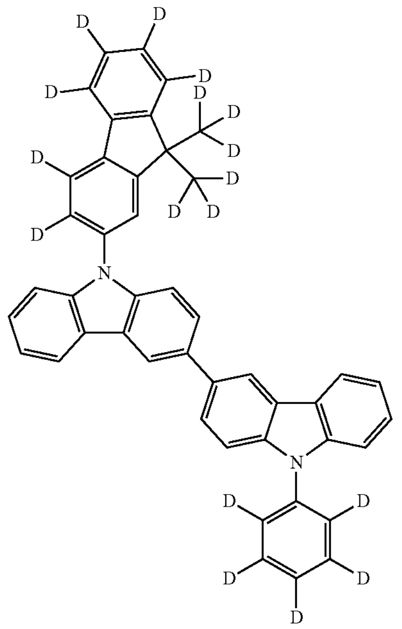
2-24
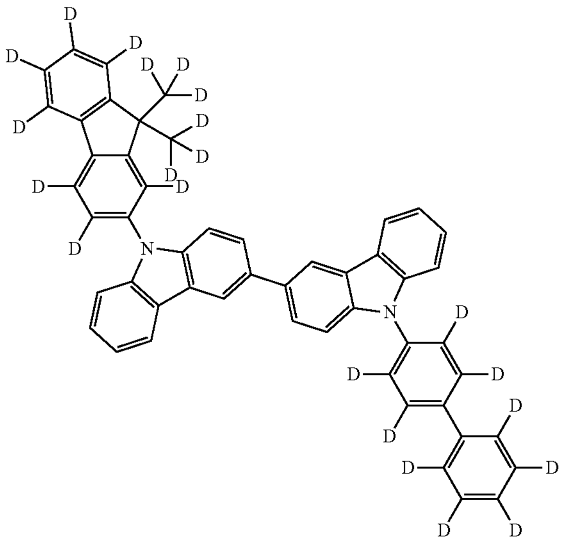

-continued
2-25
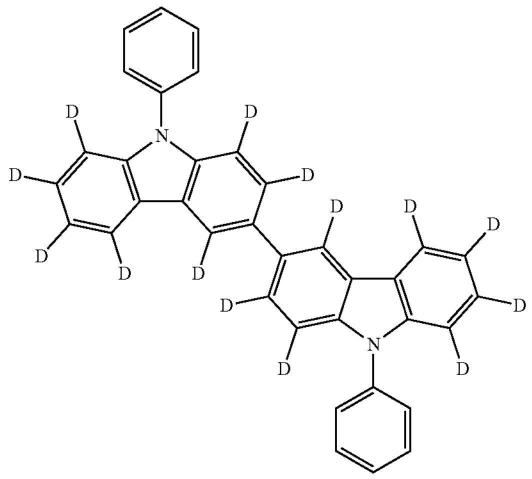
2-26
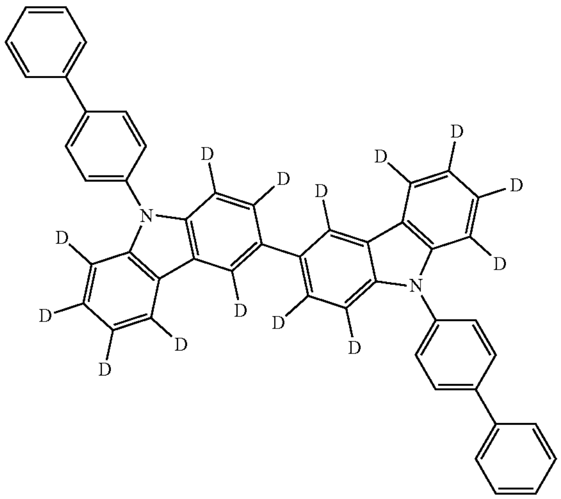
2-27
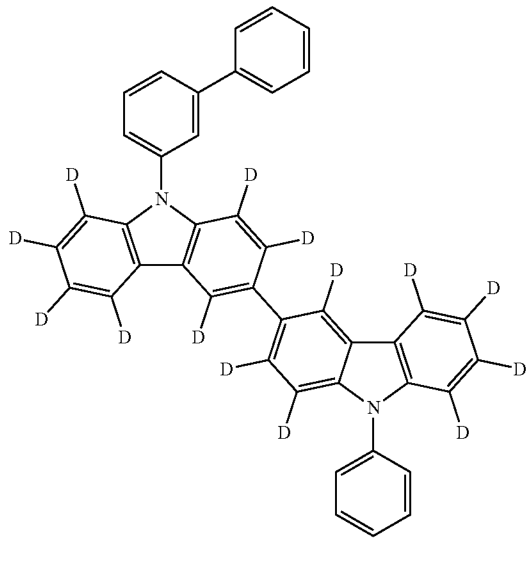
2-28
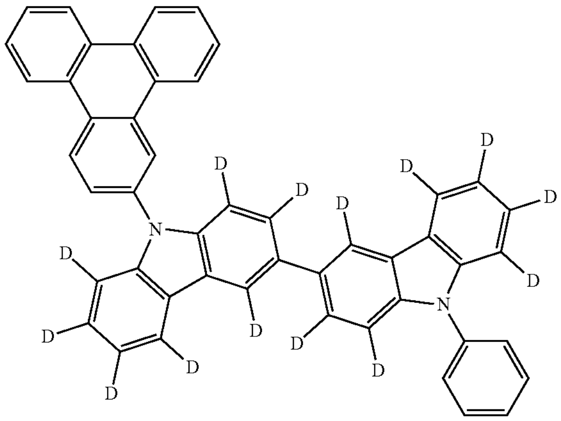

-continued
2-29
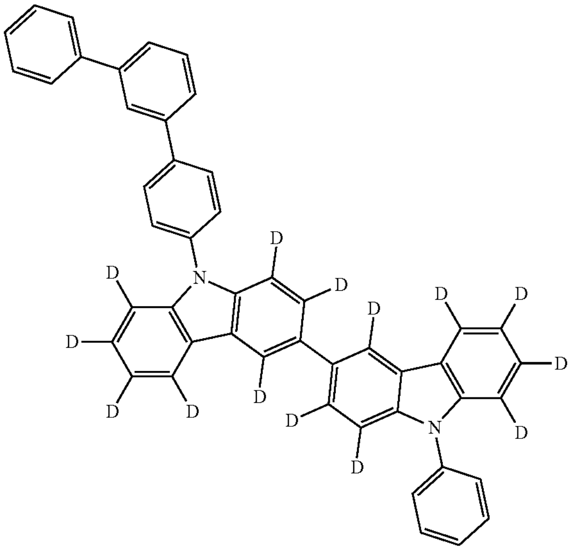
2-30
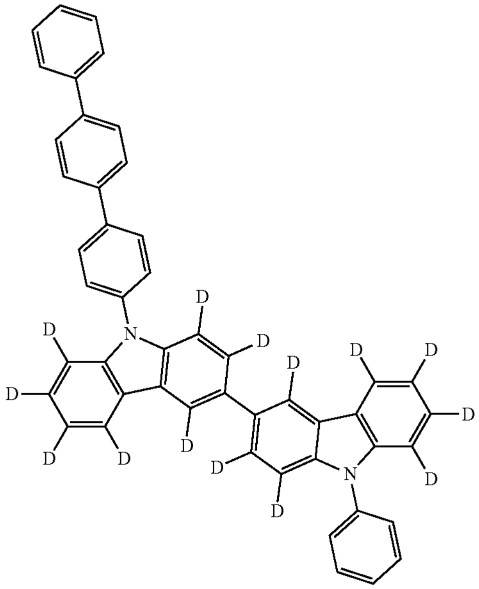
2-31
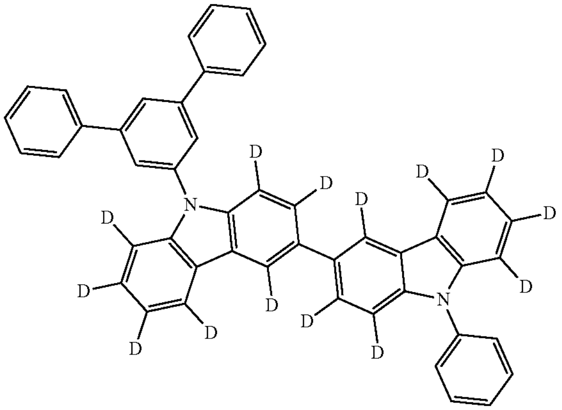
2-32
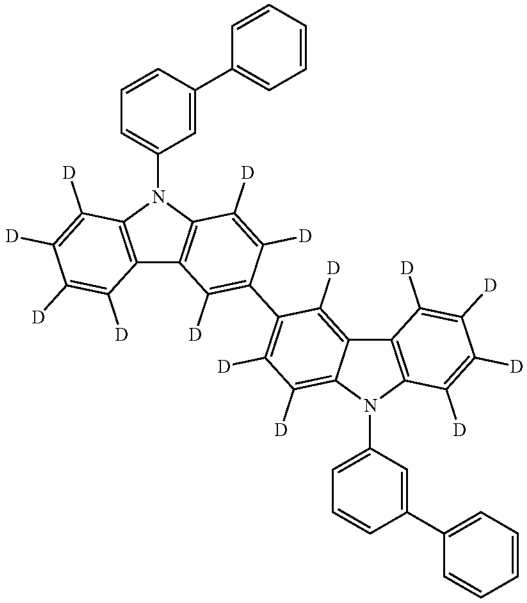

-continued
2-33
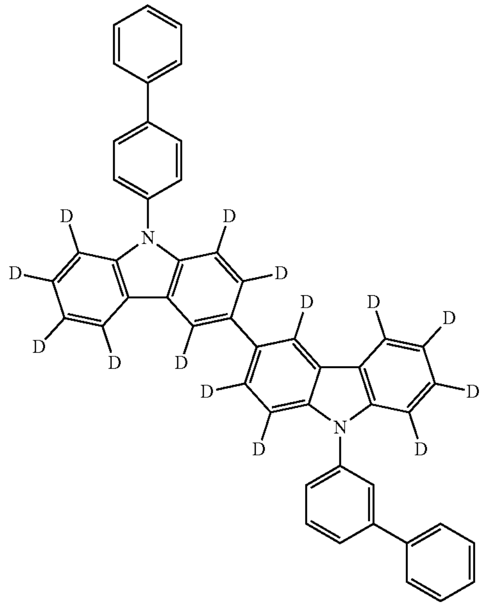
2-34
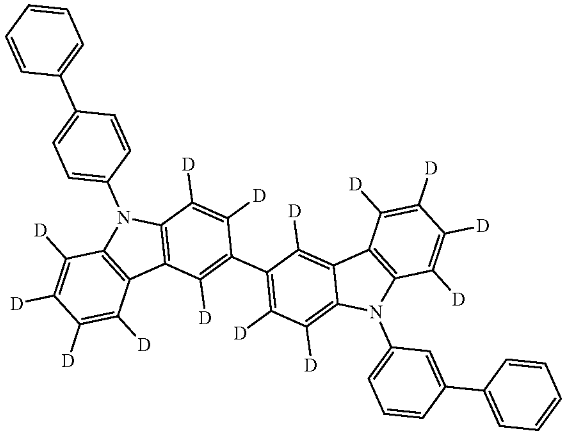
2-35
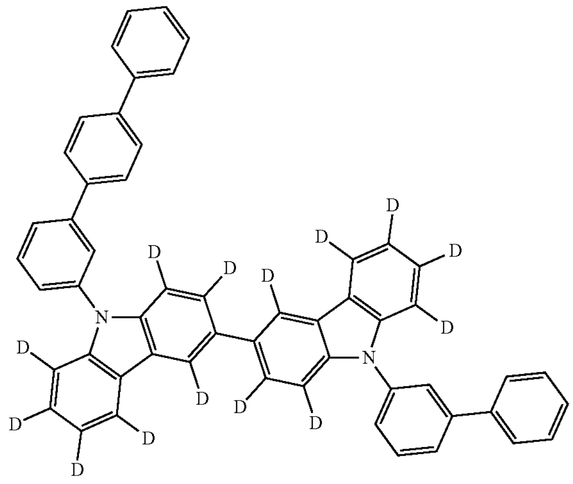
2-36
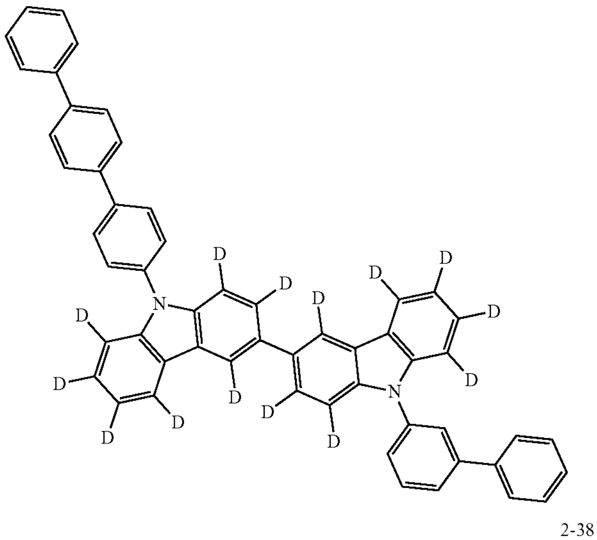
2-37
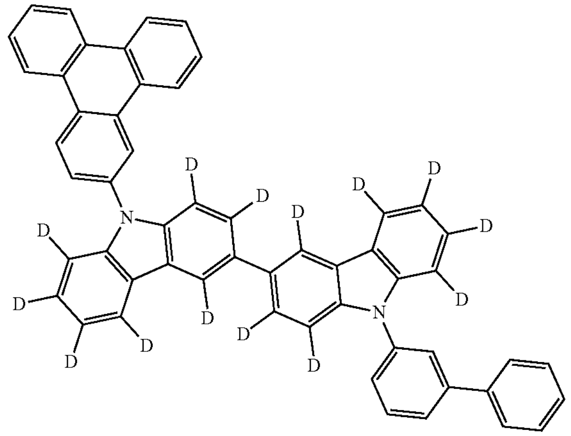
2-38
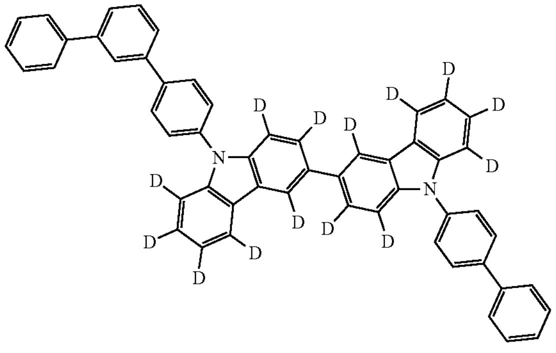

-continued
2-39
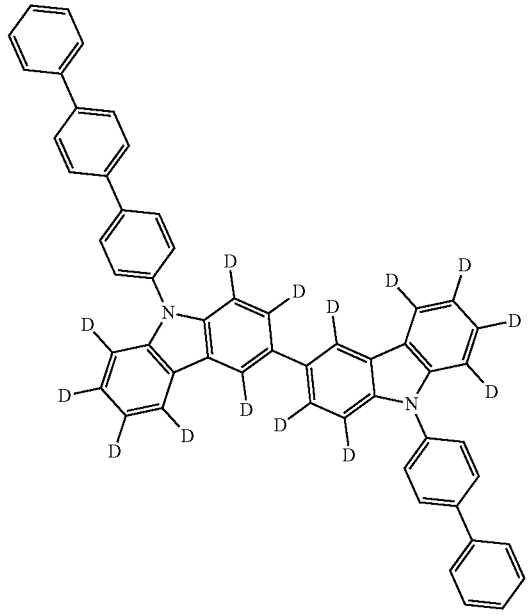
2-40
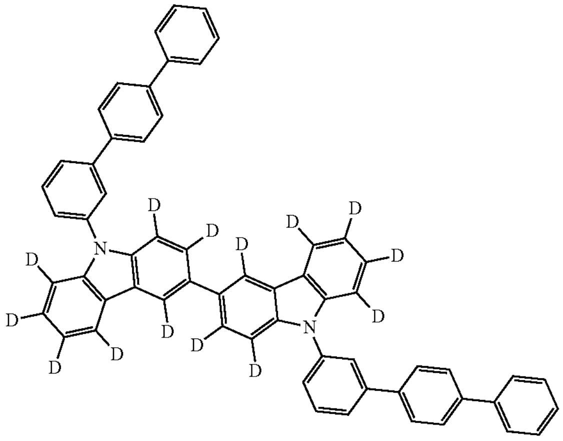
2-41
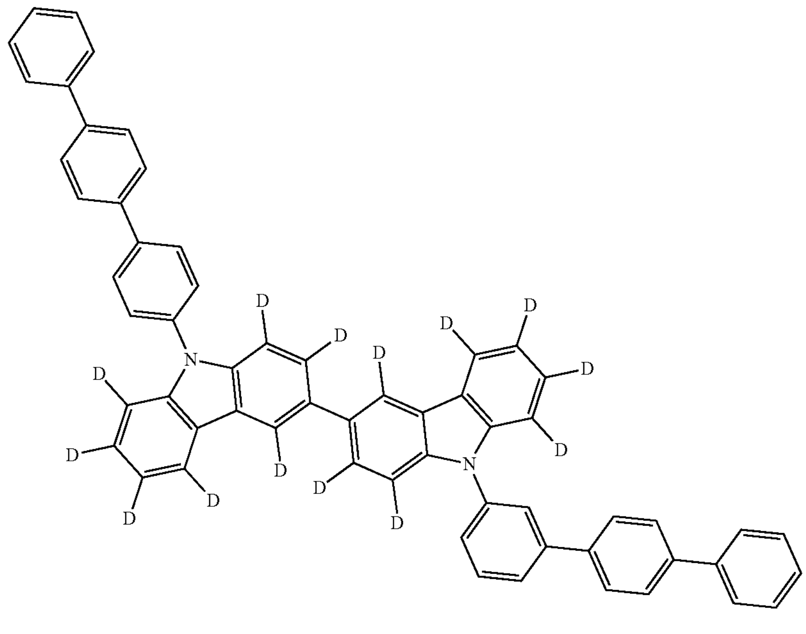

-continued
2-42
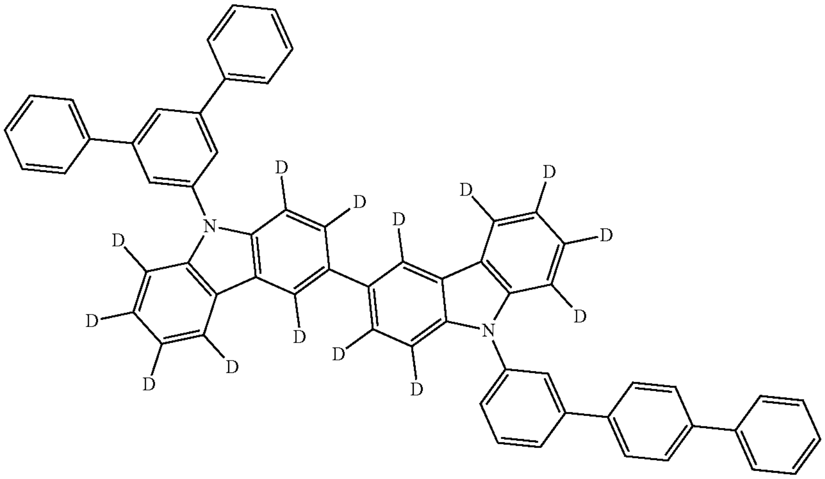
2-43
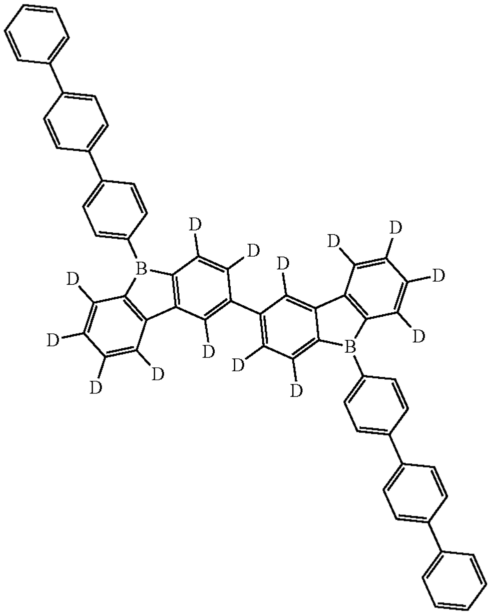
2-44
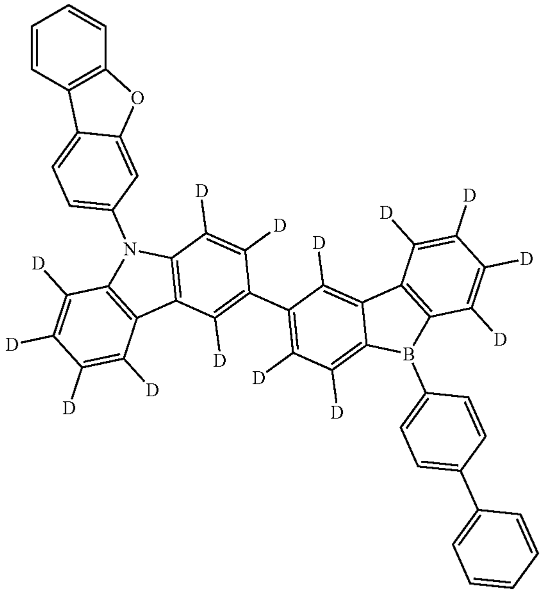

-continued
2-45
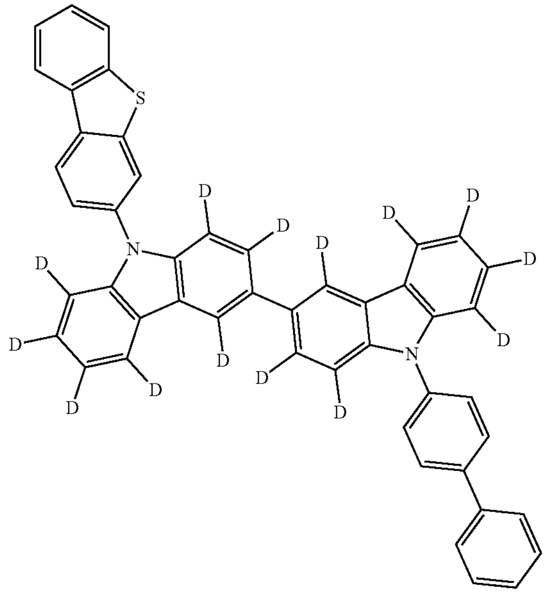
2-46
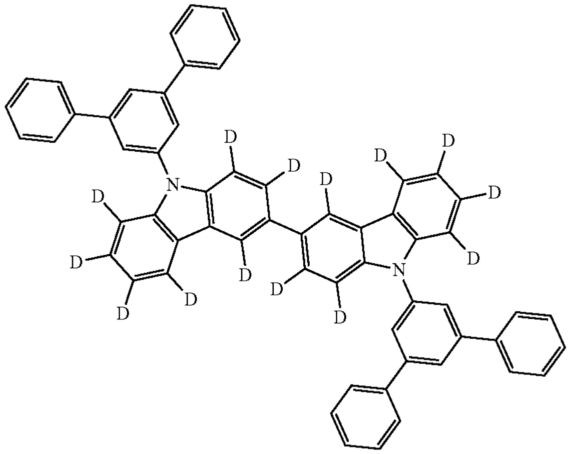
2-47
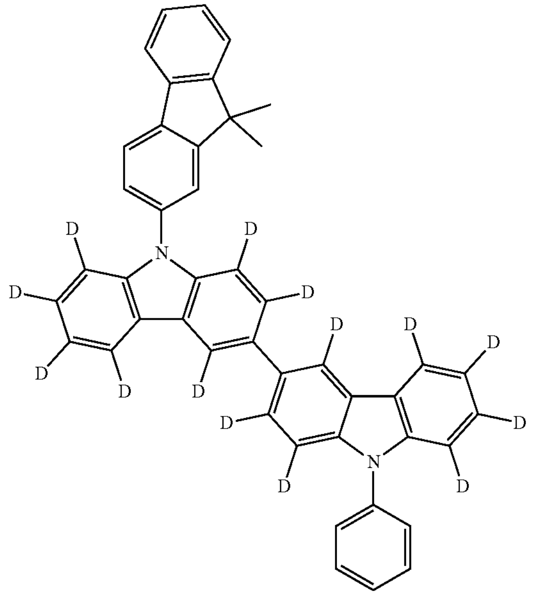
2-48
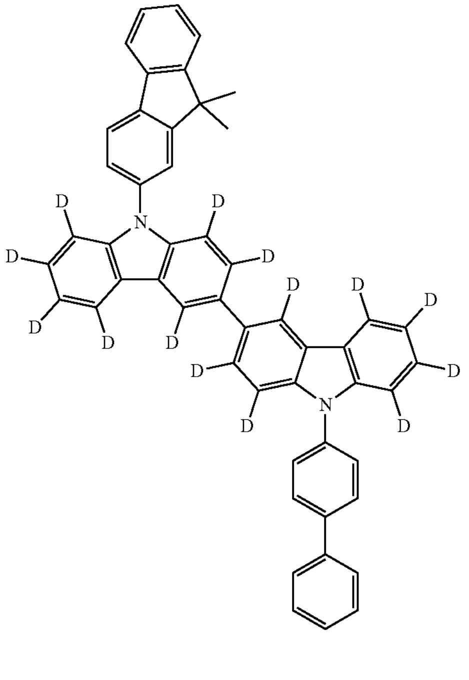

-continued
2-49
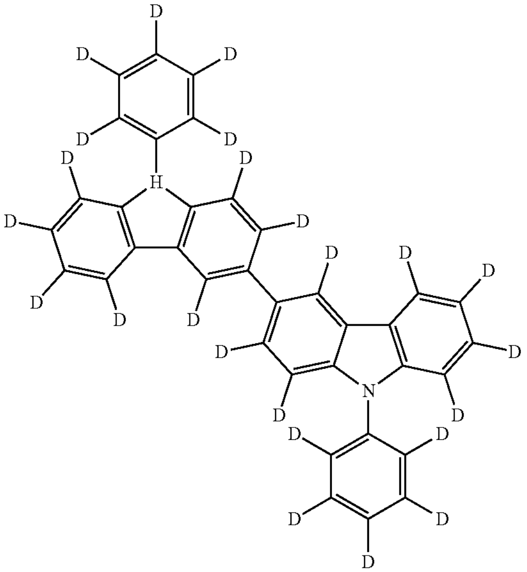
2-50
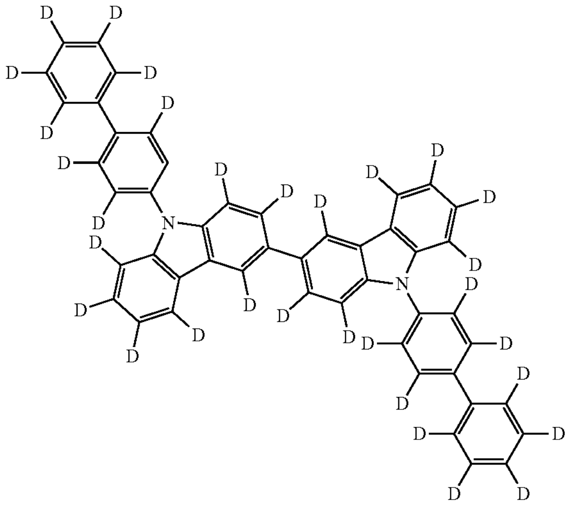
2-51
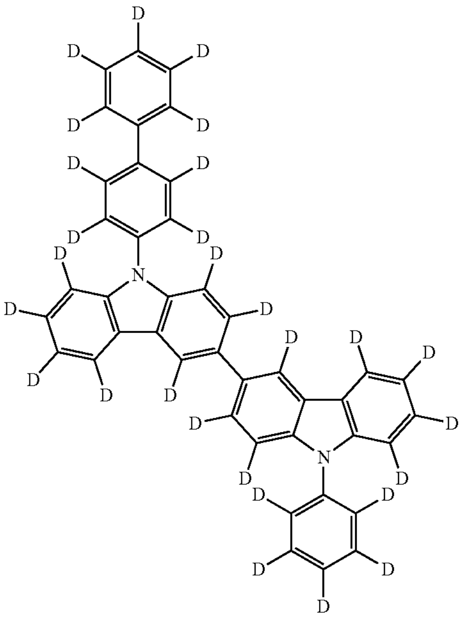
2-52
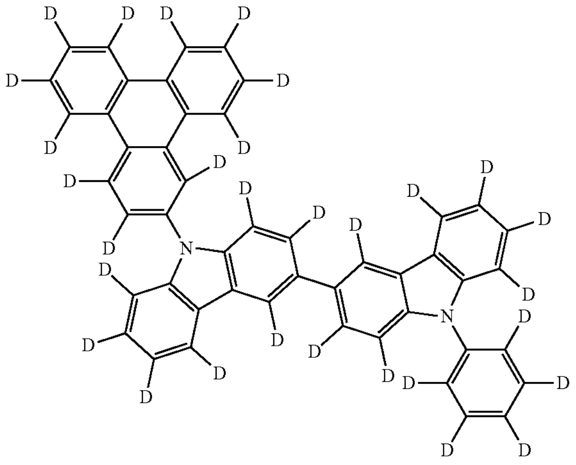

-continued
2-53
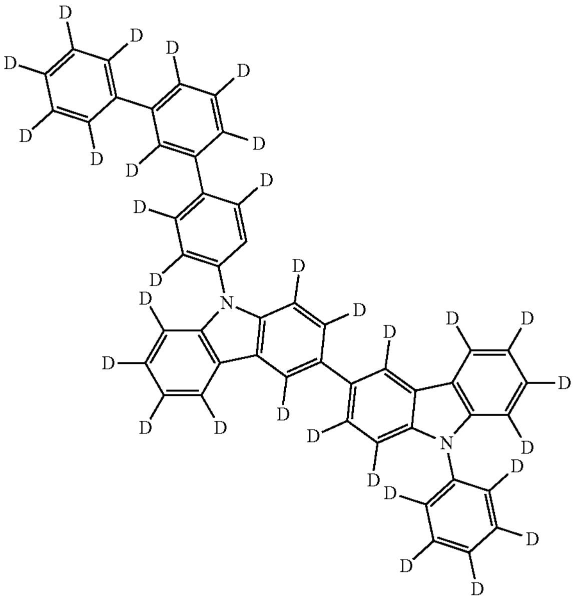
2-54
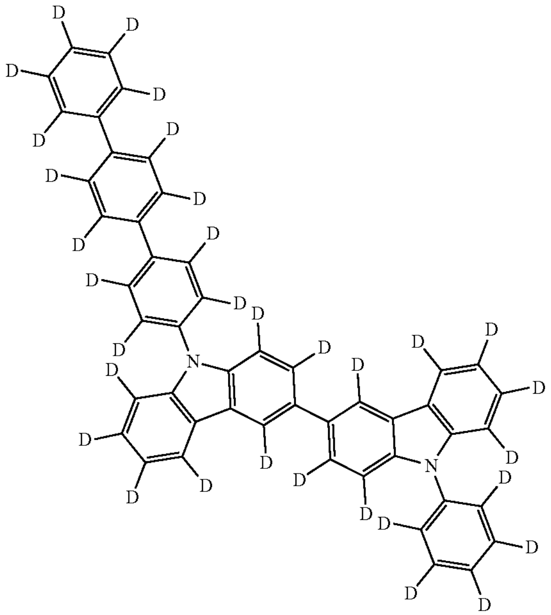
2-55
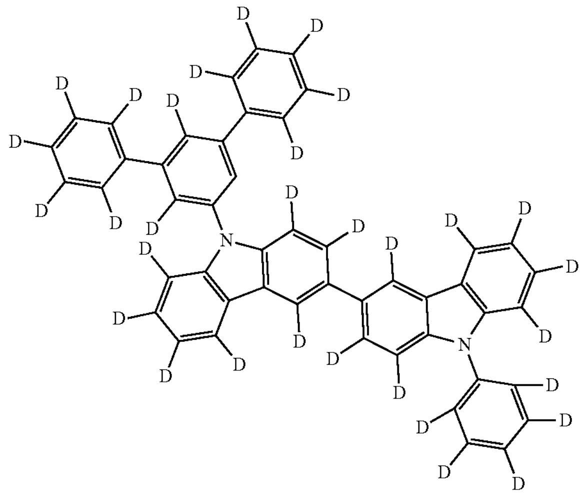
2-56
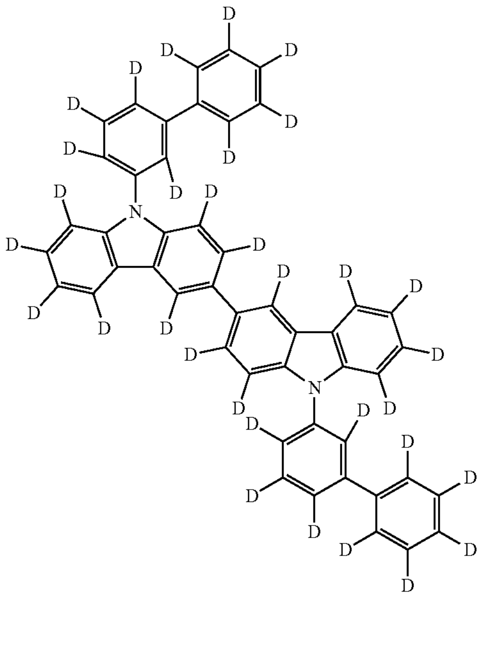

-continued
2-57
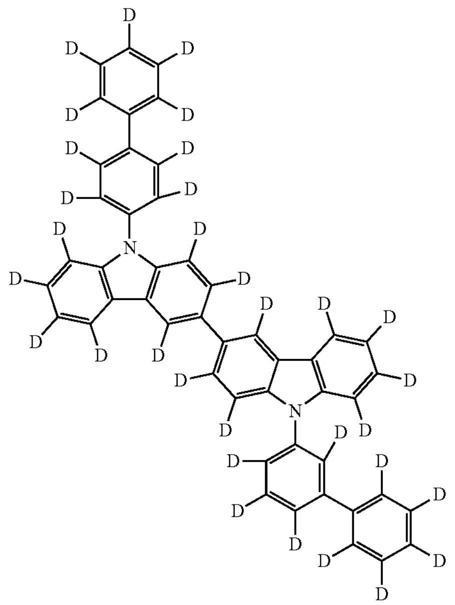
2-58
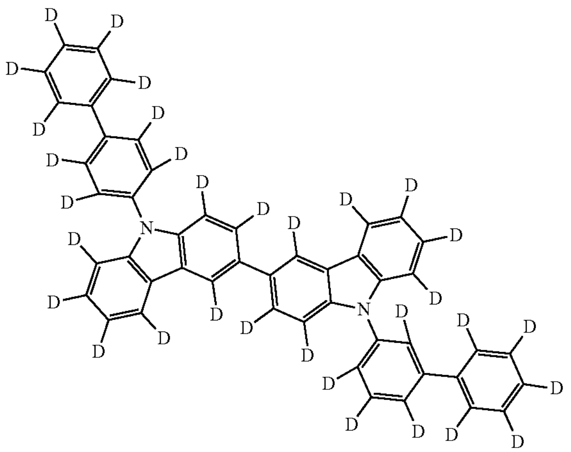
2-59
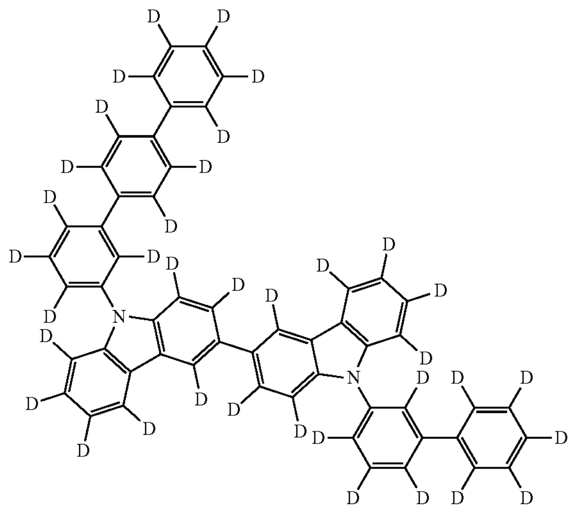
2-60
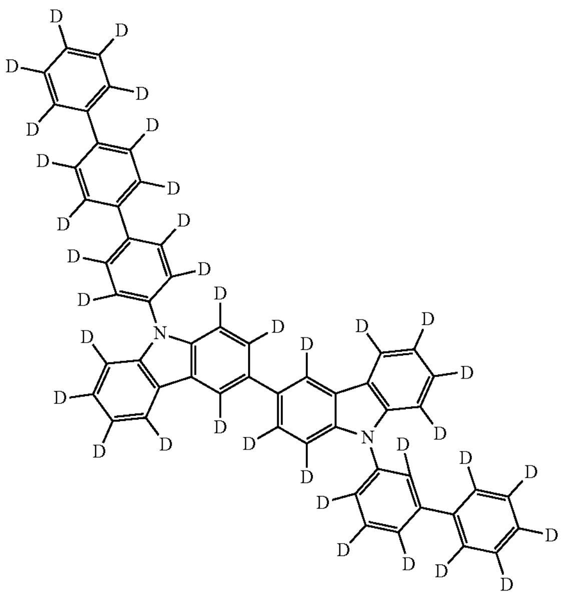

-continued
2-61
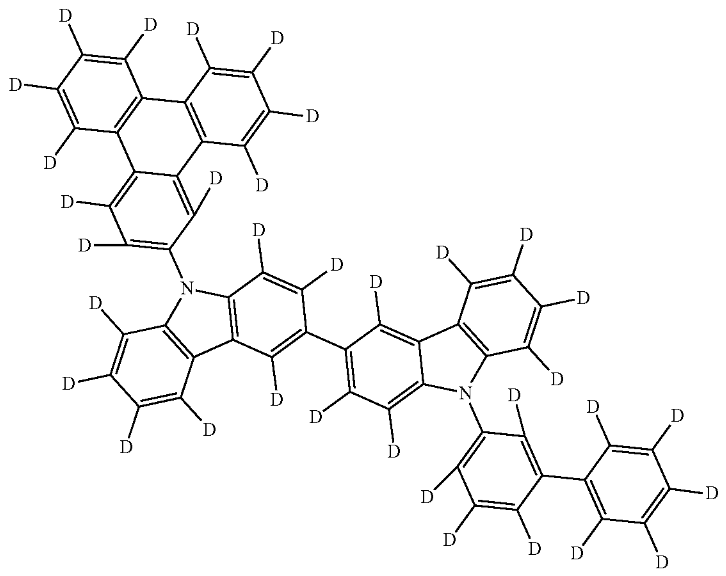
2-62
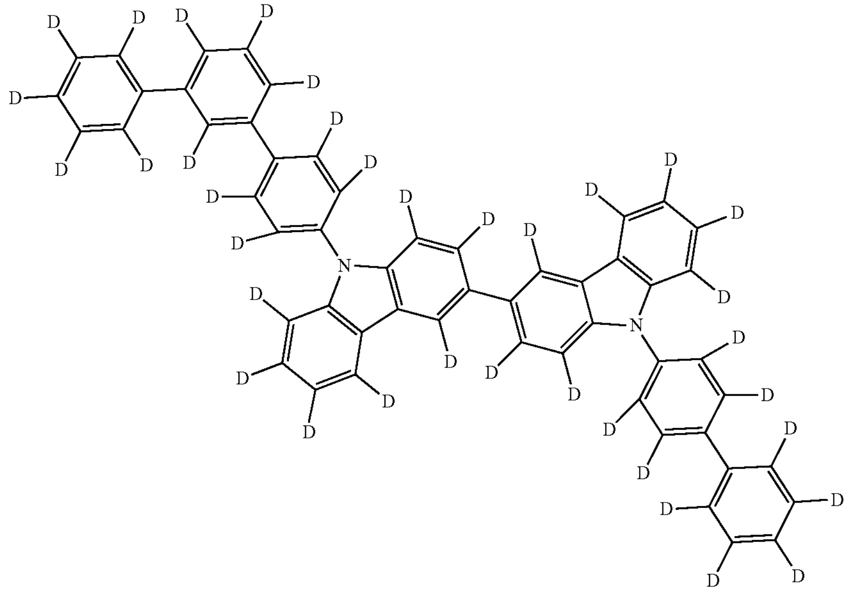

-continued
2-63
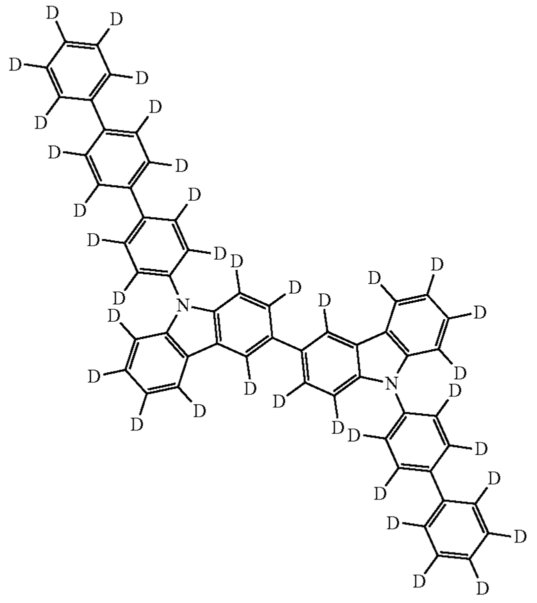
2-64
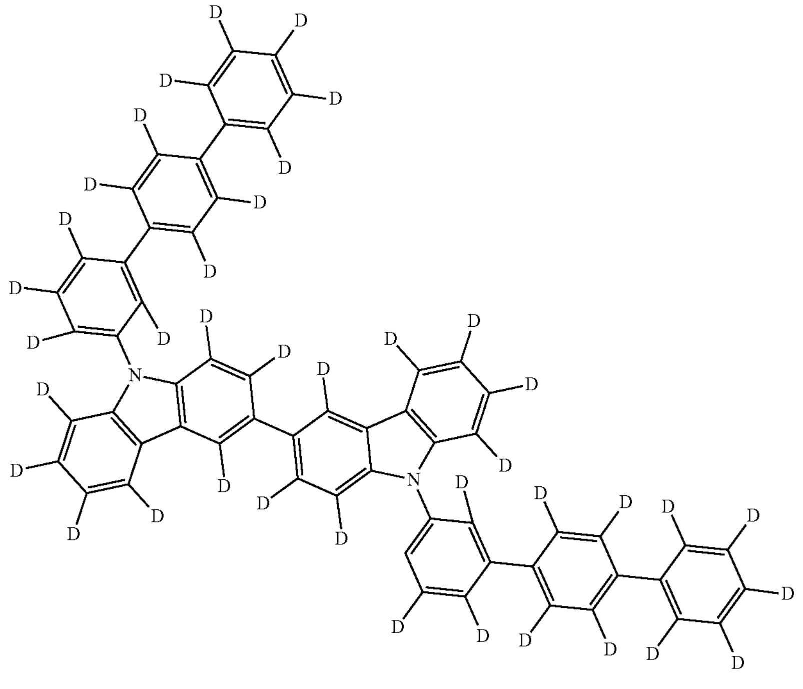

-continued
2-65
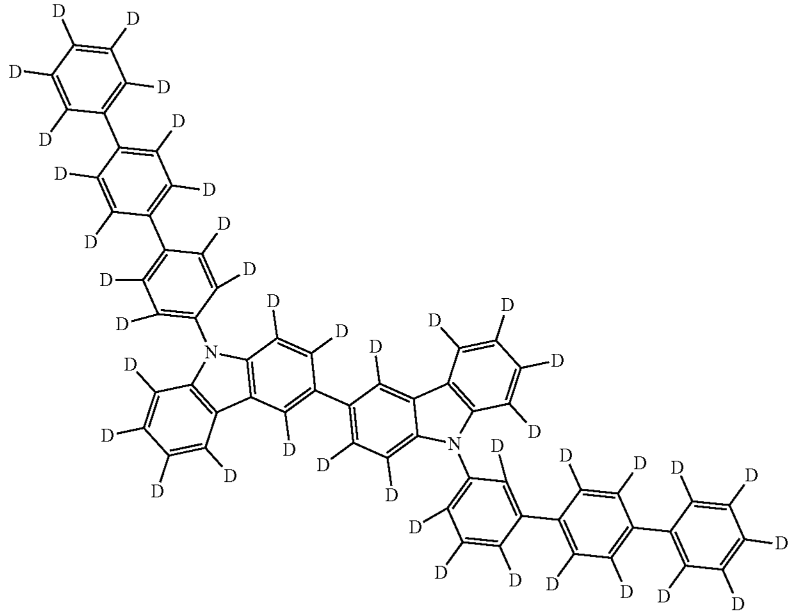
2-66
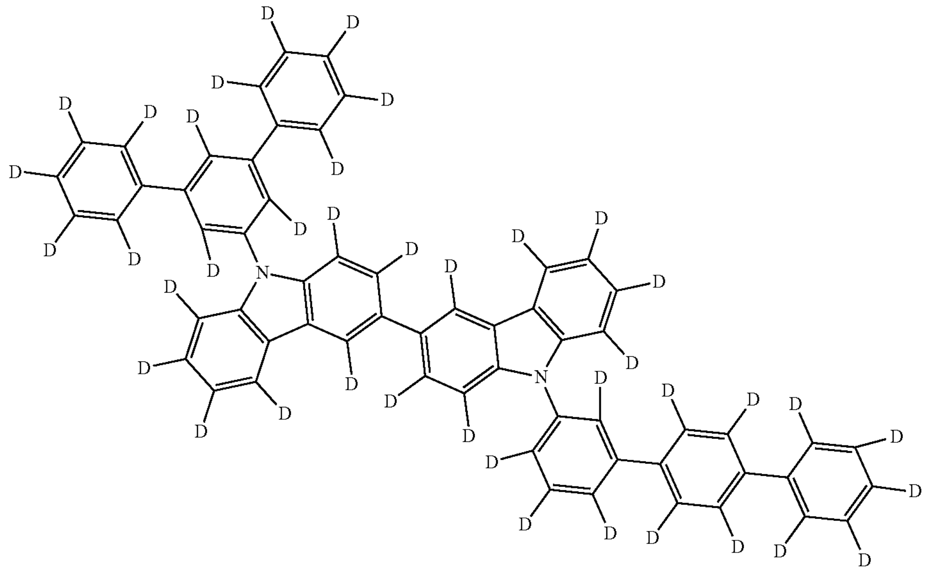

-continued
2-67
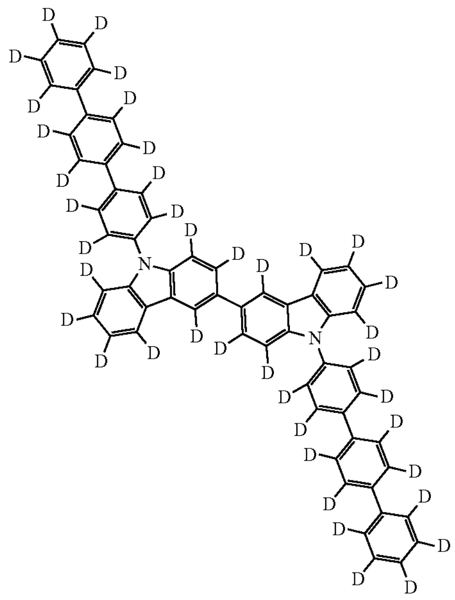
2-68
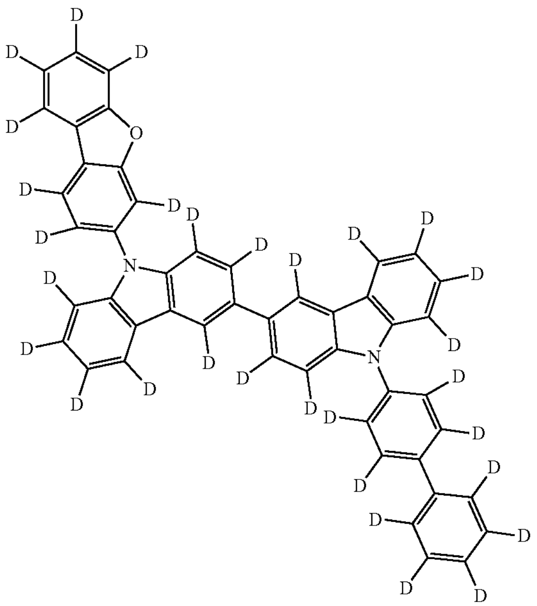
2-69
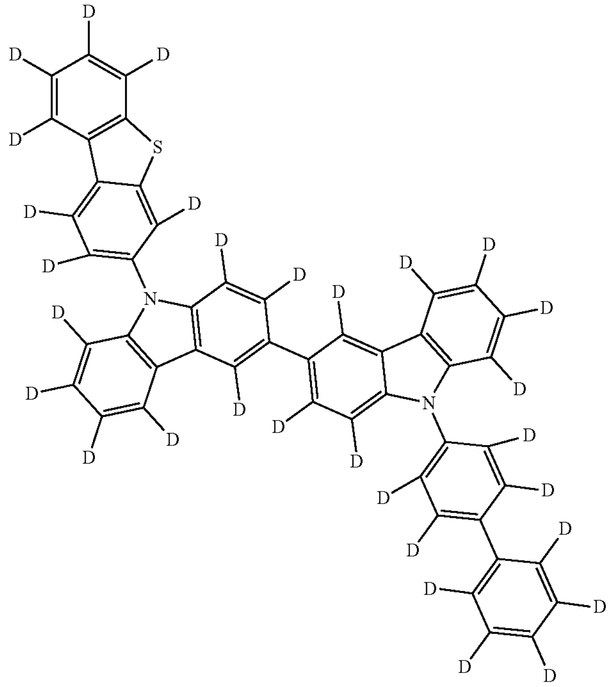

-continued
2-70
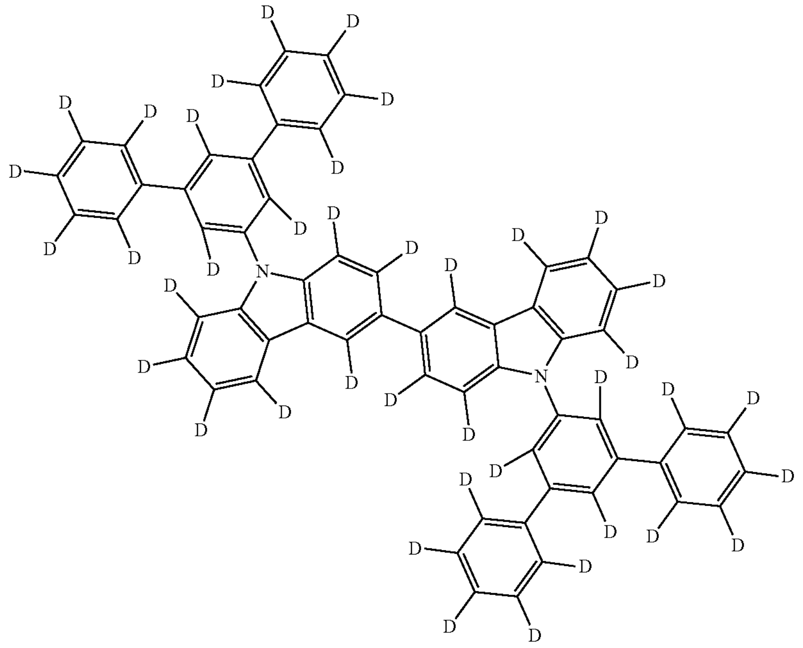
2-71
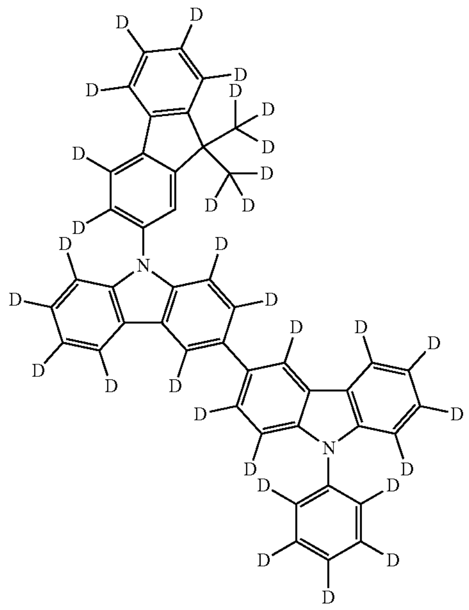
2-72
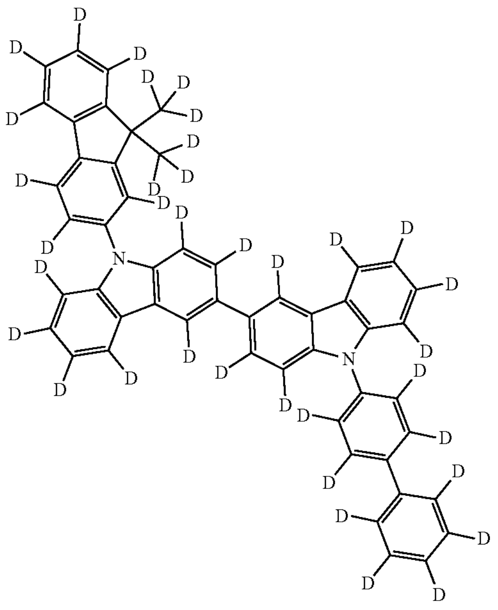

-continued
2-73
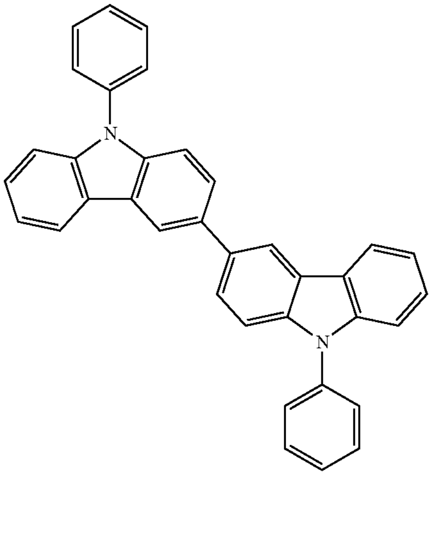
2-74
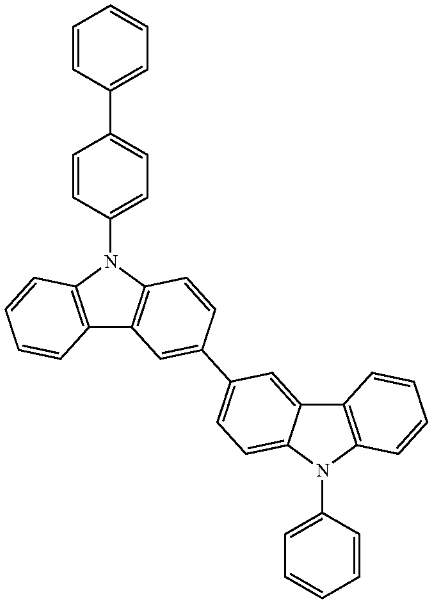
2-75
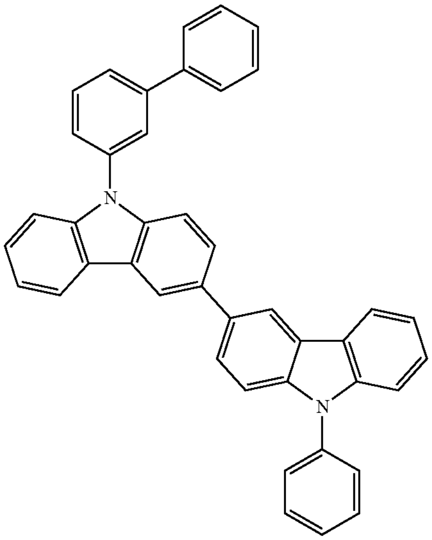
2-76
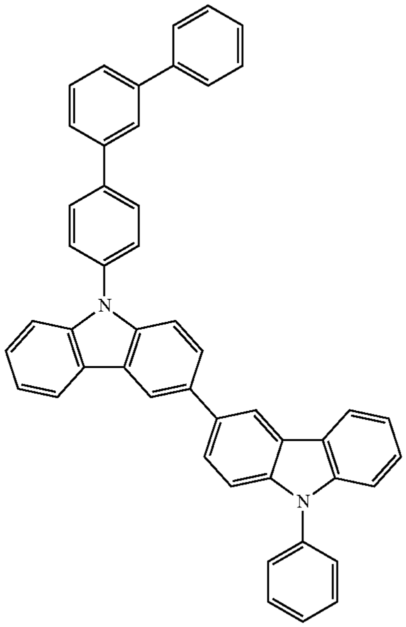

-continued
2-77
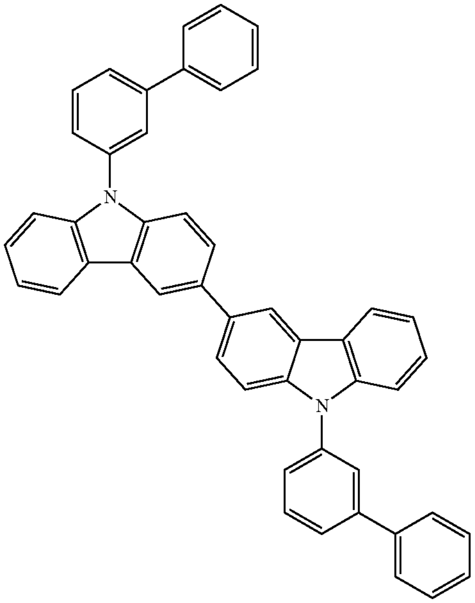
2-78
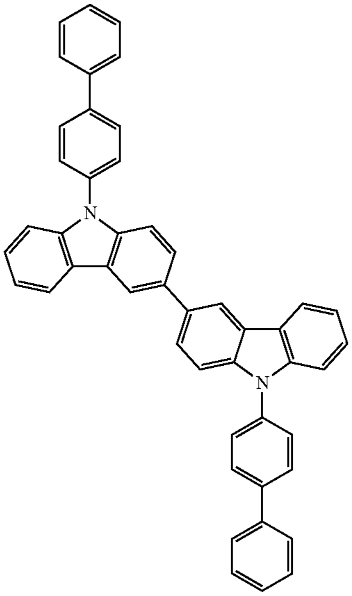
2-79
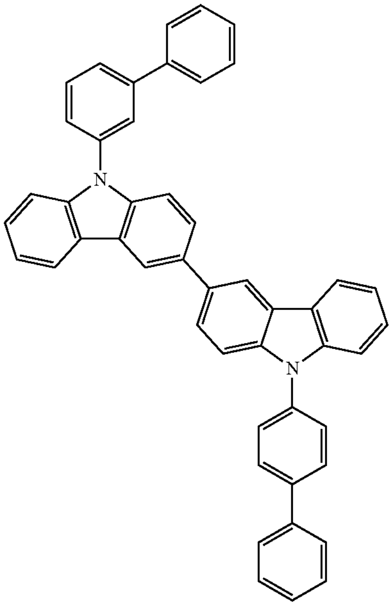
2-80
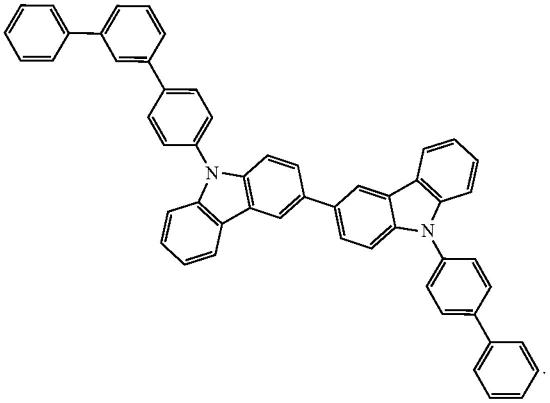

7. The organic light emitting device of claim 5, wherein Chemical Formula 2 has a deuterium content of 0%, 100%, or 10% to 80%.

8. The organic light emitting device of claim 4, wherein the organic material layer comprises a light emitting layer, and the light emitting layer comprises the heterocyclic compound of Chemical Formula 1.

9. The organic light emitting device of claim 4, wherein the organic material layer comprises a light emitting layer, the light emitting layer comprises a host material, and the host material comprises the heterocyclic compound.

10. The organic light emitting device of claim 4, further comprising one, two or more layers selected from the group consisting of a light emitting layer, a hole injection layer, a hole transfer layer, an electron injection layer, an electron transfer layer, an electron blocking layer and a hole blocking layer.

11. A composition for an organic material layer of an organic light emitting device, the composition comprising:

the heterocyclic compound of claim 1; and a heterocyclic compound represented by the following Chemical Formula 2:

[Chemical Formula 2]

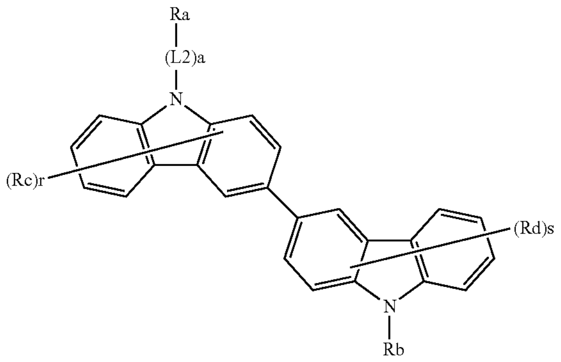

wherein, in Chemical Formula 2,

Rc and Rd are the same as or different from each other, and each independently selected from the group consisting of hydrogen; deuterium; halogen; a cyano group; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; —SiRR'R"; —P(═O)RR'; and —NRR', or two or more groups adjacent to each other bond to each other to form a substituted or unsubstituted aromatic hydrocarbon ring or a substituted or unsubstituted heteroring;

L2 is a direct bond; a substituted or unsubstituted C6 to C60 arylene group; or a substituted or unsubstituted C2 to C60 heteroarylene group;

Ra and Rb are the same as or different from each other, and each independently —CN; —SiRR'R"; a substituted or unsubstituted C6 to C60 aryl group; or a substituted or unsubstituted C2 to C60 heteroaryl group;

R, R' and R" are the same as or different from each other, and each independently hydrogen; deuterium; a substituted or unsubstituted C1 to C60 alkyl group; or a substituted or unsubstituted C6 to C60 aryl group;

a is an integer of 0 to 4;

r and s are an integer of 0 to 7; and when a, s and r are 2 or greater, substituents in the parentheses are the same as or different from each other.

12. The composition for an organic material layer of an organic light emitting device of claim 11, wherein, in the composition, the heterocyclic compound: the heterocyclic compound represented by Chemical Formula 2 have a weight ratio of 1:10 to 10:1.

* * * * *